(12) United States Patent
De Vicente Fidalgo et al.

(10) Patent No.: US 11,203,600 B2
(45) Date of Patent: Dec. 21, 2021

(54) KINASE INHIBITORS AND USES THEREOF

(71) Applicant: Denali Therapeutics Inc., South San Francisco, CA (US)

(72) Inventors: Javier De Vicente Fidalgo, South San Francisco, CA (US); Anthony A. Estrada, South San Francisco, CA (US); Jianwen A. Feng, South San Francisco, CA (US); Brian Fox, South San Francisco, CA (US); Cinzia Maria Francini, Verona (IT); Christopher R. H. Hale, South San Francisco, CA (US); Cheng Hu, South San Francisco, CA (US); Colin Philip Leslie, Verona (IT); Maksim Osipov, South San Francisco, CA (US); Elena Serra, Verona (IT); Zachary K. Sweeney, South San Francisco, CA (US); Arun Thottumkara, South San Francisco, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 16/684,340

(22) Filed: Nov. 14, 2019

(65) Prior Publication Data

US 2020/0087319 A1    Mar. 19, 2020

Related U.S. Application Data

(63) Continuation of application No. PCT/US2018/033266, filed on May 17, 2018.

(60) Provisional application No. 62/507,698, filed on May 17, 2017, provisional application No. 62/664,895, filed on Apr. 30, 2018.

(51) Int. Cl.
| | |
|---|---|
| *A61K 31/553* | (2006.01) |
| *A61P 43/00* | (2006.01) |
| *C07D 498/04* | (2006.01) |
| *C07D 223/16* | (2006.01) |
| *C07D 267/04* | (2006.01) |
| *C07D 267/14* | (2006.01) |
| *C07D 413/14* | (2006.01) |
| *C07D 519/00* | (2006.01) |

(52) U.S. Cl.
CPC ......... *C07D 498/04* (2013.01); *C07D 223/16* (2013.01); *C07D 267/04* (2013.01); *C07D 267/14* (2013.01); *C07D 413/14* (2013.01); *C07D 519/00* (2013.01)

(58) Field of Classification Search
CPC ...... A61K 31/553; A61P 43/00; C07D 498/04
See application file for complete search history.

(56) References Cited

U.S. PATENT DOCUMENTS

| | | |
|---|---|---|
| 8,586,732 B2 | 11/2013 | Corkey et al. |
| 2003/0186969 A1 | 10/2003 | Nakagawa et al. |
| 2014/0100216 A1 | 4/2014 | Savchuk et al. |
| 2016/0221973 A1 | 8/2016 | Zheng et al. |
| 2016/0222028 A1 | 8/2016 | Zheng et al. |

FOREIGN PATENT DOCUMENTS

| | | | |
|---|---|---|---|
| WO | 2014125444 A1 | 8/2014 | |
| WO | 2016185423 A1 | 11/2016 | |
| WO | WO-2016202253 A1 * | 12/2016 | ........... C07D 233/60 |

OTHER PUBLICATIONS

CAPLUS printout of RN 1785487-41-3, 2015.*
CAPLUS printout of RN 1780927-63-0, 2015.*
CAPLUS printout of RN 2055654-91-4, 2017.*
International Search Report and Written Opinion of International Application No. PCT/US2018/033266, dated Aug. 8, 2018 (9 pages).
Compound Summary for CID 63122636, PubChem, dated Aug. 11, 2018 (available from https://pubchem.ncbi.nlm.nih.gov/compound/63122636), 10 pages.
Blackburn et al., "Potent Histone Deacetylase Inhibitors Derived from 4-(Aminomethyl)-N-hydroxybenzamide with High Selectivity for the HDAC6 Isoform," J. Med. Chem. 2013, 56(18), pp. 7201-7211.
ACS Registration No. 1940092-22-7 (Jun. 27, 2016).
ACS Registration No. 1946268-10-5 (Jul. 6, 2016).
ACS Registration No. 1949684-77-8 (Jul. 11, 2016).
ACS Registration No. 1955032-20-8 (Jul. 19, 2016).
ACS Registration No. 2094850-41-4 (May 3, 2017).
CAS Registration No. 1920040-60-3 (May 29, 2016).
CAS Registration No. 1940092-21-6 (Jun. 27, 2016).
Harris et al., "Discovery of a First-in-Class receptor interacting protein 1 (RIP1) kinase specific clinical candidate (GSK2982772) for the treatment of inflammatory disease", Journal of Medicinal Chemistry, vol. 60, pp. 1247-1261 (Feb. 2, 2017).
Supplementary European Search Report in corresponding European Patent Application No. 18802127.3, dated Jun. 17, 2021 (14 pages).

\* cited by examiner

*Primary Examiner* — Brenda L Coleman
(74) *Attorney, Agent, or Firm* — McNeill Baur PLLC

(57) ABSTRACT

The present disclosure relates generally to compounds and compositions, intermediates, processes for their preparation, and their use as kinase inhibitors.

24 Claims, No Drawings

KINASE INHIBITORS AND USES THEREOF

CROSS REFERENCE TO RELATED APPLICATIONS

This application is a United States non-provisional continuation application filed under 35 U.S.C. § 111(a) of International Patent Application No. PCT/US2018/033266, filed on May 17, 2018, which claims priority under 35 U.S.C. § 119(e) of U.S. Provisional Application No. 62/507,698, filed May 17, 2017, and U.S. Provisional Application No. 62/664,895, filed on Apr. 30, 2018. The entire contents of each of these applications are incorporated by reference in their entirety into this application.

BACKGROUND

Although inflammation can be a protective mechanism in response to harmful stimuli such as invasion of pathogens and tissue damages, chronic inflammation is an important underlying factor in many human diseases such as neurodegeneration, rheumatoid arthritis, autoimmune and inflammatory diseases, and cancer. Similarly, the activation of cell death pathways, such as necrosis and apoptosis which are useful in eliminating infected or damaged cells, is also an important underlying mechanism for human diseases, including acute and chronic neurodegenerative diseases.

Receptor-interacting protein kinase 1 (UniProtKB Q13546) is a key regulator of inflammation, apoptosis and necroptosis. Receptor-interacting protein kinase 1 has an important role in modulating inflammatory responses mediated by nuclear-factor kappa-light chain enhancer of activated B cells (NF-κB). More recent research has shown that its kinase activity controls necroptosis, a form of necrotic cell death, which was traditionally thought to be passive and unregulated, and is characterized by a unique morphology. Further, receptor-interacting protein kinase 1 is part of a pro-apoptotic complex indicating its activity in regulating apoptosis.

The receptor-interacting protein kinase 1 is subject to complex and intricate regulatory mechanisms, including ubiquitylation, deubiquitylation, and phosphorylation. These regulatory events collectively determine whether a cell will survive and activate an inflammatory response or die through apoptosis or necroptosis. Dysregulation of receptor-interacting protein kinase 1 signaling can lead to excessive inflammation or cell death, and conversely, research has shown that inhibition of receptor interacting protein kinase 1 can be effective therapies for diseases involving inflammation or cell death.

DESCRIPTION

In one aspect, provided herein are compounds that are useful as inhibitors of receptor-interacting protein kinase 1.

In another aspect provided are methods for making the compounds and intermediates thereof.

In a related aspect, provided herein is a pharmaceutical composition comprising a compound as described herein and a pharmaceutically acceptable excipient.

In another aspect, provided herein is a method of inhibiting a receptor-interacting protein kinase 1. Further provided are methods for treating a receptor-interacting protein kinase 1-mediated disease or disorder comprising administering a therapeutically effective amount of a compound or a pharmaceutical composition as described herein to a subject in need thereof. The disclosure also provides uses of the compounds or compositions thereof in the manufacture of a medicament for the treatment of a disease, disorder or condition that is mediated by (or mediated, at least in part, by) receptor-interacting protein kinase.

I. DEFINITIONS

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. Unless otherwise specified, "substituted alkyl" groups can be substituted with one or more halo, hydroxy, amino, alkylamino, amido, acyl, nitro, cyano, and/or alkoxy groups.

As used herein, the term "alkoxy," by itself or as part of another substituent, refers to a group having the formula —OR, wherein R is alkyl.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Unless otherwise specified, "substituted cycloalkyl" groups can be substituted with one or more halo, hydroxy, amino, alkylamino, amido, acyl, nitro, cyano, and/or alkoxy groups. The term "lower cycloalkyl" refers to a cycloalkyl radical having from three to seven carbons including, for example, cyclopropyl, cyclobutyl, cyclopentyl, cyclohexyl, and cycloheptyl.

As used herein, the term "heteroalkyl," by itself or as part of another substituent, refers to an alkyl group of any suitable length and having from 1 to 3 heteroatoms such as N, O and S, provided that the attachment of the substituent is at a carbon atom. For example, heteroalkyl can include ethers, thioethers and alkyl-amines Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen of the alkyl group to form a hydroxy, thio, or amino group. Alternatively, the heteroatom portion can be inserted between two carbon atoms.

As used herein, the term "alkenyl," by itself or as part of another substituent, refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted. Unless otherwise specified, "substituted alkenyl" groups can be substituted with one or more halo, hydroxy, amino, alkylamino, amido, acyl, nitro, cyano, and/or alkoxy groups.

As used herein, the term "alkynyl," by itself or as part of another substituent, refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted. Unless otherwise specified, "substituted alkynyl" groups can be substituted with one or more halo, hydroxy, amino, alkylamino, amido, acyl, nitro, cyano, and/or alkoxy groups.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Unless otherwise specified, "substituted aryl" groups can be substituted with one or more halo, hydroxy, amino, alkylamino, amido, acyl, nitro, cyano, and/or alkoxy groups.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are heteroatoms such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of heteroatoms can be included in the heteroaryl groups, such as 1, 2, 3, 4; or 5, or 1 to 2, 1 to 3, 1 to 4, 1 to 5, 2 to 3, 2 to 4, 2 to 5, 3 to 4, or 3 to 5. For example, heteroaryl groups can be $C_{5-8}$ heteroaryl, wherein 1 to 4 carbon ring atoms are replaced with heteroatoms; or $C_{5-8}$ heteroaryl, wherein 1 to 3 carbon ring atoms are replaced with heteroatoms; or $C_{5-6}$ heteroaryl, wherein 1 to 4 carbon ring atoms are replaced with heteroatoms; or $C_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Unless otherwise specified, "substituted heteroaryl" groups can be substituted with one or more halo, hydroxy, amino, alkylamino, amido, acyl, nitro, cyano, and/or alkoxy groups.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6- pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. Unless otherwise specified, "substituted heterocyclyl" groups can be substituted with one or more halo, hydroxy, amino, oxo (═O), alkylamino, amido, acyl, nitro, cyano, and/or alkoxy.

The heterocyclyl groups can be linked via any position on the ring. For example, aziridine can be 1- or 2-aziridine, azetidine can be 1- or 2- azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5- isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "carbonyl," by itself or as part of another substituent, refers to —(O)—, i.e., a carbon atom double-bonded to oxygen and bound to two other groups in the moiety having the carbonyl.

As used herein, the term "amino" refers to a moiety —NR$_2$, wherein each R group is H or alkyl. An amino moiety can be ionized to form the corresponding ammonium cation. "Dialkylamino" refers to an amino moiety wherein each R group is alkyl.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O═).

As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present disclosure include, but are not limited to, binders, fillers, disintegrants, lubricants, glidants, coatings, sweeteners, flavors and colors.

As used herein, the term "salt" refers to acid or base salts of the compounds of the disclosed herein. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic.

Pharmaceutically acceptable salts of the acidic compounds disclosed herein are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, described herein are compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Any compound or Formula given herein, is also intended to represent unlabeled forms as well as isotopically labeled forms of the compounds (i.e., "isotopic analogs"). Isotopically labeled compounds have structures depicted by the formulas given herein except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2H$, $^3H$, $^{11}C$, $^1C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. Various isotopically labeled compounds of the present disclosure, for example those into which radioactive isotopes such as $^3H$, $^{13}C$ and $^{14}C$ are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^3H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

II. KINASE INHIBITORS

In one aspect, provided is a compound according to Formula A:

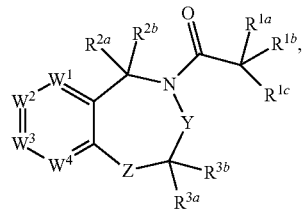

(A)

or a pharmaceutically acceptable salt, solvate, prodrug, isotopic analog, or isomer thereof, wherein $W^1$, $W^2$, $W^3$, and $W^4$ are independently N or $CR^7$;

$R^{1a}$, $R^{1b}$, and $R^{1c}$ are independently hydrogen, halogen, —CN, —$N_3$, —$NO_2$, —OH, —$SF_5$, —$SCF_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, $C_{1-8}$ haloalkoxy, 4- to 12-membered heterocyclyl, $C_{6-10}$ aryl, 5- to 12-membered heteroaryl, —$N(R^{1d})_2$, —$C(O)R^{1e}$, —$C(O)OR^{1d}$, —$C(O)N(R^{1d})_2$, —$NR^{1d}C(O)R^{1e}$, —$NR^{1d}C(O)N(R^{1d})_2$, —$NR^{1d}C(O)OR^{1d}$, —$OC(O)N(R^{1d})_2$, —$OC(O)OR^{1d}$, —$SR^{1d}$, —$S(O)R^{1e}$, —$S(O)_2R^{1e}$, —$S(O)_3R^{1d}$, —$S(O)N(R^{1d})_2$, —$S(O)_2N(R^{1d})_2$, —$NR^{1d}S(O)R^{1e}$, —$NR^{1d}S(O)_2R^{1e}$, —$NR^{1d}S(O)N(R^{1d})_2$, or —$NR^{1d}S(O)_2N(R^{1d})_2$, wherein each of $R^{1a}$, $R^{1b}$, and $R^{1c}$ is optionally and independently substituted with one or more (e.g., one to eight) $R^5$ and at least one of $R^{1a}$, $R^{1b}$, and $R^{1c}$ is other than hydrogen; or $R^{1b}$ and $R^{1c}$ are optionally taken together to form $C_{3-10}$ cycloalkyl or 4- to 12-membered heterocyclyl, each of which is optionally substituted with one or more (e.g., one to eight) $R^5$; or $R^{1a}$, $R^{1b}$, and $R^{1c}$ are optionally taken together to form $C_{5-10}$ cycloalkyl or 5- to 12-membered heterocyclyl, each which is optionally substituted with one or more (e.g., one to eight) $R^5$; or $R^{1a}$ is absent and $R^{1b}$ and $R^{1c}$ are taken together to form $C_{6-10}$ aryl or 5- to 12-membered heteroaryl or 5- to 12-membered heterocyclyl, each of which is optionally substituted with one or more (e.g., one to eight) $R^5$;

each $R^{1d}$ is independently hydrogen, $C_{1-8}$ alkyl, $C_{1-8}$ haloalkyl, $C_{3-10}$ cycloalkyl, or 4- to 12-membered heterocyclyl, or two $R^{1d}$ on the same atom are optionally taken together to form a 4- to 8-membered heterocyclyl optionally substituted by oxo, halo, or $C_{1-6}$ alkyl, wherein said alkyl is optionally substituted with one or more (e.g., one to eight) $R^5$;

each $R^{1e}$ is independently $C_{1-8}$ alkyl, $C_{1-8}$ haloalkyl, $C_{3-10}$ cycloalkyl, or 4- to 12-membered heterocyclyl;

$R^{2a}$ and $R^{2b}$ are independently hydrogen, halogen, $C_{1-8}$ alkyl, $C_{1-8}$ haloalkyl, $C_{2-8}$ alkenyl, or $C_{2-8}$ alkynyl, or $R^{2a}$ and $R^{2b}$ are optionally taken together to form $C_{3-6}$ cycloalkyl or 4- to 6-membered heterocyclyl, each of which is optionally substituted with one or more (e.g., one to eight) $R^6$;

$R^{3a}$ and $R^{3b}$ are independently hydrogen, halogen, $C_{1-8}$ alkyl, $C_{2-8}$ alkenyl, $C_{2-8}$ alkynyl, or $C_{3-6}$ cycloalkyl, or 4- to 6-membered heterocyclyl, wherein said cycloalkyl and said heterocyclyl are optionally substituted with one or more (e.g., one to eight) $R^6$, or $R^{3a}$ and $R^{3b}$ are optionally taken together to form oxo, $C_{3-6}$ cycloalkyl, or 4- to 6-membered heterocyclyl, wherein said cycloalkyl and said heterocyclyl are optionally substituted with one or more (e.g., one to eight) $R^6$;

Y is O, C(O), S, S(O), $S(O)_2$, $CR^{4a}R^{4b}$, or $NR^{4c}$;

$R^{4a}$ and $R^{4b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one or more (e.g., one to eight) $R^6$, or $R^{4a}$ and $R^{4b}$ are optionally taken together to form $C_{3-6}$ cycloalkyl or 4- to 6-membered heterocyclyl, wherein said cycloalkyl and said heterocyclyl are optionally substituted with one or more (e.g., one to eight) $R^6$, or $R^{4a}$ and $R^{1b}$ are optionally taken together to form 4- to 12-membered heterocyclyl, which is optionally substituted with one or more (e.g., one to eight) $R^6$, or $R^{4a}$ and $R^{3a}$ are optionally taken together to form $C_{3-8}$ cycloalkyl or 4- to 12-membered heterocyclyl, each of which is optionally substituted with one or more (e.g., one to eight) $R^6$, or $R^{4c}$ is hydrogen, $C_{1-8}$ alkyl, $C_{1-8}$ haloalkyl, $C_{3-10}$ cycloalkyl, or 4- to 12-membered heterocyclyl;

each $R^5$ is independently halogen, —CN, —OH, —$SF_5$, —$SCF_3$, $C_{1-8}$ alkyl, $C_{2-8}$ alkenyl, $C_{2-8}$ alkynyl, $C_{1-8}$ haloalkyl, $C_{1-8}$ heteroalkyl, $C_{3-8}$ cycloalkyl, $C_{1-8}$ haloalkyl, $C_{1-8}$ alkoxy, $C_{1-8}$ haloalkoxy, 4- to 12-membered heterocyclyl, $C_{6-10}$ aryl, 5- to 12-membered heteroaryl, (4- to 12-membered heterocyclyl)($C_{1-8}$ heteroalkyl), ($C_{6-10}$ aryl)($C_{1-8}$ heteroalkyl), (5- to 12-membered heteroaryl)($C_{1-8}$ heteroalkyl), —$N(R^{5a})_2$, —$C(O)R^{5b}$, —$C(O)OR^{5a}$, —$C(O)N(R^{5a})_2$, —$NR^{5a}C(O)R^{5b}$, —$NR^{5a}C(O)N(R^{5a})_2$, —$NR^{5a}C(O)OR^{5a}$, —$OC(O)N(R^{5a})_2$, —$OC(O)OR^{5a}$, —$SR^{5a}$, —$S(O)R^{5b}$, —$S(O)_2R^{5b}$, —$S(O)_3R^{5a}$, —$S(O)N(R^{5a})_2$, —$S(O)_2N(R^{5a})_2$, —$NR^{5a}S(O)R^{5b}$, —$NR^{5a}S(O)_2R^{5b}$, —$NR^{5a}S(O)N(R^{5a}_2$, or —$NR^{5a}S(O)_2N(R^{5a})_2$, each of which is optionally substituted with one or more (e.g., one to eight) $R^{5c}$, or two $R^5$ are optionally taken together to form oxo;

each $R^{5a}$ is independently hydrogen, $C_{1-8}$ alkyl, $C_{1-8}$ haloalkyl, $C_{3-10}$ cycloalkyl, or 4- to 12-membered heterocyclyl, and each $R^{5b}$ is independently $C_{1-8}$ alkyl, $C_{1-8}$ haloalkyl, $C_{3-10}$ cycloalkyl, 4- to 12-membered heterocyclyl, or 5- to 12-membered heteroaryl;

each $R^{5c}$ is independently halogen, cyano, $C_{1-8}$ haloalkyl, $C_{1-8}$ alkyl, $C_{1-8}$ alkoxy, $C_{1-8}$ haloalkoxy, ($C_{1-8}$ alkoxy)($C_{1-8}$ alkoxy), hydroxyl, $SR^{5d}$, $N(R^{5d})_2$, $N(R^{5d})_2(C_{1-8}$ alkoxy), $C_{3-10}$ cycloalkyl, and 4- to 12-membered heterocyclyl, or two $R^{5c}$ are optionally taken together to form oxo;

each $R^{5d}$ is independently hydrogen, $C_{1-8}$ alkyl, or $C_{1-8}$ haloalkyl;

each $R^6$ is halogen, —CN, —OH, $C_{1-8}$ alkyl, $C_{1-8}$ heteroalkyl, $C_{3-8}$ cycloalkyl, $C_{1-8}$ haloalkyl, $C_{1-8}$ alkoxy, 4- to 12-membered heterocyclyl, $C_{6-10}$ aryl, 5- to 12-membered heteroaryl, —$N(R^{6a})_2$, —$C(O)R^{6b}$, —$C(O)N(R^{6a}_2)$, or —$C(O)OR^{6a}$, or two $R^6$ are taken together to form oxo;

each $R^{6a}$ is independently hydrogen, $C_{1-8}$ alkyl, or $C_{1-8}$ haloalkyl, or two $R^{6a}$ on the same atom are optionally taken together to form 4- to 6-membered heterocyclyl;

each $R^{6b}$ is independently $C_{1-8}$ alkyl or $C_{1-8}$ haloalkyl;

each $R^7$ is independently hydrogen, halogen, —CN, —N3, —NO$_2$, —SF$_5$, —SCF$_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, 4- to 12-membered heterocyclyl, $C_{6-10}$ aryl, 5- to 12-membered heteroaryl, —OR$^{7a}$, —C(O)R$^{7b}$, —N(R$^{7a}$)$_2$, —C(O)OR$^{7a}$, —C(O)N(R$^{7a}$)$_2$, —NR$^{7a}$C(O)R$^{7b}$, —NR$^{7a}$(O)N(R$^{7a}$)$_2$, —NR$^{7a}$C(O)OR$^{7a}$, —OC(O)N(R$^{7a}$)$_2$, —OC(O)OR$^{7a}$, —SR$^{7a}$, —S(O)R$^{7b}$, —S(O)$_2$R$^{7b}$, —S(O)$_3$R$^{7a}$, —S(O)N(R$^{7a}$)$_2$, —S(O)$_2$N(R$^{7a}$)$_2$, —NR$^{7a}$S(O)R$^{7b}$, NR$^{7a}$S(O)$_2$R$^{7b}$, —NR$^{7a}$S(O)N(R$^{7a}$)$_2$, or —NR$^{7a}$S(O)$_2$N(R$^{7a}$)$_2$, each of which is optionally and independently substituted with one or more (e.g., one to eight) $R^8$;

each $R^{7a}$ is independently hydrogen, $C_{1-8}$ alkyl, $C_{1-8}$ haloalkyl, $C_{3-10}$ cycloalkyl, or 4- to 12-membered heterocyclyl, or two $R^{7a}$ on the same atom are optionally taken together to form a 4- to 8-membered heterocyclyl optionally substituted by oxo, halo, or $C_{1-6}$ alkyl, wherein said alkyl is optionally substituted with one or more (e.g., one to eight) $R^8$;

each $R^{7b}$ is independently $C_{1-8}$ alkyl, $C_{1-8}$ haloalkyl, $C_{3-10}$ cycloalkyl, or 4- to 12-membered heterocyclyl;

each $R^8$ is halogen, —CN, —OH, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, 4- to 12-membered heterocyclyl, $C_{6-10}$ aryl, 5- to 12-membered heteroaryl, —N(R$^{8a}$)$_2$, —C(O)R$^{8b}$, or —C(O)OR$^{8a}$, or two $R^8$ are optionally taken together to form oxo;

each $R^{8a}$ is independently hydrogen, $C_{1-8}$ alkyl, or $C_{1-8}$ haloalkyl;

each $R^{8b}$ is independently $C_{1-8}$ alkyl or $C_{1-8}$ haloalkyl;

Z is C(R$^9$)$_2$, C(O), O, S, S(O), S(O)$_2$, S(O)NR$^9$, or NR$^9$;

each $R^9$ is independently hydrogen, $C_{1-8}$ alkyl, $C_{2-8}$ alkenyl, $C_{2-8}$ alkynyl, $C_{1-8}$ haloalkyl, $C_{3-8}$ cycloalkyl, 4- to 8-membered heterocyclyl, or —C(O)R$^{9a}$; and $R^{9a}$ is $C_{1-8}$ alkyl, $C_{1-8}$ haloalkyl, $C_{3-8}$ cycloalkyl, or 4- to 12-membered heterocyclyl, or $R^9$ and $R^{3a}$ are optionally taken together to form $C_{3-8}$ cycloalkyl or 4- to 12-membered heterocyclyl, each of which is optionally substituted with one or more (e.g., one to eight) $R^6$.

In one aspect, provided is a compound according to Formula B:

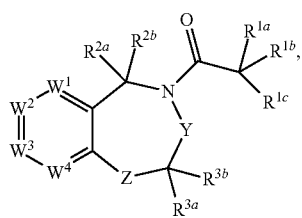

(B)

or a pharmaceutically acceptable salt, solvate, prodrug, isotopic analog, or isomer thereof, wherein $W^1$, $W^2$, $W^3$, and $W^4$ are independently N or CR$^7$;

$R^{1a}$, $R^{1b}$ and $R^{1c}$ are independently hydrogen, halogen, —CN, —N$_3$, —NO$_2$, —H, —SF$_5$, —SCF$_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, $C_{1-8}$ haloalkoxy, 4- to 12-membered heterocyclyl, $C_{6-10}$ aryl, 5- to 12-membered heteroaryl, —N(R$^{1d}$)$_2$, —C(O)R$^{1e}$, —C(O)OR$^{1d}$, —C(O)N(R$^{1d}$)$_2$, —NR$^{1d}$C(O)R$^{1e}$, —NR$^{1d}$C(O)N(R$^{1d}$)$_2$, —NR$^{1d}$C(O)OR$^{1d}$, —OC(O)N(R$^{1d}$)$_2$, —OC(O)OR$^{1d}$, —SR$^{1d}$, —S(O)R$^{1e}$, —S(O)$_2$R$^{1e}$, —S(O)$_3$R$^{1d}$, —S(O)N(R$^{1d}$)$_2$, —S(O)$_2$N(R$^{1d}$)$_2$, —NR$^{1d}$S(O)R$^{1e}$, —NR$^{1d}$S(O)$_2$R$^{1e}$, —NR$^{1d}$S(O)N(R$^{1d}$)$_2$, or —NR$^{1d}$S(O)$_2$N(R$^{1d}$)$_2$, wherein each of $R^{1a}$, $R^{1b}$, and $R^{1c}$ is optionally and independently substituted with one or more (e.g., one to eight) $R^5$ and at least one of $R^{1a}$, $R^{1b}$, and $R^{1c}$ is other than hydrogen; or $R^{1b}$ and $R^{1c}$ are optionally taken together to form $C_{3-10}$ cycloalkyl or 4- to 12-membered heterocyclyl, each of which is optionally substituted with one or more (e.g., one to eight) $R^5$; or $R^{1a}$, $R^{1b}$, and $R^{1c}$ are optionally taken together to form $C_{5-10}$ cycloalkyl, which is optionally substituted with one or more (e.g., one to eight) $R^5$; or $R^{1a}$ is absent and $R^{1b}$ and $R^{1c}$ are taken together to form $C_{6-10}$ aryl or 5- to 12-membered heteroaryl, each of which is optionally substituted with one or more (e.g., one to eight) $R^5$;

each $R^{1d}$ is independently hydrogen, $C_{1-8}$ alkyl, $C_{1-8}$ haloalkyl, $C_{3-10}$ cycloalkyl, or 4- to 12-membered heterocyclyl, or two $R^{1d}$ on the same atom are optionally taken together to form a 4- to 8-membered heterocyclyl optionally substituted by oxo, halo, or $C_{1-6}$ alkyl, wherein said alkyl is optionally substituted with one or more (e.g., one to eight) $R^5$;

each $R^{1e}$ is independently $C_{1-8}$ alkyl, $C_{1-8}$ haloalkyl, $C_{3-10}$ cycloalkyl, or 4- to 12-membered heterocyclyl;

$R^{2a}$ and $R^{2b}$ are independently hydrogen, halogen, $C_{1-8}$ alkyl, $C_{1-8}$ haloalkyl, $C_{2-8}$ alkenyl, or $C_{2-8}$ alkynyl, or $R^{2a}$ and $R^{2b}$ are optionally taken together to form $C_{3-6}$ cycloalkyl or 4- to 6-membered heterocyclyl, each of which is optionally substituted with one or more (e.g., one to eight) $R^6$;

$R^{3a}$ and $R^{3b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one or more (e.g., one to eight) $R^6$, or $R^{3a}$ and $R^{3b}$ are optionally taken together to form oxo, $C_{3-6}$ cycloalkyl, or 4- to 6-membered heterocyclyl, wherein said cycloalkyl and said heterocyclyl are optionally substituted with one or more (e.g., one to eight) $R^6$;

Y is O, C(O), S, S(O), S(O)$_2$, CR$^{4a}$R$^{4b}$, or NR$^{4c}$;

$R^{4a}$ and $R^{4b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one or more (e.g., one to eight) $R^6$, or $R^{4a}$ and $R^{4b}$ are optionally taken together to form $C_{3-6}$ cycloalkyl or 4- to 6-membered heterocyclyl, wherein said cycloalkyl and said heterocyclyl are optionally substituted with one or more (e.g., one to eight) $R^6$, or $R^{4a}$ and $R^{1b}$ are optionally taken together to form 4- to 12-membered heterocyclyl, which is optionally substituted with one or more (e.g., one to eight) $R^6$, or $R^{4a}$ and $R^{3a}$ re optionally taken together to form $C_{3-8}$ cycloalkyl or 4- to 12-membered heterocyclyl, each of which is optionally substituted with one or more (e.g., one to eight) $R^6$, or R$^{4c}$ is hydrogen, C$_{1-8}$ alkyl, C$_{1-8}$ haloalkyl, C$_{3-10}$ cycloalkyl, or 4- to 12-membered heterocyclyl;

each R$^5$ is halogen, —CN, —OH, —SF$_5$, —SCF$_3$, C$_{1-8}$ alkyl, C$_{2-8}$ alkenyl, C$_{2-8}$ alkynyl, C$_{1-8}$ heteroalkyl, C$_{3-8}$ cycloalkyl, C$_{1-8}$ haloalkyl, C$_{1-8}$ alkoxy, 4- to 12-membered heterocyclyl, C$_{6-10}$ aryl, 5- to 12-membered heteroaryl, —N(R$^{5a}$)$_2$, —C(O)R$^{5b}$, —C(O)OR$^{5a}$, —C(O)N(R$^{5a}$)$_2$, —NR$^{5a}$C(O)R$^{5b}$, —NR$^{5a}$C(O)N(R$^{5a}$)$_2$, —NR$^{5a}$C(O)OR$^{5a}$, —OC(O)N(R$^{5a}$)$_2$, —OC(O)OR$^{5a}$, —SR$^{5a}$, —S(O)R$^{5b}$, —S(O)$_2$R$^{5b}$, —S(O)$_3$R$^{5a}$, —S(O)N(R$^{5a}$)$_2$, —S(O)$_2$N(R$^{5a}$)$_2$, —NR$^{5a}$S(O)R$^{5b}$, —NR$^{5a}$S(O)$_2$R$^{5b}$, —NR$^{5a}$S(O)N(R$^{5a}$)$_2$, or —NR$^{5a}$S(O)$_2$N(R$^{5a}$)$_2$, each of which is optionally substituted with one or more (e.g., one to eight) R$^{5c}$, or two R$^5$ are optionally taken together to form oxo;

each R$^{5a}$ is independently hydrogen, C$_{1-8}$ alkyl, C$_{1-8}$ haloalkyl, C$_{3-10}$ cycloalkyl, or 4- to 12-membered heterocyclyl, and each R$^{5b}$ is independently C$_{1-8}$ alkyl, C$_{1-8}$ haloalkyl, C$_{3-10}$ cycloalkyl, or 4- to 12-membered heterocyclyl;

each R$^{5c}$ is independently halogen, C$_{1-8}$ alkyl, C$_{1-8}$ alkoxy, C$_{3-10}$ cycloalkyl, and 4- to 12-membered heterocyclyl, or two R$^{5c}$ are optionally taken together to form oxo;

each R$^6$ is halogen, —CN, —OH, C$_{1-8}$ alkyl, C$_{1-8}$ heteroalkyl, C$_{3-8}$ cycloalkyl, C$_{1-8}$ haloalkyl, C$_{1-8}$ alkoxy, 4- to 12-membered heterocyclyl, C$_{6-10}$ aryl, 5- to 12-membered heteroaryl, —N(R$^{6a}$)$_2$, —C(O)R$^{6b}$, —C(O)N(R$^{6a}$)$_2$, or —C(O)OR$^{6a}$, or two R$^6$ are taken together to form oxo;

each R$^{6a}$ is independently hydrogen, C$_{1-8}$ alkyl, or C$_{1-8}$ haloalkyl, or two R$^{6a}$ on the same atom are optionally taken together to form 4- to 6-membered heterocyclyl;

each R$^{6b}$ is independently C$_{1-8}$ alkyl or C$_{1-8}$ haloalkyl;

each R$^7$ is independently hydrogen, halogen, —CN, —N$_3$, —NO$_2$, —SF$_5$, —SCF$_3$, C$_{1-8}$ alkyl, C$_{2-8}$ alkenyl, C$_{2-8}$ alkynyl, C$_{1-8}$ heteroalkyl, C$_{3-8}$ cycloalkyl, C$_{1-8}$ haloalkyl, 4- to 12-membered heterocyclyl, C$_{6-10}$ aryl, 5- to 12-membered heteroaryl, —OR$^{7a}$, —C(O)R$^{7b}$, —N(R$^{7a}$)$_2$, —C(O)OR$^{7a}$, —C(O)N(R$^{7a}$)$_2$, —NR$^{7a}$C(O)R$^{7b}$, —NR$^{7a}$C(O)N(R$^{7a}$)$_2$,—NR$^{7a}$C(O)OR$^{7a}$, —OC(O)N(R$^{7a}$)$_2$, —OC(O)OR$^{7a}$, —SR$^{7a}$, —S(O)R$^{7b}$, —S(O)$_2$R$^{7b}$, —S(O)$_3$R$^{7a}$, —S(O)N(R$^{7a}$)$_2$, —S(O)$_2$N(R$^{7a}$)$_2$, —NR$^{7a}$S(O)R$^{7b}$, —NR$^{7a}$S(O)$_2$R$^{7b}$, —NR$^{7a}$S(O)N(R$^{7a}$)$_2$, or —NR$^{7a}$S(O)$_2$N(R$^{7a}$)$_2$, each of which is optionally and independently substituted with one or more (e.g., one to eight) R$^8$;

each R$^{7a}$ is independently hydrogen, C$_{1-8}$ alkyl, C$_{1-8}$ haloalkyl, C$_{3-10}$ cycloalkyl, or 4- to 12-membered heterocyclyl, or two R$^{7a}$ on the same atom are optionally taken together to form a 4- to 8-membered heterocyclyl optionally substituted by oxo, halo, or C$_{1-6}$ alkyl, wherein said alkyl is optionally substituted with one or more (e.g., one to eight) R$^8$;

each R$^{7b}$ is independently C$_{1-8}$ alkyl, C$_{1-8}$ haloalkyl, C$_{3-10}$ cycloalkyl, or 4- to 12-membered heterocyclyl;

each R$^8$ is halogen, —CN, —OH, C$_{1-8}$ alkyl, C$_{2-8}$ alkenyl, C$_{2-8}$ alkynyl, C$_{1-8}$ heteroalkyl, C$_{3-8}$ cycloalkyl, C$_{1-8}$ haloalkyl, C$_{1-8}$ alkoxy, 4- to 12-membered heterocyclyl, C$_{6-10}$ aryl, 5- to 12-membered heteroaryl, —N(R$^{8a}$)$_2$, —C(O)R$^{8b}$, or —C(O)OR$^{8a}$, or two R$^8$ are optionally taken together to form oxo;

each R$^{8a}$ is independently hydrogen, C$_{1-8}$ alkyl, or C$_{1-8}$ haloalkyl;

each R$^{8b}$ is independently C$_{1-8}$ alkyl or C$_{1-8}$ haloalkyl;

Z is C(R$^9$)$_2$, C(O), O, S, S(O), S(O)$_2$, S(O)NR$^9$, or NR$^9$;

each R$^9$ is independently hydrogen, C$_{1-8}$ alkyl, C$_{2-8}$ alkenyl, C$_{2-8}$ alkynyl, C$_{1-8}$ haloalkyl, C$_{3-8}$ cycloalkyl, 4- to 8-membered heterocyclyl, or C(O)R$^{9a}$; and R$^{9a}$ is C$_{1-8}$ alkyl, C$_{1-8}$ haloalkyl, C$_{3-8}$ cycloalkyl, or 4- to 12-membered heterocyclyl, or R$^9$ and R$^{3a}$ are optionally taken together to form C$_{3-8}$ cycloalkyl or 4- to 12-membered heterocyclyl, each of which is optionally substituted with one or more (e.g., one to eight) R$^6$.

In one aspect, provided is a compound according to Formula I:

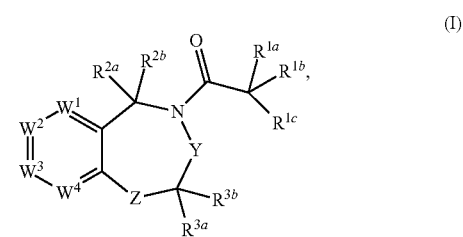

(I)

or a pharmaceutically acceptable salt, solvate, prodrug, isotopic analog, or isomer thereof, wherein W$^1$, W$^3$, and W$^4$ are CR$^7$;

W$^2$ is N or CR$^7$;

provided that when W$^2$ is CR$^7$, then either
a) W$^4$ is C—CN or
b) R$^{1a}$ is not hydrogen and R$^{1b}$ and R$^{1c}$ together form a piperidinyl ring substituted by (R$^5$)$_n$ and n is 0-9;

R$^{1a}$, R$^{1b}$, and R$^{1c}$ are independently hydrogen, halogen, —CN, —N$_3$, —NO$_2$, —OH, —SF$_5$, —SCF$_3$, C$_{1-8}$ alkyl, C$_{2-8}$ alkenyl, C$_{2-8}$ alkynyl, C$_{1-8}$ heteroalkyl, C$_{3-8}$ cycloalkyl, C$_{1-8}$ haloalkyl, C$_{1-8}$ alkoxy, C$_{1-8}$ haloalkoxy, 4- to 12-membered heterocyclyl, C$_{6-10}$ aryl, 5- to 12-membered heteroaryl, —N(R$^{1d}$)$_2$, —C(O)R$^{1d}$, —C(O)OR$^{1d}$, —C(O)N(R$^{1d}$)$_2$, —NR$^{1d}$C(O)R$^{1e}$, —NR$^{1d}$C(O)N(R$^{1d}$)$_2$, —NR$^{1d}$C(O)OR$^{1d}$, —OC(O)N(R$^{1d}$)$_2$, —OC(O)OR$^{1d}$, —SR$^{1d}$, —S(O)R$^{1e}$, —S(O)$_2$R$^{1e}$, —S(O)$_3$R$^{1d}$, —S(O)N(R$^{1d}$)$_2$, —S(O)$_2$N(R$^{1d}$)$_2$, —NR$^{1d}$S(O)R$^{1e}$, —NR$^{1d}$S(O)$_2$R$^{1e}$, —NR$^{1d}$S(O)N(R$^{1d}$)$_2$, or —NR$^{1d}$S(O)$_2$N(R$^{1d}$)$_2$, wherein each of R$^{1a}$, R$^{1b}$, and R$^{1c}$ is optionally and independently substituted with one to eight R$^5$ and at least one of R$^{1a}$, R$^{1b}$, and R$^{1c}$ is other than hydrogen; or R$^{1b}$ and R$^{1c}$ are optionally taken together to form C$_{3-10}$ cycloalkyl or 4- to 12-membered heterocyclyl, each of which is optionally substituted with one to eight R$^5$; or R$^{1a}$, R$^{1b}$, and R$^{1c}$ are optionally taken together to form C$_{5-10}$ cycloalkyl or 6- to 8-membered heterocyclyl, each of which is optionally substituted with one to eight R$^5$; or R$^{1a}$ is absent and R$^{1b}$ and R$^{1c}$ are taken together to form C$_{6-10}$ aryl or 5- to 12-membered heteroaryl, each of which is optionally substituted with one to eight R$^5$;

each R$^{1d}$ is independently hydrogen, C$_{1-8}$ alkyl, C$_{1-8}$ haloalkyl, C$_{3-10}$ cycloalkyl, or 4- to 12-membered heterocyclyl, or two R$^{1d}$ on the same atom are optionally taken together to form a 4- to 8-membered heterocyclyl optionally substituted by oxo, halo, or C$_{1-6}$ alkyl, wherein said alkyl is optionally substituted with one to eight R$^5$;

each R$^{1e}$ is independently C$_{1-8}$ alkyl, C$_{1-8}$ haloalkyl, C$_{3-10}$ cycloalkyl, or 4- to 12-membered heterocyclyl;

$R^{2a}$ and $R^{2b}$ are independently hydrogen, halogen, $C_{1-8}$ alkyl, $C_{1-7}$ haloalkyl, $C_{2-8}$ alkenyl, or $C_{2-8}$ alkynyl, or $R^{2a}$ and $R^{2b}$ are optionally taken together to form $C_{3-6}$ cycloalkyl or 4- to 6-membered heterocyclyl, each of which is optionally substituted with one to eight $R^6$;

$R^{3a}$ and $R^{3b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one to eight $R^6$, or $R^{3a}$ and $R^{3b}$ are optionally taken together to form oxo, $C_{3-6}$ cycloalkyl, or 4- to 6-membered heterocyclyl, wherein said cycloalkyl and said heterocyclyl are optionally substituted with one to eight $R^6$;

Y is O, C(O), S, S(O), $S(O)_2$, $CR^{4a}R^{4b}$, or $NR^{4c}$;

$R^{4a}$ and $R^{4b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one to eight $R^6$, or $R^{4a}$ and $R^{4b}$ are optionally taken together to form $C_{3-6}$ cycloalkyl or 4- to 6-membered heterocyclyl, wherein said cycloalkyl and said heterocyclyl are optionally substituted with one to eight $R^6$, or $R^{4a}$ and $R^{1b}$ are optionally taken together to form 4- to 12-membered heterocyclyl, which is optionally substituted with one to eight $R^6$, or $R^{4a}$ and $R^{3a}$ are optionally taken together to form $C_{3-8}$ cycloalkyl or 4- to 12-membered heterocyclyl, each of which is optionally substituted with one to eight $R^6$, or $R^{4c}$ is hydrogen, $C_{1-8}$ alkyl, $C_{1-8}$ haloalkyl, $C_{3-10}$ cycloalkyl, or 4- to 12-membered heterocyclyl;

each $R^5$ is independently halogen, —CN, —OH, —$SF_5$, —$SCF_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ alkoxy, 4- to 12-membered heterocyclyl, $C_{6-10}$ aryl, 5- to 12-membered heteroaryl, (4- to 12-membered heterocyclyl)-($C_{1-8}$ heteroalkyl), ($C_{6-10}$ aryl)($C_{1-8}$ heteroalkyl), (5- to 12-membered heteroaryl)($C_{1-8}$ heteroalkyl), —$N(R^{5a})_2$, —$C(O)R^{5b}$, —$C(O)OR^{5a}$, —$C(O)N(R^{5a})_2$, —$NR^{5a}C(O)R^{5b}$, —$NR^{5a}C(O)N(R^{5a})_2$, —$NR^{5a}C(O)OR^{5a}$, —$OC(O)N(R^{5a})_2$, —$OC(O)OR^{5a}$, —$SR^{5a}$, —$S(O)R^{5b}$, —$S(O)_2R^{5b}$, —$S(O)_3R^{5a}$, —$S(O)N(R^{5a})_2$, —$S(O)_2N(R^{5a})_2$, —$NR^{5a}S(O)R^{5b}$, —$NR^{5a}S(O)_2R^{5b}$, —$NR^{5a}S(O)N(R^{5a})_2$, or —$NR^{5a}S(O)_2N(R^{5a})_2$, each of which is optionally substituted with one to eight $R^{5c}$, or two $R^5$ are optionally taken together to form oxo;

each $R^{5a}$ is independently hydrogen, $C_{1-8}$ alkyl, $C_{1-8}$ haloalkyl, $C_{3-10}$ cycloalkyl, or 4- to 12-membered heterocyclyl, and each $R^{5b}$ is independently $C_{1-8}$ alkyl, $C_{1-8}$ haloalkyl, $C_{3-10}$ cycloalkyl, 4- to 12-membered heterocyclyl, or 5- to 12-membered heteroaryl;

each $R^{5c}$ is independently halogen, cyano, $C_{1-8}$ haloalkyl, $C_{1-8}$ alkyl, $C_{1-8}$ alkoxy, $C_{1-8}$ haloalkoxy, ($C_{1-8}$ alkoxy)($C_{1-8}$ alkoxy), hydroxyl, $SR^{5d}$, $N(R^{5d})_2$, $N(R^{5d})_2(C_{1-8}$ alkoxy), $C_{3-10}$ cycloalkyl, or 4- to 12-membered heterocyclyl, or two $R^{5c}$ are optionally taken together to form oxo;

each $R^{5d}$ is independently hydrogen, $C_{1-8}$ alkyl, or $C_{1-8}$ haloalkyl;

each $R^6$ is halogen, —CN, —OH, $C_{1-8}$ alkyl, $C_{1-8}$ heteroalkyl, $C_{3-8}$ cycloalkyl, $C_{1-8}$ haloalkyl, $C_{1-8}$ alkoxy, 4- to 12-membered heterocyclyl, $C_{6-10}$ aryl, 5- to 12-membered heteroaryl, —$N(R^{6a})_2$, —$C(O)R^{6b}$, —$C(O)N(R^{6a})_2$, or —$C(O)OR^{6a}$, or two $R^6$ are taken together to form oxo;

each $R^{6a}$ s independently hydrogen, $C_{1-8}$ alkyl, or $C_{1-8}$ haloalkyl, or two $R^a$ on the same atom are optionally taken together to form 4- to 6-membered heterocyclyl;

each $R^{6b}$ is independently $C_{1-8}$ alkyl or $C_{1-8}$ haloalkyl;

each $R^7$ is independently hydrogen, halogen, —CN, —$N_3$, —$NO_2$, —$SF_5$, —$SCF_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, 4- to 12-membered heterocyclyl, $C_{6-10}$ aryl, 5- to 12-membered heteroaryl, —$OR^{7a}$, —$C(O)R^{7b}$, —$N(R^{7a})_2$, —$C(O)OR^{7a}$, —$C(O)N(R^{7a})_2$, —$NR^{7a}C(O)R^{7b}$, —$NR^{7a}C(O)N(R^{7a})_2$, —$NR^{7a}C(O)OR^{7a}$, —$OC(O)N(R^{7a})_2$, —$OC(O)OR^{7a}$, —$SR^{7a}$, —$S(O)R^{7b}$, —$S(O)_2R^{7b}$, —$S(O)_3R^{7a}$, —$S(O)N(R^{7a})_2$, —$S(O)_2N(R^{7a})_2$, —$NR^{7a}S(O)R^{7b}$, $NR^{7a}S(O)_2R^{7b}$, —$NR^{7a}S(O)N(R^{7a})_2$, or —$NR^{7a}S(O)_2N(R^{7a})_2$, each of which is optionally and independently substituted with one to eight $R^8$;

each $R^{7a}$ is independently hydrogen, $C_{1-8}$ alkyl, $C_{1-8}$ haloalkyl, $C_{3-10}$ cycloalkyl, or 4- to 12-membered heterocyclyl, or two $R^{7a}$ on the same atom are optionally taken together to form a 4- to 8-membered heterocyclyl optionally substituted by oxo, halo, or $C_{1-6}$ alkyl, wherein said alkyl is optionally substituted with one to eight $R^8$;

each $R^{7b}$ is independently $C_{1-8}$ alkyl, $C_{1-8}$ haloalkyl, $C_{3-10}$ cycloalkyl, or 4- to 12-membered heterocyclyl;

each $R^8$ is halogen, —CN, —OH, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, 4- to 12-membered heterocyclyl, $C_{6-10}$ aryl, 5- to 12-membered heteroaryl, —$N(R^{8a})_2$, —$C(O)R^{8b}$, or —$C(O)OR^{8a}$, or two $R^8$ are optionally taken together to form oxo;

each $R^{8a}$ is independently hydrogen, $C_{1-8}$ alkyl, or $C_{1-8}$ haloalkyl;

each $R^{8b}$ is independently $C_{1-8}$ alkyl or $C_{1-8}$ haloalkyl;

Z is $C(R^9)_2$, C(O), O, S, S(O), $S(O)_2$, $S(O)NR^9$, or $NR^9$;

provided that when Z is N, then $R^{3a}$ and $R^{3b}$ are not oxo;

each $R^9$ is independently hydrogen, $C_{1-8}$ alkyl, $C_{2-8}$ alkenyl, $C_{2-8}$ alkynyl, $C_{1-8}$ haloalkyl, $C_{3-8}$ cycloalkyl, 4- to 8-membered heterocyclyl, or —$C(O)R^{9a}$; and $R^{9a}$ is $C_{1-8}$ alkyl, $C_{1-8}$ haloalkyl, $C_{3-8}$ cycloalkyl, or 4- to 12-membered heterocyclyl, or $R^9$ and $R^{3a}$ are optionally taken together to form $C_{3-8}$ cycloalkyl or 4- to 12-membered heterocyclyl, each of which is optionally substituted with one to eight $R^6$.

In some embodiments, when $R^{2a}$, $R^{2b}$, $R^{3a}$, and $R^{3b}$ are hydrogen and two of $R^{1a}$, $R^{1b}$, and $R^{1c}$ form piperidinyl or pyrrolidinyl in compounds of Formula A, Formula B, or Formula I, said piperidinyl or pyrrolidinyl is substituted with at least one $R^{1d}$ group.

In some embodiments, when $R^{2a}$, $R^{2b}$, $R^{3a}$, and $R^{3b}$ are hydrogen, $R^{1a}$ is unsubstituted methyl, $R^{1b}$ is unsubstituted methyl, chloromethyl, or unsubstituted ethyl, and $R^{1c}$ is methyl in compounds of Formula A, Formula B, and Formula I, said $R^{1c}$ is substituted with 1-3 $R^{1d}$.

In some embodiments, when $R^{2a}$, $R^{2b}$, $R^{3a}$, and $R^{3b}$ are hydrogen, $R^{1a}$ is unsubstituted aminomethyl or unsubstituted 2-aminoprop-2-yl, $R^{1b}$ is unsubstituted methyl or unsubstituted ethyl, and $R^{1c}$ is methyl or ethyl in compounds of Formula A, Formula B, and Formula I, said $R^{1c}$ is substituted with 1-4 $R^{1d}$.

In some embodiments, when $R^{3a}$ or $R^{3b}$ is methyl in compounds of Formula A, Formula B, and Formula I, at least two of $R^{1a}$, $R^{1b}$, and $R^{1c}$ are $C_{1-8}$ alkyl, $C_{1-8}$ heteroalkyl, $C_{3-8}$ cycloalkyl, $C_{6-10}$ aryl, 5- to 12-membered heterocyclyl, or 5- to 12-membered heteroaryl.

In some embodiments, $W^2$ is N in compounds of Formula A, Formula B, and Formula I.

In some embodiments, Z is O; Y is $CR^{4a}R^{4b}$; $R^{2a}$, $R^{2b}$, $R^{3a}$, $R^{3b}$, $R^{4a}$; and $R^{4b}$ are H; and $R^{1a}$, $R^{1b}$, $R^{1c}$, $R^5$, $R^7$, and $R^8$ are as defined for Formula I, Formula A, or Formula B.

In some embodiments, provided herein are compounds of Formula Ia

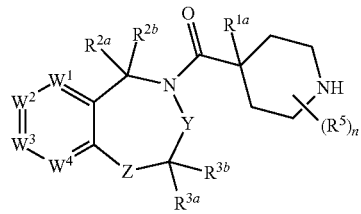

(Ia)

wherein $R^{1a}$, $R^{2a}$, $R^{b2b}$, $R^{3a}$, $R^{3b}$, $R^5$, $R^7$, $W^1$, $W^2$, $W^3$, $W^4$, Y, and Z are as defined for Formula I, Formula A, or Formula B; and n is 0-9;

provided that when $W^1$, $W^2$, $W^3$, and $W^4$ are $CR^7$, then $R^{1a}$ is not hydrogen.

In some embodiments, provided herein are compounds of Formula Ia wherein at least one of $R^5$ is 4- to 12-membered heterocyclyl or 5- to 12-membered heteroaryl, each of which is optionally substituted with one or more (e.g., one to eight) $R^{5c}$. In some embodiments, at least one of $R^5$ is a 5- to 12-membered heteroaryl optionally substituted with one or more (e.g., one to eight) $R^{5c}$. In some embodiments, at least one of $R^5$ is attached to the piperidine nitrogen.

In some embodiments, provided herein are compounds of Formula Ib

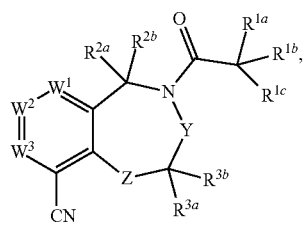

(Ib)

wherein $R^{1a}$, $R^{1b}$, $R^{1c}$, $R^{2a}$, $R^{2b}$, $R^{3a}$, $R^{3b}$, $W^1$, $W^2$, $W^3$, Y and Z are as defined for Formula I, Formula A, or Formula B.

In some embodiments, $W^2$ is N in compounds of Formula I, Formula Ia, and Formula Ib, and $W^1$, $W^3$, $W^4$ are $CR^7$. In some embodiments, $W^2$ is N in compounds of Formula I, Formula Ia, and Formula Ib, and $W^3$ is CH. In some embodiments, $W^2$ is N in compounds of Formula I, Formula Ia, and Formula Ib, and each $R^7$ is independently hydrogen, halogen, cyano, $C_{1-8}$ alkyl, $C_{1-8}$ haloalkyl, or $C_{1-8}$ alkoxy. In some embodiments $W^2$ is $CR^7$ in compounds of Formula I, Formula Ia, and Formula Ib.

In some embodiments, provided herein are compounds according to Formula Ic,

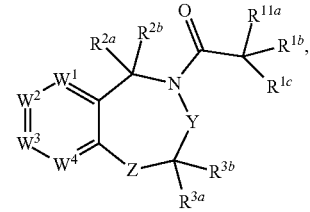

(Ic)

wherein $R^{1d}$, $R^{1e}$, $R^{2a}$, $R^{2b}$, $R^{3a}$, $R^{3b}$, $R^{4a}$, $R^5$, $R^6$, $W^1$, $W^2$, $W^3$, $W^4$, Y and Z are as defined for Formula I, Formula A, or Formula B;

$R^{11a}$ is haloalkyl;

$R^{1b}$ and $R^{1c}$ are independently —CN, $C_{1-8}$ alkyl, $C_{2-8}$ alkenyl, $C_{2-8}$ alkynyl, $C_{3-8}$ cycloalkyl, $C_{1-8}$ haloalkyl, $C_{6-10}$ aryl, 5- to 12-membered heteroaryl, —C(O)R$^{1e}$, —C(O)OR$^{1d}$, or —C(O)N(R$^{1d}$)$_2$ wherein $R^{1b}$ and $R^{1c}$ are independently substituted with one or more (e.g., one to eight) $R^5$; or $R^{1b}$ and $R^{1c}$ are optionally taken together to form $C_{3-10}$ cycloalkyl optionally substituted with one or more (e.g., one to eight) $R^5$; or $R^{1b}$ and $R^{4a}$ re optionally taken together to form 4- to 12-membered heterocyclyl, which is optionally substituted with one or more (e.g., one to eight) $R^6$; and provided that the compound is not:

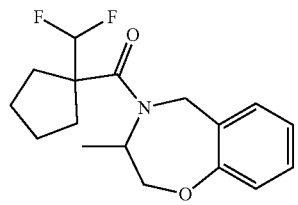

[1-(difluoromethyl)cyclopentyl](2,3-dihydro-3-methyl-1,4-benzoxazepin-4(5H)-yl)-methanone

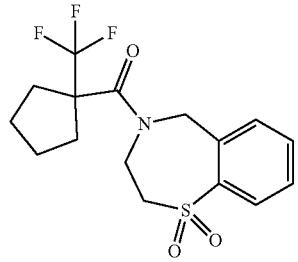

(2,3-dihydro-1,1-dioxido-1,4-benzothiazepin-4(5H)-yl)[1-(trifluoromethyl)cyclopentyl]-methanone

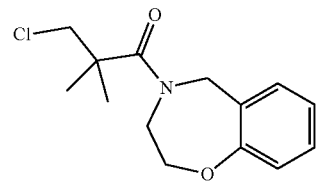

or 2-(chloromethyl)-1-(2,3-dihydro-1,4-benzoxazepin-4(5H)-yl)-2-methyl-1-propanone -continued

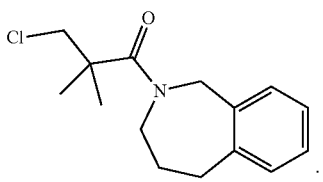

2-(chloromethyl)-2-methyl-1-(1,3,4,5-tetrahydro-2H-2-benzazepin-2-yl)-1-propanone In some embodiments, provided herein are compounds of Formula Ic wherein at least one of $W^1$, $W^2$, $W^3$, or $W^4$ is nitrogen. In some embodiments, provided herein are compound of Formula Ic wherein $R^{11a}$ is difluoromethyl.

In some embodiments, provided herein are compounds of Formula Id

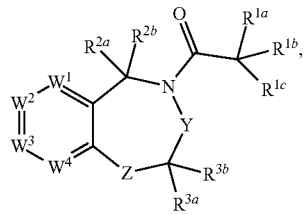

(Id)

wherein $R^{1a}$, $R^{1d}$, $R^{1e}$, $R^2$, $R^{2b}$, $R^{3a}$, $R^{3b}$, $R^{4a}$, $R^5$, $R^6$, $W^1$, $W^2$, $W^3$, $W^4$, Y and Z are as defined for Formula I, Formula A, or Formula B;

at least one of $W^1$, $W^2$, $W^3$, or $W^4$ is nitrogen (e.g., $W^1$, $W^3$, and $W^4$ are $CR^7$ and $W^2$ is N or $CR^7$);

$R^{1b}$ and $R^{1c}$ are independently —CN, $C_{1-8}$ alkyl, $C_{2-8}$ alkenyl, $C_{2-8}$ alkynyl, $C_{3-8}$ cycloalkyl, $C_{1-8}$ haloalkyl, $C_{6-10}$ aryl, 5- to 12-membered heteroaryl, —C(O)$R^{1e}$, —C(O)O$R^{1d}$, or —C(O)N($R^{1d}$)$_2$ wherein $R^{1b}$ and $R^{1c}$ are independently substituted with one or more (e.g., one to eight) $R^5$; or $R^{1b}$ and $R^{1c}$ are optionally taken together to form $C_{3-10}$ cycloalkyl optionally substituted with one or more (e.g., one to eight) $R^5$; or $R^{1b}$ and $R^{4a}$ are optionally taken together to form 4- to 12-membered heterocyclyl, which is optionally substituted with one or more (e.g., one to eight) $R^6$; or $R^{1a}$, $R^{1b}$, and $R^{1c}$ are optionally taken together form a $C_{5-10}$ cycloalkyl optionally substituted with one or more (e.g., one to eight) $R^5$; and provided that the compound is not:

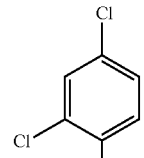

cyclopropyl[4-[[2,4-dichloro-phynyl)methyl]-amino-7, 8-dihydro-2-(methylthio)-pyrimido[5,4-f][1,4]oxazepin-6(5H)-yl]-methanone or

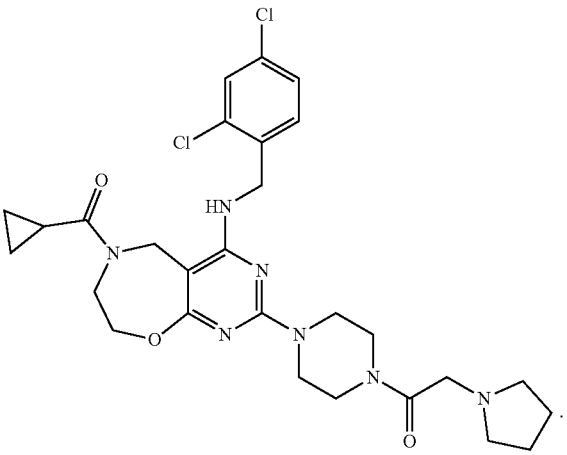

1-[4-(cyclopropyl-carbonyl)-4-[[2,4-dichlorophenyl)-methyl]amino]-5,6,7,8-tetrahydropyrimido[5,4-f][1,4]oxaxepin-2-yl]-1-piperazinyl]-2-(1-pyrrolidinyl)-ethanone In some embodiments, provided herein are compounds of Formula Id wherein two or three of $W^1$, $W^2$, $W^3$, or $W^4$ is $CR^7$, wherein $R^7$ is independently hydrogen, halogen, —CN, —N$_3$, —NO$_2$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{6-10}$ aryl, 5- to 12-membered heteroaryl, —OR$^{7a}$, —C(O)R$^{7b}$, —C(O)OR$^{7a}$, —C(O)N(R$^{7a}$)$_2$, —OC(O)N(R$^{7a}$)$_2$, or —OC(O)OR$^{7a}$, each of which is optionally and independently substituted with one or more (e.g., one to eight) $R^8$.

In some embodiments, provided herein are compounds of Formula Id wherein one of $R^{1a}$, $R^{1b}$, or $R^{1c}$ is difluoromethyl.

In some embodiments, provided herein are compounds of Formula Id wherein one of $R^{1a}$, $R^{1b}$, and $R^{1c}$ is cyclopropyl.

In some embodiments, provided herein are compounds of Formula Ie

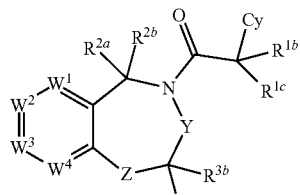

(Ie)

wherein
$R^{1b}, R^{1c}, R^{2a}, R^{2b}, R^{3a}, R^{3b}, R^5, R^7, W^1, W^2, W^3, W^4, Y$ and Z are as defined for Formula I, Formula A, or Formula B;
Cy is $C_{3-8}$ cycloalkyl, 4- to 12-membered heterocyclyl, or 5- to 12-membered heteroaryl, wherein Cy is optionally substituted with one to six substituents independently selected from halo, $C_{1-8}$ alkyl, and halo $C_{1-8}$ alkyl;
provided that when $W^1, W^2, W^3$, and $W^4$ are $CR^7$, then Cy is cyclopropyl, at least one of $R^{1b}$ or $R^{1c}$ is $C_{1-8}$ alkyl optionally substituted with one or more (e.g., one to eight) $R^5$, and at least one $R^7$ is not hydrogen.

In some embodiments, provided herein are compounds of Formula Ie wherein at least one of $W^1, W^2, W^3$, or $W^4$ is nitrogen.

In some embodiments, provided herein are compounds of Formula Ie wherein Cy is $C_{3-8}$ cycloalkyl optionally substituted with one or more (e.g., one to eight) $R^5$.

In some embodiments, provided herein are compounds according to Formula I, Formula A, Formula B, Formula Ia, Formula Ic, Formula Id, or Formula Ie, wherein $W^1$ is N. In some embodiments, provided herein are compounds according to Formula I, Formula A, Formula B, Formula Ia, Formula Ic, Formula Id, or Formula Ie, wherein $W^2$ is N. In some embodiments, provided herein are compounds according to Formula I, Formula A, Formula B, Formula Ia, Formula Ic, Formula Id, or Formula Ie, wherein $W^3$ is N. In some embodiments, provided herein are compounds according to Formula I, Formula A, Formula B, Formula Ia, Formula Ic, Formula Id, or Formula Ie, wherein $W^3$ and $W^4$ are N and $W^1$ and $W^2$ are $CR^7$. In some embodiments, provided herein are compounds according to Formula I, Formula A, Formula B, Formula Ia, Formula Ic, Formula Id, or Formula Ie, wherein $W^4$ is N and $W^1, W^2$, and $W^3$ are $CR^7$.

In some embodiments, provided herein are compounds of Formula I, wherein:
$W^2$ is N;
$W^1, W^3$, and $W^4$ are $CR^7$;
Z is O;
Y is $CR^{4a}R^{4b}$;
$R^{2a}, R^{2b}, R^{3a}, R^{3b}, R^{4a}$, and $R^{4b}$ are H; and
$R^{1a}, R^{1b}$, and $R^{1c}, R^5, R^7$, and $R^8$ are as defined as set forth above.

In some embodiments, provided herein are compounds according to Formula I, Formula A, Formula B, Formula Ia, Formula Ib, Formula Ic, Formula Id, or Formula Ie, wherein each $R^7$ is independently hydrogen, halogen, cyano, $C_{1-8}$ alkyl, $C_{1-8}$ haloalkyl, or $C_{1-9}$ alkoxy. In some embodiments, at least one $R^7$ is halo, $C_{1-6}$ alkyl, $C_{1-6}$ alkoxy, cyano, or heteroaryl. In some embodiments, at least one $R^7$ is chloro, fluoro, methyl, methoxy, cyano, bromo, triazolyl. In some embodiments, two of $R^7$ is 7-chloro, 7-methyl, 8-methoxy, 9-fluoro, 6-fluoro, 6-fluoro-9-cyano, 7-fluoro-9-cyano, 9-cyano, 6-cyano, 8-cyano, 7-fluoro-, 9-bromo-7-fluoro-, or 9-triazol-2-yl.

In some embodiments at least one $R^7$ is halo, $C_{1-6}$ alkyl, $C_{1-6}$ alkoxy, or cyano. In some embodiments, at least one $R^7$ is chloro, fluoro, methyl, methoxy, cyano, or bromo. In some embodiments, one or two of $R^7$ is 7-chloro, 7-methyl, 8-methoxy, 9-fluoro, 6-fluoro, 6-fluoro-9-cyano, 7-fluoro-9-cyano, 9-cyano, 6-cyano, 8-cyano, 7-fluoro-, or 9-bromo-7-fluoro-.

In some embodiments, provided herein are compounds according to Formula If:

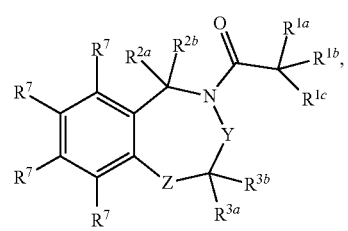

(If)

wherein
$R^{1d}, R^{1e}, R^{2a}, R^{2b}, R^{3a}, R^{3b}, R^{4a}, R^5, R^6, R^{7a}, R^{7b}, R^8, Y$, and Z are as defined for Formula I, Formula A, or Formula B;
$R^{1a}, R^{1b}$, and $R^{1c}$ are independently $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, $C_{1-8}$ haloalkoxy, $C_{6-10}$ aryl, 5- to 12-membered heteroaryl, $—C(O)R^{1e}$, or $—C(O)N(R^{1d})_2$, each of which is optionally and independently substituted with one or more (e.g., one to eight) $R^5$; or
$R^{1b}$ and $R^{1c}$ re optionally taken together to form $C_{3-10}$ cycloalkyl or 4- to 12-membered heterocyclyl, each of which is optionally and independently substituted with one or more (e.g., one to eight) $R^5$; or
$R^{1b}$ and $R^{4a}$ are optionally taken together to form 4- to 12-membered heterocyclyl, which is optionally substituted with one or more (e.g., one to eight) $R^6$; or
$R^{1a}, R^{1b}$, and $R^{1c}$ are optionally taken together form a $C_{5-10}$ cycloalkyl optionally substituted with one or more (e.g., one to eight) $R^5$; and
each $R^7$ is independently hydrogen, halogen, —CN, —SF$_5$, —SCF$_3$, $C_{2-8}$ alkyl, $C_{2-8}$ alkenyl, $C_{2-8}$ alkynyl, $C_{3-8}$ cycloalkyl, $C_{1-8}$ haloalkyl, 4- to 12-membered heterocyclyl, 5- to 12-membered heteroaryl, —C(O)$R^{7b}$, —S$R^{7a}$, —S(O)$R^{7b}$, —S(O)$_2R^{7b}$, —S(O)$_3R^{7a}$, —S(O)N($R^{7a}$)$_2$, or —S(O)$_2$N($R^{7a}$)$_2$, each of which is optionally and independently substituted with one or more (e.g., one to eight) $R^8$;
provided that at least one $R^7$ is other than hydrogen.

In some embodiments, provided herein are compounds according to Formula If wherein each $R^7$ is independently hydrogen, halogen, —CN, —SF$_5$, —SCF$_3$, $C_{2-8}$ alkyl, $C_{2-8}$ alkenyl, $C_{2-8}$ alkynyl, $C_{3-8}$ cycloalkyl, $C_{1-8}$ haloalkyl, 5- to 12-membered heteroaryl, —C(O)$R^{7b}$, —S$R^{7a}$, —S(O)$R^{7b}$, —S(O)$_2R^{7b}$, —S(O)$_3R^{7a}$, —S(O)N($R^{7a}$)$_2$, or —S(O)$_2$N($R^{7a}$)$_2$, each of which is optionally and independently substituted with one or more (e.g., one to eight) $R^8$.

In some embodiments, provided herein are compounds according to Formula If wherein at least one $R^7$ is halo, cyano, or 5- to 12-membered heteroaryl.

In some embodiments, provided herein are compounds according to Formula If wherein at least one $R^7$ is chloro, fluoro, methyl, methoxy, cyano, bromo, triazolyl.

In some embodiments, provided herein are compounds according to Formula If wherein one or two of $R^7$ is 7-chloro, 7-methyl, 8-methoxy, 9-fluoro, 6-fluoro, 6-fluoro-9-cyano, 7-fluoro-9-cyano, 9-cyano, 6-cyano, 8-cyano, 7-fluoro-, 9-bromo-7-fluoro-, or 9-triazol-2-yl.

In some embodiments, provided herein are compounds wherein Z is $CH_2$.

In some embodiments, provided herein are compounds wherein Z is O.

In some embodiments, provided herein are compounds wherein Y is $CR^{4a}R^{4b}$.

In some embodiments, provided herein are compounds according to Formula I, Formula A, or Formula B wherein $R^{1a}$, $R^{1b}$, and $R^{1c}$ are independently hydrogen, $C_{1-8}$ alkyl, $C_{1-8}$ heteroalkyl, $C_{3-8}$ cycloalkyl, $C_{6-10}$ aryl, 4- to 12-membered heterocyclyl, or 5- to 12-membered heteroaryl.

In some embodiments, provided herein are compounds according to Formula I, Formula A, or Formula B wherein $R^{1a}$ is hydrogen, $C_{1-8}$ alkyl, $C_{1-8}$ haloalkyl, and $C_{3-8}$ cycloalkyl, wherein $C_{1-8}$ alkyl, $C_{1-8}$ haloalkyl, and $C_{3-8}$ cycloalkyl are optionally substituted with halogen or —CN.

In some embodiments, at least one of $R^{1a}$, $R^{1b}$, and $R^{1c}$ is chloro, fluoro, methyl, —$CD_3$, ethyl, difluoromethyl, cyanomethyl, cyclopropyl, cyclopropylmethyl, trifluoromethyl, methoxy, trifluoromethoxymethyl, 2,2,2-trifluoroethyl, 1,1-difluoroethyl, 2-fluoroethyl, trifluoromethoxy, 1-cyanoethyl, fluoromethyl, 1-hydroxycyclopropyl, difluoromethylcyclopropyl, cyanocyclopropyl, 3,3-difluorocyclobutyl, 1,1,2,2,2-pentafluoroethyl, 1-methylethyl, methylsulfanyl, methoxymethyl, 5-fluoropyrimidin-2-ylsulfanyl, azetidin-3-yl, pyrroldin-3-yl, cyano, or hydroxyl.

In some embodiments, at least one of $R^{1a}$, $R^{1b}$, and $R^{1c}$ is chloro, methyl, —$CD_3$, ethyl, difluoromethyl, cyanomethyl, cyclopropyl, cyclopropylmethyl, trifluoromethyl, methoxy, trifluoromethoxymethyl, 2,2,2-trifluoroethyl, or 1,1-difluoroethyl. In some embodiments, $R^{1a}$, $R^{1b}$, and $R^1$ are taken together to form bicyclo[1.1.1]pentane, azabicyclo[4.1.0] heptane, azepan-4yl, 1,4-oxepane-7-yl, tetrahydropyran-2-yl, or 3,6-dihydro-2H-pyridin-4-yl. In some embodiments, $R^{1a}$, $R^{1b}$, and $R^{1c}$ are taken together to form bicyclo[1.1.1]pentane.

In some embodiments, $R^{1b}$ and $R^{1c}$ are taken together to form 4- to 12-membered heterocyclyl, each of which is optionally substituted with one or more (e.g., one to eight) $R^5$. $R^{1b}$ and $R^{1c}$ are taken together to form a 4, 5, 6, or 7 membered heterocyclyl containing a nitrogen ring atom and optionally substituted with one to eight $R^5$. In some embodiments, the heterocyclyl is substituted with one to four $R^5$. In some embodiments, at least one of $R^5$ is $C_{1-8}$ alkyl, $C_{1-8}$ haloalkyl, halogen, $C_{1-8}$ haloalkyl, $C_{1-8}$ alkoxy, —OH, or cyano. In some embodiments, at least one of $R^5$ is methyl, ethyl, fluoro, chloro, difluoromethyl, fluoromethyl, methoxy, hydroxyl, $C_{1-8}$ haloalkyl, halogen, $C_{1-8}$ haloalkyl, $C_{1-8}$ alkoxy, or cyano.

In some embodiments, at least one of $R^5$ is 4- to 12-membered heterocyclyl or 5- to 12-membered heteroaryl, each of which is optionally substituted with one to eight $R^{5c}$. In some embodiments, at least one of $R^5$ is a 5- to 12-membered heteroaryl optionally substituted with one to eight $R^{5c}$. For example, $R^5$ can be pyrimidin-2-yl, pyrimidin-4-yl, pyrazin-2-yl, [1,2,4]triazolo[1,5-a]pyrazin-8-yl, [1,2,4]triazolo[1,5-c]pyrimidin-5-yl, pyrazolo[1,5-a][1,3,5]triazin-4-yl, pyrazolo[1,5-a]pyrimidin-7-yl, pyridazin-4-yl, quinazolin-2-yl, imidazo[1,2-a]pyrazin-8-yl, pyrazolo[4,3-c]pyridin-6-yl, pyrrolo[3,2-d]pyrimidin-2-yl, imidazo[1,2-b]pyridazin-6-yl, pyrazolo[1,5-a]pyrimidin-7-yl, 6,7-dihydro-5H-cyclopenta[d]pyrimidin-2-yl, pyrid-2-yl, pyrid-3-yl, methoxypyridazin-3-yl, 5,7-dihydrofuro[3,4-d]pyrimidin-2-yl, purin-2-yl, quinazolin-2-yl, quinoxalin-2-yl, isoquinol-3-yl, quinol-2-yl, and 1,3,5-triazin-2-yl, or imidazo[2,1-f][1,2,4]triazin-4-yl, each of which can be optionally substituted with one to eight $R^{5c}$. In some embodiments, heterocyclyl in $R^5$ is substituted with one to three $R^{5c}$. In some embodiments, $R^{5c}$ is independently fluoro, methoxy, difluoromethoxy, methyl, methylamino, cyclopropylamino, 2,2-difluoroethoxy, methylsulfanyl, dimethylaminopropoxy, chloro, 2-methoxyethoxy, dimethylaminoethoxy, cyano, trifluoromethyl, ethoxy, difluoromethyl, cyclopropyl, and oxo.

In some embodiments, $R^{1b}$ and $R^{1c}$ are taken together to form 2,2-difluorocycobutyl, 3,3-difluorocycobutyl, (5-fluoropyrimidin-2-yl)piperidin-4-yl, tetrahydopyran-4-yl, tetrahydopyran-3-yl, tetrahydofuran-3-yl, cylcopropyl, or cyclobutyl.

Some embodiments provide compounds as described above wherein $R^{1a}$ is hydrogen. In some embodiments, $R^{1a}$ is chloro, fluoro, methyl, ethyl, difluoromethyl, fluoromethyl, cyano, or hydroxyl.

In some embodiments, provided herein are compounds according to Formula I, Formula A, or Formula B wherein $R^{2a}$ is hydrogen and $R^{2b}$ is $C_{1-8}$ alkyl.

In some embodiments, provided herein are compounds according to Formula I, Formula A, or Formula B wherein $R^{2a}$ and $R^{2b}$ are hydrogen.

In some embodiments, provided herein are compounds according to Formula I, Formula A, or Formula B wherein Z is O, $R^{1b}$ and $R^{1c}$ are $C_{1-8}$ alkyl, $C_{1-8}$ haloalkyl, or $C_{3-8}$ cycloalkyl, each of which is optionally substituted with halogen and/or —CN. In some embodiments, Z is $CH_2$, $R^{1b}$ and $R^{1c}$ are $C_{1-8}$ alkyl, $C_{1-8}$ haloalkyl, or $C_{3-8}$ cycloalkyl, each of which is optionally substituted with halogen and/or —CN.

In some embodiments, provided herein are compounds according to Formula I, Formula A, or Formula B wherein Z is O; $R^{2a}$ and $R^{2b}$ are hydrogen; and $R^{1b}$ and $R^{1c}$ are $C_{1-8}$ alkyl, $C_{1-8}$ haloalkyl, or $C_{3-8}$ cycloalkyl, each of which is optionally substituted with halogen and/or —CN. In some embodiments, Z is $CH_2$; $R^{2a}$ and $R^{2b}$ are hydrogen; and $R^{1b}$ and $R^{1c}$ are $C_{1-8}$ alkyl, $C_{1-8}$ haloalkyl, or $C_{3-8}$ cycloalkyl, each of which is optionally substituted with halogen and/or —CN.

In some embodiments, provided herein are compounds according to Formula I, Formula A, or Formula B wherein Z is O; $R^{2a}$ is hydrogen; $R^{2b}$ is $C_{1-4}$ alkyl; and $R^{1b}$ and $R^{1c}$ are $C_{1-8}$ alkyl, $C_{1-8}$ haloalkyl, or $C_{3-8}$ cycloalkyl, each of which is optionally substituted with halogen and/or —CN. In some such embodiments, $R^{2b}$ is methyl. In some embodiments, Z is $CH_2$; $R^{2a}$ is hydrogen; $R^{2b}$ is $C_{1-4}$ alkyl; and $R^{1b}$ and $R^{1c}$ are $C_{1-8}$ alkyl, $C_{1-8}$ haloalkyl, or $C_{3-8}$ cycloalkyl, each of which is optionally substituted with halogen and/or —CN. In some such embodiments, $R^{2b}$ is methyl.

In some embodiments, provided herein are compounds according to Formula I, Formula A, or Formula B wherein $R^{1b}$ and $R^{1c}$ are independently selected $C_{1-8}$ alkyl. For example, $R^{1b}$ and $R^{1c}$ can independently be methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, or branched octyl. In some embodiments, $R^{1b}$ and $R^{1c}$ are independently selected $C_{1-4}$ alkyl. In some embodiments, $R^{1b}$ and $R^{1c}$ are each methyl.

In some embodiments, provided herein are compounds according to Formula I, Formula A, or Formula B wherein $R^{1b}$ and $R^{1c}$ are independently selected $C_{1-4}$ alkyl, and $R^{1a}$ is $C_{1-4}$ alkyl, halo—$C_{1-4}$ alkyl, cyano—$C_{1-4}$ alkyl, or cyclopropyl. In some embodiments, $R^{1b}$ and $R^{1c}$ are independently selected $C_{1-4}$ alkyl, and $R^{1a}$ is methyl, ethyl, difluoromethyl, cyanomethyl, 1,1-difluoroethyl, 2,2-difluoroethyl, or cyclopropyl.

In some embodiments, provided herein are compounds according to Formula I, Formula A, or Formula B wherein $R^{1b}$ and $R^{1c}$ are each methyl, and $R^{1a}$ is $C_{1-4}$ alkyl, halo—$C_{1-4}$ alkyl, cyano—$C_{1-4}$ alkyl, or cyclopropyl. In some embodiments, $R^{1b}$ and $R^{1c}$ are each methyl, and $R^{1a}$ is methyl, ethyl, difluoromethyl, cyanomethyl, 1,1-difluoroethyl, 2,2-difluoroethyl, or cyclopropyl.

In some embodiments, provided herein are compounds according to Formula I, Formula A, or Formula B wherein $R^{1b}$ and $R^{1c}$ are $C_{1-8}$ haloalkyl or $C_{3-8}$ cycloalkyl. For example, $R^{1b}$ and $R^{1c}$ can independently be chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, 1,1,1,3,3,3-hexafluoropropyl, cyclopropyl, cyclobutyl, cyclopentyl, cyclohexyl, cycloheptyl, or cyclooctyl. In some embodiments, $R^{1b}$ and $R^{1c}$ are independently $C_{1-4}$ haloalkyl or $C_{3-6}$ cycloalkyl. In some embodiments, $R^{1b}$ and $R^{1c}$ are trifluoromethyl or cyclopropyl.

In some embodiments, provided herein are compounds according to Formula I, Formula A, or Formula B wherein $R^{1b}$ and $R^{1c}$ are independently $C_{1-4}$ haloalkyl or $C_{3-6}$ cycloalkyl, and $R^{1a}$ is hydrogen. In some embodiments, $R^{1b}$ and $R^{1c}$ are trifluoromethyl or cyclopropyl, and $R^{1a}$ is hydrogen.

In some embodiments, provided herein are compounds according to Formula I, Formula A, or Formula B wherein Z is O or $CH_2$; $R^{1a}$ and $R^{2b}$ are independently hydrogen or $C_{1-4}$ alkyl; $R^{1b}$ and $R^{1c}$ are independently selected $C_{1-4}$ alkyl; and $R^{1a}$ is $C_{1-4}$ alkyl, halo-$C_{1-4}$ alkyl, cyano-$C_{1-4}$ alkyl, or cyclopropyl. In some such embodiments, Y is $CR^{4a}R^{4b}$; and $R^{3a}$, $R^{3b}$, $R^{4a}$, and $R^{4b}$ are independently hydrogen or $C_{1-4}$ alkyl.

In some embodiments, provided herein are compounds according to Formula I, Formula A, or Formula B wherein Z is O or $CH_2$; $R^{2a}$ and $R^{2b}$ are independently hydrogen or $C_{1-4}$ alkyl; $R^{1b}$ and $R^{1c}$ are independently selected $C_{1-4}$ alkyl; and $R^{1a}$ is methyl, ethyl, difluoromethyl, cyanomethyl, 1,1-difluoroethyl, 2,2-difluoroethyl, or cyclopropyl. In some such embodiments, Y is $CR^{4a}R^{4b}$; and $R^{3a}$, $R^{3b}$, $R^{4a}$, and $R^{4b}$ are independently hydrogen or $C_{1-4}$ alkyl.

In some embodiments, provided herein are compounds according to Formula I, Formula A, or Formula B wherein Z is O or $CH_2$; $R^{2a}$ and $R^{2b}$ are independently hydrogen or $C_{1-4}$ alkyl; $R^{1b}$ and $R^{1c}$ are each methyl; and $R^{1a}$ is $C_{1-4}$ alkyl, halo-$C_{1-4}$ alkyl, cyano-$C_{1-4}$ alkyl, or cyclopropyl. In some such embodiments, Y is $CR^{4a}R^{4b}$; and $R^{3a}$, $R^{3b}$, $R^{4a}$, and $R^{4b}$ are independently hydrogen or $C_{1-4}$ alkyl.

In some embodiments, provided herein are compounds according to Formula I, Formula A, or Formula B wherein Z is O or $CH_2$; $R^{2a}$ and $R^{2b}$ are independently hydrogen or $C_{1-4}$ alkyl; $R^{1b}$ and $R^{1c}$ are each methyl; and $R^{1a}$ is methyl, ethyl, difluoromethyl, cyanomethyl, 1,1-difluoroethyl, 2,2-difluoroethyl, or cyclopropyl. In some such embodiments, Y is $CR^{4a}R^{4b}$; and $R^{3a}$, $R^{3b}$, $R^{4a}$, and $R^{4b}$ are independently hydrogen or $C_{1-4}$ alkyl.

In some embodiments, provided herein are compounds according to Formula I, Formula A, or Formula B wherein Z is O or $CH_2$; $R^{2a}$ and $R^{2b}$ are independently hydrogen or $C_{1-4}$ alkyl; $R^{1b}$ and $R^{1c}$ are independently $C_{1-4}$ haloalkyl or $C_{3-6}$ cycloalkyl; and $R^{1a}$ is hydrogen. In some such embodiments, Y is $CR^{4a}R^{4b}$; and $R^{3a}$, $R^{3b}$, $R^{4a}$, and $R^{4b}$ are independently hydrogen or $C_{1-4}$ alkyl.

In some embodiments, provided herein are compounds according to Formula I, Formula A, or Formula B wherein Z is O or $CH_2$; $R^{2a}$ and $R^{2b}$ are independently hydrogen or $C_{1-4}$ alkyl; $R^{1b}$ and $R^{1c}$ are trifluoromethyl or cyclopropyl; and $R^{1a}$ is hydrogen. In some such embodiments, Y is $CR^{4a}R^{4b}$; and $R^{3a}$, $R^{3b}$, $R^{4a}$, and $R^{4b}$ are independently hydrogen or $C_{1-4}$ alkyl.

In some embodiments, provided herein are compounds according to Formula I, Formula A, or Formula B wherein $R^{1b}$ and $R^{1c}$ are taken together to form 4- to 12-membered heterocyclyl.

In some embodiments, provided herein are compounds according to Formula I, Formula A, or Formula B wherein $R^{1a}$ is absent, and wherein $R^{1b}$ and $R^{1c}$ are taken together to form $C_{6-10}$ aryl or 5- to 12-membered heteroaryl.

In some embodiments, provided herein are compounds according to Formula I, Formula A, or Formula B wherein $R^{4a}$ is hydrogen or methyl.

In some embodiments, provided herein are compounds according to Formula I, Formula A, or Formula B wherein Y is O.

In some embodiments, provided herein are compounds according to Formula I, Formula A, or Formula B wherein $R^{3a}$ and $R^{3b}$ are independently hydrogen or methyl.

In some embodiments, provided herein are compounds according to Formula I, Formula A, or Formula B wherein $W^1$, $W^2$, $W^3$, and $W^4$ are $CR^7$.

In some embodiments, provided herein are compounds according to Formula I, Formula A, or Formula B wherein $W^2$, $W^3$, and $W^4$ are $CR^7$; wherein at least one $R^7$ in $W^2$, $W^3$, and $W^4$ is hydrogen; and wherein $W^1$ is $CR^7$, wherein $R^7$ in $W^1$ is halogen, —CN, —$N_3$, —$NO_2$, —$SF_5$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, 4- to 12-membered heterocyclyl, $C_{6-10}$ aryl, 5- to 12-membered heteroaryl, —$OR^{7a}$, —$C(O)R^{7b}$, —$N(R^{7a})_2$, —$C(O)OR^{7a}$, —$C(O)N(R^{7a})_2$, —$NR^{7a}C(O)R^{7b}$, —$NR^{7a}C(O)N(R^{7a})_2$, —$NR^{7a}C(O)OR^{7a}$, —$OC(O)N(R^{7a})_2$, —$OC(O)OR^{7a}$, —$SR^{7a}$, —$S(O)R^{7b}$, —$S(O)_2R^{7b}$, —$S(O)_3R^{7a}$, —$S(O)N(R^{7a})_2$, —$S(O)_2N(R^{7a})_2$, —$NR^{7a}S(O)R^{7b}$, —$NR^{7a}S(O)_2R^{7b}$, —$NR^{7a}S(O)N(R^{7a})_2$, or —$NR^{7a}S(O)_2N(R^{7a})_2$, each of which is optionally and independently substituted with one or more (e.g., one to eight) $R^8$. In some such embodiments, $R^7$ in $W^1$ is halogen, —CN, —$NO_2$, —$SF_5$, $C_{1-8}$ haloalkyl, —$C(O)R^{7b}$, —$C(O)OR^{7a}$, —$S(O)R^{7b}$, —$S(O)_2R^{7b}$, or —$S(O)_3R^{7a}$.

In some embodiments, provided herein are compounds according to Formula I, Formula A, or Formula B wherein $W^1$, $W^3$, and $W^4$ are $CR^7$; wherein at least one $R^7$ in $W^1$, $W^3$, and $W^4$ is hydrogen; and wherein $W^2$ is $CR^7$, wherein $R^7$ in $W^2$ is halogen, —CN, —$N_3$, —$NO_2$, —$SF_5$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, 4- to 12-membered heterocyclyl, $C_{6-10}$ aryl, 5- to 12-membered heteroaryl, —$OR^{7a}$, —$C(O)R^{7b}$, —$N(R^{7a})_2$, —$C(O)OR^{7a}$, —$C(O)N(R^{7a})_2$, —$NR^{7a}C(O)R^{7b}$, —$NR^{7a}C(O)N(R^{7a})_2$, —$NR^{7a}C(O)OR^{7a}$, —$OC(O)N(R^{7a})_2$, —$OC(O)OR^{7a}$, —$SR^{7a}$, —$S(O)R^{7b}$, —$S(O)_2R^{7b}$, —$S(O)_3R^{7a}$, —$S(O)N(R^{7a})_2$, —$S(O)_2N(R^{7a})_2$, —$NR^{7a}S(O)R^{7b}$, —$NR^{7a}S(O)_2R^{7b}$, —$NR^{7a}S(O)N(R^{7a})_2$, or —$NR^{7a}S(O)_2N(R^{7a})_2$, each of which is optionally and independently substituted with one or more (e.g., one to eight) $R^8$. In some such embodiments, $R^7$ in $W^2$ is halogen, —CN, —$NO_2$, —$SF_5$, $C_{1-8}$ haloalkyl, —$C(O)R^{7b}$, —$C(O)OR^{7a}$, —$S(O)R^{7b}$, —$S(O)_2R^{7b}$, or —$S(O)_3R^{7a}$.

In some embodiments, provided herein are compounds according to Formula I, Formula A, or Formula B wherein $W^1$, $W^2$, and $W^4$ are $CR^7$; wherein at least one $R^7$ in $W^1$, $W^2$, and $W^4$ is hydrogen; and wherein $W^3$ is $CR^7$, wherein $R^7$ in $W^3$ is halogen, —CN, —N$_3$, —NO$_2$, —SF$_5$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, 4- to 12-membered heterocyclyl, $C_{6-10}$ aryl, 5- to 12-membered heteroaryl, —OR$^{7a}$, —C(O)R$^{7b}$, —N(R$^{7a}$)$_2$, —C(O)OR$^{7a}$, —C(O)N(R$^{7a}$)$_2$, —NR$^{7a}$C(O)R$^{7b}$, —NR$^{7a}$C(O)N(R$^{7a}$)$_2$, —NR$^{7a}$C(O)OR$^{7a}$, —OC(O)N(R$^{7a}$)$_2$, —OC(O)OR$^{7a}$, —SR$^{7a}$, —S(O)R$^{7b}$, —S(O)$_2$R$^{7b}$, —S(O)$_3$R$^{7a}$, —S(O)N(R$^{7a}$)$_2$, —S(O)$_2$N(R$^{7a}$)$_2$, —NR$^{7a}$S(O)R$^{7b}$, —NR$^{7a}$S(O)$_2$R$^{7b}$, —NR$^{7a}$S(O)N(R$^{7a}$)$_2$, or —NR$^{7a}$S(O)$_2$N(R$^{7a}$)$_2$, each of which is optionally and independently substituted with one or more (e.g., one to eight) R$^8$. In some such embodiments, R$^7$ in W$^3$ is halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula I, Formula A, or Formula B wherein W$^1$, W$^2$, and W$^3$ are CR$^7$; wherein at least one R$^7$ in W$^1$, W$^2$, and W$^3$ is hydrogen; and wherein W$^4$ is CR$^7$, wherein R$^7$ in W$^4$ is halogen, —CN, —N$_3$, —NO$_2$, —SF$_5$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, 4- to 12-membered heterocyclyl, $C_{6-10}$ aryl, 5- to 12-membered heteroaryl, —OR$^{7a}$, —C(O)R$^{7b}$, —N(R$^{7a}$)$_2$, —C(O)OR$^{7a}$, —C(O)N(R$^{7a}$)$_2$, —NR$^{7a}$C(O)R$^{7b}$, —NR$^{7a}$C(O)N(R$^{7a}$)$_2$, —NR$^{7a}$C(O)OR$^{7a}$, —OC(O)N(R$^{7a}$)$_2$, —OC(O)OR$^{7a}$, —SR$^{7a}$, —S(O)R$^{7b}$, —S(O)$_2$R$^{7b}$, —S(O)$_3$R$^{7a}$, —S(O)N(R$^{7a}$)$_2$, —S(O)$_2$N(R$^{7a}$)$_2$, —NR$^{7a}$S(O)R$^{7b}$, —NR$^{7a}$S(O)$_2$R$^{7b}$, —NR$^{7a}$S(O)N(R$^{7a}$)$_2$, or —NR$^{7a}$S(O)$_2$N(R$^{7a}$)$_2$, each of which is optionally and independently substituted with one or more (e.g., one to eight) R$^8$. In some such embodiments, R$^7$ in W$^4$ is halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula I, Formula A, or Formula B wherein W$^1$, W$^2$, W$^3$, and W$^4$ are CR$^7$; wherein each R$^7$ in W$^2$, W$^3$, and W$^4$ is independently hydrogen, halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$; and wherein R$^7$ is in W$^1$ is halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula I, Formula A, or Formula B wherein W$^1$, W$^2$, W$^3$, and W$^4$ are CR$^7$; wherein each R$^7$ in W$^1$, W$^3$, and W$^4$ is independently hydrogen, halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$; and wherein R$^7$ is in W$^2$ is halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula I, Formula A, or Formula B wherein W$^1$, W$^2$, W$^3$, and W$^4$ are CR$^7$; wherein each R$^7$ in W$^1$, W$^2$, and W$^4$ is independently hydrogen, halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$; and wherein R$^7$ is in W$^3$ is halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula I, Formula A, or Formula B wherein W$^1$, W$^2$, W$^3$, and W$^4$ are CR$^7$; wherein each R$^7$ in W$^1$, W$^2$, and W$^3$ is independently hydrogen, halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$; and wherein R$^7$ is in W$^4$ is halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula A or Formula B wherein W$^1$ is N and W$^2$, W$^3$, and W$^4$ are CR$^7$. In some such embodiments, R$^7$ in each of W$^2$, W$^3$, and W$^4$ is independently hydrogen, halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula I, Formula A, or Formula B wherein W$^2$ is N and W$^1$, W$^3$, and W$^4$ are CR$^7$. In some such embodiments, R$^7$ in each of W$^1$, W$^3$, and W$^4$ is independently hydrogen, halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula A or Formula B wherein W$^3$ is N and W$^1$, W$^2$, and W$^4$ are CR$^7$. In some such embodiments, R$^7$ in each of W$^1$, W$^2$, and W$^4$ is independently hydrogen, halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula A or Formula B wherein W$^1$, W$^2$, and W$^3$ are CR$^7$ and W$^4$ is N. In some such embodiments, R$^7$ in each of W$^1$, W$^2$, and W$^3$ is independently hydrogen, halogen, —CN, —NO$_2$, —SF$_5$, $C_{1-8}$ haloalkyl, —C(O)R$^{7b}$, —C(O)OR$^{7a}$, —S(O)R$^{7b}$, —S(O)$_2$R$^{7b}$, or —S(O)$_3$R$^{7a}$.

In some embodiments, provided herein are compounds according to Formula A or Formula B wherein W$^4$ is CR$^7$ and R$^7$ of W$^4$ is CN or halogen. In some such embodiments, W$^4$ is C—CN. In some embodiments, W$^4$ is C—CN, and W$^2$ is N. In some embodiments, W$^4$ is C—CN, W$^2$ is N, and Z is O or S. In some embodiments, W$^4$ is C—X, wherein X is halogen; and W$^2$ is N. In some embodiments, W$^4$ is C—X, wherein X is halogen; W$^2$ is N; and Z is O or S. In some such embodiments, Z is O.

In some such embodiments, W$^4$ is C—CN; and W$^2$ is CH or C—X, wherein X is halogen. In some embodiments, W$^4$ is C—CN, W$^2$ is CH or C—X, wherein X is halogen; and Z is O or S. In some embodiments, W$^4$ is C—X, wherein X is halogen; and W$^2$ is CH or C—X, wherein X is halogen. In some embodiments, W$^4$ is C—X, wherein X is halogen; W$^2$ is CH or C—X, wherein X is halogen; and Z is O or S. In some such embodiments, Z is O.

In some embodiments, provided herein are compounds according to Formula A or Formula B wherein W$^1$ is N; R$^{1a}$ is present; and at least two of R$^{1a}$, R$^{1b}$, and R$^{1c}$ are other than hydrogen.

In some embodiments, provided herein are compounds according to Formula I wherein each R$^7$ is independently hydrogen, halogen, cyano, $C_{1-8}$ alkyl, $C_{1-8}$ haloalkyl, or $C_{1-8}$ alkoxy.

In some embodiments, provided herein is a compound which is selected from Table 1 or Examples 258-309, or a pharmaceutically acceptable salt, solvate, prodrug, isotopic analog, or isomer thereof.

III. SYNTHESIS OF COMPOUNDS

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

Scheme 1 shows the synthesis of compounds of Formula I, wherein Q is hydroxy (i.e., —OH) or a leaving group (e.g., chloride) and $W^1$, $W^2$, $W^3$, $W^4$, Y, Z, $R^{1a}$, $R^{1b}$, $R^{1c}$, $R^{2a}$, $R^{2b}$, $R^{3a}$, and $R^{3b}$ are as defined herein.

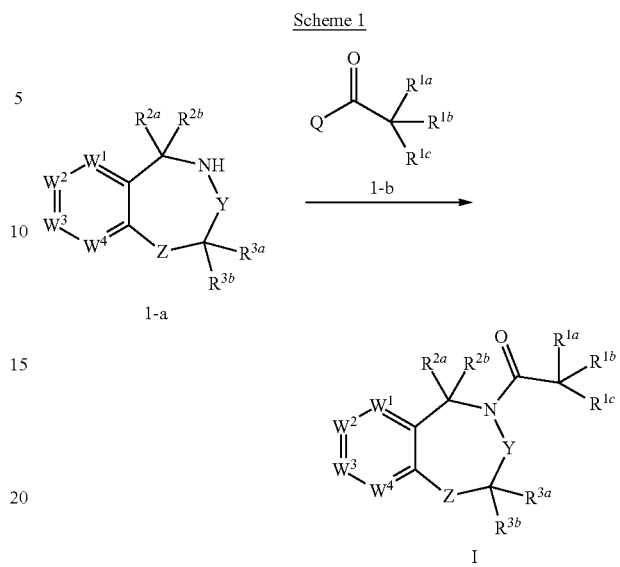

As depicted in Scheme 1, the compounds of Formula I may be prepared by contacting a suitably substituted amine 1-a with compound 1-b, under standard amide bond forming reaction conditions. When Q is hydroxy, an activating agent may be used to facilitate the reaction. Suitable coupling agents (or activating agents) are known in the art and include for example, carbodiimides (e.g., N,N'-dicyclohexylcarbodiimide (DCC), N,N'-dicyclopentylcarbodiimide, N,N'-diisopropylcarbodiimide (DIC), 1-ethyl-3-(3-dimethylaminopropyl)carbodiimide (EDC), N-t-butyl—N-methylcarbodiimide (BMC), N-t-butyl—N-ethylcarbodiimide (BEC), 1,3-bis(2,2-dimethyl-1,3-dioxolan-4-ylmethyl)carbodiimide (BDDC), etc.), phosphonium salts (HOBt, PyBOP, HOAt, etc.), aminium/uronium salts (e.g., tetramethyl aminium salts, bispyrrolidino aminium salts, bispiperidino aminium salts, imidazolium uronium salts, pyrimidinium uronium salts, uronium salts derived from N,N,N'-trimethyl-N'-phenylurea, morpholino-based aminium/uronium coupling reagents, antimoniate uronium salts, etc.), organophosphorus reagents (e.g., phosphinic and phosphoric acid derivatives), organosulfur reagents (e.g., sulfonic acid derivatives), triazine coupling reagents (e.g., 2- chloro-4,6-dimethoxy-1,3,5-triazine, 4-(4, 6-dimethoxy-1,3,5-triazin-2-yl)-4 methylmorpholinium chloride, 4-(4,6-dimethoxy-1,3,5-triazin-2-yl)-4 methylmorpholinium tetrafluoroborate, etc.), pyridinium coupling reagents (e.g., Mukaiyama's reagent, pyridinium tetrafluoroborate coupling reagents, etc.), polymer-supported reagents (e.g., polymer-bound carbodiimide, polymer-bound TBTU, polymer-bound 2,4,6-trichloro-1,3,5-triazine, polymer-bound HOBt, polymer-bound HOSu, polymer-bound IIDQ, polymer-bound EEDQ, etc.), and the like (see, e.g., El-Faham, et al. Chem. Rev., 2011, 111(11): 6557-6602; Han, et al. Tetrahedron, 2004, 60:2447-2467). Caboxylic acids where Q is —OH can also be converted to activated derivatives wherein Q is a leaving group; activated derivatives include, but are not limited to, anhydrides (including symmetric, mixed, or cyclic anhydrides), activated esters (e.g., p-nitrophenyl esters, pentafluorophenyl esters, N-succinimidyl esters, and the like), acylazoles (e.g., acylimidazoles, prepared using carbonyl diimidazole, and the like), acyl azides, and acid halides (e.g., acid chlorides).

Compounds of formula 1-a and 1-b for use in Scheme 1 may be obtained as described in the schemes and Examples provided herein or from conventional synthetic methods known in the art using appropriate starting materials. A number of unsubstituted and substituted benzapine and benzoxazepine starting materials are commercially available and can be used in the methods described herein. Examples of such starting materials include, but are not limited to: 1,2,4,5-tetrahydro-3,2-benzoxazepine; 2,3,4,5-tetrahydro-1,4-benzoxazepine; 2,3,4,5-tetrahydro-1H-2-benzazepine; 2,3,4,5-tetrahydro-1,4-benzothiazepine; 2,3,4,5-tetrahydropyrido[3,4-f][1,4]oxazepine-9-carbonitrile; 2,3,4,5-tetrahydro-1,4-benzoxazepine-6-carbonitrile; 2,3,4,5-tetrahydro-1,4-benzoxazepine-9-carbonitrile; 2-methyl-2,3,4,5-tetrahydro-1,4-benzoxazepine; 3-methyl-2,3,4,5-tetrahydro-1,4-benzoxazepine; 4-benzyl-9-bromo-6-fluoro-2,3-dihydro-1,4-benzoxazepin-5-one; 6-fluoro-2,3,4,5-tetrahydro-1,4-benzoxazepine; 7-chloro-2,3,4,5-tetrahydro-1,4-benzoxazepine; 7-fluoro-2,3,4,5-tetrahydro-1,4-benzoxazepine; 7-methyl-2,3,4,5-tetrahydro-1,4-benzoxazepine; 8-methoxy-2,3,4,5-tetrahydro-1,4-benzoxazepine; 9-bromo-7-fluoro-2,3,4,5-tetrahydro-1,4-benzoxazepine hydrochloride; 9-fluoro-2,3,4,5-tetrahydro-1,4-benzoxazepine; and salts thereof (e.g., hydrochloride salts and the like).

In some embodiments, bicyclic amines for acylation with compound 1-b are prepared as summarized in Scheme 2, wherein Q is hydroxy (i.e., —OH) or a leaving group (e.g., chloride); V is hydrogen or an amine protecting group; $Z^1$ is a first reactive functional group; $Z^2$ is a second reactive functional group; and $W^1$, $W^2$, $W^3$, $W^4$, Y, Z, $R^{1a}$, $R^{1b}$, $R^{1c}$, $R^{2a}$, $R^{2b}$, $R^{3a}$, and $R^{3b}$ are as defined herein.

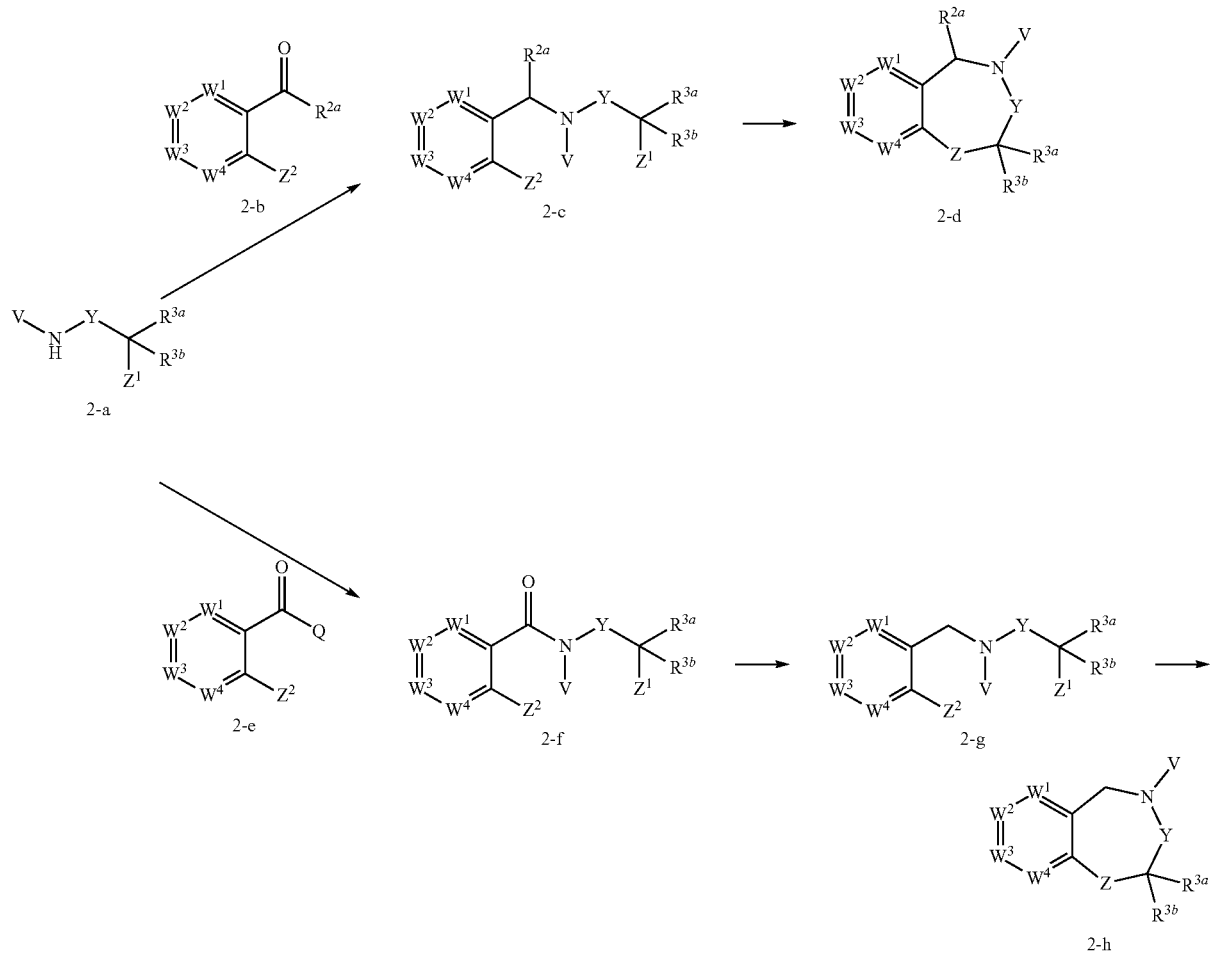

Scheme 2

A compound 2-a (e.g., a primary or secondary amine where Y is $CR^{4a}R^{4b}$, or a hydroxylamine where Y is O) can be used for reductive amination with ketone or aldehyde 2-b to provide amine 2-c, or compound 2-a can be used for acylation with compound 2-e to provide amide 2-f. The reductive amination for formation of amine 2-c is typically conducted with sodium borohydride, sodium cyanoborohydride, or another suitable reducing agent. The acylation step for formation of amide 2-f can be conducted with a carboxylic acid 2-e (wherein Q is OH) or an activated carboxylic acid derivative 2-e (wherein Q is a leaving group) as described above for Scheme 1. Amide 2-f can then be reduced to provide amine 2-g using a reducing agent such as borane, lithium aluminum hydride, or a silane reagent (e.g., diethyl silane, 1,1,3,3-tetramethyldisiloxane, etc.) with or without a suitable catalyst (e.g., zinc acetate, diethyl zinc, tris(pentafluorophenyl)boron, etc.).

Amines 2-c and 2-g contain complementary reactive groups $Z^1$ and $Z^2$, which can be reacted in a cyclization step to provide bicyclic amines 2-d and 2-h. For example, an alcohol $Z^1$ group can react with a halide $Z^2$ group (e.g., chloro) in the presence of a base (e.g., sodium hydride, lithium diisopropylamide, etc.). One of skill in the art will recognize that a $Z^1$ group can be protected with a suitable protecting group (e.g., as a silyl ether such as TBSO) to prevent unwanted reactions prior to the cyclization step. The protecting group can then be removed (e.g., with an acid such as HCl) before reaction with the $Z^2$ group. Similarly, amine 2-a can contain a protecting group V (e.g., benzyloxycarbonyl) to prevent unwanted reactions prior to acylation as shown in Scheme 1. The protecting group V can be removed (e.g., via hydrogenation) before acylation with a carboxylic acid or activated derivative thereof. Desired functional groups at $W^1$, $W^2$, $W^3$, $W^4$, Y, $R^{3a}$ and $R^{3b}$ be installed prior to, or after, the cyclization step in Scheme 2 by employing conventional synthetic methods known in the art (e.g., via halogenation, reduction, oxidation, olefination, alkylation, etc.).

In some embodiments, a method for preparing a compound according to Formula A, or a salt thereof, is provided.

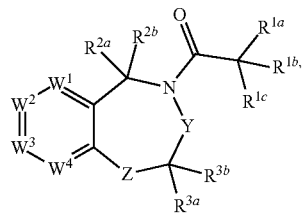

(A)

The method includes:
contacting a compound according to Formula IIa (IIa)

with a compound according to Formula IIb, (IIb)

under conditions sufficient to form a compound according to Formula IIc (IIc)

converting the compound of Formula IIc to a compound of Formula IId

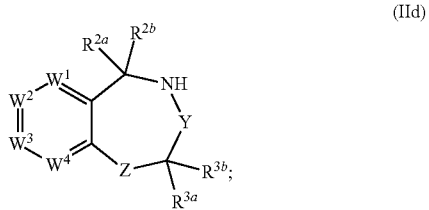

(IId)

and
contacting the compound of Formula IId with a compound of Formula IIe

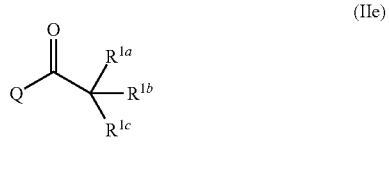

(IIe)

under conditions sufficient to form the compound of Formula A; wherein:
$Z^1$ is an optionally protected first reactive group;
$Z^2$ is an optionally protected second reactive group;
Q is —OH or a leaving group; and
$R^{1a}$, $R^{1b}$, $R^{1c}$, $R^{2a}$, $R^{2b}$, $R^{3a}$, $R^{3b}$, $W^1$, $W^2$, $W^3$, $W^4$, Y and Z are defined as set forth above.

In some embodiments, $Z^1$ is an optionally protected alcohol. In some embodiments, $Z^2$ is a halogen. In some embodiments, converting a compound of Formula IIc to a compound of Formula IId includes contacting the compound of Formula IIc with a base (e.g., sodium hydride, lithium diisopropylamide, potassium tert-butoxide, potassium carbonate, or the like). One of skill in the art will appreciate that methods for preparing compounds of Formula A can also be used for the preparation of compounds according to Formula B and/or Formula I.

Also provided herein are intermediates for the synthesis of kinase inhibitors, including compounds according to Formula Rd as set forth above. In some embodiments, compounds of Formula IId are provided wherein $W^2$ is N. In some such embodiments, $W^1$, $W^3$, and $W^4$ are $CR^7$. In some embodiments, $W^2$ is N, $W^1$ is CH, $W^3$ is CH, and $W^4$ is $CR^7$. In some embodiments, compounds of Formula Rd are provided wherein $W^2$ is N, $W^1$ is CH, $W^3$ is CH, and $W^4$ is C(CN); in some such embodiments, Y is $CH_2$ and Z is O. In some embodiments, the compound of Formula IId is:

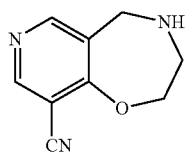 [SMILES: N#Cc1cncc2c1OCCNC2]

or a salt thereof. In some embodiments, the salt is a hydrochloride salt. In some embodiments, the salt is a dihydrochloride salt.

IV. PHARMACEUTICAL COMPOSITIONS

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical arts.

The pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual and systemic absorption, boluses, powders, granules, pastes for application to the tongue; parenteral administration, for example, by subcutaneous, intramuscular, intravenous or epidural injection as, for example, a sterile solution or suspension or sustained-release formulation; topical application, for example, as a cream, ointment or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically-acceptable carrier" as used herein means a pharmaceutically acceptable material, composition or vehicle, such as a liquid or solid filler, diluent, excipient or solvent encapsulating material, involved in carrying or transporting the subject compound from one organ or portion of the body, to another organ or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; surfactants, such as polysorbate 80 (i.e., Tween 80); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc. For example, in a certain embodiment the compounds of the disclosure can be used as 4 mM solution in 8% hydroxypropyl-beta-cyclodextrin in PBS for parenteral administration. In another certain embodiments, the compounds of the disclosure can be used as a suspension in 0.5% aqueous CMC containing 0.1% TWEEN 80.

As set out herein, certain embodiments of the present compounds may contain a basic functional group, such as amino or methylamino ($NCH_3$) and are, thus, capable of forming pharmaceutically acceptable salts with pharmaceutically-acceptable acids. The term "pharmaceutically-acceptable salts" in this respect refers to the relatively non-toxic, inorganic and organic acid addition salts of compounds of the present disclosure. These salts can be prepared in situ in the administration vehicle or the dosage form manufacturing process or by separately reacting a purified compound of the disclosure in its free base form with a suitable organic or inorganic acid and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate and laurylsulphonate salts and the like.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2- acetoxybenzoic, fumaric, toluenesulfonic, methanesulfonic, ethane disulfonic, oxalic, isothionic and the like.

In other cases, the compounds of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process or by separately reacting the purified compound in its free acid form with a suitable base, such as the hydroxide, carbonate or bicarbonate of a pharmaceutically-acceptable metal cation, with ammonia or with a pharmaceutically-acceptable organic primary, secondary or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol and the like; and metal chelating agents, such as citric acid, ethylenediamine tetraacetic acid (EDTA), sorbitol, tartaric acid, phosphoric acid and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present disclosure comprises one or more of cyclodextrins, liposomes, micelle forming agents, e.g., bile acids and polymeric carriers, e.g., polyesters and polyanhydrides; and a compound of the present disclosure. In certain embodiments, an aforementioned formulation renders orally bioavailable a compound of the present disclosure.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers or finely divided solid carriers or both and then, if necessary, shaping the product.

Formulations of the disclosure suitable for oral administration may be in the form of capsules, cachets, pills, tablets, lozenges (using a flavored basis, usually sucrose and acacia or tragacanth), powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically- acceptable carriers, such as sodium citrate or dicalcium phosphate and/or any of the following: fillers or extenders, such as starches, lactose, sucrose, glucose, mannitol and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates and sodium carbonate; solution retarding agents, such as paraffin; absorption accelerators, such as quaternary ammonium compounds; wetting agents, such as, for example, cetyl alcohol, glycerol monostearate and non-ionic surfactants; absorbents, such as kaolin and bentonite clay; lubricants, such a talc, calcium stearate, magnesium stearate, solid polyethylene glycols, sodium lauryl sulfate and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets and other solid dosage forms of the pharmaceutical compositions of the present disclosure, such as dragees, capsules, pills and granules, may optionally be scored or prepared with coatings and shells, such as enteric coatings and other coatings well known in the pharmaceutical formulating arts. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredient(s) only or preferentially, in a certain portion of the gastrointestinal tract, optionally, in a delayed manner Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier and with any preservatives, buffers or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to a compound of this disclosure, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically-acceptable sterile isotonic aqueous or nonaqueous solutions, dispersions, suspensions or emulsions or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

V. METHODS OF TREATMENT

In other embodiments, provided herein is a method of treating a receptor-interacting protein kinase 1-mediated disease or disorder. The method includes administering a therapeutically effective amount of a compound or pharmaceutical composition as described herein to a subject in need thereof. In some embodiments, the receptor-interacting protein kinase 1-mediated disease or disorder is trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis, or inflammatory bowel disease.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Experiments with knockout animal models and Necrostatin 1, a receptor-interacting protein kinase 1 inhibitor, have demonstrated the effectiveness of receptor-interacting protein kinase 1 inhibition in protecting tissues from inflammatory bowel diseases (e.g., ulcerative colitis and Crohn's disease), psoriasis, retinal-detachment-induced photoreceptor necrosis, retinitis pigmentosa, cerulein-induced acute pancreatitis, and sepsis/systemic inflammatory response syndrome (SIRS), and alleviating ischemic brain injury, retinal ischemia/reperfusion injury, Huntington's disease, renal ischemia reperfusion injury, cisplatin induced kidney injury, traumatic brain injury, hematological and solid organ malignancies, bacterial infections and viral infections (e.g., tuberculosis and influenza) and lysosomal storage diseases. The receptor-interacting protein kinase 1 inhibitors of the present disclosure are therefore useful for treating diseases and conditions mediated by receptor-interacting protein kinase 1, including but not limited to inflammatory diseases or disorders, necrotic cell diseases, neurodegenerative diseases, central nervous system (CNS) diseases, ocular diseases, infections, and malignancies. In certain embodiments, the receptor-interacting protein kinase 1 inhibitors described herein can inhibit inflammation, protect tissue or cell from damage or undesired cell death (e.g., necrosis or apoptosis), ameliorate symptoms, and improve immune response or neuronal function in a patient suffering from any of the prescribed diseases or conditions. Moreover, the compounds may be suitable for treatment of immune-mediated disease, such as but not limited to, allergic diseases, autoimmune diseases, and prevention of transplant rejection.

Provided herein are compounds and compositions for use in medicine. In certain embodiments, the compounds and compositions are for use in the treatment of a receptor-interacting protein kinase 1- mediated disease or disorder. Also provided is a method of treating a receptor-interacting protein kinase 1-mediated disease or disorder comprising administering a therapeutically effective amount of a compound or pharmaceutical composition disclosed herein to a subject in need thereof. In certain embodiments, the disease or disorder is an inflammatory disease associated with A20 SNPs.

Various specific diseases and disorders are described below. In certain embodiments, the disease or disorder is necrotizing enterocolitis, tuberous sclerosis, Tangier's Disease, Wohlman's Syndrome, inflammatory bowel disease, Crohn's disease, ulcerative colitis, psoriasis, retinal detachment, retinitis pigmentosa, macular degeneration, pancreatitis (e.g., acute pancreatitis), atopic dermatitis, rheumatoid arthritis, spondyloarthritis, gout, SoJIA, systemic lupus erythematosus, Sjogren's syndrome, systemic scleroderma, anti-phospholidpid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behget's disease, interleukin-1 converting enzyme associated fever syndrome, chronic obstructive pulmonary disease, tumor necrosis factor receptor-associated periodic syndrome, periodontitis, bacterial infection, staphylococcus infection, mycobacterium infection, retinitis pigmentosa, influenza, transplant rejection, burns or hypoxia. In certain embodiments, the disease or disorder is trauma, ischemia, stroke, cardiac infarction, infection, lysosomal storage disease, Niemann-Pick disease, Gaucher's disease, Krabbe disease, sepsis, Parkinson's disease, Alzheimer's disease, amyotrophic lateral sclerosis (ALS/Lou Gehrig's Disease), Huntington's disease, HIV-associated dementia, encephalopathy, retinal degenerative disease, glaucoma, age-related macular degeneration, rheumatoid arthritis, psoriasis, psoriatic arthritis or inflammatory bowel disease. In certain embodiments, the disease or disorder is Alzheimer's disease, ALS, Friedreich's ataxia, Huntington's disease, Lewy body disease, Parkinson's disease, Huntington's disease, multiple sclerosis, diabetic neuropathy, polyglutamine (polyQ) diseases, stroke, Fahr disease, Menke's disease, Wilson's disease, cerebral ischemia, lysosomal storage disease or a prion disorder. In certain embodiments, the disease is ALS. In certain embodiments, the disease is Alzheimer's disease. In certain embodiments, the disease is lysosomal storage disease. In certain embodiments, the disease is Parkinson's disease. In certain embodiments the disorder is an ischemic disease of organs including but not limited to brain, heart, kidney and liver. In some different embodiments, the disorder is an ocular disorder such as retinal degenerative disease, glaucoma or age-related macular degeneration. In some different embodiments, the disorder is a central nervous system (CNS) disorder.

In certain embodiments, the compounds and compositions are useful for treating psoriasis.

In certain embodiments, the disorder is an inflammatory disease of the intestines such as Crohn's disease or ulcerative colitis (both generally known together as inflammatory bowel disease). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity. Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

In certain embodiments, provided is a method of treating rheumatoid arthritis, systemic onset juvenile idiopathic arthritis (SoJIA), spondyloarthritis, osteoarthritis, psoriasis, Crohn's disease, ulcerative colitis, or multiple sclerosis, comprising administering a therapeutically effective amount of a compound as provided herein to a subject in need thereof. In certain embodiments, provided is a method of treating autoimmune hepatitis, atherosclerosis, neutrophilic dermatoses, or a rare disease driven by A20, NEMO, and/or LUBAC mutations, comprising administering a therapeutically effective amount of a compound as provided herein to a subject in need thereof. In certain embodiments, the compound is of Formula I (or any Formula described herein or tautomer thereof), wherein A is triazole. In certain embodiments, the compound is of Formula V or Va. In certain embodiments, the method comprises administering Compound 42 or tautomer thereof.

Inflammatory Diseases or Disorders

The receptor interacting protein kinase 1 inhibitors described herein may be used to treat inflammatory diseases and disorders. Inflammatory diseases and disorders typically exhibit high levels of inflammation in the connective tissues or degeneration of these tissues.

Non-limiting examples of inflammatory diseases and disorders include Alzheimer's disease, ankylosing spondylitis, arthritis including osteoarthritis, rheumatoid arthritis (RA), psoriasis, asthma, atherosclerosis, Crohn's disease, colitis, dermatitis, diverticulitis, fibromyalgia, hepatitis, irritable bowel syndrome (IBS), inflammatory bowel disease (IBD), systemic lupus erythematous (SLE), nephritis, Parkinson's disease and ulcerative colitis. In certain embodiments, the compounds and compositions of the present disclosure are useful for treating an autoimmune disorder, such as rheumatoid arthritis, psoriasis, psoriatic arthritis, encephalitis, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, sarcoidosis, scleroderma, and systemic lupus erythematosus. In an embodiment, the receptor interacting protein kinase 1 inhibitors described herein are useful for treating autoimmune encephalitis.

In certain embodiments, the compounds and compositions are useful for treating rheumatoid arthritis (RA). In certain embodiments, the compounds and compositions are useful for treating ulcerative colitis. In certain embodiments, the compounds and compositions are useful for treating psoriasis.

In certain embodiments, the disorder is an inflammatory disease of the intestines such as Crohn's disease or ulcerative colitis (both generally known together as inflammatory bowel disease). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity. Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

Necrotic Cell Diseases

The compounds described herein may be used for the treatment of diseases/disorders caused or otherwise associated with cellular necrosis. In particular, the disclosure provides methods for preventing or treating a disorder associated with cellular necrosis in a mammal, comprising the step of administering to said mammal a therapeutically effective amount of a compound or composition described herein. The term "necrotic cell disease" refers to diseases associated with or caused by cellular necrosis, for example trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis or inflammatory bowel disease.

The necrotic cell diseases can be acute diseases such as trauma, ischemia, stroke, cardiac infarction, anthrax lethal toxin induced septic shock, sepsis, cell death induced by LPS and HIV induced T-cell death leading to immunodeficiency. In certain embodiments the disorder is an ischemic disease of organs including but not limited to brain, heart, kidney and liver.

The necrotic cell diseases also include chronic neurodegenerative diseases, such as Parkinson's disease, Huntington's disease, amyotrophic lateral sclerosis, Alzheimer's disease, infectious encephalopathies, dementia such as HIV associated dementia.

In some different embodiments, the disorder is an ocular disorder such as retinal degenerative disease, glaucoma or age-related macular degeneration. In some different embodiments, the disorder is a central nervous system (CNS) disorder.

Neurodegenerative and CNS Diseases

The receptor-interacting protein kinase 1 inhibitors described herein may also be used to treat neurodegenerative diseases. Neurodegenerative diseases can affect many of the body's activities, such as balance, movement, talking, breathing, and heart function. Neurodegenerative diseases can be genetic or caused by medical conditions such as alcoholism, tumors, strokes, toxins, chemicals, and viruses.

Non-limiting examples of neurodegenerative diseases include Alzheimer's disease, amyotrophic lateral sclerosis (ALS), Friedreich's ataxia, Huntington's disease, Lewy body disease, Parkinson's disease, and spinal muscular atrophy. In certain embodiments, neurodegenerative diseases and CNS diseases include NiemannPick disease, type C1 (NPC1), Alzheimer's disease, amyotrophic lateral sclerosis (ALS), Friedreich's ataxia, Huntington's disease, Lewy body disease, Parkinson's disease, and spinal muscular atrophy.

In certain embodiments, the receptor interacting protein kinase 1 inhibitors described herein may be used to treat NPC1 via inhibiting necroptosis that causes neuronal loss. In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS).

More generally, the receptor-interacting protein kinase 1 inhibitors described herein can be used to preserve neuron viability and promote axon growth and nerve functions within the central nervous system (CNS). Accordingly, the compounds may be used to reduce or even reverse the loss of cognitive, motor, and sensory functions associated with a CNS disease or disorder, by preserving neuron viability and/or promoting axon regeneration and/or nerve functions.

The receptor-interacting protein kinase 1 inhibitors described herein can be used in a method for promoting axon regeneration in a CNS neuron, such as a CNS sensory neuron, a motor neuron, a cortical neuron, a cerebellar neuron, a hippocampal neuron, and a midbrain neuron. The receptor interacting protein kinase 1 inhibitors described herein can be used in a method for promoting nerve function or preserving the viability following injury to a CNS neuron. In another embodiments, these compounds can be used to promote regeneration of an axon in a CNS neuron that is degenerated in the CNS disease or disorder. The RIP receptor-interacting protein kinase 1 inhibitors may be administered by any conventional means, such as locally to the neuron or applied ex vivo before re-implantation.

Accordingly, in one aspect, the disclosure provides a method of treating a CNS disorder in a subject in need thereof, wherein a symptom of the CNS disorder is axon degeneration or injury within a CNS neuron. The method comprises administering to the subject an effective amount of a compound or composition disclosed herein thereby to promote regeneration of an axon in a CNS neuron affected by the CNS disorder. Following administration, neural functions may be measured, for example, as an indication of axon regeneration. It is also contemplated that, following administration of the compound or composition, the neuron function of the CNS neuron is preserved or improved relative to the neuron function prior to administration.

Non-limiting examples of CNS diseases or disorders include brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabetic neuropathy, polyglutamine (polyQ) diseases, stroke, Fahr disease, Menke's disease, Wilson's disease, cerebral ischemia, and a prion disorder.

In exemplary embodiments, the CNS disorder is brain injury or spinal cord injury.

Also provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity or other physical injury to the brain or spinal cord) or neurodegenerative CNS disease, wherein a symptom of the disorder is axon degeneration (e.g., Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, prion disorder (e.g., Creutzfeldt-Jakob disease). In certain embodiments, the CNS disorder is brain injury (e.g., traumatic brain injury) or spinal cord injury (e.g., chronic, acute or traumatic spinal cord injury). In certain embodiments, the CNS disorder affects a subject's basic vital life functions such as breathing, heart beat and blood pressure, e.g., an injury to or aneurysm in the brain stem.

In certain embodiments, the CNS disease or disorder affects a subject's cognitive ability. In certain embodiments, the CNS disease or disorder affects a subject's movement and/or strength. In certain embodiments, the CNS disease or disorder affects a subject's coordination.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy and prion disorders.

In certain embodiments, the CNS disorder affects a subject's movement and/or strength, such as injury to the brain or spinal cord or a neurodegenerative CNS disorder such as Parkinson's disease, frontotemporal dementia, dementia with Lewy bodies, corticobasal degeneration, progress supranuclear palsy, Huntington's disease, multiple system atrophy, amyotrophic lateral sclerosis and hereditary spastic paresis.

In certain embodiments, the CNS disorder affects a subject's coordination, such as brain injury to the cerebellum or a neurodegenerative CNS disorder such as spinocerebellar atrophies, Friedreich's ataxia and prion disorders.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with Lewy bodies), corticobasal degeneration, progressive supranuclear palsy, multiple system atrophy, hereditary spastic paraparesis and spinocerebellar atrophies.

Non-limiting examples of neurodegenerative diseases include Alzheimer's disease, lysosomal storage diseases, amyotrophic lateral sclerosis (ALS), Friedreich's ataxia, Huntington's disease, Lewy body disease, Parkinson's disease, and spinal muscular atrophy.

In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS). In certain embodiments, the compounds and compositions of the present disclosure are useful for treating lysosomal storage diseases.

In certain embodiments, the disorder is a brain disorders, such as, but not limited to, Alzheimer's disease, ALS, frontotemporal dementias, vascular dementia, Huntington's disease, Parkinson's disease, Lewy Body dementia, Progressive Supranuclear Palsy, multiple sclerosis, neuromyelitis optica, ischemic brain damage (stroke), hypoxic brain damage, traumatic brain injury, spinal cord injury, sepsis-induced brain damage, CNS infections, CNS abscesses, glioblastoma multiforme, epilepsy, neuropathic pain, major depression, bipolar depression, schizophrenia, autism, Niemann-Pick disease, neuro-Behget's disease.

In certain embodiments, provided is a method of treating a CNS disease or disorder, comprising administering a therapeutically effective amount of a compound as provided herein to a subject in need thereof. In certain embodiments, the disease or disorder is Alzheimer's disease or amyotrophic lateral sclerosis (ALS). In certain embodiments, the compound is of Formula I (or any Formula described herein), wherein A is other than triazole. In certain embodiments, the compound is of Formula VI.

Ocular Conditions

The receptor-interacting protein kinase 1 inhibitors described herein can also be used to treat ocular conditions, for example to reduce or prevent the loss of photoreceptor and/or retinal pigment epithelial cell viability.

In certain embodiments, the disclosure provides a method of preserving the visual function of an eye of a subject with an ocular condition, wherein a symptom of the ocular condition is the loss of photoreceptor cell viability in the retina of the eye with the condition. The method comprises administering to the eye of the subject an effective amount of a compound or composition described herein, thereby preserving the viability of the photoreceptor cells disposed within the retina of the eye. After administration, the visual function (e.g., visual acuity) of the eye may be preserved or improved relative to the visual function of the eye prior to administration.

The ocular condition may be age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity. AMD may be the neovascular or the dry form of AMD. Retinal detachment may be a rhegmatogenous, a serous, and a tractional retinal detachment. In certain embodiments, the ocular condition may be geographic atrophy, glaucoma, or another ischemic eye disease.

In certain embodiments, the disclosure provides a method of preserving the viability of retinal pigment epithelial (RPE) cells within the retina of a subject with an ocular condition with administration of a compound of the present disclosure. The subject being treated may have a loss of retinal pigment epithelial cells in the retina of the eye with the condition and the ocular condition may be age-related macular degeneration (AMD), BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE), or another uveitis disorder. In certain embodiments, the method comprises administering to the eye of the subject an effective amount of a compound or composition described herein, thereby preserving the viability of the retinal pigment epithelial cells.

Provided in another embodiment is a method of preserving the viability of photoreceptor cells disposed within a retina of a subject with age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity. Therefore, in certain embodiments, the method comprises administering to the eye an effective amount of a compound or composition described herein, thereby preserving the viability of the photoreceptor cells disposed within the retina of the subject with a condition.

Provided in another embodiment is a method of preserving the viability of photoreceptor cells disposed within a retina of a mammalian eye following retinal detachment. The retinal detachment may be a rhegmatogenous retinal detachment, tractional retinal detachment, or serous retinal detachment. In other embodiments, the retinal detachment may occur as a result of a retinal tear, retinoblastoma, melanoma or other cancers, diabetic retinopathy, uveitis, choroidal neovascularization, retinal ischemia, pathologic myopia, or trauma. In certain embodiments, the method comprises administering a compound or composition described herein to the eye in which a region of the retina has been detached in amounts sufficient to preserve the viability of photoreceptor cells disposed within the region of the detached retina.

Provided in another embodiment is a method of preserving visual function of an eye of a subject with age-related macular degeneration (AMD), retinosis pigmentosa (RP), macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis, or light-induced toxicity, wherein a symptom of the ocular condition is the loss of photoreceptor cells viability in the retina of the eye, wherein the method comprises treating the subject with a compound or composition described herein to the subject.

In another aspect, the disclosure provides a method of preserving the visual function of an eye of a subject with an ocular condition, wherein a symptom of the ocular condition is the loss of photoreceptor cell viability and/or RPE viability in the retina of the eye wherein the method comprises treating the subject with a compound or composition described herein to the subject.

In certain embodiments, provided a method of preserving the visual function of an eye of a subject with ocular conditions, wherein a symptom of the ocular condition is the loss of retinal ganglion cell viability in the retina of the eye with the conditions. The method comprises administering to the eye of the subject an effective amount of a compound or composition, thereby preserving the viability of the retinal ganglion cells disposed within the retina of the eye. After administration of the compound or composition, the visual function of the eye may be preserved or improved relative to the visual function of the eye prior to administration. Further, after the administration, the preserved retinal ganglion cell is capable of supporting axonal regeneration.

Non-limiting examples of symptoms associated with the ocular conditions include the loss of retinal ganglion cell viability in the retina of the eye, glaucoma, optic nerve injury, optic neuritis, optic neuropathies, diabetic retinopathy, central retinal artery occlusion, and central retinal vein occlusion.

The compounds described herein may also be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy, and hereditary optic neuropathy (e.g., Leber's optic neuropathy, Dominant Optic Atrophy, Behr's syndrome).

Also disclosed is a method of preserving the visual function of an eye of a subject with glaucoma, optic nerve injury, optic neuropathies, diabetic retinopathy, central retinal artery occlusion, or central retinal vein occlusion. The method comprises administering to the eye of the subject an effective amount of a compound or composition described herein, thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion and central retinal vein occlusion. The method comprises administering a compound or composition described herein to the eye in which a region of the retina has been affected in amounts sufficient to preserve the viability of retinal ganglion cells disposed within the region of the affected retina. The preserved retinal ganglion cell is capable of supporting axonal regeneration.

Also disclosed is a method for promoting axon regeneration in an eye of a subject with an ocular condition, wherein a symptom of the ocular condition is the loss of retinal ganglion cell viability in the retina of the eye with the condition. The method comprises administering to the eye of the subject an effective amount of a compound or composition described herein, thereby promoting axon regeneration of the retinal ganglion cell within the retina of the eye.

In each of the foregoing embodiments, it is understood that the methods and compositions described herein can be used to preserve the viability and/or promote axon regeneration of retinal ganglion cells during treatment of the underlying conditions including, but not limited to, glaucoma, optic nerve injury, optic neuritis, optic neuropathies, diabetic retinopathy, central retinal artery occlusion and central retinal vein occlusion.

Tissue Injuries or Damages

The ability of the compounds described herein to inhibit inflammation and cell death makes them suitable for ameliorating tissue injuries or damages. The tissue injuries or damages may be a result of any of the diseases or conditions described above. For example, the compounds may be used for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcohol steatohepatitis, alcohol steatohepatitis, autoimmune hepatitis autoimmune hepatobiliary diseases, or primary sclerosing cholangitis, or for the amelioration of liver tissue injury or damage associated with overdose of acetaminophen, or for amelioration of kidney tissue injury or damage following renal transplant or the administration of nephrotoxic drugs or substances. In certain embodiments, the For example, the compounds may be used for amelioration of brain tissue injury or damage following pulmonary injury or damage.

Non-limiting examples of brain injury or damage include stroke (e.g., hemorrhagic and nonhemorrhagic), traumatic brain injury (TBI), cerebral hemorrhage, subarachnoid hemorrhage, intracranial hemorrhage secondary to cerebral arterial malformation, cerebral infarction, perinatal brain injury, non-traumatic brain injury, Alzheimer's disease, Parkinson's disease, Huntington's disease, multiple sclerosis, amyotrophic lateral sclerosis, brain hemorrhage, brain infections, brain tumor, subclinical brain injury, spinal cord injury, anoxic-ischemic brain injury, focal cerebral ischemia, global cerebral ischemia, and hypoxic hypoxia.

In an embodiment, the compounds and compositions of the present disclosure may be used to treat peritoneal tissue injury. Non-limiting examples of peritoneal tissue injury include peritoneal deterioration, peritoneal sclerosis, and peritoneal cancer. For example, the receptor interacting protein kinase 1 inhibitors described herein may be used to treat peritoneal damage caused by peritoneal dialysis fluid (PDF) and PD-related side effects.

Liver Injury and Diseases

In an embodiment, the compounds and compositions of the present disclosure may be used to treat liver injury and diseases. Non-limiting examples of liver injury or damage include not only degeneration or necrosis of liver parenchyma cells which results from injury caused by a certain factor, but also undesirable phenomena caused by biological reactions to the injury, such as mobilization, infiltration, activation of Kupffer cells, leukocytes and the like, fibrosis of the liver tissue, etc., which reactions occur alone or in combination. In certain embodiments, the receptor interacting protein kinase 1 inhibitors described herein may be used to treat steatohepatitis and hepatocellular carcinoma via inhibiting receptor interacting protein kinase 1 activity-dependent apoptosis of hepatocytes and hepatocarcinogenesis. In an embodiment, the receptor interacting protein kinase 1 inhibitors described herein may be used to treat alcoholic hepatitis, autoimmune hepatitis, fulminent hepatic failure, acute cholestasis and liver injury.

Kidney Injury and Diseases

In an embodiment, the compounds and compositions of the present disclosure may be used to treat kidney injury and diseases. Non-limiting examples of kidney diseases include chronic kidney disease (CKD) (e.g., glomerular diseases, tubulointerstitial diseases, obstruction, polycystic kidney disease), acute kidney injury (AKI), diabetic nephropathy, fibrosis, glomerulonephritis, focal glomerulosclerosis, immune complex nephropathy, crystalline nephropathy, or lupus nephritis. Kidney disease may be caused by drug-induced renal injury or kidney graft rejection. Kidney disease may be characterized as nephrotic syndrome or renal insufficiency. In an embodiment, the receptor interacting protein kinase 1 inhibitors described herein may be used to treat kidney diseases (e.g., AKI) via inhibiting cell death pathway in kidney diseases. In an embodiment, the receptor interacting protein kinase 1 inhibitors described herein may be used to treat patient with kidney stones and to prevent crystal-induced cytotoxicity and acute kidney injury via inhibiting receptor interacting protein kinase 3-MLKL-mediated necroptosis.

Skin Diseases

In an embodiment, the compounds and compositions of the present disclosure may be used to treat dermal (or skin) diseases, including but not limited to, inflammatory skin diseases or neutrophilic dermatosis.

Malignancies

In an embodiment, the compounds and compositions of the present disclosure are useful for treating malignancies/cancers such as carcinoma, sarcoma, melanoma, lymphoma or leukemia. Nonlimiting examples of malignancies suitably treated by the receptor interacting protein kinase 1 inhibitors described herein include lung cancer (e.g., non-small cell lung cancer, small-cell lung cancer), hepatocellular cancer, melanoma, pancreatic cancer, urological cancer, bladder cancer, colorectal cancer, colon cancer, breast cancer, prostate cancer, renal cancer, thyroid cancer, gall bladder cancer, peritoneal cancer, ovarian cancer, cervical cancer, gastric cancer, endometrial cancer, esophageal cancer, head and neck cancer, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, vulval cancer, cancers of the adrenal cortex, ACTH producing tumors, lymphoma, and leukemia.

Infectious Diseases

In an embodiment, the compounds and compositions of the present disclosure are useful for treating infectious diseases resulting from the presence of pathogenic agents, including pathogenic viruses, pathogenic bacteria, fungi, protozoa, multicellular parasites and aberrant proteins known as prions. Non-limiting examples of infectious diseases suitably treated by the receptor interacting protein kinase 1 inhibitors described herein include virus infectious diseases and bacterial infectious diseases. The virus infectious disease is not particularly limited and includes, for example, infectious diseases with respiratory infectious viruses (e.g., infectious diseases due to respiratory infectious viruses such as influenza virus, rhino virus, corona virus, parainfluenza virus, RS virus, adeno virus, reo virus and the like), Staphylococcus aureus (MRSA) pneumonia, Serratia marcescens hemorrhagic pneumonia, herpes zoster caused by herpes virus, diarrhea caused by rotavirus, viral hepatitis, AIDS and the like. The bacterial infectious disease is not particularly limited and includes, for example, infectious diseases caused by *Bacillus cereus, Vibrio parahaemolyticus, Enterohemorrhagic Escherichia coli, Staphylococcus aureus*, MRSA, *Salmonella, Botulinus, Candida* and the like.

Bone Diseases

In an embodiment, the compounds and compositions of the present disclosure are useful for treating bone diseases that may result from a bone remodeling disorder whereby the balance between bone formation and bone resorption is shifted. Non-limiting examples of bone remodeling disorders include osteoporosis, Paget's disease, osteoarthritis, rheumatoid arthritis, achondroplasia, osteochondritis, hyperparathyroidism, osteogenesis imperfecta, congenital hypophosphatasia, fribromatous lesions, fibrous displasia, multiple myeloma, abnormal bone turnover, osteolytic bone disease and periodontal disease. Additional examples of bone diseases suitably treated by the receptor interacting protein kinase 1 inhibitors described herein include bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment. Additional examples of diseases affecting bone or bone joints suitably treated by the receptor interacting protein kinase 1 inhibitors described herein include metastatic bone cancer, rheumatic diseases such as rheumatoid arthritis, osteoarthritis and other inflammatory arthropathies. In an embodiment, the receptor interacting protein kinase 1 inhibitors described herein may be used to treat postmenopausal osteoporosis via inhibiting osteocyte necroptosis and trabecular deterioration.

Cardiovascular Diseases

In an embodiment, the compounds and compositions of the present disclosure are useful for treating cardiovascular diseases that may be relate to the cardiovascular disorders of fragile plaque disorder, occlusive disorder and stenosis. Non-limiting cardiovascular diseases include coronary artery disorders and peripheral arterial disorders, including, among others, atherosclerosis, arterial occlusion, aneurysm formation, thrombosis, post-traumatic aneurysm formation, restenosis, and post-operative graft occlusion. It is believed that atherosclerosis results from maladaptive inflammation driven primarily by macrophages. Thus, the compounds and compositions of the present disclosure may be used to treat atherosclerosis via inhibiting macrophage necroptosis.

Transplantation

In an embodiment, the compounds and compositions of the present disclosure are useful for treating transplant patients. Non-limiting examples of transplant patient suitably treated by the receptor interacting protein kinase 1 inhibitors described herein include patients with solid and non-solid organ and tissue transplantations and transplants, such as liver, heart, kidney, and heterologous and autologous bone marrow transplantations/transplants. Typically, immunosuppressive therapy is used to avoid graft rejection in recipients of solid organ transplants. Recipients of bone marrow transplants are usually subjected to extensive irradiation and chemotherapy prior to transplantation. It is believed that receptor interacting protein kinase 1 and NF-κB signaling in dying cells determines cross-priming of CD8+ T cells. Thus, the receptor interacting protein kinase 1 inhibitors described herein may be used to treat transplant patient and avoid graft rejection by modulating cross-priming of CD8+ T cells.

Other Diseases and Conditions

Additional examples of diseases and disorders suitably treated by the receptor interacting protein kinase 1 inhibitors described herein include Gaucher disease, organ failure, pancreatitis, atopic dermatitis, spondyloarthritis, gout, systemic onset juvenile idiopathic arthritis (SoJIA), systemic lupus erythematosus (SLE), Sjogren's syndrome, systemic scleroderma, anti-phospholipid syndrome (APS), vasculitis, primary sclerosing cholangitis (PSC), acetaminophen toxicity, kidney damage/injury (nephritis, renal transplant, surgery, administration of nephrotoxic drugs e.g., cisplatin, acute kidney injury(AKI)), Celiac disease, autoimmune idiopathic thrombocytopenic purpura (autoimmune ITP), cerebrovascular accident (CVA, stroke), myocardial infarction (MI), allergic diseases (including asthma), diabetes, Wegener's granulomatosis, pulmonary sarcoidosis, Behcet's disease, interleukin-1 converting enzyme (ICE/caspase-1) associated fever syndrome, chronic obstructive pulmonary disease (COPD), tumor necrosis factor receptor-associated periodic syndrome (TRAPS), peridontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (e.g., tuberculosis and influenza) and lysosomal storage diseases.

Non-limiting examples of lysosomal storage diseases include Gaucher disease, GM2 Gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay—Sachs and Wolman disease.

In certain embodiments, provided are compounds and compositions for use in medicine. In certain embodiments, the compounds and compositions are for use in the treatment of a receptor interacting protein kinase 1-mediated disease or disorder. Also provided is a method of treating a receptor interacting protein kinase 1-mediated disease or disorder comprising administering a therapeutically effective amount of a compound or pharmaceutical composition disclosed herein to a subject in need thereof.

In another embodiment, the present disclosure provides a method of inhibiting receptor-interacting protein kinase 1. The method includes contacting the receptor-interacting protein kinase 1 with an effective amount of a compound as described herein. Inhibiting the receptor-interacting protein kinase 1 generally include contacting the receptor-interacting protein kinase 1 with an amount of the compound sufficient to reduce the activity of the receptor-interacting protein kinase 1 as compared to the receptor-interacting protein kinase 1 activity in the absence of the compound. For example, contacting the receptor-interacting protein kinase 1 with the compound can result in from about 1% to about 99% receptor-interacting protein kinase 1 inhibition (i.e., the activity of the inhibited enzyme ranges from 99% to 1% of the enzyme activity in the absence of the compound). The level of receptor-interacting protein kinase 1 inhibition can range from about 1% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90%, or from about 90% to about 99%. The level of receptor-interacting protein kinase 1 inhibition can range from about 5% to about 95%, or from about 10% to about 90%, or from about 20% to about 80%, or from about 30% to about 70%, or from about 40% to about 60%. In some embodiments, contacting the receptor-interacting protein kinase 1 with a compound as described herein will result in complete (i.e., 100%) inhibition.

Dosing

The phrases "parenteral administration" and "administered parenterally" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient that is effective to achieve the desired therapeutic response for a particular patient, composition and mode of administration, without being toxic to the patient.

The selected dosage level will depend upon a variety of factors including the activity of the particular compound of the present disclosure employed or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated and like factors well known in the medical arts. A daily, weekly or monthly dosage (or other time interval) can be used.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required to achieve the desired therapeutic effect and then gradually increasing the dosage until the desired effect is achieved.

In general, a suitable daily dose of a compound of the disclosure will be that amount of the compound that is the lowest dose effective to produce a therapeutic effect (e.g., inhibit necrosis). Such an effective dose will generally depend upon the factors described above. Generally doses of the compounds of this disclosure for a patient, when used for the indicated effects, will range from about 0.0001 to about 100 mg per kg of body weight per day. Preferably the daily dosage will range from 0.001 to 50 mg of compound per kg of body weight and even more preferably from 0.01 to 10 mg of compound per kg of body weight.

If desired, the effective daily dose of the active compound may be administered as two, three, four, five, six or more sub-doses administered separately at appropriate intervals throughout the day, optionally, in unit dosage forms.

In certain embodiments, the present disclosure relates to compounds for inhibiting cell death, wherein the compounds are represented by structures (I). In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar and most preferably at a concentration less than 1 micromolar.

The compounds of the disclosure can be tested in standard animal models of stroke and standard protocols such as described by Hara, H., et al. *Proc. Natl. Acad. Sci. USA,* 1997. 94(5): 2007-12.

When the compounds of the present disclosure are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds of the present application or the compositions thereof may be administered once, twice, three or four times daily, using any suitable mode described above. Also, administration or treatment with the compounds may be continued for a number of days; for example, commonly treatment would continue for at least 7 days, 14 days or 28 days, for one cycle of treatment. Treatment cycles are well known and are frequently alternated with resting periods of about 1 to 28 days, commonly about 7 days or about 14 days, between cycles. The treatment cycles, in certain embodiments, may also be continuous.

When administered orally, the total daily dosage for a human subject may be between 1 mg and 1,000 mg, between about 1,000-2,000 mg/day, between about 10-500 mg/day, between about 50-300 mg/day, between about 75-200 mg/day or between about 100-150 mg/day.

The daily dosage may also be described as a total amount of a compound described herein administered per dose or per day. Daily dosage of a compound may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day or between about 15 to 150 mg/day.

In certain embodiments, the method comprises administering to the subject an initial daily dose of about 1 to 800 mg of a compound described herein and increasing the dose by increments until clinical efficacy is achieved. Increments of about 5, 10, 25, 50 or 100 mg can be used to increase the dose. The dosage can be increased daily, every other day, twice per week or once per week.

In certain embodiments, a compound or pharmaceutical preparation is administered orally. In certain embodiments, the compound or pharmaceutical preparation is administered intravenously. Alternative routes of administration include sublingual, intramuscular and transdermal administrations.

The preparations of the present disclosure may be given orally, parenterally, topically or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. In certain embodiments, the administration is oral.

VI. EXAMPLES

All solvents used were commercially available and were used without further purification. Reactions were typically run using anhydrous solvents under an inert atmosphere of nitrogen. Abbreviations: aq. (aqueous), EtOAc (ethyl acetate), DCM (dichloromethane), TFA (trifluoroacetic acid), HATU (1-lbis(dimethylamino)methylenel-1H-1,2,3-triazolo[4,5-b]pyridinium 3-oxid hexafluorophosphate), TEA (triethylamine), DMF (dimethylformamide), THF (tetrahydrofuran), MeTHF (2-methyltetrahydrofuran), PE (petroleum ether), T3P (propylphosphonic anhydride), AcOH (acetic acid), hex (hexane), DIAD (diisopropyl azodicarboxylate), IPA (isopropylalcohol), MTBE (methyl tert-butyl ether), MsCl (methanesulfonylchloride), $Boc_2O$ (di-tert-butyl dicarbonate), DMP (Dess-Martin periodinane), LDA (lithium diisopropylamide), DAST ((diethylamino)sulfur trifluoride), i-PrOH (isopropylalcohol), TBAF (tetrabutylammonium fluoride), DIEA (diisopropylethylamine), EtOH (ethanol), DMPU (1,3-dimethyl-3,4,5,6-tetrahydro-2(1H)-pyrimidinone), BAST (bis(2-methoxyethyl)aminosulfur trifluoride), XPhos (2-dicyclohexylphosphino-2',4',6'-triisopropylbiphenyl), BINAP ((2,2'-bis(diphenylphosphino)-1,1'-binaphthyl), LHMDS (lithium bis(trimethylsilyl)amide), Select F (Selectfluor, 1-chloromethyl-4-fluoro-1,4-diazoniabicyclo[2.2.2]octane bis(tetrafluoroborate)), DCE (1,2-dichloroethane), $TMSCF_3$ ((trifluoromethyl)trimethylsilane), ACN (acetonitrile, methyl cyanide), NaHMDS (sodium hexamethyldisilazide), NMI (N-methylimidazole), equiv. (equivalent), M (molar), mM (millimolar), µM (micromolar), h (hour), min. (minute), mm (millimeter) mL (milliliter), µl (microliter), N (normal), RT (room temperature), mol (mole), mmol (millimol), g (gram), mg (milligram), sat. (saturated) v/v (volume/volume), i.d. (internal diameter), psi (pounds per square inch), LC-MS (liquid chromatography mass spectroscopy), HPLC (high performance liquid chromatography), TLC (thin layer chromatograph), SFC (supercritical fluid chromatograph).

NMR Spectroscopy. $^1$H Nuclear magnetic resonance (NMR) spectroscopy was carried out using a Bruker Avance III equipped with a BBFO 300 MHz probe operating at 300 MHz or one of the following instruments: a Bruker Avance 400 instrument equipped with probe DUAL 400 MHz Si, a Bruker Avance 400 instrument equipped with probe 6 Si 400 MHz 5 mm $^1$H-$^{13}$C ID, a Bruker Avance III 400 instrument with nanobay equipped with probe Broadband BBFO 5 mm direct, a Bruker Mercury Plus 400 NMR spectrometer equipped with a Bruker 400 BBO probe with all operating at 400 MHz. All deuterated solvents contained typically 0.03% to 0.05% v/v tetramethylsilane, which was used as the reference signal (set at δ0.00 for both $^1$H and $^{13}$C). In certain cases, $^1$H Nuclear magnetic resonance (NMR) spectroscopy was carried out using a Bruker Advance 400 instrument operating at 400 megahertz (MHz) using the stated solvent at around RT unless otherwise stated. In all cases, NMR data were consistent with the proposed structures. Characteristic chemical shifts (δ) are given in parts-per-million using conventional abbreviations for designation of major peaks: e.g., s, singlet; d, doublet; t, triplet; q, quartet; dd, doublet of doublets; ddd, doublet of doublets of doublets, dt, doublet of triplets; br, broad; m, mutiplet. Chemical shifts are expressed in Hz (hertz).

Chromatography. Thin layer chromatography (TLC) was performed using silica gel F254 (Merck) plates or Alugram® (Silica gel 60 F254) from Mancherey-Nagel. Column chromatography was performed using an automatic flash chromatography system over silica gel eluting with typical solvents such as EtOAc/hexanes or MeOH/DCM. Reverse phase HPLC was performed using C18 columns eluting with typical solvents such as water and acetonitrile containing formic acid, TFA, or HCl as additives.

Liquid Chromatography-Mass Spectrometry Method A: Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ CSH, C18 column (50×2.1 mm, 1.7 µm particle size), column temperature 40° C., mobile phase: A-water+0.1% HCOOH/B—CH3CN+0.1% HCOOH, flow rate: 1.0 mL/min, run-time=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method B: Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. The column used was a Cortecs UPLC C18, 1.6 µm, 2.1×50 mm A linear gradient was applied, starting at 95% A (A: 0.1% formic acid in water) and ending at 95% B (B: 0.1% formic acid in MeCN) over 2.0 min with a total run time of 2.5 min. The column temperature was at 40° C. with the flow rate of 0.8 mL/min.

Liquid Chromatography-Mass Spectrometry Method C: LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in positive or negative mode. The mass spectrometer was scanned between m/z 90-900 with a scan time from 0.5 to 1.0 s. The column used was a Shim-pack XR-ODS, 2.2 µm, 3.0×50 mm A linear gradient was applied, starting at 95% A (A: 0.05% TFA in water) and ending at 100% B (B: 0.05% TFA in MeCN) over 2.2 min with a total run time of 2.6 min. The column temperature was at 40° C. with a flow rate of 1.0 mL/min.

Liquid Chromatography-Mass Spectrometry Method D: LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in positive or negative mode. The mass spectrometer was scanned between m/z 90-900 with a scan time from 0.5 to 1.0 s. The column used was a Kinetex EVO, 2.6 μm, 3.0×50 mm A linear gradient was applied, starting at 90% A (A: 0.05% $NH_4HCO_3$ in water) and ending at 95% B (B: MeCN) over 2.7 min with a total run time of 3.0 min. The column temperature was at 40° C. with a flow rate of 1.3 mL/min.

Liquid Chromatography-Mass Spectrometry Method E: LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in positive or negative mode. The mass spectrometer was scanned between m/z 90-900 with a scan time from 0.5 to 1.0 s. The column used was an Ascentis Express C18, 2.7 μm, 2.1×50 mm A linear gradient was applied, starting at 90% A (A: 0.1% formic acid in water) and ending at 100% B (B: 0.1% formic acid in MeCN) over 1.70 min with a total run time of 2.0 min. The column temperature was at 45° C. with a flow rate of 1.0 mL/min.

Liquid Chromatography-Mass Spectrometry Method F: LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in positive or negative mode. The mass spectrometer was scanned between m/z 90-900 with a scan time from 0.5 to 1.0 s. The column used was an Agilent Poroshell HPH-C18, 2.7 μm, 3.0×50 mm A linear gradient was applied, starting at 95% A (A: 0.05% $NH_4HCO_3$ in water) and ending at 95% B (B: 0.05% $NH_4HCO_3$ in MeCN) over 2.7 min with a total run time of 3 min. The column temperature was at 45° C. with a flow rate of 1.5 mL/min.

Liquid Chromatography-Mass Spectrometry Method G: LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in positive or negative mode. The mass spectrometer was scanned between m/z 90-900 with a scan time from 0.5 to 1.0 s. The column used was an Agilent Poroshell HPH-C18, 2.7 μm, 3.0×50 mm A linear gradient was applied, starting at 95% A (A: 0.05% $NH_4HCO_3$ in water) and ending at 95% B (B: 0.05% $NH_4HCO_3$ in MeCN) over 4.7 min with a total run time of 5.0 min. The column temperature was at 40° C. with a flow rate of 1.5 mL/min.

Liquid Chromatography-Mass Spectrometry Method H: LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Agilent Poroshell HPH-C18, 2.7 μm, 3.0×50 mm A linear gradient was applied, starting at 95% A (A: 0.05% $NH_4HCO_3$ in water) and ending at 95% B (B: 0.05% $NH_4HCO_3$ in MeCN) over 1.8 min with a total run time of 2.0 min. The column temperature was at 40° C. with a flow rate of 1.5 mL/min.

Method A, T3P coupling: To a flask containing amine (1.0 equiv.), and carboxylic acid (2.0 equiv.) in solvent (0.1 M) were added N-methylimidazole (2.0 equiv.) followed by T3P solution (2.0 equiv., 50% in EtOAc). The resulting reaction mixture was stirred at RT for 16 h, at which point 1 M NaOH solution was added followed by EtOAc. The layers were separated, and the aqueous layer was extracted with EtOAc (3×). The combined organic layers were dried over anhydrous $MgSO_4$, filtered and concentrated under reduced pressure. The crude reaction mixture was purified employing silica gel flash chromatography or reverse-phase preparatory HPLC to afford the desired product.

Method B, HATU coupling: To a flask containing amine (1.0 equiv.), carboxylic acid (1.5 equiv.), and HATU (2.0 equiv) was added DMF (0.1 M) followed by N,N-diisopropylethylamine (3-5 equiv.). The resulting reaction mixture was stirred overnight and diluted with brine and EtOAc. The layers were separated, and the aqueous layer was extracted with EtOAc (3×). The combined organic layers were dried over anhydrous $MgSO_4$, filtered and concentrated under reduced pressure. The crude reaction mixture was purified employing silica gel flash chromatography or reverse-phase preparatory HPLC to afford the desired product.

Method C, HATU coupling: To a vial containing amine (1.0 equiv.), carboxylic acid (1.5 equiv.) and HATU (2.0 equiv.) were added TEA (5.0 equiv.) and DMF (0.15 M). The resulting reaction mixture was stirred at RT for 16 h, at which point water was added. The reaction mixture was diluted with EtOAc. The layers were separated, and the aqueous layer was extracted with EtOAc (3×). The combined organic layers were dried over anhydrous $MgSO_4$, filtered and concentrated under reduced pressure. The crude reaction mixture was purified employing silica gel flash chromatography or reverse-phase preparatory HPLC to afford the desired product.

Method D: When the acid chloride needed to be prepared it was done so from the corresponding acid using standard procedures employing either $SOCl_2$ or oxalyl chloride. To a solution of acid chloride (1.5 equiv.) in THF (0.15 M) was added a solution of triethylamine (5 equiv.) and amine (1 equiv.) in THF (0.15 M) at RT. The resulting reaction mixture was stirred at RT for 16 h, at which point the mixture was diluted with EtOAc and sat. aq. $NaHCO_3$. The layers were separated and the organics were dried over sodium sulfate, filtered and concentrated under reduced pressure.

Method E: Preparation of 9-fluoro-2,3,4,5-tetrahydropyrido[3,4-f][1,4]oxazepine

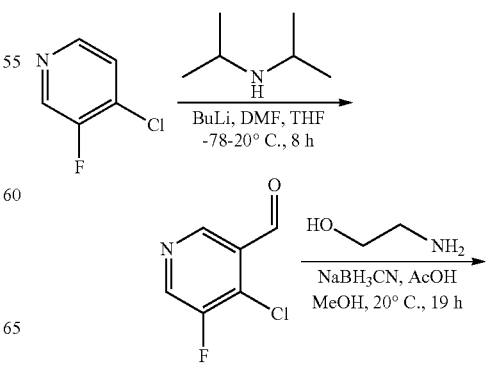

-continued

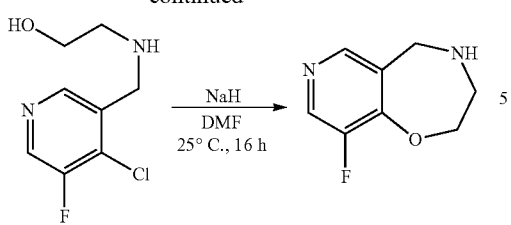

4-Chloro-5-fluoro-pyridine-3-carbaldehyde: To a solution of N-isopropylpropan-2-amine (9.23 g, 91.24 mmol) in THF (100 mL) was added n-butyllithium (2.5 M, 76.03 mmol, 36.49 mL) at −30° C. over 15 min and stirred for 15 min A solution of 4-chloro-3-fluoro-pyridine (10 g, 76.03 mmol) in THF (20 mL) was added dropwise over 15 min. at −78° C. then stirred at −78° C. for 6 h before adding DMF (7.02 mL, 91.24 mmol) and slowly warming to 20° C. The reaction mixture was quenched by the addition of sat. NH$_4$Cl (300 mL) at 0° C. and extracted with EtOAc (3×300 mL). The organic layers were combined, washed with brine (3×50 mL), dried over anhydrous Na$_2$SO$_4$, filtered and concentrated under reduced pressure. The residue was purified by silica gel column chromatography (PE:EtOAc=100:1 to 4:1) to give the title compound (12 g, 99%) as a brown oil.

2-[(4-Chloro-5-fluoro-3-pyridyl)methylamino]ethanol: To a mixture of 4-chloro-5-fluoro-pyridine-3-carbaldehyde (2 g, 12.54 mmol) in MeOH (20 mL) was added AcOH (1.51 g, 25.07 mmol), followed by 2-aminoethanol (3.83 g, 62.68 mmol), then the reaction solution was stirred at 25° C. for 3 h. NaBH$_3$CN (2.36 g, 37.61 mmol) was added and stirred at 25° C. for 16 h. The reaction mixture was quenched by the addition of water (50 mL) at 0° C. and extracted with DCM: i-PrOH (v:v=10:1, 3×50 mL). The combined organic phase was washed with brine (50 mL), dried over anhydrous Na$_2$SO$_4$, filtered and concentrated under reduced pressure to give the title compound (1.46 g, 57%) as a yellow oil.

9-Fluoro-2,3,4,5-tetrahydropyrido[3,4-f][1,4]oxazepine: To a solution of 2-[(4-chloro-5-fluoro-3-pyridyl)methylamino]ethanol (1.4 g, 6.84 mmol) in DMF (20 mL) was added NaH (60% in mineral oil) (1.37 g, 34.21 mmol) and stirred at 25° C. for 16 h. The reaction mixture was diluted with water (30 mL). The mixture was extracted with DCM: i-PrOH (v:v=3:1, 3×30 mL), washed with water (30 mL) and brine (30 mL), dried over anhydrous Na$_2$SO$_4$, filtered and concentrated under reduced pressure to provide the title compound (0.82 g, 71%) as a yellow oil.

The following intermediates were prepared using procedures analogous to those described above.

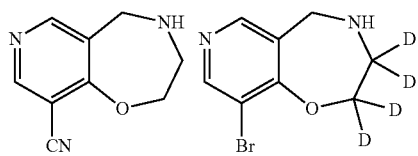

Method F: Preparation of 1-(9-Bromo-6-fluoro-3,5-dihydro-2H-1,4-benzoxazepin-4-yl)-3,3-difluoro-2,2-dimethyl-propan-1-one

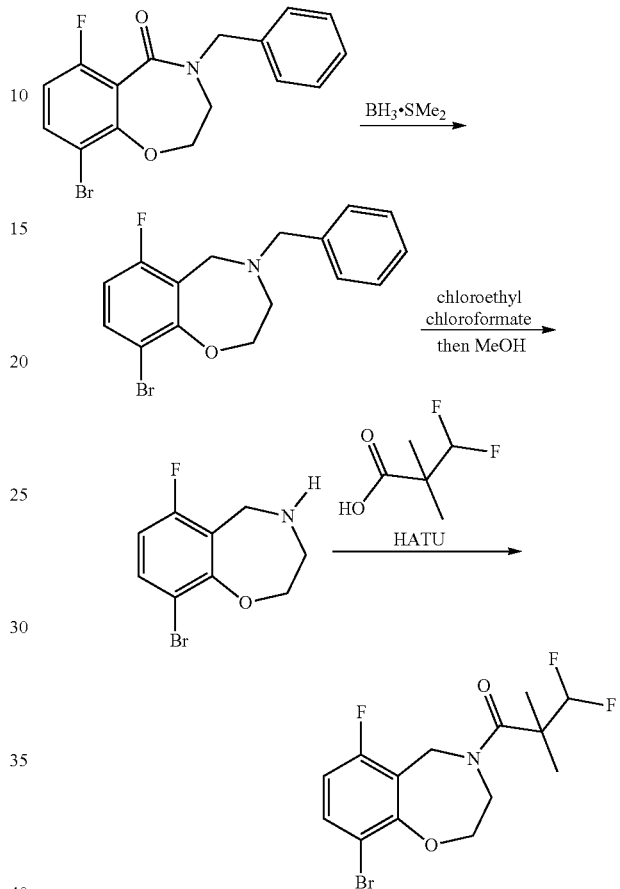

4-Benzyl-9-bromo-6-fluoro-2,3,4,5-tetrahydrobenzo[f][1,4]oxazepine. To a solution of 4-benzyl-9-bromo-6-fluoro-2,3-dihydro-1,4-benzoxazepin-5-one (1.0 g, 2.9 mmol) in THF (11.0 mL) at RT was added BH.SMea (5.7 mL, 11.4 mmol). The resulting reaction mixture was heated at 60° C. for 2 h, cooled to 0° C. and slowly treated with NaOH solution (25 mL, 1 M), and MeOH (10 mL). The resulting mixture was stirred for 15 min. and EtOAc (50 mL) was added. The layers were separated, and the aqueous layer was extracted with EtOAc (3×25 mL). The combined organic layers were dried over anhydrous MgSO$_4$, filtered and concentrated under reduced pressure. The crude reaction mixture was purified employing silica gel flash chromatography (0-30% EtOAc/hexanes) to provide the desired product as a clear oil.

9-Bromo-6-fluoro-2,3,4,5-tetrahydrobenzo[f][1,4]oxazepine. 4-Benzyl-9-bromo-6-fluoro-3,5-dihydro-2H-1,4-benzoxazepine (430 mg, 1.28 mmol) was dissolved in DCE (5.1 mL) and was treated with 1-chloroethyl chloroformate (0.28 mL, 2.56 mmol) for 1 h at 90° C. The reaction mixture was concentrated and the residue dissolved in MeOH (10 mL) and heated to 80° C. for 2h. The solution was concentrated and EtOAc (25 mL) and NaOH solution (25 mL) were added. The layers were separated, and the aqueous layer was extracted with EtOAc (3×25 mL). The combined organic layers were dried over anhydrous MgSO$_4$, filtered and concentrated under reduced pressure. The crude reaction mixture was used directly without purification.

1-(9-Bromo-6-fluoro-3,5-dihydro-2H-1,4-benzoxazepin-4-yl)-3,3-difluoro-2,2-dimethyl-propan-1-one. The title compound was prepared using General Procedure B employing 9-bromo-6-fluoro-2,3,4,5-tetrahydro-1,4-benzoxazepine (74 mg, 0.3 mmol), HATU (171 mg, 0.45 mmol), N,N-diisopropylethylamine (0.16 mL, 0.9 mmol) and 3,3-difluoro-2,2-dimethyl-propanoic acid (62 mg, 0.45 mmol) in DMF (1 mL). Purified employing column chromatography (0-40% EtOAc/hex) on combiflash and then by reverse phase HPLC to deliver the desired product as a brown solid.

Method G: Preparation of 7-Fluoro-2,3,4,5-tetrahydro-1,4-benzoxazepine-9-carbonitrile hydrochloride

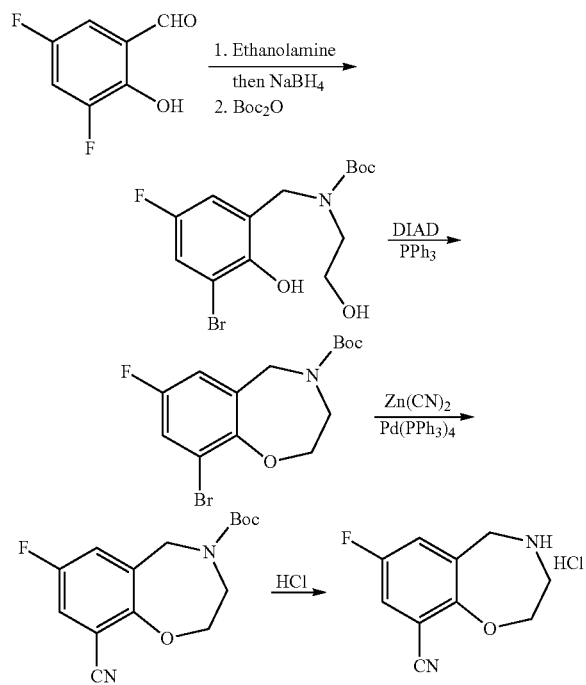

tert-Butyl (3-bromo-5-fluoro-2-hydroxybenzyl)(2-hydroxyethyl)carbamate To a solution of 3-bromo-5-fluoro-2-hydroxy-benzaldehyde (240 mg, 1.1 mmol) in THF (1.0 mL) and ethanol (1.0 mL) at RT was added ethanolamine (80 µL, 1.37 mmol). The reaction mixture was stirred at RT for 1 h and cooled to 0° C. NaBH4 (17 mg, 0.44 mmol) was added and the reaction mixture was allowed to warm to RT and was stirred for 4 h. Water (5 mL) was added and the biphasic mixture was stirred for 1 h. NH$_4$Cl solution (10 mL) and EtOAc (10 mL) were added, the layers were separated and the aqueous layer was extracted with EtOAc (3×25 mL) and DCM (3×25 mL). The combined organic layers were dried over anhydrous MgSO$_4$, filtered, and concentrated under reduced pressure. The residue was suspended in THF (4.0 mL) and MeOH (1.0 mL) and cooled to 0° C. NEt$_3$ (152 mg, 1.5 mmol) was added followed by Boc$_2$O (218 mg, 1.0 mmol) and the resulting reaction mixture was stirred overnight. The reaction mixture was concentrated and purified employing silica gel flash chromatography (25-75% EtOAc/hexanes) to provide the desired product as a clear oil.

tert-Butyl 9-bromo-7-fluoro-3,5-dihydro-2H-1,4-benzoxazepine-4-carboxylate. tert-Butyl N-[(3-bromo-5-fluoro-2-hydroxy-phenyl)methyl]-N-(2-hydroxyethyl)carbamate (200 mg, 0.55 mmol) and PPh3 (144 mg, 0.55 mmol) were dissolved in THF (2.0 mL) and cooled to 0° C. DIAD (111 mg, 0.55 mmol) was added dropwise and the reaction mixture was stirred overnight and allowed to warm to RT. The reaction mixture was concentrated and purified employing silica gel flash chromatography (0-30% EtOAc/hexanes) to provide the desired product as a clear oil.

tert-Butyl 9-cyano-7-fluoro-3,5-dihydro-2H-1,4-benzoxazepine-4-carboxylate. To a flask containing tert-butyl 9-bromo-7-fluoro-3,5-dihydro-2H-1,4-benzoxazepine-4-carboxylate (79 mg, 0.23 mmol) and Zn(CN)$_2$ (26.8 mg, 0.23 mmol) was added DMF (2.0 mL). The solution was degassed with argon for 15 min. and tetrakis(triphenylphosphine)palladium(0) (26.4 mg, 0.02 mmol) was added. The reaction mixture was heated at 100° C. overnight, cooled to RT and diluted with brine (10 mL) and EtOAc (10 mL). The layers were separated and the aqueous layer was extracted with EtOAc (3×10 mL) The combined organic layers were dried over MgSO$_4$, filtered, and concentrated under reduced pressure. The crude reaction mixture was purified employing silica gel flash chromatography (0-50% EtOAc/hexanes) to provide the desired product as a clear oil.

7-Fluoro-2,3,4,5-tetrahydro-1,4-benzoxazepine-9-carbonitrile hydrochloride. tert-butyl 9-cyano-7-fluoro-3,5-dihydro-2H-1,4-benzoxazepine-4-carboxylate (25 mg, 0.09 mmol) was dissolved in HCl solution (2.0 mL, 4 M in 1,4 dioxane) and stirred at RT for 1h. The resulting precipitate was collected and used directly.

Method H: Preparation of 2,3,4,5-Tetrahydro-1,4-benzoxazepine-8-carbonitrile hydrochloride

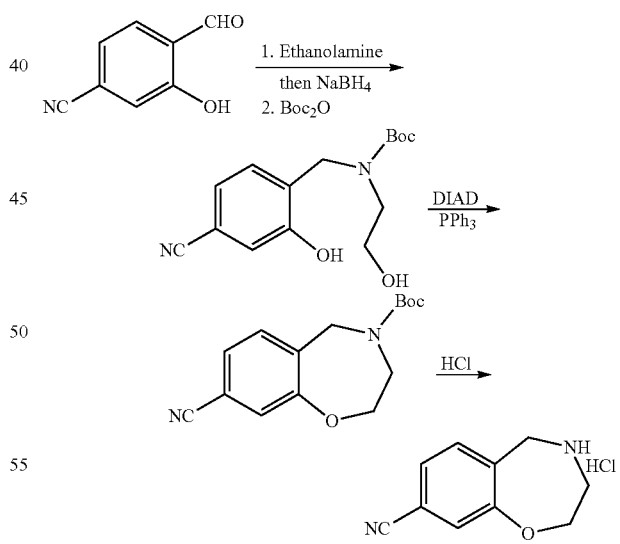

3-Hydroxy-4-[(2-hydroxyethylamino)methyl]benzonitrile. Ethanolamine (0.13 mL, 2.12 mmol) and 4-formyl-3-hydroxy-benzonitrile (250 mg, 1.7 mmol) were stirred in THF (2 mL) and ethanol (2 mL) overnight at RT. Sodium borohydride (64.3 mg, 1.7 mmol) was then added and the reaction mixture was stirred for 1 h at RT. The reaction mixture was concentrated to dryness and the resulting residue was taken up in EtOAc (25 mL) and washed with 2×mL water then 1×mL saturated brine solution. The organics were then separated and dried (MgSO₄) before concentration to dryness. The crude was taken as is to the next step. LC-MS: m/z=193.01 [M−Boc+H]⁺.

tert-Butyl N-[(4-cyano-2-hydroxy-phenyl)methyl]-N-(2-hydroxyethyl)carbamate. To a solution of 3-hydroxy-4-[(2-hydroxyethylamino)nethyl]benzonitrile (235 mg, 1.22 mmol) in THF (2 mL) and methanol (2 mL) and 0° C. was added triethylamine (0.26 mL, 1.83 mmol) and di-tert-butyl-carbonate (266.83 mg, 1.22 mmol). The reaction mixture was warmed to RT slowly and stirred overnight. The reaction mixture was concentrated and purified employing silica gel chromatography (0-60% EtOAc/hexanes) to provide the desired product as a colorless oil.

tert-Butyl 8-cyano-3,5-dihydro-2H-1,4-benzoxazepine-4-carboxylate. tert-Butyl N-[(4-cyano-2-hydroxy-phenyl)methyl]-N-(2-hydroxyethyl)carbamate (425 mg, 1.45 mmol) and triphenylphosphine (458 mg, 1.74 mmol) were dissolved in THF (10 mL) and cooled to 0° C. DIAD (0.31 mL, 1.6 mmol) was added dropwise and the reaction mixture was stirred overnight and allowed to warm to RT. The reaction mixture was concentrated and purified employing silica gel flash chromatography (0-30% gradient in ethyl acetate/hexanes) to provide the desired product as a clear oil. LC-MS: m/z=175.02 [M−Boc+H]⁺.

2,3,4,5-Tetrahydro-1,4-benzoxazepine-8-carbonitrile hydrochloride. A 4 M solution of HCl in dioxane (2.55 mL, 10.21 mmol) was added to tert-butyl 8-cyano-3,5-dihydro-2H-1,4-benzoxazepine-4-carboxylate (280 mg, 1.02 mmol). After 20 min. the reaction mixture was diluted with ether and the white solid was collected by filtration to provide the desired product. ¹H-NMR (400 MHz, DMSO-d₆): δ 9.65-9.63 (m, 2H), 7.68-7.60 (m, 3H), 4.42 (s, 2H), 4.28 (dt, J=4.5, 2.3 Hz, 2H), 3.52-3.49 (m, 2H). LC-MS: m/z=175.02 [M+H]⁺.

The following intermediate was prepared using procedures analogous to those described above.

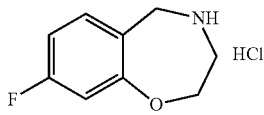

Method I: Preparation of 2,3,4,5-tetrahydropyrido[3,4-f][1,4]oxazepine-9-carbonitrile dihydrochloride and 4-(3,3-difluoro-2,2-dimethyl-propanoyl)-3,5-dihydro-2H-pyrido[3,4-f][1,4]oxazepine-9-carbonitrile

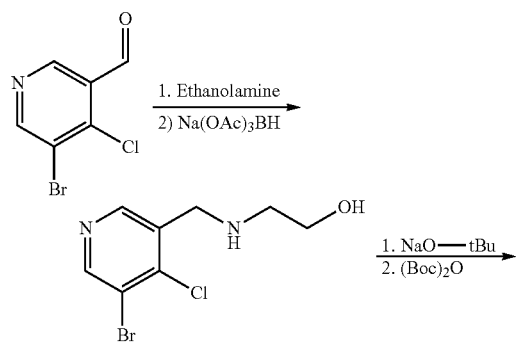

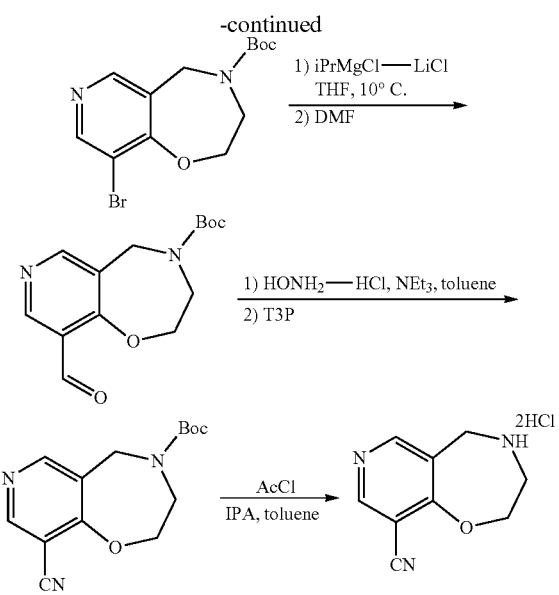

2-[(5-Bromo-4-chloro-3-pyridyl)methylamino]ethanol. 5-bromo-4-chloro-pyridine-3-carbaldehyde (1 equiv.) was dissolved in dichloroethane (0.23 M). AcOH was added along with ethanolamine (2 equiv.) and the mixture was stirred for 10 min. Sodium triacetoxyborohydride (3 equiv.) was added, and the mixture was stirred at RT overnight. The volatiles were removed under reduced pressure. The residue was treated with 1N NaOH until pH basic and extracted with DCM, dried over magnesium sulfate and concentrated under reduced pressure to provide the desired material as a white solid. ¹H-NMR (400 MHz, CDCl₃): δ 8.70 (s, IFl), 8.54 (d, J=0.6 Hz, 1H), 4.03 (s, 2H), 3.75-3.70 (m, 2H), 2.88-2.85 (m, 2H). LCMS: m/z=266.87 [M+H]⁺.

tert-Butyl 9-bromo-3,5-dihydro-2H-pyrido[3,4-f][1,4]oxazepine-4-carboxylate. To a solution of sodium tert-butoxide (3.0 equiv.) in MeTHF (2.25 M) at 10° C. was added a solution of 2-[(5-bromo-4-chloro-3-pyridyl)methylamino]ethanol (1.0 equiv.) in MeTHF (0.38 M) while maintaining a temperature of less than 15° C. The reaction mixture was stirred at 10-15° C. for 1 hour before quenching with a solution of AcOH (2.0 equiv.) in MeTHF (1.5 M). A solution of (Boc)₂O (1.0 equiv.) in MeTHF (0.38 M) was added. The reaction mixture was stirred at 10-15° C. for 3.5 hours before diluting with water. The layers were separated and the aqueous layer was extracted with MeTHF. The combined organics were washed with brine and concentrated in vacuo to provide the title compound. ¹H-NMR (400 MHz, CDCl₃): δ 8.62-8.60 (m, 1H), 8.31-8.29 (m, 1H), 4.66-4.52 (m, 2H), 4.39-4.32 (m, 2H), 3.93-3.90 (m, 2H), 1.43 (dd, J=1.3, 0.7 Hz, 9H). LCMS: m/z=330.40 [M+H]⁺.

tert-Butyl 9-formyl-3,5-dihydro-2H-pyrido[3,4-f][1,4]oxazepine-4-carboxylate. To a solution of tert-butyl 9-bromo-3,5-dihydro-2H-pyrido[3,4-f][1,4]oxazepine-4-carboxylate (1 equiv.) in THF (0.75 M) at 0° C. under an inert atmosphere was added i-PrMgCl—LiCl 1.3 M solution in THF (1.3 equiv.) while maintaining a temperature below 10° C. The reaction mixture was stirred at 20° C. for 1 hour, cooled to 10° C. and DMF was added (1.5 equiv.) via addition funnel. The reaction mixture was stirred at 20° C. for 15 minutes before concentrating in vacuo. The resulting residue was partitioned between water and EtOAc 1:1 v/v. The layers were separated and the organic solution was concentrated in vacuo to provide the title compound as a yellow solid (95% yield). $^1$H-NMR (400 MHz, CDCl$_3$): δ 10.47 (s, 1H), 8.85 (s, 1H), 8.56-8.49 (m, 1H), 4.66-4.53 (m, 2H), 4.41 (br s, 2H), 3.91-3.89 (m, 2H), 1.40 (br s, 9H). LCMS: m/z=279 [M+H]$^+$.

tert-Butyl 9-cyano-3,5-dihydro-2H-pyrido[3,4-f][1,4]oxazepine-4-carboxylate. A mixture of tert-butyl 9-formyl-3,5-dihydro-2H-pyrido[3,4-f][1,4]oxazepine-4-carboxylate (1 equiv.), hydroxylamine hydrochloride (1.1 equiv.) and NEt$_3$ (2 equiv.) in toluene (0.6 M) was heated at 90° C. for 30 minutes and then cooled to 50° C. A 50% solution of T3P in EtOAc (2 equiv.) was added and the reaction mixture was heated at 90° C. for 30 minutes and then cooled to RT. The mixture was added to 10% K$_2$CO$_3$ and the layers were separated. The organic layer was washed with 10% aq. K$_2$CO$_3$ and 5% aq. KH$_2$PO$_4$ and then concentrated in vacuo to provide the title compound as a yellow oil (78% yield). $^1$H-NMR (CDCl$_3$)=8.62 (br s, 1H), 8.45 (br s, 1H), 4.40-4.70 (m, 4H), 3.84-3.91 (m, 2H), 1.34-1.46 (m, 9H) ppm. LCMS: m/z=276.2 [M+H]$^+$.

2,3,4,5-Tetrahydropyrido[3,4-f][1,4]oxazepine-9-carbonitrile dihydrochloride. To a solution of tert-butyl 9-cyano-3,5-dihydro-2H-pyrido[3,4-f][1,4]oxazepine-4-carboxylate (1 equiv.) in toluene and IPA 1:1 v/v (0.5 M) at 10° C. was added acetyl chloride (6 equiv.). The reaction mixture was stirred at RT for 3 hours. LCMS indicated the reaction was incomplete. Additional acetyl chloride (3 equiv.) was added and the mixture was stirred overnight. The resulting precipitate was collected by vacuum filtration and washed with MTBE to provide the title compound as a white solid (87% yield). $^1$H-NMR (400 MHz, CDCl$_3$): δ 10.17 (br s, 2H), 8.89 (s, 1H), 8.74 (s, 1H), 4.54-4.74 (m, 2H), 4.54 (s, 2H), 3.60 (s, 2H). LCMS: m/z=176 [M+H]$^+$.

4-(3,3-Difluoro-2,2-dimethyl-propanoyl)-3,5-dihydro-2H-pyrido[3,4-f][1,4]oxazepine-9-carbonitrile. To a solution of 3,3-difluoro-2,2-dimethyl-propanoic acid (1.3 equiv.) in CH$_3$CN (1 M) was added N-methylimidazole (7 equiv.) followed by the addition of MsCl (1.3 equiv.). The reaction mixture was heated at 55° C. for 90 minutes. The reaction mixture was cooled to 20° C. and 2,3,4,5-tetrahydropyrido[3,4-f][1,4]oxazepine-9-carbonitrile dihydrochloride (1 equiv.) was added and the reaction mixture was stirred for 45 minutes. 10% aq. K$_2$CO$_3$ and DCM (1:1 v/v) were added and the layers were separated. The organic layer was washed with 10% aq. K$_2$CO$_3$ and then concentrated in vacuo. The resulting solid was crystallized from IPA to provide the title compound.

2-[(5-Bromo-4-chloro-3-pyridyl)methylamino]ethanol. 5-bromo-4-chloro-pyridine-3-carbaldehyde (600 mg, 2.72 mmol) was dissolved in dichloroethane (12 mL). AcOH was added along with ethanolamine (332 mg, 5.44 mmol) and the mixture was stirred for 10 min. Sodium triacetoxyborohydride (1730 mg, 8.16 mmol) was added, and the mixture was stirred at RT overnight. The volatiles were removed under reduced pressure. The residue was treated with 1N NaOH until pH basic and extracted with DCM (40 mL), dried over magnesium sulfate and concentrated under reduced pressure to provide the desired material as a white solid. $^1$H-NMR (400 MHz, CDCl$_3$): δ 8.70 (s, 1H), 8.54 (d, J=0.6 Hz, 1H), 4.03 (s, 2H), 3.75-3.70 (m, 2H) 2.88-2.85 (m, 2H). LCMS (Method B): m/z [M+H]$^+$=266.87, 268.76.

tert-Butyl 9-bromo-3,5-dihydro-2H-pyrido[3,4-f][1,4]oxazepine-4-carboxylate. To a solution of 2-[(5-bromo-4-chloro-3-pyridyl)methylamino]ethanol (0.48 g, 1.81 mmol) in DMF was added NaH (0.36 g, 9.04 mmol). After stirring at rt overnight, the reaction was carefully treated with water at 0° C. The reaction mixture was diluted with EtOAc (30 mL). The organics were then separated and dried (MgSO$_4$) before concentration to dryness to provide the desired cyclized intermediate (LCMS (Method B): m/z [M+H]$^+$=228.95, 230.93). The crude material was then dissolved in DMF (10 mL) and treated with di-tert-butyl dicarbonate (0.79 g, 3.62 mmol) at rt. The reaction mixture was stirred at rt for 2h. The reaction mixture was then diluted with water (20 mL) and EtOAc (20 mL). The organics were then separated and dried (MgSO$_4$) before concentration to dryness. The crude was then purified by flash column chromatography eluting with 0-100% EtOAc/hexanes to provide the desired product as a colorless oil. $^1$H-NMR (400 MHz, CDCl$_3$): δ 8.62-8.60 (m, 1H), 8.31-8.29 (m, 1H), 4.66-4.52 (m, 2H), 4.39-4.32 (m, 2H), 3.93-3.90 (m, 2H), 1.43 (dd, J=1.3, 0.7 Hz, 9H). LC-MS (Method B): m/z=330.40 [M+H]$^+$.

tert-Butyl 9-cyano-3,5-dihydro-2H-pyrido[3,4-f][1,4]oxazepine-4-carboxylate. To a flask containing tert-butyl 9-bromo-3,5-dihydro-2H-pyrido[3,4-f][1,4]oxazepine-4-carboxylate (230 mg, 0.7 mmol), and zinc cyanine (82 mg, 0.7 mmol) was added DMF (5 mL). The solution was sparged with argon for 15 min and tetrakis(triphenylphosphine)palladium(0) (242 mg, 0.21 mmol) was then added. The reaction mixture was heated at 100° C. overnight, cooled to rt and diluted with water (10 mL) and EtOAc (10 mL). The organics were then separated and dried (MgSO$_4$) before concentration to dryness. The crude was then purified by flash column chromatography eluting with 0-100% EtOAc/hexanes to provide the desired product as a colorless oil. LC-MS (Method B): m/z=276.48 [M+H]$^+$.

2,3,4,5-Tetrahydropyrido[3,4-f][1,4]oxazepine-9-carbonitrile hydrochloride. 10 mL of 4 M HCl dioxane (40 mmol) was added to tert-butyl 9-cyano-3,5-dihydro-2H-pyrido[3,4-f][1,4]oxazepine-4-carboxylate (120 mg, 0.44 mmol). After 20 mins, the reaction mixture was diluted with ether (10 mL) and the solid was collected by filtration to provide the desired product as an orange solid. $^1$H-NMR (400 MHz, DMSO-d$_6$): δ 10.04-10.03 (m, 2H), 8.90 (s, 1H), 8.74 (s, 1H), 4.74-4.72 (m, 2H), 4.55-4.54 (m, 2H), 3.64-3.59 (m, 2H). LC-MS (Method B): m/z=176.37 [M+H]$^+$.

4-(3,3-Difluoro-2,2-dimethyl-propanoyl)-3,5-dihydro-2H-pyrido[3,4-f][1,4]oxazepine-9-carbonitrile. Prepared using general procedure C employing 2,3,4,5-tetrahydropyrido[3,4-f][1,4]oxazepine-9-carbonitrile hydrochloride (35 mg, 0.17 mmol), 3,3-difluoro-2,2-dimethyl-propanoic acid (34 mg, 0.248 mmol), TEA (0.230 mL, 1.65 mmol) and HATU (125 mg, 0.33 mmol) in DMF (1 mL). Purified employing reverse-phase HPLC to provide the desired product as a white solid. $^1$H-NMR (400 MHz, CDCl$_3$): δ 8.67 (s, 1H), 8.61 (s, 1H), 6.11 (t, J=56.5 Hz, 1H), 4.80 (s, 2H), 4.62-4.60 (m, 2H), 4.13 (t, J=5.0 Hz, 2H), 1.39 (t, J=1.3 Hz, 6H). LC-MS (Method B): m/z=296.29 [M+H]$^+$.

Method J: Preparation of 2,3,4,5-tetrahydropyrido[3,2-f][1,4]oxazepine

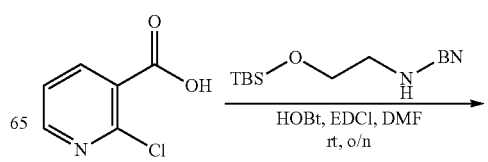

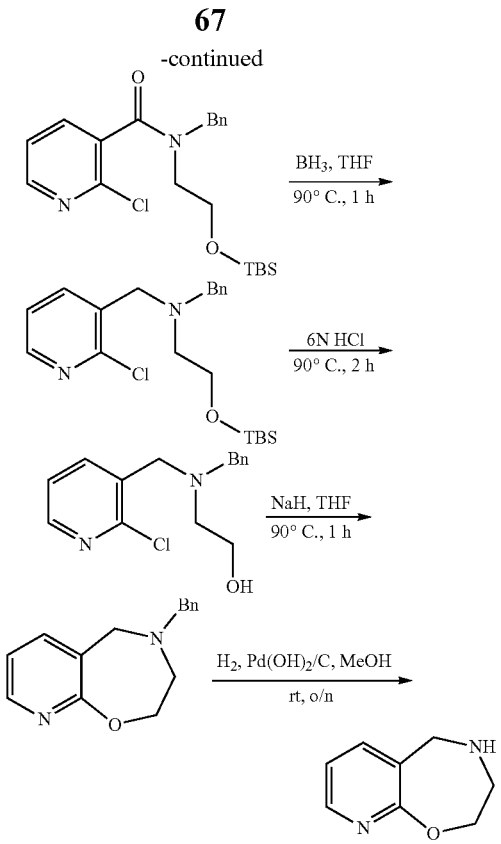

N-Benzyl-N-(2-(tert-butyldimethylsilyloxy)ethyl)-2-chloronicotinamide. To a mixture of 2-chloropyridine-3-carboxylic acid (1.0 g, 6.37 mmol) in N,N-dimethylformamide (15 mL) were added N-benzyl-2-(tert-butyldimethylsilyloxy)ethanamine (1.69 g, 6.37 mmol), 1-hydroxybenzotriazole (1.29 g, 9.55 mmol) and N-(3-dimethylaminopropyl))-N'-ethylcarbodiimide hydrochloride (1.83 g, 9.55 mmol). After stirring overnight at RT, the reaction mixture was quenched by addition of water (100 mL) and extracted with ethyl acetate (3×100 mL). The combined organic layers were dried over anhydrous sodium sulfate, filtered and concentrated under vacuum. The residue was purified by column chromatography (ethyl acetate/petroleum ether, 1/2) to afford the title compound (2.2 g, 85%) as a yellow oil. LC-MS: m/z=405.00 [M+H]$^+$.

N-Benzyl-2-(tert-butyldimethylsilyloxy)-N-((2-chloropyridin-3-yl)methyl) ethanamine. To a mixture of N-benzyl-N-(2-(tert-butyldimethylsilyloxy)ethyl)-2-chloronicotinamide (1.4 g, 3.46 mmol) in tetrahydrofuran (30 mL) was added a solution of borane in tetrahydrofuran (1 M, 17.3 mL). The resulting mixture was heated at 90° C. and stirred for 1 hour under nitrogen. After cooling to RT, the reaction mixture was quenched by the slow addition of methanol (20 mL) and concentrated under vacuum to afford the title compound (1.7 g crude) as a white oil. LC-MS: m/z=391.15 [M+H]$^+$.

2-(Benzyl((2-chloropyridin-3-yl)methyl)amino)ethanol. N-Benzyl-2-(tert-butyldimethylsilyloxy)-N-((2-chloropyridin-3-yl)methyl)ethanamine (1.7 g, 3.46 mmol) was added to hydrochloric acid (6 N, 15 mL). The resulting mixture was heated at 90° C. and stirred for 2 hours. After cooling to RT, the pH value of the reaction mixture was adjusted to 8 with aqueous sodium hydroxide (1 M, 15 mL). The resulting mixture was then extracted with ethyl acetate (3×20 mL). The combined organic layers were dried over anhydrous sodium sulfate, and filtered. The filtrate was concentrated under vacuum to afford the title compound (550 mg, 57% yield for two steps) as a white oil. LC-MS: m/z=277.05 [M+H]$^+$.

4-Benzyl-2,3,4,5-tetrahydropyrido[3,2-f][1,4]oxazepine. Sodium hydride (96 mg, 4.0 mmol) was added to a stirring mixture of 2-(benzyl((2-chloropyridin-3-yl)methyl)amino)ethanol (550 mg, 1.99 mmol) in tetrahydrofuran (10 mL) at 0° C. Then the resulting mixture was heated to 90° C. and stirred for 1 hour. After cooling to RT, the reaction mixture was quenched by the addition of water (20 mL) and extracted with ethyl acetate (3×15 mL). The combined organic layers were dried over anhydrous sodium sulfate, filtered and concentrated under vacuum. The residue was purified by Prep-TLC (ethyl acetate) to afford the title compound (470 mg, 98%) as a white oil. LC-MS: m/z=241.2 [M+H]$^+$.

2,3,4,5-Tetrahydropyrido[3,2-f][1,4]oxazepine. A mixture of 4-benzyl-2,3,4,5-tetrahydropyridol[3,2-f][1,4]oxazepine (200 mg, 0.83 mmol) in methanol (5 mL) was hydrogenated in the presence of palladium hydroxide (20%, 120 mg) under a hydrogen atmosphere (2-3 atm). After stirring overnight at RT, the reaction mixture was filtered through Celite. The filtrate was concentrated under vacuum to afford the title compound (110 mg, 88%) as a white oil. LC-MS: m/z=150.88 [M+H]$^+$.

The following intermediate was prepared using procedures analogous to those described above.

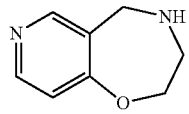 [SMILES: c1cc2c(cn1)CNCCO2]

Method K: Preparation of
2-cyclopropyl-3,3-difluoro-2-methyl-propanoic acid

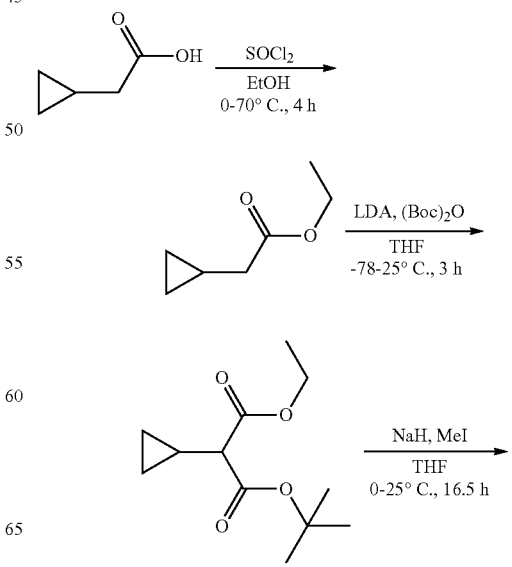

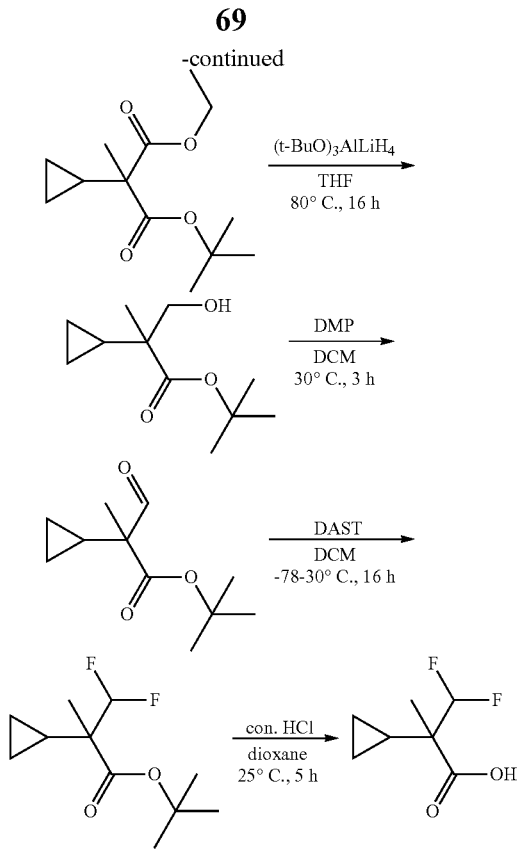

Ethyl 2-cyclopropylacetate: To a solution of 2-cyclopropylacetic acid (10.00 g, 99.88 mmol) in EtOH (40 mL) was added SOCl$_2$ (17.82 g, 149.83 mmol) at 0° C. The reaction solution was stirred at 70° C. for 4 h before concentrating directly to give the desired product (7 g, 55%) as a colorless oil.

1-tert-Butyl 3-ethyl 2-cyclopropylmalonate: To a solution of LDA (2 M, 43.89 mL) in THF (10 mL) was added ethyl 2-cyclopropylacetate (4.50 g, 35.11 mmol) in THF (5 mL) at −78° C. under N$_2$. The reaction solution was stirred at −78° C. for 30 min and at 0° C. for 30 min. Then Boc$_2$O (8.05 g, 36.87 mmol) was added dropwise at −78° C. The reaction solution was stirred at 25° C. for 2 h. The reaction mixture was quenched with sat. NH$_4$Cl (30 mL) at 0° C. and then extracted with EtOAc (3×30 mL). The combined organic layers were washed with brine (30 mL), dried over anhydrous Na$_2$SO$_4$, filtered and concentrated under vacuum. The residue was purified by silica gel column chromatography (PE:EtOAc=1:0 to 10:1) to provide the title compound (5.55 g, 69%) as a colorless oil.

1-tert-Butyl 3-ethyl 2-cyclopropyl-2-methylmalonate: To a stirred solution of 1-tert-butyl 3-ethyl 2-cyclopropylmalonate (5.55 g, 24.31 mmol) in THF (100 mL), was added NaH (1.46 g, 36.47 mmol, 60% purity) at 0° C. slowly. After 30 min., MeI (6.90 g, 48.62 mmol) was added. The mixture was stirred at 25° C. for 16 h. The reaction solution was quenched with sat. NH$_4$Cl (50 mL), extracted with EtOAc (3×50 mL), dried over anhydrous Na$_2$SO$_4$, filtered and concentrated under vacuum. The residue was purified by silica gel column chromatography (PE:EtOAc=50:1) to yield the title compound (3.6 g, 61%) as a yellow oil.

tert-Butyl 2-cyclopropyl-3-hydroxy-2-methyl-propanoate: A mixture of 1-tert-butyl 3-ethyl 2-cyclopropyl-2-methylmalonate (1.8 g, 7.43 mmol) and lithium tri-tert-butoxyaluminum hydride (1 M, 44.57 mmol) in THF (30 mL) was heated at reflux for 16 h. The reaction was quenched with sat. NH$_4$Cl solution (200 mL) and extracted with EtOAc (3×100 mL). The combined organic layers were washed with brine (200 mL), dried over anhydrous Na$_2$SO$_4$, filtered and concentrated to give the desired compound (1.3 g, crude) as a yellow oil.

tert-Butyl 2-cyclopropyl-2-methyl-3-oxo-propanoate: To a stirred solution of tert-butyl 2-cyclopropyl-3-hydroxy-2-methyl-propanoate (1.3 g, 6.5 mmol) in DCM (20 mL) was added DMP (3.30 g, 7.79 mmol). The reaction mixture was stirred at 30° C. for 3 h before quenching with sat. NaHCO$_3$ (30 mL). The mixture was extracted with EtOAc (3×20 mL) and the combined organic layers were washed with brine (20 mL), dried over anhydrous Na$_2$SO$_4$, filtered and concentrated under reduced pressure. The residue was purified by silica gel column chromatography (PE:EtOAc=50:1 to 20:1) to provide the title compound (0.7 g, 55%) as a yellow solid.

tert-Butyl 2-cyclopropyl-3,3-difluoro-2-methyl-propanoate: To a stirred solution of tert-butyl 2-cyclopropyl-2-methyl-3-oxo-propanoate (0.3 g, 1.51 mmol) in DCM (10 mL) was added DAST (610 mg, 3.78 mmol) at −78° C. The mixture was stirred at 30° C. for 16 h. The reaction was quenched with sat. NaHCO$_3$ solution (30 mL) and extracted with DCM (3×20 mL). The combined organics were washed with brine (30 mL), dried over anhydrous Na$_2$SO$_4$, filtered and concentrated to give the title compound (0.31 g) as a yellow oil.

2-Cyclopropyl-3,3-difluoro-2-methyl-propanoic acid: To a solution of tert-butyl 2-cyclopropyl-3,3-difluoro-2-methyl-propanoate (0.15 g, 0.68 mmol) in 1,4-dioxane (3 mL) was added conc. HCl (1.5 mL). The reaction solution was stirred at 25° C. for 5 h, diluted with H$_2$O (10 mL) and extracted with DCM (2×30 mL). The combined organic layers were washed with brine (20 mL), dried over anhydrous Na$_2$SO$_4$, filtered and concentrated to provide the title compound (0.08 g) as a dark yellow oil that was used without further purification. LCMS: m/z=163.1 [M−H]$^−$.

Method L: Preparation of 2-(difluoromethyl)-2-methylbutanoyl chloride

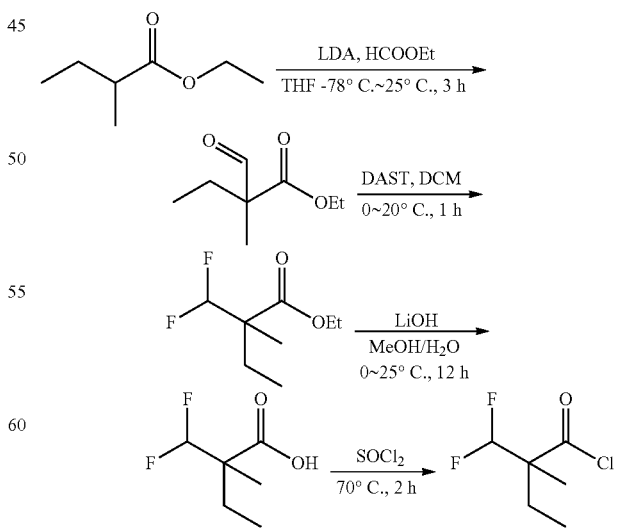

Ethyl-2-formyl-2-methyl-butanoate: To a solution of ethyl 2-methylbutanoate (10 g, 76.81 mmol) in THF (100 mL) was added LDA (2 M, 46.09 mL) dropwise at −78° C. under N₂. The mixture was stirred at −78° C. for 30 min., and then ethyl formate (6.83 g, 92.18 mmol) was added dropwise at −78° C. The mixture was stirred at 25° C. for 2.5 h, poured into water (100 mL) and extracted with EtOAc (3×80 mL). The combined organic layers were washed with brine (50 mL), dried over anhydrous Na₂SO₄, filtered and concentrated to give the title compound (7 g, 58%) as a yellow oil. ¹H NMR (400 MHz, CDCl₃): δ 9.66 (s, 1H), 4.15-4.21 (m, 2H), 1.79-1.95 (m, 2H), 1.22-1.24 (m, 6H), 1.07-1.10 (m, 3H).

Ethyl 2-(difluoromethyl)-2-methylbutanoate: To a solution of ethyl 2-formyl-2-methyl-butanoate (0.5 g, 3.16 mmol) in DCM (10 mL) was added DAST (1.02 g, 6.32 mmol) at 0° C. The reaction mixture was warmed to 25° C. and stirred for 12 h. The reaction mixture was quenched with sat. NaHCO₃ (15 mL) and extracted with EtOAc (3×10 mL). The organic layers were washed with brine (10 mL), dried over anhydrous Na₂SO₄, filtered and concentrated to provide the title compound (350 mg, 61%) as a yellow oil, which was used in the next step without further purification. ¹H NMR (400 MHz, CDCl₃): δ 6.00 (t, J=56.0 Hz, 1H), 4.23-4.12 (m, 2H), 1.82-1.77 (m, 1H), 1.62-1.58 (m, 1H), 1.30-1.23 (m, 6H), 0.92-0.88 (t, J=7.60 Hz, 3H).

2-(Difluoromethyl)-2-methylbutanoic acid: To a solution of ethyl 2-(difluoromethyl)-2-methyl-butanoate (350 mg, 1.94 mmol) in MeOH (3 mL) and H₂O (1 mL) was added NaOH (233.07 mg, 5.83 mmol) at 0° C. The mixture was stirred at 25° C. for 12 h. The solvent was removed under reduced pressure and water (10 mL) was added. The aqueous was washed with EtOAc (3×10 mL) and the aqueous solution was adjusted to pH=4 with 2 N HCl and extracted with DCM:i-PrOH (3×10 mL, v:v=3:1). The combined organic layers were washed with brine (10 mL), dried over anhydrous Na₂SO₄, filtered and concentrated under reduced pressure to provide the title compound (150 mg, 51%) as a yellow oil. The crude product was used in the next step without further purification. ¹H NMR (400 MHz, CDCl₃): δ 6.02 (t, J=56 Hz, 1H), 1.97-1.82 (m, 1H), 1.69-1.64 (m, 1H), 1.28 (s, 3H), 1.00-0.96 (t, J=7.60 Hz, 3H).

2-(Difluoromethyl)-2-methylbutanoyl chloride: A solution of 2-(difluoromethyl)-2-methyl-butanoic acid (100 mg, 657.29 μmol) in SOCl₂ (4.37 g, 36.76 mmol) was stirred at 70° C. for 2 h. The reaction mixture was concentrated under reduced pressure to give the title compound (110 mg) as a yellow oil. The crude product was used in the next step without further purification.

Method M: Preparation of 8-chloro-2,3,4,5-tetrahydropyrido[3,4-f][1,4]oxazepine-9-carbonitrile

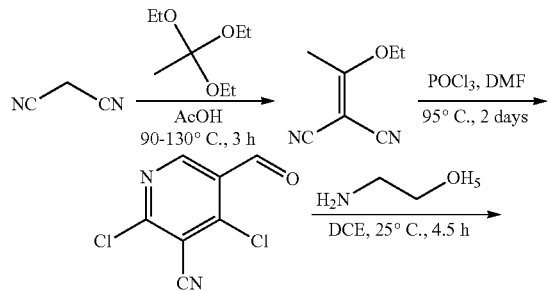

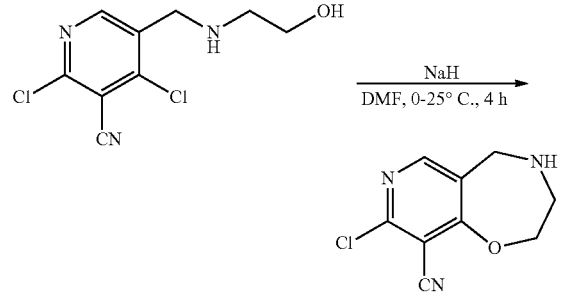

2-(1-Ethoxyethylidene)propanedinitrile: 1,1,1-triethoxyethane (134 g, 826 mmol) and AcOH (2.1 g, 34.97 mmol) were added sequentially to malononitrile (45.5 g, 688.75 mmol) at 20° C. under N₂. The mixture was stirred and gently heated to 90° C. for 2 h to remove the ethanol by distillation. Then the reaction was stirred at 130° C. for another 1 h to ensure complete reaction. The reaction mixture was cooled to RT and to the resulting solid was added hexane (200 mL). The solid was triturated, collected by filtration and the filter cake was washed with EtOH (50 mL) to give the title compound (87 g, 93%) as a white solid.

2,4-Dichloro-5-formyl-pyridine-3-carbonitrile: To a solution of 2-(1-ethoxyethylidene)propanedinitrile (35 g, 257.07 mmol) in DMF (80 g, 1.08 mol) was added POCl₃ (165.6 g, 1.08 mol) dropwise at 95° C. slowly. The mixture was stirred at 95° C. for 2 days. The reaction mixture was diluted with DCM (1 L) and stirred for 1 h before the solution was slowly poured into H₂O (1 L) and stirred for another 1 h. The reaction mixture was extracted with DCM (3×600 mL). The organic layers were combined, washed with brine (800 mL), dried over anhydrous Na₂SO₄, filtered and concentrated under reduced pressure. The resulting residue was purified by silica gel column chromatography (PE: EtOAc=20:1 to 3:1) to provide the title compound (37 g, 36%) as a yellow solid.

2,4-Dichloro-5-[(2-hydroxyethylamino)methyl]pyridine-3-carbonitrile: To a solution of 2,4-dichloro-5-formyl-pyridine-3-carbonitrile (5 g, 24.87 mmol) in DCE (50 mL) was added AcOH (3 g, 49.75 mmol) at 25° C., then the solution was stirred for 30 min. 2-aminoethanol (1.7 g, 27.36 mmol) was added at 25° C. and stirred at 25° C. for 2 h. Then NaBH(OAc)₃ (15.8 g, 74.62 mmol) was added in portions. The reaction solution was stirred at 25° C. for 2 h. The reaction mixture was quenched by the addition of sat. NH₄Cl (10 mL) at 0° C., and then the aqueous phase was neutralized to pH=7 with sat. NaHCO₃ and extracted with EtOAc (3×20 mL). The combined organic layers were dried over anhydrous Na₂SO₄, filtered and concentrated under reduced pressure. The resulting residue was purified by silica gel column chromatography (PE: EtOAc=1:1 to DCM: MeOH=1:1) to provide the title compound (2.7 g, 44%) as a yellow solid. LCMS: m/z=246.1 [M+H]⁺.

8-Chloro-2,3,4,5-tetrahydropyrido[3,4-f][1,4]oxazepine-9-carbonitrile: To a solution of 2,4-dichloro-5-[(2-hydroxyethylamino)methyl]pyridine-3-carbonitrile (0.5 g, 2.03 mmol) in DMF (10 mL) was added NaH (60% in mineral oil) (163 mg, 4.06 mmol) at 0° C. The reaction mixture was stirred at 25° C. for 4 h. The reaction mixture was quenched by the addition of sat. NH₄Cl (20 mL) at 0° C., and then extracted with EtOAc (4×10 mL). The combined organic layers were dried over anhydrous Na₂SO₄, filtered and concentrated under reduced pressure. The residue was purified by silica gel column chromatography (PE: EtOAc=1:1

Method N: Preparation of
4-fluoro-2,2-dimethyl-butanoic acid

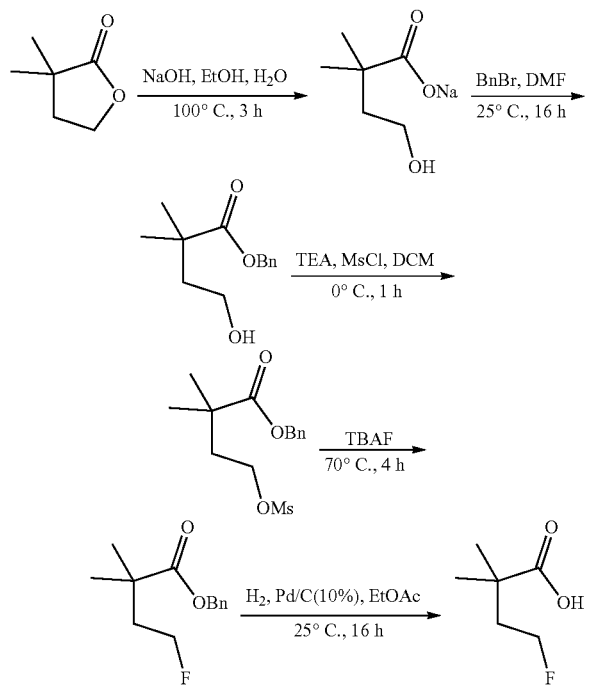

(4-Hydroxy-2,2-dimethyl-butanoyl)oxysodium: To a solution of 3,3-dimethyltetrahydrofuran-2-one (0.7 g, 6.13 mmol) in EtOH (6 mL) was added H$_2$O (3 mL) and NaOH (245.31 mg, 6.13 mmol). The reaction mixture was heated at 100° C. and stirred for 3 h. The mixture was concentrated to afford the title compound (1.1 g) as a white solid, which was used in the next step directly.

Benzyl 4-hydroxy-2,2-dimethyl-butanoate: To a solution of (4-hydroxy-2,2-dimethyl-butanoyl)oxysodium (1.1 g, 7.14 mmol) in DMF (10 mL) was added bromomethylbenzene (1.28 g, 7.49 mmol) at 25° C. The solution was stirred at 25° C. for 16 h before it was quenched with water (20 mL) at 0° C., and then extracted with EtOAc (3×20 mL). The combined organic layers were washed with brine (20 mL), dried over anhydrous Na$_2$SO$_4$, filtered and concentrated under reduced pressure. The residue was purified by prep-TLC (SiO$_2$, PE:EtOAc=3:1) to afford the title compound (254 mg, 16%) as a yellow oil.

Benzyl 2,2-dimethyl-4-methylsulfonyloxy-butanoate: To a solution of benzyl 4-hydroxy-2,2-dimethyl-butanoate (0.09 g, 405 µmol) in DCM (1 mL) was added TEA (61.46 mg, 607 µmol, 85 µL) and MsCl (69.57 mg, 607 µmol, 47 µL) at 0° C. under N$_2$. The mixture was stirred at 0° C. for 1 h. The mixture was diluted with DCM (10 mL), washed with water (3 mL) and brine (3 mL). The organic layer was dried over anhydrous Na$_2$SO$_4$, filtered and concentrated to afford the title compound (0.12 g, 99%) as a colorless oil, which was used in the next step directly.

4-Fluoro-2,2-dimethyl-butanoate: A solution of benzyl 2,2-dimethyl-4-methylsulfonyloxy-butanoate (0.12 g, 399 µmol) in TBAF (1 M in THF, 4 mL) was heated at 70° C. and stirred for 4 h. The mixture was diluted with EtOAc (10 mL) and washed with water (3 mL) and brine (3 mL). The organic layer was dried over anhydrous Na$_2$SO$_4$, filtered and concentrated. The resulting residue was purified by prep-TLC (SiO$_2$, PE:EtOAc=20:1) to afford the title compound (0.07 g, 78%) as a colorless oil.

4-Fluoro-2,2-dimethyl-butanoic acid: To a solution of benzyl 4-fluoro-2,2-dimethyl-butanoate (0.07 g, 312 µmol) in EtOAc (2 mL) was added 10% Pd/C (0.02 g) under N$_2$. The suspension was degassed under vacuum and purged with H$_2$ three times. The mixture was stirred under H$_2$ (50 psi) at 25° C. for 16 h. The reaction mixture was filtered and the filtrate was concentrated to afford the title compound (0.03 g, 72%) as a colorless oil, which was used in the next step without further purification.

Method O: Preparation of 9-methyl-2,3,4,5-tetrahydropyrido[3,4-f][1,4]oxazepine dihydrochloride

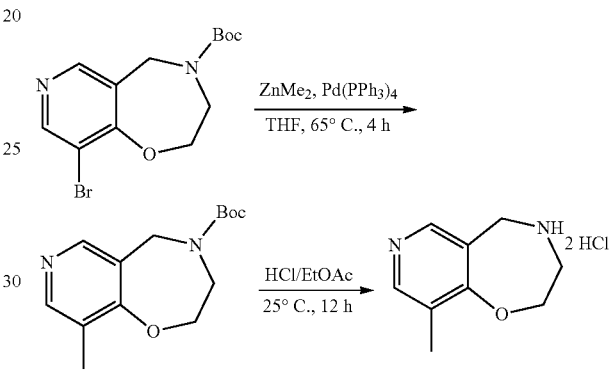

tert-Butyl 9-methyl-3,5-dihydro-2H-pyrido[3,4-f][1,4] oxazepine-4-carboxylate: To a solution of tert-butyl 9-bromo-3,5-dihydro-2H-pyrido[3,4-f][1,4]oxazepine-4-carboxylate (300 mg, 911 µmol) in THF (10 mL) was added Pd(PPh$_3$)$_4$ (105 mg, 91 µmol) and ZnMe$_2$ (1 M, 1.8 mL), then stirred at 65° C. for 4 h under N$_2$. The reaction mixture was quenched by addition of sat. NH$_4$Cl (10 mL) and extracted with EtOAc (3×10 mL). The combined organic layers were washed with brine (10 mL), dried over anhydrous Na$_2$SO$_4$, filtered and concentrated under reduced pressure. The residue was purified by silica gel column chromatography (PE:EtOAc=3:1) to provide the title compound (233 mg, 73%) as a yellow oil.

9-Methyl-2,3,4,5-tetrahydropyrido[3,4-f][1,4]oxazepine dihydrochloride: A solution of tert-butyl 9-methyl-3,5-dihydro-2H-pyrido[3,4-f][1,4]oxazepine-4-carboxylate (230 mg, 765 µmol) in HCl/EtOAc (3 mL) was stirred at 25° C. for 12 h. The reaction solution was concentrated under reduced pressure to give the title compound (72%) as a brown solid.

Method P: Preparation of 8-(trifluoromethyl)-2,3,4,5-tetrahydropyrido[3,4-f][1,4]oxazepine

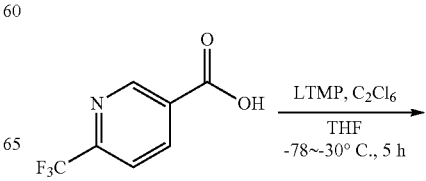

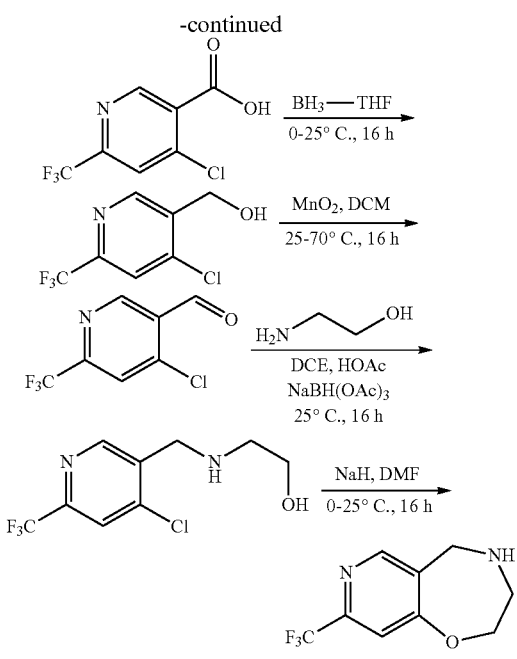

4-Chloro-6-(trifluoromethyl)pyridine-3-carboxylic acid: To a mixture of 2,2,6,6-tetramethylpiperidine (33.26 g, 235.47 mmol, 39.98 mL) in anhydrous THF (700 mL) was added n-butyllithium (235.47 mmol, 2.5 M, 94.19 mL) dropwise at −78° C. under $N_2$. The mixture was stirred at −78° C. for 30 min. The mixture was added to a solution of 6-(trifluoromethyl)pyridine-3-carboxylic acid (15 g, 78.49 mmol) in THF (700 mL) dropwise at −78° C. The mixture was stirred at −78° C. for 1 h, then added to a solution of hexachloroethane (37.16 g, 156.98 mmol, 17.78 mL) in THF (700 mL) and stirred at −78° C. for 3 h. The reaction mixture was quenched with sat. $NH_4Cl$ (500 mL) at −40° C. and warmed to 25° C. The mixture was diluted with water (200 mL) and extracted with EtOAc (3×300 mL). The combined organics were washed with brine (200 mL), dried over anhydrous $Na_2SO_4$, filtered and concentrated under reduced pressure. The residue was triturated in MTBE (100 mL) to provide the title compound (10 g, 27%) as a yellow solid. LCMS: m/z=225.9 $[M+H]^+$.

4-Chloro-6-(trifluoromethyl)-3-pyridyl]methanol: To a mixture of 4-chloro-6-(trifluoromethyl)pyridine-3-carboxylic acid (5 g, 22.17 mmol) in THF (50 mL) was added $BH_3 \cdot THF$ (66.50 mmol, 1 M, 66.50 mL) at 0° C. under $N_2$. The mixture was stirred at 25° C. for 16 h. The mixture was quenched with MeOH (10 mL) and poured into water (100 mL). The mixture was extracted with EtOAc (3×30 mL). The combined organics were washed with brine (30 mL), dried over anhydrous $Na_2SO_4$, filtered and concentrated under reduced pressure. The residue was purified by silica gel column chromatography (PE:EtOAc=20:1 to 5:1) to give the title compound (1.5 g, 32%) as a colorless oil. LCMS: m/z=211.9 $[M+H]^+$.

4-Chloro-6-(trifluoromethyl)pyridine-3-carbaldehyde: To a mixture of [4-chloro-6-(trifluoromethyl)-3-pyridyl]methanol (700 mg, 3.31 mmol) in $CHCl_3$ (20 mL) was added $MnO_2$ (1.44 g, 16.54 mmol) at 25° C. under $N_2$. The mixture was stirred at 70° C. for 16 h. The mixture was filtered and the filtrate was concentrated under reduced pressure to afford the title compound (460 mg, 66%) as a yellow oil.

2-[(4-Chloro-6-(trifluoromethyl)-3-pyridyl)methylamino]ethanol: To a mixture of 4-chloro-6-(trifluoromethyl) pyridine-3-carbaldehyde (460 mg, 2.20 mmol) and 2-aminoethanol (134 mg, 2.20 mmol) in DCE (25 mL) was added AcOH (264 mg, 4.39 mmol) at 25° C. under $N_2$. The mixture was stirred at 25° C. for 30 min., before adding NaBH (OAc)$_3$ (1.40 g, 6.59 mmol) and stirring for 16 h. The mixture was poured into water (20 mL) and the organic phase was separated. The aqueous phase was adjusted to pH=7 with sat. $NaHCO_3$ and extracted with DCM/i-PrOH (3×10 mL, v:v=3:1). The combined organic layers were dried over anhydrous $Na_2SO_4$, filtered and concentrated under reduced pressure to provide the title compound (163 mg, 29%) as a colorless oil.

8-(Trifluoromethyl)-2,3,4,5-tetrahydropyrido[3,4-f][1,4]oxazepine: To a mixture of 2-[(4-chloro-6-(trifluoromethyl)-3-pyridyl)methylamino]ethanol (163 mg, 640.13 μmol) in DMF (3 mL) was added NaH (64 mg, 1.60 mmol, 60% purity) at 0° C. under $N_2$. The mixture was stirred at 25° C. for 16 h. The mixture was poured into ice water (10 mL) and extracted with DCM/i-PrOH (3×5 mL, v:v=3:1). The combined organic layers were dried over anhydrous $Na_2SO_4$, filtered and concentrated under reduced pressure. The resulting residue was purified by prep-TLC ($SiO_2$, EtOAc) to give the title compound (34 mg, 24%) as a yellow oil. LCMS: m/z=219.1 $[M+H]^+$.

Method Q: Preparation of 2-methyl-2-(trifluoromethoxy)propanoic acid

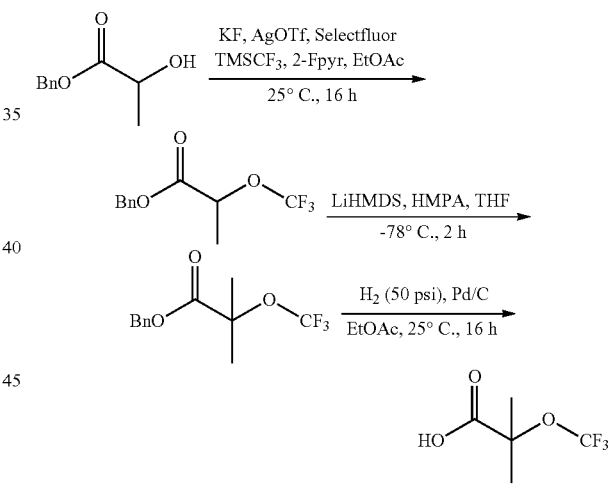

Benzyl 2-(trifluoromethoxy)propanoate: To a mixture of AgOTf (12.83 g, 49.94 mmol), Selectfluor (8.85 g, 24.97 mmol) and KF (3.87 g, 66.59 mmol) in EtOAc (30 mL) was added benzyl 2-hydroxypropanoate (3 g, 16.65 mmol) at 25° C. under $N_2$. Then 2-fluoropyridine (4.85 g, 49.94 mmol, 4.29 mL) and TMSCF$_3$ (7.1 g, 49.94 mmol) were added. The mixture was stirred at 25° C. for 16 h. The reaction mixture was filtered and the filtrate was concentrated. The crude product was purified by silica gel column chromatography (PE:EtOAc=100:1 to 10:1) to give the title compound (1.7 g, 41%) as a colorless oil.

Benzyl 2-methyl-2-(trifluoromethoxy)propanoate: To a mixture of LiHMDS (1 M, 12.09 mL) in THF (5 mL) was added HMPA (722 mg, 4.03 mmol, 708 μL) and benzyl 2-(trifluoromethoxy)propanoate (1 g, 4.03 mmol) at −78° C. under $N_2$. The mixture was stirred at −78° C. for 5 min., and then MeI (572 mg, 4.03 mmol) was added. The mixture remained at −78° C. and stirred for 2 h. The mixture was quenched with sat. NH₄Cl (50 mL). The aqueous phase was extracted with EtOAc (3×15 mL). The combined organic phase was washed with brine (10 mL), dried over anhydrous Na₂SO₄, filtered and concentrated under reduced pressure. The residue was purified by silica gel column chromatography (PE:EtOAc=100:1 to 50:1) to provide the title compound (0.3 g, 28%) as a colorless oil.

2-Methyl-2-(trifluoromethoxy)propanoic acid: To a solution of benzyl 2-methyl-2-(trifluoromethoxy)propanoate (200 mg, 762.71 μmol) in EtOAc (5 mL) was added 10% Pd/C (0.07 g) under N₂. The suspension was degassed under vacuum and purged with H₂ three times. The mixture was stirred under H₂ (50 psi) at 25° C. for 16 h. The mixture was filtered and the filtrate was concentrated under reduced pressure to afford the title compound (0.12 g, 91%) as a colorless oil, which was used in the next step directly.

Method R: Preparation of 3-cyano-2,2-dimethylbutanoic acid

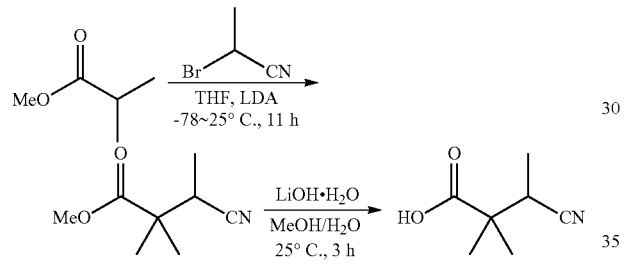

Methyl 3-cyano-2,2-dimethylbutanoate: To a solution of LDA (2 M, 3.50 mL) in THF (15 mL) was added dropwise methyl 2-methylpropanoate (0.65 g, 6.36 mmol) at −78° C. under N₂. The mixture was stirred for 1 h, and then 2-bromopropanenitrile (1.02 g, 7.64 mmol) was added dropwise at −78° C. The resulting mixture was stirred at 25° C. for 10 h. The reaction mixture was quenched with aq. HCl (3 mL, 1N) at 0° C., and then diluted with H₂O (10 mL) and extracted with EtOAc (2×15 mL). The combined organics were washed with brine (30 mL), dried over Na₂SO₄, filtered and concentrated under reduced pressure to provide the title compound (0.84 g, 85%) as a yellow oil, which was used in the next step without further purification.

3-Cyano-2,2-dimethylbutanoic acid: To a solution of methyl 3-cyano-2,2-dimethyl-butanoate (400 mg, 2.58 mmol) in MeOH (3 mL) and H₂O (1 mL) was added LiOH H₂O (433 mg, 10.31 mmol). The mixture was stirred at 25° C. for 3 h. The reaction mixture was concentrated under reduced pressure to remove MeOH. The residue was diluted with water (2 mL) and adjusted to pH=4 with aq. HCl (2 N) and extracted with EtOAc (2×5 mL). The combined organics were washed with brine (10 mL), dried over Na₂SO₄, filtered and concentrated under reduced pressure to give the title compound (270 mg, 74%) as a yellow oil that was used into the next step directly. LCMS: m/z=140.1 [M−H]⁻.

The following intermediate was prepared using procedures analogous to those described above.

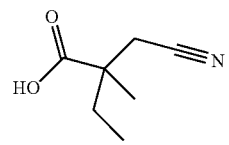

Method S: Preparation of 3,3-difluoro-2-methoxycarbonyl-2-methyl-butanoic acid and 2-(difluoromethyl)-3-methoxy-2-methyl-3-oxo-propanoic acid

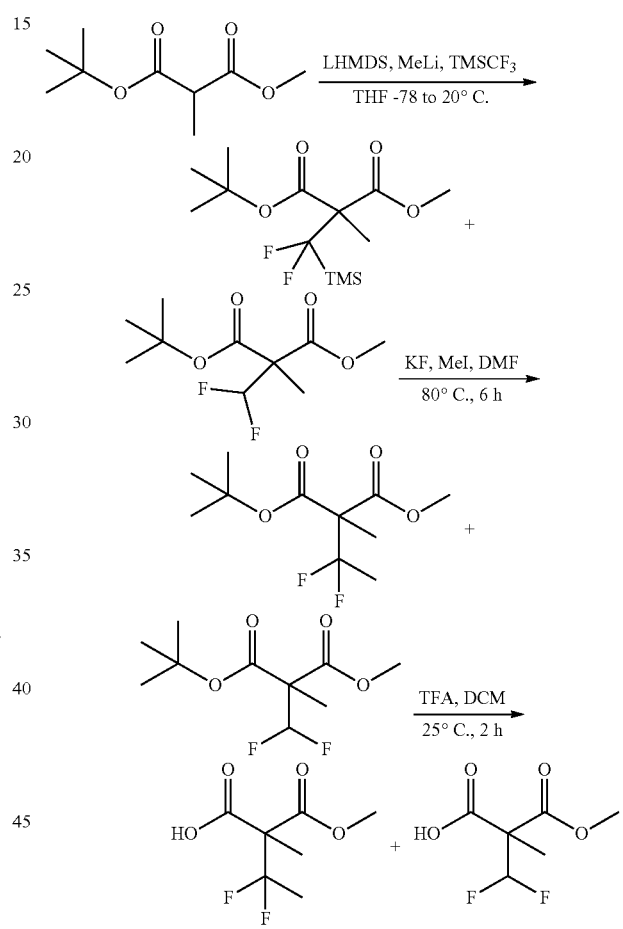

1-tert-Butyl 3-methyl 2-(difluoro(trimethylsilyl)methyl)-2-methylmalonate and 1-tert-butyl 3-methyl 2-(difluoromethyl)-2-methylmalonate: To a solution of 1-tert-butyl 3-methyl 2-methylmalonate (20 g, 106.26 mmol) in THF (200 mL) was added LiHMDS (1 M in THF, 106.26 mL) at −78° C. under N₂. The mixture was stirred at −78° C. for 30 min., then MeLi (1 M in THF, 106.26 mL) was added. The mixture was stirred for 10 min then TMSCF₃ (75.55 g, 531.29 mmol) was added. The reaction mixture was stirred for 16 h while slowly warming to 20° C. The mixture was quenched slowly with sat. aqueous NH₄Cl (200 mL). The organic phase was separated and the aqueous phase was extracted with MTBE (2×100 mL). The combined organic phase was washed with brine (100 mL), dried with anhydrous Na₂SO₄, filtered and concentrated under reduced pressure to provide the title compounds (40 g, crude) as a colorless liquid.

1-tert-Butyl 3-methyl 2-(1,1-difluoroethyl)-2-methylmalonate and 1-tert-butyl 3-methyl 2-(difluoromethyl)-2-methylmalonate: KF (1.68 g, 28.99 mmol) was vacuum dried and added to a mixture of 1-tert-butyl 3-methyl 2-(difluoro(trimethylsilyl)methyl)-2-methylmalonate and 1-tert-butyl 3-methyl 2-(difluoromethyl)-2-methylmalonate (3 g, 9.66 mmol) and MeI (4.12 g, 28.99 mmol, 1.80 mL) in DMF (20 mL) at 25° C. under $N_2$. Then the mixture was heated to 80° C. and stirred for 6 h. This was conducted in 4 equal batches. The mixture was filtered through a pad of celite and the filter cake was washed with MTBE (3×20 mL). The filtrate was poured into water (200 mL). The aqueous phase was extracted with MTBE (3×50 mL). The combined organic phase was washed with brine (50 mL), dried over $Na_2SO_4$, filtered and concentrated to give a residue. The residue was purified by silica gel column chromatography (PE:MTBE=30:1 to 10:1) to afford a mixture of 1-tert-butyl 3-methyl 2-(1,1-difluoroethyl)-2-methylmalonate and 1-tert-butyl 3-methyl 2-(difluoromethyl)-2-methylmalonate (6.5 g, 67%; ratio=2:3) as a colorless liquid.

3,3-Difluoro-2-methoxycarbonyl-2-methyl-butanoic acid and 2-(difluoromethyl)-3-methoxy-2-methyl-3-oxo-propanoic acid: To a mixture of 1-tert-butyl 3-methyl 2-(1,1-difluoroethyl)-2-methylmalonate and 1-tert-butyl 3-methyl 2-(difluoromethyl)-2-methylmalonate (2 g, 7.93 mmol) in DCM (20 mL) was added TFA (20 mL) at 25° C. under $N_2$. The reaction mixture was stirred at 25° C. for 2 h. The reaction mixture was concentrated under reduced pressure. The residue was diluted with water (20 mL) and extracted with EtOAc (3×20 mL). The combined organic layers were washed with brine (10 mL), dried over $Na_2SO_4$, filtered and concentrated under reduced pressure to give a mixture of 3,3-difluoro-2-methoxycarbonyl-2-methyl-butanoic acid and 2-(difluoromethyl)-3-methoxy-2-methyl-3-oxo-propanoic acid (2.7 g, crude; ratio=2:3) as a light yellow oil. The residue was used in the next step without purification.

Method T: Preparation of 3-fluoro-2,2-dimethyl-butanoic acid and 2,2-dimethylbut-3-enoic acid

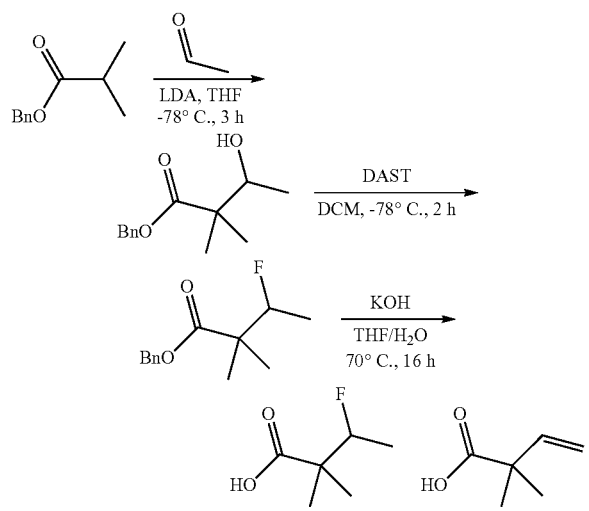

Benzyl 3-hydroxy-2,2-dimethyl-butanoate: To a mixture of benzyl 2-methylpropanoate (10.0 g, 56.11 mmol) in THF (200 mL) was added LDA (1 M, 56.11 mL) dropwise at −78° C. under $N_2$. The mixture was stirred at −78° C. for 1 h. Then to the mixture was added acetaldehyde (3.0 g, 67.33 mmol) dropwise with stirring at −78° C., and the mixture was stirred at −78° C. for 2 h. The reaction mixture was quenched with saturated $NH_4Cl$ (150 mL) at 0° C., diluted with water (50 mL) and extracted with DCM (3×100 mL). The combined organic layers were washed with brine (50 mL), dried over anhydrous $Na_2SO_4$, filtered and concentrated under reduced pressure. The residue was purified by column chromatography (PE:EtOAc=1:0 to 20:1) to afford the title compound (4 g, 32%) as a yellow oil.

Benzyl 3-fluoro-2,2-dimethyl-butanoate: To a mixture of benzyl 3-hydroxy-2,2-dimethyl-butanoate (2.00 g, 9.00 mmol) in DCM (40 mL) was added DAST (1.74 g, 10.80 mmol) dropwise at −78° C. under $N_2$. The mixture was stirred at −78° C. for 2 h. The reaction mixture was quenched with saturated $NaHCO_3$ (40 mL) at 0° C., diluted with water (40 mL) and extracted with DCM (3×20 mL). The combined organic layers were washed with brine (20 mL), dried over anhydrous $Na_2SO_4$, filtered and concentrated under reduced pressure. The residue was purified by silica gel column chromatography (PE:EtOAc=100:1 to 20:1) to provide the title compound (500 mg, 25%) as a yellow oil.

3-Fluoro-2,2-dimethyl-butanoic acid and 2,2-dimethyl-but-3-enoic acid: To a mixture of benzyl 3-fluoro-2,2-dimethyl-butanoate (500 mg, 2.23 mmol) in THF (5 mL) and $H_2O$ (2 mL) was added KOH (375 mg, 6.69 mmol) in one portion at 20° C. under $N_2$. The mixture was stirred at 20° C. for 10 min., then heated to 70° C. and stirred for 16 h. The reaction mixture was diluted with water (14 mL) and extracted with EtOAc (5 mL). The organic phase was separated. The aqueous phase was adjusted to pH=4-5 and extracted with DCM/i-PrOH (3×8 mL, v:v=3/1). The combined organic layers were washed with brine (10 mL), dried over anhydrous $Na_2SO_4$, filtered and concentrated under reduced pressure to afford a mixture of the title compounds (250 mg) as a colorless oil.

Method U: Preparation of 2-(1-hydroxycyclopropyl)-2-methylpropanoic acid

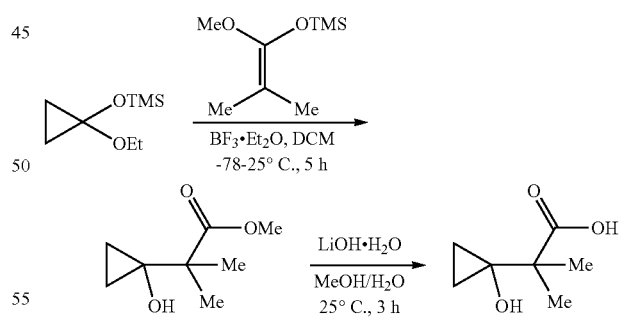

Methyl 2-(1-hydroxycyclopropyl)-2-methylpropanoate: To a mixture of (1-ethoxycyclopropoxy)-trimethyl-silane (5.0 g, 28.68 mmol) and (1-methoxy-2-methyl-prop-1-enoxy)-trimethyl-silane (10.0 g, 57.37 mmol) in DCM (50 mL) was added $BF_3Et_2O$ (6.5 g, 45.89 mmol) at −78° C. The mixture was warmed to 25° C. slowly over 5 h. The reaction mixture was quenched with sat. $NaHCO_3$ (20 mL) at 0° C., and then diluted with DCM (20 mL) and extracted with DCM (2×25 mL). The combined organics were washed with brine (2×30 mL), dried over anhydrous $Na_2SO_4$, filtered and concentrated under reduced pressure. The residue was purified by silica gel column chromatography (PE:MTBE=20:1 to 3:1) to give the title compound (3.0 g, 66%) as a yellow oil.

2-(1-Hydroxycyclopropyl)-2-methylpropanoic acid: To a solution of methyl 2-(1-hydroxycyclopropyl)-2-methyl-propanoate (500 mg, 3.16 mmol) in MeOH (3 mL) and H$_2$O (1 mL) was added LiOH H$_2$O (398 mg, 9.48 mmol). The mixture was stirred at 25° C. for 3 h. The reaction mixture was concentrated under reduced pressure to remove MeOH. The residue was diluted with H$_2$O (2 mL) and extracted with EtOAc (2×3 mL). The aqueous phase was adjusted to pH=5 by addition of 1 N HCl and extracted with EtOAc (2×3 mL). The combined organics were dried over anhydrous Na$_2$SO$_4$, filtered and concentrated under reduced pressure to provide the title compound (240 mg, 42%) as a yellow oil. LCMS: m/z=143.1 [M–H]$^-$.

Method V: Preparation of (2,3-dihydrobenzo[f][1,4]oxazepin-4(5H)-yl)(1-(5-fluoropyrimidin-2-yl)piperidin-4-yl)methanone

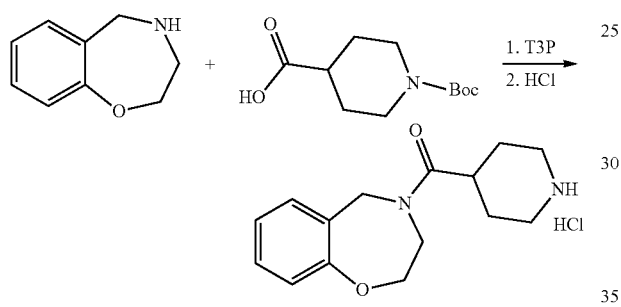

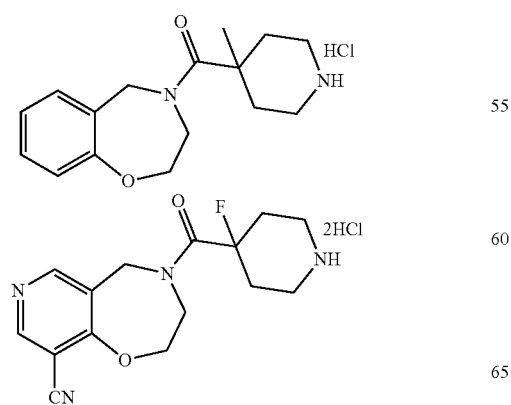

The title compound was prepared using general procedure A employing 2,3,4,5-tetrahydro-1,4-benzoxazepine (149 mg, 1.0 mmol), 1-tert-butoxycarbonylpiperidine-4-carboxylic acid (343 mg, 1.5 mmol), N-methylimidazole (246 mg, 3.0 mmol) and T3P solution (954 mg, 1.5 mmol) in EtOAc (5 mL). Purified employing silica gel flash chromatography (0-40% EtOAc/hexanes) to provide the desired Boc-protected intermediate as a white foam. This material was dissolved in HCl solution (4 mL, 4 M in dioxane). The solution was stirred for 1 h at RT and was concentrated to provide the desired compound as the HCl salt.

The following intermediates were prepared using general procedure A, B or C followed by deprotection using HCl.

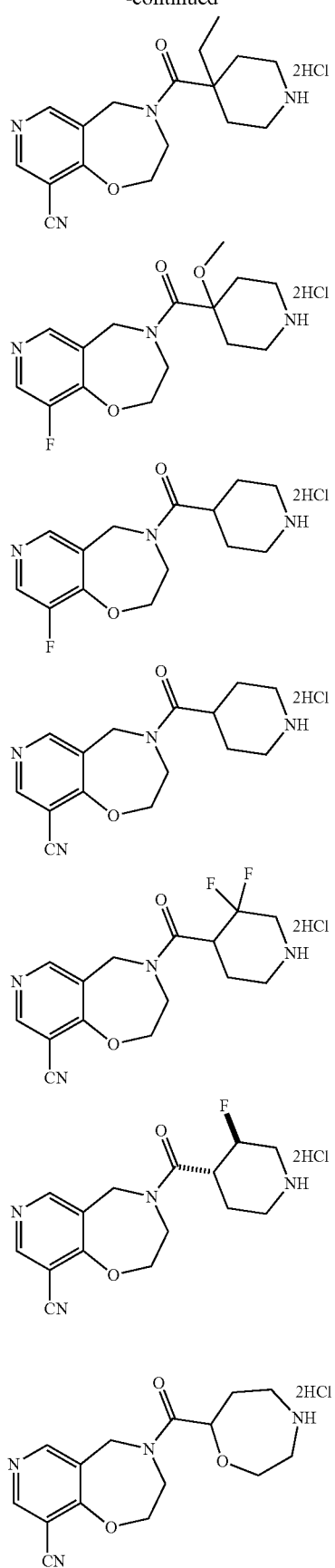

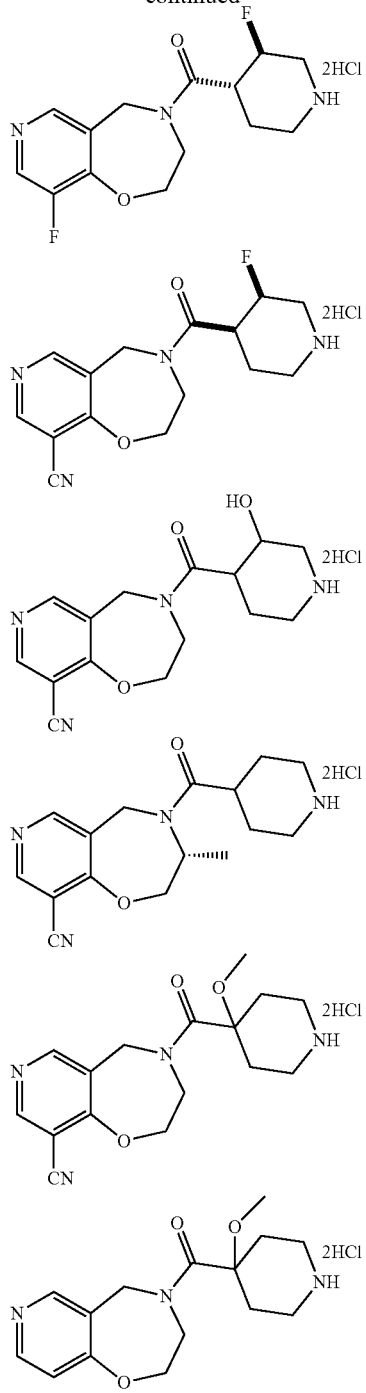

Method W: Nucleophilic Aromatic Substitution

A mixture of the amine (1 equiv), heteroaryl halide (2 equiv) and Cs$_2$CO$_3$ (3 equiv) in DMF (0.2 M) was heated at 100° C. until the reaction was complete. The reaction mixture was cooled to RT and sat. NH$_4$Cl was added followed by EtOAc. The layers were separated and the aqueous layer was extracted with EtOAc three times. The combined organics were dried over MgSO$_4$, filtered and concentrated under reduced pressure. The resulting residue was purified by flash column chromatography or HPLC. In some cases DIPEA, K$_2$CO$_3$ or NEt$_3$ were used as the base and acetonitrile, dioxane or IPA were used as solvent.

Method X: Preparation of 2-(2-(difluoromethyl) cyclopropyl)-2-methyl-propanoic acid

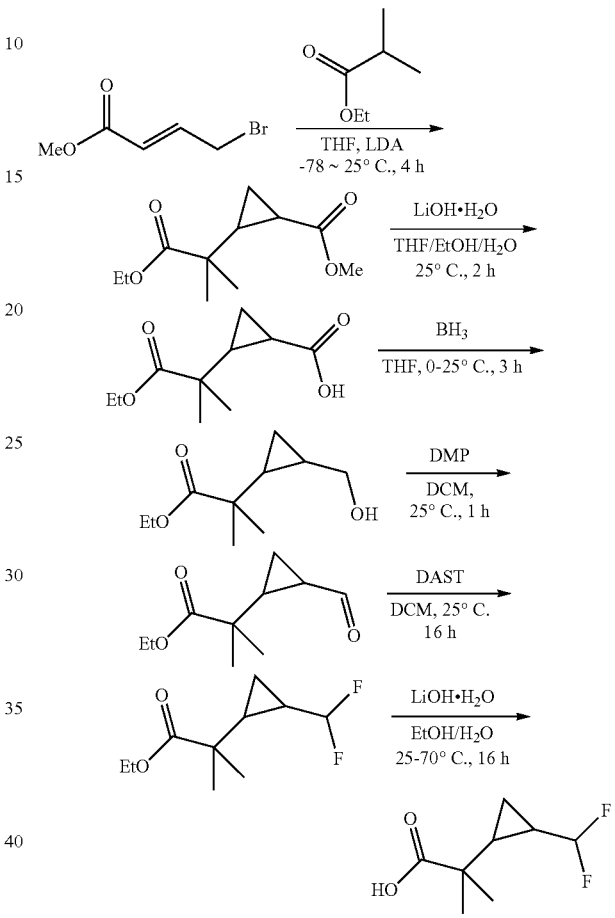

Methyl 2-(2-ethoxy-1,1-dimethyl-2-oxo-ethyl)cyclopropanecarboxylate: To a solution of i-Pr$_2$NH (22.65 g, 223.83 mmol) in anhydrous THF (200 mL) was added n-BuLi (2.5 M, 89.53 mL) dropwise at −78° C. under N$_2$. The reaction mixture was warmed to 0° C. and stirred for 30 min. Then a solution of ethyl 2-methylpropanoate (20 g, 172.18 mmol) in anhydrous THF (50 mL) was added dropwise at −78° C. under N$_2$. The mixture was stirred for 30 min. Then a solution of methyl (E)-4-bromobut-2-enoate (30.82 g, 172.18 mmol) in THF (50 mL) was added dropwise. The mixture was warmed to 25° C. slowly and stirred for 3 h. The mixture was quenched with sat. NH$_4$Cl (200 mL). The mixture was diluted with water (100 mL) and extracted with EtOAc (3×200 mL). The combined organics were washed with brine (200 mL), dried over anhydrous Na$_2$SO$_4$, filtered and concentrated under reduced pressure to afford the title compound (30 g, 81%) as a yellow oil.

2-(2-Ethoxy-1,1-dimethyl-2-oxo-ethyl)cyclopropanecarboxylic acid: To a mixture of methyl 2-(2-ethoxy-1,1-dimethyl-2-oxo-ethyl)cyclopropanecarboxylate (30 g, 140.02 mmol) in THF (100 mL), EtOH (100 mL) and H$_2$O (100 mL) was added LiOH.H$_2$O (11.75 g, 280.04 mmol) in one portion at 25° C. The mixture was stirred at 25° C. for 2 h.

The reaction mixture was concentrated under reduced pressure. The residue was diluted with water (50 mL), and then extracted with MTBE (25 mL). The organic phase was adjusted to pH=3~4 with aq. HCl (1 N). The aqueous phase was extracted with EtOAc (3×30 mL). The combined organics were washed with brine (100 mL), dried over anhydrous $Na_2SO_4$, filtered and concentrated under reduced pressure to afford the title compound (21 g, 75%) as a yellow oil.

Ethyl 2-(2-(hydroxymethyl)cyclopropyl)-2-methyl-propanoate: To a solution of 2-(2-ethoxy-1,1-dimethyl-2-oxo-ethyl)cyclopropanecarboxylic acid (10 g, 49.94 mmol) in THF (100 mL) was added $BH_3$.THF (1 M, 149.83 mL) dropwise at 0° C. under $N_2$. The mixture was stirred at 0° C. for 30 min., then warmed to 25° C. and stirred for 3 h. The reaction mixture was quenched with water (100 mL) and extracted with EtOAc (3×50 mL).

The combined organics were washed with brine (5 mL) and dried over anhydrous $Na_2SO_4$, filtered and concentrated under reduced pressure to provide the title compound (6 g, 65%) as a yellow oil.

Ethyl 2-(2-formylcyclopropyl)-2-methyl-propanoate: To a solution of ethyl 2-(2-(hydroxymethyl)cyclopropyl)-2-methyl-propanoate (0.5 g, 2.68 mmol) in DCM (40 mL) was added DMP (1.37 g, 3.22 mmol) at 0° C. under $N_2$. The reaction mixture was stirred at 25° C. for 1 h. The mixture was washed with sat. $NaHCO_3$ (10 mL), aq. $Na_2SO_3$ (10 mL, 10%) and brine (10 mL), dried over anhydrous $Na_2SO_4$, filtered and concentrated under reduced pressure. The resulting residue was purified by silica gel column chromatography (PE:EtOAc=100 to 10:1) to afford the title compound (0.25 g, 51%) as a colorless oil.

Ethyl 2-(2-(difluoromethyl)cyclopropyl)-2-methyl-propanoate: To a mixture of ethyl 2-(2-formylcyclopropyl)-2-methyl-propanoate (150 mg, 814.19 mmol) in DCM (2 mL) was added DAST (328 mg, 2.04 mmol) dropwise at 0° C. under $N_2$. The mixture was stirred at 0° C. for 30 min., then warmed to 25° C. and stirred for 16 h. The reaction mixture was poured into ice-cold $NaHCO_3$ solution slowly, then extracted with EtOAc (3×10 mL). The combined organics were washed with brine (5 mL), dried over anhydrous $Na_2SO_4$, filtered and concentrated under reduced pressure to afford the title compound (150 mg, 89%) as a yellow oil.

2-(2-(Difluoromethyl)cyclopropyl)-2-methyl-propanoic acid: To a mixture of ethyl 2-(2-(difluoromethyl)cyclopropyl)-2-methyl-propanoate (150 mg, 727.35 mmol) in EtOH (2 mL) and $H_2O$ (1 mL) was added $LiOH.H_2O$ (183.13 mg, 4.36 mmol) in one portion at 25° C. The mixture was stirred at 25° C. for 30 min., then heated to 70° C. and stirred for 16 h. The mixture was cooled to 25° C. and concentrated under reduced pressure. The residue was diluted with water (3 mL) and extracted with MTBE (5 mL). The aqueous phase was adjusted to pH=3~4 with aq. HCl (1 N) and extracted with EtOAc (3×5 mL). The combined organics were washed with brine (5 mL), dried over anhydrous $Na_2SO_4$, filtered and concentrated under reduced pressure to the title compound (70 mg, 54%) as a yellow oil.

Method Y: Preparation of
2-(2-cyanocyclopropyl)-2-methyl-propanoic acid

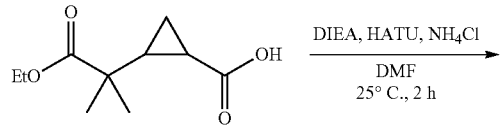

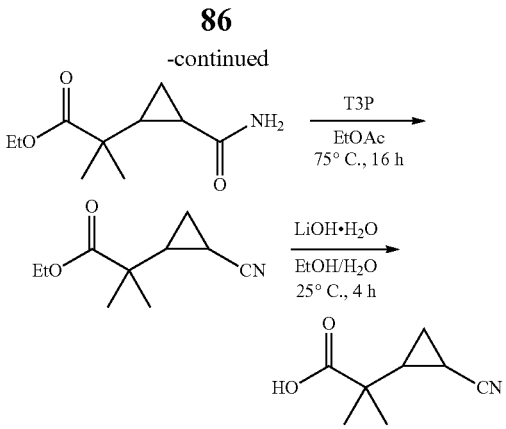

Ethyl 2-(2-carbamoylcyclopropyl)-2-methyl-propanoate: To a solution of 2-(2-ethoxy-1,1-dimethyl-2-oxo-ethyl)cyclopropanecarboxylic acid (280 mg, 1.40 mmol) in DMF (2 mL) was added $NH_4Cl$ (449 mg, 8.39 mmol, 293.33 µL) and DIEA (1.08 g, 8.39 mmol, 1.46 mL) at 25° C. and stirred for 10 min. HATU (1.06 g, 2.80 mmol) was added at 25° C., and then the mixture was stirred at 25° C. for 2 h. The reaction mixture was quenched with water (10 mL) at 0° C., and then extracted with EtOAc (3×10 mL). The combined organic layers were washed with brine (10 mL), dried over anhydrous $Na_2SO_4$, filtered and concentrated under reduced pressure to provide the title compound (220 mg, 79%) as a light yellow oil.

Ethyl 2-(2-cyanocyclopropyl)-2-methyl-propanoate: To a solution of ethyl 2-(2-carbamoylcyclopropyl)-2-methyl-propanoate (0.22 g, 1.10 mmol) in EtOAc (2 mL) was added T3P (3.51 g, 5.52 mmol, 3.28 mL, 50% in EtOAc) at 25° C., and then the solution was stirred at 75° C. for 16 h. The reaction mixture was quenched with water (10 mL) at 0° C., and then extracted with EtOAc (3×10 mL). The combined organic layers were washed with brine (10 mL), dried over anhydrous $Na_2SO_4$, filtered and concentrated under reduced pressure. The resulting residue was purified by silica gel column chromatography (PE:EtOAc=100:1 to 5:1) to afford the title compound (220 mg, 55%) as a light yellow oil. LC-MS: m/z=182.2 $[M+H]^+$.

2-(2-Cyanocyclopropyl)-2-methyl-propanoic acid: To a solution of ethyl 2-(2-cyanocyclopropyl)-2-methyl-propanoate (50 mg, 275.89 µmol) in EtOH (2 mL) and $H_2O$ (2 mL) was added $LiOH.H_2O$ (46 mg, 1.10 mmol) at 25° C., and then the solution was stirred at 25° C. for 4 h. The reaction mixture was washed with EtOAc (3×10 mL). The aqueous layer was adjusted to pH=4~5 by the addition of HCl (1 M), and then extracted with EtOAc (3×10 mL). The combined organic layers were washed with brine (10 mL), dried over anhydrous $Na_2SO_4$, filtered and concentrated under reduced pressure to provide the title compound (40 mg, 95%) as a light yellow oil.

Method Z: Preparation of
2-(3,3-difluorocyclobutyl)-2-methyl-propanoic acid

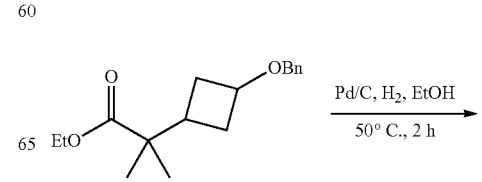

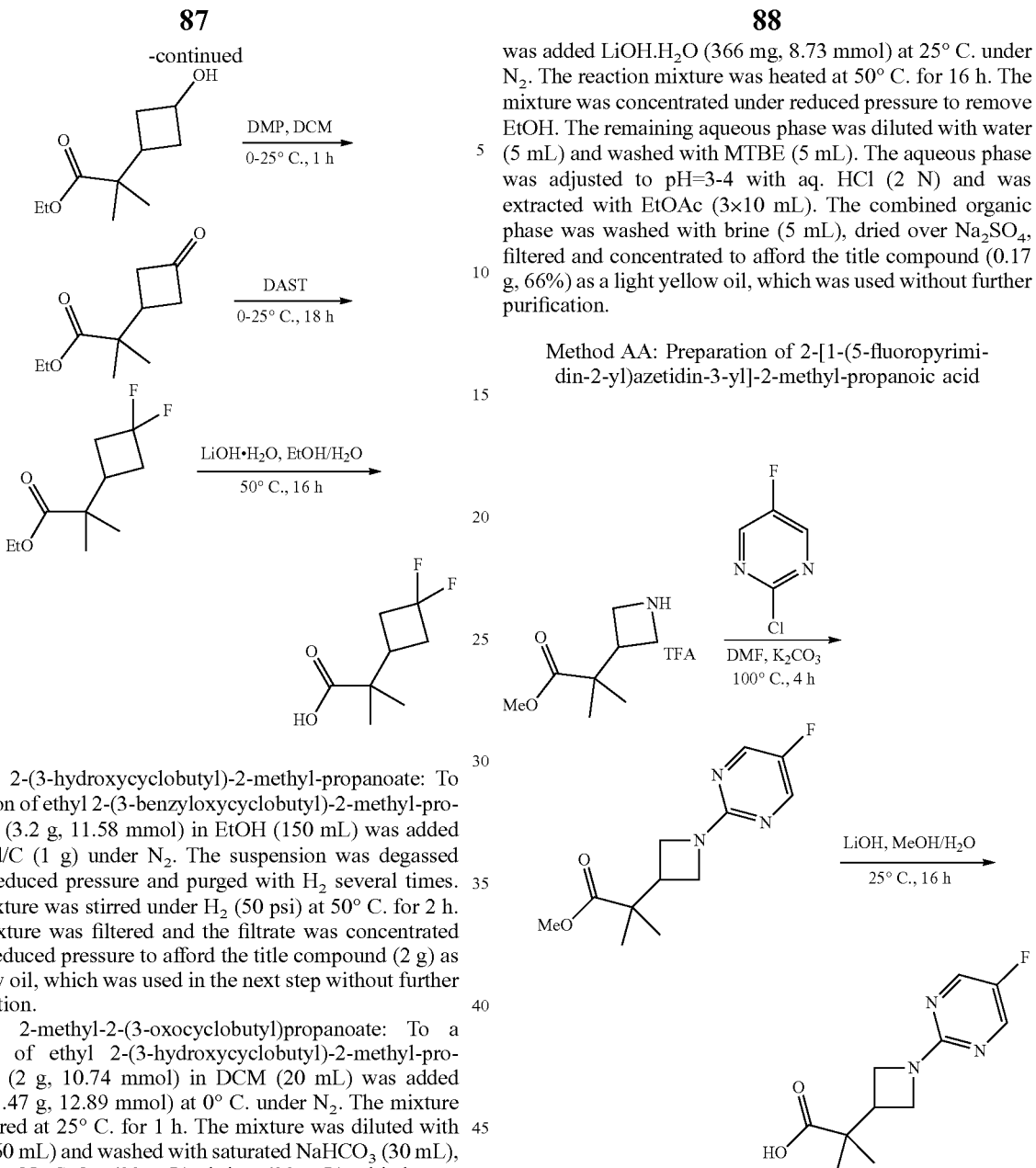

Ethyl 2-(3-hydroxycyclobutyl)-2-methyl-propanoate: To a solution of ethyl 2-(3-benzyloxycyclobutyl)-2-methyl-propanoate (3.2 g, 11.58 mmol) in EtOH (150 mL) was added 10% Pd/C (1 g) under $N_2$. The suspension was degassed under reduced pressure and purged with $H_2$ several times. The mixture was stirred under $H_2$ (50 psi) at 50° C. for 2 h. The mixture was filtered and the filtrate was concentrated under reduced pressure to afford the title compound (2 g) as a yellow oil, which was used in the next step without further purification.

Ethyl 2-methyl-2-(3-oxocyclobutyl)propanoate: To a mixture of ethyl 2-(3-hydroxycyclobutyl)-2-methyl-propanoate (2 g, 10.74 mmol) in DCM (20 mL) was added DMP (5.47 g, 12.89 mmol) at 0° C. under $N_2$. The mixture was stirred at 25° C. for 1 h. The mixture was diluted with DCM (60 mL) and washed with saturated $NaHCO_3$ (30 mL), 10% aq. $Na_2S_2O_3$ (30 mL), brine (30 mL), dried over anhydrous $Na_2SO_4$, filtered and concentrated. The residue was purified by silica gel column chromatography (PE:EtOAc=20:1 to 10:1) to afford the title compound (1 g, 51%) as a colorless oil.

Ethyl 2-(3,3-difluorocyclobutyl)-2-methyl-propanoate: To a solution of ethyl 2-methyl-2-(3-oxocyclobutyl)propanoate (0.3 g, 1.63 mmol) in DCM (3 mL) was added DAST (787 mg, 4.89 mmol) at 0° C. under $N_2$. The reaction mixture was stirred at 25° C. for 16 h. The mixture was cooled to 0° C. and poured into ice-water (30 mL). The aqueous phase was adjusted to pH=8 with saturated $NaHCO_3$, and extracted with MTBE (3×20 mL). The combined organic phase was washed with brine (10 mL), dried over $Na_2SO_4$, filtered and concentrated. The resulting residue was purified by silica gel column chromatography (PE:MTBE=30:1 to 20:1) to provide the title compound (0.3 g, 89%) as a light yellow oil.

2-(3,3-Difluorocyclobutyl)-2-methyl-propanoic acid: To a solution of ethyl 2-(3,3-difluorocyclobutyl)-2-methyl-propanoate (0.3 g, 1.45 mmol) in EtOH (4 mL) and $H_2O$ (2 mL) was added LiOH·$H_2O$ (366 mg, 8.73 mmol) at 25° C. under $N_2$. The reaction mixture was heated at 50° C. for 16 h. The mixture was concentrated under reduced pressure to remove EtOH. The remaining aqueous phase was diluted with water (5 mL) and washed with MTBE (5 mL). The aqueous phase was adjusted to pH=3-4 with aq. HCl (2 N) and was extracted with EtOAc (3×10 mL). The combined organic phase was washed with brine (5 mL), dried over $Na_2SO_4$, filtered and concentrated to afford the title compound (0.17 g, 66%) as a light yellow oil, which was used without further purification.

Method AA: Preparation of 2-[1-(5-fluoropyrimidin-2-yl)azetidin-3-yl]-2-methyl-propanoic acid Methyl 2-[1-(5-fluoropyrimidin-2-yl)azetidin-3-yl]-2-methyl-propanoate: To a mixture of methyl 2-(azetidin-3-yl)-2-methyl-propanoate trifluoroacetate (0.2 g, 737.37 wnol) and 2-chloro-5-fluoro-pyrimidine (195 mg, 1.47 mmol) in DMF (2 mL) was added $K_2CO_3$ (407 mg, 2.95 mmol) at 25° C. under $N_2$. The reaction mixture was heated at 100° C. for 4 h. The reaction mixture was cooled to 25° C. and poured into ice-water (60 mL). The aqueous phase was extracted with EtOAc (3×20 mL). The combined organic phase was washed with brine (10 mL), dried over $Na_2SO_4$, filtered and concentrated under reduced pressure. The resulting residue was purified by prep-TLC ($SiO_2$, PE:EtOAc=10:1) to afford the title compound (0.11 g, 59%) as a light yellow oil.

2-[1-(5-Fluoropyrimidin-2-yl)azetidin-3-yl]-2-methyl-propanoic acid: To a solution of methyl 2-[1-(5-fluoropyrimidin-2-yl)azetidin-3-yl]-2-methyl-propanoate (0.11 g, 434.32 µmol) in MeOH (4 mL) and $H_2O$ (1 mL) was added LiOH·$H_2O$ (182 mg, 4.34 mmol) at 25° C. under $N_2$. The reaction mixture was stirred at 25° C. for 16 h. The reaction mixture was cooled to 0° C., adjusted to pH=3-4 with aq. HCl (2 N), and concentrated to dryness under reduced pressure to provide the title compounds (0.103 g) as a yellow solid that was used in the next step without further purification. LC-MS: m/z=240.2 [M+H]$^+$.

The following intermediates were prepared using procedures analogous to those described above. In some cases the first step was conducted using TEA or DIPEA as base and EtOH as solvent with heating via microwave irradiation.

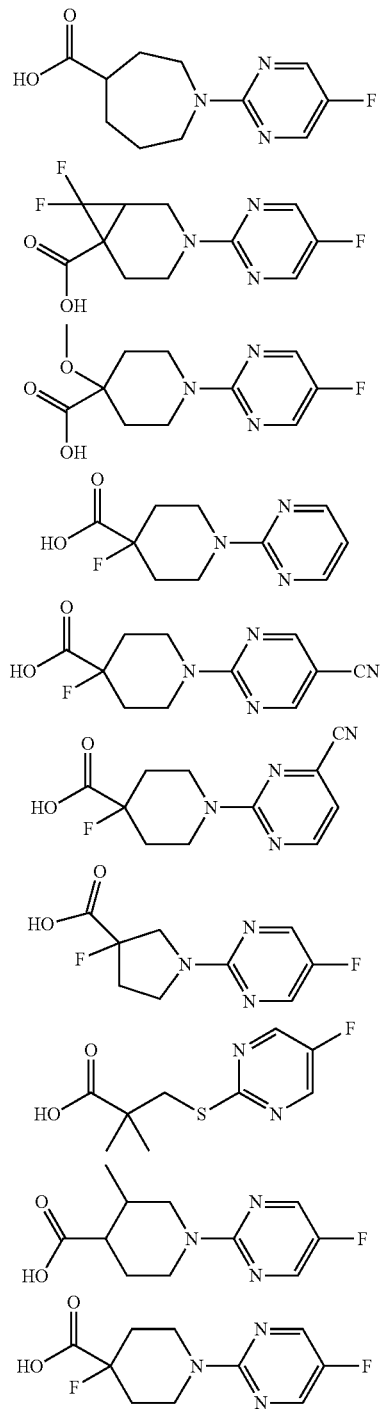

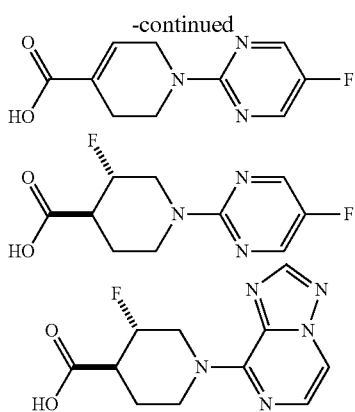

Method AB: Preparation of 4-fluoro-1-(5-fluoropyrimidin-2-yl)piperidine-4-carboxylic acid hydrochloride

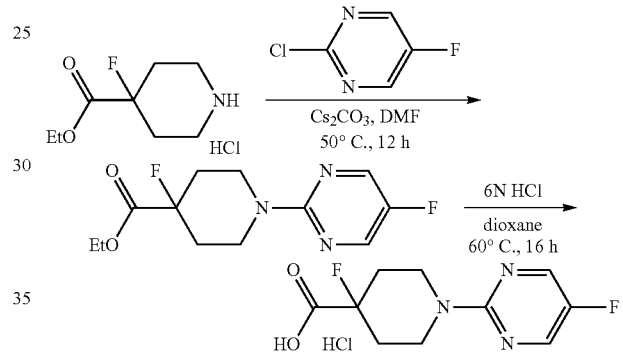

Ethyl 4-fluoro-1-(5-fluoropyrimidin-2-yl)piperidine-4-carboxylate: To a solution of ethyl 4-fluoropiperidine-4-carboxylate hydrochloride (500 mg, 2.36 mmol) in DMF (5 mL) was added Cs$_2$CO$_3$ (1.54 g, 4.72 mmol) and 2-chloro-5-fluoro-pyrimidine (313 mg, 2.36 mmol). The reaction mixture was stirred at 50° C. for 12 h. The reaction mixture was diluted with H$_2$O (5 mL) and extracted with EtOAc (3×5 mL). The combined organic layers were washed with brine (10 mL), dried over anhydrous Na$_2$SO$_4$, filtered and concentrated under reduced pressure. The resulting residue was purified by silica gel column chromatography (SiO$_2$, PE:EtOAc=10:1 to 0:1) to provide the title compound (370 mg, 58%) as a yellow oil. LCMS: m/z=272.1 [M+H]$^+$.

4-Fluoro-1-(5-fluoropyrimidin-2-yl)piperidine-4-carboxylic acid hydrochloride: To a solution of ethyl 4-fluoro-1-(5-fluoropyrimidin-2-yl)piperidine-4-carboxylate (190 mg, 700.43 μmol) in 1,4-dioxane (2 mL) was added HCl (6 M, 2 mL). The reaction mixture was stirred at 60° C. for 12 h and then concentrated under reduced pressure to afford the title compound (170 mg, 90%) as a white solid. LCMS: m/z=244.1, [M+H]$^+$.

The following intermediates were prepared using procedures analogous to those described above.

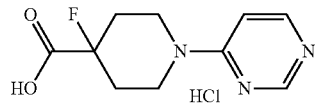

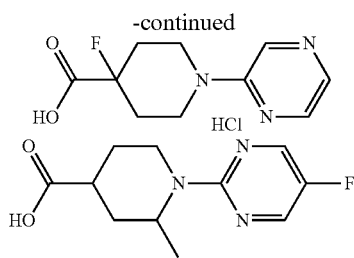

Method AC: Preparation of cis-3-(5-fluoropyrimidin-2-yl)3-azabicyclo[4.1.0]heptane-6-carboxylic acid

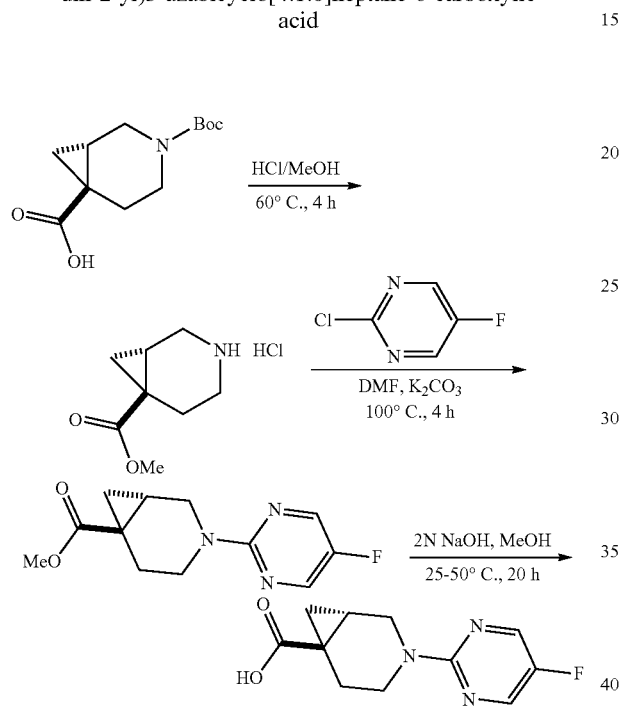

cis-3-Azabicyclo[4.1.0]heptane-6-carboxylate hydrochloride: A mixture of cis-3-tert-butoxycarbonyl-3-azabicyclo[4.1.0]heptane-6-carboxylic acid (100 mg, 414.45 µmol) in HCl/MeOH (1 mL, 4 N) was heated at 60° C. for 4 h. The reaction mixture was concentrated under reduced pressure to provide the title compound (0.096 g) as a white solid, which was used in the next step directly.

Methyl cis-3-(5-fluoropyrimidin-2-yl)-3-azabicyclo[4.1.0]heptane-6-carboxylate: To a mixture of methyl cis-3-azabicyclo[4.1.0]heptane-6-carboxylate hydrochloride (0.09 g, 469.59 µmol) and 2-chloro-5-fluoro-pyrimidine (124 mg, 939.19 µmol) in DMF (4 mL) was added $K_2CO_3$ (259 mg, 1.88 mmol). The reaction mixture was heated at 100° C. for 4 h. The mixture was cooled to 25° C., poured into water (20 mL) and extracted with EtOAc (3×10 mL). The combined organic phase was washed with brine (10 mL), dried over $Na_2SO_4$, filtered and concentrated under reduced pressure. The resulting residue was purified by prep-TLC ($SiO_2$, PE:EtOAc=9:1) to afford the title compound (0.1 g, 85%) as a white solid. LC-MS: m/z=252.1 [M+H]$^+$.

cis-3-(5-Fluoropyrimidin-2-yl)-3-azabicyclo[4.1.0]heptane-6-carboxylic acid: To a mixture of methyl cis-3-(5-fluoropyrimidin-2-yl)-3-azabicyclo[4.1.0]heptane-6-carboxylate (0.1 g, 398.00 µmol) in MeOH (4 mL) was added NaOH (2 N, 0.8 mL) at 25° C. under $N_2$. The reaction mixture was stirred at 25° C. for 16 h and then at 50° C. for 4 h. The mixture was cooled to 25° C. and concentrated under reduced pressure. The resulting residue was diluted with water (10 mL). The solution was adjusted to pH=3-4 with aq. $KHSO_4$ (1 N) and extracted with DCM (3×10 mL). The combined organic phase was washed with brine (10 mL), dried over $Na_2SO_4$, filtered and concentrated under reduced pressure to provide the title compound (0.09 g, 95%) as a white solid, which was used without further purification.

Method AD: Preparation of 2-(1-(5-fluoropyrimidin-2-yl)pyrrolidin-3-yl)-2-methylpropanoic acid

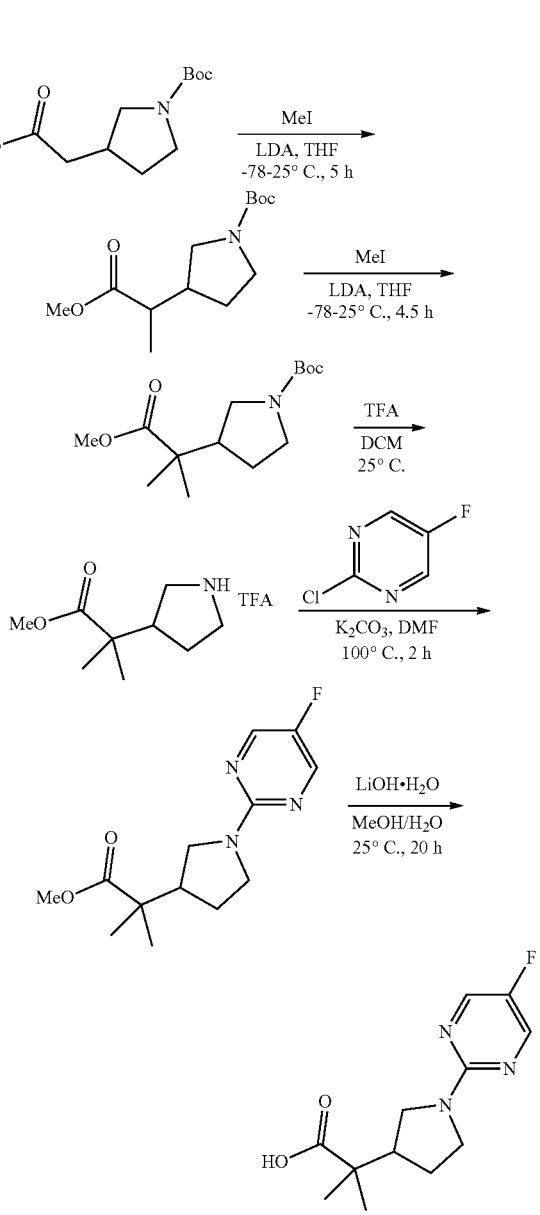

tert-Butyl 3-(2-methoxy-1-methyl-2-oxo-ethyl)pyrrolidine-1-carboxylate and tert-butyl 3-(2-methoxy-1,1-dimethyl-2-oxo-ethyl)pyrrolidine-1-carboxylate: To a mixture of DIPEA (645 mg, 6.37 mmol, 900 µL) in THF (5 mL) was added n-BuLi (2.5 M, 2.47 mL) at −40° C. under $N_2$. The mixture was stirred at −40° C. for 1 h. The mixture was cooled to −78° C., and then added to a solution of tert-butyl 3-(2-methoxy-2-oxo-ethyl)pyrrolidine-1-carboxylate (500 mg, 2.06 mmol) in THF (5 mL) dropwise. The reaction mixture was stirred at −78° C. for 1 h. To the mixture was added MeI (1.75 g, 12.33 mmol, 768 μL) and the reaction mixture was stirred at −78° C. for 1 h, then warmed to 25° C. and stirred for 2 h. The reaction mixture was diluted with H₂O (5 mL) and extracted with EtOAc (3×5 mL). The combined organics were washed with brine (10 mL), dried over Na₂SO₄, filtered and concentrated under reduced pressure. The resulting residue was purified by silica gel column chromatography (PE:EtOAc=10:1 to 3:1) to provide a mixture of the title compounds (0.5 g) as a yellow oil.

tert-Butyl 3-(2-methoxy-1,1-dimethyl-2-oxo-ethyl)pyrrolidine-1-carboxylate: To a mixture of DIPEA (610 mg, 6.02 mmol, 851 μL) in THF (5 mL) was added n-BuLi (2.5 M, 2.33 mL) at −40° C. under N₂. The mixture was stirred at −40° C. for 1 h. The mixture was cooled to −78° C., and then added to a solution of tert-butyl 3-(2-methoxy-1-methyl-2-oxo-ethyl)pyrrolidine-1-carboxylate and tert-butyl 3-(2-methoxy-1,1-dimethyl-2-oxo-ethyl)pyrrolidine-1-carboxylate (0.50 g, 1.94 mmol) in THF (5 mL). The mixture was stirred at −78° C. for 1 h. To the mixture was added MeI (1.65 g, 11.66 mmol, 726 μL) and the reaction mixture was stirred at −78° C. for 30 min. Then the mixture was warmed to 25° C. and stirred for 2 h. The reaction mixture was diluted with H₂ (5 mL) and extracted with EtOAc (3×5 mL). The combined organics were washed with brine (10 mL), dried over Na₂SO₄, filtered and concentrated under reduced pressure. The resulting residue was purified by silica gel column chromatography (PE:EtOAc=10:1 to 3:1) to provide the title compound (0.2 g) as a yellow oil.

Methyl 2-methyl-2-pyrrolidin-3-yl-propanoate trifluoroacetate: To a solution of tert-butyl 3-(2-methoxy-1,1-dimethyl-2-oxo-ethyl)pyrrolidine-1-carboxylate (0.2 g, 737 μmol) in DCM (6 mL) was added TFA (1 mL). The mixture was stirred at 25° C. for 4 h and then concentrated under reduced pressure to afford the title compound (390 mg) as a brown solid.

Methyl 2-(1-(5-fluoropyrimidin-2-yl)pyrrolidin-3-yl)-2-methylpropanoate: To a solution of methyl 2-methyl-2-pyrrolidin-3-yl-propanoate trifluoroacetate (390 mg, 684 wnol) in DMF (5 mL) was added K₂CO₃ (380 mg, 2.73 mmol) and 2-chloro-5-fluoro-pyrimidine (181 mg, 1.37 mmol, 169 μL). The mixture was stirred at 100° C. for 2 h. The reaction mixture was diluted with water (5 mL) and extracted with EtOAc (3×5 mL). The combined organic layers were washed with brine (10 mL), dried over Na₂SO₄, filtered and concentrated under reduced pressure. The residue was purified by prep-TLC (SiO₂, PE:EtOAc=5:1) to provide the title compound (140 mg) as a yellow oil. LCMS: m/z=268.1 [M+H]⁺.

2-(1-(5-Fluoropyrimidin-2-yl)pyrrolidin-3-yl)-2-methylpropanoic acid: To a solution of methyl 2-(1-(5-fluoropyrimidin-2-yl)pyrrolidin-3-yl)-2-methylpropanoate (140 mg, 524 μmol) in MeOH (4 mL) and H₂O (1 mL) was added LiOH.H₂O (659 mg, 15.71 mmol). The mixture was stirred at 25° C. for 20 h. The reaction mixture was concentrated under reduced pressure. The resulting residue was diluted with H₂O (3 mL) and adjusted to pH=4. The mixture was concentrated under reduced pressure to provide the title compound (132 mg, 99%) as a white solid.

Method AE: Preparation of 3-((5-fluoropyrimidin-2-yl)oxy)methyl)bicyclo[1.1.1]-pentane-1-carboxylic acid

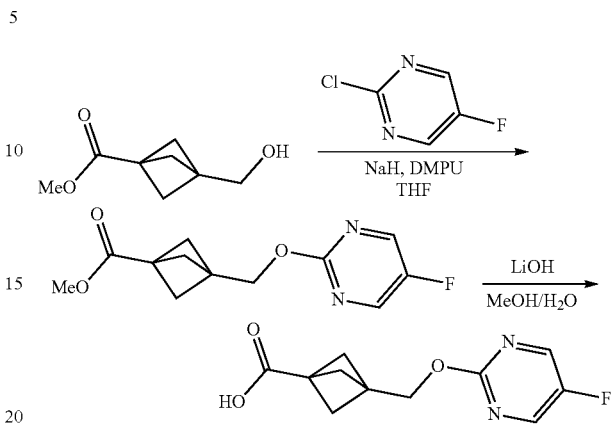

Methyl 3-(((5-fluoropyrimidin-2-yl)oxy)methyl)bicyclo[1.1.1]pentane-1-carboxylate: To a solution of methyl 1-(hydroxymethyl)bicyclo[1.1.1]pentane-3-carboxylate (300 mg, 1.92 mmol) and 2-chloro-5-fluoro-pyrimidine (254.6 mg, 1.92 mmol) in THF (10 mL) at 0° C. under nitrogen was added DMPU (984.8 mg, 7.68 mmol), 4A molecular sieves, and NaH (153.7 mg, 3.84 mmol, 60% in mineral oil). The reaction mixture was stirred at 20° C. for 3 h. The mixture was filtered through a pad of celite, the filtrate was quenched by addition of sat. NH₄Cl (10 mL) at 0° C. The aqueous mixture was extracted with EtOAc (2×10 mL) and the combined organic layers were washed with brine (2×10 mL), dried over anhydrous Na₂SO₄, filtered and concentrated under reduced pressure. The resulting residue was purified by prep-TLC (SiO₂, 3:1 PE/EtOAc) to provide the title compound (60 mg, 13%) as a white solid. LCMS: m/z=253.1 [M+H]⁺.

3-(((5-Fluoropyrimidin-2-yl)oxy)methyl)bicyclo[1.1.1]pentane-1-carboxylic acid: To a solution of methyl 1-[(5-fluoropyrimidin-2-yl)oxymethyl]bicyclo[1.1.1]pentane-3-carboxylate (60 mg, 0.237 mmol) in MeOH (2 mL) and H₂O (1 mL) was added LiOH.H₂O (49.9 mg, 1.19 mmol).The mixture was stirred at 25° C. for 12 h. The reaction mixture was concentrated under reduced pressure to remove MeOH. The residue was diluted with H₂O (3 mL) and adjusted to pH=4 with HCl and then concentrated under reduced pressure to give the title compound (60 mg) as a white solid. LCMS: m/z=239.1 [M+H]⁺.

Method AF: Preparation of 4-(difluoromethyl)-1-(5-fluoropyrimidin-2-yl)piperidine-4-carboxylic acid

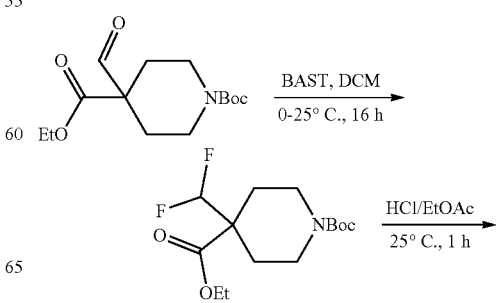

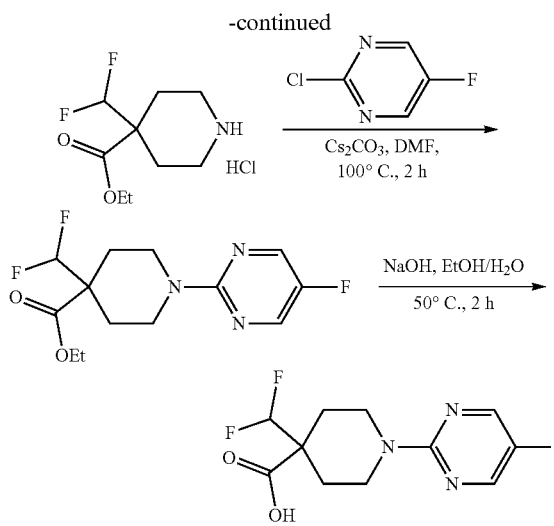

1-tert-Butyl 4-ethyl 4-(difluoromethyl)piperidine-1,4-dicarboxylate: To a solution of 1-tert-butyl 4-ethyl 4-formylpiperidine-1,4-dicarboxylate (1.2 g, 4.21 mmol) in DCM (24 mL) was added BAST (2.05 g, 9.25 mmol, 2.03 mL) at 0° C. under $N_2$. The reaction mixture was stirred at 25° C. for 16 h. The mixture was poured into ice-water (50 mL). The aqueous phase was adjusted to pH=7-8 with saturated aqueous $NaHCO_3$. The organic phase was separated and the aqueous phase was extracted with DCM (30 mL). The combined organics were washed with brine (20 mL), dried over anhydrous $Na_2SO_4$, filtered and concentrated under reduced pressure. The resulting residue was purified by silica gel column chromatography (PE:EtOAc=10:1) to afford the title compound (0.8 g, 62%) as a colorless oil.

Ethyl 4-(difluoromethyl)piperidine-4-carboxylate hydrochloride: A mixture of 1-tert-butyl 4-ethyl 4-(difluoromethyl)piperidine-1,4-dicarboxylate (0.6 g, 1.95 mmol) in HCl/EtOAc (4 M, 10 mL) was stirred at 25° C. for 1 h. The reaction mixture was concentrated under reduced pressure to provide the title compound (0.5 g) as a colorless oil, which was used in the next step directly. LC-MS: m/z=208.1 [M+H]$^+$.

Ethyl 4-(difluoromethyl)-1-(5-fluoropyrimidin-2-yl)piperidine-4-carboxylate: To a solution of ethyl 4-(difluoromethyl)piperidine-4-carboxylate hydrochloride (0.5 g, 2.05 mmol) in DMF (10 mL) was added $Cs_2CO_3$ (2.67 g, 8.21 mmol) and 2-chloro-5-fluoro-pyrimidine (543 mg, 4.10 mmol) at 25° C. under $N_2$. The reaction mixture was heated at 100° C. for 2 h. The mixture was cooled to 25° C. and poured into ice-water (60 mL). The aqueous phase was extracted with EtOAc (3×20 mL). The combined organic phase was washed with brine (10 mL), dried over anhydrous $Na_2SO_4$, filtered and concentrated under reduced pressure. The resulting residue was purified by silica gel column chromatography (PE:EtOAc=10:1) to afford the title compound (0.52 g, 84%) as a colorless oil. LC-MS: m/z=304.1 [M+H]$^+$.

4-(Difluoromethyl)-1-(5-fluoropyrimidin-2-yl)piperidine-4-carboxylic acid: To a mixture of ethyl 4-(difluoromethyl)-1-(5-fluoropyrimidin-2-yl)piperidine-4-carboxylate (0.28 g, 0.92 mmol) in EtOH (4 mL) and $H_2O$ (2 mL) was added NaOH (147.71 mg, 3.69 mmol) at 25° C. under $N_2$. The mixture was stirred at 50° C. for 2 h. The mixture was cooled to 25° C. and diluted with water (30 mL). The aqueous phase was washed with MTBE (10 mL) and the pH was adjusted to 3-4 with 2 N aqueous $KHSO_4$. The aqueous phase was extracted with DCM (3×15 mL) and the combined organic phase was washed with brine (10 mL), dried over anhydrous $Na_2SO_4$, filtered and concentrated under reduced pressure to provide the title compound (0.24 g, 95%) as a white solid which was used in the next step directly. LC-MS: m/z=276.3 [M+H]$^+$.

Method AG: Preparation of 4-fluoro-1-(pyridine-3-carbonyl)piperidine-4-carboxylic acid

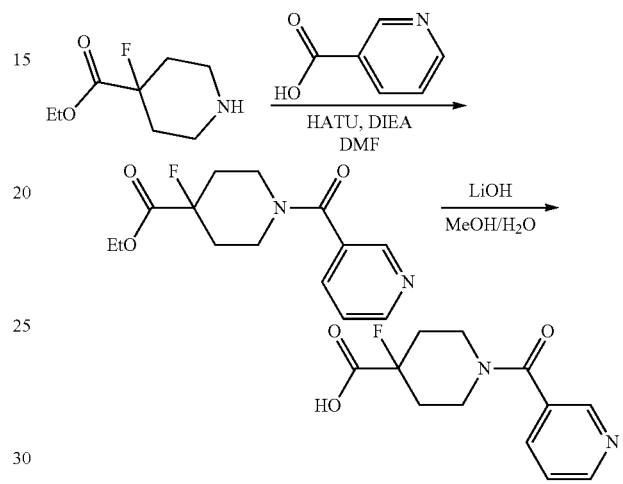

Ethyl 4-fluoro-1-(pyridine-3-carbonyl)piperidine-4-carboxylate: To a solution of ethyl 4-fluoropiperidine-4-carboxylate (200 mg, 0.94 mmol) and nicotinic acid (151 mg, 1.23 mmol) in DMF (10 mL) was added DIEA (366 mg, 2.83 mmol) and HATU (431 mg, 1.13 mmol). The reaction mixture was stirred at 20° C. for 2 h. The reaction mixture was diluted with $H_2O$ (20 mL) and extracted with EtOAc (3×20 mL). The combined organic layers were washed with brine (2×10 mL), dried over anhydrous $Na_2SO_4$, filtered and concentrated under reduced pressure. The resulting residue was purified by prep-TLC ($SiO_2$, DCM:MeOH=20:1) to provide the title compound (200 mg, 76%). LCMS: m/z=281.2[M+H]$^+$.

4-Fluoro-1-(pyridine-3-carbonyl)piperidine-4-carboxylic acid: To a mixture of ethyl 4-fluoro-1-(pyridine-3-carbonyl) piperidine-4-carboxylate (45 mg, 0.16 mmol) in MeOH (2 mL) and $H_2O$ (1 mL) was added $LiOH·H_2O$ (34 mg, 0.80 mol). The reaction mixture was stirred at 20° C. for 12 h. The reaction mixture was adjusted to pH=5 and concentrated under reduced pressure to the title compound (38 mg) as a yellow oil that was used in the next step without further purification. LCMS: m/z=253.2 [M+H]$^+$.

Method AH: Preparation of 3,3-difluoro-1-(5-fluoropyrimidin-2-yl)-4-methyl-piperidine-4-carboxylic acid

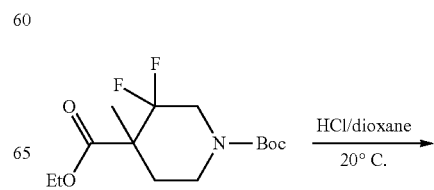

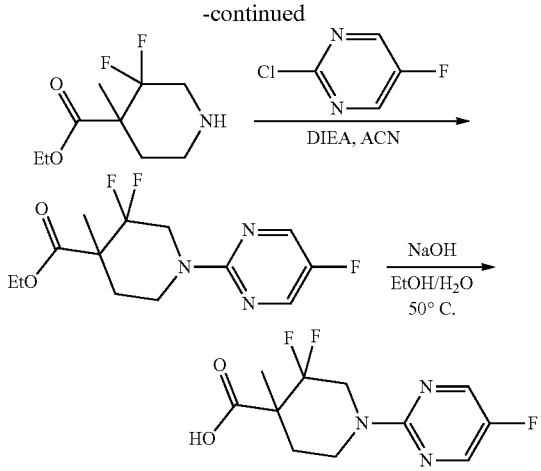

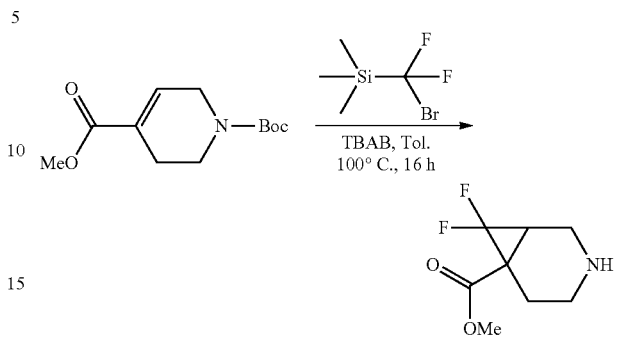

Method AI: Preparation of methyl 7,7-difluoro-3-azabicyclo[4.1.0]heptane-6-carboxylate To a solution of 1-tert-butyl 4-methyl 3,6-dihydro-2H-pyridine-1,4-dicarboxylate (500 mg, 2.07 mmol) in toluene (2.5 mL) was added tetrabutylammoniumbromide (33 mg, 0.10 mmol) under $N_2$, then [bromo(difluoro)methyl]-trimethyl-silane (842 mg, 4.14 mmol) was added drop-wise under $N_2$. The reaction mixture was heated at 110° C. and stirred for 16 h in a sealed tube. The residue was filtered and concentrated under reduced pressure to provide the title compound (700 mg) as a brown oil, which was used in the next step without further purification. LC-MS: m/z=192.1 $[M+H]^+$.

Method AJ: Palladium Catalyzed Coupling

A mixture of amine (1 equiv), haloaryl (1 equiv), XPhos (0.1 equiv), $Pd_2(dba)_3$ (0.1 equiv) and NaOt-Bu (4 equiv) in 1,4-dioxane (0.2 M) was heated at 120° C. for 120 min. under microwave irradiation. The reaction mixture was filtered and the filtrate was concentrated under reduced pressure. The resulting residue was purified by chromatography. In some cases the ligand used was BINAP and the solvent was toluene or RuPhos Pd G3 was used in THF as solvent.

Method AK: Preparation of 2-chloro-4-(2,2-difluoroethoxy)-5-fluoro-pyrimidine

Ethyl 3,3-difluoro-4-methylpiperidine-4-carboxylate hydrochloride: A solution of 1-tert-butyl 4-ethyl 3,3-difluoro-4-methyl-piperidine-1,4-dicarboxylate (200 mg, 0.65 mmol) in HCl/1,4-dioxane (5 mL, 4 N) was stirred for 1 h at 20° C. The mixture was concentrated under reduced pressure to give the title compound (150 mg) as a white solid.

Ethyl 3,3-difluoro-1-(5-fluoropyrimidin-2-yl)-4-methyl-piperidine-4-carboxylate: To a mixture of 2-chloro-5-fluoro-pyrimidine (150 mg, 1.13 mmol) and ethyl 3,3-difluoro-4-methyl-piperidine-4-carboxylate hydrochloride (235 mg, 0.96 mmol) in MeCN (5 mL) was added DIEA (146 mg, 1.13 mmol) in one portion at 15° C. The mixture was heated at 120° C. in a sealed tube and stirred for 16 h. The mixture was concentrated under reduced pressure and the resulting residue was purified by prep-TLC (SiO$_2$, PE:EtOAc=5:1) to give the title compound (60 mg, 18%) as a light yellow oil. LCMS: m/z=304.1 $[M+H]^+$.

3,3-Difluoro-1-(5-fluoropyrimidin-2-yl)-4-methyl-piperidine-4-carboxylic acid: To a mixture of ethyl 3,3-difluoro-1-(5-fluoropyrimidin-2-yl)-4-methyl-piperidine-4-carboxylate (60 mg, 198 µmol) in EtOH (2 mL) and H$_2$O (0.4 mL) was added NaOH (32 mg, 0.79 mmol) in one portion. The mixture was heated at 50° C. for 4 h. The mixture was concentrated under reduced pressure and the resulting residue was dissolved in water (2 mL). The aqueous phase was adjusted to pH=3 by addition of aq. HCl (2 N). The aqueous phase was extracted with EtOAc (2×5 mL). The combined organics were washed with brine (5 mL), dried over Na$_2$SO$_4$, filtered and concentrated under reduced pressure to provide the title compound (50 mg, 92%) as a light yellow solid.

The following intermediates were prepared using procedures analogous to those described above.

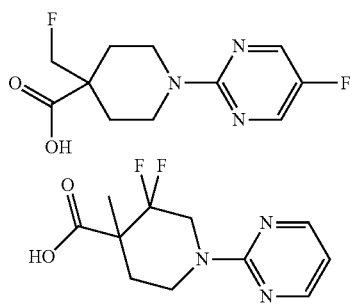

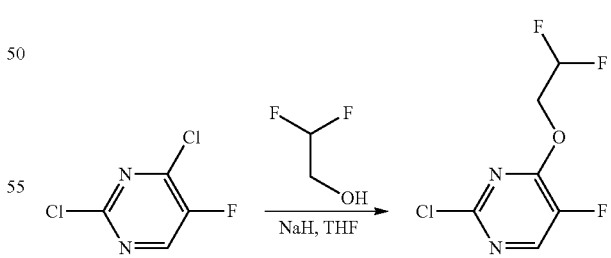

To a solution of 2,4-dichloro-5-fluoro-pyrimidine (1 g, 5.99 mmol) and 2,2-difluoroethanol (540 mg, 6.59 mmol) in THF (20 mL) was added NaH (287 mg, 7.19 mmol, 60% in mineral oil) in portions at 0° C. The mixture was warmed to 15° C. and stirred for 1 h. The mixture was quenched with sat. NH$_4$Cl (20 mL) and extracted with EtOAc (2×10 mL). The organic layers were combined, washed with brine (20 mL), dried over anhydrous Na$_2$SO$_4$, filtered and concentrated under reduced pressure to provide the title compound (1.2 g, 94%) as a light yellow solid. LCMS: m/z=213.0 [M+H]+.

The following intermediates were prepared using procedures analogous to those described above.

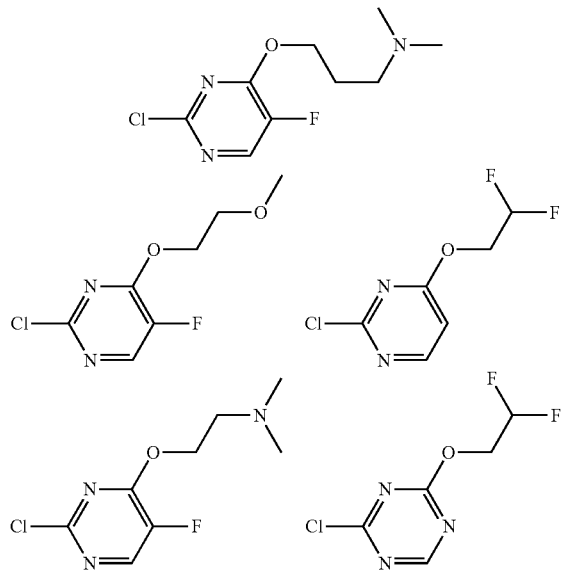

Method AL: Preparation of 1-tert-butyl 4-ethyl 4-(fluoromethyl)piperidine-1,4-dicarboxylate

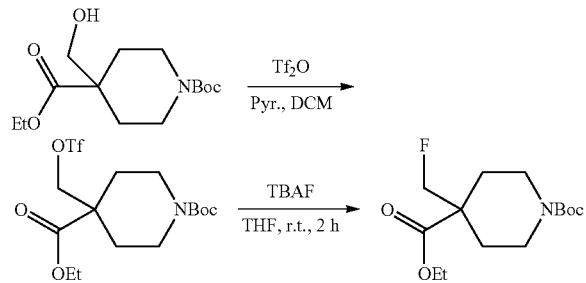

tert-Butyl 4-ethyl 4-(trifluoromethylsulfonyloxymethyl) piperidine-1,4-dicarboxylate: To a solution of 1-tert-butyl 4-ethyl 4-(hydroxymethyl)piperidine-1,4-dicarboxylate (300 mg, 1.04 mmol) and pyridine (248 mg, 3.13 mmol) in DCM (3 mL) was added Tf$_2$O (324 mg, 1.15 mmol) at 0° C. The reaction mixture was stirred at 20° C. for 2 h. The mixture was poured into H$_2$O (10 mL) and extracted with DCM (2×5 mL). The combined organic layers were washed with brine (15 mL), dried over anhydrous Na$_2$SO$_4$, filtered and concentrated under reduced pressure to provide the title compound (340 mg, 78%) as a yellow oil. The product was used in the next step without further purification.

1-tert-Butyl 4-ethyl 4-(fluoromethyl)piperidine-1,4-dicarboxylate: To a solution of 1-tert-butyl 4-ethyl 4-(trifluoromethylsulfonyloxymethyl)piperidine-1,4-dicarboxylate (300 mg, 0.72 mmol) in THF (10 mL) was added TBAF (1.07 mmol, 1 M in THF, 1.07 mL). The mixture was stirred at 20° C. for 1 h. The reaction mixture was concentrated under reduced pressure and the resulting residue was purified by silica gel column chromatography (PE:EtOAc=10:1) to give the title compound (180 mg, 87%) as a colorless oil.

Method AM: Preparation of 4-chloro-(5-fluoropyrimidin-2-yl)piperidine-4-carboxylic acid

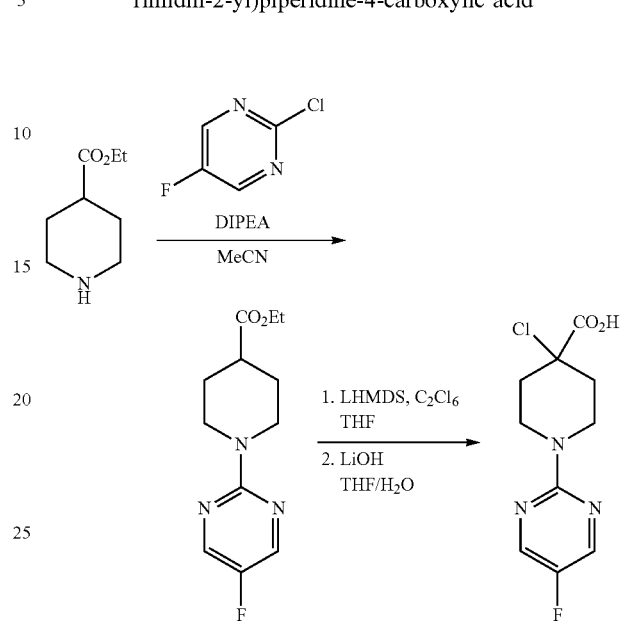

Ethyl 1-(5-fluoropyrimidin-2-yl)piperidine-4-carboxylate: To a dry round bottom flask containing ethyl piperidine-4-carboxylate (2.0 g, 12.72 mmol) and 2-chloro-5-fluoropyrimidine (1.57 mL, 12.72 mmol) in MeCN (31.8 mL) was added DIPEA (6.65 mL, 38.17 mmol). The reaction mixture was stirred at reflux overnight and then concentrated under reduced pressure. The crude reaction mixture was purified employing silica gel chromatography (0-10% EtOAc/hexanes) to provide the desired product as a colorless oil.

Ethyl 4-chloro-(5-fluoropyrimidin-2-yl)piperidine-4-carboxylate: To a solution of ethyl 1-(5-fluoropyrimidin-2-yl)piperidine-4-carboxylate (426.0 mg, 1.68 mmol) in THF (8.41 mL) at −78° C. was added LHMDS (2.02 mL, 1 M solution in THF) dropwise. The reaction mixture was warmed from −78° C. to 0° C. over 3 h, at which time the reaction mixture was cooled to −78° C. and hexachloroethane (478 mg, 2.02 mmol) was added. The reaction mixture was warmed from −78° C. to RT overnight, at which time the reaction mixture was diluted with sat. aq. NH$_4$Cl (20 mL) and EtOAc (20 mL). The layers were separated and the aqueous layer was extracted with EtOAc (3×20 mL). The combined organic layers were dried over anhydrous Na$_2$SO$_4$, filtered and concentrated under reduced pressure. The crude reaction mixture was purified employing silica gel flash chromatography (0-25% EtOAc/hexanes) to provide the desired product as a colorless oil.

4-Chloro-(5-fluoropyrimidin-2-yl)piperidine-4-carboxylic acid: To a solution of ethyl 4-chloro-(5-fluoropyrimidin-2-yl)piperidine-4-carboxylate (81 mg, 0.282 mmol) in THF (1 mL) and water (1 mL) was added lithium hydroxide (67 mg, 2.82 mmol). The reaction mixture was stirred overnight at RT and then diluted with EtOAc (10 mL). The organic layer was extracted with water (2×10 mL). The aqueous layer was acidified to pH=1 with 1 M aq. HCl and extracted with EtOAc (3×10 mL). The combined organic layers were dried over anhydrous Na$_2$SO$_4$, filtered, and concentrated

Method AN: Preparation of 3,3,4-trifluoro-1-(5-fluoropyrimidin-2-yl)piperidine-4-carboxylic acid

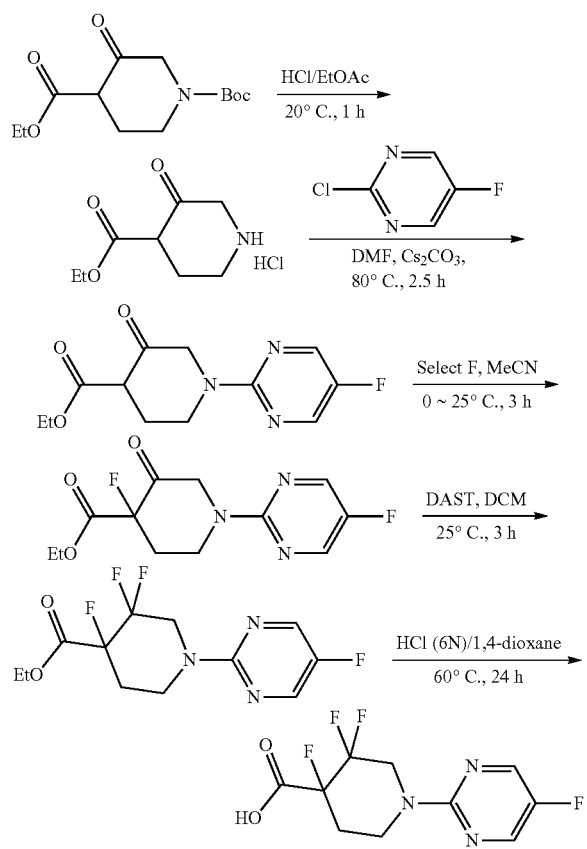

Ethyl 3-oxopiperidine-4-carboxylate hydrochloride: A solution of 1-tert-butyl 4-ethyl 3-oxopiperidine-1,4-dicarboxylate (2 g, 7.37 mmol) in HCl/EtOAc (4 M, 20 mL) was stirred at 20° C. for 1 h. The mixture was concentrated under reduced pressure to provide the title compound (1.4 g, 91%) as a white solid.

Ethyl 1-(5-fluoropyrimidin-2-yl)-3-oxo-piperidine-4-carboxylate: To a mixture of ethyl 3-oxopiperidine-4-carboxylate hydrochloride (200 mg, 1.17 mmol) and 2-chloro-5-fluoro-pyrimidine (310 mg, 2.34 mmol) in DMF (5 mL) was added $Cs_2CO_3$ (1.14 g, 3.51 mmol) at 20° C. under $N_2$. The reaction mixture was stirred at 80° C. for 2.5 h. The mixture was poured into water (20 mL) and extracted with EtOAc (3×10 mL). The combined organic phase was washed with brine (3×10 mL), dried over anhydrous $Na_2SO_4$, filtered and concentrated under reduced pressure. The resulting residue was purified by column chromatography (PE:EtOAc=20:1 to 10:1) to give the title compound (330 mg, 15%) as a yellow oil. LCMS: m/z=268.1 [M+H]$^+$.

Ethyl 4-fluoro-1-(5-fluoropyrimidin-2-yl)-3-oxo-piperidine-4-carboxylate: To a solution of ethyl 1-(5-fluoropyrimidin-2-yl)-3-oxo-piperidine-4-carboxylate (0.35 g, 1.31 mmol) in $CH_3CN$ (20 mL) was added Selectfluor (464 mg, 1.31 mmol) at 0° C. under $N_2$. The reaction mixture was stirred at 25° C. for 3 h. The mixture was poured into ice-water (60 mL) and sat. $NaHCO_3$ (3 mL) was added. The aqueous phase was extracted with EtOAc (3×20 mL) and the combined organic phase was washed with brine (20 mL), dried over anhydrous $Na_2SO_4$, filtered and concentrated under reduced pressure to provide the title compound (0.37 g) as a light-yellow oil. LCMS: m/z=286.0 [M+H]$^+$.

Ethyl 3,3,4-trifluoro-1-(5-fluoropyrimidin-2-yl)piperidine-4-carboxylate: To a solution of ethyl 4-fluoro-1-(5-fluoropyrimidin-2-yl)-3-oxo-piperidine-4-carboxylate (0.37 g, 1.30 mmol) in DCM (5 mL) was added DAST (418 mg, 2.59 mmol) at 25° C. under $N_2$. The reaction mixture was stirred at 25° C. for 3 h. The mixture was poured into ice-water (30 mL). The pH was adjusted to 7 with sat. $NaHCO_3$ and extracted with EtOAc (3×20 mL). The combined organic phase was washed with brine (20 mL), dried over anhydrous $Na_2SO_4$, filtered and concentrated under reduced pressure to provide the title compound (0.4 g) as a light yellow oil. LCMS: m/z=308.1 [M+H]$^+$.

3,3,4-Trifluoro-1-(5-fluoropyrimidin-2-yl)piperidine-4-carboxylic acid hydrochloride: To a solution of ethyl 3,3,4-trifluoro-1-(5-fluoropyrimidin-2-yl)piperidine-4-carboxylate (0.2 g, 651 µmol) in 1,4-dioxane (5 mL) was added 6 N HCl (0.65 mmol, 10 mL) at 25° C. under $N_2$. The reaction mixture was heated at 60° C. and stirred for 24 h. The mixture was cooled to 25° C. and concentrated under reduced pressure to provide the title compound (0.18 g, 88%) as a red solid. LCMS: m/z=280.2 [M+H]$^+$.

Method AO: Preparation of 1-(5-chloropyrimidin-2-yl)-3,3-difluoro-4-methylpiperidine-4-carbonyl chloride

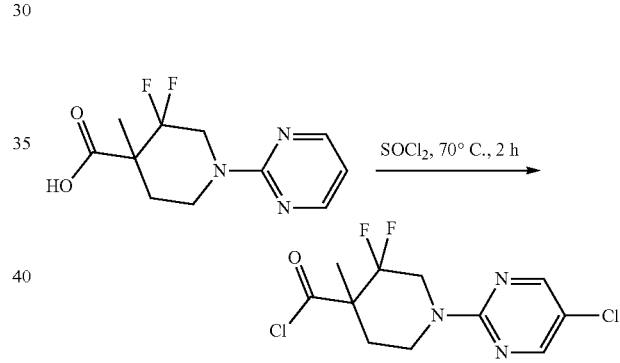

A solution of 3,3-difluoro-4-methyl-1-pyrimidin-2-yl-piperidine-4-carboxylic acid (140 mg, 0.55 mmol) in $SOCl_2$ (6 mL) was heated at 70° C. and stirred for 2 h. The reaction mixture was concentrated under reduced pressure to provide the title compound (75 mg, 44%) as a brown oil.

Method AP: Preparation of 3-fluoro-1-(5-fluoropyrimidin-2-yl)-4-methyl-piperidine-4-carbonyl chloride

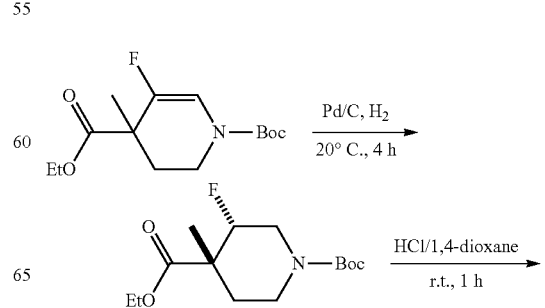

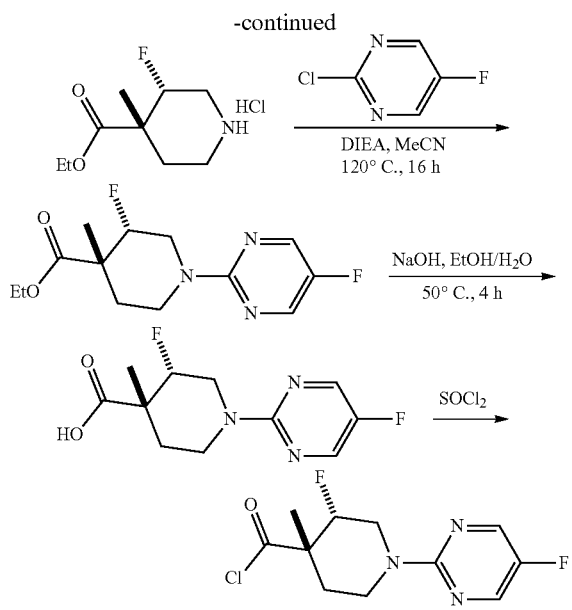

1-tert-Butyl 4-ethyl 3-fluoro-4-methyl-piperidine-1,4-dicarboxylate: To a solution of 1-tert-butyl 4-ethyl 5-fluoro-4-methyl-2,3-dihydropyridine-1,4-dicarboxylate (225 mg, 0.78 mmol) in EtOAc (3 mL) was added 10% Pd/C (100 mg) under N₂. The suspension was degassed under vacuum and purged with H₂ several times. The mixture was stirred under H₂ (50 psi) at 20° C. for 2 h. The reaction mixture was filtered through a pad of celite and the filtrate was concentrated under reduced pressure to provide the title compound (220 mg, 97%) as a yellow oil.

Ethyl 3-fluoro-4-methyl-piperidine-4-carboxylate hydrochloride: A solution of 1-tert-butyl 4-ethyl 3-fluoro-4-methyl-piperidine-1,4-dicarboxylate (380 mg, 1.31 mmol) in HCl/1,4-dioxane (10 mL) was stirred at 10° C. for 2 h. The reaction solution was concentrated under reduced pressure to provide the title compound (280 mg, 95%) as a white solid. The solid was used in next step without further purification.

Ethyl 3-fluoro-1-(5-fluoropyrimidin-2-yl)-4-methyl-piperidine-4-carboxylate: To a solution of ethyl 3-fluoro-4-methyl-piperidine-4-carboxylate hydrochloride (280 mg, 1.24 mmol) and 2-chloro-5-fluoro-pyrimidine (329 mg, 2.48 mmol) in MeCN (10 mL) was added DIEA (802 mg, 6.20 mmol, 1.08 mL). The reaction mixture was heated at 120° C. for 16 h in a sealed tube. The reaction solution was then concentrated under reduced pressure and the resulting residue was purified by silica gel column chromatography (PE:EtOAc=20:1 to 3:1) to provide the title compound (170 mg, 48%) as a yellow solid.

3-Fluoro-1-(5-fluoropyrimidin-2-yl)-4-methyl-piperidine-4-carboxylic acid: To a solution of ethyl 3-fluoro-1-(5-fluoropyrimidin-2-yl)-4-methyl-piperidine-4-carboxylate (170 mg, 0.59 mmol) in H₂O (2 mL) and EtOH (10 mL) was added NaOH (119 mg, 2.98 mmol), the reaction solution was stirred at 50° C. for 12 h. The reaction mixture was concentrated under reduced pressure and the resulting residue was adjusted to pH=3 with sat. KHSO₄ solution. The aqueous solution was extracted with EtOAc (3×5 mL) and the combined organic layers were washed with brine (5 mL), dried over anhydrous Na₂SO₄, filtered and concentrated under reduced pressure to provide the title compound (130 mg, 85%) as a yellow solid.

3-Fluoro-1-(5-fluoropyrimidin-2-yl)-4-methyl-piperidine-4-carbonyl chloride: A solution of 3-fluoro-1-(5-fluoropyrimidin-2-yl)-4-methyl-piperidine-4-carboxylic acid (112 mg, 0.44 mmol) in SOCl₂ (155 mmol, 11 mL) was heated at 70° C. for 2 h. The reaction mixture was concentrated under reduced pressure to provide the title compound (120 mg, quant.) as a yellow oil.

Method AQ: Preparation of 7-chloro-3-fluoro-pyrazolo[1,5-a]pyrimidine and 3,7-dichloropyrazolo[1,5-a]pyrimidine

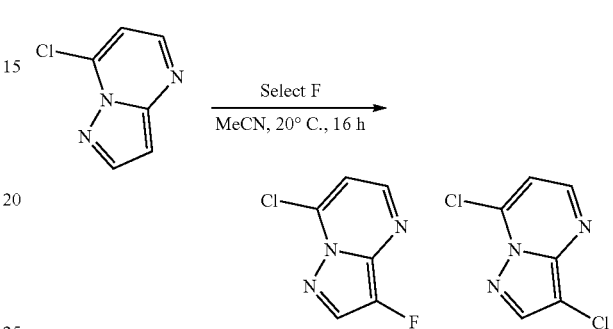

7-Chloro-3-fluoro-pyrazolo[1,5-a]pyrimidine and 3,7-dichloropyrazolo[1,5-a]pyrimidine: To a mixture of 7-chloropyrazolo[1,5-a]pyrimidine (200 mg, 1.30 mmol) in MeCN (5 mL) was added Selectfluor (554 mg, 1.56 mmol) at 20° C. under N₂. The mixture was stirred at 20° C. for 16 h. The mixture was poured into water (10 mL) and extracted with EtOAc (3×3 mL). The combined organic phase was dried over anhydrous Na₂SO₄, filtered and concentrated under reduced pressure. The residue was purified by prep-TLC (SiO₂, PE:EtOAc=3:1) to provide a mixture of 7-chloro-3-fluoro-pyrazolo[1,5-a]pyrimidine and 3,7-dichloropyrazolo[1,5-a]pyrimidine (110 mg, F:Cl=~5:2) as a yellow solid.

Method AR: Preparation of spiro[4,5-dihydro-2H-pyrido[3,4-f][1,4]oxazepine-3,1'-cyclopropane]-9-carbonitrile

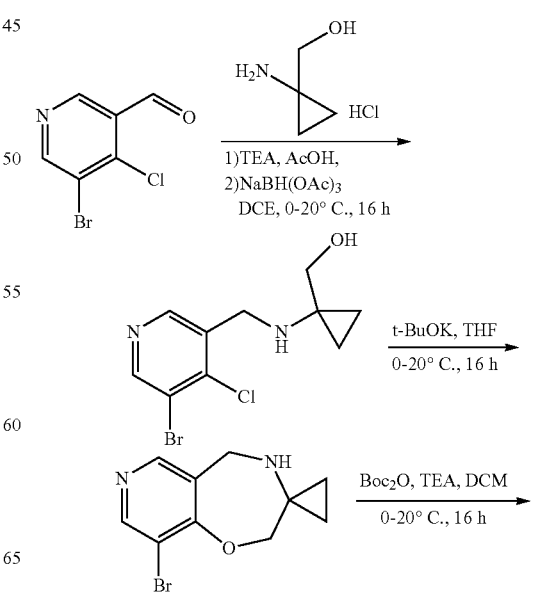

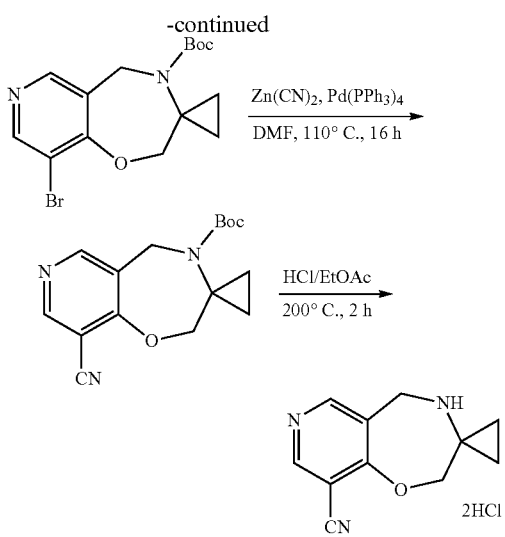

[1-[(5-Bromo-4-chloro-3-pyridyl)methylamino]cyclopropyl]methanol: To a mixture of 5-bromo-4-chloro-pyridine-3-carbaldehyde (3.5 g, 15.88 mmol) and (1-aminocyclopropyl)methanol HCl salt (2.94 g, 23.81 mmol) in DCE (150 mL) was added TEA (2.73 g, 26.99 mmol, 3.76 mL) at 0° C. under N₂. The mixture was stirred at 20° C. for 1 h before adding AcOH (3.15 g, 52.39 mmol, 3 mL) and stirring for 1 h. To the mixture was added NaBH(OAc)₃ (10.09 g, 47.63 mmol) at 0° C. and stirred at 20° C. for 16 h. The mixture was poured into sat. NaHCO₃ (100 mL) and extracted with DCM:i-PrOH (3×30 mL, v:v=3:1). The combined organic phase was dried over anhydrous Na₂SO₄, filtered and concentrated under reduced pressure to provide the title compound (4.68 g) as a yellow gum. LCMS: m/z=292.9 [M+H]⁺.

9-Bromospiro[4,5-dihydro-2H-pyrido[3,4-f][1,4]oxazepine-3,1'-cyclopropane]: To a mixture of [1-[(5-bromo-4-chloro-3-pyridyl)methylamino]cyclopropyl]methanol (4.6 g, 15.78 mmol) in THF (300 mL) was added t-BuOK (5.49 g, 48.91 mmol) at 0° C. under N₂. The mixture was stirred at 20° C. for 16 h. The mixture was poured into water (100 mL) and extracted with DCM:i-PrOH (3×30 mL, v:v=3:1). The combined organic phase was dried over anhydrous Na₂SO₄, filtered and concentrated under reduced pressure to provide the title compound (3.78 g, 93%) as a yellow oil. LCMS: m/z=255.0 [M+H]⁺.

tert-Butyl 9-bromospiro[2,5-dihydropyrido[3,4-f][1,4]oxazepine-3,1'-cyclopropane]-4-carboxylate: To a mixture of 9-bromospiro[4,5-dihydro-2H-pyrido[3,4-f][1,4]oxazepine-3,1'-cyclopropane] (3.78 g, 14.82 mmol) and TEA (3 g, 29.63 mmol, 4.12 mL) in DCM (50 mL) was added Boc₂O (4.85 g, 22.23 mmol, 5.11 mL) at 20° C. under N₂. The reaction mixture was stirred at 20° C. for 16 h. The mixture was poured into water (50 mL) and extracted with DCM (3×20 mL). The combined organic phase was dried over anhydrous Na₂SO₄, filtered and concentrated under reduced pressure. The resulting residue was purified by silica gel column chromatography (PE:EtOAc=3:1 to 1:1) to provide the title compound (1.7 g, 32%) as a yellow solid. LCMS: m/z=355.0 [M+H]⁺.

tert-Butyl 9-cyanospiro[2,5-dihydropyrido[3,4-f][1,4]oxazepine-3,1'-cyclopropane]-4-carboxylate: To a mixture of tert-butyl 9-bromospiro[2,5-dihydropyrido[3,4-f][1,4]oxazepine-3,1'-cyclopropane]-4-carboxylate (1 g, 2.82 mmol) and Zn(CN)₂ (331 mg, 2.82 mmol, 179 μL) in DMF (15 mL) was added Pd(PPh₃)₄ (325 mg, 0.28 mmol) at 20° C. under N₂. The mixture was stirred at 110° C. for 16 h. The mixture was filtered and the filtrate was poured into water (50 mL) and extracted with EtOAc (3×15 mL). The combined organic phase was dried over anhydrous Na₂SO₄, filtered and concentrated under reduced pressure. The resulting residue was purified by silica gel column chromatography (PE:EtOAc=3:1 to 1:1) to provide the title compound (670 mg, 79%) as a yellow oil.

Spiro[4,5-dihydro-2H-pyrido[3,4-f][1,4]oxazepine-3,1'-cyclopropane]-9-carbonitrile dihydrochloride: A solution of tert-butyl 9-cyanospiro[2,5-dihydropyrido[3,4-f][1,4]oxazepine-3,1'-cyclopropane]-4-carboxylate (670 mg, 2.22 mmol) in HCl/EtOAc (60 mmol, 4 M, 15 mL) at 20° C. under N₂ was stirred at 20° C. for 1 h and then concentrated under reduced pressure to provide the title compound (600 mg, 98%) as a white solid.

Method AS: Preparation of 4-tert-butoxycarbonyl-1,4-oxazepane-7-carboxylic acid

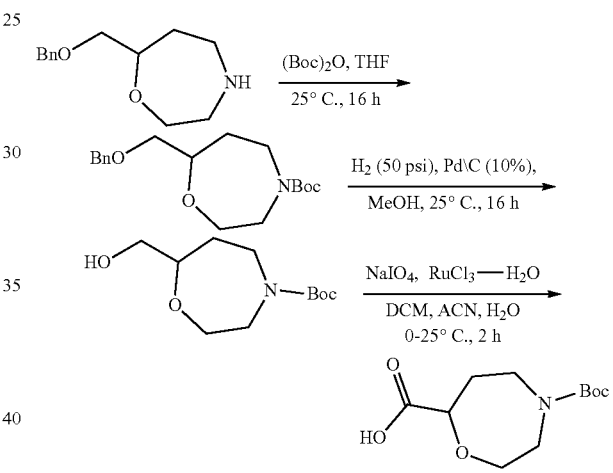

tert-Butyl 7-(benzyloxymethyl)-1,4-oxazepane-4-carboxylate: To a solution of 7-(benzyloxymethyl)-1,4-oxazepane (3.2 g, 14.46 mmol) in THF (50 mL) was added Boc₂O (3.79 g, 17.35 mmol, 3.99 mL) at 25° C. under N₂. The mixture was stirred at 25° C. for 16 h. The mixture was concentrated under reduced pressure. The resulting residue was purified by silica gel column chromatography (PE:EtOAc=10:1 to 5:1) to provide the title compound (4.2 g, 90%) as a colorless oil.

tert-Butyl 7-(hydroxymethyl)-1,4-oxazepane-4-carboxylate: To a solution of tert-butyl 7-(benzyloxymethyl)-1,4-oxazepane-4-carboxylate (4.2 g, 13.07 mmol) in MeOH (84 mL) was added 10% Pd/C (2 g) under N₂. The suspension was degassed under reduced pressure and purged with H₂ three times. The mixture was stirred under H₂ (50 psi) at 25° C. for 16 h. The reaction mixture was filtered through a pad of celite and the filtrate was concentrated under reduced pressure to provide the title compound (2.9 g, 96%) as a colorless oil.

4-tert-Butoxycarbonyl-1,4-oxazepane-7-carboxylic acid: To a solution of tert-butyl 7-(hydroxymethyl)-1,4-oxazepane-4-carboxylate (0.5 g, 2.16 mmol) in DCM (4 mL), CH₃CN (4 mL) and H₂O (8 mL) was added NaIO₄ (1.39 g, 6.49 mmol, 359 μL) at 0° C. under N₂. RuCl₃·H₂O (10 mg, 43 μmol) was added and the mixture was stirred at 25° C. for 2 h. The mixture was cooled to 0° C. and sat. Na$_2$S$_2$O$_3$ was added. The mixture was adjusted to pH~4-5 with 2 N HCl and extracted with EtOAc (3×30 mL). The combined organic phase was washed with brine (20 mL), dried over anhydrous Na$_2$SO$_4$, filtered and concentrated under reduced pressure to provide the title compound (0.32 g, 60%) as a gray oil.

Method AT: Preparation of 3-fluoro-1-(5-fluoropyrimidin-2-yl)-4-hydroxy-piperidine-4-carboxylic acid

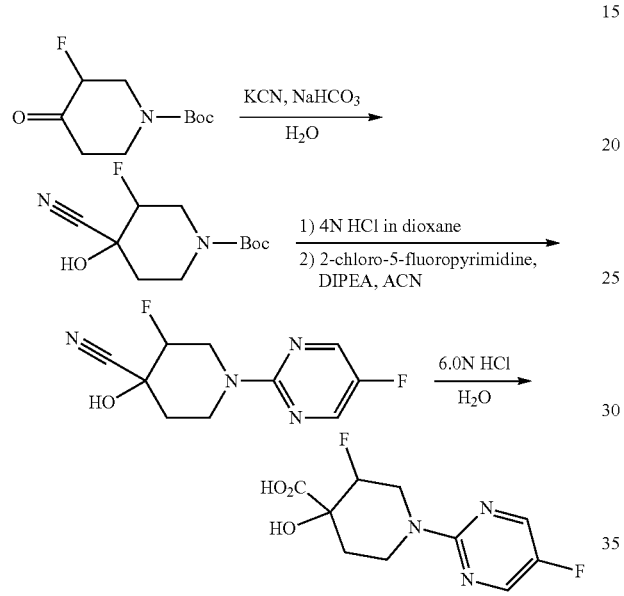

tert-Butyl 4-cyano-3-fluoro-4-hydroxy-piperidine-1-carboxylate: A solution of potassium cyanide (1.6 g, 25.3 mmol) and NaHCO$_3$ (3.9 g, 46.0 mmol) in water (60 mL) was added dropwise to a vigorously stirring solution of tert-butyl 3-fluoro-4-oxo-piperidine-1-carboxylate (5.0 g, 23.0 mmol) in ether (92 mL) at RT. The reaction mixture was stirred for 15 h and the layers were separated. The aqueous layer was extracted with CH$_2$Cl$_2$ (3×100 mL) and the combined organic layers were dried (MgSO$_4$) and concentrated reduced under pressure to provide the title compound (4.9 g, 86% yield) as a colorless solid. LCMS: m/z=245.3 [M+H]$^+$.

3-Fluoro-1-(5-fluoropyrimidin-2-yl)-4-hydroxy-piperidine-4-carbonitrile: tert-butyl 4-cyano-3-fluoro-4-hydroxy-piperidine-1-carboxylate (2.2 g, 9.01 mmol) was dissolved in 4.0 N HCl in dioxane (20 mL, 80 mmol) and the mixture was stirred at RT for 2 h. The reaction mixture was concentrated to dryness. To the resulting residue was added MeCN (10 mL) followed by 2-chloro-5-fluoropyrimidine (1.31 g, 9.91 mmol) and triethylamine (3.77 mL, 27.0 mmol). The mixture was heated at 80° C. for 16 h and then concentrated in vacuo to provide a yellow solid. Purification by flash chromatography (0-20% methanol in dichloromethane) provided the title compound as a colorless solid. (1.31 g, 61% yield). LCMS: m/z=241.3 [M+H]$^+$.

3-Fluoro-1-(5-fluoropyrimidin-2-yl)-4-hydroxy-piperidine-4-carboxylic acid: 3-fluoro-1-(5-fluoropyrimidin-2-yl)-4-hydroxy-piperidine-4-carbonitrile (350 mg, 1.46 mmol) was added to 6.0 N HCl in water (20 mL, 120 mmol) and the mixture was heated at 70° C. for 6 h. The mixture was concentrated to dryness, dissolved in water (50 mL). The pH was adjusted to 4.0 using sodium bicarbonate aqueous solution and it was extracted with ethyl acetate (50 mL×2). The organic layers were combined and concentrated to yield the title compound, which was used directly in the next step. LC-MS: m/z=260.3 [M+H]$^+$.

Method AU: Preparation of (3R)-3-methyl-2,3,4,5-tetrahydropyrido[3,4-f][1,4]oxazepine-9-carbonitrile

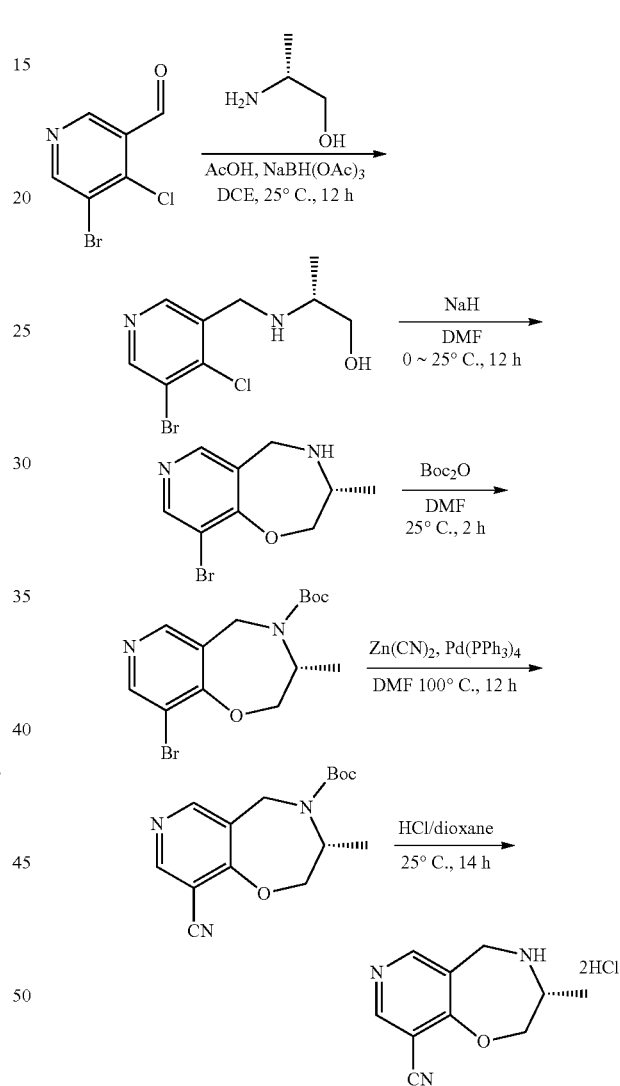

(2R)-2-[(5-Bromo-4-chloro-3-pyridyl)methylamino]propan-1-ol: To a solution of 5-bromo-4-chloro-pyridine-3-carbaldehyde (5 g, 22.68 mmol) in DCE (100 mL) at 25° C. was added (2R)-2-aminopropan-1-ol (3.41 g, 45.36 mmol, 3.54 mL) followed by AcOH (2.72 g, 45.36 mmol, 2.59 mL) and the mixture was stirred for 10 min. NaBH(OAc)$_3$ (14.42 g, 68.04 mmol,) was added and the mixture was stirred at 25° C. for 12 h. The reaction mixture was diluted with water (100 mL) and stirred for 20 min. The layers were separated and the aqueous layer was extracted with a mixture of i-PrOH/DCM (v:v=1:3, 3×50 mL). The aqueous layer was adjusted to pH=7~8 by sat. NaHCO$_3$. The aqueous layer was extracted with a mixture of i-PrOH:DCM (v:v=1:3; 3×100 mL). The combined organic layers were washed with brine (2×100 mL), dried over anhydrous $Na_2SO_4$, filtered and concentrated under reduced pressure to provide the title compound (3.77 g, 59%) as a yellow solid.

(3R)-9-Bromo-3-methyl-2,3,4,5-tetrahydropyrido[3,4-f] [1,4]oxazepine: To a solution of (2R)-2[(5-bromo-4-chloro-3-pyridyl)methylamino]propan-1-ol (3.4 g, 12.16 mmol,) in DMF (70 mL) was added NaH (486 mg, 12.16 mmol, 60% in mineral oil) at 0° C. under $N_2$, and then the mixture was stirred at 25° C. for 12 h. The reaction mixture was quenched by addition of sat. $NH_4Cl$ (50 mL) at 0° C., and then extracted with i-PrOH:DCM (v:v=1:3; 3×50 mL). The combined organic layers were washed with brine (50 mL), dried over anhydrous $Na_2SO_4$, filtered and concentrated under reduced pressure to provide the title compound (27 g, 82%) as a yellow oil. LCMS: m/z=243.1 $[M+H]^+$.

tert-Butyl (3R)-9-bromo-3-methyl-3,5-dihydro-2H-pyrido[3,4-f][1,4]oxazepine-4-carboxylate: To a solution of (3R)-9-bromo-3-methyl-2,3,4,5-tetrahydropyrido[3,4-f][1,4]oxazepine (27 g, 9.44 mmol,) in DMF (20 mL) was added $Boc_2O$ (4.12 g, 18.88 mmol, 4.34 mL) at 25° C., and the solution was stirred at 25° C. for 2 h. The reaction mixture was diluted with water (100 mL) at 25° C., and the aqueous phase was extracted with EtOAc (3×100 mL). The combined organic layers were washed with brine (2×50 mL), dried over anhydrous $Na_2SO_4$, filtered and concentrated under reduced pressure. The resulting residue was purified by silica gel column chromatography (PE:EA=10:1 to 0:1) to give the title compound (2.5 g, 77%) as a yellow oil. LCMS: m/z=344.2 $[M+H]^+$.

tert-Butyl (3R)-9-cyano-3-methyl-3,5-dihydro-2H-pyrido[3,4-f][1,4]oxazepine-4-carboxylate: To a mixture of tert-butyl (3R)-9-bromo-3-methyl-3,5-dihydro-2H-pyrido[3,4-f][1,4]oxazepine-4-carboxylate (2.5 g, 7.28 mmol) in DMF (50 mL) was added $Pd(PPh_3)_4$ (2.53 g, 2.19 mmol) and $Zn(CN)_2$ (855 mg, 7.28 mmol) at 25° C., and then the solution was stirred at 100° C. for 12 h. The reaction mixture was poured into $H_2O$ (50 mL). The mixture was extracted with EtOAc (3×20 mL). The combined organic phase was washed with brine (20 mL), dried over anhydrous $Na_2SO_4$, filtered and concentrated under reduced pressure. The resulting residue was purified by silica gel column chromatography (PE:EtOAc=30:1 to 0:1) to provide the title compound (2.19 g, 83%) as a yellow oil. LCMS: m/z=290.0 $[M+H]^+$.

(3R)-3-Methyl-2,3,4,5-tetrahydropyrido[3,4-f][1,4]oxazepine-9-carbonitrile dihydrochloride: A solution of tert-butyl (3R)-9-cyano-3-methyl-3,5-dihydro-2H-pyrido[3,4-f][1,4]oxazepine- 4-carboxylate (2.19 g, 6.06 mmol) in HCl/1,4-dioxane (4 M, 23.36 mL) was stirred at 25° C. for 14 h. The reaction mixture was filtered and washed with MTBE (50 mL) to provide the title compound (1.2 g, 76%) as a white solid.

Example 1

Preparation of (3,3-difluorocyclobutyl)(2,3-dihydrobenzo[f][1,4]oxazepin-4(5H)-yl)methanone

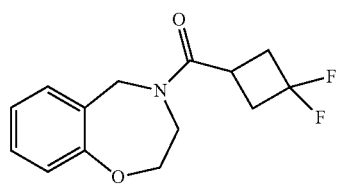 [SMILES: O=C(C1CC(F)(F)C1)N1CCOc2ccccc2C1]

To a solution of 2,3,4,5-tetrahydro-1,4-benzoxazepine (75 mg, 0.5 mmol) in THF (2.0 mL) at 0° C. was added $^i$PrMgBr solution (183 μM, 3M/THF). The solution was warmed to RT and methyl 3,3-difluorocyclobutanecarboxylate (113 mg, 0.75 mmol) was added and the resulting reaction mixture was stirred overnight. A saturated aqueous $NH_4Cl$ solution (10 mL) was added followed by EtOAc (10 mL). The layers were separated, and the aqueous layer was extracted with EtOAc (3×10 mL). The combined organic layers were dried over anhydrous $MgSO_4$, filtered and concentrated under reduced pressure. The crude reaction mixture was purified employing silica gel flash chromatography (0-100% EtOAc/hexanes) to provide the desired product as a clear oil. $^1$H NMR (400 MHz, $CDCl_3$): δ 7.39-7.02 (m, 4H), 4.68-4.51 (m, 2H), 4.13-3.79 (m, 4H), 3.25-2.83 (m, 3H), 2.81-2.61 (m, 2H). LC-MS: m/z=268.0 $[M+H]^+$.

Example 2

Preparation of 4-(3,3-difluoro-2,2-dimethyl-propanoyl)-6-fluoro-3,5-dihydro-2H-1,4-benzoxazepine-9-carbonitrile

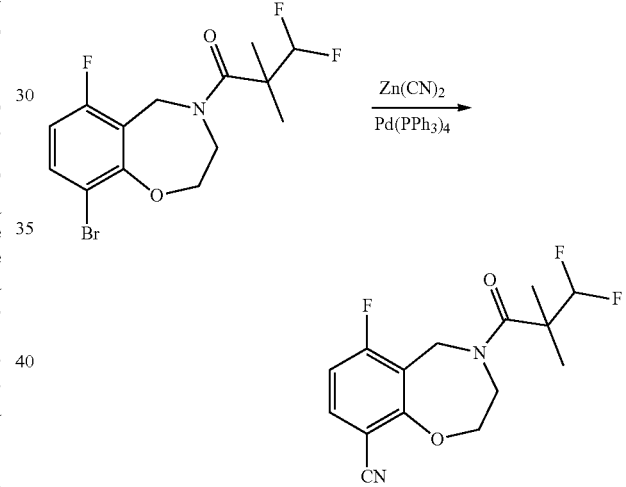

4-(3,3-Difluoro-2,2-dimethyl-propanoyl)-6-fluoro-3,5-dihydro-2H-1,4-benzoxazepine-9-carbonitrile. To a flask containing 1-(9-bromo-6-fluoro-3,5-dihydro-2H-1,4-benzoxazepin-4-yl)-3,3-difluoro-2,2-dimethyl-propan-1-one (43.0 mg, 0.12 mmol) and $Zn(CN)_2$ (13.8 mg, 0.12 mmol) was added DMF (1.0 mL). The solution was degassed with argon for 15 min and tetrakis(triphenylphosphine)palladium(0) (27.0 mg, 0.02 mmol) was added. The reaction mixture was heated to 100° C. overnight, cooled to RT and diluted with brine (10 mL) and EtOAc (10 mL). The layers were separated and the aqueous layer was extracted with EtOAc (3×10 mL). The combined organic layers were dried over $MgSO_4$, filtered, and concentrated under reduced pressure. The crude reaction mixture was purified employing reverse-phase HPLC to provide the desired product as a clear oil. $^1$H NMR (400 MHz, $CDCl_3$): δ 7.50 (dd, J=8.7, 6.0 Hz, 1H), 6.90 (t, J=8.7 Hz, 1H), 6.12 (t, J=56.5 Hz, 1H), 4.80 (s, 2H), 4.48 (dd, J=5.6, 4.4 Hz, 2H), 4.09 (t, J=5.0 Hz, 2H), 1.37 (t, J=1.3 Hz, 6H). LC-MS: m/z=313.27 $[M+H]^+$.

The compounds of Table 1 can be prepared according to the methods described herein.

TABLE 1

| Ex | Name | Structure | ¹H NMR | MS (M + H)⁺ | Method |
|----|------|-----------|--------|-------------|--------|
| 3 | 2,2-dimethyl-1-(1,3,4,5-tetrahydro-2-benzazepin-2-yl)propan-1-one | 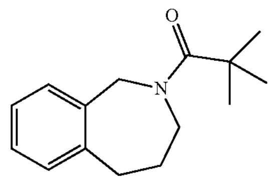 [SMILES: CC(C)(C)C(=O)N1CCCc2ccccc2C1] | ¹H-NMR (400 MHz, CDCl₃): δ 7.42 (dd, J = 4.8, 3.9 Hz, 1H), 7.19-7.13 (m, 3H), 4.58-4.52 (m, 2H), 3.96-3.91 (m, 2H), 3.02-2.99 (m, 2H),1.90-1.85 (m, 2H),1.27-1.25 (m, 9H) | 233.5 | D |
| 4 | 2,2-dimethyl-1-(1,3,4,5-tetrahydro-2-benzazepin-2-yl)butan-1-one | 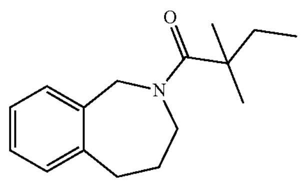 [SMILES: CCC(C)(C)C(=O)N1CCCc2ccccc2C1] | ¹H NMR (400 MHz, CDCl₃): δ 7.41 (dd, J = 5.5, 3.1 Hz, 1H), 7.19-7.11 (m, 3H), 4.56 (s, 2H), 3.92 (s, 2H), 2.99 (dd, J = 7.1, 4.4 Hz, 2H), 1.85 (dt, J = 11.1, 5.6 Hz, 2H), 1.62 (q, J = 7.5 Hz, 2H), 1.22 (s, 6H), 0.77 (t, J = 7.5 Hz, 3H) | 246.5 | A |
| 5 | 3,3-difluoro-2,2-dimethyl-1-(1,3,4,5-tetrahydro-2-benzazepin-2-yl)propan-1-one | 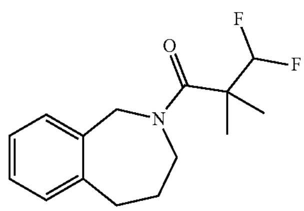 [SMILES: CC(C)(C(=O)N1CCCc2ccccc2C1)C(F)F] | ¹H-NMR (400 MHz, CDCl₃): δ 7.41-7.39 (m, 1H), 7.21-7.15 (m, 3H), 6.16 (t, J = 56.5 Hz, 1H), 4.57 (d, J = 0.3 Hz, 2H), 3.89 (d, J = 0.6 Hz, 2H), 3.01 (dd, J = 7.1, 4.4 Hz, 2H), 1.93-1.87 (m, 2H), 1.35 (d, J = 2.7 Hz, 6H) | 268.5 | C |
| 6 | 1-(3,5-dihydro-2H-1,4-benzoxazepin-4-yl)-2,2-dimethyl-butan-1-one | 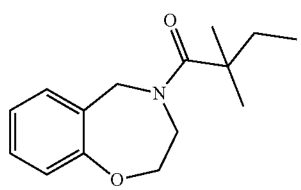 [SMILES: CCC(C)(C)C(=O)N1CCOc2ccccc2C1] | ¹H-NMR (400 MHz, CDCl₃): δ 7.35 (dd, J = 7.5, 1.5 Hz, 1H), 7.22-7.18 (m, 1H), 7.03 (qd, J = 7.4, 1.3 Hz, 2H), 4.66 (s, 2H), 4.17-4.14 (m, 2H), 4.06-4.03 (m, 2H), 1.63 (dq, J = 11.9, 7.5 Hz, 2H), 1.24 (s, 6H), 0.80 (t, J = 7.5 Hz, 3H) | 248.5 | A |
| 7 | 1-(3,5-dihydro-2H-1,4-benzoxazepin-4-yl)-3,3-difluoro-2,2-dimethyl-propan-1-one | 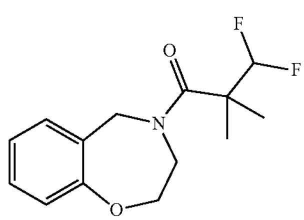 [SMILES: CC(C)(C(=O)N1CCOc2ccccc2C1)C(F)F] | ¹H-NMR (400 MHz, CDCl₃): δ 7.33 (dd, J = 7.4, 1.4 Hz, 1H), 7.25-7.21 (m, 1H), 7.08-7.02 (m, 2H), 6.15 (t, J = 56.5 Hz, 1H), 4.66 (s, 2H), 4.19-4.17 (m, 2H), 4.01 (dd, J = 5.4, 3.6 Hz, 2H), 1.38 (d, J = 1.3 Hz, 6H) | 270.5 | C |
| 8 | 3,5-dihydro-2H-1,4-benzoxazepin-4-yl-[1-(5-fluoropyrimidin-2-yl)-4-piperidyl]methanone | 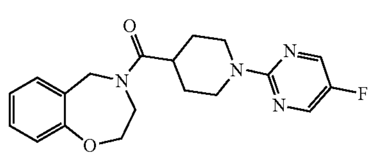 [SMILES: O=C(C1CCN(c2ncc(F)cn2)CC1)N1CCOc2ccccc2C1] | ¹H NMR (400 MHz, CDCl₃): δ 8.22-8.18 (m, 2H), 7.38-7.19 (m, 2H), 7.12-7.02 (m, 2H), 4.75-4.63 (m, 4H), 4.20-3.93 (m, 4H), 3.01-2.66 (m, 3H), 1.85-1.66 (m, 4H) | 357.9 | W |

TABLE 1-continued

| Ex | Name | Structure | ¹H NMR | MS (M + H)⁺ | Method |
|---|---|---|---|---|---|
| 9 | 3,5-dihydro-2H-1,4-benzoxazepin-4-yl-[1-(5-fluoropyrimidin-2-yl)-4-methyl-4-piperidyl]methanone | 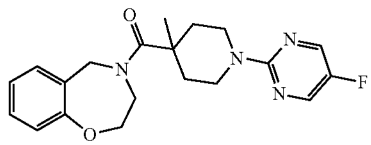 [SMILES: CC1(C(=O)N2CCOc3ccccc3C2)CCN(c2ncc(F)cn2)CC1] | ¹H NMR (400 MHz, CDCl₃): δ 8.18 (d, J = 0.6 Hz, 2H), 7.36-7.34 (m, 1H), 7.24-7.20 (m, 1H), 7.08-7.01 (m, 2H), 4.68 (s, 2H), 4.19-4.17 (m, 2H), 4.08-3.99 (m, 4H), 3.50-3.43 (m, 2H), 2.27-2.22 (m, 2H), 1.54 (ddd, J = 13.7, 9.7, 3.9 Hz, 2H), 1.33 (s, 3H) | 371.7 | W |
| 10 | 1-(7-chloro-2,3-dihydrobenzo[f][1,4]oxazepin-4(5H)-yl)-3,3-difluoro-2,2-dimethylpropan-1-one | 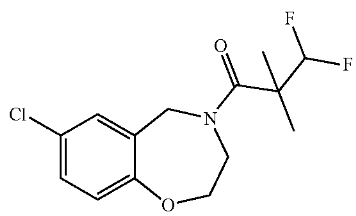 [SMILES: CC(C)(C(=O)N1CCOc2ccc(Cl)cc2C1)C(F)F] | ¹H N MR (400 MHz, CDCl₃): δ 7.32 (d, J = 2.6 Hz, 1H), 7.18 (dd, J = 8.5, 2.6 Hz, 1H), 6.96 (d, J = 8.5 Hz, 1H), 6.13 (t, J = 56.5 Hz, 1H), 4.59 (s, 2H), 4.17-4.15 (m, 2H), 4.01 (dd, J = 5.4, 3.6 Hz, 2H), 1.36 (t, J = 1.3 Hz, 6H). | 304.10 | A |
| 11 | 3,3-difluoro-2,2-dimethyl-1-(7-methyl-2,3-dihydrobenzo[f][1,4]oxazepin-4(5H)-yl)propan-1-one | 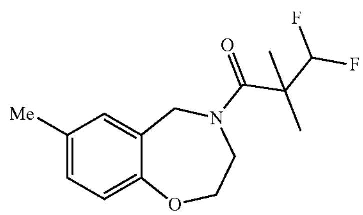 [SMILES: Cc1ccc2c(c1)CN(C(=O)C(C)(C)C(F)F)CCO2] | ¹H N MR (400 MHz, CDCl₃): δ 7.14-7.14 (m, 1H), 7.02 (ddd, J = 8.1, 2.2, 0.6 Hz, 1H), 6.92 (d, J = 8.1 Hz, 1H), 6.16 (t, J = 56.5 Hz, 1H), 4.61 (s, 2H), 4.15-4.13 (m, 2H), 4.00 (dd, J = 5.4, 3.5 Hz, 2H), 2.31 (s, 3H), 1.37 (t, J = 1.3 Hz, 6H) | 284.5 | A |
| 12 | 3,3-difluoro-1-(8-methoxy-3,5-dihydro-2H-14-benzoxazepin-4-yl)-2,2-dimethyl-propan-1-one | 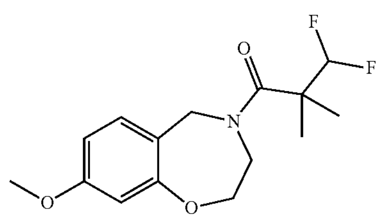 [SMILES: COc1ccc2c(c1)OCCN(C(=O)C(C)(C)C(F)F)C2] | ¹H-NMR (400 MHz, CDCl₃): δ 7.22-7.20 (m, 1H), 6.62-6.60 (m, 2H), 6.16 (t, J = 56.6 Hz, 1H), 4.60 (s, 2H), 4.19-4.17 (m, 2H), 3.99 (dd, J = 5.4, 3.7 Hz, 2H), 3.80 (s, 3H), 1.37 (t, J = 1.3 Hz, 6H) | 300.5 | C |
| 13 | 3,3-difluoro-1-(9-fluoro-2,3-dihydrobenzo[f][1,4]oxazepin-4(5H)-yl)-2,2-dimethylpropan-1-one | 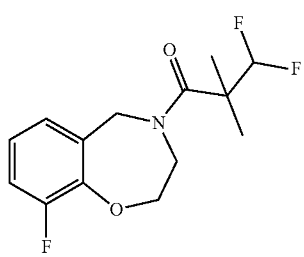 [SMILES: CC(C)(C(=O)N1CCOc2c(F)cccc2C1)C(F)F] | ¹H N MR (400 MHz, CDCl₃): δ 7.12-7.10 (m, 1H), 7.07-6.97 (m, 2H), 6.14 (t, J = 56.5 Hz, 1H), 4.67 (s, 2H), 4.25 (dd, J = 5.3, 3.8 Hz, 2H), 4.05 (t, J = 4.5 Hz, 2H), 1.37 (t, J = 1.3 Hz, 6H) | 288.1 | A |
| 14 | 4-(9-fluoro-3,5-dihydro-2H-1,4-benzoxazepin-4-yl)-3,3-dimethyl-4-oxo-butanenitrile | 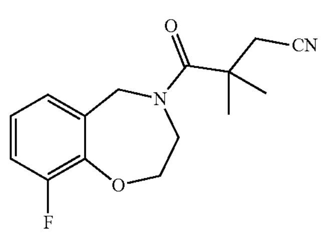 [SMILES: CC(C)(CC#N)C(=O)N1CCOc2c(F)cccc2C1] | ¹H-NMR (400 MHz, CDCl₃): δ 7.11-6.98 (m, 3H), 4.66 (s, 2H), 4.24 (dd, J = 5.3, 3.8 Hz, 2H), 4.08-4.05 (m, 2H), 2.02 (s, 2H), 1.48-1.46 (m, 6H) | 277.4 | C |

TABLE 1-continued

| Ex | Name | Structure | ¹H NMR | MS (M + H)⁺ | Method |
|---|---|---|---|---|---|
| 15 | 2-cyclopropyl-1-(9-fluoro-3,5-dihydro-2H-1,4-benzoxazepin-4-yl)-2-methyl-propan-1-one | 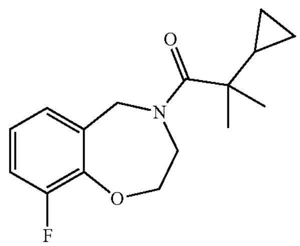 [SMILES: CC(C)(C(=O)N1CCOc2c(F)cccc2C1)C1CC1] | ¹H-NMR (400 MHz, CDCl₃): δ 7.16-7.14 (m, 1H), 7.04-6.95 (m, 2H), 4.70 (s, 2H), 4.24-4.21 (m, 4H), 1.09 (s, 6H), 0.98 (tt, J = 8.5, 5.8 Hz, 1H), 0.58-0.53 (m, 2H), 0.44-0.40 (m, 2H) | 278.5 | C |
| 16 | 4,4-difluoro-1-(9-fluoro-3,5-dihydro-2H-1,4-benzoxazepin-4-yl)-2,2-dimethyl-butan-1-one | 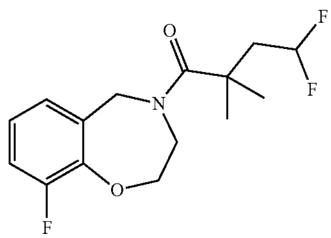 [SMILES: CC(C)(CC(F)F)C(=O)N1CCOc2c(F)cccc2C1] | ¹H-NMR (400 MHz, CDCl₃): δ 7.13-7.11 (m, 1H), 7.06-6.97 (m, 2H), 6.00 (tt, J = 56.8, 4.5 Hz, 1H), 4.67 (s, 2H), 4.26-4.24 (m, 2H), 4.08 (dd, J = 5.4, 3.6 Hz, 2H), 2.15 (td, J = 16.9, 4.5 Hz, 2H), 1.37 (d, J = 1.7 Hz, 6H) | 302.5 | C |
| 17 | 3,3,3-trifluoro-1-(9-fluoro-3,5-dihydro-2H-1,4-benzoxazepin-4-yl)-2-methyl-propan-1-one | 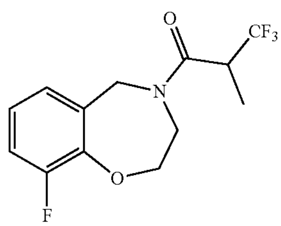 [SMILES: CC(C(=O)N1CCOc2c(F)cccc2C1)C(F)(F)F] | | 292.4 | C |
| 18 | 3,3-difluoro-1-(9-fluoro-3,5-dihydro-2H-1,4-benzoxazepin-4-yl)-2,2-dimethyl-butan-1-one | 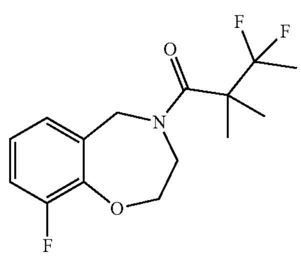 [SMILES: CC(F)(F)C(C)(C)C(=O)N1CCOc2c(F)cccc2C1] | ¹H-NMR (400 MHz, CDCl₃): δ 7.14 (d, J = 7.2 Hz, 1H), 7.05-6.96 (m, 2H), 4.68 (s, 2H), 4.21-4.18 (m 2H), 4.13 (dd, J = 5.6, 3.2 Hz, 2H), 1.58 (t, J = 19.3 Hz, 3H), 1.43 (d, J = 0.7 Hz, 6H) | 302.4 | C |
| 19 | 2,2-dicyclopropyl-1-(9-fluoro-3,5-dihydro-2H-1,4-benzoxazepin-4-yl)ethanone | 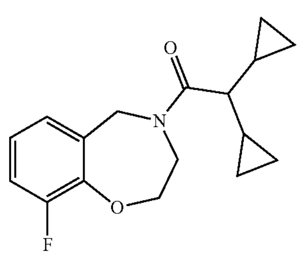 [SMILES: O=C(C(C1CC1)C1CC1)N1CCOc2c(F)cccc2C1] | | 290.4 | C |
| 20 | 3,3-difluoro-1-(6-fluoro-2,3-dihydrobenzo[f][1,4]oxazepin-4(5H)-yl)-2,2-dimethylpropan-1-one | 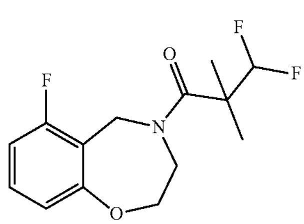 [SMILES: CC(C)(C(=O)N1CCOc2cccc(F)c2C1)C(F)F] | ¹H NMR (400 MHz, CDCl₃): δ 7.16 (td, J = 8.3, 6.5 Hz, 1H), 6.83-6.79 (m, 2H), 6.17 (t, J = 56.6 Hz, 1H), 4.80 (s, 2H), 4.26 (dd, J = 5.4, 4.3 Hz, 2H), 4.01 (t, J = 4.9 Hz, 2H), 1.37 (d, J = 1.4 Hz, 6H) | 288.5 | A |

TABLE 1-continued

| Ex | Name | Structure | ¹H NMR | MS (M + H)⁺ | Method |
|----|------|-----------|--------|-------------|--------|
| 21 | 3,3-difluoro-2,2-dimethyl-1-(3-methyl-2,3-dihydrobenzo[f][1,4]oxazepin-4(5H)-yl)propan-1-one | 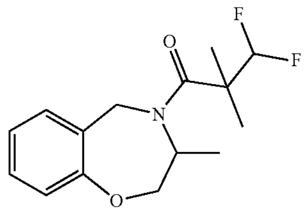 [SMILES: CC1COc2ccccc2CN1C(=O)C(C)(C)C(F)F] | ¹H N MR (400 MHz, CDCl₃): δ 7.20-7.15 (m, 2H), 7.00 (td, J = 7.4, 1.2 Hz, 1H), 6.92 (dd, J = 8.2, 1.1 Hz, 1H), 6.32-6.04 (m, 1H), 4.86-4.40 (m, 3H), 4.15 (qd, J = 13.9, 7.1 Hz, 2H), 1.36-1.31 (m, 9H) | 284.4 | A |
| 22 | 4-(3,3-difluoro-2,2-dimethyl-propanoyl)-7-fluoro-3,5-dihydro-2H-1,4-benzoxazepine-9-carbonitrile | 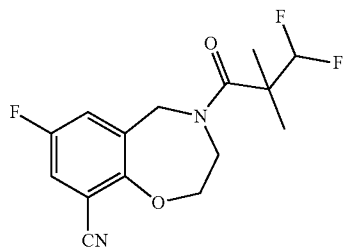 [SMILES: CC(C)(C(=O)N1CCOc2c(C#N)cc(F)cc2C1)C(F)F] | ¹H-NMR (400 MHz, CDCl₃): δ 7.33 (dd, J = 7.9, 3.1 Hz, 1H), 7.20 (dd, J = 7.3, 3.1 Hz, 1H), 6.08 (t, J = 56.4 Hz, 1H), 4.60 (s, 2H), 4.31 (dd, J = 5.3, 4.0 Hz, 2H), 4.09 (t, J = 4.6 Hz, 2H), 1.36 (t, J = 1.3 Hz, 6H) | 313.1 | B |
| 23 | 4-(3,3-difluoro-2,2-dimethyl-propanoyl)-3,5-dihydro-2H-1,4-benzoxazepine-9-carbonitrile | 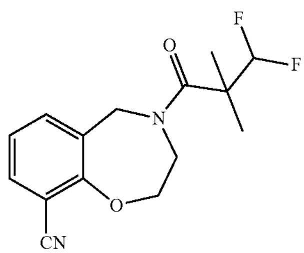 [SMILES: CC(C)(C(=O)N1CCOc2c(C#N)cccc2C1)C(F)F] | ¹H-NMR (400 MHz, CDCl₃): δ 7.33 (dd, J = 7.6, 1.6 Hz, 1H), 7.28 (dd, J = 7.8, 1.7 Hz, 1H), 6.90 (t, J = 7.7 Hz, 1H), 5.88 (t, J = 56.5 Hz, 1H), 4.44 (s, 2H), 4.15-4.13 (m, 2H), 3.86 (dd, J = 5.4, 3.9 Hz, 2H), 1.13 (t, J = 1.3 Hz, 6H) | 295.3 | B |
| 24 | 4-[1-(5-fluoropyrimidin-2-yl)-4-methyl-piperidine-4-carbonyl]-3,5-dihydro-2H-1,4-benzoxazepine-9-carbonitrile | 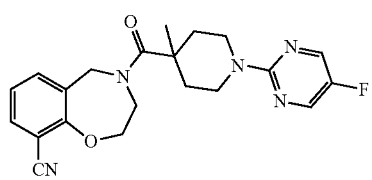 [SMILES: CC1(C(=O)N2CCOc3c(C#N)cccc3C2)CCN(c2ncc(F)cn2)CC1] | ¹H N MR (400 MHz, CDCl₃): δ 8.18 (d, J = 0.5 Hz, 2H), 7.59 (dd, J = 7.6, 1.5 Hz, 1H), 7.50 (dd, J = 7.8, 1.7 Hz, 1H), 7.13 (t, J = 7.7 Hz, 1H), 4.67 (s, 2H), 4.35 (dd, J = 5.3, 4.0 Hz, 2H), 4.13 (t, J = 4.6 Hz, 2H), 4.02 (ddd, J = 13.6, 6.0, 3.9 Hz, 2H), 3.48 (ddd, J = 13.3, 9.6, 3.3 Hz, 2H), 2.23-2.17 (m, 2H), 1.55 (ddd, J = 13.7, 9.6, 4.0 Hz, 2H), 1.32 (s, 3H) | 396.7 | B |
| 25 | 4-(3-cyano-2,2-dimethyl-propanoyl)-3,5-dihydro-2H-1,4-benzoxazepine-9-carbonitrile | 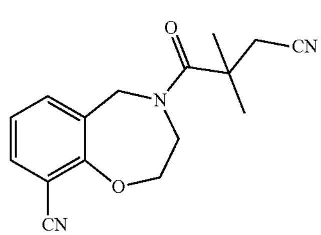 [SMILES: CC(C)(CC#N)C(=O)N1CCOc2c(C#N)cccc2C1] | ¹H NMR (400 MHz, CDCl₃): δ 7.58 (dd, J = 7.6, 1.6 Hz, 1H), 7.52 (dd, J = 7.8, 1.7 Hz, 1H), 7.14 (t, J = 7.7 Hz, 1H), 4.68 (s, 2H), 4.37 (dd, J = 5.4, 4.0 Hz, 2H), 4.11 (t, J = 4.7 Hz, 2H), 2.65 (s, 2H), 1.47 (s, 6H) | 284.3 | B |

TABLE 1-continued

| Ex | Name | Structure | ¹H NMR | MS (M + H)⁺ | Method |
|---|---|---|---|---|---|
| 26 | 4-(2-cyclopropyl-2-methyl-propanoyl)-3,5-dihydro-2H-1,4-benzoxazepine-9-carbonitrile | 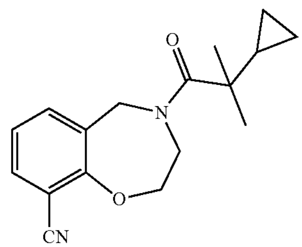 [SMILES: CC(C)(C(=O)N1CCOc2c(C#N)cccc2C1)C1CC1] | ¹H N MR (400 MHz, CDCl₃): δ 7.60 (dd, J = 7.6, 1.7 Hz, 1H), 7.49 (dd, J = 7.8, 1.7 Hz, 1H), 7.12 (t, J = 7.7 Hz, 1H), 4.67 (s, 2H), 4.33-4.31 (m, 2H), 4.26 (dd, J = 5.6, 3.1 Hz, 2H), 1.08 (s, 6H), 0.96 (tt, J = 8.5, 5.7 Hz, 1H), 0.59-0.54 (m, 2H), 0.43-0.39 (m, 2H) | 285.4 | B |
| 27 | 4-(3,3-difluoro-2,2-dimethyl-propanoyl)-3,5-dihydro-2H-1,4-benzoxazepine-6-carbonitrile | 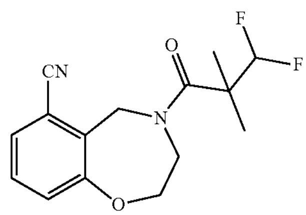 [SMILES: CC(C)(C(=O)N1CCOc2cccc(C#N)c2C1)C(F)F] | ¹H N MR (400 MHz, CDCl₃): δ 7.35 (dd, J = 7.6, 1.4 Hz, 1H), 7.26 (t, J = 7.9 Hz, 1H), 7.19 (dd, J = 8.2, 1.4 Hz, 1H), 6.10 (t, J = 56.5 Hz, 1H), 4.87 (s, 2H), 4.25-4.23 (m, 2H), 4.02 (dd, J = 6.5, 3.4 Hz, 2H), 1.33 (t, J = 1.3 Hz, 6H) | 295.5 | B |
| 28 | 4-(3,3-difluoro-2,2-dimethyl-propanoyl)-3,5-dihydro-2H-1,4-benzoxazepine-8-carbonitrile | 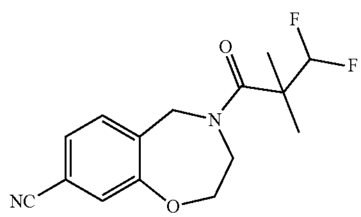 [SMILES: CC(C)(C(=O)N1CCOc2cc(C#N)ccc2C1)C(F)F] | ¹H-NMR (400 MHz, CDCl₃): δ 7.46 (d, J = 7.8 Hz, 1H), 7.36 (dd, J = 7.8, 1.6 Hz, 1H), 7.31 (d, J = 1.5 Hz, 1H), 6.10 (t, J = 56.4 Hz, 1H), 4.66 (s, 2H), 4.24-4.21 (m, 2H), 4.05 (t, J = 4.6 Hz, 2H), 1.36 (d, J = 2.6 Hz, 6H) | 295.3 | C |
| 29 | 4-(3,3-difluoro-2,2-dimethyl-propanoyl)-3,5-dihydro-2H-pyrido[3,4-f][1,4]oxazepine-9-carbonitrile | 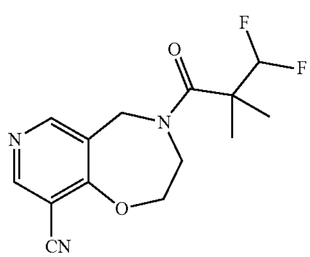 [SMILES: CC(C)(C(=O)N1CCOc2c(C#N)cncc2C1)C(F)F] | ¹H-NMR (400 MHz, CDCl₃): δ 8.67 (s, 1H), 8.61 (s, 1H), 6.11 (t, J = 56.5 Hz, 1H), 4.80 (s, 2H), 4.62-4.60 (m, 2H), 4.13 (t, J = 5.0 Hz, 2H), 1.39 (t, J = 1.3 Hz, 6H) | 296.3 | I |
| 30 | 4-(2-cyclopropyl-2-methyl-propanoyl)-3,5-dihydro-2H-pyrido[3,4-f][1,4]oxazepine-9-carbonitrile | 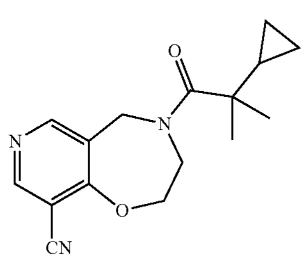 [SMILES: CC(C)(C(=O)N1CCOc2c(C#N)cncc2C1)C1CC1] | ¹H-NMR (400 MHz, DMSO-d₆): δ 8.73 (s, 1H), 8.64 (s, 1H), 4.85 (d, J = 3.6 Hz, 2H), 4.71 (dd, J = 5.6, 4.7 Hz, 2H), 4.16-4.11 (m, 2H), 1.03 (s, 1H), 1.01-0.95 (m, 6H), 0.45-0.41 (m, 2H), 0.34 (dd, J = 6.0, 4.5 Hz, 2H) | 286.5 | C |
| 31 | 4-(3-cyano-2,2-dimethyl-propanoyl)-3,5-dihydro-2H-pyrido[3,4-f][1,4]oxazepine-9-carbonitrile | 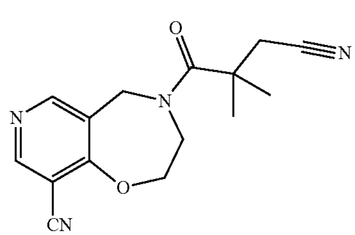 [SMILES: CC(C)(CC#N)C(=O)N1CCOc2c(C#N)cncc2C1] | ¹H-NMR (400 MHz, DMSO-d₆): δ 8.74 (s, 1H), 8.70 (d, J = 0.3 Hz, 1H), 4.89-4.85 (m, 2H), 4.73-4.71 (m, 2H), 4.06-4.03 (m, 2H), 2.68 (s, 2H), 1.33 (s, 6H) | 285.2 | C |

TABLE 1-continued

| Ex | Name | Structure | ¹H NMR | MS (M + H)⁺ | Method |
|---|---|---|---|---|---|
| 32 | 1-(7-fluoro-2,3,4,5-tetrahydro-1,4-benzoxazepin-4-yl)-2,2-dimethylbutan-1-one | 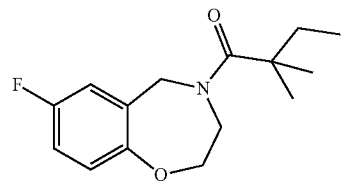 [SMILES: CCC(C)(C)C(=O)N1CCOc2ccc(F)cc2C1] | ¹H NMR (400 MHz, CDCl₃) δ 7.08 (dd, J = 8.3, 3.0 Hz, 1H), 6.97 (dd, J = 8.8, 5.0 Hz, 1H), 6.91-6.84 (m, 1H), 4.59 (s, 2H), 4.13-4.08 (m, 2H), 4.07-4.02 (m, 2H), 1.64 (q, J = 7.4 Hz, 2H), 1.24 (s, 6H), 0.82 (t, J = 7.5 Hz, 3H) | 266.2 | A |
| 33 | 3,3-difluoro-1-(7-fluoro-2,3,4,5-tetrahydro-1,4-benzoxazepin-4-yl)-2,2-dimethylpropan-1-one | 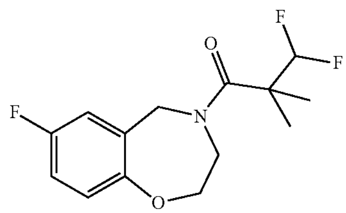 [SMILES: CC(C)(C(=O)N1CCOc2ccc(F)cc2C1)C(F)F] | ¹H NMR (400 MHz, CDCl₃) δ 7.06 (dd, J = 8.3, 3.0 Hz, 1H), 7.01-6.96 (m, 1H), 6.93-6.86 (m, 1H), 6.13 (t, J = 57.0 Hz, 1H), 4.59 (s, 2H), 4.16-4.11 (m, 2H), 4.05-3.98 (m, 2H), 1.37 (s, 6H) | 288.2 | A |
| 34 | 1-(2,3-dihydropyrido[3,2-f][1,4]oxazepin-4(5H)-yl)-3,3-difluoro-2,2-dimethylpropan-1-one | 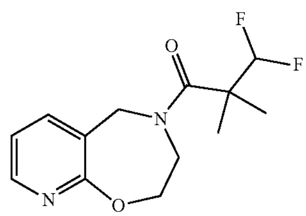 [SMILES: CC(C)(C(=O)N1CCOc2ncccc2C1)C(F)F] | ¹H NMR (300 MHz, DMSO-d₆) δ 8.08 (dd, J = 4.8, 1.8 Hz, 1H), 7.76 (d, J = 7.2 Hz, 1H), 7.06 (dd, J = 7.5, 4.8 Hz, 1H), 6.24 (t, J = 56.4 Hz, 1H), 4.67 (s, 2H), 4.38 (t, J = 4.8 Hz, 2H), 3.97 (t, J = 5.1 Hz, 2H), 1.25 (s, 6H) | 271.0 | B |
| 35 | 1-(2,3-dihydropyrido[3,4-f][1,4]oxazepin-4(5H)-yl)-3,3-difluoro-2,2-dimethylpropan-1-one | 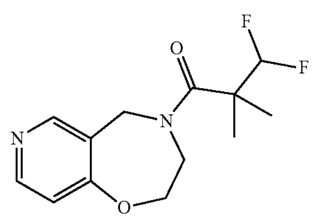 [SMILES: CC(C)(C(=O)N1CCOc2ccncc2C1)C(F)F] | ¹H NMR (300 MHz, DMSO-d₆) δ 8.41 (s, 1H), 8.26 (d, J = 5.7 Hz, 1H), 6.88 (d, J = 5.4 Hz, 1H), 6.24 (t, J = 56.7 Hz, 1H), 4.76 (s, 2H), 4.50-4.41 (m, 2H), 4.00-3.93 (m, 2H), 1.25 (s, 6H) | 271.1 | B |
| 36 | 3,3-difluoro-2,2-dimethyl-1-(2-methyl-2,3-dihydrobenzo[f][1,4]oxazepin-4(5H)-yl)propan-1-one | 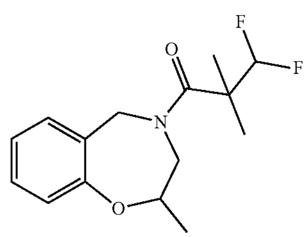 [SMILES: CC1CN(C(=O)C(C)(C)C(F)F)Cc2ccccc2O1] | ¹H-NMR (400 MHz, CDCl₃): δ 7.32-7.29 (m, 1H), 7.23 (td, J = 7.7, 1.7 Hz, 1H), 7.08-7.01 (m, 2H), 6.15 (t, J = 56.5 Hz, 1H), 4.96 (dd, J = 14.6, 0.8 Hz, 1H) 4.33-4.30 (m, 1H), 4.14 (dt, J = 14.4, 1.6 Hz, 1H), 4.07-4.00 (m, 1H), 3.53 (dd, J = 14.4, 9.5 Hz, 1H), 1.43 (d, J = 6.4 Hz, 3H), 1.40 (t, J = 1.3 Hz, 3H), 1.32 (s, 3H). | 284.2 | A |
| 37 | 1-(9-bromo-7-fluoro-3,5-dihydro-2H-1,4-benzoxazepin-4-yl)-3,3-difluoro-2,2-dimethyl-propan-1-one | 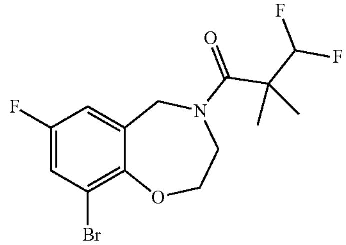 [SMILES: CC(C)(C(=O)N1CCOc2c(Br)cc(F)cc2C1)C(F)F] | | 365.97 | B |

TABLE 1-continued

| Ex | Name | Structure | ¹H NMR | MS (M + H)⁺ | Method |
|---|---|---|---|---|---|
| 38 | 3,3-difluoro-2,2-dimethyl-1-(1,2,4,5-tetrahydro-3,2-benzoxazepin-2-yl)propan-1-one | 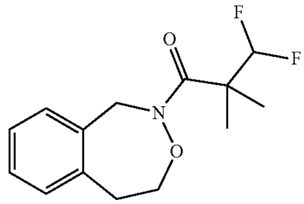 [SMILES: CC(C)(C(=O)N1Cc2ccccc2CCO1)C(F)F] | ¹H N MR (400 MHz, CDCl₃) δ 7.35-7.15 (m, 4H), 6.25 (t, J = 57.2 Hz, 1H), 4.96 (s, 2H), 4.22-4.16 (m, 2H), 3.27-3.21 (m, 2H), 1.35 (t, J = 1.3 Hz, 6H) | 270.2 | D |
| 39 | 2-[1-(5-fluoropyrimidin-2-yl)piperidine-4-carbonyl]-1,2,4,5-tetrahydro-3,2-benzoxazepine | 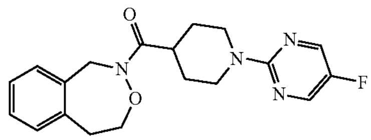 [SMILES: O=C(C1CCN(c2ncc(F)cn2)CC1)N1Cc2ccccc2CCO1] | ¹H NMR (400 MHz, CDCl₃) δ 8.20 (s, 2H), 7.35-7.30 (m, 1H), 7.27-7.15 (m, 3H), 4.95 (s, 2H), 4.69 (td, J = 3.0, 13.3 Hz, 2H), 4.24-4.18 (m, 2H), 3.27-3.22 (m, 2H), 3.03-2.91 (m, 3H), 1.87-1.69 (m, 4H) | 357.3 | B |
| 40 | 4-[1-(5-fluoropyrimidin-2-yl)-4-methyl-piperidine-4-carbonyl]-3,5-dihydro-2H-pyrido[3,4-f][1,4]oxazepine-9-carbonitrile | 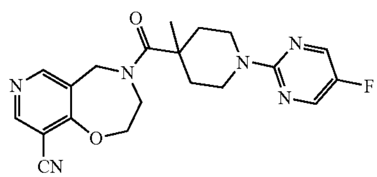 [SMILES: CC1(C(=O)N2CCOc3c(C#N)cncc3C2)CCN(c2ncc(F)cn2)CC1] | ¹H-NMR (400 MHz, CDCl₃): δ 8.66 (s, 1H), 8.63 (s, 1H), 8.19 (d, J = 0.5 Hz, 2H), 4.80 (s, 2H), 4.59 (dd, J = 5.6, 4.4 Hz, 2H), 4.17 (t, J = 5.0 Hz, 2H), 4.03 (ddd, J = 13.7, 6.1, 3.9 Hz, 2H), 3.48 (ddd, J = 13.4, 9.7, 3.4 Hz, 2H), 2.25-2.19 (m, 2H), 1.59 (ddd, J = 13.7, 9.6, 3.9 Hz, 2H), 1.36 (s, 3H) | 397.3 | C |
| 41 | 4-(4-methyltetrahydropyran-4-carbonyl)-3,5-dihydro-2H-pyrido[3,4-f][1,4]oxazepine-9-carbonitrile | 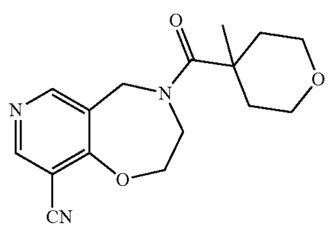 [SMILES: CC1(C(=O)N2CCOc3c(C#N)cncc3C2)CCOCC1] | ¹H-NMR (400 MHz, CDCl₃): δ 8.69-8.66 (m, 2H), 4.82 (d, J = 1.0 Hz, 2H), 4.65-4.61 (m, 2H), 4.18-4.15 (m, 2H), 3.78-3.73 (m, 2H), 3.62-3.56 (m, 2H), 2.16-2.10 (m, 2H), 1.63-1.57 (m, 2H), 1.35 (s, 3H) | 302.2 | C |
| 42 | 4-(3-methyltetrahydrofuran-3-carbonyl)-3,5-dihydro-2H-pyrido[3,4-f][1,4]oxazepine-9-carbonitrile | 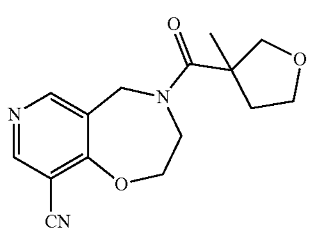 [SMILES: CC1(C(=O)N2CCOc3c(C#N)cncc3C2)CCOC1] | ¹H-NMR (400 MHz, CDCl₃): δ 8.67 (s, 1H), 8.61 (s, 1H), 4.81 (s, 2H), 4.64-4.61 (m, 2H), 4.10-4.04 (m, 3H), 3.97-3.88 (m, 2H), 3.69 (d, J = 9.0 Hz, 1H), 2.38-2.31 (m, 1H), 1.91 (ddd, J = 12.3, 7.0, 5.2 Hz, 1H), 1.41 (s, 3H) | 288.4 | C |
| 43 | 4-(2-methoxy-2-methyl-propanoyl)-3,5-dihydro-2H-pyrido[3,4-f][1,4]oxazepine-9-carbonitrile | 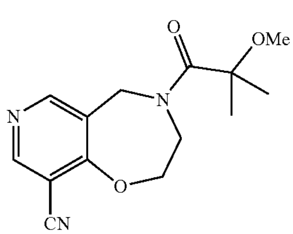 [SMILES: COC(C)(C)C(=O)N1CCOc2c(C#N)cncc2C1] | ¹H-NMR (400 MHz, CDCl₃): δ 8.68-8.54 (m, 2H), 5.27-5.19 (m, 1H), 4.83-4.75 (m, 1H), 4.64-4.48 (m, 3H), 4.13-4.05 (m, 1H), 3.26-2.96 (m, 3H), 1.59-1.46 (m, 6H) | 276.5 | C |

TABLE 1-continued

| Ex | Name | Structure | ¹H NMR | MS (M + H)⁺ | Method |
|---|---|---|---|---|---|
| 44 | 4-(bicyclo[1.1.1]pentane-3-carbonyl)-3,5-dihydro-2H-pyrido[3,4-f][1,4]oxazepine-9-carbonitrile | 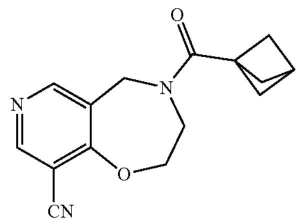 [SMILES: N#Cc1cncc2c1OCCN(C(=O)C13CC(C1)C3)C2] | ¹H-NMR (400 MHz, CDCl₃): δ 8.68-8.53 (m, 2H), 4.94-4.75 (m, 2H), 4.60-4.53 (m, 2H), 4.15-4.02 (m, 2H), 2.54-2.52 (m, 1H), 2.19-2.16 (m, 6H) | 270.5 | C |
| 45 | 4-(3,3,3-trifluoro-2,2-dimethyl-propanoyl)-3,5-dihydro-2H-pyrido[3,4-f][1,4]oxazepine-9-carbonitrile | 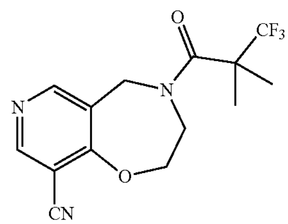 [SMILES: CC(C)(C(=O)N1CCOc2c(C#N)cncc2C1)C(F)(F)F] | ¹H-NMR (400 MHz, CDCl₃): δ 8.67 (s, 1H), 8.61 (s, 1H), 4.80 (s, 2H), 4.57-4.55 (m, 2H), 4.17-4.14 (m, 2H), 1.53 (d, J = 0.6 Hz, 6H) | 314.3 | C |
| 46 | 4-(1-cyclopropylcyclo-propanecarbonyl)-3,5-dihydro-2H-pyrido[3,4-f][1,4]oxazepine-9-carbonitrile | 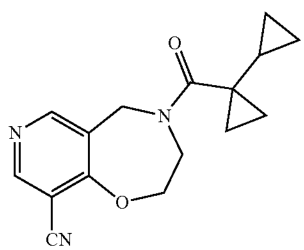 [SMILES: N#Cc1cncc2c1OCCN(C(=O)C1(C3CC3)CC1)C2] | ¹H-NMR (400 MHz, DMSO-d₆): δ 8.76-8.72 (m, 1H), 8.70-8.63 (m, 1H), 5.15-4.78 (m, 2H), 4.27-4.11 (m, 1H), 3.92-3.83 (m, 1H), 3.55-3.39 (m, 2H), 1.20-1.12 (m, 1H), 0.67-0.60 (m, 2H), 0.59-0.54 (m, 2H), 0.37-0.31 (m, 2H), 0.15-0.04 (m, 2H) | 284.2 | C |
| 47 | 4-(4,4,4-trifluoro-2,2-dimethyl-butanoyl)-3,5-dihydro-2H-pyrido[3,4-f][1,4]oxazepine-9-carbonitrile | 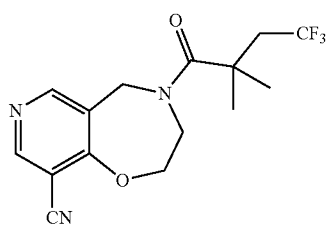 [SMILES: CC(C)(CC(F)(F)F)C(=O)N1CCOc2c(C#N)cncc2C1] | ¹H-NMR (400 MHz, DMSO-d₆): δ 8.72 (s, 1H), 8.67 (s, 1H), 4.86 (s, 2H), 4.72 (t, J = 5.2 Hz, 2H), 4.03-4.01 (m, 2H), 2.75-2.66 (m, 2H), 1.31-1.25 (m, 6H) | 328.5 | C |
| 48 | 4-[1-(trifluoromethyl)cyclo-propanecarbonyl]-3,5-dihydro-2H-pyrido[3,4-f][1,4]oxazepine-9-carbonitrile | 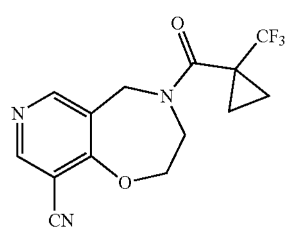 [SMILES: N#Cc1cncc2c1OCCN(C(=O)C1(C(F)(F)F)CC1)C2] | ¹H-NMR (400 MHz, DMSO-d₆): δ 8.75 (s, 1H), 8.69-8.68 (m, 1H), 5.09-4.80 (m, 2H), 4.77-4.74 (m, 2H), 4.16-3.93 (m, 2H), 1.37-1.34 (m, 2H), 1.16-1.11 (m, 2H) | 312.1 | C |
| 49 | 4-[1-(difluoromethyl)cyclo-butanecarbonyl]-3,5-dihydro-2H-pyrido[3,4-f][1,4]oxazepine-9-carbonitrile | 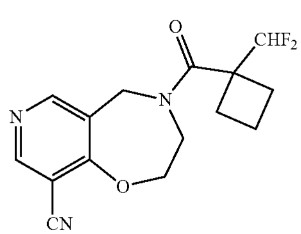 [SMILES: N#Cc1cncc2c1OCCN(C(=O)C1(C(F)F)CCC1)C2] | ¹H-NMR (400 MHz, DMSO-d₆): δ 8.76-8.74 (m, 1H), 8.66-8.64 (m, 1H), 6.52-6.23 (m, 1H), 4.81-4.73 (m, 3H), 4.69-4.66 (m, 1H), 3.87-3.84 (m, 1H), 3.83-3.80 (m, 1H), 2.49-2.25 (m, 4H), 1.92-1.85 (m, 1H), 1.72-1.60 (m, 1H) | 308.3 | C |

TABLE 1-continued

| Ex | Name | Structure | ¹H NMR | MS (M + H)⁺ | Method |
|---|---|---|---|---|---|
| 50 | 4-(2,2-difluoro-1-methyl-cyclo-propanecarbonyl)-3,5-dihydro-2H-pyrido[3,4-f][1,4]oxazepine-9-carbonitrile | 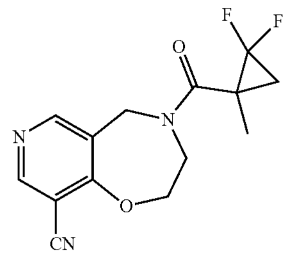 [SMILES: CC1(C(=O)N2CCOc3c(C#N)cncc3C2)CC1(F)F] | ¹H-NMR (400 MHz, DMSO-d₆): δ 8.78-8.72 (m, 1H), 8.68-8.63 (m, 1H), 4.95-4.68 (m, 4H), 4.03-3.86 (m, 2H), 1.82-1.70 (m, 1H), 1.66-1.33 (m, 3H) | 294.3 | C |
| 51 | 4-[2,2-dimethyl-3-(trifluoromethoxy)propanoyl]-3,5-dihydro-2H-pyrido[3,4-f][1,4]oxazepine-9-carbonitrile | 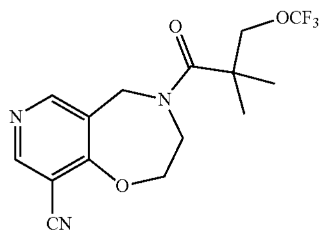 [SMILES: CC(C)(COC(F)(F)F)C(=O)N1CCOc2c(C#N)cncc2C1] | ¹H-NMR (400 MHz, CDCl₃): δ 8.66 (s, 1H), 8.61 (s, 1H), 4.80 (s, 2H), 4.60 (t, J = 5.0 Hz, 2H), 4.15 (t, J = 5.0 Hz, 2H), 4.02 (s, 2H), 1.39-1.36 (m, 6H) | 344.3 | C |
| 52 | (3R)-4-(3,3-difluoro-2,2-dimethyl-propanoyl)-3-methyl-3,5-dihydro-2H-pyrido[3,4-f][1,4]oxazepine-9-carbonitrile | 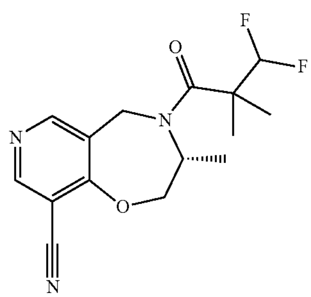 [SMILES: C[C@@H]1COc2c(C#N)cncc2CN1C(=O)C(C)(C)C(F)F] | ¹H-NMR (400 MHz, CDCl₃): δ 8.63 (s, 1H), 8.55 (s, 1H), 6.10 (dd, J = 57.3, 55.9 Hz, 1H), 4.97 (d, J = 16.5 Hz, 1H), 4.88-4.80 (m, 1H), 4.54 (dd, J = 13.3, 5.4 Hz, 1H), 4.49-4.41 (m, 1H), 4.34 (dd, J = 13.3, 11.1 Hz, 1H), 1.35 (d, J = 21.2 Hz, 9H) | 310.4 | D |
| 53 | 4-[1-(trifluoromethyl)cyclobutanecarbonyl]-3,5-dihydro-2H-pyrido[3,4-f][1,4]oxazepine-9-carbonitrile | 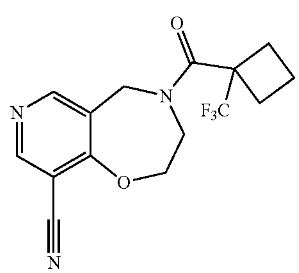 [SMILES: N#Cc1cncc2c1OCCN(C(=O)C1(C(F)(F)F)CCC1)C2] | ¹H-NMR (400 MHz; CDCl₃): δ 8.72-8.40 (m, 2H), 4.81-3.84 (m, 6H), 2.71-1.81 (m, 6H) | 326.5 | C |
| 54 | 4-(2,2-dimethylbutanoyl)-3,5-dihydro-2H-pyrido[3,4-f][1,4]oxazepine-9-carbonitrile | 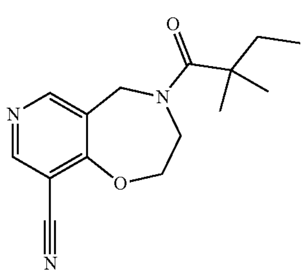 [SMILES: CCC(C)(C)C(=O)N1CCOc2c(C#N)cncc2C1] | ¹H-NMR (400 MHz; CDCl₃): δ 8.66 (s, 1H), 8.61 (s, 1H), 4.80 (s, 2H), 4.59 (t, J = 5.0 Hz, 2H), 4.15 (t, J = 5.0 Hz, 2H), 1.67 (q, J = 7.5 Hz, 2H), 1.26 (s, 6H), 0.81 (t, J = 7.5 Hz, 3H) | 274.18 | C |
| 55 | 3,3-difluoro-1-(9-fluoro-3,5-dihydro-2H-pyrido[3,4-f][1,4]oxazepin-4-yl)-2,2-dimethyl-propan-1-one | 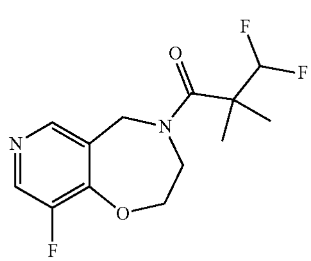 [SMILES: CC(C)(C(=O)N1CCOc2c(F)cncc2C1)C(F)F] | ¹H NMR (400 MHz, CDCl₃): δ 8.36 (d, J = 2.0 Hz, 1H), 8.28 (s, 1H), 6.27-5.95 (t, J = 56.0 Hz, 1H), 4.76 (s, 2H), 4.46-4.41 (m, 2H), 4.11-4.05 (m, 2H), 1.38 (s, 6H) | 289.3 | D |

TABLE 1-continued

| Ex | Name | Structure | ¹H NMR | MS (M + H)⁺ | Method |
|---|---|---|---|---|---|
| 56 | 4-(2-cyclopropyl-3,3-difluoro-2-methyl-propanoyl)-3,5-dihydro-2H-pyrido[3,4-f][1,4]oxazepine-9-carbonitrile | 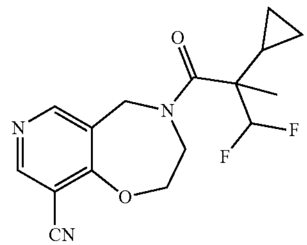 [SMILES: CC(C(=O)N1CCOc2c(C#N)cncc2C1)(C(F)F)C1CC1] | | 322.2 | C |
| 57 | 4-(2-(difluoromethyl)-2-methylbutanoyl)-2,3,4,5-tetrahydropyrido[3,4-f][1,4]oxazepine-9-carbonitrile | 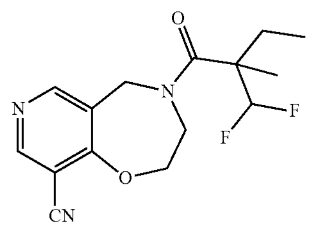 [SMILES: CCC(C)(C(=O)N1CCOc2c(C#N)cncc2C1)C(F)F] | | 310.3 | D |
| 58 | 4-(3-cyclopropyl-2,2-dimethyl-propanoyl)-3,5-dihydro-2H-pyrido[3,4-f][1,4]oxazepine-9-carbonitrile | 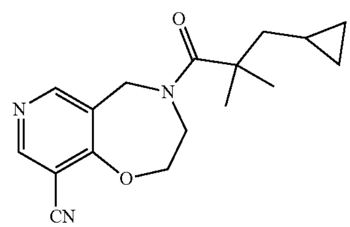 [SMILES: CC(C)(CC1CC1)C(=O)N1CCOc2c(C#N)cncc2C1] | | 300.4 | D |
| 59 | 8-chloro-4-(3,3-difluoro-2,2-dimethyl-propanoyl)-3,5-dihydro-2H-pyrido[3,4-f][1,4]oxazepine-9-carbonitrile | 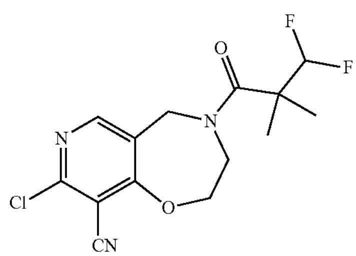 [SMILES: CC(C)(C(=O)N1CCOc2c(cnc(Cl)c2C#N)C1)C(F)F] | | 330.3 | D |
| 60 | 4-(4-fluoro-2,2-dimethyl-butanoyl)-3,5-dihydro-2H-pyrido[3,4-f][1,4]oxazepine-9-carbonitrile | 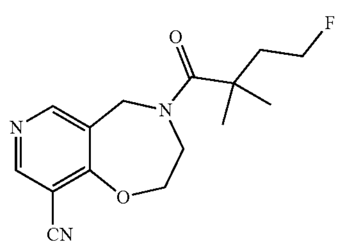 [SMILES: CC(C)(CCF)C(=O)N1CCOc2c(C#N)cncc2C1] | | 292.3 | C |
| 61 | 1-(9-chloro-3,5-dihydro-2H-pyrido[3,4-f][1,4]oxazepin-4-yl)-3,3-difluoro-2,2-dimethyl-propan-1-one | 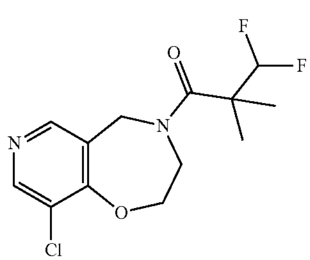 [SMILES: CC(C)(C(=O)N1CCOc2c(Cl)cncc2C1)C(F)F] | | 305.2 | C |

TABLE 1-continued

| Ex | Name | Structure | ¹H NMR | MS (M + H)⁺ | Method |
|---|---|---|---|---|---|
| 62 | 3,3-difluoro-2,2-dimethyl-1-(9-methyl-3,5-dihydro-2H-pyrido[3,4-f][1,4]oxazepin-4-yl)propan-1-one | 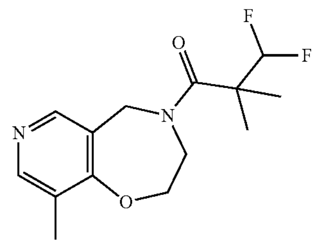 [SMILES: Cc1cncc2c1OCCN(C(=O)C(C)(C)C(F)F)C2] | | 285.3 | C |
| 63 | 4-(1-ethylcyclo-propanecarbonyl)-3,5-dihydro-2H-pyrido[3,4-f][1,4]oxazepine-9-carbonitrile | 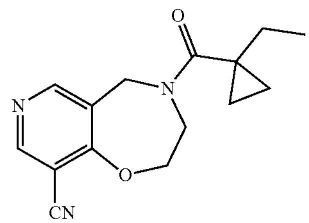 [SMILES: CCC1(C(=O)N2CCOc3c(C#N)cncc3C2)CC1] | | 272.3 | C |
| 64 | 4-(1-ethylcyclo-butanecarbonyl)-3,5-dihydro-2H-pyrido[3,4-f][1,4]oxazepine-9-carbonitrile | 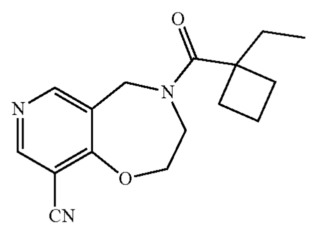 [SMILES: CCC1(C(=O)N2CCOc3c(C#N)cncc3C2)CCC1] | | 286.3 | C |
| 65 | 4-[(1S,2R)-1,2-dimethylcyclo-propanecarbonyl]-3,5-dihydro-2H-pyrido[3,4-f][1,4]oxazepine-9-carbonitrile | 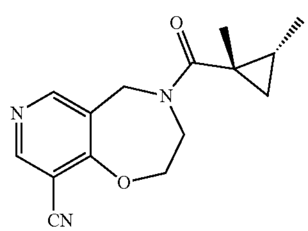 [SMILES: C[C@@H]1C[C@]1(C)C(=O)N1CCOc2c(C#N)cncc2C1] | | 272.3 | C |
| 66 | 3,3-difluoro-2,2-dimethyl-1-[8-(trifluoromethyl)-3,5-dihydro-2H-pyrido[3,4-f][1,4]oxazepin-4-yl]propan-1-one | 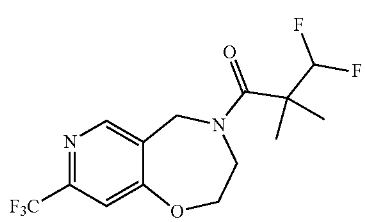 [SMILES: CC(C)(C(=O)N1CCOc2cc(C(F)(F)F)ncc2C1)C(F)F] | | 339.3 | C |
| 67 | 4-[2-methyl-2-(trifluoromethyl)butanoyl]-3,5-dihydro-2H-pyrido[3,4f][1,4]oxazepine-9-carbonitrile | 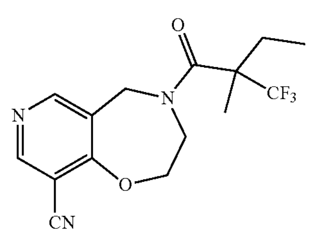 [SMILES: CCC(C)(C(=O)N1CCOc2c(C#N)cncc2C1)C(F)(F)F] | | 328.3 | B |

TABLE 1-continued

| Ex | Name | Structure | ¹H NMR | MS (M + H)⁺ | Method |
|---|---|---|---|---|---|
| 68 | 3,3-difluoro-1-(8-fluoro-3,5-dihydro-2H-1,4-benzoxazepin-4-yl)-2,2-dimethyl-propan-1-one | 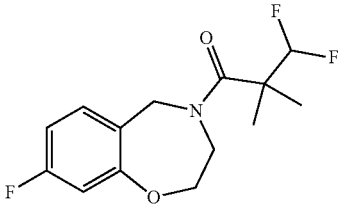 [SMILES: CC(C)(C(=O)N1CCOc2cc(F)ccc2C1)C(F)F] | | 288.3 | C |
| 69 | 4-[2-methyl-2-(trifluoromethoxy)propanoyl]-3,5-dihydro-2H-pyrido[3,4-f][1,4]oxazepine-9-carbonitrile | 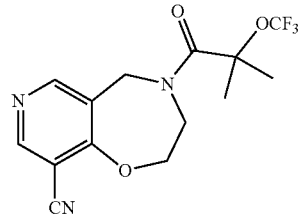 [SMILES: CC(C)(OC(F)(F)F)C(=O)N1CCOc2c(C#N)cncc2C1] | | 330.3 | C |
| 70 | 4-(9-fluoro-2,3-dihydropyrido[3,4-f][1,4]oxazepin-4(5H)-yl)-3,3-dimethyl-4-oxobutanenitrile | 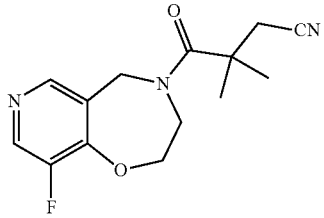 [SMILES: CC(C)(CC#N)C(=O)N1CCOc2c(F)cncc2C1] | | 278.3 | C |
| 71 | 4-(9-fluoro-2,3-dihydropyrido[3,4-f][1,4]oxazepin-4(5H)-yl)-2,3,3-trimethyl-4-oxobutanenitrile | 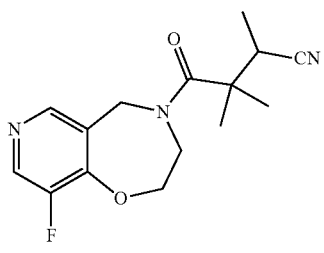 | | 292.3 | C |
| 72 | 4-(3-cyano-2,2-dimethylpropanoyl)-2,3,4,5-tetrahydropyrido[3,4-f][1,4]oxazepine-9-carbonitrile | 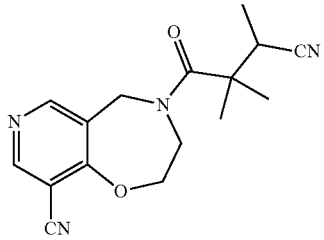 [SMILES: CC(C#N)C(C)(C)C(=O)N1CCOc2c(C#N)cncc2C1] | | 299.3 | C |
| 73 | 3-(9-fluoro-3,5-dihydro-2H-pyrido[3,4-f][1,4]oxazepine-4-carbonyl)-3-methyl-pentanenitrile | 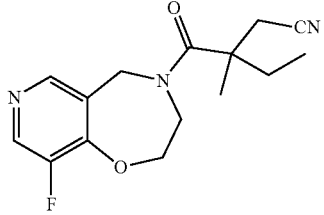 [SMILES: CCC(C)(CC#N)C(=O)N1CCOc2c(F)cncc2C1] | | 292.3 | C |

TABLE 1-continued

| Ex | Name | Structure | ¹H NMR | MS (M + H)⁺ | Method |
|----|------|-----------|--------|-------------|--------|
| 74 | 4-[2-(cyanomethyl)-2-methyl-butanoyl]-3,5-dihydro-2H-pyrido[3,4-f][1,4]oxazepine-9-carbonitrile | 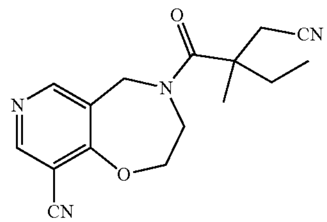 [SMILES: CCC(C)(CC#N)C(=O)N1CCOc2c(C#N)cncc2C1] | | 299.3 | C |
| 75 | (3R)-4-(2,2-dimethylbutanoyl)-3-methyl-3,5-dihydro-2H-pyrido[3,4-f][1,4]oxazepine-9-carbonitrile | 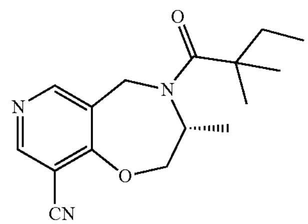 [SMILES: CCC(C)(C)C(=O)N1Cc2cncc(C#N)c2OC[C@H]1C] | | 288.3 | C |
| 76 | (3R)-3-methyl-4-(2-methylbutanoyl)-3,5-dihydro-2H-pyrido[3,4-f][1,4]oxazepine-9-carbonitrile | 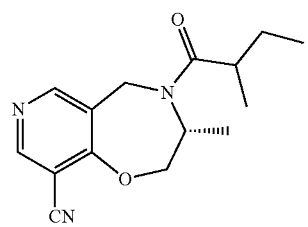 [SMILES: CCC(C)C(=O)N1Cc2cncc(C#N)c2OC[C@H]1C] | | 274.3 | C |
| 77 | (3R)-4-(3-fluoro-2,2-dimethyl-propanoyl)-3-methyl-3,5-dihydro-2H-pyrido[3,4-f][1,4]oxazepine-9-carbonitrile | 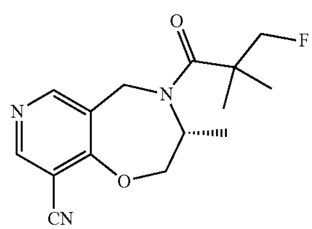 [SMILES: C[C@@H]1COc2c(C#N)cncc2CN1C(=O)C(C)(C)CF] | | 292.3 | D |
| 78 | (3R)-4-(2,2-dimethylpropanoyl)-3-methyl-3,5-dihydro-2H-pyrido[3,4-f][1,4]oxazepine-9-carbonitrile | 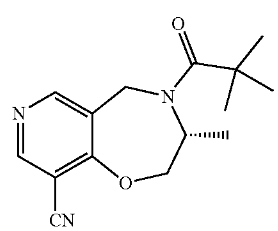 [SMILES: C[C@@H]1COc2c(C#N)cncc2CN1C(=O)C(C)(C)C] | | 274.1 | D |
| 79 | 3,3,3-trifluoro-1-(9-fluoro-3,5-dihydro-2H-pyrido[3,4-f][1,4]oxazepin-4-yl)-2,2-dimethyl-propan-1-one | 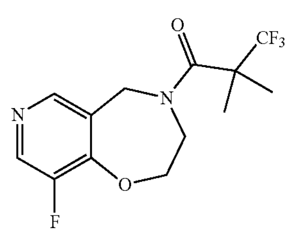 [SMILES: CC(C)(C(=O)N1CCOc2c(F)cncc2C1)C(F)(F)F] | | 307.1 | B |

TABLE 1-continued

| Ex | Name | Structure | ¹H NMR | MS (M + H)⁺ | Method |
|---|---|---|---|---|---|
| 80 | 1-(9-fluoro-3,5-dihydro-2H-pyrido[3,4-f][1,4]oxazepin-4-yl)-2,2-dimethyl-propan-1-one | 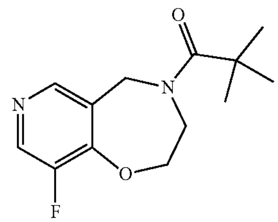 [SMILES: CC(C)(C)C(=O)N1CCOc2c(F)cncc2C1] | | 253.3 | D |
| 81 | 4-(2-(1-hydroxycyclo-propyl)-2-methylpropanoyl)-2,3,4,5-tetrahydropyrido[3,4-f][1,4]oxazepine-9-carbonitrile | 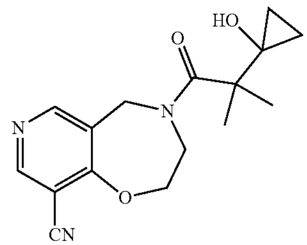 [SMILES: CC(C)(C(=O)N1CCOc2c(C#N)cncc2C1)C1(O)CC1] | | 302.3 | C |
| 82 | 4-[2-(-2-(difluoromethyl)cyclopropyl)-2-methyl-propanoyl]-3,5-dihydro-2H-pyrido[3,4-f][1,4]oxazepine-9-carbonitrile | 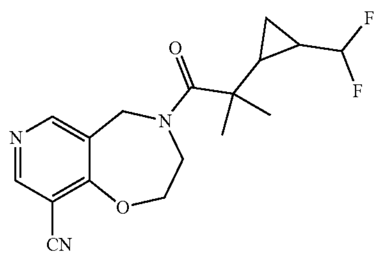 [SMILES: CC(C)(C(=O)N1CCOc2c(C#N)cncc2C1)C1CC1C(F)F] | | 335.4 | C |
| 83 | 4-[2-(2-cyanocyclopropyl)-2-methyl-propanoyl]-3,5-dihydro-2H-pyrido[3,4-f][1,4]oxazepine-9-carbonitrile | 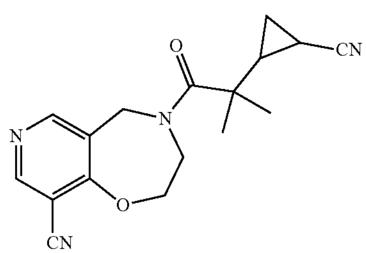 [SMILES: CC(C)(C(=O)N1CCOc2c(C#N)cncc2C1)C1CC1C#N] | | 311.3 | C |
| 84 | 4-[2-(3,3-difluorocyclobutyl)-2-methyl-propanoyl]-3,5-dihydro-2H-pyrido[3,4-f][1,4]oxazepine-9-carbonitrile | 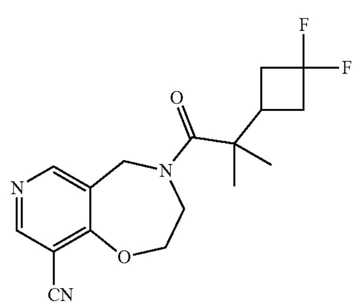 [SMILES: CC(C)(C(=O)N1CCOc2c(C#N)cncc2C1)C1CC(F)(F)C1] | | 336.2 | C |
| 85 | 4-[2-[1-(5-fluoropyrimidin-2-yl)azetidin-3-yl]-2-methyl-propanoyl]-3,5-dihydro-2H-pyrido[3,4-f][1,4]oxazepine-9-carbonitrile | 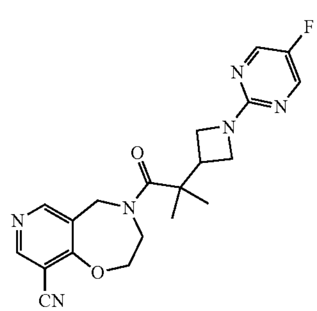 [SMILES: CC(C)(C(=O)N1CCOc2c(C#N)cncc2C1)C1CN(c2ncc(F)cn2)C1] | | 397.4 | C |

TABLE 1-continued

| Ex | Name | Structure | ¹H NMR | MS (M + H)⁺ | Method |
|---|---|---|---|---|---|
| 86 | (3R)-4-[4-fluoro-1-(5-fluoropyrimidin-2-yl)piperidine-4-carbonyl]-3-methyl-3,5-dihydro-2H-pyrido[3,4-f][1,4]oxazepine-9-carbonitrile | 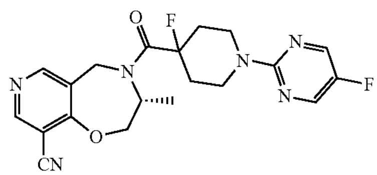 [SMILES: C[C@@H]1COc2c(C#N)cncc2CN1C(=O)C1(F)CCN(c2ncc(F)cn2)CC1] | | 415.4 | B |
| 87 | 4-(4-fluoro-1-pyrazin-2-yl-piperidine-4-carbonyl)-3,5-dihydro-2H-pyrido[3,4-f][1,4]oxazepine-9-carbonitrile | 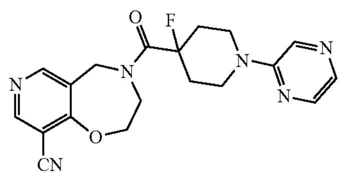 [SMILES: N#Cc1cncc2c1OCCN(C(=O)C1(F)CCN(c3cnccn3)CC1)C2] | | 383.4 | B |
| 88 | 4-(4-fluoro-1-pyrimidin-4-yl-piperidine-4-carbonyl)-3,5-dihydro-2H-pyrido[3,4-f][1,4]oxazepine-9-carbonitrile | 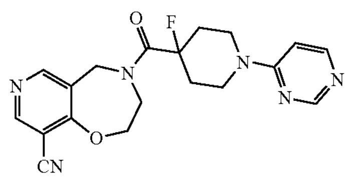 [SMILES: N#Cc1cncc2c1OCCN(C(=O)C1(F)CCN(c3ccncn3)CC1)C2] | | 383.4 | B |
| 89 | 4-(cis-3-(5-fluoropyrimidin-2-yl)-3-azabicyclo[4.1.0]heptane-6-carbonyl)-3,5-dihydro-2H-pyrido[3,4-f][1,4]oxazepine-9-carbonitrile | 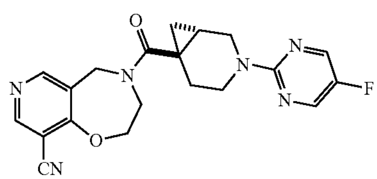 | | 395.4 | C |
| 90 | 4-[2-[1-(5-fluoropyrimidin-2-yl)pyrrolidin-3-yl]-2-methyl-propanoyl]-3,5-dihydro-2H-pyrido[3,4-f][1,4]oxazepine-9-carbonitrile | 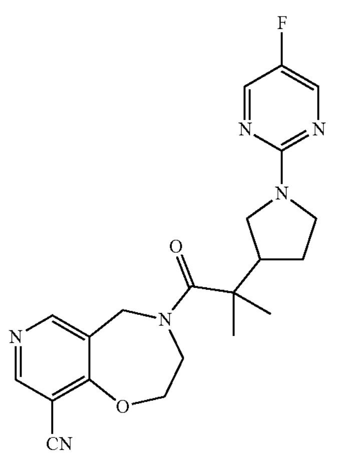 [SMILES: CC(C)(C(=O)N1CCOc2c(C#N)cncc2C1)C1CCN(c2ncc(F)cn2)C1] | | 411.4 | C |
| 91 | 4-[1-(5-fluoropyrimidin-2-yl)-2-methyl-piperidine-4-carbonyl]-3,5-dihydro-2H-pyrido[3,4-f][1,4]oxazepine-9-carbonitrile | 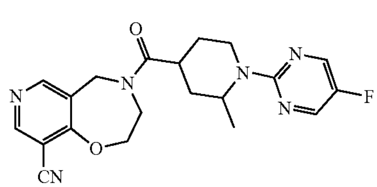 [SMILES: CC1CC(C(=O)N2CCOc3c(C#N)cncc3C2)CCN1c1ncc(F)cn1] | | 397.4 | C |

TABLE 1-continued

| Ex | Name | Structure | ¹H NMR | MS (M + H)⁺ | Method |
|---|---|---|---|---|---|
| 92 | 4-[1-(5-fluoropyrimidin-2-yl)azepane-4-carbonyl]-3,5-dihydro-2H-pyrido[3,4-f][1,4]oxazepine-9-carbonitrile | 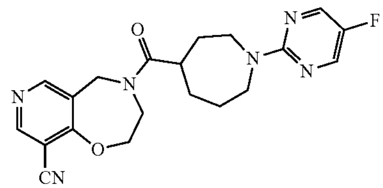 [SMILES: N#Cc1cncc2c1OCCN(C(=O)C1CCCN(c3ncc(F)cn3)CC1)C2] | | 397.4 | C |
| 93 | 4-(3-(((5-fluoropyrimidin-2-yl)oxy)methyl)bicyclo[1.1.1]pentane-1-carbonyl)-2,3,4,5-tetrahydropyrido[3,4-f][1,4]oxazepine-9-carbonitrile | 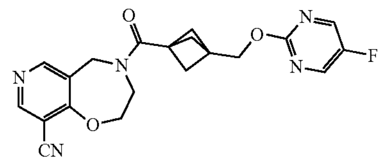 [SMILES: N#Cc1cncc2c1OCCN(C(=O)C13CC(COc4ncc(F)cn4)(C1)C3)C2] | | 396.3 | C |
| 94 | 4-[4-(difluoromethyl)-1-(5-fluoropyrimidin-2-yl)piperidine-4-carbonyl]-3,5-dihydro-2H-pyrido[3,4-f][1,4]oxazepine-9-carbonitrile | 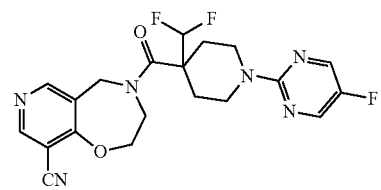 [SMILES: N#Cc1cncc2c1OCCN(C(=O)C1(C(F)F)CCN(c3ncc(F)cn3)CC1)C2] | | 433.3 | C |
| 95 | 4-[4-fluoro-1-(pyridine-3-carbonyl)piperidine-4-carbonyl]-3,5-dihydro-2H-pyrido[3,4-f][1,4]oxazepine-9-carbonitrile | 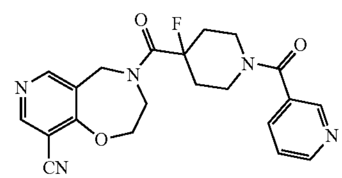 [SMILES: N#Cc1cncc2c1OCCN(C(=O)C1(F)CCN(C(=O)c3cccnc3)CC1)C2] | | 410.3 | B |
| 96 | 4-[3,3-difluoro-1-(5-fluoropyrimidin-2-yl)-4-methyl-piperidine-4-carbonyl]-3,5-dihydro-2H-pyrido[3,4-f][1,4]oxazepine-9-carbonitrile | 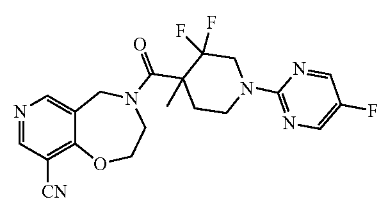 [SMILES: CC1(C(=O)N2CCOc3c(C#N)cncc3C2)CCN(c2ncc(F)cn2)CC1(F)F] | | 433.3 | D |
| 97 | 4-(4-fluoro-1-quinazolin-2-yl-piperidine-4-carbonyl)-3,5-dihydro-2H-pyrido[3,4-f][1,4]oxazepine-9-carbonitrile | 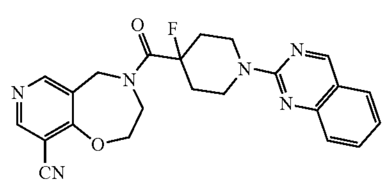 [SMILES: N#Cc1cncc2c1OCCN(C(=O)C1(F)CCN(c3ncc4ccccc4n3)CC1)C2] | | 433.4 | W |
| 98 | 4-[4-ethyl-1-(5-fluoropyrimidin-2-yl)piperidine-4-carbonyl]-3,5-dihydro-2H-pyrido[3,4-f][1,4]oxazepine-9-carbonitrile | 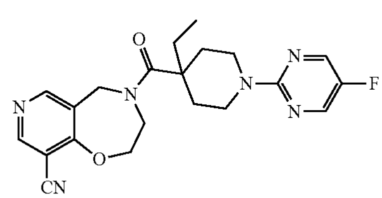 [SMILES: CCC1(C(=O)N2CCOc3c(C#N)cncc3C2)CCN(c2ncc(F)cn2)CC1] | | 411.4 | W |
| 99 | 4-[7,7-difluoro-3-(5-fluoropyrimidin-2-yl)-3-azabicyclo[4.1.0]heptane-6-carbonyl]-3,5-dihydro-2H-pyrido[3,4-f][1,4]oxazepine-9-carbonitrile | 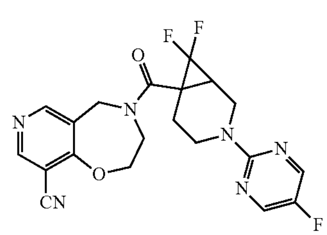 [SMILES: N#Cc1cncc2c1OCCN(C(=O)C13CCN(c4ncc(F)cn4)CC1C3(F)F)C2] | | 431.1 | C |

TABLE 1-continued

| Ex | Name | Structure | ¹H NMR | MS (M + H)⁺ | Method |
|---|---|---|---|---|---|
| 100 | 4-[1-(5-cyclopropylpyrimidin-2-yl)-4-fluoro-piperidine-4-carbonyl]-3,5-dihydro-2H-pyrido[3,4-f][1,4]oxazepine-9-carbonitrile | 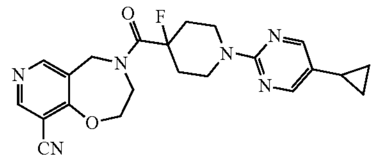 [SMILES: N#Cc1cncc2c1OCCN(C(=O)C1(F)CCN(c3ncc(C4CC4)cn3)CC1)C2] | | 423.4 | W |
| 101 | 4-[4-fluoro-1-(5-methoxypyrimidin-2-yl)piperidine-4-carbonyl]-3,5-dihydro-2H-pyrido[3,4-f][1,4]oxazepine-9-carbonitrile | 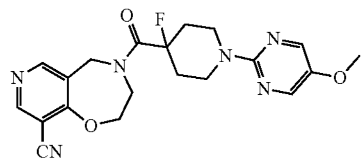 [SMILES: COc1cnc(N2CCC(F)(C(=O)N3CCOc4c(C#N)cncc4C3)CC2)nc1] | | 413.4 | W |
| 102 | 4-[1-[5-(difluoromethoxy)pyrimidin-2-yl]-4-fluoro-piperidine-4-carbonyl]-3,5-dihydro-2H-pyrido[3,4-f][1,4]oxazepine-9-carbonitrile | 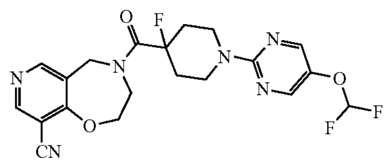 [SMILES: N#Cc1cncc2c1OCCN(C(=O)C1(F)CCN(c3ncc(OC(F)F)cn3)CC1)C2] | | 449.4 | W |
| 103 | 4-[4-fluoro-1-(4-methoxypyrimidin-2-yl)piperidine-4-carbonyl]-3,5-dihydro-2H-pyrido[3,4-f][1,4]oxazepine-9-carbonitrile | 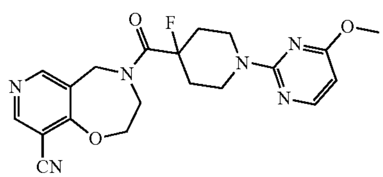 [SMILES: COc1ccnc(N2CCC(F)(C(=O)N3CCOc4c(C#N)cncc4C3)CC2)n1] | | 413.3 | W |
| 104 | (3R)-4-(1-(5-fluoropyrimidin-2-yl)piperidine-4-carbonyl)-3-methyl-2,3,4,5-tetrahydropyrido[3,4-f][1,4]oxazepine-9-carbonitrile | 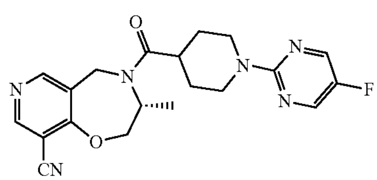 [SMILES: C[C@@H]1COc2c(C#N)cncc2CN1C(=O)C1CCN(c2ncc(F)cn2)CC1] | | 397.3 | B |
| 105 | (3R)-4-[1-(5-fluoropyrimidin-2-yl)-4-methoxy-piperidine-4-carbonyl]-3-methyl-3,5-dihydro-2H-pyrido[3,4-f][1,4]oxazepine-9-carbonitrile | 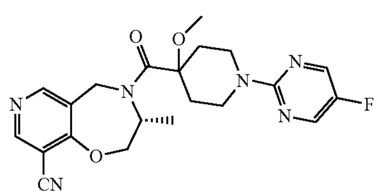 [SMILES: COC1(C(=O)N2Cc3cncc(C#N)c3OC[C@H]2C)CCN(c2ncc(F)cn2)CC1] | | 427.4 | D |
| 106 | 4-(4-fluoro-1-imidazo[1,2-a]pyrazin-8-yl-piperidine-4-carbonyl)-3,5-dihydro-2H-pyrido[3,4-f][1,4]oxazepine-9-carbonitrile | 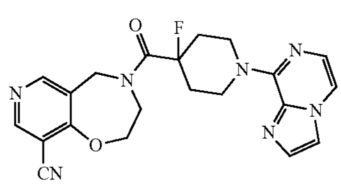 [SMILES: N#Cc1cncc2c1OCCN(C(=O)C1(F)CCN(c3nccn4ccnc34)CC1)C2] | | 422.3 | W |
| 107 | 4-[4-fluoro-1-(1-methylpyrazolo[4,3-c]pyridin-6-yl)piperidine-4-carbonyl]-3,5-dihydro-2H-pyrido[3,4-f][1,4]oxazepine-9-carbonitrile | 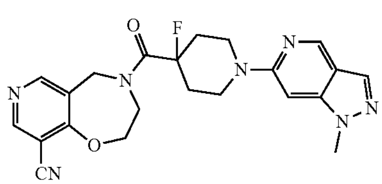 [SMILES: Cn1ncc2cnc(N3CCC(F)(C(=O)N4CCOc5c(C#N)cncc5C4)CC3)cc21] | | 436.4 | AJ |

TABLE 1-continued

| Ex | Name | Structure | ¹H NMR | MS (M + H)⁺ | Method |
|---|---|---|---|---|---|
| 108 | 4-[4-fluoro-1-(5-methylpyrrolo[3,2-d]pyrimidin-2-yl)piperidine-4-carbonyl]-3,5-dihydro-2H-pyrido[3,4-f][1,4]oxazepine-9-carbonitrile | 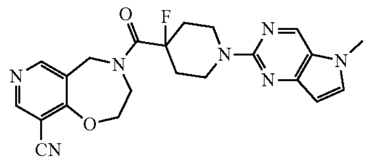 [SMILES: Cn1ccc2nc(N3CCC(F)(C(=O)N4CCOc5c(C#N)cncc5C4)CC3)ncc21] | | 436.2 | AJ |
| 109 | 4-(4-fluoro-1-imidazo[1,2-b]pyridazin-6-yl-piperidine-4-carbonyl)-3,5-dihydro-2H-pyrido[3,4-f][1,4]oxazepine-9-carbonitrile | 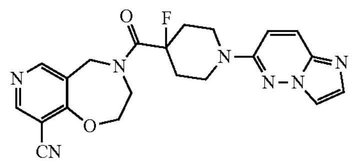 [SMILES: N#Cc1cncc2c1OCCN(C(=O)C1(F)CCN(c3ccc4nccn4n3)CC1)C2] | | 422.3 | AJ |
| 110 | 4-(4-fluoro-1-(pyrazolo[1,5-a]pyrimidin-7-yl)piperidine-4-carbonyl)-2,3,4,5-tetrahydropyrido[3,4-f][1,4]oxazepine-9-carbonitrile | 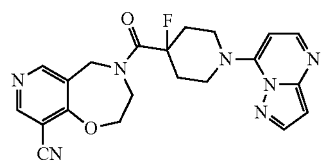 [SMILES: N#Cc1cncc2c1OCCN(C(=O)C1(F)CCN(c3ccnc4ccnn34)CC1)C2] | | 422.3 | W |
| 111 | 4-[1-(6,7-dihydro-5H-cyclopenta[d]pyrimidin-2-yl)-4-fluoro-piperidine-4-carbonyl]-3,5-dihydro-2H-pyrido[3,4-f][1,4]oxazepine-9-carbonitrile | 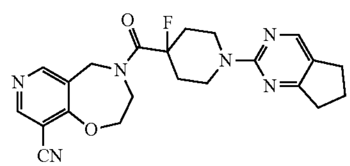 [SMILES: N#Cc1cncc2c1OCCN(C(=O)C1(F)CCN(c3ncc4c(n3)CCC4)CC1)C2] | | 423.4 | W |
| 112 | 4-(4-fluoro-1-(5-fluoropyrimidin-4-yl)piperidine-4-carbonyl)-2,3,4,5-tetrahydropyrido[3,4-f][1,4]oxazepine-9-carbonitrile | 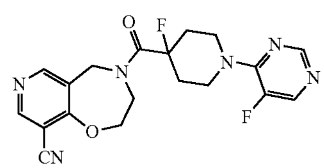 [SMILES: N#Cc1cncc2c1OCCN(C(=O)C1(F)CCN(c3ncncc3F)CC1)C2] | | 401.1 | W |
| 113 | 4-[4-fluoro-1-(3-fluoro-2-pyridyl)piperidine-4-carbonyl]-3,5-dihydro-2H-pyrido[3,4-f][1,4]oxazepine-9-carbonitrile | 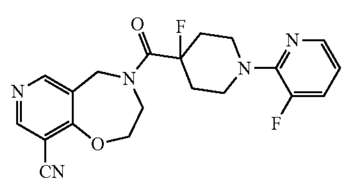 [SMILES: N#Cc1cncc2c1OCCN(C(=O)C1(F)CCN(c3ncccc3F)CC1)C2] | | 400.3 | AJ |
| 114 | 4-[4-fluoro-1-(5-fluoro-2-methoxy-pyrimidin-4-yl)piperidine-4-carbonyl]-3,5-dihydro-2H-pyrido[3,4-f][1,4]oxazepine-9-carbonitrile | 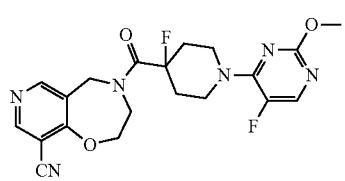 [SMILES: COc1ncc(F)c(N2CCC(F)(C(=O)N3CCOc4c(C#N)cncc4C3)CC2)n1] | | 431.3 | W |
| 115 | 4-[4-fluoro-1-(6-methoxypyridazin-3-yl)piperidine-4-carbonyl]-3,5-dihydro-2H-pyrido[3,4-f][1,4]oxazepine-9-carbonitrile | 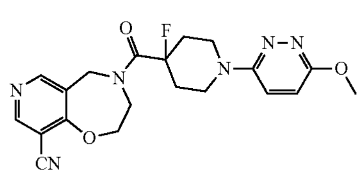 [SMILES: COc1ccc(N2CCC(F)(C(=O)N3CCOc4c(C#N)cncc4C3)CC2)nn1] | | 413.4 | AJ |

TABLE 1-continued

| Ex | Name | Structure | ¹H NMR | MS (M + H)⁺ | Method |
|---|---|---|---|---|---|
| 116 | 4-(4-fluoro-1-pyridazin-3-yl-piperidine-4-carbonyl)-3,5-dihydro-2H-pyrido[3,4-f][1,4]oxazepine-9-carbonitrile | 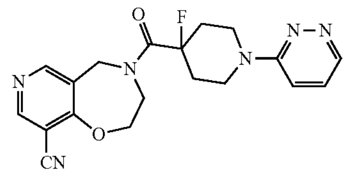 [SMILES: N#Cc1cncc2c1OCCN(C(=O)C1(F)CCN(c3cccnn3)CC1)C2] | | 383.3 | AJ |
| 117 | 4-[1-(4-methoxypyrimidin-2-yl)piperidine-4-carbonyl]-3,5-dihydro-2H-pyrido[3,4-f][1,4]oxazepine-9-carbonitrile | 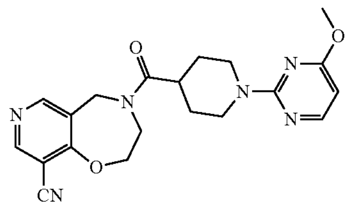 [SMILES: COc1ccnc(N2CCC(C(=O)N3CCOc4c(C#N)cncc4C3)CC2)n1] | | 395.3 | W |
| 118 | 4-[1-(5-fluoro-4-methoxy-pyrimidin-2-yl)piperidine-4-carbonyl]-3,5-dihydro-2H-pyrido[3,4-f][1,4]oxazepine-9-carbonitrile | 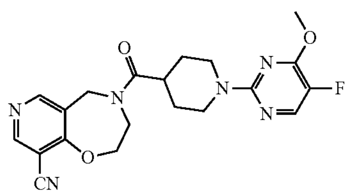 [SMILES: COc1nc(N2CCC(C(=O)N3CCOc4c(C#N)cncc4C3)CC2)ncc1F] | | 413.3 | W |
| 119 | (3R)-4-(1-(4-methoxypyrimidin-2-yl)piperidine-4-carbonyl)-3-methyl-2,3,4,5-tetrahydropyrido[3,4-f][1,4]oxazepine-9-carbonitrile | 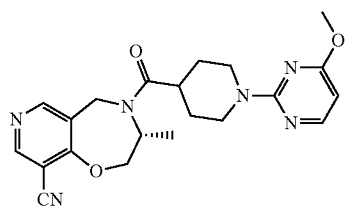 [SMILES: COc1ccnc(N2CCC(C(=O)N3Cc4cncc(C#N)c4OC[C@H]3C)CC2)n1] | | 409.4 | W |
| 120 | (3R)-4-(1-(5-fluoro-4-methoxypyrimidin-2-yl)piperidine-4-carbonyl)-3-methyl-2,3,4,5-tetrahydropyrido[3,4-f][1,4]oxazepine-9-carbonitrile | 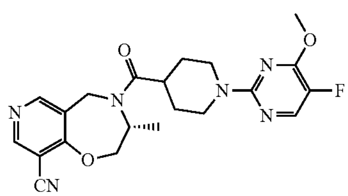 [SMILES: COc1nc(N2CCC(C(=O)N3Cc4cncc(C#N)c4OC[C@H]3C)CC2)ncc1F] | | 427.3 | W |
| 121 | (9-fluoro-3,5-dihydro-2H-pyrido[3,4-f][1,4]oxazepin-4-yl)41-(5-fluoropyrimidin-2-yl)-4-methoxy-4-piperidyl]methanone | 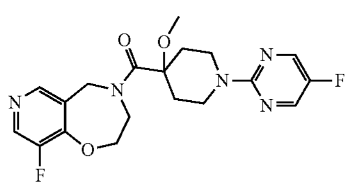 [SMILES: COC1(C(=O)N2CCOc3c(F)cncc3C2)CCN(c2ncc(F)cn2)CC1] | | 406.3 | W |
| 122 | (9-fluoro-3,5-dihydro-2H-pyrido[3,4-f][1,4]oxazepin-4-yl)-[1-(5-fluoro-4-methoxy-pyrimidin-2-yl)-4-methoxy-4-piperidyl]methanone | 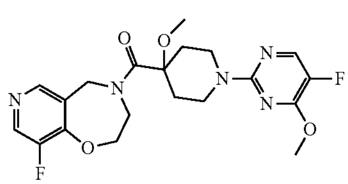 [SMILES: COc1nc(N2CCC(OC)(C(=O)N3CCOc4c(F)cncc4C3)CC2)ncc1F] | | 436.3 | W |
| 123 | 4-[4-fluoro-1-[5-fluoro-4-(methylamino)pyrimidin-2-yl]piperidine-4-carbonyl]-3,5-dihydro-2H-pyrido[3,4- | 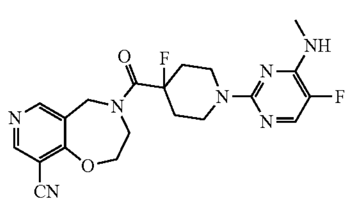 [SMILES: CNc1nc(N2CCC(F)(C(=O)N3CCOc4c(C#N)cncc4C3)CC2)ncc1F] | | 430.4 | W |

TABLE 1-continued

| Ex | Name | Structure | ¹H NMR | MS (M + H)⁺ | Method |
|---|---|---|---|---|---|
| | f][1,4]oxazepine-9-carbonitrile | | | | |
| 124 | 4-[1-[4-(cyclopropylamino)-5-fluoro-pyrimidin-2-yl]-4-fluoro-piperidine-4-carbonyl]-3,5-dihydro-2H-pyrido[3,4-f][1,4]oxazepine-9-carbonitrile | 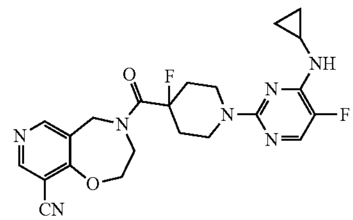 [SMILES: N#Cc1cncc2c1OCCN(C(=O)C1(F)CCN(c3ncc(F)c(NC4CC4)n3)CC1)C2] | | 456.4 | W |
| 125 | 4-[1-[4-(2,2-difluoroethoxy)-5-fluoro-pyrimidin-2-yl]-4-fluoro-piperidine-4-carbonyl]-3,5-dihydro-2H-pyrido[3,4-f][1,4]oxazepine-9-carbonitrile | 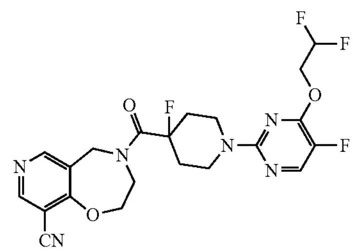 [SMILES: N#Cc1cncc2c1OCCN(C(=O)C1(F)CCN(c3ncc(F)c(OCC(F)F)n3)CC1)C2] | | 481.4 | W |
| 126 | 4-[4-fluoro-1-(5-fluoro-4-methylsulfanyl-pyrimidin-2-yl)piperidine-4-carbonyl]-3,5-dihydro-2H-pyrido[3,4-f][1,4]oxazepine-9-carbonitrile | 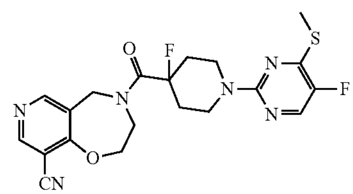 [SMILES: CSc1nc(N2CCC(F)(C(=O)N3CCOc4c(C#N)cncc4C3)CC2)ncc1F] | | 447.3 | W |
| 127 | 4-[1-[4-[3-(dimethylamino)propoxy]-5-fluoro-pyrimidin-2-yl]-4-fluoro-piperidine-4-carbonyl]-3,5-dihydro-2H-pyrido[3,4-f][1,4]oxazepine-9-carbonitrile | 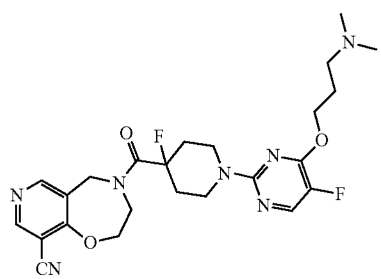 [SMILES: CN(C)CCCOc1nc(N2CCC(F)(C(=O)N3CCOc4c(C#N)cncc4C3)CC2)ncc1F] | | 502.5 | W |
| 128 | 4-[1-(5-chloro-4-methoxy-pyrimidin-2-yl)-4-fluoro-piperidine-4-carbonyl]-3,5-dihydro-2H-pyrido[3,4-f][1,4]oxazepine-9-carbonitrile | 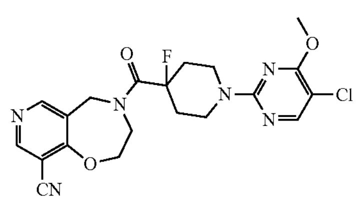 [SMILES: COc1nc(N2CCC(F)(C(=O)N3CCOc4c(C#N)cncc4C3)CC2)ncc1Cl] | | 447.3 | W |
| 129 | 4-[1-(5-chloro-4-methoxy-pyrimidin-2-yl)piperidine-4-carbonyl]-3,5-dihydro-2H-pyrido[3,4-f][1,4]oxazepine-9-carbonitrile | 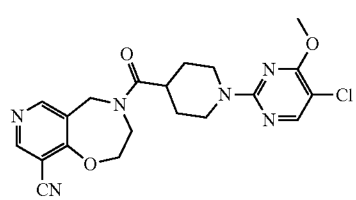 [SMILES: COc1nc(N2CCC(C(=O)N3CCOc4c(C#N)cncc4C3)CC2)ncc1Cl] | | 429.3 | W |

TABLE 1-continued

| Ex | Name | Structure | ¹H NMR | MS (M + H)⁺ | Method |
|---|---|---|---|---|---|
| 130 | (9-fluoro-3,5-dihydro-2H-pyrido[3,4-f][1,4]oxazepin-4-yl)-[1-[5-fluoro-4-(2-methoxyethoxy)pyrimidin-2-yl]-4-piperidyl]methanone | 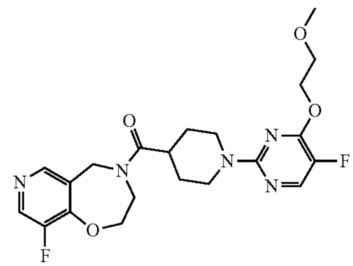 [SMILES: COCCOc1nc(N2CCC(C(=O)N3CCOc4c(F)cncc4C3)CC2)ncc1F] | | 450.4 | W |
| 131 | 4-(1-(4-(2,2-difluoroethoxy)-5-fluoropyrimidin-2-yl)piperidine-4-carbonyl)-2,3,4,5-tetrahydropyrido[3,4-f][1,4]oxazepine-9-carbonitrile | 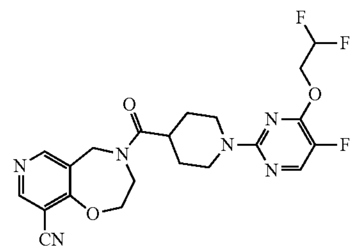 [SMILES: N#Cc1cncc2c1OCCN(C(=O)C1CCN(c3ncc(F)c(OCC(F)F)n3)CC1)C2] | | 463.4 | W |
| 132 | (1-(4-(2,2-difluoroethoxy)-5-fluoropyrimidin-2-yl)-4-methoxypiperidin-4-yl)(9-fluoro-2,3-dihydropyrido[3,4-f][1,4]oxazepin-4(5H)-yl)methanone | 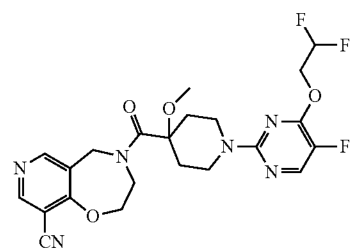 [SMILES: COC1(C(=O)N2CCOc3c(C#N)cncc3C2)CCN(c2ncc(F)c(OCC(F)F)n2)CC1] | | 486.4 | W |
| 133 | 4-[1-[4-(2,2-difluoroethoxy)pyrimidin-2-yl]piperidine-4-carbonyl]-3,5-dihydro-2H-pyrido[3,4-f][1,4]oxazepine-9-carbonitrile | 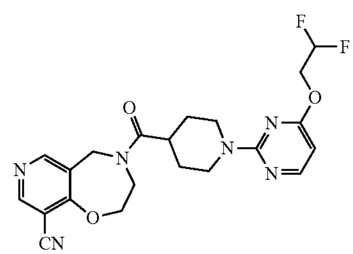 [SMILES: N#Cc1cncc2c1OCCN(C(=O)C1CCN(c3nccc(OCC(F)F)n3)CC1)C2] | | 445.4 | W |
| 134 | [1-[4-(2,2-difluoroethoxy)pyrimidin-2-yl]-4-methoxy-4-piperidyl]-(9-fluoro-3,5-dihydro-2H-pyrido[3,4-f][1,4]oxazepin-4-yl)methanone | 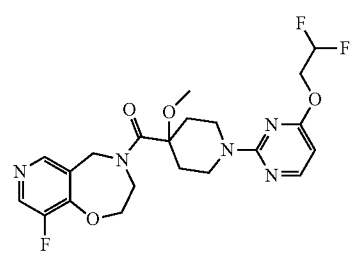 [SMILES: COC1(C(=O)N2CCOc3c(F)cncc3C2)CCN(c2nccc(OCC(F)F)n2)CC1] | | 468.4 | W |
| 135 | (9-fluoro-3,5-dihydro-2H-pyrido[3,4-f][1,4]oxazepin-4-yl)-(4-methoxy-1-pyrimidin-2-yl-4-piperidyl)methanone | 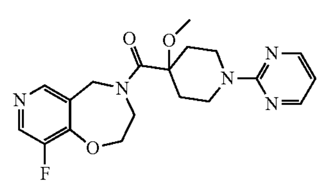 [SMILES: COC1(C(=O)N2CCOc3c(F)cncc3C2)CCN(c2ncccn2)CC1] | | 388.2 | W |

TABLE 1-continued

| Ex | Name | Structure | ¹H NMR | MS (M + H)⁺ | Method |
|---|---|---|---|---|---|
| 136 | [1-[4-[2-(dimethylamino)ethoxyl-5-fluoro-pyrimidin-2-yl]-4-methoxy-4-piperidyl]-(9-fluoro-3,5-dihydro-2H-pyrido[3,4-f][1,4]oxazepin-4-yl)methanone | 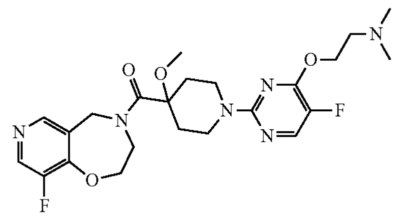 [SMILES: COC1(C(=O)N2CCOc3c(F)cncc3C2)CCN(c2ncc(F)c(OCCN(C)C)n2)CC1] | | 493.3 | W |
| 137 | 4-(4-(fluoromethyl)-1-(5-fluoropyrimidin-2-yl)piperidine-4-carbonyl)-2,3,4,5-tetrahydropyrido[3,4-f][1,4]oxazepine-9-carbonitrile | 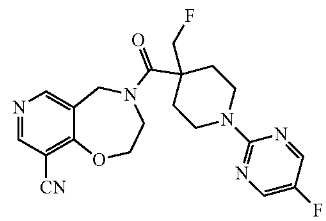 [SMILES: N#Cc1cncc2c1OCCN(C(=O)C1(CF)CCN(c3ncc(F)cn3)CC1)C2] | | 415.4 | C |
| 138 | 4-(3,3-difluoro-1-methyl-cyclobutanecarbonyl)-3,5-dihydro-2H-pyrido[3,4-f][1,4]oxazepine-9-carbonitrile | 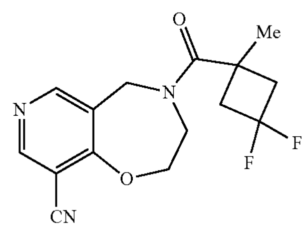 [SMILES: CC1(C(=O)N2CCOc3c(C#N)cncc3C2)CC(F)(F)C1] | | 308.5 | C |
| 139 | 4-[1-(difluoromethyl)cyclopropanecarbonyl]-3,5-dihydro-2H-pyrido[3,4-f][1,4]oxazepine-9-carbonitrile | 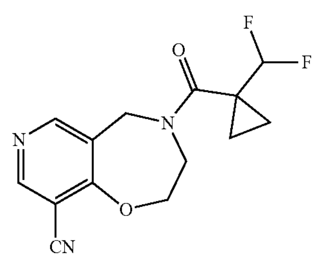 [SMILES: N#Cc1cncc2c1OCCN(C(=O)C1(C(F)F)CC1)C2] | | 294.2 | C |
| 140 | 4-(1-fluorocyclopropanecarbonyl)-3,5-dihydro-2H-pyrido[3,4-f][1,4]oxazepine-9-carbonitrile | 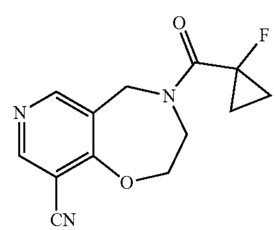 [SMILES: N#Cc1cncc2c1OCCN(C(=O)C1(F)CC1)C2] | | 262.5 | C |
| 141 | 4-(4,4,4-trifluoro-2-methyl-butanoyl)-3,5-dihydro-2H-pyrido[3,4-f][1,4]oxazepine-9-carbonitrile | 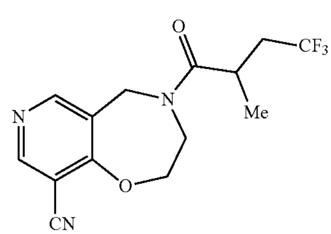 [SMILES: CC(CC(F)(F)F)C(=O)N1CCOc2c(C#N)cncc2C1] | | 314.6 | C |

TABLE 1-continued

| Ex | Name | Structure | ¹H NMR | MS (M + H)⁺ | Method |
|---|---|---|---|---|---|
| 142 | 4-(3,3-difluoro-2,2-dimethyl-butanoyl)-3,5-dihydro-2H-pyrido[3,4-f][1,4]oxazepine-9-carbonitrile | 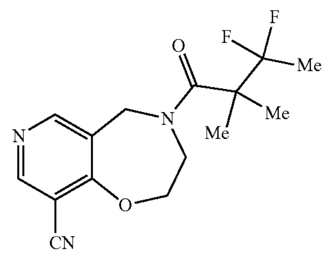 [SMILES: CC(F)(F)C(C)(C)C(=O)N1CCOc2c(C#N)cncc2C1] | | 310.6 | C |
| 143 | 4-(2,2,3,3,4,4,4,-heptafluorobutanoyl)-3,5-dihydro-2H-pyrido[3,4-f][1,4]oxazepine-9-carbonitrile | 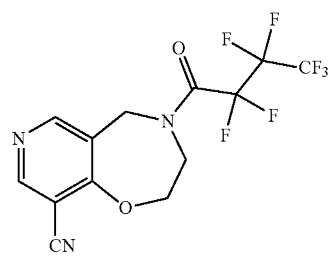 [SMILES: N#Cc1cncc2c1OCCN(C(=O)C(F)(F)C(F)(F)C(F)(F)F)C2] | | 372.5 | C |
| 144 | 4-(3-fluoro-2,2-dimethyl-propanoyl)-3,5-dihydro-2H-pyrido[3,4-f][1,4]oxazepine-9-carbonitrile | 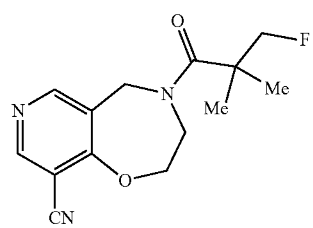 [SMILES: CC(C)(CF)C(=O)N1CCOc2c(C#N)cncc2C1] | | 278.6 | C |
| 145 | 4-(2,2,3-trimethylbutanoyl)-3,5-dihydro-2H-pyrido[3,4-f][1,4]oxazepine-9-carbonitrile | 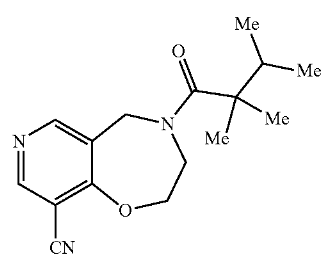 [SMILES: CC(C)C(C)(C)C(=O)N1CCOc2c(C#N)cncc2C1] | | 288.6 | C |
| 146 | 4-(2-cyclopropylpropanoyl)-3,5-dihydro-2H-pyrido[3,4-f][1,4]oxazepine-9-carbonitrile | 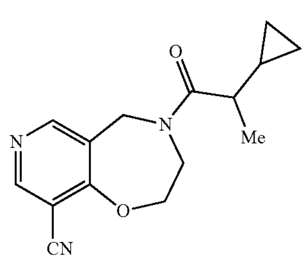 [SMILES: CC(C(=O)N1CCOc2c(C#N)cncc2C1)C1CC1] | | 272.5 | C |
| 147 | 4-[3-fluoro-2-(fluoromethyl)-2-methyl-propanoyl]-3,5-dihydro-2H-pyrido[3,4-f][1,4]oxazepine-9-carbonitrile | 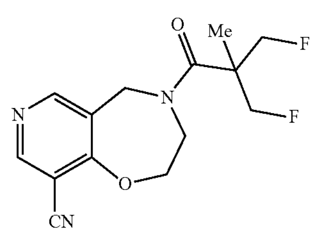 [SMILES: CC(CF)(CF)C(=O)N1CCOc2c(C#N)cncc2C1] | | 296.6 | C |

TABLE 1-continued

| Ex | Name | Structure | ¹H NMR | MS (M + H)⁺ | Method |
|---|---|---|---|---|---|
| 148 | 4-(2-methyl-2-methylsulfanyl-propanoyl)-3,5-dihydro-2H-pyrido[3,4-f][1,4]oxazepine-9-carbonitrile | 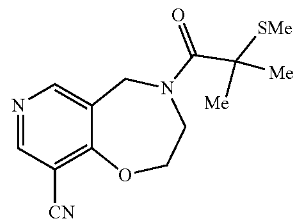 [SMILES: CSC(C)(C)C(=O)N1CCOc2c(C#N)cncc2C1] | | 292.6 | C |
| 149 | 4-(4,4-difluoro-2,2-dimethyl-butanoyl)-3,5-dihydro-2H-pyrido[3,4-f][1,4]oxazepine-9-carbonitrile | 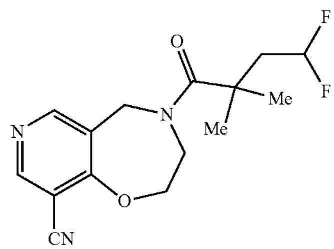 [SMILES: CC(C)(CC(F)F)C(=O)N1CCOc2c(C#N)cncc2C1] | | 310.5 | C |
| 150 | 4-(3-methoxy-2,2-dimethyl-propanoyl)-3,5-dihydro-2H-pyrido[3,4-f][1,4]oxazepine-9-carbonitrile | 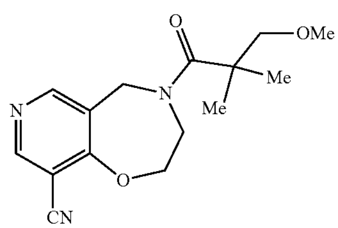 [SMILES: COCC(C)(C)C(=O)N1CCOc2c(C#N)cncc2C1] | | 290.5 | C |
| 151 | 4-(2-ethyl-2-methyl-butanoyl)-3,5-dihydro-2H-pyrido[3,4-f][1,4]oxazepine-9-carbonitrile | 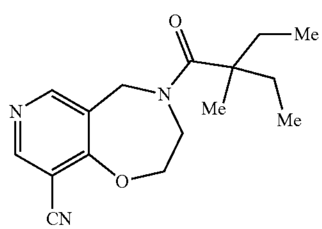 [SMILES: CCC(C)(CC)C(=O)N1CCOc2c(C#N)cncc2C1] | | 288.6 | C |
| 152 | 4-[3,3,3-trifluoro-2-methyl-2-(trifluoromethyl)propanoyl]-3,5-dihydro-2H-pyrido[3,4-f][1,4]oxazepine-9-carbonitrile | 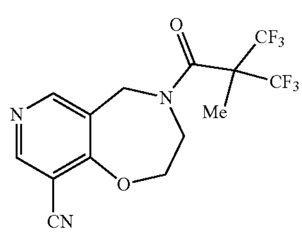 [SMILES: CC(C(=O)N1CCOc2c(C#N)cncc2C1)(C(F)(F)F)C(F)(F)F] | | 368.2 | C |
| 153 | 4-(2-methoxy-2-methyl-butanoyl)-3,5-dihydro-2H-pyrido[3,4-f][1,4]oxazepine-9-carbonitrile | 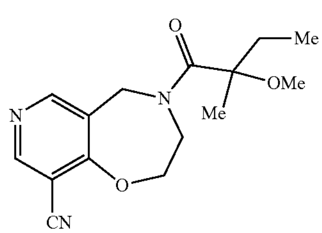 [SMILES: CCC(C)(OC)C(=O)N1CCOc2c(C#N)cncc2C1] | | 290.7 | C |

TABLE 1-continued

| Ex | Name | Structure | ¹H NMR | MS (M + H)⁺ | Method |
|---|---|---|---|---|---|
| 154 | 4-(2-cyclopropyl-2-methoxy-propanoyl)-3,5-dihydro-2H-pyrido[3,4-f][1,4]oxazepine-9-carbonitrile | 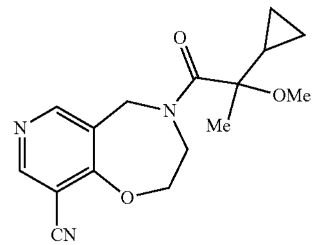 [SMILES: COC(C)(C(=O)N1CCOc2c(C#N)cncc2C1)C1CC1] | | 302.8 | C |
| 155 | 4-[1-(5-fluoropyrimidin-2-yl)piperidine-4-carbonyl]-3,5-dihydro-2H-pyrido[3,4-f][1,4]oxazepine-9-carbonitrile | 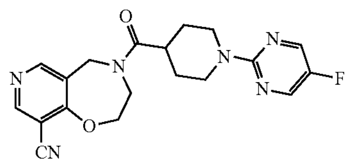 [SMILES: N#Cc1cncc2c1OCCN(C(=O)C1CCN(c3ncc(F)cn3)CC1)C2] | | 383.5 | C |
| 156 | (9-fluoro-3,5-dihydro-2H-pyrido[3,4-f][1,4]oxazepin-4-yl)-[1-(5-fluoropyrimidin-2-yl)-4-piperidyl]methanone | 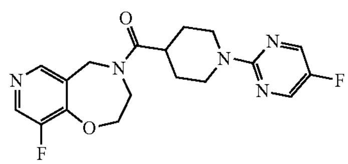 [SMILES: O=C(C1CCN(c2ncc(F)cn2)CC1)N1CCOc2c(F)cncc2C1] | | 376.6 | C |
| 157 | 4-(4-fluoro-1-pyrimidin-2-yl-piperidine-4-carbonyl)-3,5-dihydro-2H-pyrido[3,4-f][1,4]oxazepine-9-carbonitrile | 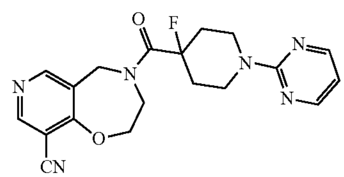 [SMILES: N#Cc1cncc2c1OCCN(C(=O)C1(F)CCN(c3ncccn3)CC1)C2] | | 383.66 | C |
| 158 | 4-(2-chloro-2-methyl-propanoyl)-3,5-dihydro-2H-pyrido[3,4-f][1,4]oxazepine-9-carbonitrile | 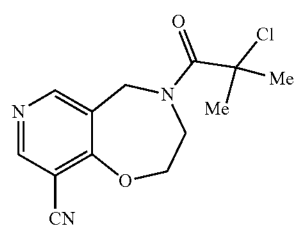 [SMILES: CC(C)(Cl)C(=O)N1CCOc2c(C#N)cncc2C1] | | 280.19 | C |
| 159 | 2-[4-fluoro-4-(9-fluoro-3,5-dihydro-2H-pyrido[3,4-f][1,4]oxazepine-4-carbonyl)-1-piperidyl]pyrimidine-5-carbonitrile | 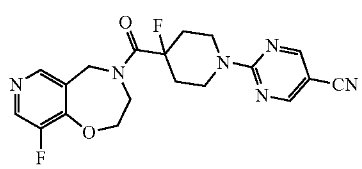 [SMILES: N#Cc1cnc(N2CCC(F)(C(=O)N3CCOc4c(F)cncc4C3)CC2)nc1] | | 401.64 | C |
| 160 | 2-[4-fluoro-4-(9-fluoro-3,5-dihydro-2H-pyrido[3,4-f][1,4]oxazepine-4-carbonyl)-1-piperidyl]pyrimidine-4-carbonitrile | 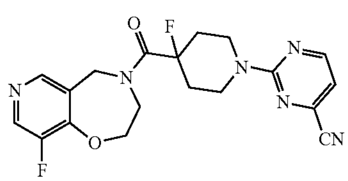 [SMILES: N#Cc1ccnc(N2CCC(F)(C(=O)N3CCOc4c(F)cncc4C3)CC2)n1] | | 401.69 | C |
| 161 | 4-[4-fluoro-1-(5-fluoropyrimidin-2-yl)piperidine-4-carbonyl]-3,5-dihydro-2H-pyrido[3,4-f][1,4]oxazepine-9-carbonitrile | 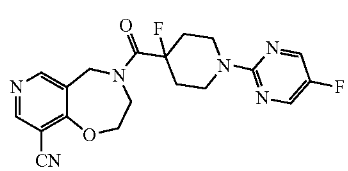 [SMILES: N#Cc1cncc2c1OCCN(C(=O)C1(F)CCN(c3ncc(F)cn3)CC1)C2] | | 401.64 | W |

TABLE 1-continued

| Ex | Name | Structure | ¹H NMR | MS (M + H)⁺ | Method |
|----|------|-----------|--------|-------------|--------|
| 162 | 4-[4-fluoro-1-(4-methylpyrimidin-2-yl)piperidine-4-carbonyl]-3,5-dihydro-2H-pyrido[3,4-f][1,4]oxazepine-9-carbonitrile | 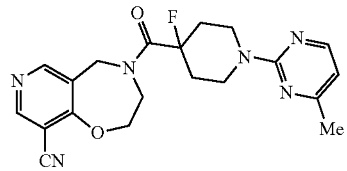 [SMILES: Cc1ccnc(N2CCC(F)(C(=O)N3CCOc4c(C#N)cncc4C3)CC2)n1] | | 397.69 | W |
| 163 | 4-[4-fluoro-1-(5-methylpyrimidin-2-yl)piperidine-4-carbonyl]-3,5-dihydro-2H-pyrido[3,4-f][1,4]oxazepine-9-carbonitrile | 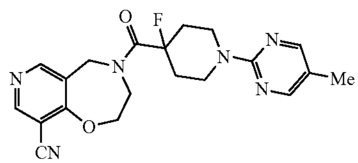 [SMILES: Cc1cnc(N2CCC(F)(C(=O)N3CCOc4c(C#N)cncc4C3)CC2)nc1] | | 397.69 | W |
| 164 | 4-[1-(5-chloropyrimidin-2-yl)-4-fluoro-piperidine-4-carbonyl]-3,5-dihydro-2H-pyrido[3,4-f][1,4]oxazepine-9-carbonitrile | 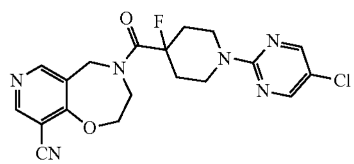 [SMILES: N#Cc1cncc2c1OCCN(C(=O)C1(F)CCN(c3ncc(Cl)cn3)CC1)C2] | | 417.32 | W |
| 165 | 4-[1-(5,7-dihydrofuro[3,4-d]pyrimidin-2-yl)-4-fluoro-piperidine-4-carbonyl]-3,5-dihydro-2H-pyrido[3,4-f][1,4]oxazepine-9-carbonitrile | 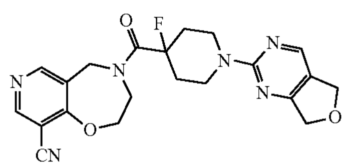 [SMILES: N#Cc1cncc2c1OCCN(C(=O)C1(F)CCN(c3ncc4c(n3)COC4)CC1)C2] | | 425.72 | W |
| 166 | 4-[4-fluoro-1-([1,2,4]triazolo[1,5-c]pyrimidin-5-yl)piperidine-4-carbonyl]-3,5-dihydro-2H-pyrido[3,4-f][1,4]oxazepine-9-carbonitrile | 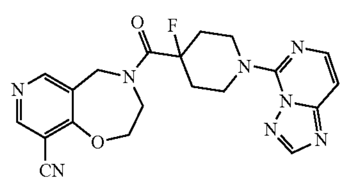 [SMILES: N#Cc1cncc2c1OCCN(C(=O)C1(F)CCN(c3nccc4ncnn34)CC1)C2] | | 423.71 | W |
| 167 | 4-[4-fluoro-1-[4-(trifluoromethyl)pyrimidin-2-yl]piperidine-4-carbonyl]-3,5-dihydro-2H-pyrido[3,4-f][1,4]oxazepine-9-carbonitrile | 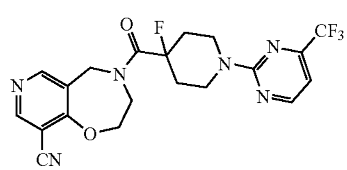 [SMILES: N#Cc1cncc2c1OCCN(C(=O)C1(F)CCN(c3nccc(C(F)(F)F)n3)CC1)C2] | | 451.52 | W |
| 168 | 4-[4-fluoro-1-[4-methyl-6-(trifluoromethyl)pyrimidin-2-yl]piperidine-4-carbonyl]-3,5-dihydro-2H-pyrido[3,4-f][1,4]oxazepine-9-carbonitrile | 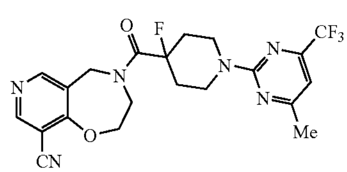 [SMILES: Cc1cc(C(F)(F)F)nc(N2CCC(F)(C(=O)N3CCOc4c(C#N)cncc4C3)CC2)n1] | | 465.64 | W |

TABLE 1-continued

| Ex | Name | Structure | ¹H NMR | MS (M + H)⁺ | Method |
|---|---|---|---|---|---|
| 169 | 4-[4-fluoro-1-(9-methylpurin-2-yl)piperidine-4-carbonyl]-3,5-dihydro-2H-pyrido[3,4-f][1,4]oxazepine-9-carbonitrile | 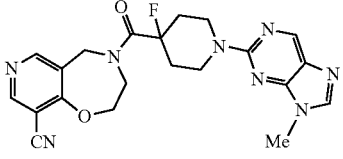 [SMILES: Cn1cnc2cnc(N3CCC(F)(C(=O)N4CCOc5c(C#N)cncc5C4)CC3)nc21] | | 437.70 | W |
| 170 | 4-[4-fluoro-1-[5-(trifluoromethyl)pyrimidin-2-yl]piperidine-4-carbonyl]-3,5-dihydro-2H-pyrido[3,4-f][1,4]oxazepine-9-carbonitrile | 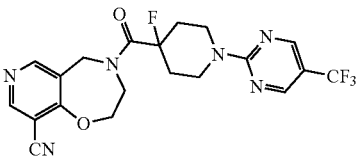 [SMILES: N#Cc1cncc2c1OCCN(C(=O)C1(F)CCN(c3ncc(C(F)(F)F)cn3)CC1)C2] | | 451.56 | W |
| 171 | 4-[4-fluoro-1-[2-(trifluoromethyl)pyrimidin-4-yl]piperidine-4-carbonyl]-3,5-dihydro-2H-pyrido[3,4-f][1,4]oxazepine-9-carbonitrile | 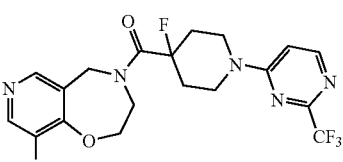 | | 451.61 | W |
| 172 | 4-[4-fluoro-1-(2-methoxypyrimidin-4-yl)piperidine-4-carbonyl]-3,5-dihydro-2H-pyrido[3,4-f][1,4]oxazepine-9-carbonitrile | 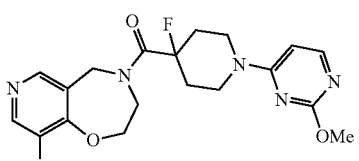 | | 413.7 | W |
| 173 | 4-[4-fluoro-1-(5-methyloxazole-4-carbonyl)piperidine-4-carbonyl]-3,5-dihydro-2H-pyrido[3,4-f][1,4]oxazepine-9-carbonitrile | 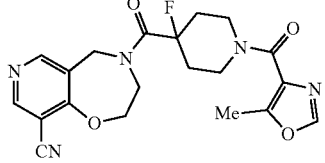 | | 414.42 | C |
| 174 | isobutyl 4-(9-cyano-3,5-dihydro-2H-pyrido[3,4-f][1,4]oxazepine-4-carbonyl)-4-fluoro-piperidine-1-carboxylate | 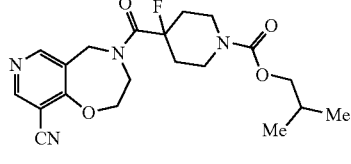 | | 405.76 | D |
| 175 | 4-(2,2-dimethylpropanoyl)-3,5-dihydro-2H-pyrido[3,4-f][1,4]oxazepine-9-carbonitrile | 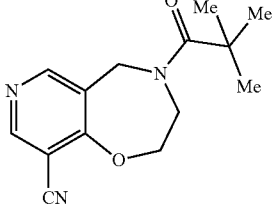 | | 260.56 | D |
| 176 | 4-[3-fluoro-1-(5-fluoropyrimidin-2-yl)pyrrolidine-3-carbonyl]-3,5-dihydro-2H-pyrido[3,4-f][1,4]oxazepine-9-carbonitrile | 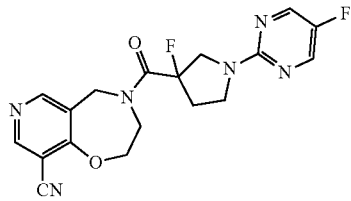 [SMILES: N#Cc1cncc2c1OCCN(C(=O)C1(F)CCN(c3ncc(F)cn3)C1)C2] | | 387.57 | C |

TABLE 1-continued

| Ex | Name | Structure | ¹H NMR | MS (M + H)⁺ | Method |
|---|---|---|---|---|---|
| 177 | 4-[4-chloro-1-(5-fluoropyrimidin-2-yl)piperidine-4-carbonyl]-3,5-dihydro-2H-pyrido[3,4-f][1,4]oxazepine-9-carbonitrile | 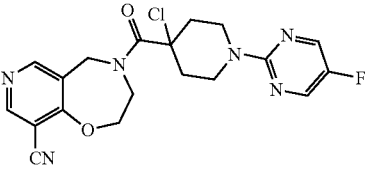 | | 417.23 | C |
| 178 | 4-[1-(4-ethoxy-5-fluoro-pyrimidin-2-yl)-4-fluoro-piperidine-4-carbonyl]-3,5-dihydro-2H-pyrido[3,4-f][1,4]oxazepine-9-carbonitrile | 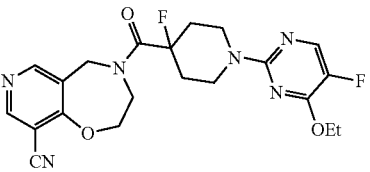 [SMILES: CCOc1nc(N2CCC(F)(C(=O)N3CCOc4c(C#N)cncc4C3)CC2)ncc1F] | | 445.47 | W |
| 179 | 4-[4-fluoro-1-(8-fluoro-[1,2,4]triazolo[1,5-c]pyrimidin-5-yl)piperidine-4-carbonyl]-3,5-dihydro-2H-pyrido[3,4-f][1,4]oxazepine-9-carbonitrile | 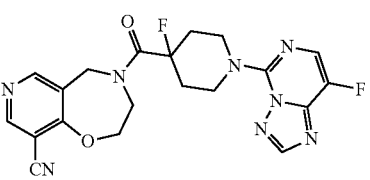 [SMILES: N#Cc1cncc2c1OCCN(C(=O)C1(F)CCN(c3ncc(F)c4ncnn34)CC1)C2] | | | |
| 180 | 4-(4-fluoro-1-imidazo[1,2-a]pyrimidin-5-yl-piperidine-4-carbonyl)-3,5-dihydro-2H-pyrido[3,4-f][1,4]oxazepine-9-carbonitrile | 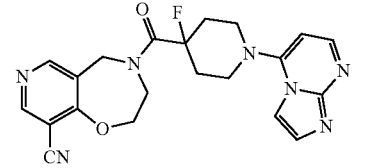 [SMILES: N#Cc1cncc2c1OCCN(C(=O)C1(F)CCN(c3ccnc4nccn34)CC1)C2] | | 422.7 | W |
| 181 | 4-[3-(5-fluoropyrimidin-2-yl)sulfanyl-2,2-dimethyl-propanoyl]-3,5-dihydro-2H-pyrido[3,4-f][1,4]oxazepine-9-carbonitrile | 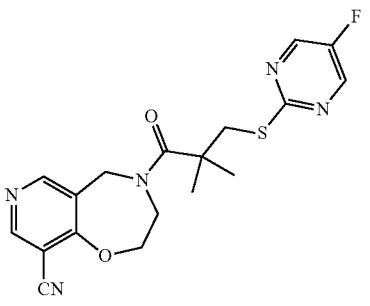 [SMILES: CC(C)(CSc1ncc(F)cn1)C(=O)N1CCOc2c(C#N)cncc2C1] | | 388.4 | C |
| 182 | 4-[4-cyano-1-(5-fluoropyrimidin-2-yl)piperidine-4-carbonyl]-3,5-dihydro-2H-pyrido[3,4-f][1,4]oxazepine-9-carbonitrile | 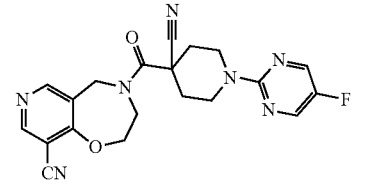 [SMILES: N#Cc1cncc2c1OCCN(C(=O)C1(C#N)CCN(c3ncc(F)cn3)CC1)C2] | | 408.4 | C |
| 183 | 4-[1-(5-fluoropyrimidin-2-yl)piperidine-4-carbonyl]-3,5-dihydro-2H-1,4-benzoxazepine-9-carbonitrile | 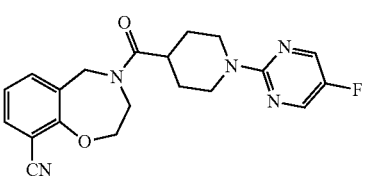 [SMILES: N#Cc1cccc2c1OCCN(C(=O)C1CCN(c3ncc(F)cn3)CC1)C2] | | 382.4 | B |

TABLE 1-continued

| Ex | Name | Structure | ¹H NMR | MS (M + H)⁺ | Method |
|---|---|---|---|---|---|
| 184 | 4-[4-fluoro-1-(5-fluoro-4-methyl-pyrimidin-2-yl)piperidine-4-carbonyl]-3,5-dihydro-2H-pyrido[3,4-f][1,4]oxazepine-9-carbonitrile | 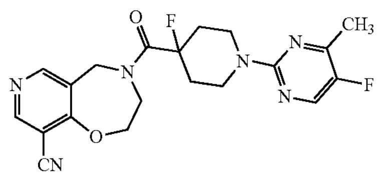 [SMILES: Cc1nc(N2CCC(F)(C(=O)N3CCOc4c(C#N)cncc4C3)CC2)ncc1F] | | 414.4 | W |
| 185 | 4-[1-(5-fluoropyrimidin-2-yl)-4-methoxy-piperidine-4-carbonyl]-3,5-dihydro-2H-pyrido[3,4-f][1,4]oxazepine-9-carbonitrile | 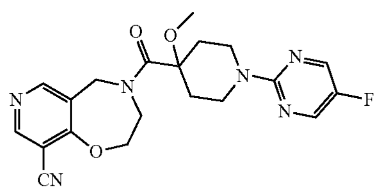 [SMILES: COC1(C(=O)N2CCOc3c(C#N)cncc3C2)CCN(c2ncc(F)cn2)CC1] | | 413.4 | W |
| 186 | 4-[1-(2-chloro-5-methoxy-pyrimidin-4-yl)-4-fluoro-piperidine-4-carbonyl]-3,5-dihydro-2H-pyrido[3,4-f][1,4]oxazepine-9-carbonitrile | 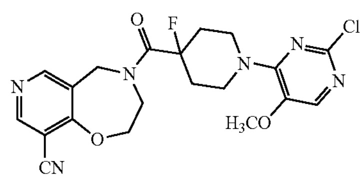 [SMILES: COc1cnc(Cl)nc1N1CCC(F)(C(=O)N2CCOc3c(C#N)cncc3C2)CC1] | | 447.4 | W |
| 187 | 4-[1-(5-fluoropyrimidin-2-yl)-3-methyl-piperidine-4-carbonyl]-3,5-dihydro-2H-pyrido[3,4-f][1,4]oxazepine-9-carbonitrile | 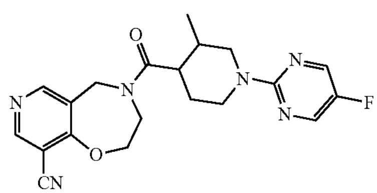 [SMILES: CC1CN(c2ncc(F)cn2)CCC1C(=O)N1CCOc2c(C#N)cncc2C1] | | 397.4 | C |
| 188 | 4-[4-fluoro-1-(5-fluoro-2-pyridyl)piperidine-4-carbonyl]-3,5-dihydro-2H-pyrido[3,4-f][1,4]oxazepine-9-carbonitrile | 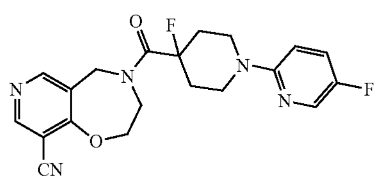 [SMILES: N#Cc1cncc2c1OCCN(C(=O)C1(F)CCN(c3ccc(F)cn3)CC1)C2] | | 400.4 | W |
| 189 | 4-[1-[5-(difluoromethyl)pyrimidin-2-yl]-4-fluoro-piperidine-4-carbonyl]-3,5-dihydro-2H-pyrido[3,4-f][1,4]oxazepine-9-carbonitrile | 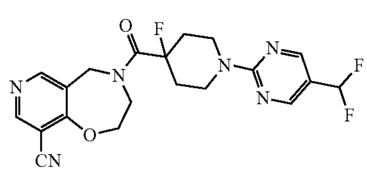 [SMILES: N#Cc1cncc2c1OCCN(C(=O)C1(F)CCN(c3ncc(C(F)F)cn3)CC1)C2] | | 433.4 | W |
| 190 | 4-[1-(5-fluoro-2-pyridyl)-4-methoxy-piperidine-4-carbonyl]-3,5-dihydro-2H-pyrido[3,4-f][1,4]oxazepine-9-carbonitrile | 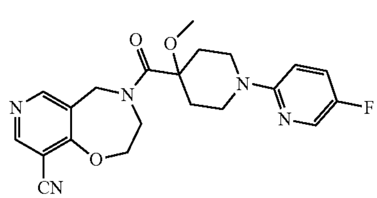 [SMILES: COC1(C(=O)N2CCOc3c(C#N)cncc3C2)CCN(c2ccc(F)cn2)CC1] | | 412.4 | W |

TABLE 1-continued

| Ex | Name | Structure | ¹H NMR | MS (M + H)⁺ | Method |
|---|---|---|---|---|---|
| 191 | 4-[4-fluoro-1-(5-fluoro-4-methoxy-pyrimidin-2-yl)piperidine-4-carbonyl]-3,5-dihydro-2H-pyrido[3,4-f][1,4]oxazepine-9-carbonitrile | 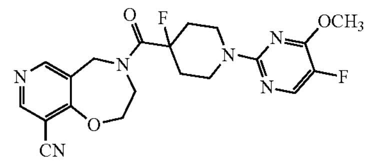 [SMILES: COc1nc(N2CCC(F)(C(=O)N3CCOc4c(C#N)cncc4C3)CC2)ncc1F] | | 431.4 | W |
| 192 | 4-[1-(3,5-difluoro-2-pyridyl)-4-fluoro-piperidine-4-carbonyl]-3,5-dihydro-2H-pyrido[3,4-f][1,4]oxazepine-9-carbonitrile | 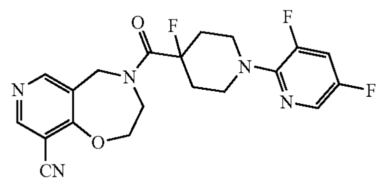 [SMILES: N#Cc1cncc2c1OCCN(C(=O)C1(F)CCN(c3ncc(F)cc3F)CC1)C2] | | 418.4 | W |
| 193 | 4-[1-(5,6-difluoro-3-pyridyl)-4-fluoro-piperidine-4-carbonyl]-3,5-dihydro-2H-pyrido[3,4-f][1,4]oxazepine-9-carbonitrile | 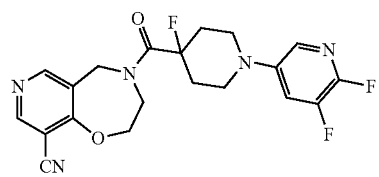 [SMILES: N#Cc1cncc2c1OCCN(C(=O)C1(F)CCN(c3cnc(F)c(F)c3)CC1)C2] | | 418.4 | AJ |
| 194 | 4-[1-(5-fluoro-4-methoxy-pyrimidin-2-yl)-4-methoxy-piperidine-4-carbonyl]-3,5-dihydro-2H-pyrido[3,4-f][1,4]oxazepine-9-carbonitrile | 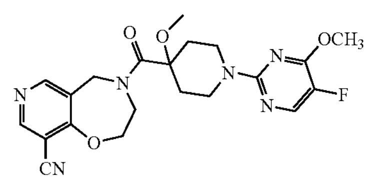 [SMILES: COc1nc(N2CCC(OC)(C(=O)N3CCOc4c(C#N)cncc4C3)CC2)ncc1F] | | 443.4 | W |
| 195 | 4-[1-(5-fluoro-4-methoxy-6-methyl-pyrimidin-2-yl)-4-methoxy-piperidine-4-carbonyl]-3,5-dihydro-2H-pyrido[3,4-f][1,4]oxazepine-9-carbonitrile | 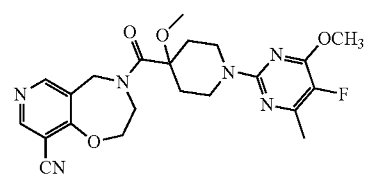 [SMILES: COc1nc(N2CCC(OC)(C(=O)N3CCOc4c(C#N)cncc4C3)CC2)nc(C)c1F] | | 457.4 | W |
| 196 | 4-[4-fluoro-1-(5-fluoro-4-methoxy-6-methyl-pyrimidin-2-yl)piperidine-4-carbonyl]-3,5-dihydro-2H-pyrido[3,4-f][1,4]oxazepine-9-carbonitrile | 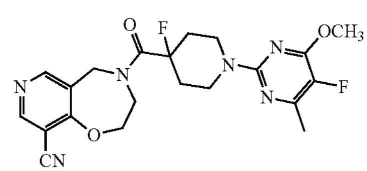 [SMILES: COc1nc(N2CCC(F)(C(=O)N3CCOc4c(C#N)cncc4C3)CC2)nc(C)c1F] | | 445.4 | W |
| 197 | 4-[4-fluoro-1-(4-methoxyquinazolin-2-yl)piperidine-4-carbonyl]-3,5-dihydro-2H-pyrido[3,4-f][1,4]oxazepine-9-carbonitrile | 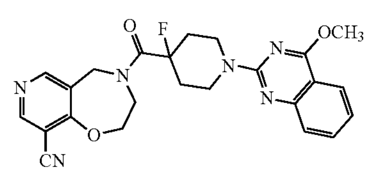 [SMILES: COc1nc(N2CCC(F)(C(=O)N3CCOc4c(C#N)cncc4C3)CC2)nc2ccccc12] | | 463.4 | AJ |
| 198 | 4-(4-fluoro-1-quinoxalin-2-yl-piperidine-4-carbonyl)-3,5-dihydro-2H-pyrido[3,4-f][1,4]oxazepine-9-carbonitrile | 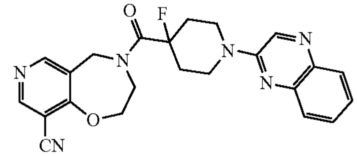 [SMILES: N#Cc1cncc2c1OCCN(C(=O)C1(F)CCN(c3cnc4ccccc4n3)CC1)C2] | | 433.4 | AJ |

TABLE 1-continued

| Ex | Name | Structure | ¹H NMR | MS (M + H)⁺ | Method |
|---|---|---|---|---|---|
| 199 | 4-[4-fluoro-1-(3-isoquinolyl)piperidine-4-carbonyl]-3,5-dihydro-2H-pyrido[3,4-f][1,4]oxazepine-9-carbonitrile | 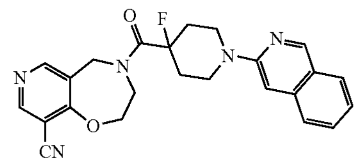 [SMILES: N#Cc1cncc2c1OCCN(C(=O)C1(F)CCN(c3cc4ccccc4cn3)CC1)C2] | | 432.4 | AJ |
| 200 | 4-[4-fluoro-1-(2-quinolyl)piperidine-4-carbonyl]-3,5-dihydro-2H-pyrido[3,4-f][1,4]oxazepine-9-carbonitrile | 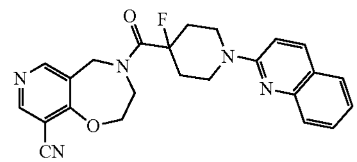 [SMILES: N#Cc1cncc2c1OCCN(C(=O)C1(F)CCN(c3ccc4ccccc4n3)CC1)C2] | | 432.4 | AJ |
| 201 | 4-[1-(4-cyclopropyl-5-fluoro-pyrimidin-2-yl)-4-fluoro-piperidine-4-carbonyl]-3,5-dihydro-2H-pyrido[3,4-f][1,4]oxazepine-9-carbonitrile | 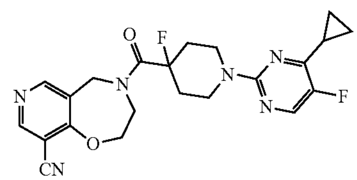 [SMILES: N#Cc1cncc2c1OCCN(C(=O)C1(F)CCN(c3ncc(F)c(C4CC4)n3)CC1)C2] | | 441.4 | W |
| 202 | 4-[1-(2-chloro-5-fluoro-pyrimidin-4-yl)-4-fluoro-piperidine-4-carbonyl]-3,5-dihydro-2H-pyrido[3,4-f][1,4]oxazepine-9-carbonitrile | 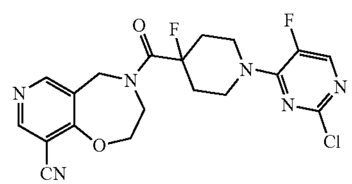 [SMILES: N#Cc1cncc2c1OCCN(C(=O)C1(F)CCN(c3nc(Cl)ncc3F)CC1)C2] | | 435.4 | W |
| 203 | [1-(5-fluoropyrimidin-2-yl)-4-piperidyl]-(1,3,4,5-tetrahydro-2-benzazepin-2-yl)methanone | 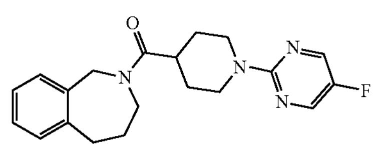 [SMILES: O=C(C1CCN(c2ncc(F)cn2)CC1)N1CCCc2ccccc2C1] | | 355.4 | C |
| 204 | 4-[1-(8-fluoro-[1,2,4]triazolo[1,5-c]pyrimidin-5-yl)piperidine-4-carbonyl]-3,5-dihydro-2H-pyrido[3,4-f][1,4]oxazepine-9carbonitrile | 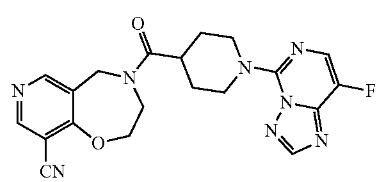 [SMILES: N#Cc1cncc2c1OCCN(C(=O)C1CCN(c3ncc(F)c4ncnn34)CC1)C2] | | | |
| 205 | 4-(1-pyrazolo[1,5-a]pyrimidin-7-ylpiperidine-4-carbonyl)-3,5-dihydro-2H-pyrido[3,4-f][1,4]oxazepine-9-carbonitrile | 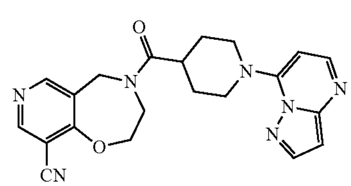 [SMILES: N#Cc1cncc2c1OCCN(C(=O)C1CCN(c3ccnc4ccnn34)CC1)C2] | | 404.4 | W |
| 206 | 4-[4-fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile | 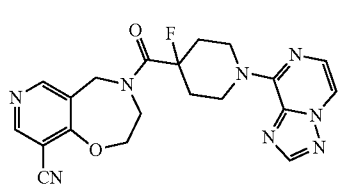 [SMILES: N#Cc1cncc2c1OCCN(C(=O)C1(F)CCN(c3nccn4ncnc34)CC1)C2] | | 423.1 | W |

TABLE 1-continued

| Ex | Name | Structure | ¹H NMR | MS (M + H)⁺ | Method |
|---|---|---|---|---|---|
| 207 | 1-(9-fluoro-3,5-dihydro-2H-pyrido[3,4-f][1,4]oxazepin-4-yl)-2,2-dimethyl-butan-1-one | 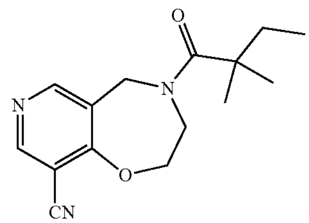 [SMILES: CCC(C)(C)C(=O)N1CCOc2c(C#N)cncc2C1] | | 267.3 | B |
| 208 | 4-[3-fluoro-1-(5-fluoropyrimidin-2-yl)-4-hydroxy-piperidine-4-carbonyl]-3,5-dihydro-2H-pyrido[3,4-f][1,4]oxazepine-9-carbonitrile | 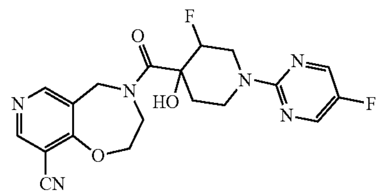 [SMILES: N#Cc1cncc2c1OCCN(C(=O)C1(O)CCN(c3ncc(F)cn3)CC1F)C2] | | 417.4 | B |
| 209 | [1-[4-(2,2-difluoroethoxy)-1,3,5-triazin-2-yl]-4-methoxy-4-piperidyl]-(9-fluoro-3,5-dihydro-2H-pyrido[3,4-f][1,4]oxazepin-4-yl)methanone | 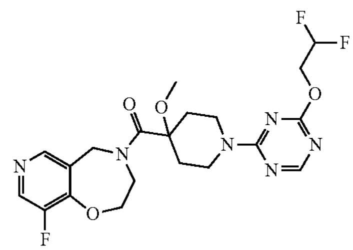 [SMILES: COC1(C(=O)N2CCOc3c(F)cncc3C2)CCN(c2ncnc(OCC(F)F)n2)CC1] | | 469.4 | W |
| 210 | [1-[4-(2,2-difluoroethoxy)-1,3,5-triazin-2-yl]-4-piperidyl]-(9-fluoro-3,5-dihydro-2H-pyrido[3,4-f][1,4]oxazepin-4-yl)methanone | 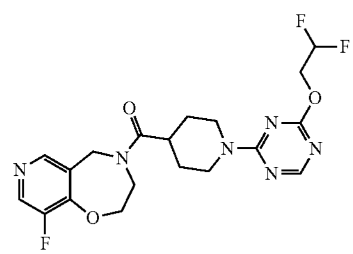 [SMILES: O=C(C1CCN(c2ncnc(OCC(F)F)n2)CC1)N1CCOc2c(F)cncc2C1] | | 439.4 | W |
| 211 | 4-[1-(5-fluoropyrimidin-2-yl)-3-hydroxy-piperidine-4-carbonyl]-3,5-dihydro-2H-pyrido[3,4-f][1,4]oxazepine-9-carbonitrile | 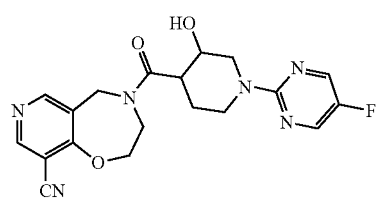 [SMILES: N#Cc1cncc2c1OCCN(C(=O)C1CCN(c3ncc(F)cn3)CC1O)C2] | | 399.4 | W |
| 212 | 4-[4-fluoro-1-([1,2,4]triazolo[1,5-a]pyrimidin-7-yl)piperidine-4-carbonyl]-3,5-dihydro-2H-pyrido[3,4-f][1,4]oxazepine-9-carbonitrile | 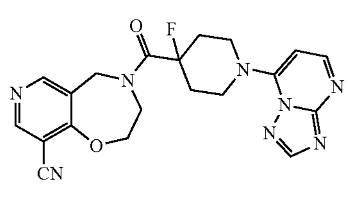 [SMILES: N#Cc1cncc2c1OCCN(C(=O)C1(F)CCN(c3ccnc4ncnn34)CC1)C2] | | 423.2 | W |
| 213 | 4-[3,3,4-trifluoro-1-(5-fluoropyrimidin-2-yl)piperidine-4-carbonyl]-3,5-dihydro-2H-pyrido[3,4-f][1,4]oxazepine-9-carbonitrile | 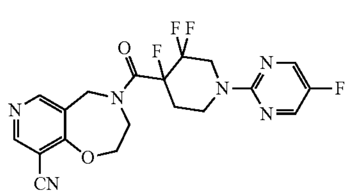 [SMILES: N#Cc1cncc2c1OCCN(C(=O)C1(F)CCN(c3ncc(F)cn3)CC1(F)F)C2] | | 437.3 | D |

TABLE 1-continued

| Ex | Name | Structure | ¹H NMR | MS (M + H)⁺ | Method |
|---|---|---|---|---|---|
| 214 | 4-[3,3-difluoro-4-methyl-1-pyrimidin-2-yl-piperidine-4-carbonyl]-3,5-dihydro-2H-pyrido[3,4-f][1,4]oxazepine-9-carbonitrile | 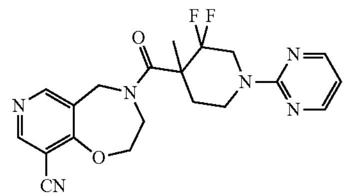 [SMILES: CC1(C(=O)N2CCOc3c(C#N)cncc3C2)CCN(c2ncccn2)CC1(F)F] | | 415.3 | D |
| 215 | 4-(1-(5-chloropyrimidin-2-yl)-3,3-difluoro-4-methylpiperidine-4-carbonyl)-2,3,4,5-tetrahydropyrido[3,4-f][1,4]oxazepine-9-carbonitrile | 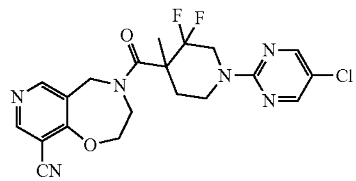 [SMILES: CC1(C(=O)N2CCOc3c(C#N)cncc3C2)CCN(c2ncc(Cl)cn2)CC1(F)F] | | 449.3 | D |
| 216 | 4-[3,3-difluoro-1-(5-fluoro-6-oxo-1H-pyrimidin-2-yl)-4-methyl-piperidine-4-carbonyl]-3,5-dihydro-2H-pyrido[3,4-f][1,4]oxazepine-9-carbonitrile | 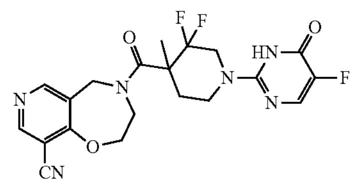 [SMILES: CC1(C(=O)N2CCOc3c(C#N)cncc3C2)CCN(c2ncc(F)c(=O)[nH]2)CC1(F)F] | | 449.3 | W |
| 217 | 4-[3,3-difluoro-1-[5-fluoro-4-(2-methoxyethoxy)pyrimidin-2-yl]-4-methyl-piperidine-4-carbonyl]-3,5-dihydro-2H-pyrido[3,4-f][1,4]oxazepine-9-carbonitrile | 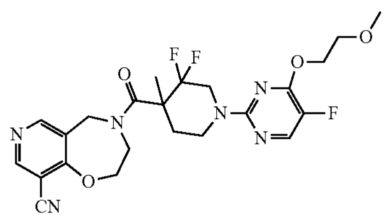 [SMILES: COCCOc1nc(N2CCC(C)(C(=O)N3CCOc4c(C#N)cncc4C3)C(F)(F)C2)ncc1F] | | 507.4 | W |
| 218 | 4-(3,3-difluoro-1-imidazo[2,1-f][1,2,4]triazin-4-yl-piperidine-4-carbonyl)-3,5-dihydro-2H-pyrido[3,4-f][1,4]oxazepine-9-carbonitrile) | 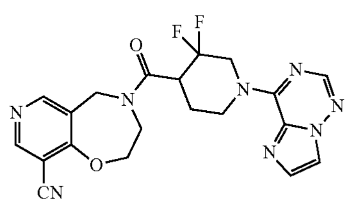 [SMILES: N#Cc1cncc2c1OCCN(C(=O)C1CCN(c3ncnn4ccnc34)CC1(F)F)C2] | | 441.4 | W |
| 219 | 4-[3,3-difluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile | 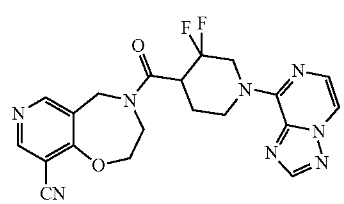 [SMILES: N#Cc1cncc2c1OCCN(C(=O)C1CCN(c3nccn4ncnc34)CC1(F)F)C2] | | 441.3 | W |
| 220 | 4-(3,3-difluoro-1-pyrazolo[1,5-a][1,3,5]triazin-4-yl-piperidine-4-carbonyl)-3,5-dihydro-2H-pyrido[3,4-f][1,4]oxazepine-9-carbonitrile | 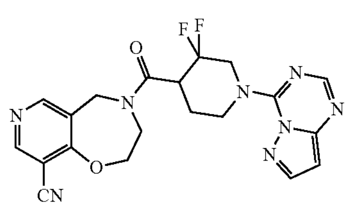 [SMILES: N#Cc1cncc2c1OCCN(C(=O)C1CCN(c3ncnc4ccnn34)CC1(F)F)C2] | | 441.4 | W |

TABLE 1-continued

| Ex | Name | Structure | ¹H NMR | MS (M + H)+ | Method |
|---|---|---|---|---|---|
| 221 | 4-(3,3-difluoro-1-pyrazolo[1,5-a]pyrimidin-7-yl-piperidine-4-carbonyl)-3,5-dihydro-2H-pyrido[3,4-f][1,4]oxazepine-9-carbonitrile | 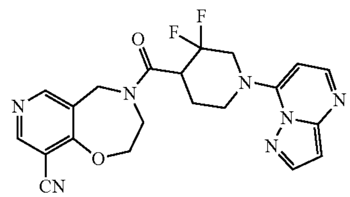 [SMILES: N#Cc1cncc2c1OCCN(C(=O)C1CCN(c3ccnc4ccnn34)CC1(F)F)C2] | | 440.4 | W |
| 222 | 4-[3,3-difluoro-4-methyl-1-([1,2,4]triazolo[1,5-a]pyrazin-8-yl)piperidine-4-carbonyl]-3,5-dihydro-2H-pyrido[3,4-f][1,4]oxazepine-9-carbonitrile | 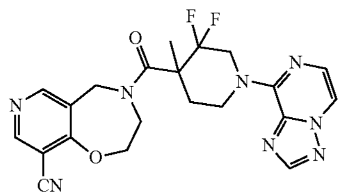 [SMILES: CC1(C(=O)N2CCOc3c(C#N)cncc3C2)CCN(c2nccn3ncnc23)CC1(F)F] | | 455.1 | W |
| 223 | 4-[(3,4)-trans-3-fluoro-1-(5-fluoropyrimidin-2-yl)-4-methyl-piperidine-4-carbonyl]-3,5-dihydro-2H-pyrido[3,4-f][1,4]oxazepine-9-carbonitrile | 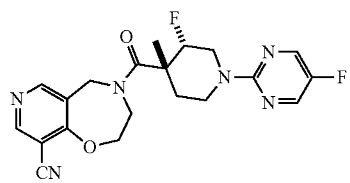 [SMILES: C[C@]1(C(=O)N2CCOc3c(C#N)cncc3C2)CCN(c2ncc(F)cn2)C[C@H]1F] | | 415.4 | D |
| 224 | 4-[(3,4)-trans-3-fluoro-1-(2-methyl-3-oxo-pyridazin-4-yl)piperidine-4-carbonyl]-3,5-dihydro-2H-pyrido[3,4-f][1,4]oxazepine-9-carbonitrile | 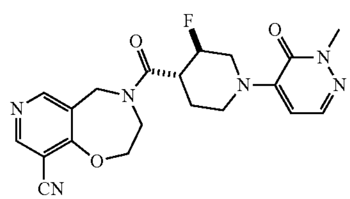 | | 435.0 [M + Na]+ | AJ |
| 225 | 4-[(3,4)-trans-3-fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile | 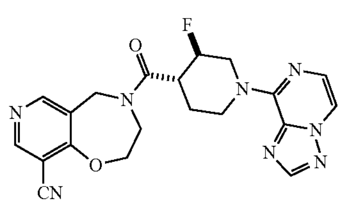 | | 423.1 | W |
| 226 | 4-[(3,4)-trans-3-fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile | 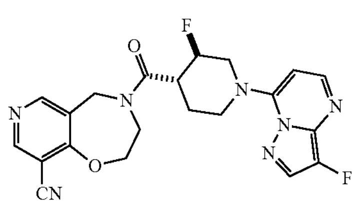 | | 440.1 | W |
| 227 | 4-[1-(3-chloropyrazolo[1,5-a]pyrimidin-7-yl)-(3,4)-trans-3-fluoro-piperidine-4-carbonyl]-3,5-dihydro-2H-pyrido[3,4-f][1,4]oxazepine-9-carbonitrile | 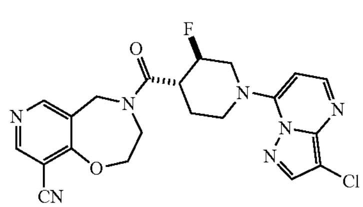 | | 456.1 | W |

TABLE 1-continued

| Ex | Name | Structure | ¹H NMR | MS (M + H)⁺ | Method |
|---|---|---|---|---|---|
| 228 | 4-[1-(3-fluoropyrazolo[1,5-a]pyrimidin-7-yl)piperidine-4-carbonyl]-3,5-dihydro-2H-pyrido[3,4-f][1,4]oxazepine-9-carbonitrile | 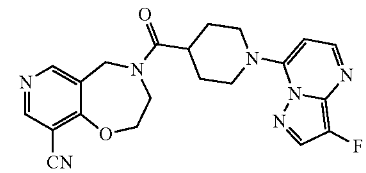 [SMILES: N#Cc1cncc2c1OCCN(C(=O)C1CCN(c3ccnc4c(F)cnn34)CC1)C2] | | 422.1 | W |
| 229 | 4-[1-(3-chloropyrazolo[1,5-a]pyrimidin-7-yl)piperidine-4-carbonyl]-3,5-dihydro-2H-pyrido[3,4-f][1,4]oxazepine-9-carbonitrile | 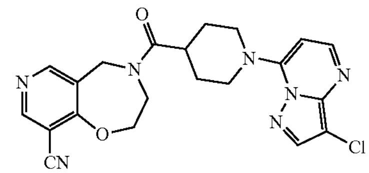 [SMILES: N#Cc1cncc2c1OCCN(C(=O)C1CCN(c3ccnc4c(Cl)cnn34)CC1)C2] | | 438.2 | W |
| 230 | 4-[1-(5-fluoropyrimidin-2-yl)piperidine-4-carbonyl]spiro[2,5-dihydropyrido[3,4-f][1,4]oxazepine-3,1'-cyclopropane]-9-carbonitrile | 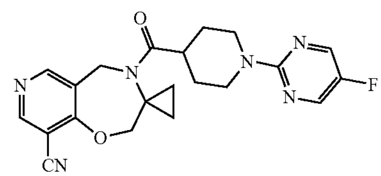 [SMILES: N#Cc1cncc2c1OCC1(CC1)N(C(=O)C1CCN(c3ncc(F)cn3)CC1)C2] | | 409.1 | D |
| 231 | 4-[4-(5-fluoropyrimidin-2-yl)-1,4-oxazepane-7-carbonyl]-3,5-dihydro-2H-pyrido[3,4-f][1,4]oxazepine-9-carbonitrile | 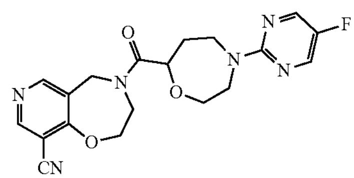 [SMILES: N#Cc1cncc2c1OCCN(C(=O)C1CCN(c3ncc(F)cn3)CCO1)C2] | | 399.4 | W |
| 232 | 4-[4-fluoro-1-[4-methoxy-6-(trifluoromethyl)pyrimidin-2-yl]piperidine-4-carbonyl]-3,5-dihydro-2H-pyrido[3,4-f][1,4]oxazepine-9-carbonitrile | 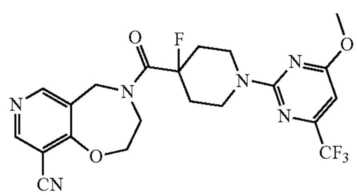 [SMILES: COc1cc(C(F)(F)F)nc(N2CCC(F)(C(=O)N3CCOc4c(C#N)cncc4C3)CC2)n1] | | 481.4 | W |
| 233 | 4-[1-(4-cyclopropyl-5-fluoro-pyrimidin-2-yl)-4-methoxy-piperidine-4-carbonyl]-3,5-dihydro-2H-pyrido[3,4-f][1,4]oxazepine-9-carbonitrile | 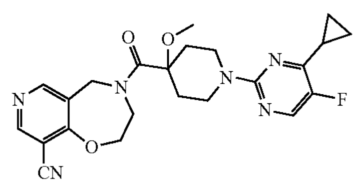 [SMILES: COC1(C(=O)N2CCOc3c(C#N)cncc3C2)CCN(c2ncc(F)c(C3CC3)n2)CC1] | | 453.4 | W |
| 234 | 3,5-dihydro-2H-pyrido[3,4-f][1,4]oxazepin-4-yl-[1-(5-fluoropyrimidin-2-yl)-4-methoxy-4-piperidyl]methanone | 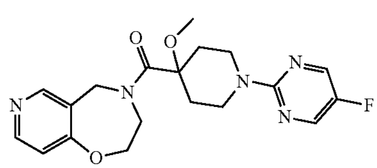 [SMILES: COC1(C(=O)N2CCOc3ccncc3C2)CCN(c2ncc(F)cn2)CC1] | | 388.4 | W |
| 235 | 3,5-dihydro-2H-pyrido[3,4-f][1,4]oxazepin-4-yl-[1-(5-fluoro-4-methoxy-pyrimidin-2-yl)-4-methoxy-4-piperidyl]methanone | 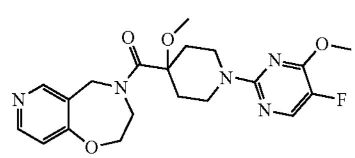 [SMILES: COc1nc(N2CCC(OC)(C(=O)N3CCOc4ccncc4C3)CC2)ncc1F] | | 418.4 | W |

TABLE 1-continued

| Ex | Name | Structure | ¹H NMR | MS (M + H)⁺ | Method |
|---|---|---|---|---|---|
| 236 | (9-fluoro-3,5-dihydro-2H-pyrido[3,4-f][1,4]oxazepin-4-yl)-[1-(5-fluoro-4-methoxy-pyrimidin-piperidyl]methanone | 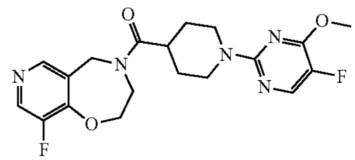 [SMILES: COc1nc(N2CCC(C(=O)N3CCOc4c(F)cncc4C3)CC2)ncc1F] | | 406.4 | W |
| 237 | [1-(5-fluoro-4-methoxy-pyrimidin-2-yl)-4-piperidyl]-(1,3,4,5-tetrahydro-2-benzazepin-2-yl)methanone | 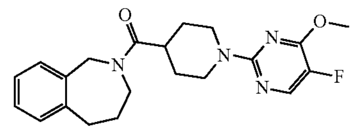 [SMILES: COc1nc(N2CCC(C(=O)N3CCCc4ccccc4C3)CC2)ncc1F] | | 385.4 | W |
| 238 | 3,5-dihydro-2H-pyrido[3,4-f][1,4]oxazepin-4-yl-[1-(5-fluoro-4-methoxy-pyrimidin-piperidyl]methanone | 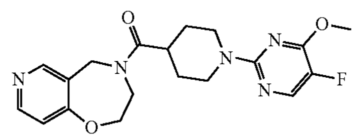 [SMILES: COc1nc(N2CCC(C(=O)N3CCOc4ccncc4C3)CC2)ncc1F] | | 388.4 | W |
| 239 | 4-(4-methoxy-1-pyrimidin-2-yl-piperidine-4-carbonyl)-3,5-dihydro-2H-pyrido[3,4-f][1,4]oxazepine-9-carbonitrile | 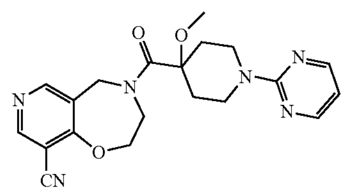 [SMILES: COC1(C(=O)N2CCOc3c(C#N)cncc3C2)CCN(c2ncccn2)CC1] | | 395.4 | W |
| 240 | 4-(2-methyltetrahydropyran-2-carbonyl)-3,5-dihydro-2H-pyrido[3,4-f][1,4]oxazepine-9-carbonitrile | 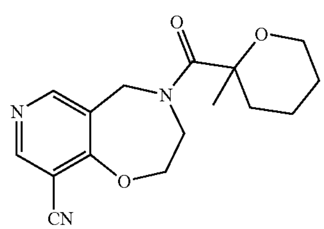 [SMILES: CC1(C(=O)N2CCOc3c(C#N)cncc3C2)CCCCO1] | | 301.3 | B |
| 241 | 4-[(3,4)-cis-3-fluoro-1-(5-fluoropyrimidin-2-yl)piperidine-4-carbonyl]-3,5-dihydro-2H-pyrido[3,4-f][1,4]oxazepine-9-carbonitrile | 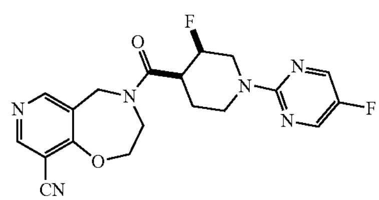 | | 401.4 | W |
| 242 | 4-[(3,4)-trans-3-fluoro-1-(5-fluoropyrimidin-2-yl)piperidine-4-carbonyl]-3,5-dihydro-2H-pyrido[3,4-f][1,4]oxazepine-9-carbonitrile | 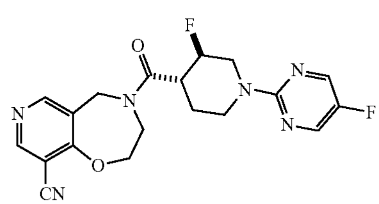 | | 401.4 | B |
| 243 | 4-[3,3-difluoro-1-(5-fluoropyrimidin-2-yl)piperidine-4-carbonyl]-3,5-dihydro-2H-pyrido[3,4-f][1,4]oxazepine-9-carbonitrile | 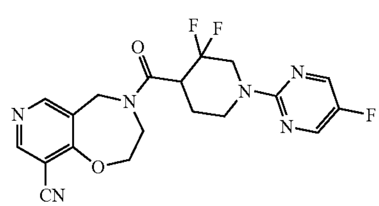 [SMILES: N#Cc1cncc2c1OCCN(C(=O)C1CCN(c3ncc(F)cn3)CC1(F)F)C2] | | 419.4 | W |

TABLE 1-continued

| Ex | Name | Structure | ¹H NMR | MS (M + H)⁺ | Method |
|---|---|---|---|---|---|
| 244 | [3,3-difluoro-1-(5-fluoropyrimidin-2-yl)-4-methyl-4-piperidyl]-(3,5-dihydro-2H-pyrido[3,4-f][1,4]oxazepin-4-yl)methanone | 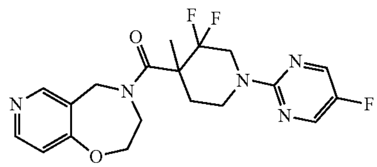 [SMILES: CC1(C(=O)N2CCOc3ccncc3C2)CCN(c2ncc(F)cn2)CC1(F)F] | | 407.4 | B |
| 245 | 4-[1-(5-fluoropyrimidin-2-yl)-3,6-dihydro-2H-pyridine-4-carbonyl]-3,5-dihydro-2H-pyrido[3,4-f][1,4]oxazepine-9-carbonitrile | 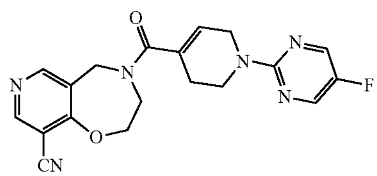 [SMILES: N#Cc1cncc2c1OCCN(C(=O)C1=CCN(c3ncc(F)cn3)CC1)C2] | | 381.4 | B |
| 246 | 4-[3,3-difluoro-1-([1,2,4]triazolo[1,5-c]pyrimidin-5-yl)piperidine-4-carbonyl]-3,5-dihydro-2H-pyrido[3,4-f][1,4]oxazepine-9-carbonitrile | 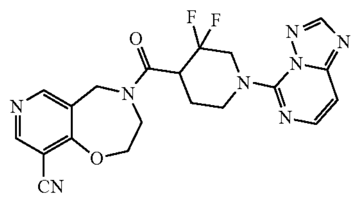 [SMILES: N#Cc1cncc2c1OCCN(C(=O)C1CCN(c3nccc4ncnn34)CC1(F)F)C2] | | 441.4 | W |
| 247 | 9-fluoro-3,5-dihydro-2H-pyrido[3,4-f][1,4]oxazepin-4-yl)-[(3,4)-trans-3-fluoro-1-(5-fluoropyrimidin-2-yl)-4-piperidyl]methanone | 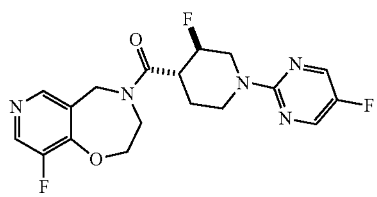 | | 394.4 | B |
| 248 | (9-fluoro-3,5-dihydro-2H-pyrido[3,4-f][1,4]oxazepin-4-yl)-[1-(5-fluoropyrimidin-2-yl)-3,6-dihydro-2H-pyridin-4-yl]methanone | 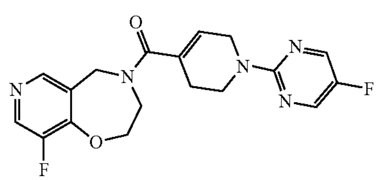 [SMILES: O=C(C1=CCN(c2ncc(F)cn2)CC1)N1CCOc2c(F)cncc2C1] | | 374.4 | B |
| 249 | 4-[(3,4)-trans-3-fluoro-1-pyrazolo[1,5-a]pyrimidin-7-yl-piperidine-4-carbonyl]-3,5-dihydro-2H-pyrido[3,4-f][1,4]oxazepine-9-carbonitrile | 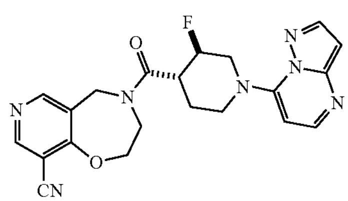 | | 422.4 | W |
| 250 | 4-[(3,4)-trans-3-fluoro-1-([1,2,4]triazolo[1,5-c]pyrimidin-5-yl)piperidine-4-carbonyl]-3,5-dihydro-2H-pyrido[3,4-f][1,4]oxazepine-9-carbonitrile | 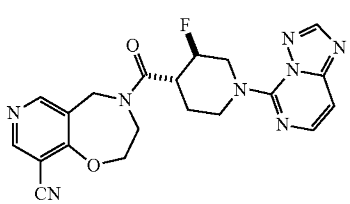 | | 423.4 | W |

TABLE 1-continued

| Ex | Name | Structure | ¹H NMR | MS (M + H)⁺ | Method |
|---|---|---|---|---|---|
| 251 | [3,3-difluoro-1-([1,2,4]triazolo[1,5-c]pyrimidin-5-yl)-4-piperidyl]-(9-fluoro-3,5-dihydro-2H-pyrido[3,4-f][1,4]oxazepin-4-yl)methanone | 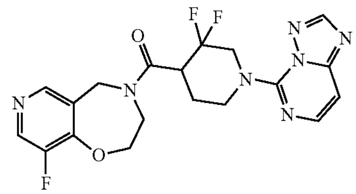 [SMILES: O=C(C1CCN(c2nccc3ncnn23)CC1(F)F)N1CCOc2c(F)cncc2C1] | | 434.4 | W |
| 252 | (3,3-difluoro-1-pyrazolo[1,5-a]pyrimidin-7-yl-4-piperidyl)-(9-fluoro-3,5-dihydro-2H-pyrido[3,4-f][1,4]oxazepin-4-yl)methanone | 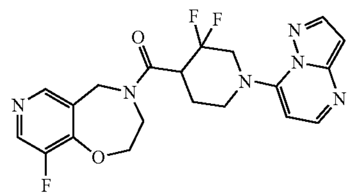 [SMILES: O=C(C1CCN(c2ccnc3ccnn23)CC1(F)F)N1CCOc2c(F)cncc2C1] | | 433.4 | W |
| 253 | (9-fluoro-3,5-dihydro-2H-pyrido[3,4-f][1,4]oxazepin-4-yl)-[(3,4)-trans-3-fluoro-1-pyrazolo[1,5-a]pyrimidin-7-yl-4-piperidyl]methanone | 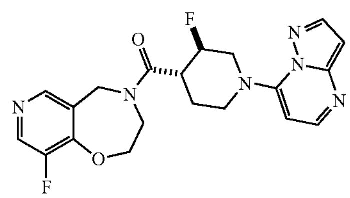 | | 415.4 | W |
| 254 | 3,5-dihydro-2H-pyrido[3,4-f][1,4]oxazepin-4-yl-[(3,4)-trans-3-fluoro-1-(5-fluoropyrimidin-2-yl)-4-piperidyl]methanone | 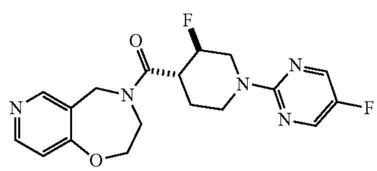 | | 376.4 | B |
| 255 | (9-fluoro-3,5-dihydro-2H-pyrido[3,4-f][1,4]oxazepin-4-yl)-[(3,4)-trans-3-fluoro-1-([1,2,4]triazolo[1,5-c]pyrimidin-5-yl-4-piperidyl]methanone | 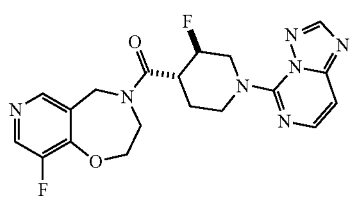 | | 416.4 | W |
| 256 | (9-fluoro-3,5-dihydro-2H-pyrido[3,4-f][1,4]oxazepin-4-yl)-[(3,4)-trans-3-fluoro-1-(3-fluoropyrazolo[1,5-a]pyrimidin-7-yl)-4-piperidyl]methanone | 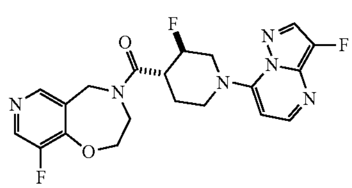 | | 433.4 | W |
| 257 | (9-fluoro-3,5-dihydro-2H-pyrido[3,4-f][1,4]oxazepin-4-yl)-[(3,4)-trans-3-fluoro-1-([1,2,4]triazolo[1,5-a]pyrazin-8-yl)-4-piperidyl]methanone | 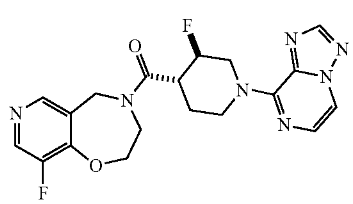 | | 416.4 | B |

Examples 258 and 259

Preparation of 4-[(2S)-2-cyclopropyl-3,3-difluoro-2-methyl-propanoyl)]-3,5-dihydro-2H-pyrido[3,4-f][1,4]oxazepine-9-carbonitrile and 4-[(2R)-2-cyclopropyl-3,3-difluoro-2-methyl-propanoyl)]-3,5-dihydro-2H-pyrido[3,4-f][1,4]oxazepine-9-carbonitrile

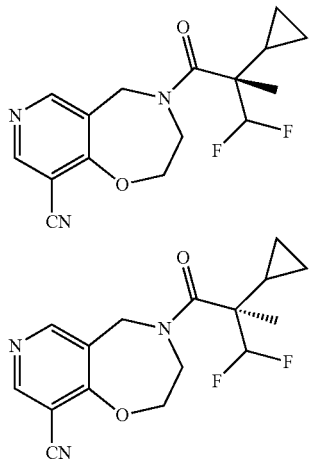

Racemic 4-(2-cyclopropyl-3,3-difluoro-2-methyl-propanoyl)-3,5-dihydro-2H-pyrido[3,4-f][1,4]oxazepine-9-carbonitrile was separated by SFC with the following conditions: Instrument: Thar SFC80 preparative SFC; Column Chiralpak AD-H 250×30 mm i.d. 5 μm; Mobile phase A: $CO_2$, Mobile phase B: EtOH; Gradient: B %=25%; Flow rate: 65 g/min.; Wavelength: 220 nm; Column temperature: 40° C.; System back pressure: 100 bar; to provide the two enantiomers.

4-(2-Cyclopropyl-3,3-difluoro-2-methyl-propanoyl)-3,5-dihydro-2H-pyrido[3,4-f][1,4]oxazepine-9-carbonitrile (first eluting peak, Example 258) Isolated as a light yellow oil. LCMS: m/z=322.3 $[M+H]^+$.

4-(2-Cyclopropyl-3,3-difluoro-2-methyl-propanoyl)-3,5-dihydro-2H-pyrido[3,4-f][1,4]oxazepine-9-carbonitrile (second eluting peak, Example 259) Isolated as a light yellow oil. LCMS: m/z=322.3 $[M+H]^+$.

Examples 260 and 261

Preparation of 4-[(2S)-2-(difluoromethyl)-2-methylbutanoyl)]-2,3,4,5-tetrahydropyrido[3,4-f][1,4]oxazepine-9-carbonitrile and 4-[(2R)-2-(difluoromethyl)-2-methylbutanoyl)]-2,3,4,5-tetrahydropyrido[3,4-f][1,4]oxazepine-9-carbonitrile

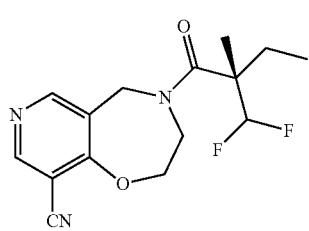

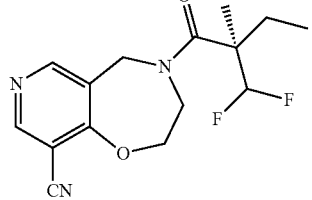

Racemic 4-(2-(difluoromethyl)-2-methylbutanoyl)-2,3,4,5-tetrahydropyrido[3,4-f][1,4]oxazepine-9-carbonitrile was separated by SFC column with the following conditions: Instrument: Thar SFC80 preparative SFC; Column: Chiralpak AD-H 250×30 mm i.d. 5 μm; Mobile phase A: $CO_2$, Mobile phase B: EtOH; Gradient: B %=35% Flow rate: 65 g/min.; Wavelength: 220 nm; Column temperature: 40° C.; System back pressure: 100 bar to provide the two enantiomers.

4-(2-(Difluoromethyl)-2-methylbutanoyl)-2,3,4,5-tetrahydropyrido[3,4-f][1,4]oxazepine-9-carbonitrile (first eluting peak, Example 260) Isolated as a yellow oil. LCMS: m/z=310.3 $[M+H]^+$.

4-(2-(Difluoromethyl)-2-methylbutanoyl)-2,3,4,5-tetrahydropyrido[3,4-f][1,4]oxazepine-9-carbonitrile (second eluting peak, Example 261) Isolated as a yellow oil. LCMS: m/z=310.3 $[M+H]^+$.

Example 262

Preparation of 4-(3,3-difluoro-2,2-dimethyl-propanoyl)-8-methyl-3,5-dihydro-2H-pyrido[3,4-f][1,4]oxazepine-9-carbonitrile

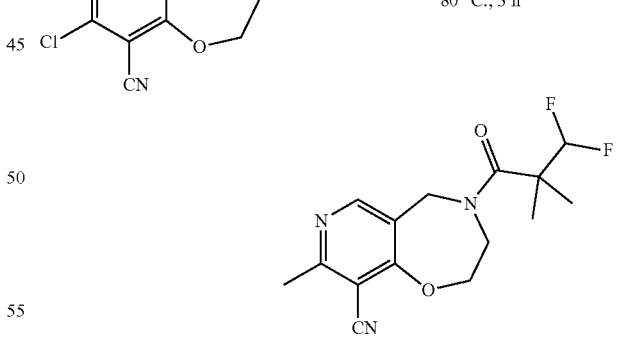

To a mixture of 8-chloro-4-(3,3-difluoro-2,2-dimethyl-propanoyl)-3,5-dihydro-2H-pyrido[3,4-f][1,4]oxazepine-9-carbonitrile (30 mg, 0.091 mmol) in THF (3 mL) was added Pd(PPh₃)₄ (11 mg, 0.0091 mmol), followed by Zn(Me)₂ (1 M, 91 μL) under N₂, and the reaction mixture was stirred at 80° C. for 3 h. Then the reaction mixture was diluted with water (5 mL) and extracted with EtOAc (3×5 mL). The organic layers were combined, washed with brine (5 mL), dried over anhydrous Na₂SO₄, filtered and concentrated under reduced pressure. The resulting residue was purified by prep-HPLC with the following conditions prep-HPLC (column Nano-micro Kromasil C18 100×30 mm 5 µm; Mobile phase: [A-TFA/H₂O=0.075% v/v; B-ACN], gradient B %: 15%-40% over 10 min.). The fractions containing desired product were adjusted to pH=7 with sat. NaHCO₃ solution and extracted with EtOAc (3×10 mL). The combined organic layers were washed with brine (10 mL), dried over anhydrous Na₂SO₄, filtered and concentrated under reduced pressure to give the title compound as a white solid. LCMS: m/z=310.3 [M+H]⁺.

Example 263

Preparation of 2,2,3,3-tetradeuterio-4-(3,3-difluoro-2,2-dimethyl-propanoyl)-5H-pyrido[3,4-f][1,4]oxazepine-9-carbonitrile

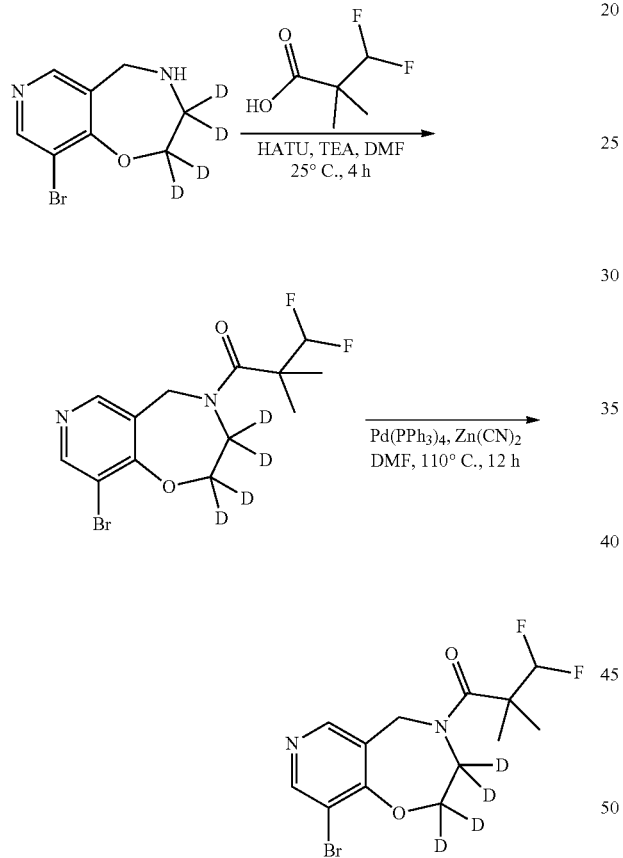

9-Bromo-2,2,3,3-tetradeuterio-4,5-dihydropyrido[3,4-f][1,4]oxazepine: The title compound was prepared using Method C employing 9-bromo-2,2,3,3-tetradeuterio-4,5-dihydropyrido[3,4-f][1,4]oxazepine (600 mg, 2.57 mmol) and 3,3-difluoro-2,2-dimethyl-propanoic acid (391 mg, 2.83 mmol). The crude product was purified by silica gel column chromatography (PE:EtOAc=5:1 to 1:1) to afford the title compound as a yellow syrup. LCMS: m/z=352.9 [M+H]⁺.

2,2,3,3-Tetradeuterio-4-(3,3-difluoro-2,2-dimethyl-propanoyl)-5H-pyrido[3,4-f][1,4]oxazepine-9-carbonitrile: To a solution of 1-(9-bromo-2,2,3,3-tetradeuterio-5H-pyrido[3,4-f][1,4]oxazepin-4-yl)-3,3-difluoro-2,2-dimethyl-propan-1-one (500 mg, 1.42 mmol) in anhydrous DMF (20 mL) was added Pd(PPh₃)₄ (491 mg, 424.69 µmol) and Zn(CN)₂ (183 mg, 1.56 mmol). The reaction mixture was heated to 100° C. and stirred for 12 h under N₂. The reaction mixture was diluted with EtOAc (20 mL), filtered and concentrated under reduced pressure. The filtrate was washed with water (40 mL) and brine (40 mL), dried over anhydrous Na₂SO₄, filtered and concentrated under reduced pressure. The residue was purified by silica gel column chromatography (PE:EtOAc=5:1 to 1:1) to provide crude product (92% HPLC purity). The crude product was further purified by prep-HPLC with the following conditions: column: Xtimate C18 150×25 mm 5 µm; mobile phase: [water (10 mM NH₄HCO₃)-ACN];B %: 20%-50% over 10.5 min. The eluent was extracted with EtOAc (3×10 mL). The combined organics were washed with brine (10 mL), dried over anhydrous Na₂SO₄, filtered and concentrated under reduced pressure to provide the title compound as a white solid. ¹H NMR (400 MHz, CDCl₃): δ 8.65 (s, 1H), 8.59 (s, 1H), 6.09 (t, J=56.0 Hz,1H), 4.78 (s, 2H), 1.38 (s, 6H). LCMS: m/z=300.3 [M+H]⁺.

Examples 264 and 265

Preparation of 4-[(2S)-2-(cyanomethyl)-2-methyl-butanoyl]-3,5-dihydro-2H-pyrido[3,4-f][1,4]oxazepine-9-carbonitrile and 4-[(2R)-2-(cyanomethyl)-2-methyl-butanoyl]-3,5-dihydro-2H-pyrido[3,4-f][1,4]oxazepine-9-carbonitrile

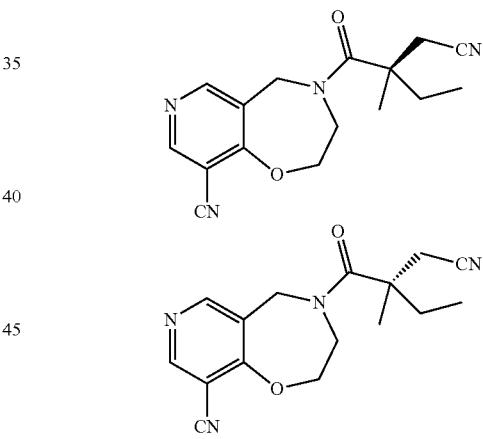

Racemic 4-[2-(cyanomethyl)-2-methyl-butanoyl]-3,5-dihydro-2H-pyrido[3,4-f][1,4]oxazepine-9-carbonitrile was separated by SFC under the following conditions: Instrument: Thar SFC80 preparative SFC; Column: Chiralpak AD-H 250×30 mm i.d. 5 µm; Mobile phase A: CO₂, Mobile phase B: MeOH; Gradient: B %=42%; Flow rate: 70 g/min; Wavelength: 220 nm; Column temperature: 40° C.; System back pressure: 100 bar to provide the two enantiomers.

4-[2-(Cyanomethyl)-2-methyl-butanoyl]-3,5-dihydro-2H-pyrido[3,4-f][1,4]oxazepine-9-carbonitrile (first eluting peak, Example 264) Isolated as a colorless oil. LCMS: m/z=299.1, [M+H]⁺.

4-[2-(Cyanomethyl)-2-methyl-butanoyl]-3,5-dihydro-2H-pyrido[3,4-f][1,4]oxazepine-9-carbonitrile (second eluting peak, Example 265) Isolated as a colorless oil. LCMS: m/z=299.1 [M+H]⁺.

Example 266 and 267

Preparation of 4-[3,3-difluoro-2-(fluoromethyl)-2-methyl-propanoyl]-3,5-dihydro-2H-pyrido[3,4-f][1,4]oxazepine-9-carbonitrile (Example 266) and 4-[3,3-difluoro-2-(fluoromethyl)-2-methyl-butanoyl]-3,5-dihydro-2H-pyrido[3,4-f][1,4]oxazepine-9-carbonitrile (Example 267)

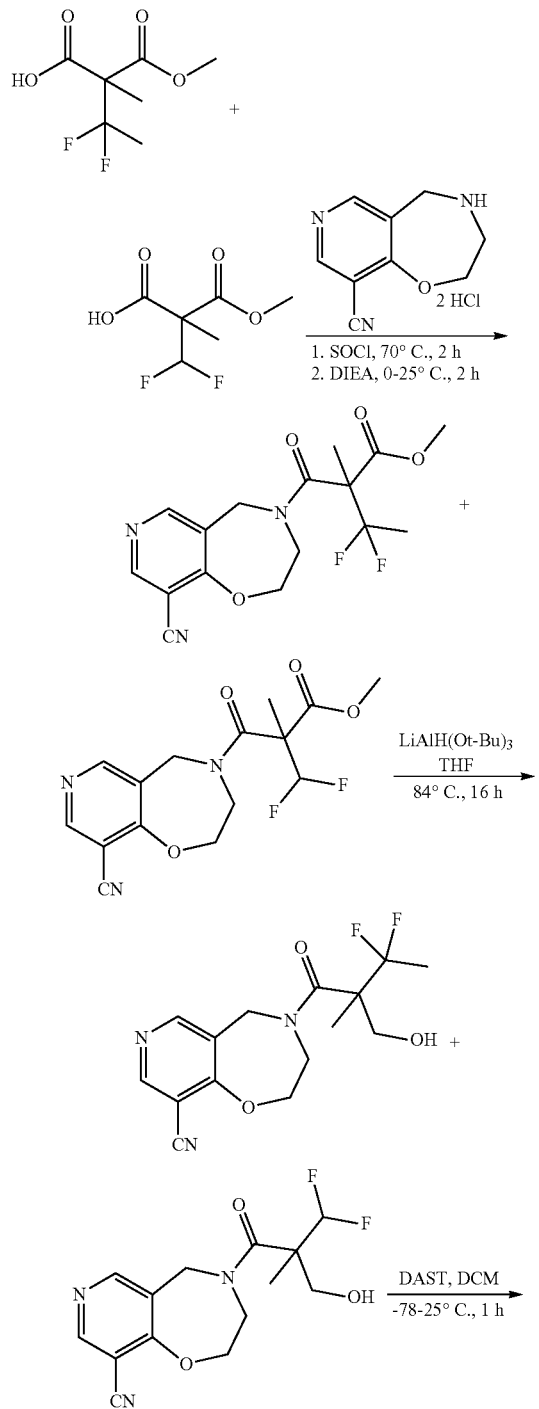

-continued

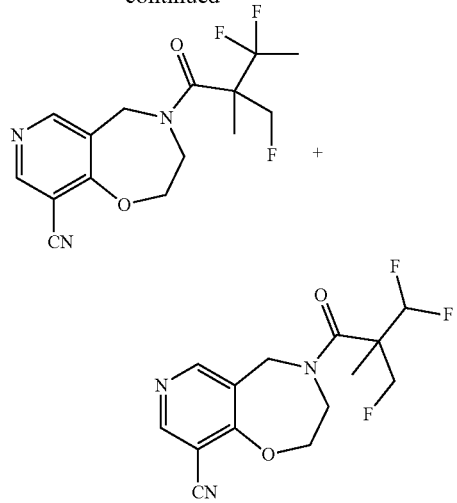

2-(9-Cyano-3,5-dihydro-2H-pyrido[3,4-f][1,4]oxazepine-4-carbonyl)-3,3-difluoro-2-methyl-butanoate and methyl 2-(9-cyano-3,5-dihydro-2H-pyrido[3,4-f][1,4]oxazepine-4-carbonyl)-3,3-difluoro-2-methyl-propanoate: The title compounds were prepared using Method D to afford a mixture of methyl 2-(9-cyano-3,5-dihydro-2H-pyrido[3,4-f][1,4]oxazepine-4-carbonyl)-3,3-difluoro-2-methyl-butanoate and methyl 2-(9-cyano-3,5-dihydro-2H-pyrido[3,4-f][1,4]oxazepine-4-carbonyl)-3,3-difluoro-2-methyl-propanoate (290 mg, 29%; ratio=4:5) as a colorless oil. LC-MS: m/z=340.3 [M+H]$^+$; m/z=354.3 [M+H]$^+$.

4-[3,3-Difluoro-2-(hydroxymethyl)-2-methyl-butanoyl]-3,5-dihydro-2H-pyrido[3,4-f][1,4]oxazepine-9-carbonitrile and 4-[3,3-difluoro-2-(hydroxymethyl)-2-methyl-propanoyl]-3,5-dihydro-2H-pyrido[3,4-f][1,4]oxazepine-9-carbonitrile: To a mixture of methyl 2-(9-cyano-3,5-dihydro-2H-pyrido[3,4-f][1,4]oxazepine-4-carbonyl)-3,3-difluoro-2-methyl-butanoate and methyl 2-(9-cyano-3,5-dihydro-2H-pyrido[3,4-f][1,4]oxazepine-4-carbonyl)-3,3-difluoro-2-methyl-propanoate (0.29 g, 0.82 mmol) in THF (7 mL) was added a solution of lithium tri-tert-butoxyaluminum hydride (4.1 mmol, 4.1 mL, 1 M in THF) at 25° C. under N$_2$. The mixture was then heated to 84° C. and stirred for 16 h. The mixture was cooled to 25° C., poured into aq. ice-cold NH$_4$Cl (20 mL) and filtered through a pad of celite. The filter cake was washed with EtOAc (3×10 mL). The filtrate was washed with brine (10 mL), dried over Na$_2$SO$_4$, filtered and concentrated in vacuo. The resulting residue was purified by prep-TLC (SiO$_2$, PE:EtOAc=1:3) to afford a mixture of the title compounds (100 mg, 38%; ratio=1:1) as a colorless oil. LC-MS: m/z=312.0 [M+H]$^+$; m/z=326.0 [M+H]$^+$.

4-[3,3-Difluoro-2-(fluoromethyl)-2-methyl-butanoyl]-3,5-dihydro-2H-pyrido[3,4-f][1,4]oxazepine-9-carbonitrile and 4-[3,3-difluoro-2-(fluoromethyl)-2-methyl-propanoyl]-3,5-dihydro-2H-pyrido[3,4-f][1,4]oxazepine-9-carbonitrile: To a mixture of 4-[3,3-difluoro-2-(hydroxymethyl)-2-methyl-butanoyl]-3,5-dihydro-2H-pyrido[3,4-f][1,4]oxazepine-9-carbonitrile and 4-[3,3-difluoro-2-(hydroxymethyl)-2-methyl-propanoyl]-3,5-dihydro-2H-pyrido[3,4-f][1,4]oxazepine-9-carbonitrile (80 mg, 0.25 mmol) in DCM (2 mL) was added DAST (198 mg, 1.23 mmol) at −78° C. under N$_2$. The mixture was allowed to warm to 25° C. and stirred for 1 h. The mixture was diluted with DCM (20 mL) and adjusted to pH=8 with sat. NaHCO$_3$ at 0° C. The organic phase was separated, washed with brine (5 mL), dried over Na₂SO₄, filtered and concentrated under reduced pressure. The resulting residue was purified by prep-HPLC with the following conditions: column: Xtimate C18 150×25 mm×5 μm; mobile phase: [water (10 mM NH₄HCO₃)-ACN]; B %: 25%-45%, over 10.5 mM. to afford the title compounds.

4-[3,3-Difluoro-2-(fluoromethyl)-2-methyl-propanoyl]-3,5-dihydro-2H-pyrido[3,4-f][1,4]oxazepine-9-carbonitrile (first eluting peak in HPLC, Example 266). Isolated as a colorless oil. LCMS: m/z=314.3 [M+H]⁺.

4-[3,3-Difluoro-2-(fluoromethyl)-2-methyl-butanoyl]-3,5-dihydro-2H-pyrido[3,4-f][1,4]oxazepine-9-carbonitrile (second eluting peak in HPLC, Example 267). Isolated as a light yellow oil. LCMS: m/z=328.3 [M+H]⁺.

Examples 268 and 269

Preparation of 4-[2-(difluoromethyl)-3,3-difluoro-2-methyl-propanoyl]-3,5-dihydro-2H-pyrido[3,4-f][1,4]oxazepine-9-carbonitrile (Example 268) and 4-[2-(difluoromethyl)-3,3-difluoro-2-methyl-butanoyl]-3,5-dihydro-2H-pyrido[3,4-f][1,4]oxazepine-9-carbonitrile (Example 269)

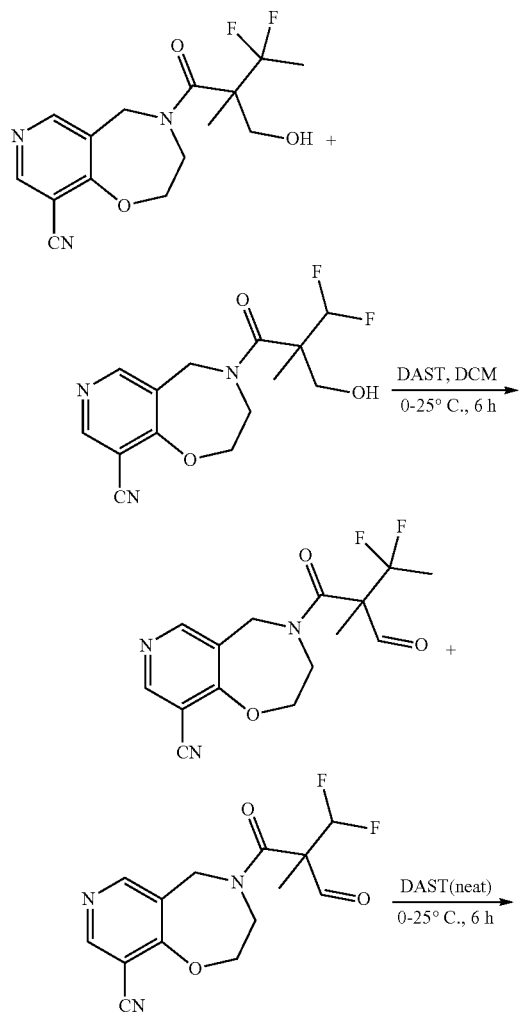

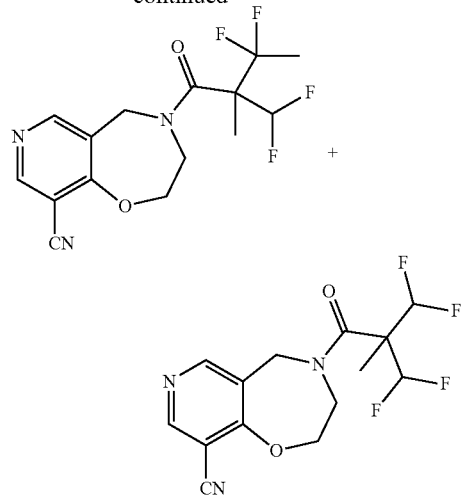

4-(3,3-Difluoro-2-formyl-2-methyl-butanoyl)-3,5-dihydro-2H-pyrido[3,4-f][1,4]oxazepine-9-carbonitrile and 4-(3,3-difluoro-2-formyl-2-methyl-propanoyl)-3,5-dihydro-2H-pyrido[3,4-f][1,4]oxazepine-9-carbonitrile: To a mixture of 4-[3,3-difluoro-2-(hydroxymethyl)-2-methyl-butanoyl]-3,5-dihydro-2H-pyrido[3,4-f][1,4]oxazepine-9-carbonitrile and 4-[3,3-difluoro-2-(hydroxymethyl)-2-methyl-propanoyl]-3,5-dihydro-2H-pyrido[3,4-f][1,4]oxazepine-9-carbonitrile (0.1 g, 307.4 μmol) in DCM (3 mL) was added DMP (143 mg, 338.14 μmol) at 0° C. under N₂. The mixture was stirred at 0° C. for 3 h. Additional DMP (143 mg, 338.14 μmol) was added to the mixture at 0° C. and the mixture was stirred for another 3 h. The mixture was added to EtOAc (50 mL) and washed with aq. Na₂S₂O₃ (10 mL), aq. NaHCO₃ (10 mL), brine (10 mL), dried over anhydrous Na₂SO₄, filtered and concentrated under reduced pressure. The residue was purified by prep-TLC (SiO₂, PE:EtOAc=3:1) to give a mixture of the title compounds (0.07 g, 71%) as a colorless oil. LCMS: m/z=310.0 [M+H]⁺; m/z=324.0 [M+H]⁺.

4-[2-(Ditluoromethyl)-3,3-ditluoro-2-methyl-butanoyl]-3,5-dihydro-2H-pyrido[3,4-f][1,4]oxazepine-9-carbonitrile and 4-[2-(difluoromethyl)-3,3-ditluoro-2-methyl-propanoyl]-3,5-dihydro-2H-pyrido[3,4-f][1,4]oxazepine-9-carbonitrile: To a mixture of 4-(3,3-difluoro-2-formyl-2-methyl-butanoyl)-3,5-dihydro-2H-pyrido[3,4-f][1,4]oxazepine-9-carbonitrile and 4-(3,3-difluoro-2-formyl-2-methyl-propanoyl)-3,5-dihydro-2H-pyrido[3,4-f][1,4]oxazepine-9-carbonitrile (0.12 g, 371.18 μmol) was added DAST (2 mL) neat at 0° C. under N₂. The mixture was stirred at 25° C. for 6 h. The mixture was diluted with EtOAc (10 mL), and then poured into sat. NaHCO₃ (50 mL) slowly at 0° C. The aqueous phase was extracted with EtOAc (3×10 mL). The combined organic phase was washed with brine (10 mL), dried over anhydrous Na₂SO₄, filtered and concentrated under reduced pressure. The residue was purified by prep-HPLC with the following conditions: Column: Waters Xbridge 150×25 mm 5 μm; mobile phase: [water (10 mM NH₄HCO₃)-ACN]; B %: 25%-35% over 10 min. to provide the title compounds.

4-[2-(Ditluoromethyl)-3,3-ditluoro-2-methyl-propanoyl]-3,5-dihydro-2H-pyrido[3,4-f][1,4]oxazepine-9-carbonitrile (first eluting peak in HPLC, Example 268) Isolated as a light yellow solid. LCMS: m/z=332.3 [M+H]⁺.

4-[2-(Difluoromethyl)-3,3-difluoro-2-methyl-butanoyl]-3,5-dihydro-2H-pyrido[3,4-f][1,4]oxazepine-9-carbonitrile (second eluting peak in HPLC, Example 269) Isolated as a light yellow solid. LCMS: m/z=346.3 [M+H]⁺.

Examples 270 and 271

Preparation of 4-(3-fluoro-2,2-dimethyl-butanoyl)-3,5-dihydro-2H-pyrido[3,4-f][1,4]oxazepine-9-carbonitrile (Example 270) and 4-(2,2-dimethylbut-3-enoyl)-3,5-dihydro-2H-pyrido[3,4-f][1,4]oxazepine-9-carbonitrile (Example 271)

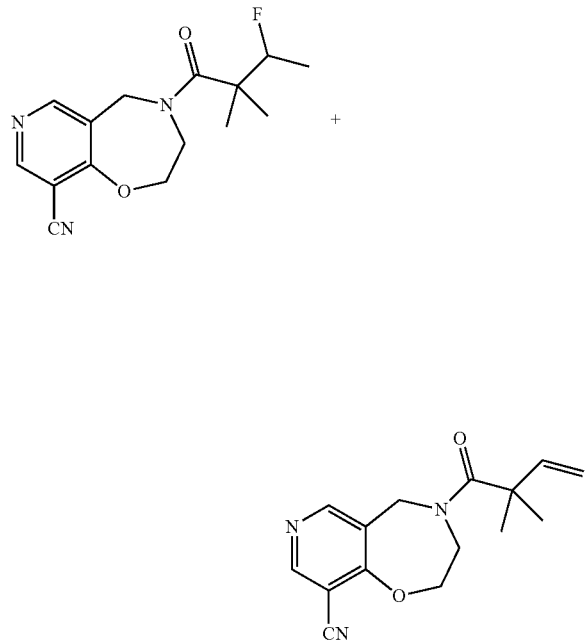

The title compounds were prepared using general procedure C and were purified by prep-TLC (PE:EtOAc=1:1) followed by purification by SFC with the following conditions: Instrument: Thar SFC80 preparative SFC; Column: Chiralcel OJ-H 250×30 mm i.d. 5 μm; Mobile phase A: CO₂, Mobile phase B: MeOH; Gradient: B %=20%; Flow rate: 48 g/min.; Wavelength: 220 nm; Column temperature: 40° C.; System back pressure: 100 bar to afford the title compounds.

4-(3-Fluoro-2,2-dimethyl-butanoyl)-3,5-dihydro-2H-pyrido[3,4-f][1,4]oxazepine-9-carbonitrile (second eluting peak, Example 270) Isolated as a yellow oil. LCMS: m/z: 292.3, [M+H]⁺.

4-(2,2-Dimethylbut-3-enoyl)-3,5-dihydro-2H-pyrido[3,4-f][1,4]oxazepine-9-carbonitrile (the first eluting peak, Example 271) Isolated as a yellow oil. LCMS: m/z=272.3 [M+H]⁺.

Examples 272 and 273

Preparation of 4-[(3S)-3-fluoro-2,2-dimethyl-butanoyl]-3,5-dihydro-2H-pyrido[3,4-f][1,4]oxazepine-9-carbonitrile and 4-[(3R)-3-fluoro-2,2-dimethyl-butanoyl]-3,5-dihydro-2H-pyrido[3,4-f][1,4]oxazepine-9-carbonitrile

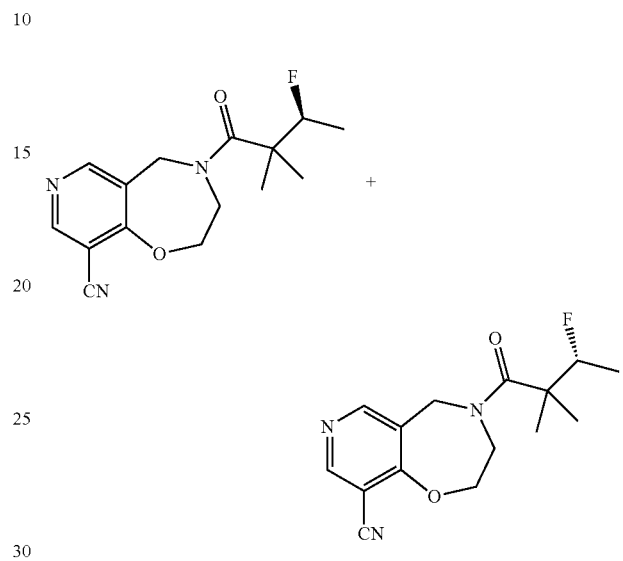

Racemic 4-(3-fluoro-2,2-dimethyl-butanoyl)-3,5-dihydro-2H-pyrido[3,4-f][1,4]oxazepine-9-carbonitrile was separated by SFC with the following conditions: Instrument: Thar SFC80 preparative SFC; Column: Chiralpak AD-H 250×30 mm i.d. 5 μm; Mobile phase A: CO₂, Mobile phase B: MeOH (0.1% NH₃H₂O); Gradient: B %=25%; Flow rate: 65 g/min.; Wavelength: 220 nm; Column temperature: 40° C.; System back pressure: 100 bar; Cycle time: 4 min.; Injection amount: 3 mg per injection to afford the pure enantiomers.

4-(3-Fluoro-2,2-dimethyl-butanoyl)-3,5-dihydro-2H-pyrido[3,4-f][1,4]oxazepine-9-carbonitrile (first eluting peak, Example 272) Isolated as a yellow oil. LCMS: m/z=292.3 [M+H]⁺.

4-(3-Fluoro-2,2-dimethyl-butanoyl)-3,5-dihydro-2H-pyrido[3,4-f][1,4]oxazepine-9-carbonitrile (second eluting peak, Example 273) isolated as a yellow oil. LCMS: m/z=292.3 [M+H]⁺.

Example 274

Preparation of 4-(2-methyl-2-(2-((trifluoromethoxy)methyl)cyclopropyl)propanoyl)-2,3,4,5-tetrahydro-pyrido[3,4-f][1,4]oxazepine-9-carbonitrile

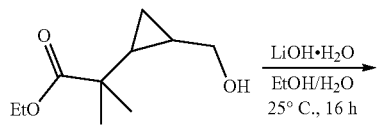

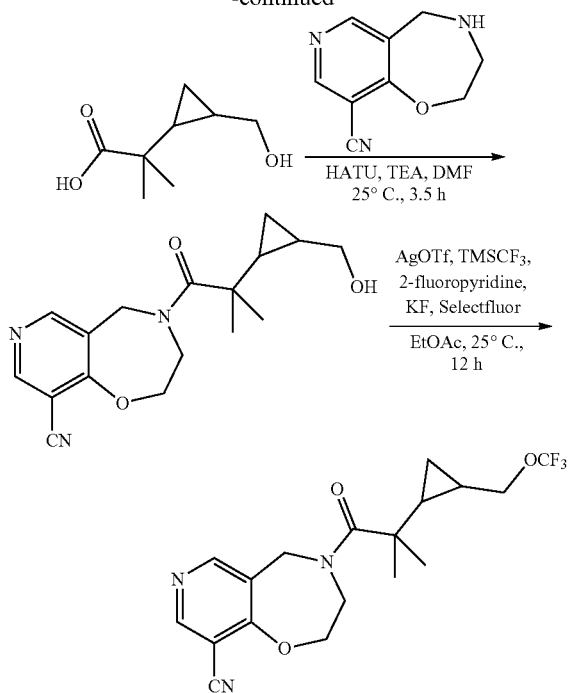

2-(2-(Hydroxymethyl)cyclopropyl)-2-methyl-propanoic acid: To a mixture of ethyl 2-(2-(hydroxymethyl)cyclopropyl)-2-methyl-propanoate (6.5 g, 34.90 mmol) in EtOH (60 mL) and H₂O (20 mL) was added LiOH.H₂O (8.8 g, 209.40 mmol) in one portion at 25° C. under N₂. The mixture was stirred at 25° C. for 16 h. The reaction mixture was partitioned between MTBE (5 mL) and water (2 mL). The organic phase was separated and the aqueous phase was adjusted to pH=3-4 with aq. HCl (2 N). The mixture was extracted with EtOAc (3×50 mL). The combined organics were washed with brine (50 mL), dried over Na₂SO₄, filtered and concentrated under reduced pressure to afford the title compound (1.5 g, 27%) as a yellow oil.

4-(2-(2-(Hydroxymethyl)cyclopropyl)-2-methylpropanoyl)-2,3,4,5-tetrahydropyrido[3,4-f][1,4]oxazepine-9-carbonitrile: Prepared using Method C and purified by silica gel column chromatography (MTBE:MeOH=1:0 to 30:1) to provide the title compound (0.7 g, 27%) as a white solid. LCMS: m/z=316.2 [M+H]⁺.

4-(2-Methyl-2-(2-(((trifluoromethoxy)methyl)cyclopropyl)propanoyl)-2,3,4,5-tetrahydropyrido[3,4-f][1,4]oxazepine-9-carbonitrile: To a reaction flask equipped with a stir bar and covered with tin foil, AgOTf (733 mg, 2.85 mmol), Selectfluor (506 mg, 1.43 mmol), KF (221 mg, 3.81 mmol) and 4-(2-(2-(hydroxymethyl)cyclopropyl)-2-methyl-propanoyl)-2,3,4,5-tetrahydropyrido[3,4-f][1,4]oxazepine-9-carbonitrile (0.3 g, 0.95 mmol) were added under N₂. EtOAc (5 mL), 2-fluoropyridine (277 mg, 2.85 mmol) and TMSCF₃ (406 mg, 2.85 mmol) were added dropwise at 25° C. successively under water bath while keeping the internal temperature below 30° C. The reaction mixture was stirred at 25° C. for 12 h. The reaction mixture was filtered through a plug of silica and washed with MeOH. The filtrate was concentrated and the resulting residue was purified by prep-HPLC with the following conditions: column: Xtimate C18 150×25 mm 5 μm; mobile phase: [water (10 mM NH₄HCO₃)-ACN]; B %: 35%-65%, 10.5 mM. to afford the title compound. LCMS: m/z=384.2 [M+H]⁺.

Examples 275 and 276

Preparation of 4-[2-methyl-2-[3-(triazol-2-yl)cyclobutyl]propanoyl]-3,5-dihydro-2H-pyrido[3,4-f][1,4]oxazepine-9-carbonitrile (Example 275) and 4-[2-methyl-2-[3-(triazol-1-yl)cyclobutyl]propanoyl]-3,5-dihydro-2H-pyrido[3,4-f][1,4]oxazepine-9-carbonitrile (Example 276)

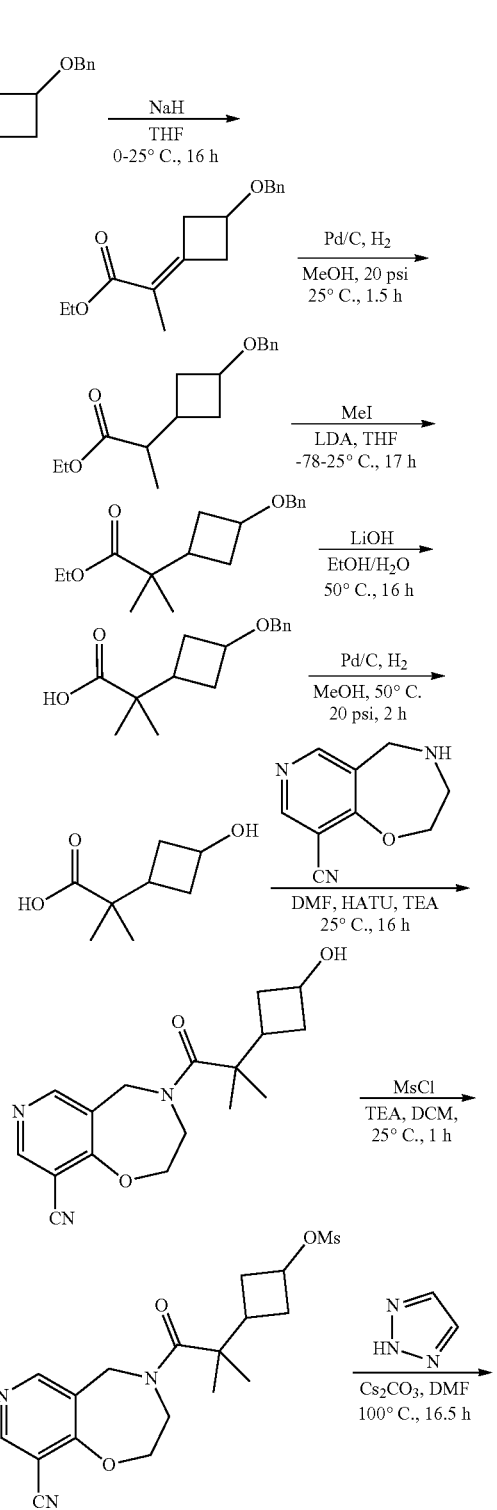

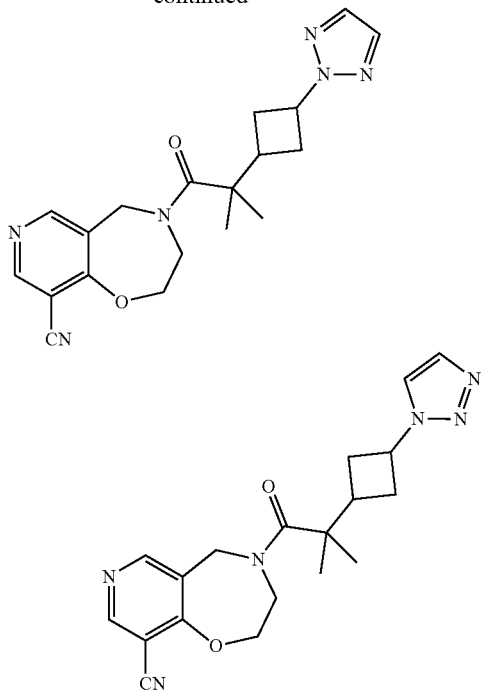

Ethyl 2-(3-benzyloxycyclobutylidene)propanoate: To a mixture of NaH (2.7 g, 68.10 mmol, 60% in mineral oil) in anhydrous THF (100 mL) was added ethyl 2-diethoxyphosphorylpropanoate (20.3 g, 85.12 mmol) dropwise at 0° C. under N$_2$. The mixture was stirred at 0° C. for 1 h. To the mixture was added 3-benzyloxycyclobutanone (10.0 g, 56.75 mmol) dropwise with stirring at 0° C., then warmed to 25° C. and stirred for 16 h. The reaction mixture was quenched with saturated aqueous NH$_4$Cl (40 mL) at 0° C., diluted with water (20 mL) and extracted with EtOAc (3×50 mL). The combined organics were washed with brine (50 mL), dried over anhydrous Na$_2$SO$_4$, filtered and concentrated under reduced pressure. The resulting residue was purified by silica gel column chromatography (PE:EtOAc=1:0 to 30:1) to afford the title compound (14 g, 95%) as a yellow oil. LCMS: m/z=261. [M+H]$^+$.

Ethyl 2-(3-benzyloxycyclobutyl)propanoate: To a solution of ethyl 2-(3-benzyloxycyclobutylidene)propanoate (5.0 g, 19.21 mmol) in MeOH (400 mL) was added 10% Pd/C (1.0 g) under N$_2$. The suspension was degassed under reduced pressure and purged with H$_2$ several times. The mixture was stirred under H$_2$ (20 psi) at 25° C. for 1.5 h. The mixture was filtered and the filtrate was concentrated under reduced pressure to provide the title compound (5.0 g, 99%) as a colorless oil. LCMS: m/z=263.1 [M+H]$^+$.

Ethyl 2-(3-benzyloxycyclobutyl)-2-methyl-propanoate: To a mixture of LDA (2 M, 14.29 mL) in THF (100 mL) was added ethyl 2-(3-benzyloxycyclobutyl)propanoate (5.0 g, 19.06 mmol) dropwise at −78° C. under N$_2$. The mixture was stirred at −78° C. for 1 h. MeI (4.1 g, 28.59 mmol) was added dropwise and the mixture was warmed to 25° C. and stirred for 16 h. The reaction mixture was quenched with saturated NH$_4$Cl (100 mL) at 0° C. and extracted with EtOAc (3×50 mL). The combined organic layers were washed with brine (40 mL), dried over anhydrous Na$_2$SO$_4$, filtered and concentrated under reduced pressure. The crude product was purified by silica gel column chromatography (PE:EtOAc=1:0 to 30:1) to afford the title compound (3.7 g, 70%) as a white solid. LCMS: m/z=277.2 [M+H]$^+$.

2-(3-Benzyloxycyclobutyl)-2-methyl-propanoic acid: To a solution of ethyl 2-(3-benzyloxycyclobutyl)-2-methyl-propanoate (1.2 g, 4.34 mmol) in EtOH (12 mL) and H$_2$O (4 mL) was added LiOH.H$_2$O (1.1 g, 26.05 mmol) in one portion at 25° C. under N$_2$. The mixture was heated at 50° C. and stirred for 16 h. The mixture was concentrated under reduced pressure and the resulting residue was diluted with water (10 mL) and extracted with MTBE (5 mL). The aqueous phase was adjusted to pH=3~4 by 1 N HCl and extracted with EtOAc (3×15 mL). The combined organics were washed with brine (15 mL), dried over anhydrous Na$_2$SO$_4$, filtered and concentrated under reduced pressure to provide the title compound (620 mg, 58%) as a colorless oil. LCMS: m/z=247.1 [M−H]$^+$.

2-(3-Hydroxycyclobutyl)-2-methyl-propanoic acid: To a solution of 2-(3-benzyloxycyclobutyl)-2-methyl-propanoic acid (620 mg, 2.50 mmol) in MeOH (20 mL) was added 10% Pd/C (200 mg) under N$_2$. The suspension was degassed under reduced pressure and purged with H$_2$ several times. The mixture was stirred under H$_2$ (20 psi) at 50° C. for 2 h. The mixture was filtered and the filtrate was concentrated under reduced pressure to afford the title compound (350 mg, 88%) as a colorless oil. LCMS: m/z=157.1 [M−H]$^+$.

4-[2-(3-Hydroxycyclobutyl)-2-methyl-propanoyl]-3,5-dihydro-2H-pyrido[3,4-f][1,4]oxazepine-9-carbonitrile: Prepared using Method C and purified by silica gel column chromatography (DCM:MeOH=1:0 to 30:1) to afford the title compound (280 mg, 70%) as a white solid. LCMS: m/z=316.2 [M+H]$^+$.

[3-[2-(9-Cyano-3,5-dihydro-2H-pyrido[3,4-f][1,4]oxazepin-4-yl)-1,1-dimethyl-2-oxo-ethyl]cyclobutyl] methanesulfonate: To a mixture of 4-[2-(3-hydroxycyclobutyl)-2-methyl-propanoyl]-3,5-dihydro-2H-pyrido[3,4-f][1,4]oxazepine-9-carbonitrile (270 mg, 856.15 μmol) and TEA (260 mg, 2.57 mmol) in DCM (1 mL) was added MsCl (108 mg, 941.76 μmol) dropwise at 0° C. under N$_2$. The reaction mixture was stirred at 0° C. for 30 min., then warmed to 25° C. and stirred for 1 h. The reaction mixture was diluted with water (3 mL) and extracted with DCM (3×3 mL). The combined organics were washed with brine (2 mL), dried over anhydrous Na$_2$SO$_4$, filtered and concentrated under reduced pressure to afford the title compound (300 mg, 89%) as a yellow oil. LCMS: m/z=394.2 [M+H]$^+$.

4-[2-Methyl-2-[3-(triazol-2-yl)cyclobutyl]propanoyl]-3,5-dihydro-2H-pyrido[3,4-f][1,4]oxazepine-9-carbonitrile and 4-[2-methyl-2-[3-(triazol-1-yl)cyclobutyl]propanoyl]-3,5-dihydro-2H-pyrido[3,4-f][1,4]oxazepine-9-carbonitrile: To a mixture of 2H-triazole (70.21 mg, 1.02 mmol) and [3-[2-(9-cyano-3,5-dihydro-2H-pyrido[3,4-f][1,4]oxazepin-4-yl)-1,1-dimethyl-2-oxo-ethyl]cyclobutyl] methanesulfonate (200 mg, 508.32 μmol) in DMF (2 mL) was added Cs$_2$CO$_3$ (497 mg, 1.52 mmol) in one portion at 25° C. under N$_2$. The mixture was stirred at 25° C. for 30 min., then heated to 100° C. and stirred for 16 h. The reaction mixture was diluted with water (5 mL) and extracted with EtOAc (3×3 mL). The combined organics were washed with brine (2 mL), dried over anhydrous Na$_2$SO$_4$, filtered and concentrated under reduced pressure. The residue was purified by prep-HPLC with the following conditions: column: Xtimate C18 150×25 mm 5 μm; mobile phase: [water (10 mM NH$_4$HCO$_3$)-ACN]; B %: 24%-44%, 10.5 min to provide the title compounds.

4-[2-Methyl-2-[3-(triazol-2-yl)cyclobutyl]propanoyl]-3,5-dihydro-2H-pyrido[3,4-f][1,4]oxazepine-9-carbonitrile (second eluting peak, Example 275) Isolated as a white solid. ¹H NMR (400 MHz, CDCl₃) δ 8.63 (s, 1H), 8.60 (s, 1H), 7.62 (s, 2H), 5.12-4.99 (m, 1H), 4.76 (s, 2H), 4.60-4.50 (m, 2H), 4.20-4.09 (m, 2H), 3.23-3.12 (m, 1H), 2.71-2.61 (m, 2H), 2.52-2.42 (m, 2H), 1.31 (s, 6H). LCMS: m/z=367.2 [M+H]⁺.

4-[2-Methyl-2-[3-(triazol-1-yl)cyclobutyl]propanoyl]-3,5-dihydro-2H-pyrido[3,4-f][1,4]oxazepine-9-carbonitrile (first eluting peak, Example 276) Isolated as a white solid. ¹H NMR (400 MHz, CDCl₃) δ 8.64 (s, 1H), 8.59 (s, 1H), 7.72 (d, J=0.8 Hz, 1H), 7.63 (d, J=0.8 Hz, 1H), 5.02-4.98 (m, 1H), 4.76 (s, 2H), 4.61-4.49 (m, 2H), 4.20-4.10 (m, 2H), 3.17 (t, J=8.8 Hz, 1H), 2.69-2.46 (m, 4H), 1.31 (s, 6H). LCMS: m/z=367.2 [M+H]⁺.

Example 277

Preparation of 4-[2-[3-(4-fluoropyrazol-1-yl)cyclobutyl]-2-methyl-propanoyl]-3,5-dihydro-2H-pyrido[3,4-f][1,4]oxazepine-9-carbonitrile

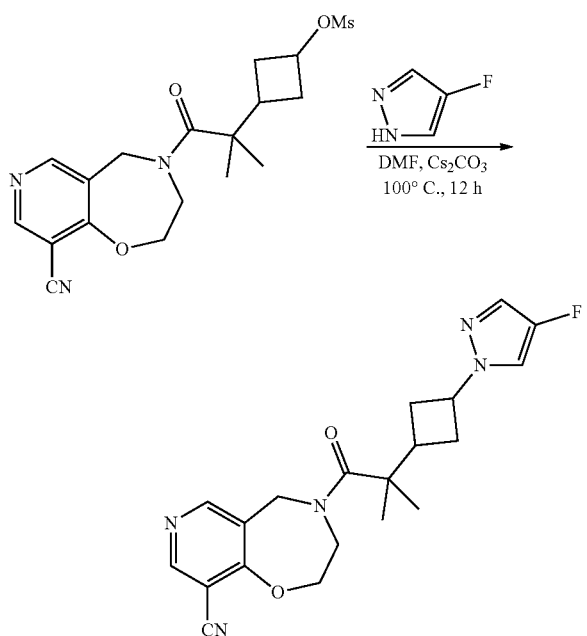

4-[2-[3-(4-Fluoropyrazol-1-yl)cyclobutyl]-2-methyl-propanoyl]-3,5-dihydro-2H-pyrido[3,4f][1,4]oxazepine-9-carbonitrile: To a solution of [3-[2-(9-cyano-3,5-dihydro-2H-pyrido[3,4-f][1,4]oxazepin-4-yl)-1,1-dimethyl-2-oxo-ethyl]cyclobutyl]methanesulfonate (200 mg, 0.51 mmol) and 4-fluoro-1H-pyrazole (88 mg, 1.02 mmol) in DMF (2 mL) was added Cs₂CO₃ (331 mg, 1.02 mmol) at 25° C., and then the solution was stirred at 100° C. for 12 h. The reaction mixture was partitioned between DCM/i-PrOH (v:v=3:1, 3×10 mL) and water (5 mL). The organic phase was separated, washed with brine (5 mL), dried over anhydrous Na₂SO₄, filtered and concentrated under reduced pressure. The residue was purified by prep-HPLC with the following conditions: column: Xtimate C18 150×25 mm 5 μm; mobile phase: [water (10 mM NH₄HCO₃)-ACN]; B %: 30%-50% over 10.5 min to provide the title compound as a light yellow oil. LCMS: m/z=384.4 [M+H]⁺.

Example 278

Preparation of 4-[2-(3-chlorocyclobutyl)-2-methyl-propanoyl]-3,5-dihydro-2H-pyrido[3,4-f][1,4]oxazepine-9-carbonitrile

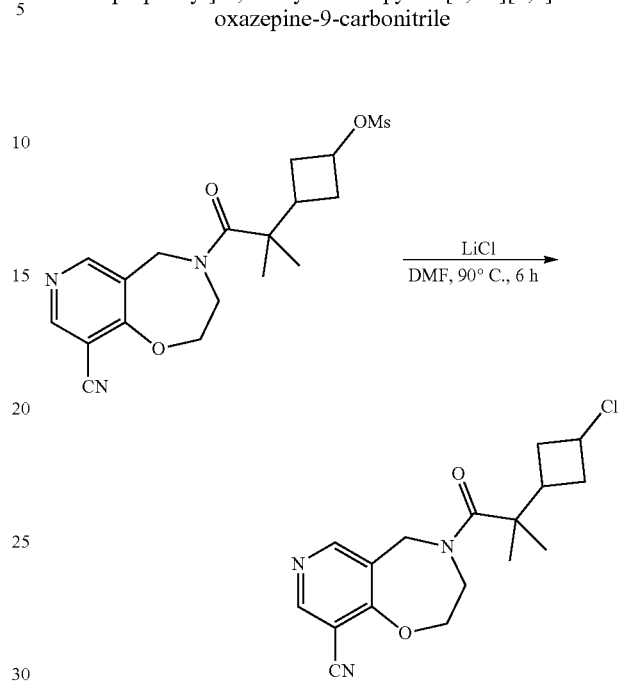

To a solution of [3-[2-(9-cyano-3,5-dihydro-2H-pyrido[3,4-f][1,4]oxazepin-4-yl)-1,1-dimethyl-2-oxo-ethyl]cyclobutyl]methanesulfonate (60 mg, 0.15 mmol) in DMF (1 mL) was added LiCl (13 mg, 0.31 mmol) in one portion at 25° C. under N₂. The mixture was heated at 90° C. for 6 h. The reaction mixture was diluted with water (2 mL) and extracted with EtOAc (3×3 mL). The combined organics were washed with brine (2 mL), dried over anhydrous Na₂SO₄, filtered and concentrated under reduced pressure. The residue was purified by prep-HPLC with the following conditions: column: Xtimate C18 150×25 mm 5 μm; mobile phase: [water (10 mM NH₄HCO₃)-ACN]; B %: 28%-58% over 10.5 min. to afford the title compound as a white solid. LCMS: m/z=334.1 [M+H]⁺.

Example 279

Preparation of 4-[2-methyl-2-[3-(trifluoromethoxy)cyclobutyl]propanoyl]-3,5-dihydro-2H-pyrido[3,4-f][1,4]oxazepine-9-carbonitrile

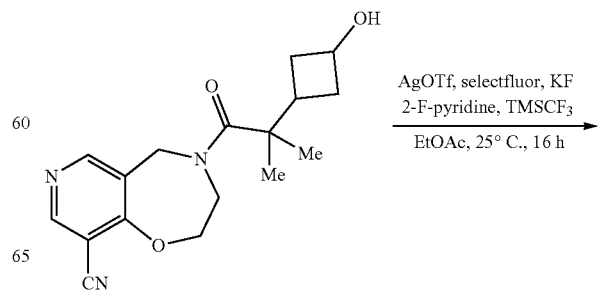

-continued

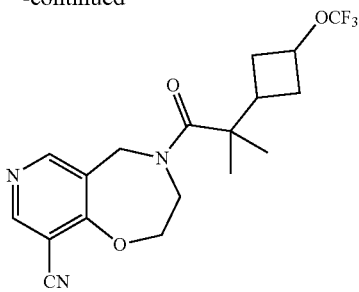

4-[2-Methyl-2-[3-(trifluoromethoxy)cyclobutyl]propanoyl]-3,5-dihydro-2H-pyrido[3,4-f][1,4]oxazepine-9-carbonitrile: To a mixture of AgOTf (433 mg, 1.68 mmol), selectfluor (298 mg, 0.84 μmol) and KF (130.43 mg, 2.25 mmol) in EtOAc (20 mL) was added 4-[2-(3-hydroxycyclobutyl)-2-methyl-propanoyl]-3,5-dihydro-2H-pyrido[3,4-f][1,4]oxazepine-9-carbonitrile (177 mg, 0.56 mmol), 2-fluoropyridine (163 mg, 1.68 mmol) and trimethyl(trifluoromethyl)silane (239 mg, 1.68 mmol) under $N_2$. The reaction mixture was stirred at 20° C. for 16 h. The reaction mixture was filtered and concentrated under reduced pressure. The resulting residue was purified by prep-HPLC with the following conditions: column Xtimate C18 150×25 mm 5 μm; mobile phase: [water (10 mM $NH_4HCO_3$)-ACN]; B %: 38%-58% over 10.5 min to afford the title compound as a colorless oil. LCMS: m/z=384.3 [M+H]$^+$.

Examples 280 and 281

Preparation of 4-[2-[(3S)-1-(5-fluoropyrimidin-2-yl) pyrrolidin-3-yl]-2-methyl-propanoyl]-3,5-dihydro-2H-pyrido[3,4-f][1,4]oxazepine-9-carbonitrile and 4-[2-[(3R)-1-(5-fluoropyrimidin-2-yl)pyrrolidin-3-yl]-2-methyl-propanoyl]-3,5-dihydro-2H-pyrido[3,4-f][1,4]oxazepine-9-carbonitrile

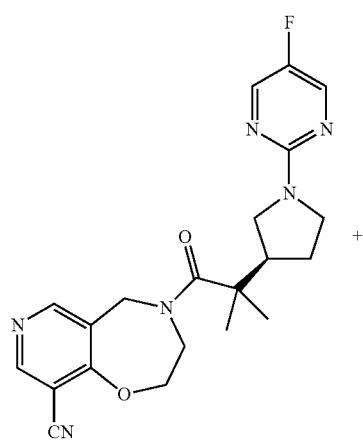

Racemic 4-(2-(1-(5-fluoropyrimidin-2-yl)pyrrolidin-3-yl)-2-methylpropanoyl)-2,3,4,5-tetrahydropyrido[3,4-f][1,4]oxazepine-9-carbonitrile was separated by SFC under the following conditions: Instrument: Thar SFC80 preparative SFC; Column: Chiralpak AY-H 250×30 mm i.d. 5 μm; Mobile phase A: $CO_2$, Mobile phase B: EtOH (0.1% $NH_3H_2O$); Gradient: B %=35%; Flow rate: 62 g/min.; Wavelength: 220 nm; Column temperature: 40° C.; System back pressure: 100 bar to provide the title compounds as pure enantiomers.

4-[2-(-1-(5-Fluoropyrimidin-2-yl)pyrrolidin-3-yl)-2-methyl-propanoyl]-3,5-dihydro-2H-pyrido[3,4-f][1,4] oxazepine-9-carbonitrile (first eluting peak, Example 280) Isolated as a white solid. LCMS: m/z=411.4 [M+H]$^+$.

4-[2-(-1-(5-Fluoropyrimidin-2-yl)pyrrolidin-3-yl)-2-methyl-propanoyl]-3,5-dihydro-2H-pyrido[3,4-f][1,4] oxazepine-9-carbonitrile (second eluting peak, Example 281) as a white solid. LCMS: m/z=411.4 [M+H]$^+$.

Examples 282 and 283

Preparation of 4-[(2S)-2-methoxy-2-methyl-butanoyl]-3,5-dihydro-2H-pyrido[3,4-f][1,4]oxazepine-9-carbonitrile and 4-[(2R)-2-methoxy-2-methyl-butanoyl]-3,5-dihydro-2H-pyrido[3,4-f][1,4] oxazepine-9-carbonitrile

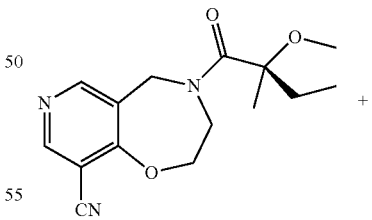

+

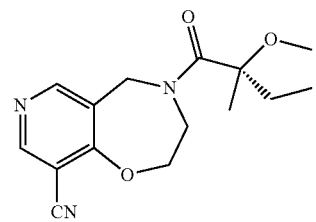

Racemic 4-(2-methoxy-2-methyl-butanoyl)-3,5-dihydro-2H-pyrido[3,4-f][1,4]oxazepine-9-carbonitrile was separated by SFC with the following conditions: Instrument: Thar SFC80 preparative SFC; Column: Chiralpak AD-H 250×30 mm i.d. 5 µm; Mobile phase A: $CO_2$ Mobile phase B: EtOH (0.1% $NH_3H_2O$); Gradient: B %=25%; Flow rate: 67 g/min.; Wavelength: 220 nm; Column temperature: 40° C.; System back pressure: 100 bar; Cycle time: 2.5 min. to provide the title compounds as pure enantiomers.

4-(2-Methoxy-2-methyl-butanoyl)-3,5-dihydro-2H-pyrido[3,4-f][1,4]oxazepine-9-carbonitrile (first eluting peak, Example 282). LCMS: m/z=290.7 $[M+H]^+$.

4-(-2-Methoxy-2-methyl-butanoyl)-3,5-dihydro-2H-pyrido[3,4-f][1,4]oxazepine-9-carbonitrile (second eluting peak, Example 283). LCMS: m/z=290.7 $[M+H]^+$.

Examples 284 and 285

Preparation of 4-[(4R)-3,3-difluoro-1-(5-fluoropyrimidin-2-yl)-4-methyl-piperidine-4-carbonyl]-3,5-dihydro-2H-pyrido [3,4-f][1,4]oxazepine-9-carbonitrile and 4-[(4S)-3,3-difluoro-1-(5-fluoropyrimidin-2-yl)-4-methyl-piperidine-4-carbonyl]-3,5-dihydro-2H-pyrido [3,4-f][1,4]oxazepine-9-carbonitrile

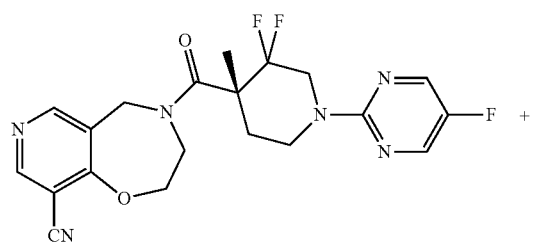

+

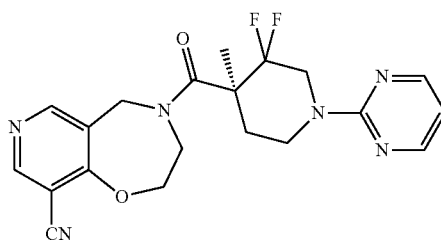

Racemic 4- [3,3-difluoro-1-(5-fluoropyrimidin-2-yl)-4-methyl-piperidine-4-carbonyl]-3,5-dihydro-2H-pyrido[3,4-f][1,4]oxazepine-9-carbonitrile was separated by SFC with the following conditions: column: DAICEL CHIRALPAK AD-H (250 mm×30 mm, 5 µm); mobile phase A: $CO_2$, mobile phase B: [0.1% $NH_3H_2O$ IPA]; B %: 45%-45%, over 4 min to provide the pure enantiomers.

4-[3,3-Difluoro-1-(5-fluoropyrimidin-2-yl)-4-methyl-piperidine-4-carbonyl]-3,5-dihydro-2H-pyrido[3,4-f][1,4] oxazepine-9-carbonitrile (first eluting peak, Example 284) Isolated as a colorless oil. LCMS: m/z=433.3 $[M+H]^+$.

4-[-3,3-Difluoro-1-(5-fluoropyrimidin-2-yl)-4-methyl-piperidine-4-carbonyl]-3,5-dihydro-2H-pyrido[3,4-f][1,4] oxazepine-9-carbonitrile (second eluting peak, Example 285) Isolated as a colorless oil. LCMS: m/z=433.3 $[M+H]^+$.

Example 286

Preparation of 4-[1-(6,7-dihydro-5H-pyrrolo[3,4-b]pyridin-2-yl)-4-fluoro-piperidine-4-carbonyl]-3,5-dihydro-2H-pyrido[3,4-f][1,4]oxazepine-9-carbonitrile

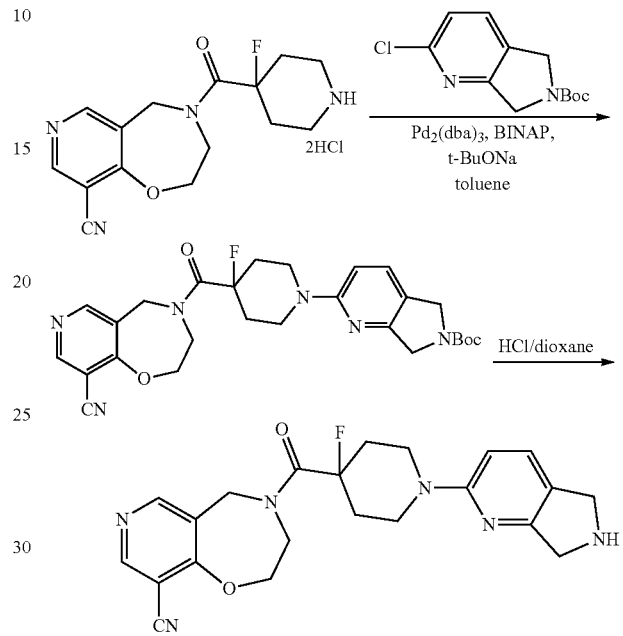

tert-Butyl 2-[4-(9-cyano-3,5-dihydro-2H-pyrido[3,4-f][1,4]oxazepine-4-carbonyl)-4-fluoro-1-piperidyl]-5,7-dihydropyrrolo[3,4-b]pyridine-6-carboxylate: To a mixture of 4-(4-fluoropiperidine-4-carbonyl)-3,5-dihydro-2H-pyrido [3,4-f][1,4]oxazepine-9-carbonitrile dihydrochloride (100 mg, 0.265 mmol) and tert-butyl 2-chloro-5,7-dihydropyrrolo [3,4-b]pyridine-6-carboxylate (101 mg, 0.398 mmol) in toluene (2 mL) was added $Pd_2(dba)_3$ (24 mg, 0.026 mmol), BINAP (33 mg, 0.053 mmol) and sodium 2-methylpropan-2-olate (153 mg, 1.59 mmol) in one portion at 15° C. The mixture was heated at 110° C. and stirred for 2 h under $N_2$. The mixture was diluted with water (5 mL) and extracted with EtOAc (2×3 mL). The combined organics were washed with brine (10 mL), dried over anhydrous $Na_2SO_4$, filtered and concentrated under reduced pressure to provide the title compound (50 mg, 36%) as a brown oil. LCMS: m/z=523.3 $[M+H]^+$.

4-[1-(6,7-Dihydro-5H-pyrrolo[3,4-b]pyridin-2-yl)-4-fluoro-piperidine-4-carbonyl]-3,5-dihydro-2H-pyrido[3,4-f] [1,4]oxazepine-9-carbonitrile: A solution of tert-butyl 2-[4-(9-cyano-3,5-dihydro-2H-pyrido[3,4-f][1,4]oxazepine-4-carbonyl)-4-fluoro-1-piperidyl]-5,7-dihydropyrrolo[3,4-b] pyridine-6-carboxylate (50 mg, 0.96 mmol) in HCl/1,4-dioxane (10 mL, 4 M) was stirred for 1 h at 15° C. The mixture was diluted with water (10 mL) and concentrated under reduced pressure to remove 1,4-dioxane. The aqueous phase was washed with EtOAc (2×5 mL) and the pH was adjusted to 9 and extracted with DCM:i-PrOH (5×5 mL, v:v=3:1). The combined organics were dried over anhydrous $Na_2SO_4$, filtered and concentrated under reduced pressure. The residue was purified by prep-HPLC with the following conditions: column: Xtimate C18 150×25 mm×5 µm; mobile phase A: water (10 mM NH₄HCO₃) mobile phase B: ACN; B %: 15%-45% over 10.5 min. to provide the title compound as a colorless oil. LCMS: m/z=423.4 [M+H]⁺.

Examples 287 and 288

Preparation of 4-[1-(3,5-difluoro-6-methoxy-2-pyridyl)piperidine-4-carbonyl]-3,5-dihydro-2H-pyrido[3,4-f][1,4]oxazepine-9-carbonitrile (Example 287) and 4-[1-(3,5,6-trifluoro-2-pyridyl)piperidine-4-carbonyl]-3,5-dihydro-2H-pyrido[3,4-f][1,4] oxazepine-9-carbonitrile (Example 288)

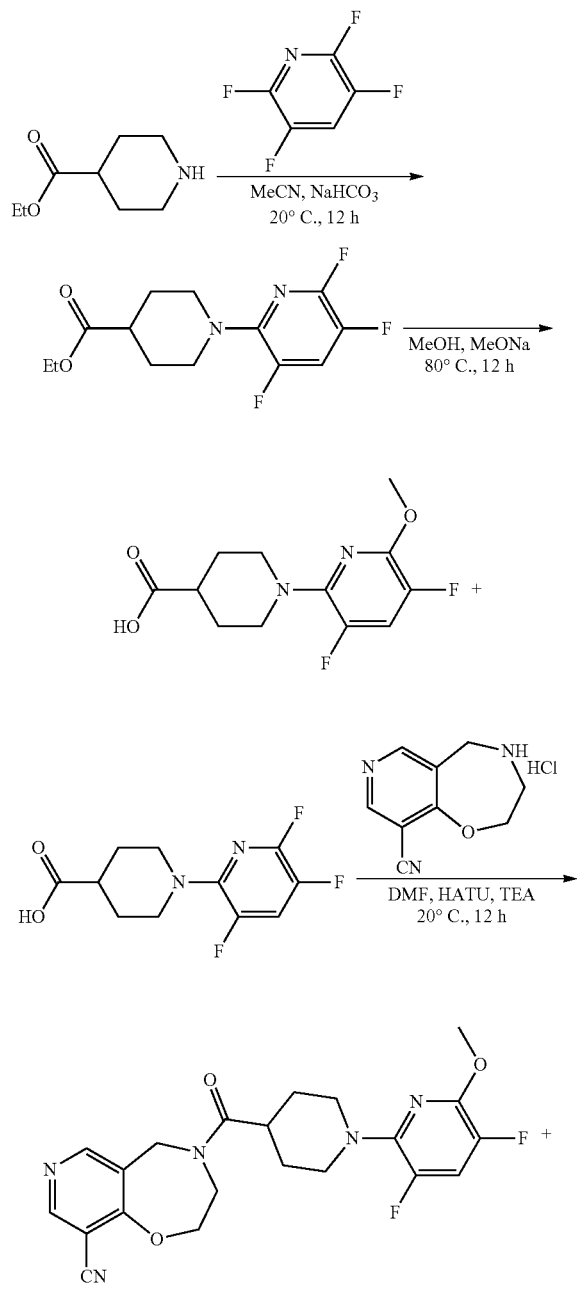

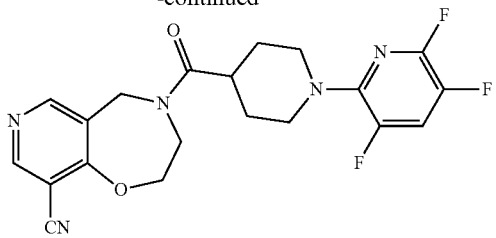

Ethyl 1-(3,5,6-trifluoro-2-pyridyl)piperidine-4-carboxylate: To a solution of 2,3,5,6-tetrafluoropyridine (961 mg, 6.36 mmol) in MeCN (20 mL) was added NaHCO₃ (267 mg, 3.18 mmol) and ethyl piperidine-4-carboxylate (0.5 g, 3.18 mmol). The reaction mixture was stirred at 20° C. for 12 h before concentrating under reduced pressure. The resulting residue was purified by silica gel column chromatography (PE:EtOAc=20:1 to 3:1) to give the title compound (0.3 g, 33%) as a colorless oil. LCMS: m/z=289.1 [M+H]⁺.

1-(3,5,6-Trifluoro-2-pyridyl)piperidine-4-carboxylic acid and 1-(3,5-difluoro-6-methoxy-2-pyridyl)piperidine-4-carboxylic acid: To a solution of ethyl 1-(3,5,6-trifluoro-2-pyridyl)piperidine-4-carboxylate (150 mg, 0.52 mmol) in MeOH (5 mL) was added MeONa (281 mg, 5.20 mmol). The reaction solution was heated at 80° C. for 12 h before concentrating under reduced pressure. The resulting residue was taken up in water and the pH adjusted to 4 with HCl. The aqueous solution was extracted with EtOAc (3×10 mL) and the combined organic layers were washed with brine (10 mL), dried over anhydrous Na₂SO₄, filtered and concentrated under reduced pressure to provide a mixture of the title compounds (130 mg, 96%) as a white solid, which was used directly in next step. LCMS: m/z=261.1, 273.1 [M+H]⁺.

4-[1-(3,5-Difluoro-6-methoxy-2-pyridyl)piperidine-4-carbonyl]-3,5-dihydro-2H-pyrido[3,4-f][1,4]oxazepine-9-carbonitrile and 4-[1-(3,5,6-trifluoro-2-pyridyl)piperidine-4-carbonyl]-3,5-dihydro-2H-pyrido[3,4-f][1,4]oxazepine-9-carbonitrile: To a solution of 1-(3,5-difluoro-6-methoxy-2-pyridyl)piperidine-4-carboxylic acid, 1-(3,5,6-trifluoro-2-pyridyl)piperidine-4-carboxylic acid (120 mg, 0.44 mmol) and 2,3,4,5-tetrahydropyrido[3,4-f][1,4]oxazepine-9-carbonitrile dihydrochloride (109 mg, 0.44 mmol) in DMF (5 mL) was added TEA (178 mg, 1.76 mmol, 245 µL) and HATU (201 mg, 0.53 mmol). The reaction mixture was stirred at 20° C. for 12 h, diluted with water (10 mL) and extracted with EtOAc (3×10 mL). The organic layers were combined, washed with brine (3×5 mL), dried over anhydrous Na₂SO₄, filtered and concentrated under reduced pressure. The resulting residue was purified by prep-HPLC with the following conditions: column: Nano-micro Kromasil C18 100×30 mm 5 µm; mobile phase A: water (0.1% TFA), mobile phase B: ACN; B %: 40%-50% over 10 min. to provide the title compounds.

4-[1-(3,5-Difluoro-6-methoxy-2-pyridyl)piperidine-4-carbonyl]-3,5-dihydro-2H-pyrido[3,4-f][1,4]oxazepine-9-carbonitrile (second eluting peak, Example 287) Obtained as a white solid. LCMS: m/z=430.4 [M+H]⁺.

4-[1-(3,5,6-Trifluoro-2-pyridyl)piperidine-4-carbonyl]-3,5-dihydro-2H-pyrido [3,4-f][1,4]oxazepine-9-carbonitrile (first eluting peak, Example 288) Obtained as a white solid. LCMS: m/z=418.3 [M+H].

Example 289

Preparation of 4-[1-(3,5-difluoro-6-methoxy-2-pyridyl)-4-methoxy-piperidine-4-carbonyl]-3,5-dihydro-2H-pyrido [3,4-f][1,4]oxazepine-9-carbonitrile

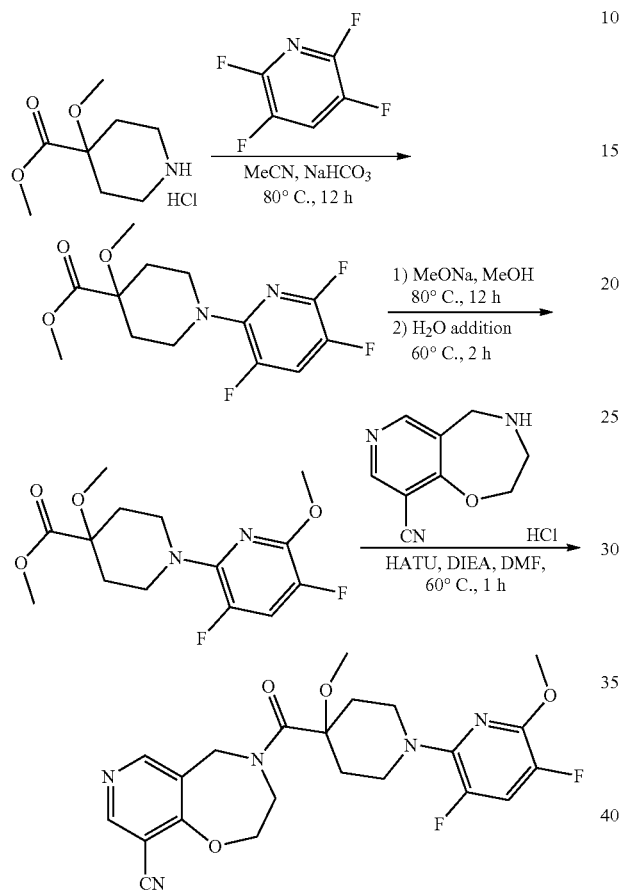

Methyl 4-methoxy-1-(3,5,6-trifluoropyridin-2-yl)piperidine-4-carboxylate. To a solution of methyl 4-methoxypiperidine-4-carboxylate hydrochloride (200 mg, 0.95 mmol) and 2,3,5,6-tetrafluoropyridine (288 mg, 1.91 mmol) in MeCN (5 mL) was added NaHCO$_3$ (240 mg, 2.86 mmol). The mixture was stirred at 80° C. for 12 h. The reaction mixture was filtered and the filtrate was concentrated to provide the title compound (287 mg, 99%) as a yellow oil, which was used in the next step without further purification. LCMS: m/z=305.1 [M+H]$^+$.

1-(3,5-Difluoro-6-methoxypyridin-2-yl)-4-methoxypiperidine-4-carboxylic acid. To a solution of methyl 4-methoxy-1-(3,5,6-trifluoro-2-pyridyl)piperidine-4-carboxylate (280 mg, 0.92 mmol) in MeOH (10 mL) was added NaOMe (249 mg, 4.60 mmol). The mixture was stirred at 80° C. for 12 h before diluting with H$_2$O (4 mL). The mixture was stirred at 60° C. for 2 h. The reaction mixture was concentrated under reduced pressure to remove MeOH. The residue was diluted with H$_2$O (4 mL) and adjusted to pH=4 with 1N HCl, The mixture was concentrated under reduced pressure to provide the title compound (300 mg) as a white solid, which was used in the next step without further purification. LCMS: m/z=303.1 [M+H]$^+$.

4-(1-(3,5-Difluoro-6-methoxypyridin-2-yl)-4-methoxypiperidine-4-carbonyl)-2,3,4,5-tetrahydropyrido[3,4-f][1,4]oxazepine-9-carbonitrile. To a solution of 2,3,4,5-tetrahydropyrido[3,4-f][1,4]oxazepine-9-carbonitrile hydrochloride (50 mg, 0.24 mmol) and 1-(3,5-difluoro-6-methoxy-2-pyridyl)-4-methoxy-piperidine-4-carboxylic acid (143 mg, 0.24 mmol) in DMF (2 mL) was added DIEA (122 mg, 0.94 mmol) and HATU (108 mg, 0.28 mmol). The mixture was stirred at 60° C. for 1 h. The reaction mixture was quenched with H$_2$O (1 mL) and extracted with EtOAc. The organics were washed with brine, dried over Na$_2$SO$_4$, filtered and concentrated in vacuo. The resulting residue was purified by prep-HPLC with the following conditions: column: Xtimate C18 150×25 mm×5 μm; mobile phase A: water (10 mM NH$_4$HCO$_3$), mobile phase B: ACN; B %: 43%-63% over 10.5 min) to provide the title compound as a white solid. LCMS: m/z=460.4 [M+H]$^+$.

Examples 290 and 291

Preparation of trans-4-[2-methyl-2-[3-(triazol-2-ylmethyl)cyclobutyl]propanoyl]-3,5-dihydro-2H-pyrido [3,4-f][1,4]oxazepine-9-carbonitrile (Example 290) and cis-4-[2-methyl-2-[3-(triazol-2-ylmethyl)cyclobutyl]propanoyl]-3,5-dihydro-2H-pyrido[3,4-f][1,4]oxazepine-9-carbonitrile (Example 291)

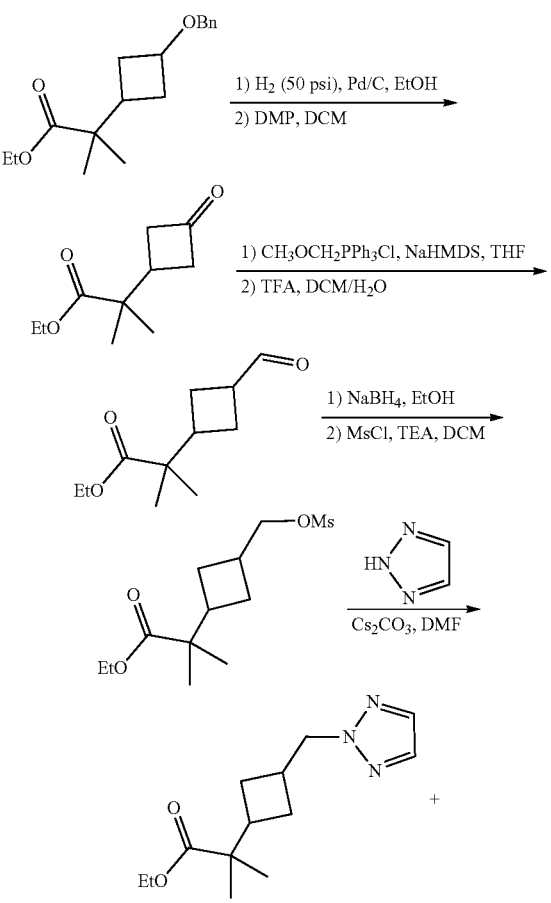

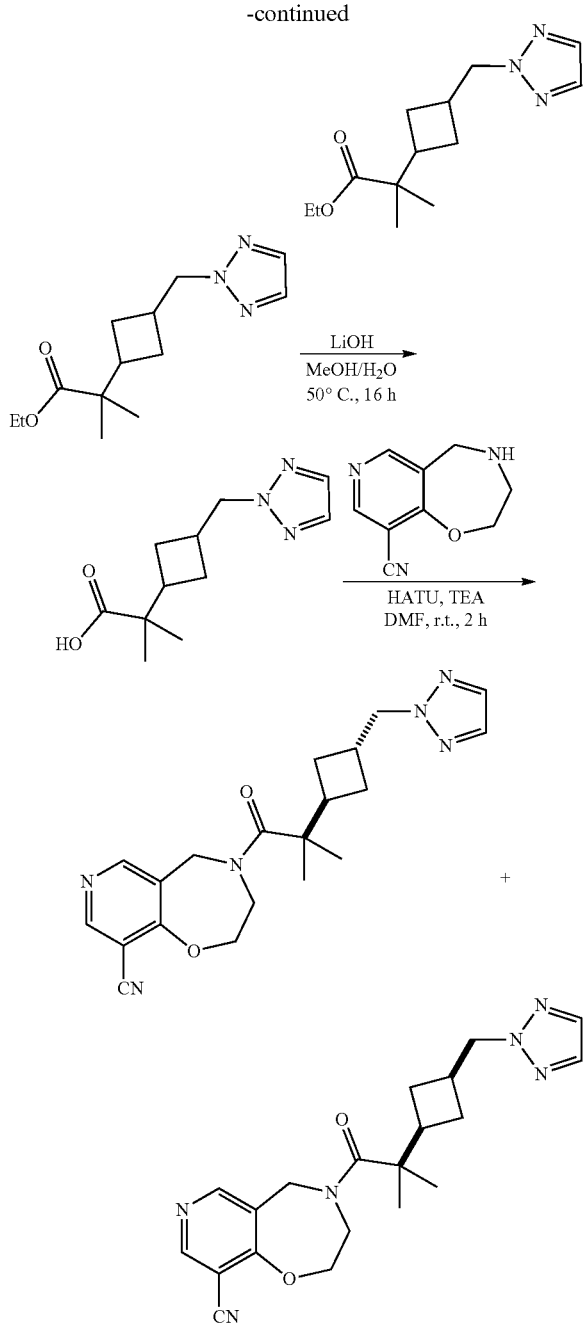

Ethyl 2-(3-hydroxycyclobutyl)-2-methyl-propanoate: To a solution of ethyl 2-(3-benzyloxycyclobutyl)-2-methyl-propanoate (9 g, 32.57 mmol) in EtOH (200 mL) was added 10% Pd/C (3 g) under $N_2$. The suspension was degassed under vacuum and purged with $H_2$ three times. The mixture was stirred under $H_2$ (50 psi) at 50° C. for 16 h. The reaction mixture was filtered through a pad of celite and the filtrate was concentrated under reduced pressure to provide the title compound (6.3 g) as a colorless oil, which was used in the next step without purification.

Ethyl 2-methyl-2-(3-oxocyclobutyl)propanoate: To a solution of ethyl 2-(3-hydroxycyclobutyl)-2-methyl-propanoate (6.3 g, 33.83 mmol) in DCM (150 mL) was added DMP (17.22 g, 40.59 mmol) at 0° C. under $N_2$. The reaction mixture was warmed to 25° C. and stirred for 1 h. The mixture was diluted with DCM (50 mL) and washed with 10% aq. $Na_2S_2O_3$ (2×50 mL), sat. $NaHCO_3$ (2×50 mL) and brine (50 mL). The organic layer was dried over anhydrous $Na_2SO_4$, filtered and concentrated under reduced pressure. The resulting residue was purified by silica gel column chromatography (PE:EtOAc=30:1 to 15:1) to afford the title compound (4.5 g, 72%) as a colorless oil.

Ethyl 2-[3-(methoxymethylene)cyclobutyl]-2-methyl-propanoate: To a mixture of methoxymethyl(triphenyl)phosphonium chloride (13.4 g, 39.08 mmol) in THF (80 mL) was added NaHMDS (36.64 mmol, 36.6 mL, 1 M in THF) at −40° C. under $N_2$. The mixture was stirred at 0° C. for 30 min., then cooled to −40° C. and a solution of ethyl 2-methyl-2-(3-oxocyclobutyl)propanoate (4.5 g, 24.43 mmol) in THF (20 mL) was added. The reaction mixture was stirred at 25° C. for 16 h and was then poured into sat. $NH_4Cl$ (100 mL). The aqueous phase was extracted with MTBE (3×30 mL). The combined organics were washed with brine (50 mL), dried over anhydrous $Na_2SO_4$, filtered and concentrated under reduced pressure. The resulting residue was purified by silica gel column chromatography (PE:EtOAc=50:1 to 20:1) to give the title compound (4.3 g, 83%) as a colorless oil.

Ethyl 2-(3-formylcyclobutyl)-2-methyl-propanoate: To a solution of ethyl 2-[3-(methoxymethylene)cyclobutyl]-2-methyl-propanoate (4.3 g, 20.26 mmol) in DCM (80 mL) was added TFA (3 mL) and $H_2O$ (9 mL) at 25° C. under $N_2$. The mixture was stirred at 25° C. for 3 h and the layers were separated. The aqueous phase was extracted with DCM (10 mL). The combined organics were washed with brine (20 mL), dried over anhydrous $Na_2SO_4$, filtered and concentrated under reduced pressure. The resulting residue was purified by silica gel column chromatography (PE:EtOAc=30:1 to 20:1) to afford the title compound (3 g, 75%) as a 1:1 mixture of cis and trans isomers isolated as a colorless oil.

Ethyl 2-[3-(hydroxymethyl)cyclobutyl]-2-methyl-propanoate: To a solution of ethyl 2-(3-formylcyclobutyl)-2-methyl-propanoate (3 g, 15.13 mmol) in EtOH (30 mL) was added $NaBH_4$ (859 mg, 22.70 mmol) at 0° C. under $N_2$. The mixture was stirred at 0° C. for 1 h and was quenched by the addition of water (50 mL) at 0° C. The solution was concentrated under reduced pressure to remove EtOH. The remaining aqueous phase was extracted with EtOAc (3×15 mL). The combined organic phase was washed with brine (10 mL), dried over anhydrous $Na_2SO_4$, filtered and concentrated under reduced pressure. The resulting residue was purified by silica gel column chromatography (PE:EtOAc=7:1) to provide the title compound (2.2 g, 73%) as a 1:1 mixture of cis and trans isomers isolated as a colorless oil.

Ethyl 2-methyl-2-[3-(methylsulfonyloxymethyl)cyclobutyl]propanoate: To a solution of ethyl 2-[3-(hydroxymethyl)cyclobutyl]-2-methyl-propanoate (1.1 g, 5.49 mmol) in DCM (20 mL) was added TEA (834 mg, 8.24 mmol, 1.15 mL) and MsCl (755 mg, 6.59 mmol) at 0° C. under $N_2$. The reaction mixture was stirred at 0° C. for 1 h and was then washed with water (20 mL), brine (20 mL), dried over anhydrous $Na_2SO_4$, filtered and concentrated under reduced pressure to afford the title compound (1.4 g, 92%) as a 1:1 mixture of cis and trans isomers isolated as a colorless oil. The residue was used in the next step without further purification.

Ethyl 2-methyl-2-[3-(triazol-2-ylmethyl)cyclobutyl]propanoate and ethyl 2-methyl-2-[3-(triazol-1-ylmethyl)cyclobutyl]propanoate: To a mixture of ethyl 2-methyl-2-[3-(methylsulfonyloxymethyl)cyclobutyl]propanoate (1.4 g, 5.03 mmol) and 2H-triazole (521 mg, 7.54 mmol) in DMF (28 mL) was added Cs$_2$CO$_3$ (3.28 g, 10.06 mmol) at 25° C. under N$_2$. The mixture was heated to 70° C. and stirred for 16 h. The mixture was cooled to 25° C. and poured into ice-water (140 mL). The aqueous phase was extracted with EtOAc (3×40 mL). The combined organic phase was washed with brine (30 mL), dried over anhydrous Na$_2$SO$_4$, filtered and concentrated under reduced pressure. The resulting residue was purified by silica gel column chromatography (PE: EtOAc=20:1 to 1:1) to afford the first eluting product, ethyl 2-methyl-2-[3-(triazol-2-ylmethyl)cyclobutyl]propanoate (0.7 g, 55%) as a 1:1 mixture of cis and trans isomers isolated as a colorless oil and the second eluting product, ethyl 2-methyl-2-[3-(triazol-1-ylmethyl)cyclobutyl]propanoate (0.5 g, 40%) as a 1:1 mixture of cis and trans isomers isolated as a colorless oil.

2-Methyl-2-[3-(triazol-2-ylmethyl)cyclobutyl]propanoic acid: To a mixture of ethyl 2-methyl-2-[3-(triazol-2-ylmethyl)cyclobutyl]propanoate (250 mg, 1 mmol) in H$_2$O (2 mL) and EtOH (4 mL) was added LiOH.H$_2$O (167 mg, 3.98 mmol) at 25° C. The mixture was heated at 50° C. for 16 h. The mixture was added to water (40 mL). The aqueous phase was washed with MTBE (10 mL), the pH was adjusted to 3-4 with dilute HCl and extracted with EtOAc (3×20 mL). The combined organic phase was washed with brine (10 mL), dried over anhydrous Na$_2$SO$_4$, filtered and concentrated to provide the title compound (0.19 g, 86%) as a colorless oil, which was used in the next step without further purification. LC-MS: m/z=224.1 [M+H]$^+$.

trans-4-[2-Methyl-2-[3-(triazol-2-ylmethyl)cyclobutyl]propanoyl]-3,5-dihydro-2H-pyrido[3,4-f][1,4]oxazepine-9-carbonitrile and cis-4-[2-methyl-2-[3-(triazol-2-ylmethyl)cyclobutyl]propanoyl]-3,5-dihydro-2H-pyrido[3,4-f][1,4]oxazepine-9-carbonitrile: To a mixture of 2-methyl-2-[3-(triazol-2-ylmethyl)cyclobutyl]propanoic acid (190 mg, 0.85 mmol) and 2,3,4,5-tetrahydropyrido[3,4-f][1,4]oxazepine-9-carbonitrile dihydrochloride (422 mg, 1.70 mmol) in DMF (10 mL) was added TEA (430 mg, 4.25 mmol) and HATU (388 mg, 1.02 mmol) at 0° C. under N$_2$. The reaction mixture was stirred at 25° C. for 2 h. The mixture was poured into water (60 mL). The aqueous phase was extracted with EtOAc (3×20 mL). The combined organic phase was washed with brine (15 mL), dried over anhydrous Na$_2$SO$_4$, filtered and concentrated under reduced pressure. The resulting residue was purified by silica gel column chromatography (MTBE:MeOH=50:1 to 30:1) to afford a mixture of the cis and trans isomers as a colorless syrup. Purification by SFC with the following conditions: (column: DAICEL CHIRALCEL OJ-H (250 mm×30 mm, 5 μm); mobile phase: [0.1% NH$_3$H$_2$O IPA]; B %: 35%-35% over 3 min.) to afford the two isomers.

trans 4-[2-Methyl-2-[3-(triazol-2-ylmethyl)cyclobutyl]propanoyl]-3,5-dihydro-2H-pyrido[3,4-f][1,4]oxazepine-9-carbonitrile (first eluting peak, Example 290) Isolated as a white solid. LCMS: m/z=381.2 [M+H]$^+$.

cis-4-[2-Methyl-2-[3-(triazol-2-ylmethyl)cyclobutyl]propanoyl]-3,5-dihydro-2H-pyrido[3,4-f][1,4]oxazepine-9-carbonitrile (second eluting peak, Example 291) Isolated as a white solid. LCMS: m/z=381.4 [M+H]$^+$.

Examples 292 and 293

Preparation of trans-4-[2-methyl-2-[3-(triazol-1-ylmethyl)cyclobutyl]propanoyl]-3,5-dihydro-2H-pyrido[3,4-f][1,4]oxazepine-9-carbonitrile (Example 292) and cis-4-[2-methyl-2-[3-(triazol-1-ylmethyl)cyclobutyl]propanoyl]-3,5-dihydro-2H-pyrido[3,4-f][1,4]oxazepine-9-carbonitrile (Example 293)

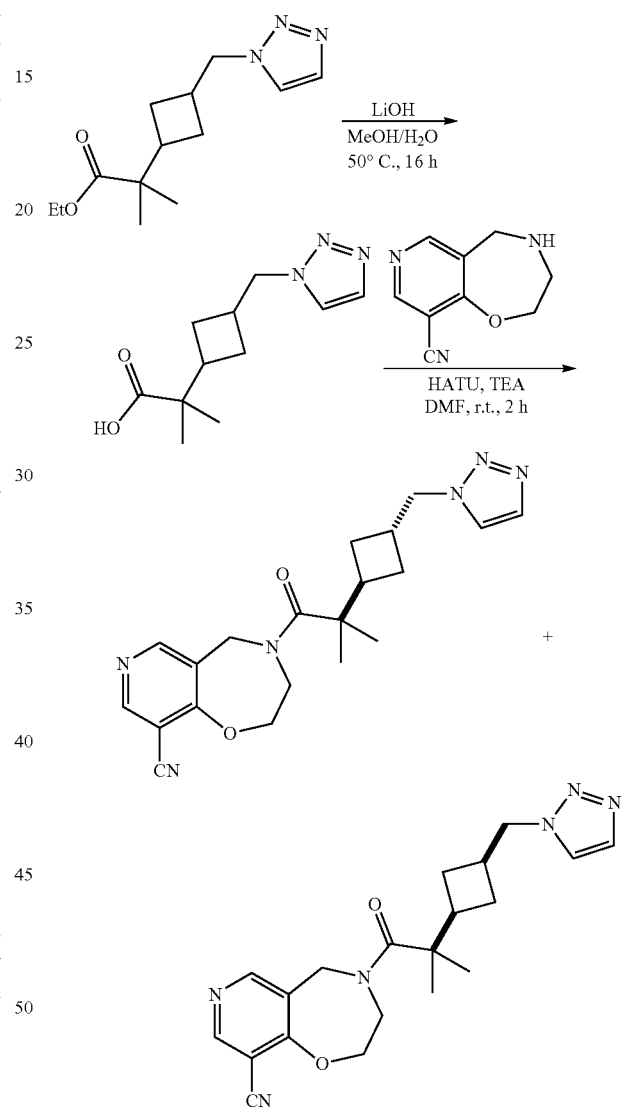

2-Methyl-2-[3-(triazol-1-ylmethyl)cyclobutyl]propanoic acid: To a mixture of ethyl 2-methyl-2-[3-(triazol-1-ylmethyl)cyclobutyl]propanoate (250 mg, 1 mmol) in H$_2$(2 mL) and EtOH (4 mL) was added LiOH.H$_2$O (167 mg, 3.98 mmol) at 25° C. under N$_2$. The reaction mixture was heated at 50° C. for 16 h. The mixture was added to water (40 mL) and washed with MTBE (10 mL). The aqueous phase was adjusted to pH=3-4 with dilute HCl and extracted with EtOAc (3×20 mL). The combined organic phase was washed with brine (10 mL), dried over anhydrous Na$_2$SO$_4$, filtered and concentrated under reduced pressure to provide the title compound (0.18 g, 81%) as a mixture of cis and trans isomers isolated as a colorless oil, which was used in the next step without further purification. LC-MS: m/z=224.2 [M+H]+.

trans-4-[2-Methyl-2-[3-(triazol-1-ylmethyl)cyclobutyl] propanoyl]-3,5-dihydro-2H-pyrido[3,4-f][1,4]oxazepine-9-carbonitrile and cis-4-[2-methyl-2-[3-(triazol-1-ylmethyl) cyclobutyl]propanoyl]-3,5-dihydro-2H-pyrido[3,4-f][1,4] oxazepine-9-carbonitrile: To a mixture of 2-methyl-2-[3-(triazol-1-ylmethyl)cyclobutyl]propanoic acid (180 mg, 0.81 mmol) and 2,3,4,5-tetrahydropyrido[3,4-f][1,4] oxazepine-9-carbonitrile dihydrochloride (400 mg, 1.61 mmol) in DMF (10 mL) was added TEA (408 mg, 4.03 mmol) and HATU (368 mg, 0.97 mmol) at 0° C. under $N_2$. The mixture was stirred at 25° C. for 2 h. The mixture was poured into water (60 mL). The aqueous phase was extracted with EtOAc (3×20 mL). The combined organic phase was washed with brine (20 mL), dried over anhydrous $Na_2SO_4$, filtered and concentrated. The residue was purified by silica gel column chromatography (MTBE:MeOH=10:1 to 5:1) to afford a mixture of the cis and trans isomers as a colorless oil. Purification by SFC with the following conditions: (column DAICEL CHIRALCEL OJ-H (250 mm×30 mm, 5 μm); mobile phase: [0.1% $NH_3H_2O$ IPA]; B %: 40%-40% over 3 min.) provided the two isomers.

trans-4-[2-Methyl-2-[3-(triazol-1-ylmethyl)cyclobutyl] propanoyl]-3,5-dihydro-2H-pyrido[3,4-f][1,4]oxazepine-9-carbonitrile (first eluting peak, Example 292) Isolated as a white solid. LCMS: m/z=381.2 [M+H]+.

cis-4-[2-Methyl-2-[3-(triazol-1-ylmethyl)cyclobutyl]propanoyl]-3,5-dihydro-2H-pyrido[3,4-f][1,4]oxazepine-9-carbonitrile (second eluting peak, Example 293) as white solid. LCMS: m/z=381.4 [M+H]+.

Example 294

Preparation of 4-[4-fluoro-1-(5-fluoro-[1,2,4]triazolo[1,5-a]pyrazin-8-yl)piperidine-4-carbonyl]-3,5-dihydro-2H-pyrido [3,4-f][1,4]oxazepine-9-carbonitrile

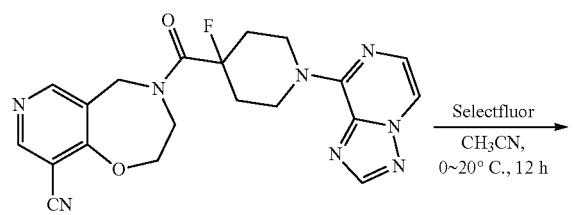

To a solution of 4-[4-fluoro-1-([1,2,4]triazolo[1,5-a] pyrazin-8-yl)piperidine-4-carbonyl]-3,5-dihydro-2H-pyrido [3,4-f][1,4]oxazepine-9-carbonitrile (45 mg, 0.11 mmol) in MeCN (5 mL) was added Selectfluor (34 mg, 95.88 μmol) at −30° C. The reaction solution was stirred at 20° C. for 12 h and then concentrated under reduced pressure. The resulting residue was purified by prep-TLC (DCM:MeOH=10:1) to provide the title compound as a colorless syrup. LCMS: m/z=441.1 [M+H]+.

Examples 295 and 296

Preparation of 4-[(4S)-3,3,4-trifluoro-1-(5-fluoropyrimidin-2-yl)piperidine-4-carbonyl]-3,5-dihydro-2H-pyrido[3,4-f][1,4]oxazepine-9-carbonitrile and 4-[(4R)-3,3,4-trifluoro-1-(5-fluoropyrimidin-2-yl) piperidine-4-carbonyl]-3,5-dihydro-2H-pyrido[3,4-f] [1,4]oxazepine-9-carbonitrile

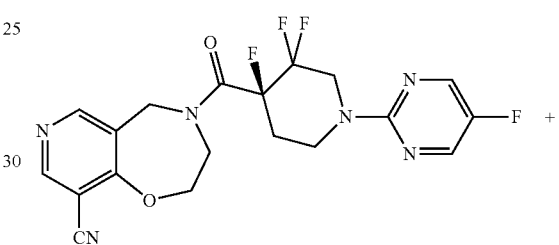

+

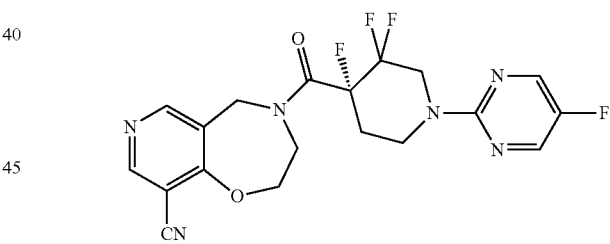

Racemic 4-[3,3,4-trifluoro-1-(5-fluoropyrimidin-2-yl)piperidine-4-carbonyl]-3,5-dihydro-2H-pyrido[3,4-f][1,4] oxazepine-9-carbonitrile was separated by SFC under the following conditions: column: DAICEL CHIRALPAK IC (250 mm×30 mm 5 μm); mobile phase: [0.1% $NH_3H_2O$ EtOH]; B %: 29%-29%, over 5.76 min) to provide the two enantiomers.

4-[3,3,4-Trifluoro-1-(5-fluoropyrimidin-2-yl)piperidine-4-carbonyl]-3,5-dihydro-2H-pyrido[3,4-f][1,4]oxazepine-9-carbonitrile (first eluting peak, Example 295) Isolated as a colorless gum. LCMS: m/z=437.3 [M+H]+.

4-[3,3,4-Trifluoro-1-(5-fluoropyrimidin-2-yl)piperidine-4-carbonyl]-3,5-dihydro-2H-pyrido[3,4-f][1,4]oxazepine-9-carbonitrile (second eluting peak, Example 296) Isolated as a white solid. LCMS: m/z=437.3 [M+H]+.

Examples 297 and 298

Preparation of 4-[(4R)-3,3-difluoro-4-methyl-1-pyrimidin-2-yl-piperidine-4-carbonyl]-3,5-dihydro-2H-pyrido[3,4-f][1,4]oxazepine-9-carbonitrile and 4-[(4S)-3,3-difluoro-4-methyl-1-pyrimidin-2-yl-piperidine-4-carbonyl]-3,5-dihydro-2H-pyrido [3,4-f][1,4]oxazepine-9-carbonitrile

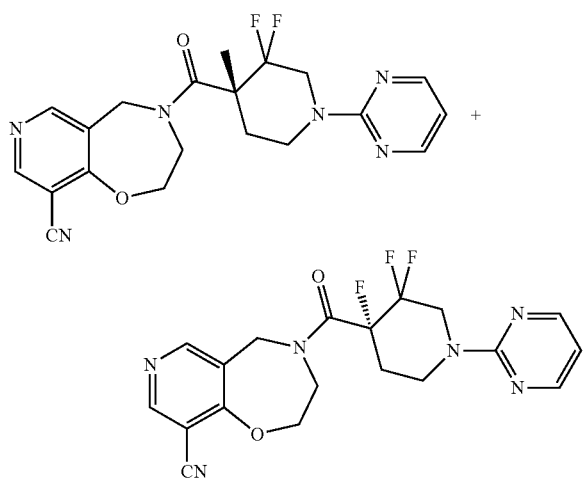

Racemic 4- [3,3-difluoro-4-methyl- 1-pyrimidin-2-yl-piperidine-4-carbonyl]-3,5-dihydro-2H-pyrido[3,4-f][1,4] oxazepine-9-carbonitrile was purified by SFC (column: DAICEL CHIRALPAK AD-H (250 mm×30 mm, 5 μm); mobile phase: [0.1% NH$_3$H$_2$O EtOH]; B %: 24%-24%, over 12 min) to provide the two enantiomers.

4-[3,3-Difluoro-4-methyl-1-pyrimidin-2-yl-piperidine-4-carbonyl]-3,5-dihydro-2H-pyrido[3,4-f][1,4]oxazepine-9-carbonitrile (first eluting peak, Example 297) Isolated as a white solid. LCMS: m/z=415.3 [M+H]$^+$.

4-[3,3-Difluoro-4-methyl-1-pyrimidin-2-yl-piperidine-4-carbonyl]-3,5-dihydro-2H-pyrido[3,4-f][1,4]oxazepine-9-carbonitrile (second eluting peak, Example 298) Isolated as a white solid. LCMS: m/z=415.4 [M+H]$^+$.

Examples 299 and 300

Preparation of 4-[(3S,4R)-3-fluoro-1-(5-fluoropyrimidin-2-yl)-4-methyl-piperidine-4-carbonyl]-3,5-dihydro-2H-pyrido[3,4-f][1,4]oxazepine-9-carbonitrile and 4-[(3R,4S)-3-fluoro-1-(5-fluoropyrimidin-2-yl)-4-methyl-piperidine-4-carbonyl]-3,5-dihydro-2H-pyrido[3,4-f][1,4]oxazepine-9-carbonitrile

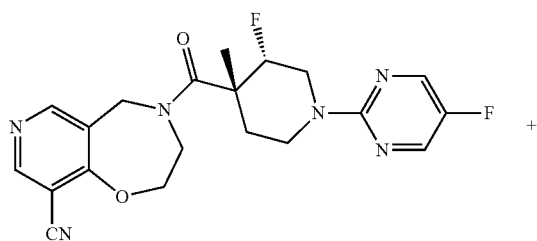

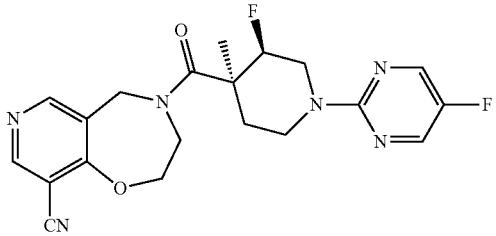

Racemic 4-[3-fluoro-1-(5-fluoropyrimidin-2-yl)-4-methyl-piperidine-4-carbonyl]-3,5-dihydro-2H-pyrido[3,4-f][1,4]oxazepine-9-carbonitrile was separated by SFC with the following conditions: column: DAICEL CHIRALPAK AD-H (250 mm×30 mm, 5 μm); mobile phase: [0.1% NH$_3$H$_2$O IPA]; B %: 28%-28% over 13.5 min. to provide the two enantiomers.

4-[3-Fluoro-1-(5-fluoropyrimidin-2-yl)-4-methyl-piperidine-4-carbonyl]-3,5-dihydro-2H-pyrido[3,4-f][1,4]oxazepine-9-carbonitrile (first eluting peak, Example 299) Isolated as white solid. LCMS: m/z=415.4 [M+H]$^+$.

4-[3-Fluoro-1-(5-fluoropyrimidin-2-yl)-4-methyl-piperidine-4-carbonyl]-3,5-dihydro-2H-pyrido[3,4-f][1,4]oxazepine-9-carbonitrile (second eluting peak, Example 300) Isolated as a white solid. LCMS: m/z=415.4 [M+H]$^+$.

Examples 301 and 302

Preparation of 4-[(3R,4R)-3-fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile and 4-[(3S,4S)-3-fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile

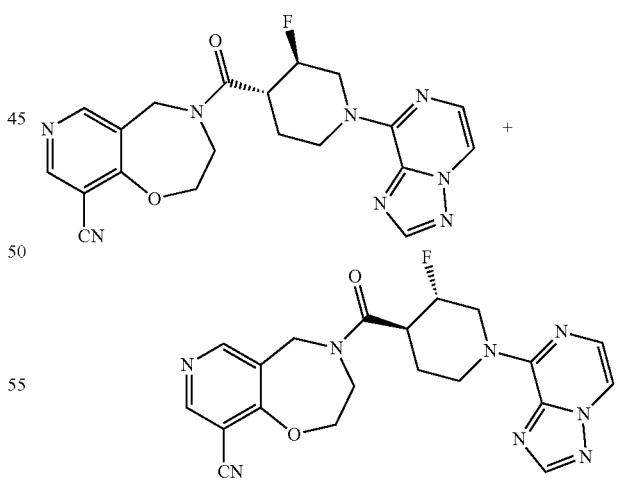

Racemic 4-[3-fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile was separated by SFC with the following conditions: column: DAICEL CHIRALPAK AS-H (250 mm×30 mm, 5 μm); mobile phase: [0.1% NH$_3$H$_2$O IPA]; B %: 35%-35% over 5 min. to provide the two enantiomers.

4-[3-Fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile (first eluting peak, Example 301) Obtained as a colorless oil. LCMS: m/z=423.3 [M+H]$^+$.

4-[3-Fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile (second eluting peak, Example 302) Obtained as a colorless oil. LCMS: m/z=423.1 [M+H]$^+$.

Examples 303 and 304

Preparation of 4-[(3R,4R)-3-fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile and 4-[(3S, 4S)-3-fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile

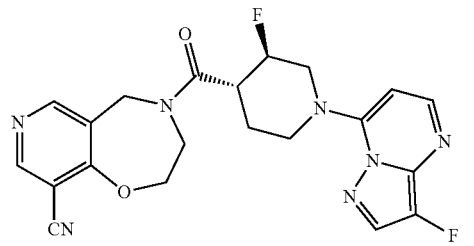

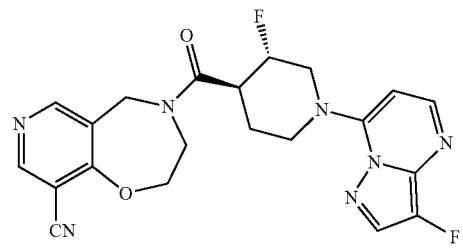

Racemic 4-[3-fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile was separated by SFC with the following conditions: column: DAICEL CHIRALCEL OJ (250 mm×30 mm, 10 μm); mobile phase: [0.1% NH$_3$H$_2$O MeOH]; B %: 40%-40% over 4.5 min to provide the two enantiomers.

4-[3-Fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile (first eluting peak, Example 303) Obtained as a white solid. LCMS: m/z=440.2 [M+H]$^+$.

4-[3-Fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile (second eluting peak, Example 304) Obtained as white solid. LCMS: m/z=440.1 [M+H]$^+$.

Examples 305 and 306

Preparation of 4-[(3R,4R)-3-fluoro-1-(5-fluoropyrimidin-2-yl)piperidine-4-carbonyl]-3,5-dihydro-2H-pyrido[3,4-f][1,4]oxazepine-9-carbonitrile and 4-[(3S,4S)-3-fluoro-1-(5-fluoropyrimidin-2-yl)piperidine-4-carbonyl]-3,5-dihydro-2H-pyrido[3,4-f][1,4]oxazepine-9-carbonitrile

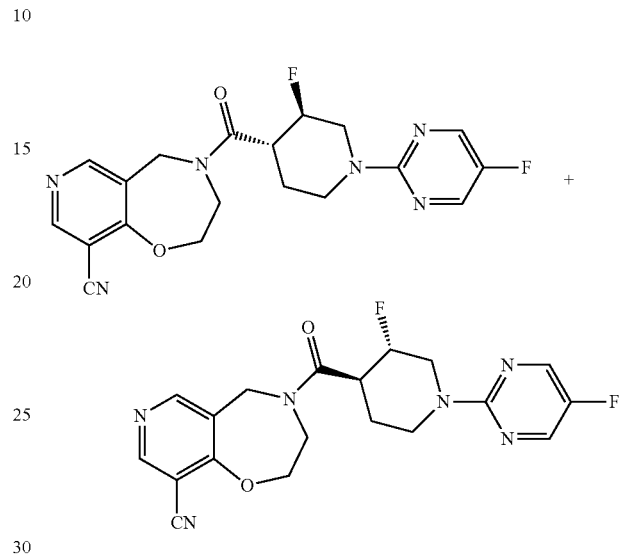

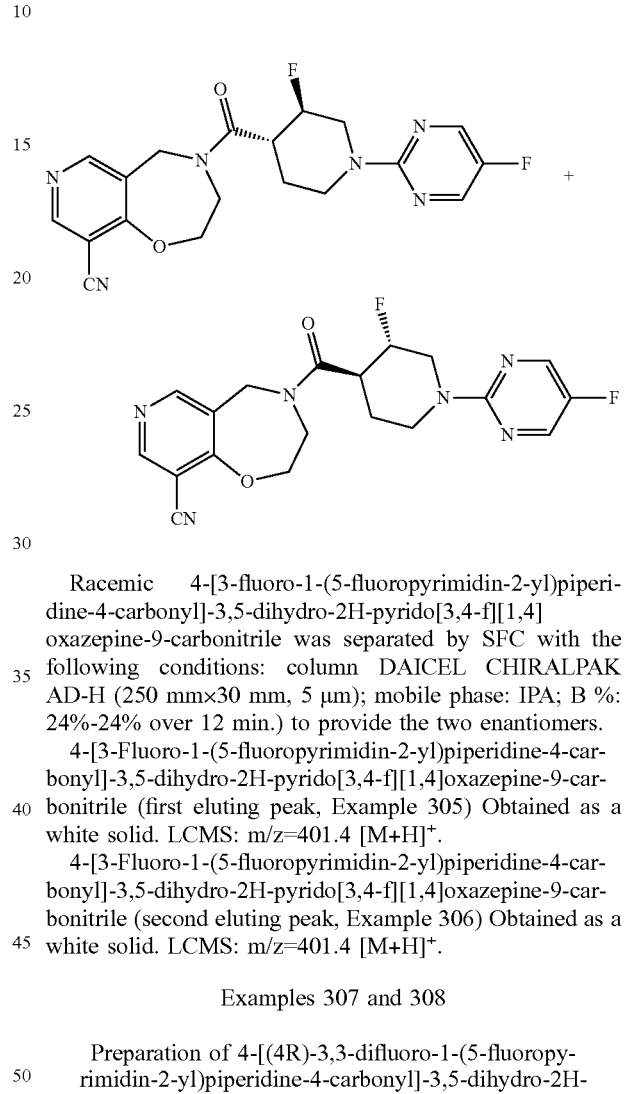

Racemic 4-[3-fluoro-1-(5-fluoropyrimidin-2-yl)piperidine-4-carbonyl]-3,5-dihydro-2H-pyrido[3,4-f][1,4]oxazepine-9-carbonitrile was separated by SFC with the following conditions: column DAICEL CHIRALPAK AD-H (250 mm×30 mm, 5 μm); mobile phase: IPA; B %: 24%-24% over 12 min.) to provide the two enantiomers.

4-[3-Fluoro-1-(5-fluoropyrimidin-2-yl)piperidine-4-carbonyl]-3,5-dihydro-2H-pyrido[3,4-f][1,4]oxazepine-9-carbonitrile (first eluting peak, Example 305) Obtained as a white solid. LCMS: m/z=401.4 [M+H]$^+$.

4-[3-Fluoro-1-(5-fluoropyrimidin-2-yl)piperidine-4-carbonyl]-3,5-dihydro-2H-pyrido[3,4-f][1,4]oxazepine-9-carbonitrile (second eluting peak, Example 306) Obtained as a white solid. LCMS: m/z=401.4 [M+H]$^+$.

Examples 307 and 308

Preparation of 4-[(4R)-3,3-difluoro-1-(5-fluoropyrimidin-2-yl)piperidine-4-carbonyl]-3,5-dihydro-2H-pyrido[3,4-f][1,4]oxazepine-9-carbonitrile and 4-[(4S)-3,3-difluoro-1-(5-fluoropyrimidin-2-yl)piperidine-4-carbonyl]-3,5-dihydro-2H-pyrido[3,4-f][1,4]oxazepine-9-carbonitrile

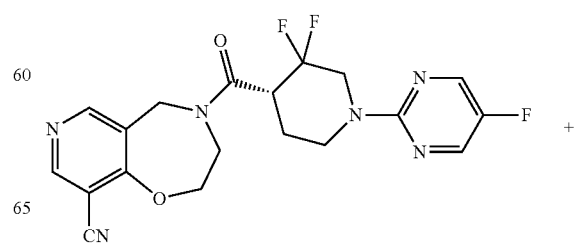

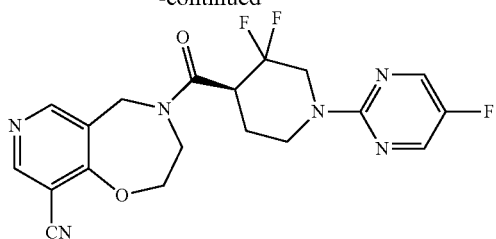

Racemic 4-[3,3-difluoro-1-(5-fluoropyrimidin-2-yl)piperidine-4-carbonyl]-3,5-dihydro-2H-pyrido[3,4-f][1,4]oxazepine-9-carbonitrile was separated by SFC with the following conditions: (column: DAICEL CHIRALPAK AD-H (250 mm×30 mm, 5 μm); mobile phase: IPA; B %: 24%-24%, over 12 min.) to provide the two enantiomers.

4-[3,3-Difluoro-1-(5-fluoropyrimidin-2-yl)piperidine-4-carbonyl]-3,5-dihydro-2H-pyrido[3,4-f][1,4]oxazepine-9-carbonitrile (first eluting peak, Example 307) was obtained as white solid. LCMS: m/z=419.3 [M+H]+.

4-[3,3-Difluoro-1-(5-fluoropyrimidin-2-yl)piperidine-4-carbonyl]-3,5-dihydro-2H-pyrido[3,4-f][1,4]oxazepine-9-carbonitrile (second eluting peak, Example 308) Obtained as a white solid. LCMS: m/z=419.4 [M+H]+.

Example 309

Preparation of 4-[1-(5-fluoropyrimidin-2-yl)-3-methoxy-piperidine-4-carbonyl]-3,5-dihydro-2H-pyrido[3,4-f][1,4]oxazepine-9-carbonitrile

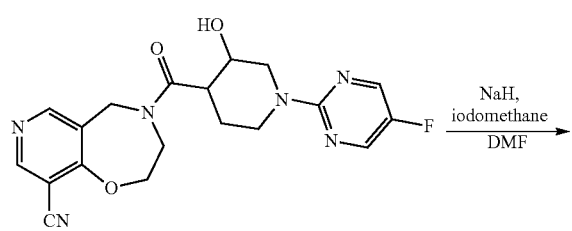

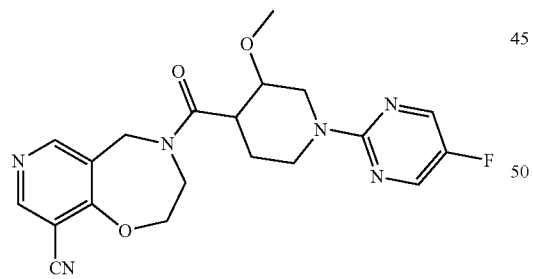

To a solution of 4-[1-(5-fluoropyrimidin-2-yl)-3-hydroxy-piperidine-4-carbonyl]-3,5-dihydro-2H-pyrido[3,4-f][1,4]oxazepine-9-carbonitrile (50.0 mg, 0.130 mmol) in DMF (5 mL) was added sodium hydride (7.5 mg, 0.19 mmol). The mixture was stirred at RT for 30 min before iodomethane (21.4 mg, 0.15 mmol) was added. The mixture was stirred at RT for 2 h. The reaction mixture was diluted with water (25 mL) then extracted with ethyl acetate (30 mL×2). The organic layers were combined and concentrated in vacuo. The resulting residue was purified employing reverse-phase HPLC to provide the title product as a colorless solid. LCMS: m/z=413.4 [M+H]+.

Example 310

Evaluation of Receptor-Interacting Protein Kinase 1 Inhibition

Fluorescent Polarization Binding (FP Binding) assay (Berger S. B. et al. (2015) Cell Death Discovery, 1: 15009; Maki J. L. et al. (2012) Anal Biochem., 427(2): 164-174) was performed in polystyrene low volume 384-well black plate, at RT in a final volume of 10.1 μl/well using 10 nM of GST-hRIPK1 (8-327) enzyme and 5 nM of fluorescent-labeled ligand (14-(2-{[3-({2-{[4-(cyanomethyl)phenyl]amino]-6-[(5-cyclopropyl-1H-pyrazol-3-yl)amino]-4-pyrimidinyl}amino) propyl}amino}-2-oxoethyl)-16,16,18,18-tetramethyl-6,7,7a,8a,9,10,16,18-octahydrobenzo [2",3"]indolizino[8",7":5',6']pyrano [3',2':3,4]pyrido[1,2-a]indol-5-ium-2-sulfonate.

Test compounds were serially diluted in DMSO at 100 fold final concentrations in the assay (1% DMSO final). In each well of a 384-well Plate were dispensed 0.1 μL of compound solution (or DMSO for controls) followed by 5 μL of GST-hRIPK1 (8-327) at twice the final concentrations in assay buffer (50 mM HEPES pH 7.5, 10 mM NaCl, 50 mM $MgCl_2$, 0.02% CHAPS, 0.5 mM DTT and 0.01% Pluronic F127). For negative control the enzyme addition was replaced by assay buffer only.

After addition of 5 μL of fluorescentlabeled ligand at twice the final concentrations in assay buffer, the plate was incubated at RT for 30 mM. At the end, the binding was measured as FP value with the Envision (PerkinElmer) plate reader using filter for an excitation λ=531 nm FP and an emission λ=595 nm FP (S & P-pol). GST-hRIPK1 (8-327) enzyme was produced via Baculovirus expression.

Test compound inhibition was expressed as percent inhibition of internal assay controls. For concentration response curves, normalized data is fit and $IC_{50}$ determined using XL-fit (IDBS) for Excel. The $IC_{50}$ values were averaged to determine a mean value, for a minimum of two independent experiments. Results are shown in Table 2 (RIPK1 $IC_{50}$) values: +++=0.1 nM<$IC_{50}$<100 nM; ++=100 nM<$IC_{50}$<1 μM; +=1 μM<$IC_{50}$).

TABLE 2A

| Example | RIPK1 $IC_{50}$ |
|---------|-----------------|
| 1       | +               |
| 2       | +++             |
| 3       | ++              |
| 4       | ++              |
| 5       | ++              |
| 6       | +++             |
| 7       | +++             |
| 8       | +++             |
| 9       | +++             |
| 10      | ++              |
| 11      | ++              |
| 12      | ++              |
| 13      | +++             |
| 14      | +++             |
| 15      | +++             |
| 16      | +++             |
| 17      | +               |
| 18      | +++             |
| 19      | +               |
| 20      | +++             |
| 21      | +++             |
| 22      | +++             |
| 23      | +++             |
| 24      | +++             |

TABLE 2A-continued

| Example | RIPK1 IC$_{50}$ |
|---|---|
| 25 | +++ |
| 26 | +++ |
| 27 | + |
| 28 | ++ |
| 29 | +++ |
| 30 | +++ |
| 31 | ++ |
| 32 | +++ |
| 33 | +++ |
| 34 | + |
| 35 | ++ |
| 36 | + |
| 37 | ++ |
| 38 | + |
| 39 | ++ |
| 40 | +++ |
| 41 | ++ |
| 42 | ++ |
| 43 | ++ |
| 44 | + |
| 45 | +++ |
| 46 | ++ |
| 47 | +++ |
| 48 | ++ |
| 49 | +++ |
| 50 | ++ |
| 51 | +++ |
| 52 | +++ |
| 53 | ++ |
| 54 | +++ |
| 55 | ++ |
| 56 | +++ |
| 57 | +++ |
| 58 | ++ |
| 59 | ++ |
| 60 | ++ |
| 61 | ++ |
| 62 | + |
| 63 | ++ |
| 64 | ++ |
| 65 | ++ |
| 66 | + |
| 67 | +++ |
| 68 | ++ |
| 69 | +++ |
| 70 | ++ |
| 71 | + |
| 72 | ++ |
| 73 | ++ |
| 74 | +++ |
| 75 | +++ |
| 76 | ++ |
| 77 | +++ |
| 78 | +++ |
| 79 | ++ |
| 80 | ++ |
| 81 | + |
| 82 | ++ |
| 83 | + |
| 84 | +++ |
| 85 | ++ |
| 86 | +++ |
| 87 | ++ |
| 88 | ++ |
| 89 | +++ |
| 90 | +++ |
| 91 | ++ |
| 92 | ++ |
| 93 | ++ |
| 94 | ++ |
| 95 | + |
| 96 | +++ |
| 97 | +++ |
| 98 | ++ |
| 99 | ++ |

TABLE 2B

| Example | RIPK1 IC$_{50}$ |
|---|---|
| 100 | ++ |
| 101 | ++ |
| 102 | ++ |
| 103 | +++ |
| 104 | +++ |
| 105 | +++ |
| 106 | ++ |
| 107 | ++ |
| 108 | ++ |
| 109 | ++ |
| 110 | +++ |
| 111 | ++ |
| 112 | ++ |
| 113 | ++ |
| 114 | +++ |
| 115 | ++ |
| 116 | ++ |
| 117 | +++ |
| 118 | +++ |
| 119 | +++ |
| 120 | +++ |
| 121 | +++ |
| 122 | +++ |
| 123 | ++ |
| 124 | +++ |
| 125 | +++ |
| 126 | +++ |
| 127 | ++ |
| 128 | +++ |
| 129 | +++ |
| 130 | +++ |
| 131 | +++ |
| 132 | +++ |
| 133 | ++ |
| 134 | ++ |
| 135 | +++ |
| 136 | + |
| 137 | ++ |
| 138 | ++ |
| 139 | + |
| 140 | + |
| 141 | ++ |
| 142 | +++ |
| 143 | + |
| 144 | +++ |
| 145 | +++ |
| 146 | ++ |
| 147 | +++ |
| 148 | +++ |
| 149 | ++ |
| 150 | ++ |
| 151 | +++ |
| 152 | ++ |
| 153 | +++ |
| 154 | ++ |
| 155 | +++ |
| 156 | +++ |
| 157 | +++ |
| 158 | +++ |
| 159 | ++ |
| 160 | ++ |
| 161 | +++ |
| 162 | ++ |
| 163 | ++ |
| 164 | +++ |
| 165 | ++ |
| 166 | ++ |
| 167 | ++ |
| 168 | ++ |
| 169 | ++ |
| 170 | ++ |
| 171 | ++ |
| 172 | ++ |
| 173 | ++ |
| 174 | + |
| 175 | +++ |
| 176 | + |
| 177 | +++ |

TABLE 2B-continued

| Example | RIPK1 IC$_{50}$ |
| --- | --- |
| 178 | +++ |
| 180 | ++ |
| 181 | + |
| 182 | ++ |
| 183 | +++ |
| 184 | +++ |
| 185 | +++ |
| 186 | + |
| 187 | +++ |
| 188 | +++ |
| 189 | ++ |
| 190 | ++ |
| 191 | +++ |
| 192 | +++ |
| 193 | + |
| 194 | +++ |
| 195 | + |
| 196 | ++ |
| 197 | ++ |
| 198 | ++ |
| 199 | +++ |

TABLE 2C

| Example | RIPK1 IC$_{50}$ |
| --- | --- |
| 200 | +++ |
| 201 | +++ |
| 202 | +++ |
| 203 | ++ |
| 205 | ++ |
| 206 | +++ |
| 207 | ++ |
| 208 | ++ |
| 209 | ++ |
| 210 | ++ |
| 211 | ++ |
| 212 | ++ |
| 215 | +++ |
| 216 | ++ |
| 217 | +++ |
| 218 | ++ |
| 219 | ++ |
| 220 | ++ |
| 221 | ++ |
| 222 | +++ |
| 224 | + |
| 225 | +++ |
| 226 | +++ |
| 227 | +++ |
| 228 | +++ |
| 229 | +++ |
| 230 | ++ |
| 231 | + |
| 232 | ++ |
| 233 | +++ |
| 234 | +++ |
| 235 | +++ |
| 236 | +++ |
| 237 | +++ |
| 238 | +++ |
| 239 | +++ |
| 240 | ++ |
| 241 | ++ |
| 242 | +++ |
| 243 | ++ |
| 244 | +++ |
| 245 | ++ |
| 246 | ++ |
| 247 | +++ |
| 248 | ++ |
| 249 | +++ |
| 250 | ++ |
| 251 | ++ |
| 252 | ++ |

TABLE 2C-continued

| Example | RIPK1 IC$_{50}$ |
| --- | --- |
| 253 | +++ |
| 254 | ++ |
| 255 | ++ |
| 256 | +++ |
| 257 | ++ |
| 258 | +++ |
| 259 | ++ |
| 260 | +++ |
| 261 | +++ |
| 262 | ++ |
| 263 | +++ |
| 264 | +++ |
| 265 | +++ |
| 244 | +++ |
| 245 | ++ |
| 246 | ++ |
| 247 | +++ |
| 248 | ++ |
| 249 | +++ |
| 250 | ++ |
| 251 | ++ |
| 252 | ++ |
| 253 | +++ |
| 254 | ++ |
| 255 | ++ |
| 256 | +++ |
| 257 | ++ |
| 258 | +++ |
| 259 | ++ |
| 260 | +++ |
| 261 | +++ |
| 262 | ++ |
| 263 | +++ |
| 264 | +++ |
| 265 | +++ |
| 266 | ++ |
| 267 | ++ |
| 268 | ++ |
| 269 | ++ |
| 270 | +++ |
| 271 | +++ |
| 272 | +++ |
| 273 | ++ |
| 274 | + |
| 275 | ++ |
| 276 | + |
| 277 | ++ |
| 278 | +++ |
| 279 | +++ |
| 280 | + |
| 281 | +++ |
| 282 | ++ |
| 283 | ++ |
| 284 | +++ |
| 285 | ++ |
| 286 | + |
| 287 | +++ |
| 288 | +++ |
| 289 | +++ |
| 290 | ++ |
| 291 | ++ |
| 292 | + |
| 293 | + |
| 294 | +++ |
| 295 | ++ |
| 296 | +++ |
| 297 | +++ |
| 298 | + |
| 299 | +++ |
| 300 | +++ |
| 301 | ++ |
| 302 | +++ |
| 303 | ++ |

TABLE 2C-continued

| Example | RIPK1 IC$_{50}$ |
|---------|-----------------|
| 304 | +++ |
| 305 | ++ |
| 306 | +++ |
| 307 | ++ |
| 308 | +++ |
| 309 | ++ |

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A compound according to Formula I:

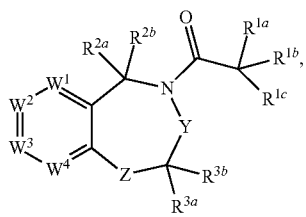

or a pharmaceutically acceptable salt, isotopic analog, or isomer thereof, wherein $W^1$, $W^3$, and $W^4$ are $CR^7$;

$W^2$ is N;

$R^{1a}$, $R^{1b}$, and $R^{1c}$ are independently hydrogen, halogen, —CN, —N$_3$, —NO$_2$, —OH, —SF$_5$, —SCF$_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, $C_{1-8}$ haloalkoxy, 4- to 12-membered heterocyclyl, $C_{6-10}$ aryl, 5- to 12-membered heteroaryl, —N(R$^{1d}$)$_2$, —C(O)R$^{1e}$, —C(O)OR$^{1d}$, —C(O)N(R$^{1d}$)$_2$, —NR$^{1d}$C(O)R$^{1e}$, —NR$^{1d}$C(O)N(R$^{1d}$)$_2$, —NR$^{1d}$C(O)OR$^{1d}$, —OC(O)N(R$^{1d}$)$_2$, —OC(O)OR$^{1d}$, —SR$^{1d}$, —S(O)R$^{1e}$, —S(O)$_2$R$^{1e}$, —S(O)$_3$R$^{1d}$, —S(O)N(R$^{1d}$)$_2$, —S(O)$_2$N(R$^{1d}$)$_2$, —NR$^{1d}$S(O)R$^{1e}$, —NR$^{1d}$S(O)$_2$R$^{1e}$, —NR$^{1d}$S(O)N(R$^{1d}$)$_2$, or —NR$^{1d}$S(O)$_2$N(R$^{1d}$)$_2$, wherein each of R$^{1a}$, R$^{1b}$, and R$^{1c}$ is optionally and independently substituted with one to eight R$^5$ and at least one of R$^{1a}$, R$^{1b}$, and R$^{1c}$ is other than hydrogen; or $R^{1b}$ and $R^{1c}$ are optionally taken together to form $C_{3-10}$ cycloalkyl or 4- to 12-membered heterocyclyl, each of which is optionally substituted with one to eight R$^5$; or $R^{1a}$, $R^{1b}$, and $R^{1c}$ are optionally taken together to form $C_{5-10}$ cycloalkyl or 6- to 8-membered heterocyclyl, each of which is optionally substituted with one to eight R$^5$;

each R$^{1d}$ is independently hydrogen, $C_{1-8}$ alkyl, $C_{1-8}$ haloalkyl, $C_{3-10}$ cycloalkyl, or 4- to 12-membered heterocyclyl, or two R$^{1d}$ on the same atom are optionally taken together to form a 4- to 8-membered heterocyclyl optionally substituted by oxo, halo, or $C_{1-6}$ alkyl, wherein said alkyl is optionally substituted with one to eight R$^5$;

each R$^{1e}$ is independently $C_{1-8}$ alkyl, $C_{1-8}$ haloalkyl, $C_{3-10}$ cycloalkyl, or 4- to 12-membered heterocyclyl;

$R^{2a}$ and $R^{2b}$ are independently hydrogen, halogen, $C_{1-8}$ alkyl, $C_{1-8}$ haloalkyl, $C_{2-8}$ alkenyl, or $C_{2-8}$ alkynyl, or $R^{2a}$ and $R^{2b}$ are optionally taken together to form $C_{3-6}$ cycloalkyl or 4- to 6-membered heterocyclyl, each of which is optionally substituted with one to eight R$^6$;

$R^{3a}$ and $R^{3b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one to eight R$^6$, or $R^{3a}$ and $R^{3b}$ are optionally taken together to form oxo, $C_{3-6}$ cycloalkyl, or 4- to 6-membered heterocyclyl, wherein said cycloalkyl and said heterocyclyl are optionally substituted with one to eight R$^6$;

Y is $CR^{4a}R_{4b}$;

$R^{4a}$ and $R^{4b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one to eight R$^6$, or $R^{4a}$ and $R^{4b}$ are optionally taken together to form $C_{3-6}$ cycloalkyl or 4- to 6-membered heterocyclyl, wherein said cycloalkyl and said heterocyclyl are optionally substituted with one to eight R$^6$, or $R^{4a}$ and $R^{1b}$ are optionally taken together to form 4- to 12-membered heterocyclyl, which is optionally substituted with one to eight R$^6$, or $R^{4a}$ and $R^{3a}$ are optionally taken together to form $C_{3-8}$ cycloalkyl or 4- to 12-membered heterocyclyl, each of which is optionally substituted with one to eight R$^6$, each R$^5$ is independently halogen, —CN, —OH, —SF$_5$, —SCF$_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ alkoxy, 4- to 12-membered heterocyclyl, $C_{6-10}$ aryl, 5- to 12-membered heteroaryl, (4- to 12-membered heterocyclyl)($C_{1-8}$ heteroalkyl), ($C_{6-10}$ aryl)($C_{1-8}$ heteroalkyl), (5- to 12-membered heteroaryl)($C_{1-8}$ heteroalkyl), —N(R$^{5a}$)$_2$, —C(O)R$^{5b}$, —C(O)OR$^{5a}$, —C(O)N(R$^{5a}$)$_2$, —NR$^{5a}$C(O)R$^{5b}$, —NR$^{5a}$C(O)N(R$^{5a}$)$_2$, —NR$^{5a}$C(O)OR$^{5a}$, —OC(O)N(R$^{5a}$)$_2$, —OC(O)OR$^{5a}$, —SR$^{5a}$, —S(O)R$^{5b}$, —S(O)$_2$R$^{5b}$, —S(O)$_3$R$^{5a}$, —S(O)N(R$^{5a}$)$_2$, —S(O)$_2$N(R$^{5a}$)$_2$, —NR$^{5a}$S(O)R$^{5b}$, —NR$^{5a}$S(O)$_2$R$^{5b}$, —NR$^{5a}$S(O)N(R$^{5a}$)$_2$, or —NR$^{5a}$S(O)$_2$N(R$^{5a}$)$_2$, each of which is optionally substituted with one to eight R$^{5c}$, or two R$^5$ are optionally taken together to form oxo;

each R$^{5a}$ is independently hydrogen, $C_{1-8}$ alkyl, $C_{1-8}$ haloalkyl, $C_{3-10}$ cycloalkyl, or 4- to 12-membered heterocyclyl, and each R$^{5b}$ is independently $C_{1-8}$ alkyl, $C_{1-8}$ haloalkyl, $C_{3-10}$ cycloalkyl, 4- to 12-membered heterocyclyl, or 5- to 12-membered heteroaryl;

each R$^{5c}$ is independently halogen, cyano, $C_{1-8}$ haloalkyl, $C_{1-8}$ alkyl, $C_{1-8}$ alkoxy, $C_{1-8}$ haloalkoxy, ($C_{1-8}$ alkoxy)($C_{1-8}$ alkoxy), hydroxyl, SR$^{5d}$, N(R$^{5d}$)$_2$, N(R$^{5d}$)$_2$($C_{1-8}$ alkoxy), $C_{3-10}$ cycloalkyl, or 4- to 12-membered heterocyclyl, or two R$^{5c}$ are optionally taken together to form oxo;

each R$^{5d}$ is independently hydrogen, $C_{1-8}$ alkyl, or $C_{1-8}$ haloalkyl;

each R⁶ is halogen, —CN, —OH, $C_{1-8}$ alkyl, $C_{1-8}$ heteroalkyl, $C_{3-8}$ cycloalkyl, $C_{1-8}$ haloalkyl, $C_{1-8}$ alkoxy, 4- to 12-membered heterocyclyl, $C_{6-10}$ aryl, 5- to 12-membered heteroaryl, —N(R⁶ᵃ)₂, —C(O)R⁶ᵇ, —C(O)N(R⁶ᵃ)₂, or —C(O)OR⁶ᵃ, or two R⁶ are taken together to form oxo;

each R⁶ᵃ is independently hydrogen, $C_{1-8}$ alkyl, or $C_{1-8}$ haloalkyl, or two R⁶ᵃ on the same atom are optionally taken together to form 4- to 6-membered heterocyclyl;

each R⁶ᵇ is independently $C_{1-8}$ alkyl or $C_{1-8}$ haloalkyl;

each R⁷ is independently hydrogen, halogen, —CN, —N₃, —NO₂, —SF₅, —SCF₃, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, 4- to 12-membered heterocyclyl, $C_{6-10}$ aryl, 5- to 12-membered heteroaryl, —OR⁷ᵃ, —C(O)R⁷ᵇ, —N(R⁷ᵃ)₂, —C(O)OR⁷ᵃ, —C(O)N(R⁷ᵃ)₂, —NR⁷ᵃC(O)R⁷ᵇ, —NR⁷ᵃC(O)N(R⁷ᵃ)₂, —NR⁷ᵃC(O)OR⁷ᵃ, —OC(O)N(R⁷ᵃ)₂, —OC(O)OR⁷ᵃ, —SR⁷ᵃ, —S(O)R⁷ᵇ, —S(O)₂R⁷ᵇ, —S(O)₃R⁷ᵃ, —S(O)N(R⁷ᵃ)₂, —S(O)₂N(R⁷ᵃ)₂, —NR⁷ᵃS(O)R⁷ᵇ, —NR⁷ᵃS(O)₂R⁷ᵇ, —NR⁷ᵃS(O)N(R⁷ᵃ)₂, or —NR⁷ᵃS(O)₂N(R⁷ᵃ)₂, each of which is optionally and independently substituted with one to eight R⁸;

each R⁷ᵃ is independently hydrogen, $C_{1-8}$ alkyl, $C_{1-8}$ haloalkyl, $C_{3-10}$ cycloalkyl, or 4- to 12-membered heterocyclyl, or two R⁷ᵃ on the same atom are optionally taken together to form a 4- to 8-membered heterocyclyl optionally substituted by oxo, halo, or $C_{1-6}$ alkyl, wherein said alkyl is optionally substituted with one to eight R⁸;

each R⁷ᵇ is independently C1-8 alkyl, $C_{1-8}$ haloalkyl, $C_{3-10}$ cycloalkyl, or 4- to 12-membered heterocyclyl;

each R⁸ is halogen, —CN, —OH, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, 4- to 12-membered heterocyclyl, $C_{6-10}$ aryl, 5- to 12-membered heteroaryl, —N(R⁸ᵃ)₂, —C(O)R⁸ᵇ, or —C(O)OR⁸ᵃ, or two R⁸ are optionally taken together to form oxo;

each R⁸ᵃ is independently hydrogen, $C_{1-8}$ alkyl, or $C_{1-8}$ haloalkyl;

each R⁸ᵇ is independently $C_{1-8}$ alkyl or $C_{1-8}$ haloalkyl; and Z is O.

2. The compound of claim 1, wherein R²ᵃ, R²ᵇ, R³ᵃ, R⁴ᵃ, and R⁴ᵇ are H.

3. The compound of claim 1, according to Formula Ib:

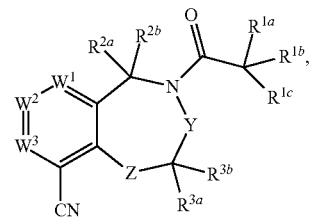

(Ib)

wherein R¹ᵃ, R¹ᵇ, R²ᵃ, R²ᵇ, R³ᵃ, R³ᵇ, W¹, W¹, W¹, Y, and Z are as defined for Formula I; or a pharmaceutically acceptable salt, isotopic analog, or isomer thereof.

4. The compound of claim 1, wherein each R⁷ is independently hydrogen, halogen, cyano, $C_{1-8}$ alkyl, $C_{1-8}$ haloalkyl, or $C_{1-8}$ alkoxy.

5. The compound of claim 1, wherein R¹ᵃ is (a) hydrogen, $C_{1-8}$ alkyl, $C_{1-8}$ haloalkyl, or $C_{3-8}$ cycloalkyl, each of which is optionally substituted with halogen and —CN; or (b) chloro, fluoro, methyl, ethyl, difluoromethyl, fluoromethyl, cyano, or hydroxyl.

6. The compound of claim 1, wherein R¹ᵇ and R¹ᶜ are independently $C_{1-8}$ alkyl, $C_{1-8}$ haloalkyl, or $C_{3-8}$ cycloalkyl, each of which is optionally substituted with halogen and —CN or R¹ᵇ and R¹ᶜ are taken together to form 4- to 12-membered heterocyclyl, which is optionally substituted with one to eight R⁵.

7. The compound of claim 1, wherein (a) at least one of R⁵ is $C_{1-8}$ alkyl, $C_{1-8}$ haloalkyl, halogen, $C_{1-8}$ haloalkyl, $C_{1-8}$ alkoxy, —OH, or cyano; or (b) at least one of R⁵ is 4- to 12-membered heterocyclyl or 5- to 12-membered heteroaryl, each of which is optionally substituted with one to eight R⁵ᶜ.

8. The compound of claim 1, wherein R¹ᵃ, and R¹ᶜ are taken together to form bicyclo[1.1.1[pentane, azabicyclo[4.1.0[heptane, azepan-4yl, 1,4-oxepane-7-yl, tetrahydropyran-2-yl, or 3,6-dihydro-2H-pyridin-4-yl.

9. The compound of claim 1, wherein (a) R²ᵃ is hydrogen and R²ᵇ is $C_{1-8}$ alkyl, or (b) R²ᵃ and R²ᵇ are hydrogen.

10. The compound of claim 1, wherein R⁴ᵃ is hydrogen or methyl.

11. The compound of claim 1, wherein R³ᵃ and Rᵃᵇ are independently hydrogen or methyl.

12. A compound selected from

| Name | Structure |
|---|---|
| 4-(3,3-difluoro-2,2-dimethyl-propanoyl)-3,5-dihydro-2H-pyrido[3,4-f][1,4]oxazepine-9-carbontrile | 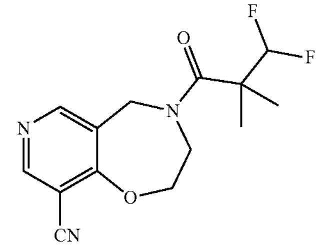 [SMILES: CC(C)(C(=O)N1CCOc2c(C#N)cncc2C1)C(F)F] |

-continued

| Name | Structure |
|---|---|
| 4-(2-cyclopropyl-2-methyl-propanoyl)-3,5-dihydro-2H-pyrido[3,4-f][1,4]oxazepine-9-carbonitrile | 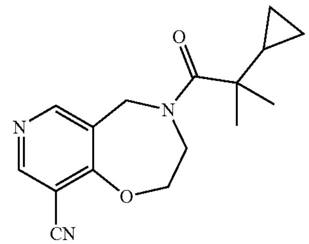 [SMILES: CC(C)(C(=O)N1CCOc2c(C#N)cncc2C1)C1CC1] |
| 4-(3-cyano-2,2-dimethyl-propanoyl)-3,5-dihydro-2H-pyrido[3,4-f][1,4]oxazepine-9-carbonitrile | 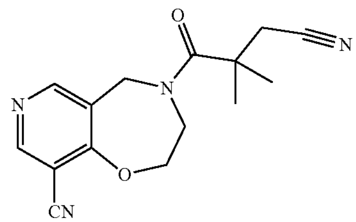 [SMILES: CC(C)(CC#N)C(=O)N1CCOc2c(C#N)cncc2C1] |
| 1-(2,3-dihydropyrido[3,4-f][1,4]oxazepin-4(5H)-yl)-3,3-difluoro-2,2-dimethylpropan-1-one | 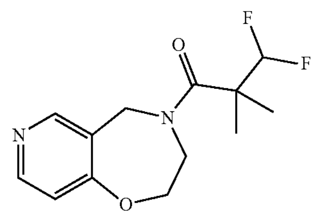 [SMILES: CC(C)(C(=O)N1CCOc2ccncc2C1)C(F)F] |
| 4-[1-(5-fluoropyrimidin-2-yl)-4-methyl-piperidine-4-carbonyl]-3,5-dihydro-2H-pyrido[3,4-f][1,4]oxazepine-9-carbonitrile | 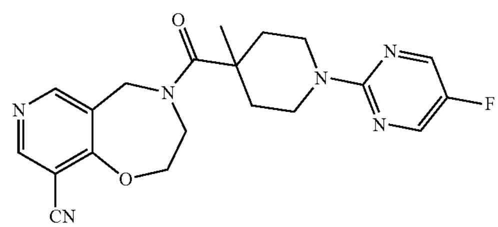 [SMILES: CC1(C(=O)N2CCOc3c(C#N)cncc3C2)CCN(c2ncc(F)cn2)CC1] |
| 4-(4-methyltetrahydropyran-4-carbonyl)-3,5-dihydro-2H-pyrido[3,4-f][1,4]oxazepine-9-carbonitrile | 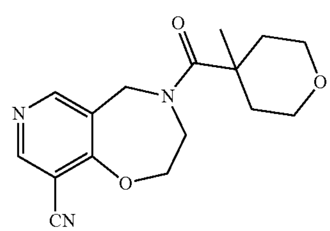 [SMILES: CC1(C(=O)N2CCOc3c(C#N)cncc3C2)CCOCC1] |
| 4-(3-methyltetrahydrofuran-3-carbonyl)-3,5-dihydro-2H-pyrido[3,4-f][1,4]oxazepine-9-carbonitrile | 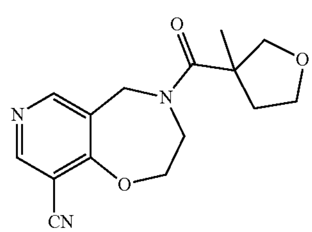 [SMILES: CC1(C(=O)N2CCOc3c(C#N)cncc3C2)CCOC1] |
| 4-(2-methoxy-2-methyl-propanoyl)-3,5-dihydro-2H-pyrido[3,4-f][1,4]oxazepine-9-carbonitrile | 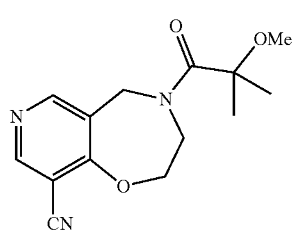 [SMILES: COC(C)(C)C(=O)N1CCOc2c(C#N)cncc2C1] |

-continued

| Name | Structure |
|---|---|
| 4-(bicyclo [1.1.1]pentane-3-carbonyl)-3,5-dihydro-2H-pyrido[3,4-f][1,4]oxazepine-9-carbonitrile | 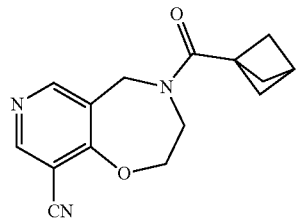 [SMILES: N#Cc1cncc2c1OCCN(C(=O)C13CC(C1)C3)C2] |
| 4-(3,3,3-trifluoro-2,2-dimethyl-propanoyl)-3,5-dihydro-2H-pyrido[3,4-f][1,4]oxazepine-9-carbonitrile | 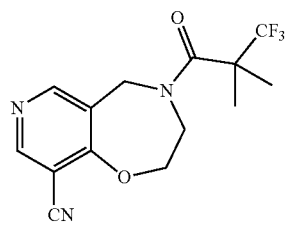 [SMILES: CC(C)(C(=O)N1CCOc2c(C#N)cncc2C1)C(F)(F)F] |
| 4-(1-cyclopropylcyclopropanecarbonyl)-3,5-dihydro-2H-pyrido[3,4-f][1,4]oxazepine-9-carbonitrile | 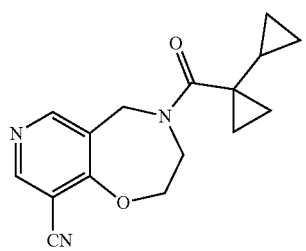 [SMILES: N#Cc1cncc2c1OCCN(C(=O)C1(C3CC3)CC1)C2] |
| 4-(4,4,4-trifluoro-2,2-dimethyl-butanoyl)-3,5-dihydro-2H-pyrido[3,4-f][1,4]oxazepine-9-carbonitrile | 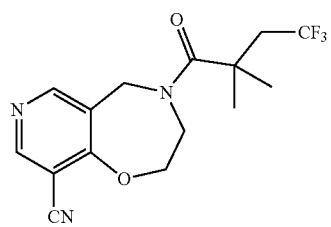 [SMILES: CC(C)(CC(F)(F)F)C(=O)N1CCOc2c(C#N)cncc2C1] |
| 4-[1-(trifluoromethyl)cyclopropanecarbonyl]-3,5-dihydro-2H-pyrido[3,4-f][1,4]oxazepine-9-carbonitrile | 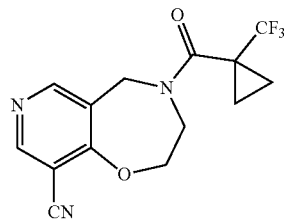 [SMILES: N#Cc1cncc2c1OCCN(C(=O)C1(C(F)(F)F)CC1)C2] |
| 4-[1-(difluoromethyl)cyclobutanecarbonyl]-3,5-dihydro-2H-pyrido[3,4-f][1,4]oxazepine-9-carbonitrile | 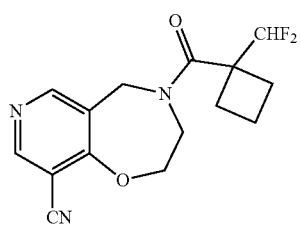 [SMILES: N#Cc1cncc2c1OCCN(C(=O)C1(C(F)F)CCC1)C2] |

-continued

| Name | Structure |
|---|---|
| 4-(2,2-difluoro-1-methyl-cyclopropanecarbonyl)-3,5-dihydro-2H-pyrido[3,4-f][1,4]oxazepine-9-carbonitrile | 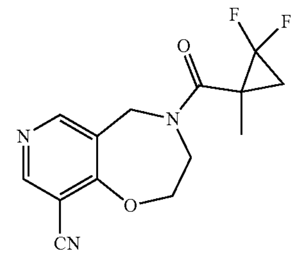 [SMILES: CC1(C(=O)N2CCOc3c(C#N)cncc3C2)CC1(F)F] |
| 4-[2,2-dimethyl-3-(trifluoromethoxy)propanoyl]-3,5-dihydro-2H-pyrido[3,4-f][1,4]oxazepine-9-carbonitrile | 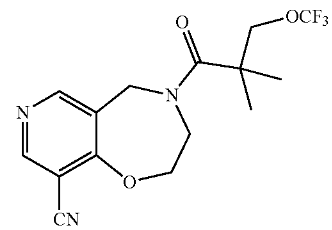 [SMILES: CC(C)(COC(F)(F)F)C(=O)N1CCOc2c(C#N)cncc2C1] |
| (3R)-4-(3,3-difluoro-2,2-dimethyl-propanoyl)-3-methyl-3,5-dihydro-2H-pyrido[3,4-f][1,4]oxazepine-9-carbonitrile | 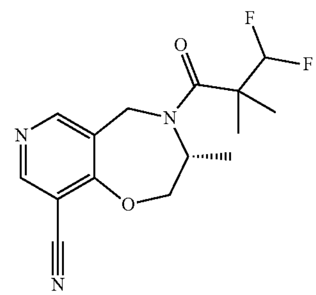 [SMILES: C[C@@H]1COc2c(C#N)cncc2CN1C(=O)C(C)(C)C(F)F] |
| 4-[1-(trifluoromethyl)cyclobutanecarbonyl]-3,5-dihydro-2H-pyrido[3,4-f][1,4]oxazepine-9-carbonitrile | 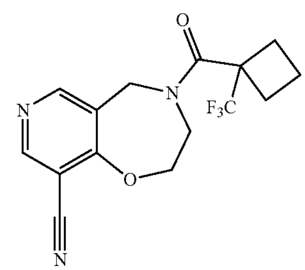 [SMILES: N#Cc1cncc2c1OCCN(C(=O)C1(C(F)(F)F)CCC1)C2] |
| 4-(2,2-dimethylbutanoyl)-3,5-dihydro-2H-pyrido[3,4-f][1,4]oxazepine-9-carbonitrile | 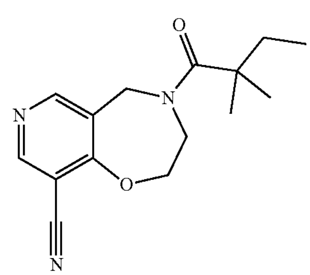 [SMILES: CCC(C)(C)C(=O)N1CCOc2c(C#N)cncc2C1] |
| 3,3-difluoro-1-(9-fluoro-3,5-dihydro-2H-pyrido[3,4-f][1,4]oxazepin-4-yl)-2,2-dimethyl-propan-1-one | 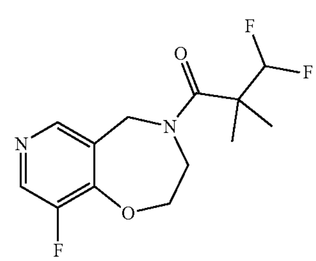 [SMILES: CC(C)(C(=O)N1CCOc2c(F)cncc2C1)C(F)F] |

| Name | Structure |
|---|---|
| 4-(2-cyclopropyl-3,3-difluoro-2-methyl-propanoyl)-3,5-dihydro-2H-pyrido[3,4-f][1,4]oxazepine-9-carbonitrile | 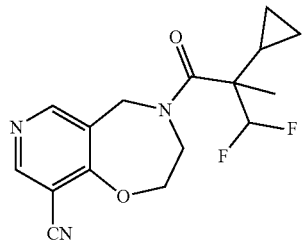 [SMILES: CC(C(=O)N1CCOc2c(C#N)cncc2C1)(C(F)F)C1CC1] |
| 4-(2-(difluoromethyl)-2-methylbutanoyl)-2,3,4,5-tetrahydropyrido[3,4-f][1,4]oxazepine-9-carbonitrile | 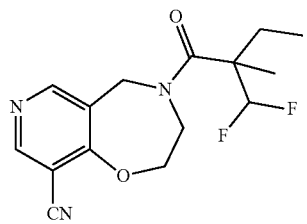 [SMILES: CCC(C)(C(=O)N1CCOc2c(C#N)cncc2C1)C(F)F] |
| 4-(3-cyclopropyl-2,2-dimethyl-propanoyl)-3,5-dihydro-2H-pyrido[3,4-f][1,4]oxazepine-9-carbonitrile | 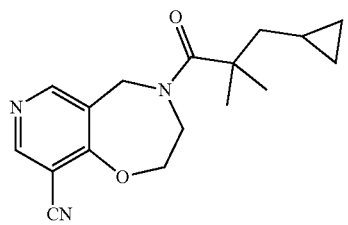 [SMILES: CC(C)(CC1CC1)C(=O)N1CCOc2c(C#N)cncc2C1] |
| 8-chloro-4-(3,3-difluoro-2,2-dimethyl-propanoyl)-3,5-dihydro-2H-pyrido[3,4-f][1,4]oxazepine-9-carbonitrile | 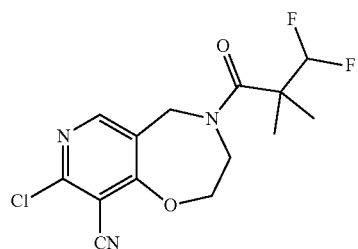 [SMILES: CC(C)(C(=O)N1CCOc2c(cnc(Cl)c2C#N)C1)C(F)F] |
| 4-(4-fluoro-2,2-dimethyl-butanoyl)-3,5-dihydro-2H-pyrido[3,4-f][1,4]oxazepine-9-carbonitrile | 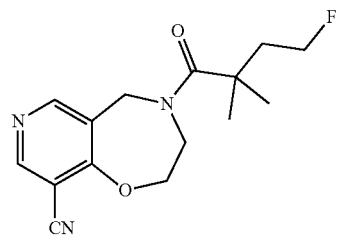 [SMILES: CC(C)(CCF)C(=O)N1CCOc2c(C#N)cncc2C1] |
| 1-(9-chloro-3,5-dihydro-2H-pyrido[3,4-f][1,4]oxazepin-4-yl)-3,3-difluoro-2,2-dimethyl-propan-1-one | 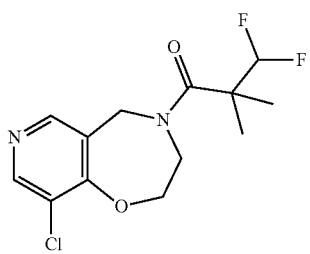 [SMILES: CC(C)(C(=O)N1CCOc2c(Cl)cncc2C1)C(F)F] |

| Name | Structure |
|---|---|
| 3,3-difluoro-2,2-dimethyl-1-(9-methyl-3,5-dihydro-2H-pyrido[3,4-f][1,4]oxazepin-4-yl)propan-1-one | |
| 4-(1-ethylcyclopropanecarbonyl)-3,5-dihydro-2H-pyrido[3,4-f][1,4]oxazepine-9-carbonitrile | 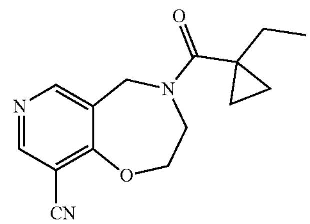 [SMILES: CCC1(C(=O)N2CCOc3c(C#N)cncc3C2)CC1] |
| 4-(1-ethylcyclobutanecarbonyl)-3,5-dihydro-2H-pyrido[3,4-f][1,4]oxazepine-9-carbonitrile | 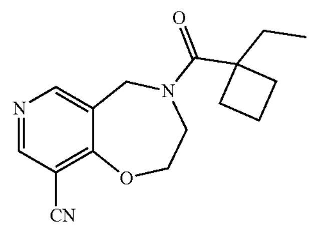 [SMILES: CCC1(C(=O)N2CCOc3c(C#N)cncc3C2)CCC1] |
| 4-[(1S,2R)-1,2-dimethylcyclopropanecarbonyl]-3,5-dihydro-2H-pyrido[3,4-f][1,4]oxazepine-9-carbonitrile | 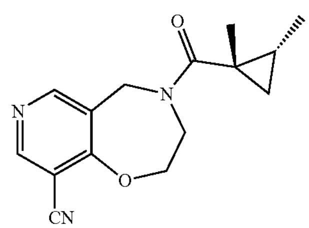 [SMILES: C[C@@H]1C[C@]1(C)C(=O)N1CCOc2c(C#N)cncc2C1] |
| 3,3-difluoro-2,2-dimethyl-1-[8-(trifluoromethyl)-3,5-dihydro-2H-pyrido[3,4-f][1,4]oxazepin-4-yl]propan-1-one | 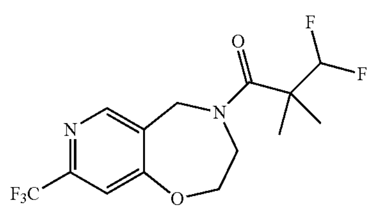 [SMILES: CC(C)(C(=O)N1CCOc2cc(C(F)(F)F)ncc2C1)C(F)F] |
| 4-[2-methyl-2-(trifluoromethyl)butanoyl]-3,5-dihydro-2H-pyrido[3,4-f][1,4]oxazepine-9-carbonitrile | |
| 4-[2-methyl-2-(trifluoromethoxy)propanoyl]-3,5-dihydro-2H-pyrido[3,4-f][1,4]oxazepine-9-carbonitrile | 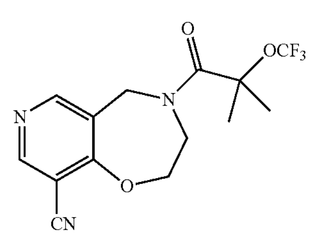 [SMILES: CC(C)(OC(F)(F)F)C(=O)N1CCOc2c(C#N)cncc2C1] |

| Name | Structure |
|---|---|
| 4-(9-fluoro-2,3-dihydropyrido[3,4-f][1,4]oxazepin-4(5H)-yl)-3,3-dimethyl-4-oxobutanenitrile | 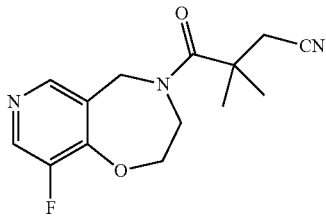 [SMILES: CC(C)(CC#N)C(=O)N1CCOc2c(F)cncc2C1] |
| 4-(9-fluoro-2,3-dihydropyrido[3,4-f][1,4]oxazepin-4(5H)-yl)-2,3,3-trimethyl-4-oxobutanenitrile | 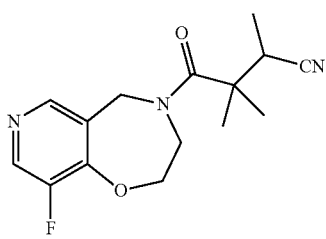 [SMILES: CC(C#N)C(C)(C)C(=O)N1CCOc2c(F)cncc2C1] |
| 4-(3-cyano-2,2-dimethylpropanoyl)-2,3,4,5-tetrahydropyrido[3,4-f][1,4]oxazepine-9-carbonitrile | 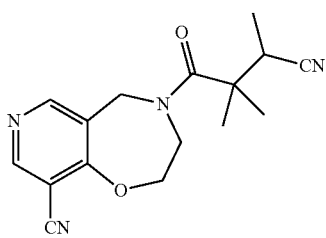 [SMILES: CC(C#N)C(C)(C)C(=O)N1CCOc2c(C#N)cncc2C1] |
| 3-(9-fluoro-3,5-dihydro-2H-pyrido[3,4-f][1,4]oxazepine-4-carbonyl)-3-methyl-pentanenitrile | 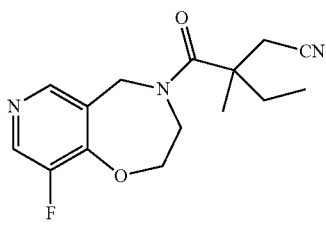 [SMILES: CCC(C)(CC#N)C(=O)N1CCOc2c(F)cncc2C1] |
| 4-[2-(cyanomethyl)-2-methyl-butanoyl]-3,5-dihydro-2H-pyrido[3,4-f][1,4]oxazepine-9-carbonitrile | 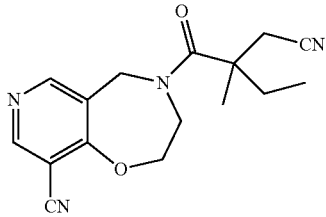 [SMILES: CCC(C)(CC#N)C(=O)N1CCOc2c(C#N)cncc2C1] |
| (3R)-4-(2,2-dimethylbutanoyl)-3-methyl-3,5-dihydro-2H-pyrido[3,4-f][1,4]oxazepine-9-carbonitrile | 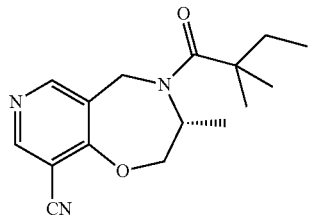 [SMILES: CCC(C)(C)C(=O)N1Cc2cncc(C#N)c2OC[C@H]1C] |

| Name | Structure |
|---|---|
| (3R)-3-methyl-4-(2-methylbutanoyl)-3,5-dihydro-2H-pyrido[3,4-f][1,4]oxazepine-9-carbonitrile | 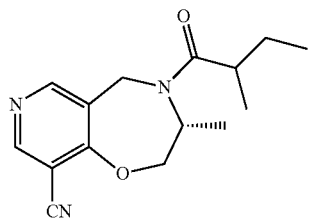 [SMILES: CCC(C)C(=O)N1Cc2cncc(C#N)c2OC[C@H]1C] |
| (3R)-4-(3-fluoro-2,2-dimethyl-propanoyl)-3-methyl-3,5-dihydro-2H-pyrido[3,4-f][1,4]oxazepine-9-carbonitrile | 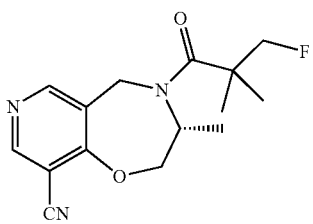 [SMILES: C[C@@H]1COc2c(C#N)cncc2CN1C(=O)C(C)(C)CF] |
| (3R)-4-(2,2-dimethylpropanoyl)-3-methyl-3,5-dihydro-2H-pyrido[3,4-f][1,4]oxazepine-9-carbonitrile | 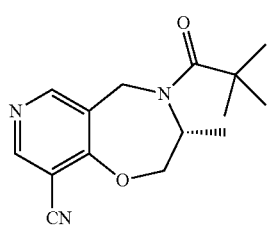 [SMILES: C[C@@H]1COc2c(C#N)cncc2CN1C(=O)C(C)(C)C] |
| 3,3,3-trifluoro-1-(9-fluoro-3,5-dihydro-2H-pyrido[3,4-f][1,4]oxazepin-4-yl)-2,2-dimethyl-propan-1-one | 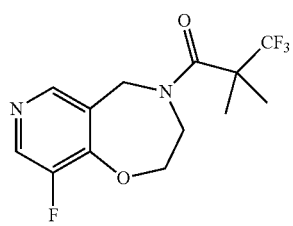 [SMILES: CC(C)(C(=O)N1CCOc2c(F)cncc2C1)C(F)(F)F] |
| 1-(9-fluoro-3,5-dihydro-2H-pyrido[3,4-f][1,4]oxazepin-4-yl)-2,2-dimethyl-propan-1-one | 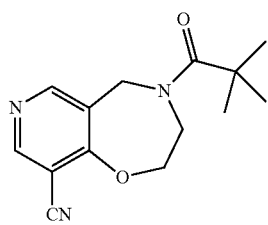 [SMILES: CC(C)(C)C(=O)N1CCOc2c(C#N)cncc2C1] |
| 4-(2-(1-hydroxycyclopropyl)-2-methylpropanoyl)-2,3,4,5-tetrahydropyrido[3,4-f][1,4]oxazepine-9-carbonitrile | 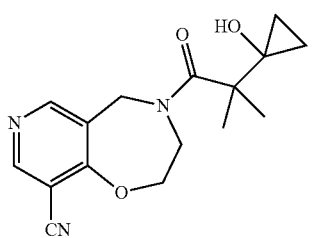 [SMILES: CC(C)(C(=O)N1CCOc2c(C#N)cncc2C1)C1(O)CC1] |

| Name | Structure |
|---|---|
| 4-[2-(-2-(difluoromethyl)cyclopropyl)-2-methyl-propanoyl]-3,5-dihydro-2H-pyrido[3,4-f][1,4]oxazepine-9-carbonitrile | 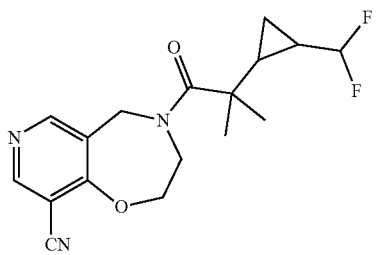 [SMILES: CC(C)(C(=O)N1CCOc2c(C#N)cncc2C1)C1CC1C(F)F] |
| 4-[2-(2-cyanocyclopropyl)-2-methyl-propanoyl]-3,5-dihydro-2H-pyrido[3,4-f][1,4]oxazepine-9-carbonitrile | 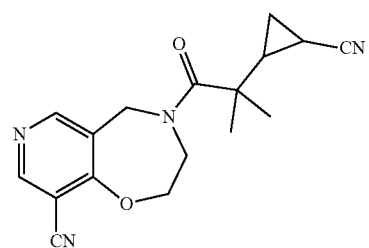 [SMILES: CC(C)(C(=O)N1CCOc2c(C#N)cncc2C1)C1CC1C#N] |
| 4-[2-(3,3-difluorocyclobutyl)-2-methyl-propanoyl]-3,5-dihydro-2H-pyrido[3,4-f][1,4]oxazepine-9-carbonitrile | 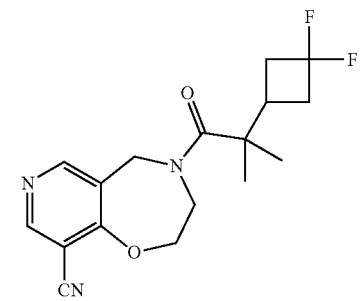 [SMILES: CC(C)(C(=O)N1CCOc2c(C#N)cncc2C1)C1CC(F)(F)C1] |
| 4-[2-[1-(5-fluoropyrimidin-2-yl)azetidin-3-yl]-2-methyl-propanoyl]-3,5-dihydro-2H-pyrido[3,4-f][1,4]oxazepine-9-carbonitrile | 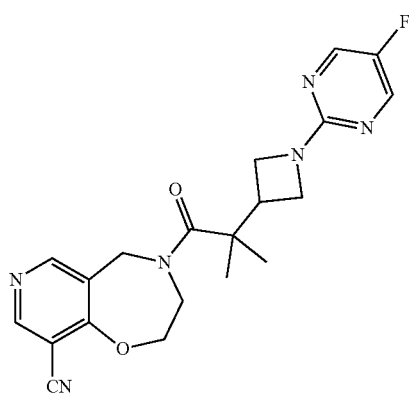 [SMILES: CC(C)(C(=O)N1CCOc2c(C#N)cncc2C1)C1CN(c2ncc(F)cn2)C1] |
| (3R)-4-[4-fluoro-1-(5-fluoropyrimidin-2-yl)piperidine-4-carbonyl]-3-methyl-3,5-dihydro-2H-pyrido[3,4-f][1,4]oxazepine-9-carbonitrile | 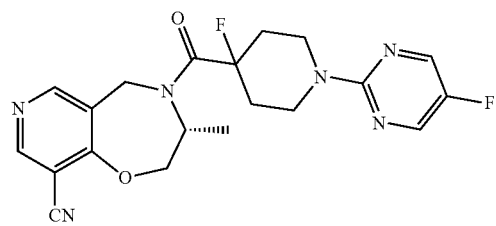 [SMILES: C[C@@H]1COc2c(C#N)cncc2CN1C(=O)C1(F)CCN(c2ncc(F)cn2)CC1] |

| Name | Structure |
|---|---|
| 4-(4-fluoro-1-pyrazin-2-yl-piperidine-4-carbonyl)-3,5-dihydro-2H-pyrido[3,4-f][1,4]oxazepine-9-carbonitrile | 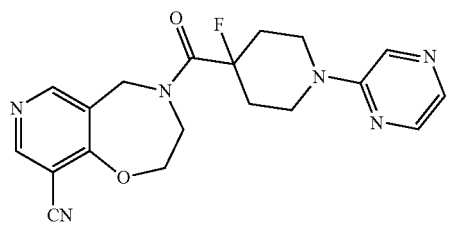 [SMILES: N#Cc1cncc2c1OCCN(C(=O)C1(F)CCN(c3cnccn3)CC1)C2] |
| 4-(4-fluoro-1-pyrimidin-4-yl-piperidine-4-carbonyl)-3,5-dihydro-2H-pyrido[3,4-f][1,4]oxazepine-9-carbonitrile | 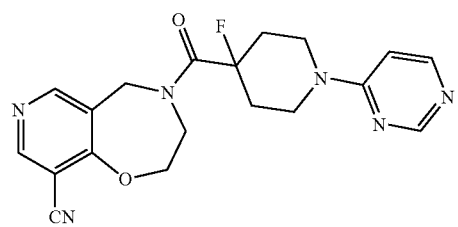 [SMILES: N#Cc1cncc2c1OCCN(C(=O)C1(F)CCN(c3ccncn3)CC1)C2] |
| 4-(cis-3-(5-fluoropyrimidin-2-yl)-3-azabicyclo[4.1.0]heptane-6-carbonyl)-3,5-dihydro-2H-pyrido[3,4-f][1,4]oxazepine-9-carbonitrile | 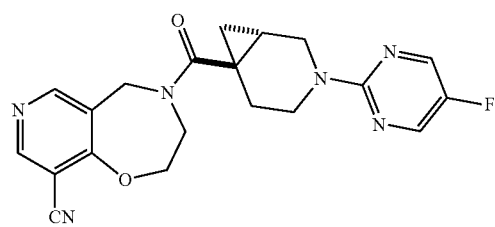 |
| 4-[2-[1-(5-fluoropyrimidin-2-yl)pyrrolidin-3-yl]-2-methyl-propanoyl]-3,5-dihydro-2H-pyrido[3,4-f][1,4]oxazepine-9-carbonitrile | 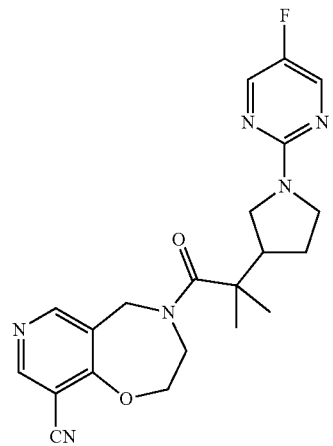 [SMILES: CC(C)(C(=O)N1CCOc2c(C#N)cncc2C1)C1CCN(c2ncc(F)cn2)C1] |
| 4-[1-(5-fluoropyrimidin-2-yl)-2-methyl-piperidine-4-carbonyl]-3,5-dihydro-2H-pyrido[3,4-f][1,4]oxazepine-9-carbonitrile | 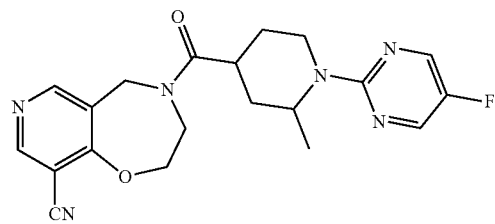 [SMILES: CC1CC(C(=O)N2CCOc3c(C#N)cncc3C2)CCN1c1ncc(F)cn1] |

-continued

| Name | Structure |
|---|---|
| 4-[1-(5-fluoropyrimidin-2-yl)azepane-4-carbonyl]-3,5-dihydro-2H-pyrido[3,4-f][1,4]oxazepine-9-carbonitrile | 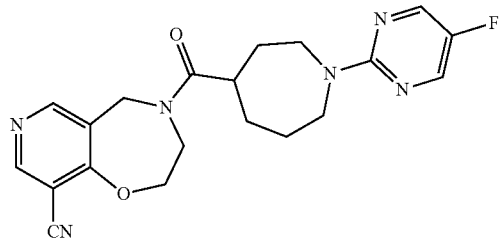 [SMILES: N#Cc1cncc2c1OCCN(C(=O)C1CCCN(c3ncc(F)cn3)CC1)C2] |
| 4-(3-(((5-fluoropyrimidin-2-yl)oxy)methyl)bicyclo[1.1.1]pentane-1-carbonyl)-2,3,4,5-tetrahydropyrido[3,4-f][1,4]oxazepine-9-carbonitrile | 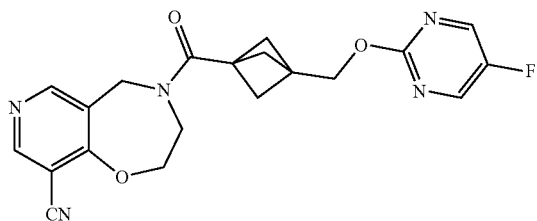 [SMILES: N#Cc1cncc2c1OCCN(C(=O)C13CC(COc4ncc(F)cn4)(C1)C3)C2] |
| 4-[4-(difluoromethyl)-1-(5-fluoropyrimidin-2-yl)piperidine-4-carbonyl]-3,5-dihydro-2H-pyrido[3,4-f][1,4]oxazepine-9-carbonitrile | 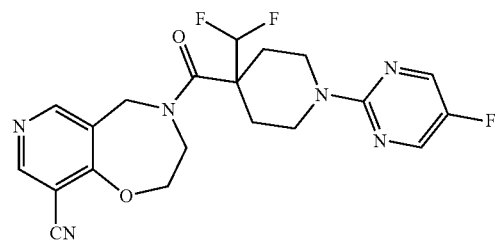 [SMILES: N#Cc1cncc2c1OCCN(C(=O)C1(C(F)F)CCN(c3ncc(F)cn3)CC1)C2] |
| 4-[4-fluoro-1-(pyridine-3-carbonyl)piperidine-4-carbonyl]-3,5-dihydro-2H-pyrido[3,4-f][1,4]oxazepine-9-carbonitrile | 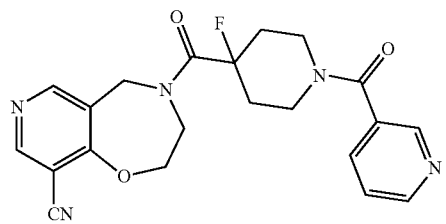 [SMILES: N#Cc1cncc2c1OCCN(C(=O)C1(F)CCN(C(=O)c3cccnc3)CC1)C2] |
| 4-[3,3-difluoro-1-(5-fluoropyrimidin-2-yl)-4-methyl-piperidine-4-carbonyl]-3,5-dihydro-2H-pyrido[3,4-f][1,4]oxazepine-9-carbonitrile | 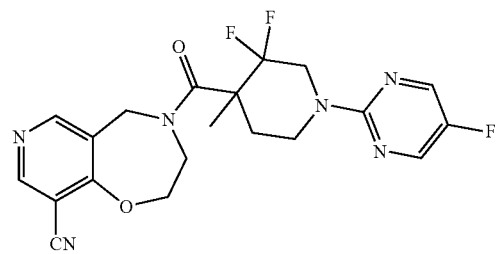 [SMILES: CC1(C(=O)N2CCOc3c(C#N)cncc3C2)CCN(c2ncc(F)cn2)CC1(F)F] |
| 4-(4-fluoro-1-quinazolin-2-yl-piperidine-4-carbonyl)-3,5-dihydro-2H-pyrido[3,4-f][1,4]oxazepine-9-carbonitrile | 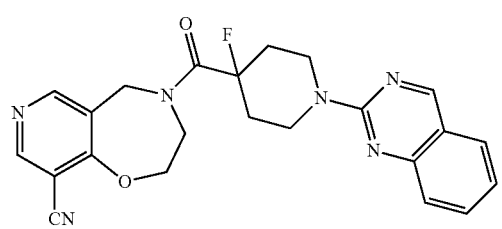 [SMILES: N#Cc1cncc2c1OCCN(C(=O)C1(F)CCN(c3ncc4ccccc4n3)CC1)C2] |

-continued

| Name | Structure |
|---|---|
| 4-[4-ethyl-1-(5-fluoropyrimidin-2-yl)piperidine-4-carbonyl]-3,5-dihydro-2H-pyrido[3,4-f][1,4]oxazepine-9-carbonitrile | 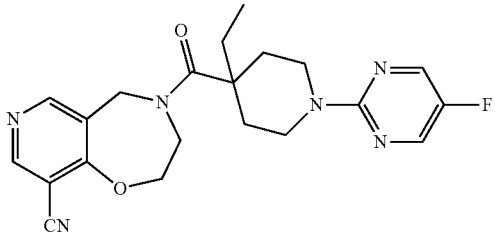 [SMILES: CCC1(C(=O)N2CCOc3c(C#N)cncc3C2)CCN(c2ncc(F)cn2)CC1] |
| 4-[7,7-difluoro-3-(5-fluoropyrimidin-2-yl)-3-azabicyclo[4.1.0]heptane-6-carbonyl]-3,5-dihydro-2H-pyrido[3,4-f][1,4]oxazepine-9-carbonitrile | 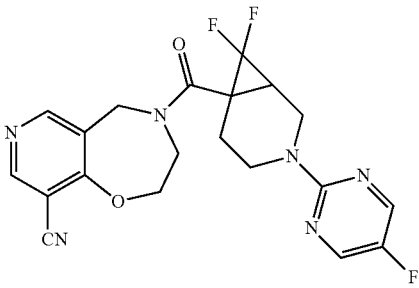 [SMILES: N#Cc1cncc2c1OCCN(C(=O)C13CCN(c4ncc(F)cn4)CC1C3(F)F)C2] |
| 4-[1-(5-cyclopropylpyrimidin-2-yl)-4-fluoro-piperidine-4-carbonyl]-3,5-dihydro-2H-pyrido[3,4-f][1,4]oxazepine-9-carbonitrile | 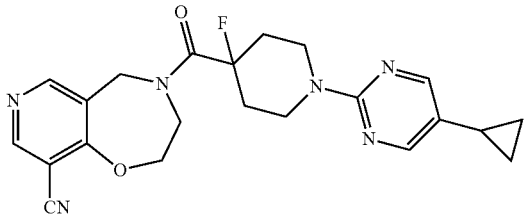 [SMILES: N#Cc1cncc2c1OCCN(C(=O)C1(F)CCN(c3ncc(C4CC4)cn3)CC1)C2] |
| 4-[4-fluoro-1-(5-methoxypyrimidin-2-yl)piperidine-4-carbonyl]-3,5-dihydro-2H-pyrido[3,4-f][1,4]oxazepine-9-carbonitrile | 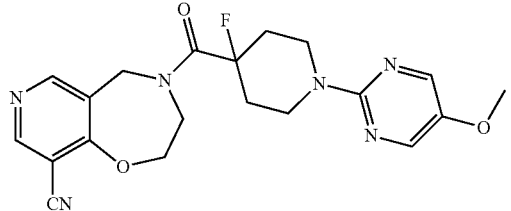 [SMILES: COc1cnc(N2CCC(F)(C(=O)N3CCOc4c(C#N)cncc4C3)CC2)nc1] |
| 4-[1-[5-(difluoromethoxy)pyrimidin-2-yl]-4-fluoro-piperidine-4-carbonyl]-3,5-dihydro-2H-pyrido[3,4-f][1,4]oxazepine-9-carbonitrile | 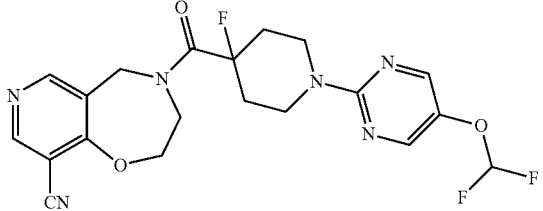 [SMILES: N#Cc1cncc2c1OCCN(C(=O)C1(F)CCN(c3ncc(OC(F)F)cn3)CC1)C2] |
| 4-[4-fluoro-1-(4-methoxypyrimidin-2-yl)piperidine-4-carbonyl]-3,5-dihydro-2H-pyrido[3,4-f][1,4]oxazepine-9-carbonitrile | 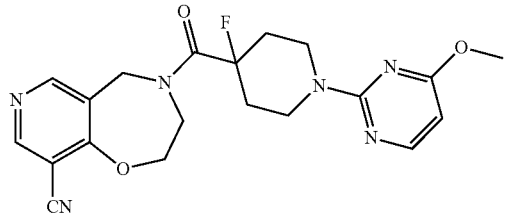 [SMILES: COc1ccnc(N2CCC(F)(C(=O)N3CCOc4c(C#N)cncc4C3)CC2)n1] |

| Name | Structure |
|------|-----------|
| (3R)-4-(1-(5-fluoropyrimidin-2-yl)piperidine-4-carbonyl)-3-methyl-2,3,4,5-tetrahydropyrido[3,4-f][1,4]oxazepine-9-carbonitrile | 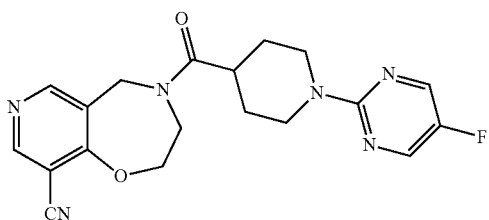 [SMILES: N#Cc1cncc2c1OCCN(C(=O)C1CCN(c3ncc(F)cn3)CC1)C2] |
| (3R)-4-[1-(5-fluoropyrimidin-2-yl)-4-methoxy-piperidine-4-carbonyl]-3-methyl-3,5-dihydro-2H-pyrido[3,4-f][1,4]oxazepine-9-carbonitrile | 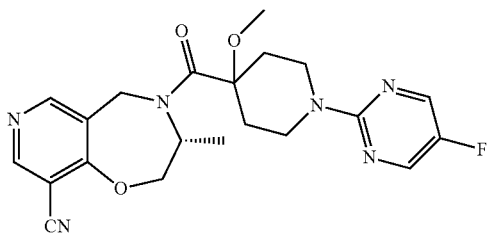 [SMILES: COC1(C(=O)N2Cc3cncc(C#N)c3OC[C@H]2C)CCN(c2ncc(F)cn2)CC1] |
| 4-(4-fluoro-1-imidazo[1,2-a]pyrazin-8-yl-piperidine-4-carbonyl)-3,5-dihydro-2H-pyrido[3,4-f][1,4]oxazepine-9-carbonitrile | 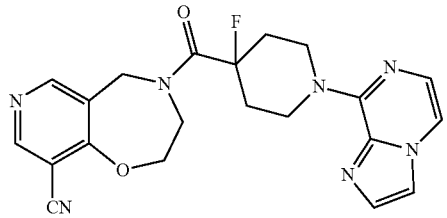 [SMILES: N#Cc1cncc2c1OCCN(C(=O)C1(F)CCN(c3nccn4ccnc34)CC1)C2] |
| 4-[4-fluoro-1-(1-methylpyrazolo[4,3-c]pyridin-6-yl)piperidine-4-carbonyl]-3,5-dihydro-2H-pyrido[3,4-f][1,4]oxazepine-9-carbonitrile | 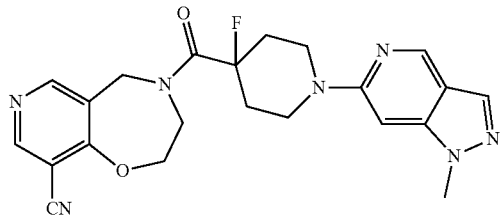 [SMILES: Cn1ncc2cnc(N3CCC(F)(C(=O)N4CCOc5c(C#N)cncc5C4)CC3)cc21] |
| 4-[4-fluoro-1-(5-methylpyrrolo[3,2-d]pyrimidin-2-yl)piperidine-4-carbonyl]-3,5-dihydro-2H-pyrido[3,4-f][1,4]oxazepine-9-carbonitrile | 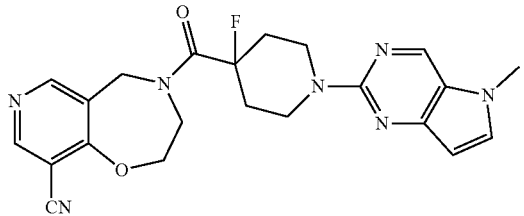 [SMILES: Cn1ccc2nc(N3CCC(F)(C(=O)N4CCOc5c(C#N)cncc5C4)CC3)ncc21] |
| 4-(4-fluoro-1-imidazo[1,2-b]pyridazin-6-yl-piperidine-4-carbonyl)-3,5-dihydro-2H-pyrido[3,4-f][1,4]oxazepine-9-carbonitrile | 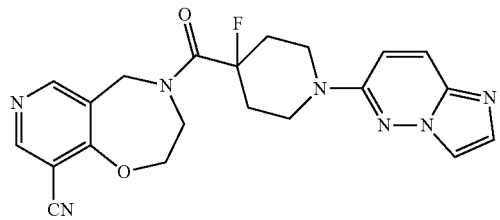 [SMILES: N#Cc1cncc2c1OCCN(C(=O)C1(F)CCN(c3ccc4nccn4n3)CC1)C2] |
| 4-(4-fluoro-1-(pyrazolo[1,5-a]pyrimidin-7-yl)piperidine-4-carbonyl)-2,3,4,5-tetrahydropyrido[3,4-f][1,4]oxazepine-9-carbonitrile | 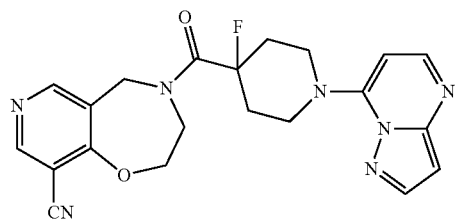 [SMILES: N#Cc1cncc2c1OCCN(C(=O)C1(F)CCN(c3ccnc4ccnn34)CC1)C2] |

| Name | Structure |
|---|---|
| 4-[1-(6,7-dihydro-5H-cyclopenta[d]pyrimidin-2-yl)-4-fluoro-piperidine-4-carbonyl]-3,5-dihydro-2H-pyrido[3,4-f][1,4]oxazepine-9-carbonitrile | 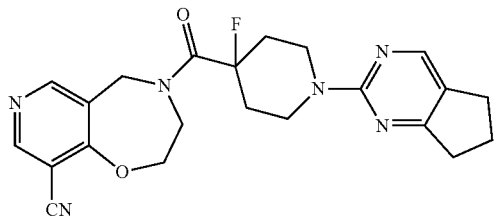 [SMILES: N#Cc1cncc2c1OCCN(C(=O)C1(F)CCN(c3ncc4c(n3)CCC4)CC1)C2] |
| 4-(4-fluoro-1-(5-fluoropyrimidin-4-yl)piperidine-4-carbonyl)-2,3,4,5-tetrahydropyrido[3,4-f][1,4]oxazepine-9-carbonitrile | 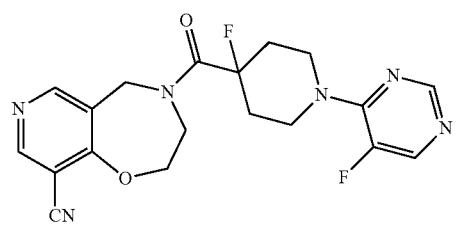 [SMILES: N#Cc1cncc2c1OCCN(C(=O)C1(F)CCN(c3ncncc3F)CC1)C2] |
| 4-[4-fluoro-1-(3-fluoro-2-pyridyl)piperidine-4-carbonyl]-3,5-dihydro-2H-pyrido[3,4-f][1,4]oxazepine-9-carbonitrile | 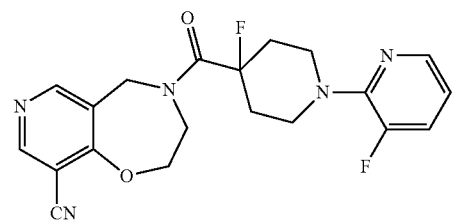 [SMILES: N#Cc1cncc2c1OCCN(C(=O)C1(F)CCN(c3ncccc3F)CC1)C2] |
| 4-[4-fluoro-1-(5-fluoro-2-methoxy-pyrimidin-4-yl)piperidine-4-carbonyl]-3,5-dihydro-2H-pyrido[3,4-f][[1,4]oxazepine-9-carbonitrile | 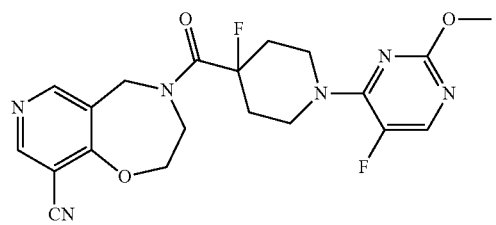 [SMILES: COc1ncc(F)c(N2CCC(F)(C(=O)N3CCOc4c(C#N)cncc4C3)CC2)n1] |
| 4-[4-fluoro-1-(6-methoxypyridazin-3-yl)piperidine-4-carbonyl]-3,5-dihydro-2H-pyrido[3,4-f][1,4]oxazepine-9-carbonitrile | 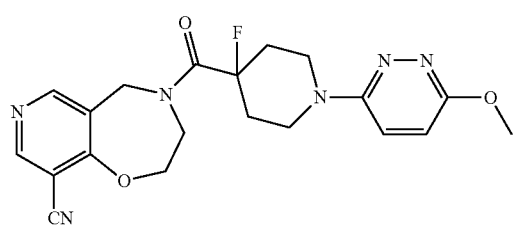 [SMILES: COc1ccc(N2CCC(F)(C(=O)N3CCOc4c(C#N)cncc4C3)CC2)nn1] |
| 4-(4-fluoro-1-pyridazin-3-yl-piperidine-4-carbonyl)-3,5-dihydro-2H-pyrido[3,4-f][1,4]oxazepine-9-carbonitrile | 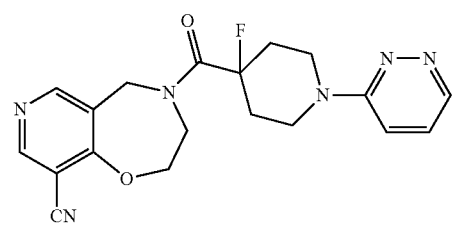 [SMILES: N#Cc1cncc2c1OCCN(C(=O)C1(F)CCN(c3cccnn3)CC1)C2] |

| Name | Structure |
|---|---|
| 4-[1-(4-methoxypyrimidin-2-yl)piperidine-4-carbonyl]-3,5-dihydro-2H-pyrido[3,4-f][1,4]oxazepine-9-carbonitrile | 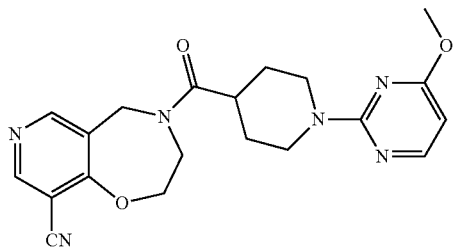 [SMILES: COc1ccnc(N2CCC(C(=O)N3CCOc4c(C#N)cncc4C3)CC2)n1] |
| 4-[1-(5-fluoro-4-methoxy-pyrimidin-2-yl)piperidine-4-carbonyl]-3,5-dihydro-2H-pyrido[3,4-f][1,4]oxazepine-9-carbonitrile | 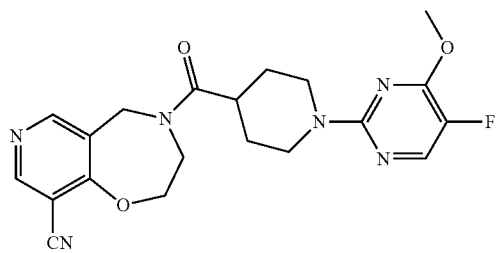 [SMILES: COc1nc(N2CCC(C(=O)N3CCOc4c(C#N)cncc4C3)CC2)ncc1F] |
| (3R)-4-(1-(4-methoxypyrimidin-2-yl)piperidine-4-carbonyl)-3-methyl-2,3,4,5-tetrahydropyrido[3,4-f][1,4]oxazepine-9-carbonitrile | 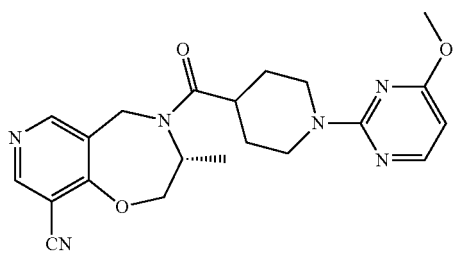 [SMILES: COc1ccnc(N2CCC(C(=O)N3Cc4cncc(C#N)c4OC[C@H]3C)CC2)n1] |
| (3R)-4-(1-(5-fluoro-4-methoxypyrimidin-2-yl)piperidine-4-carbonyl)-3-methyl-2,3,4,5-tetrahydropyrido[3,4-f][1,4]oxazepine-9-carbonitrile | 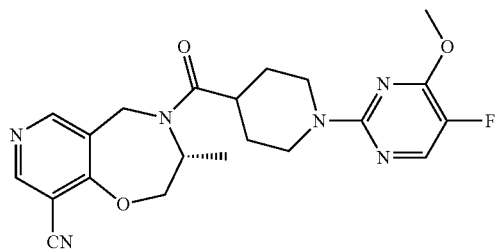 [SMILES: COc1nc(N2CCC(C(=O)N3Cc4cncc(C#N)c4OC[C@H]3C)CC2)ncc1F] |
| (9-fluoro-3,5-dihydro-2H-pyrido[3,4-f][1,4]oxazepin-4-yl)[1-(5 fluoropyrimidin-2-yl)-4-methoxy-4-piperidyl]methanone | 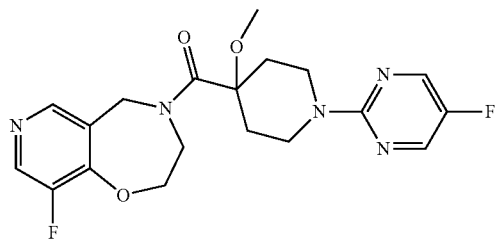 [SMILES: COC1(C(=O)N2CCOc3c(F)cncc3C2)CCN(c2ncc(F)cn2)CC1] |
| (9-fluoro-3,5-dihydro-2H-pyrido[3,4-f][1,4]oxazepin-4-yl)-[1-(5-fluoro-4-methoxy-pyrimidin-2-yl)-4-methoxy-4-piperidyl]methanone | 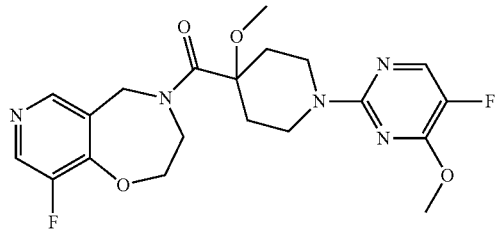 [SMILES: COc1nc(N2CCC(OC)(C(=O)N3CCOc4c(F)cncc4C3)CC2)ncc1F] |

| Name | Structure |
|---|---|
| 4-[4-fluoro-1-[5-fluoro-4-(methylamino)pyrimidin-2-yl]piperidine-4-carbonyl]-3,5-dihydro-2H-pyrido[3,4-f][1,4]oxazepine-9-carbonitrile | 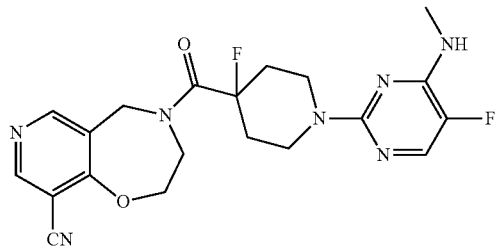 |
| 4-[1-[4-(cyclopropylamino)-5-fluoro-pyrimidin-2-yl]-4-fluoro-piperidine-4-carbonyl]-3,5-dihydro-2H-pyrido[3,4-f][1,4]oxazepine-9-carbonitrile | 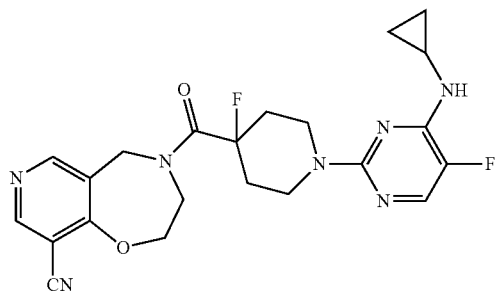 [SMILES: N#Cc1cncc2c1OCCN(C(=O)C1(F)CCN(c3ncc(F)c(NC4CC4)n3)CC1)C2] |
| 4-[1-[4-(2,2-difluoroethoxy)-5-fluoro-pyrimidin-2-yl]-4-fluoro-piperidine-4-carbonyl]-3,5-dihydro-2H-pyrido[3,4-f][1,4]oxazepine-9-carbonitrile | 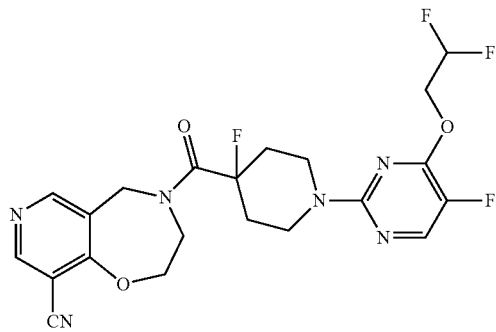 [SMILES: N#Cc1cncc2c1OCCN(C(=O)C1(F)CCN(c3ncc(F)c(OCC(F)F)n3)CC1)C2] |
| 4-[4-fluoro-1-(5-fluoro-4-methylsulfanyl-pyrimidin-2-yl)piperidine-4-carbonyl]-3,5-dihydro-2H-pyrido[3,4-f][1,4]oxazepine-9-carbonitrile | 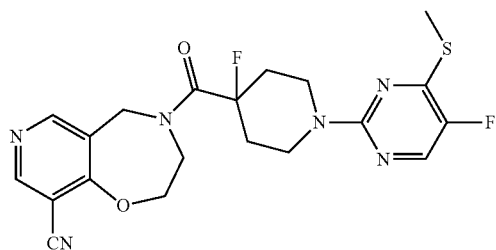 [SMILES: CSc1nc(N2CCC(F)(C(=O)N3CCOc4c(C#N)cncc4C3)CC2)ncc1F] |
| 4-[1-[4-[3-(dimethylamino)propoxy]-5-fluoro-pyrimidin-2-yl]-4-fluoro-piperidine-4-carbonyl]-3,5-dihydro-2H-pyrido[3,4-f][1,4]oxazepine-9-carbonitrile | 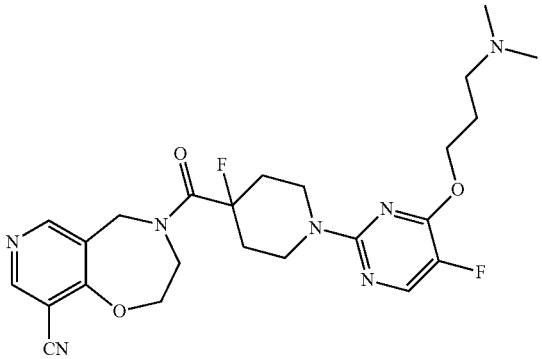 [SMILES: CN(C)CCCOc1nc(N2CCC(F)(C(=O)N3CCOc4c(C#N)cncc4C3)CC2)ncc1F] |

-continued

| Name | Structure |
|---|---|
| 4-[1-(5-chloro-4-methoxy-pyrimidin-2-yl)-4-fluoro-piperidine-4-carbonyl]-3,5-dihydro-2H-pyrido[3,4-f][1,4]oxazepine-9-carbonitrile | 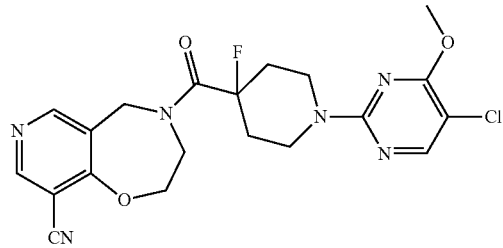 [SMILES: COc1nc(N2CCC(F)(C(=O)N3CCOc4c(C#N)cncc4C3)CC2)ncc1Cl] |
| 4-[1-(5-chloro-4-methoxy-pyrimidin-2-yl)piperidine-4-carbonyl]-3,5-dihydro-2H-pyrido[3,4-f][1,4]oxazepine-9-carbonitrile | 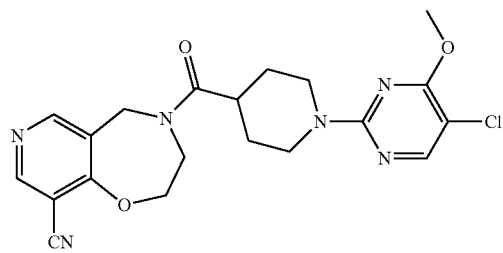 [SMILES: COc1nc(N2CCC(C(=O)N3CCOc4c(C#N)cncc4C3)CC2)ncc1Cl] |
| (9-fluoro-3,5-dihydro-2H-pyrido[3,4-f][1,4]oxazepin-4-yl)-[1-[5-fluoro-4-(2-methoxyethoxy)pyrimidin-2-yl]-4-piperidyl]methanone | 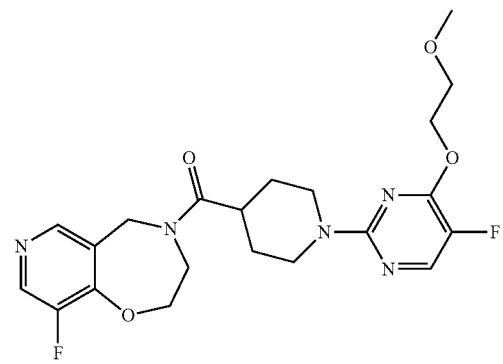 [SMILES: COCCOc1nc(N2CCC(C(=O)N3CCOc4c(F)cncc4C3)CC2)ncc1F] |
| 4-(1-(4-(2,2-difluoroethoxy)-5-fluoropyrimidin-2-yl)piperidine-4-carbonyl)-2,3,4,5-tetrahydropyrido[3,4-f][1,4]oxazepine-9-carbonitrile | 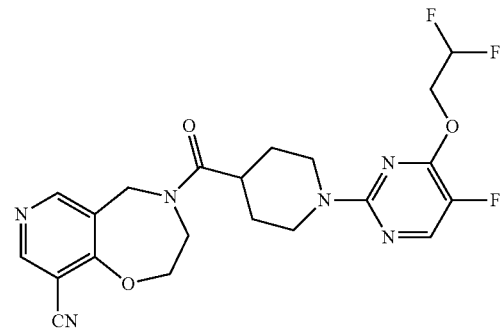 [SMILES: N#Cc1cncc2c1OCCN(C(=O)C1CCN(c3ncc(F)c(OCC(F)F)n3)CC1)C2] |
| (1-(4-(2,2-difluoroethoxy)-5-fluoropyrimidin-2-yl)-4-methoxypiperidin-4-yl)(9-fluoro-2,3-dihydropyrido[3,4-f][1,4]oxazepin-4(5H)-yl)methanone | 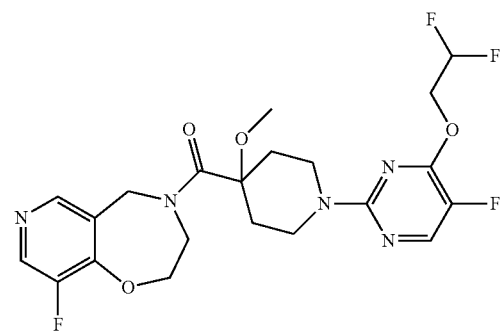 [SMILES: COC1(C(=O)N2CCOc3c(F)cncc3C2)CCN(c2ncc(F)c(OCC(F)F)n2)CC1] |

-continued

| Name | Structure |
|------|-----------|
| 4-[1-[4-(2,2-difluoroethoxy)pyrimidin-2-yl]piperidine-4-carbonyl]-3,5-dihydro-2H-pyrido[3,4-f][1,4]oxazepine-9-carbonitrile | 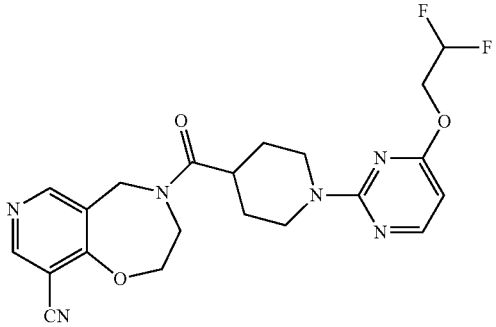 [SMILES: N#Cc1cncc2c1OCCN(C(=O)C1CCN(c3nccc(OCC(F)F)n3)CC1)C2] |
| [1- [4-(2,2-difluoroethoxy)pyrimidin-2-yl]-4-methoxy-4-piperidyl]-(9-fluoro-3,5-dihydro-2H-pyrido[3,4-f][1,4]oxazepin-4-yl)methanone | 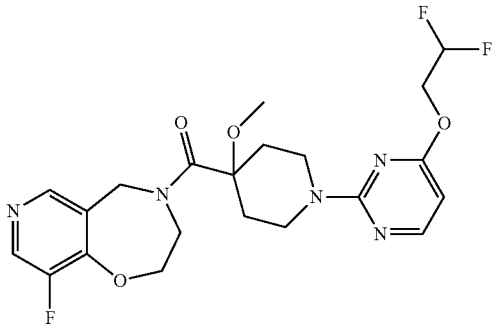 [SMILES: COC1(C(=O)N2CCOc3c(F)cncc3C2)CCN(c2nccc(OCC(F)F)n2)CC1] |
| (9-fluoro-3,5-dihydro-2H-pyrido[3,4-f][1,4]oxazepin-4-yl)-(4-methoxy-1-pyrimidin-2-yl-4-piperidyl)methanone | 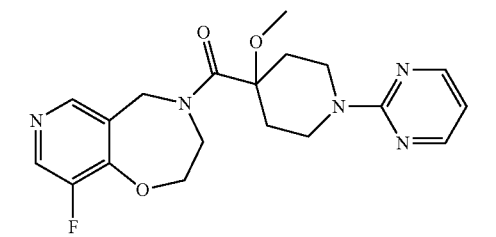 [SMILES: COC1(C(=O)N2CCOc3c(F)cncc3C2)CCN(c2ncccn2)CC1] |
| [1- [4-[2-(dimethylamino)ethoxy]-5-fluoro-pyrimidin-2-yl]-4-methoxy-4-piperidyl]-(9-fluoro-3,5-dihydro-2H-pyrido[3,4-f][1,4]oxazepin-4-yl)methanone | 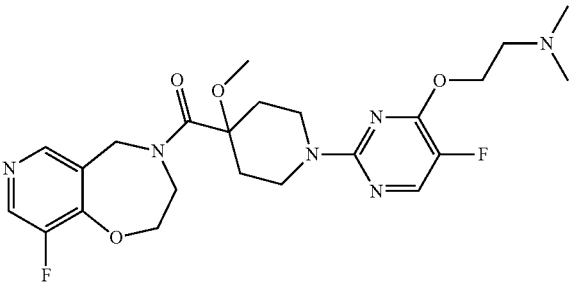 [SMILES: COC1(C(=O)N2CCOc3c(F)cncc3C2)CCN(c2ncc(F)c(OCCN(C)C)n2)CC1] |
| 4-(4-(fluoromethyl)-1-(5-fluoropyrimidin-2-yl)piperidine-4-carbonyl)-2,3,4,5-tetrahydropyrido[3,4-f][1,4]oxazepine-9-carbonitrile | 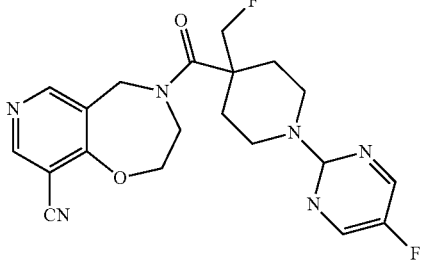 |

| Name | Structure |
|---|---|
| 4-(3,3-difluoro-1-methyl-cyclobutanecarbonyl)-3,5-dihydro-2H-pyrido[3,4-f][1,4]oxazepine-9-carbonitrile | 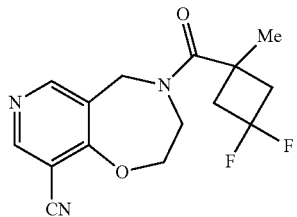 [SMILES: CC1(C(=O)N2CCOc3c(C#N)cncc3C2)CC(F)(F)C1] |
| 4-(1-(difluoromethyl)cyclopropane-1-carbonyl)-2,3,4,5-tetrahydropyrido[3,4-f][1,4]oxazepine-9-carbonitrile | 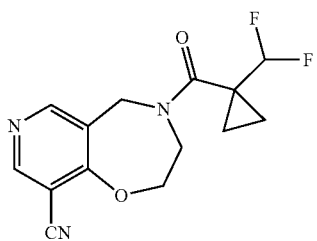 [SMILES: N#Cc1cncc2c1OCCN(C(=O)C1(C(F)F)CC1)C2] |
| 4-(1-fluorocyclopropanecarbonyl)-3,5-dihydro-2H-pyrido[3,4-f][1,4]oxazepine-9-carbonitrile | 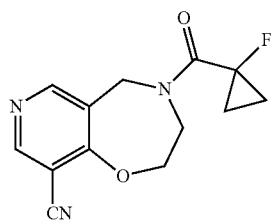 [SMILES: N#Cc1cncc2c1OCCN(C(=O)C1(F)CC1)C2] |
| 4-(4,4,4-trifluoro-2-methyl-butanoyl)-3,5-dihydro-2H-pyrido[3,4-f][1,4]oxazepine-9-carbonitrile | 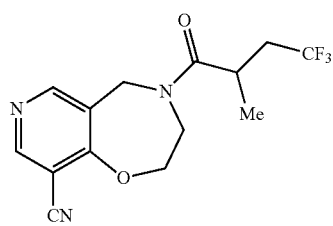 [SMILES: CC(CC(F)(F)F)C(=O)N1CCOc2c(C#N)cncc2C1] |
| 4-(3,3-difluoro-2,2-dimethyl-butanoyl)-3,5-dihydro-2H-pyrido[3,4-f][1,4]oxazepine-9-carbonitrile | 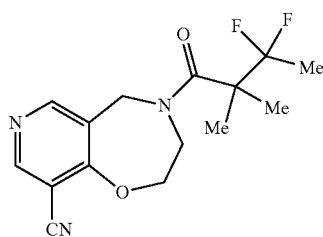 [SMILES: CC(F)(F)C(C)(C)C(=O)N1CCOc2c(C#N)cncc2C1] |
| 4-(2,2,3,3,4,4,4,-heptafluorobutanoyl)-3,5-dihydro-2H-pyrido[3,4-f][1,4]oxazepine-9-carbonitrile | 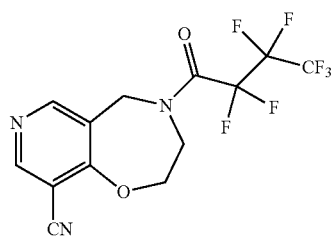 [SMILES: N#Cc1cncc2c1OCCN(C(=O)C(F)(F)C(F)(F)C(F)(F)F)C2] |

-continued

| Name | Structure |
|---|---|
| 4-(3-fluoro-2,2-dimethyl-propanoyl)-3,5-dihydro-2H-pyrido[3,4-f][1,4]oxazepine-9-carbonitrile | 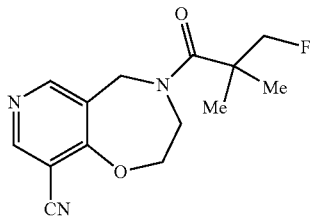 [SMILES: CC(C)(CF)C(=O)N1CCOc2c(C#N)cncc2C1] |
| 4-(2,2,3-trimethylbutanoyl)-3,5-dihydro-2H-pyrido[3,4-f][1,4]oxazepine-9-carbonitrile | 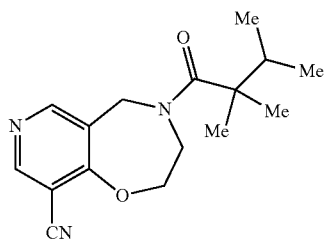 [SMILES: CC(C)C(C)(C)C(=O)N1CCOc2c(C#N)cncc2C1] |
| 4-(2-cyclopropylpropanoyl)-3,5-dihydro-2H-pyrido[3,4-f][1,4]oxazepine-9-carbonitrile | 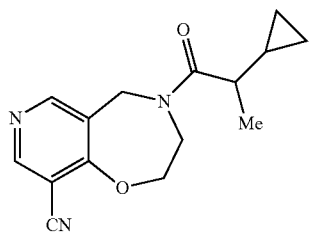 [SMILES: CC(C(=O)N1CCOc2c(C#N)cncc2C1)C1CC1] |
| 4-[3-fluoro-2-(fluoromethyl)-2-methyl-propanoyl]-3,5-dihydro-2H-pyrido[3,4-f][1,4]oxazepine-9-carbonitrile | 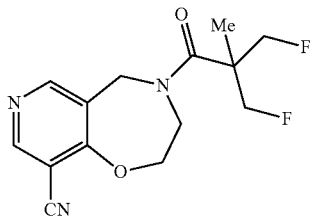 [SMILES: CC(CF)(CF)C(=O)N1CCOc2c(C#N)cncc2C1] |
| 4-(2-methyl-2-methylsulfanyl-propanoyl)-3,5-dihydro-2H-pyrido[3,4-f][1,4]oxazepine-9-carbonitrile | 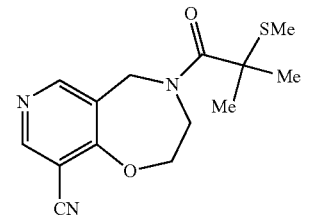 [SMILES: CSC(C)(C)C(=O)N1CCOc2c(C#N)cncc2C1] |
| 4-(4,4-difluoro-2,2-dimethyl-butanoyl)-3,5-dihydro-2H-pyrido[3,4-f][1,4]oxazepine-9-carbonitrile | 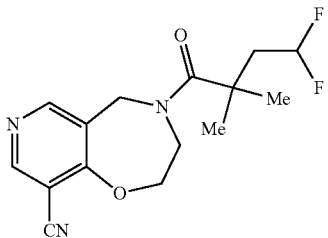 [SMILES: CC(C)(CC(F)F)C(=O)N1CCOc2c(C#N)cncc2C1] |

-continued

| Name | Structure |
|---|---|
| 4-(3-methoxy-2,2-dimethyl-propanoyl)-3,5-dihydro-2H-pyrido[3,4-f][1,4]oxazepine-9-carbonitrile | 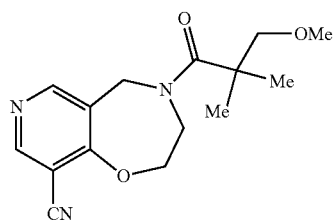 [SMILES: COCC(C)(C)C(=O)N1CCOc2c(C#N)cncc2C1] |
| 4-(2-ethyl-2-methyl-butanoyl)-3,5-dihydro-2H-pyrido[3,4-f][1,4]oxazepine-9-carbonitrile | 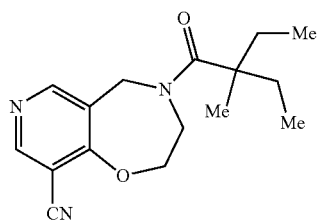 [SMILES: CCC(C)(CC)C(=O)N1CCOc2c(C#N)cncc2C1] |
| 4-[3,3,3-trifluoro-2-methyl-2-(trifluoromethyl)propanoyl]-3,5-dihydro-2H-pyrido[3,4-f][1,4]oxazepine-9-carbonitrile | 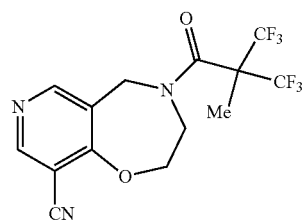 [SMILES: CC(C(=O)N1CCOc2c(C#N)cncc2C1)(C(F)(F)F)C(F)(F)F] |
| 4-(2-methoxy-2-methyl-butanoyl)-3,5-dihydro-2H-pyrido[3,4-f][1,4]oxazepine-9-carbonitrile | 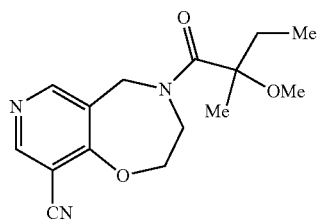 [SMILES: CCC(C)(OC)C(=O)N1CCOc2c(C#N)cncc2C1] |
| 4-(2-cyclopropyl-2-methoxy-propanoyl)-3,5-dihydro-2H-pyrido[3,4-f][1,4]oxazepine-9-carbonitrile | 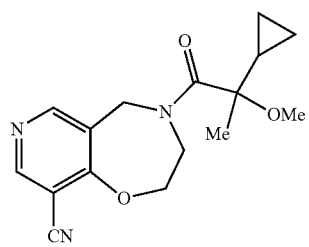 [SMILES: COC(C)(C(=O)N1CCOc2c(C#N)cncc2C1)C1CC1] |
| 4-[1-(5-fluoropyrimidin-2-yl)piperidine-4-carbonyl]-3,5-dihydro-2H-pyrido[3,4-f][1,4]oxazepine-9-carbonitrile | 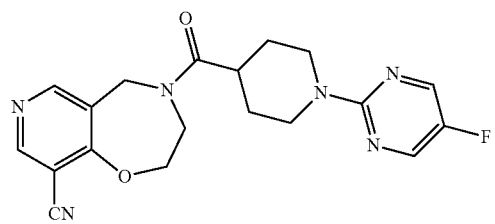 [SMILES: N#Cc1cncc2c1OCCN(C(=O)C1CCN(c3ncc(F)cn3)CC1)C2] |
| (9-fluoro-3,5-dihydro-2H-pyrido[3,4-f][1,4]oxazepin-4-yl)-[1-(5-fluoropyrimidin-2-yl)-4-piperidyl]methanone | 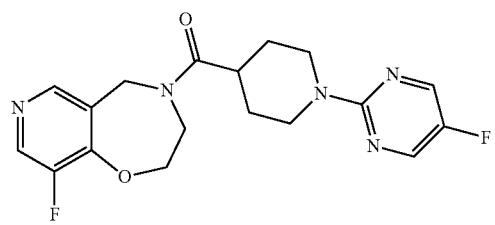 [SMILES: O=C(C1CCN(c2ncc(F)cn2)CC1)N1CCOc2c(F)cncc2C1] |

-continued

| Name | Structure |
|---|---|
| 4-(4-fluoro-1-pyrimidin-2-yl-piperidine-4-carbonyl)-3,5-dihydro-2H-pyrido[3,4-f][1,4]oxazepine-9-carbonitrile | 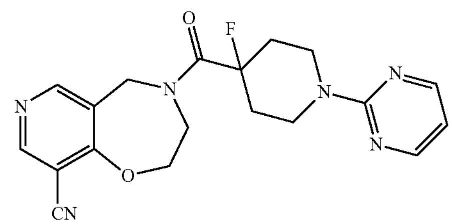 [SMILES: N#Cc1cncc2c1OCCN(C(=O)C1(F)CCN(c3ncccn3)CC1)C2] |
| 4-(2-chloro-2-methyl-propanoyl)-3,5-dihydro-2H-pyrido[3,4-f][1,4]oxazepine-9-carbonitrile | 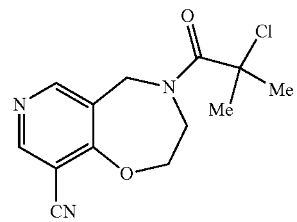 [SMILES: CC(C)(Cl)C(=O)N1CCOc2c(C#N)cncc2C1] |
| 2-[4-fluoro-4-(9-fluoro-3,5-dihydro-2H-pyrido[3,4-f][1,4]oxazepine-4-carbonyl)-1-piperidyl]pyrimidine-5-carbonitrile | 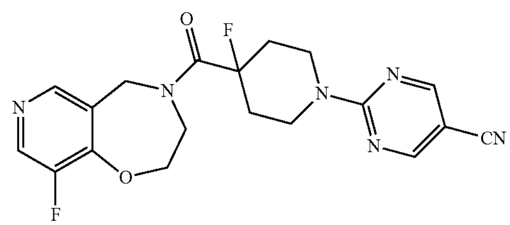 [SMILES: N#Cc1cnc(N2CCC(F)(C(=O)N3CCOc4c(F)cncc4C3)CC2)nc1] |
| 2-[4-fluoro-4-(9-fluoro-3,5-dihydro-2H-pyrido[3,4-f][1,4]oxazepine-4-carbonyl)-1-piperidyl]pyrimidine-4-carbonitrile | 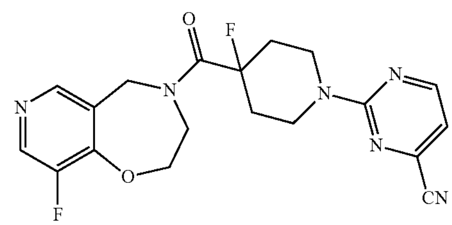 [SMILES: N#Cc1ccnc(N2CCC(F)(C(=O)N3CCOc4c(F)cncc4C3)CC2)n1] |
| 4-[4-fluoro-1-(5-fluoropyrimidin-2-yl)piperidine-4-carbonyl]-3,5-dihydro-2H-pyrido[3,4-f][1,4]oxazepine-9-carbonitrile | 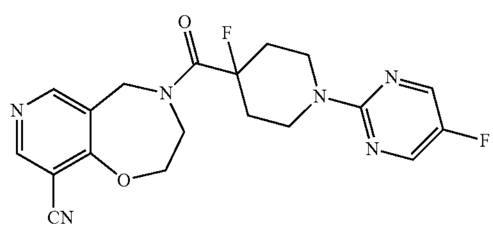 [SMILES: N#Cc1cncc2c1OCCN(C(=O)C1(F)CCN(c3ncc(F)cn3)CC1)C2] |
| 4-[4-fluoro-1-(4-methylpyrimidin-2-yl)piperidine-4-carbonyl]-3,5-dihydro-2H-pyrido[3,4-f][1,4]oxazepine-9-carbonitrile | 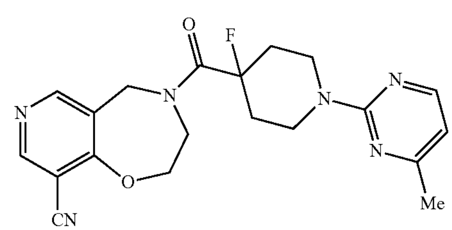 [SMILES: Cc1ccnc(N2CCC(F)(C(=O)N3CCOc4c(C#N)cncc4C3)CC2)n1] |
| 4-[4-fluoro-1-(5-methylpyrimidin-2-yl)piperidine-4-carbonyl]-3,5-dihydro-2H-pyrido[3,4-f][1,4]oxazepine-9-carbonitrile | 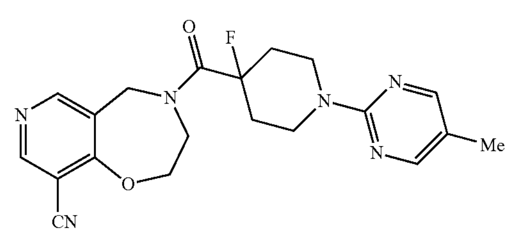 [SMILES: Cc1cnc(N2CCC(F)(C(=O)N3CCOc4c(C#N)cncc4C3)CC2)nc1] |

| Name | Structure |
|---|---|
| 4-[1-(5-chloropyrimidin-2-yl)-4-fluoro-piperidine-4-carbonyl]-3,5-dihydro-2H-pyrido[3,4-f][1,4]oxazepine-9-carbonitrile | 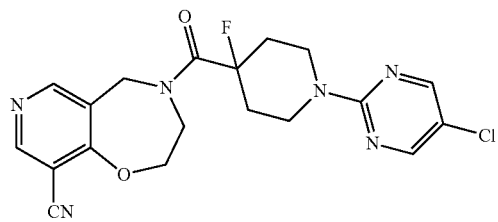 [SMILES: N#Cc1cncc2c1OCCN(C(=O)C1(F)CCN(c3ncc(Cl)cn3)CC1)C2] |
| 4-[1-(5,7-dihydrofuro[3,4-d]pyrimidin-2-yl)-4-fluoro-piperidine-4-carbonyl]-3,5-dihydro-2H-pyrido[3,4-f][1,4]oxazepine-9-carbonitrile | 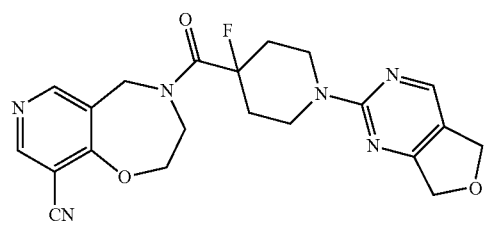 [SMILES: N#Cc1cncc2c1OCCN(C(=O)C1(F)CCN(c3ncc4c(n3)COC4)CC1)C2] |
| 4-[4-fluoro-1-([1,2,4]triazolo[1,5-c]pyrimidin-5-yl)piperidine-4-carbonyl]-3,5-dihydro-2H-pyrido[3,4-f][1,4]oxazepine-9-carbonitrile | 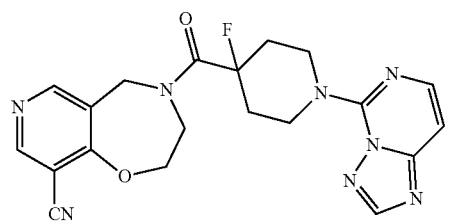 [SMILES: N#Cc1cncc2c1OCCN(C(=O)C1(F)CCN(c3nccc4ncnn34)CC1)C2] |
| 4-[4-fluoro-1-[4-(trifluoromethyl)pyrimidin-2-yl]piperidine-4-carbonyl]-3,5-dihydro-2H-pyrido[3,4-f][1,4]oxazepine-9-carbonitrile | 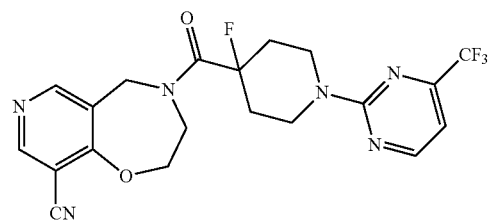 [SMILES: N#Cc1cncc2c1OCCN(C(=O)C1(F)CCN(c3nccc(C(F)(F)F)n3)CC1)C2] |
| 4-[4-fluoro-1-[4-methyl-6-(trifluoromethyl)pyrimidin-2-yl]piperidine-4-carbonyl]-3,5-dihydro-2H-pyrido[3,4-f][1,4]oxazepine-9-carbonitrile | 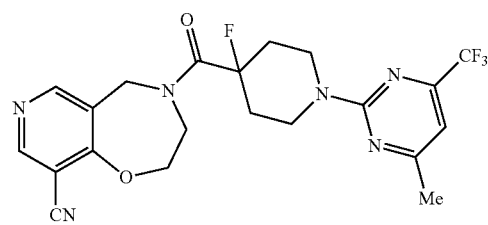 [SMILES: Cc1cc(C(F)(F)F)nc(N2CCC(F)(C(=O)N3CCOc4c(C#N)cncc4C3)CC2)n1] |
| 4-[4-fluoro-1-(9-methylpurin-2-yl)piperidine-4-carbonyl]-3,5-dihydro-2H-pyrido[3,4-f][1,4]oxazepine-9-carbonitrile | 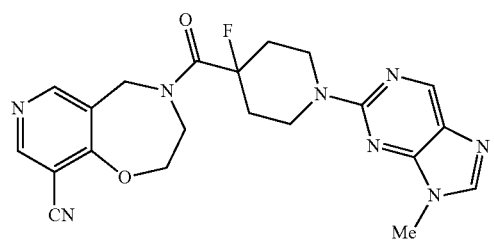 [SMILES: Cn1cnc2cnc(N3CCC(F)(C(=O)N4CCOc5c(C#N)cncc5C4)CC3)nc21] |

| Name | Structure |
|---|---|
| 4-[4-fluoro-1-[5-(trifluoromethyl)pyrimidin-2-yl]piperidine-4-carbonyl]-3,5-dihydro-2H-pyrido[3,4-f][1,4]oxazepine-9-carbonitrile | 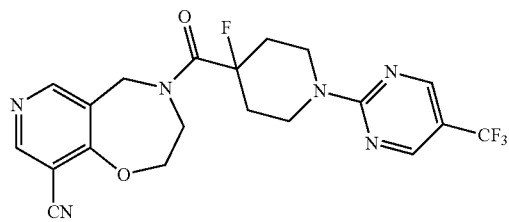 [SMILES: N#Cc1cncc2c1OCCN(C(=O)C1(F)CCN(c3ncc(C(F)(F)F)cn3)CC1)C2] |
| 4-[4-fluoro-1-[2-(trifluoromethyl)pyrimidin-4-yl]piperidine-4-carbonyl]-3,5-dihydro-2H-pyrido[3,4-f][1,4]oxazepine-9-carbonitrile | 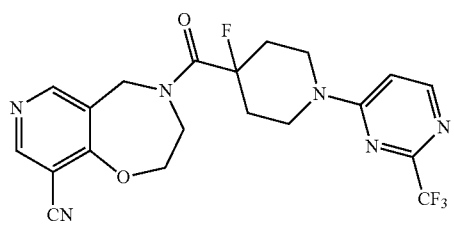 [SMILES: N#Cc1cncc2c1OCCN(C(=O)C1(F)CCN(c3ccnc(C(F)(F)F)n3)CC1)C2] |
| 4-[4-fluoro-1-(2-methoxypyrimidin-4-yl)piperidine-4-carbonyl]-3,5-dihydro-2H-pyrido[3,4-f][1,4]oxazepine-9-carbonitrile | 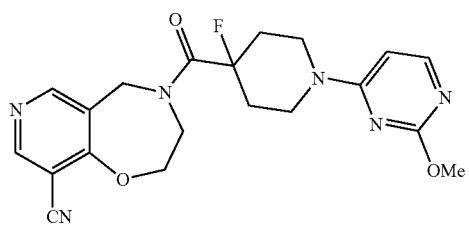 [SMILES: COc1nccc(N2CCC(F)(C(=O)N3CCOc4c(C#N)cncc4C3)CC2)n1] |
| 4-[4-fluoro-1-(5-methyloxazole-4-carbonyl)piperidine-4-carbonyl]-3,5-dihydro-2H-pyrido[3,4-f][1,4]oxazepine-9-carbonitrile | 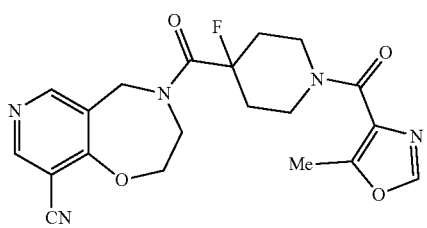 [SMILES: Cc1ocnc1C(=O)N1CCC(F)(C(=O)N2CCOc3c(C#N)cncc3C2)CC1] |
| isobutyl 4-(9-cyano-3,5-dihydro-2H-pyrido[3,4-f][1,4]oxazepine-4-carbonyl)-4-fluoro-piperidine-1-carboxylate | 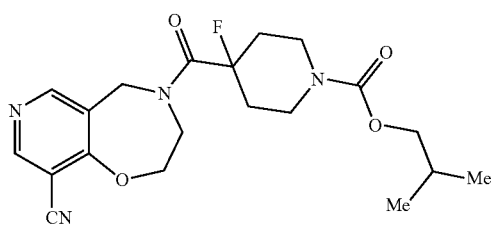 [SMILES: CC(C)COC(=O)N1CCC(F)(C(=O)N2CCOc3c(C#N)cncc3C2)CC1] |
| 4-(2,2-dimethylpropanoyl)-3,5-dihydro-2H-pyrido[3,4-f][1,4]oxazepine-9-carbonitrile | 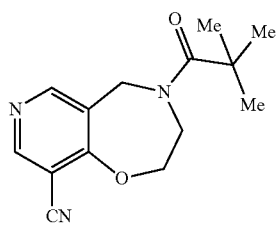 [SMILES: CC(C)(C)C(=O)N1CCOc2c(C#N)cncc2C1] |

| Name | Structure |
|---|---|
| 4-[3-fluoro-1-(5-fluoropyrimidin-2-yl)pyrrolidine-3-carbonyl]-3,5-dihydro-2H-pyrido[3,4-f][1,4]oxazepine-9-carbonitrile | 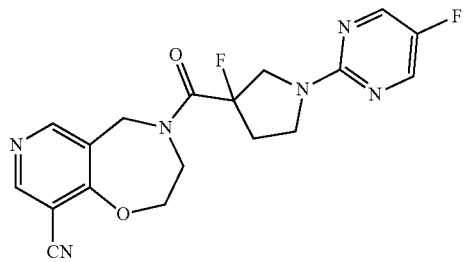 [SMILES: N#Cc1cncc2c1OCCN(C(=O)C1(F)CCN(c3ncc(F)cn3)C1)C2] |
| 4-[4-chloro-1-(5-fluoropyrimidin-2-yl)piperidine-4-carbonyl]-3,5-dihydro-2H-pyrido[3,4-f][1,4]oxazepine-9-carbonitrile | 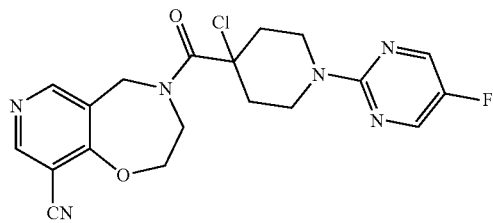 [SMILES: N#Cc1cncc2c1OCCN(C(=O)C1(Cl)CCN(c3ncc(F)cn3)CC1)C2] |
| 4-[1-(4-ethoxy-5-fluoro-pyrimidin-2-yl)-4-fluoro-piperidine-4-carbonyl]-3,5-dihydro-2H-pyrido[3,4-f][1,4]oxazepine-9-carbonitrile | 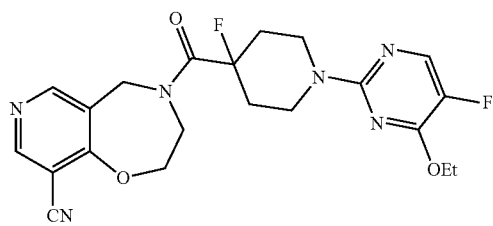 [SMILES: CCOc1nc(N2CCC(F)(C(=O)N3CCOc4c(C#N)cncc4C3)CC2)ncc1F] |
| 4-[4-fluoro-1-(8-fluoro-[1,2,4]triazolo[1,5-c]pyrimidin-5-yl)piperidine-4-carbonyl]-3,5-dihydro-2H-pyrido[3,4-f][1,4]oxazepine-9-carbonitrile | 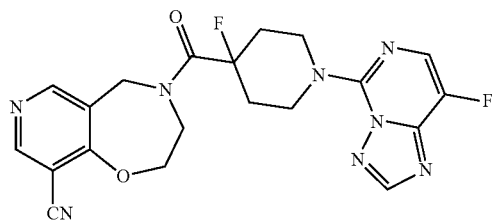 [SMILES: N#Cc1cncc2c1OCCN(C(=O)C1(F)CCN(c3ncc(F)c4ncnn34)CC1)C2] |
| 4-(4-fluoro-1-imidazo[1,2-a]pyrimidin-5-yl-piperidine-4-carbonyl)-3,5-dihydro-2H-pyrido[3,4-f][1,4]oxazepine-9-carbonitrile | 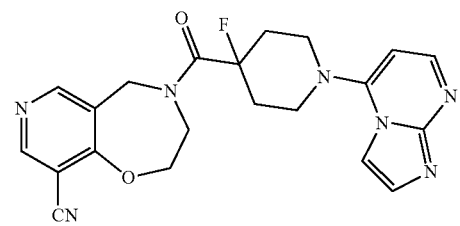 [SMILES: N#Cc1cncc2c1OCCN(C(=O)C1(F)CCN(c3ccnc4nccn34)CC1)C2] |
| 4-(3-((5-fluoropyrimidin-2-yl)thio)-2,2-dimethylpropanoyl)-2,3,4,5-tetrahydropyrido[3,4-f][1,4]oxazepine-9-carbonitrile | 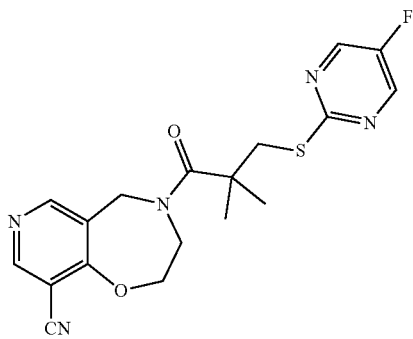 [SMILES: CC(C)(CSc1ncc(F)cn1)C(=O)N1CCOc2c(C#N)cncc2C1] |

| Name | Structure |
|---|---|
| 4-[4-cyano-1-(5-fluoropyrimidin-2-yl)piperidine-4-carbonyl]-3,5-dihydro-2H-pyrido[3,4-f][1,4]oxazepine-9-carbonitrile | 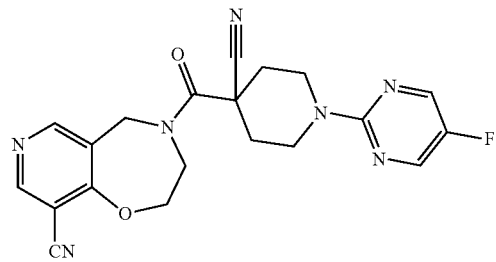 [SMILES: N#Cc1cncc2c1OCCN(C(=O)C1(C#N)CCN(c3ncc(F)cn3)CC1)C2] |
| 4-[4-fluoro-1-(5-fluoro-4-methyl-pyrimidin-2-yl)piperidine-4-carbonyl]-3,5-dihydro-2H-pyrido[3,4-f][1,4]oxazepine-9-carbonitrile | 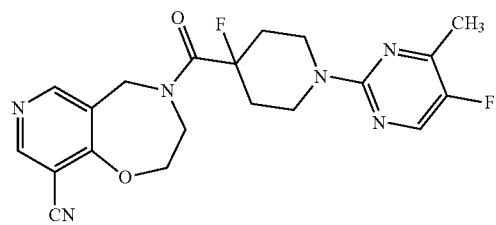 [SMILES: Cc1nc(N2CCC(F)(C(=O)N3CCOc4c(C#N)cncc4C3)CC2)ncc1F] |
| 4-[1-(5-fluoropyrimidin-2-yl)-4-methoxy-piperidine-4-carbonyl]-3,5-dihydro-2H-pyrido[3,4-f][1,4]oxazepine-9-carbonitrile | 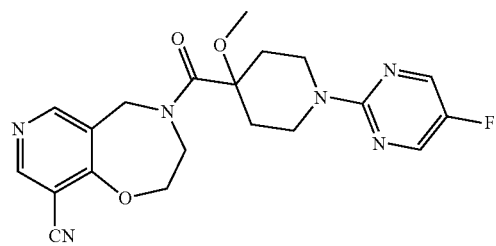 [SMILES: COC1(C(=O)N2CCOc3c(C#N)cncc3C2)CCN(c2ncc(F)cn2)CC1] |
| 4-[1-(2-chloro-5-methoxy-pyrimidin-4-yl)-4-fluoro-piperidine-4-carbonyl]-3,5-dihydro-2H-pyrido[3,4-f][1,4]oxazepine-9-carbonitrile | 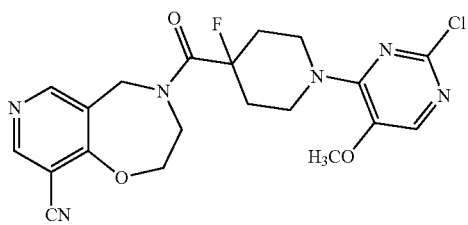 [SMILES: COc1cnc(Cl)nc1N1CCC(F)(C(=O)N2CCOc3c(C#N)cncc3C2)CC1] |
| 4-[1-(5-fluoropyrimidin-2-yl)-3-methyl-piperidine-4-carbonyl]-3,5-dihydro-2H-pyrido[3,4-f][1,4]oxazepine-9-carbonitrile | 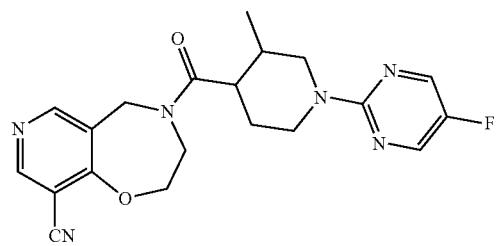 [SMILES: CC1CN(c2ncc(F)cn2)CCC1C(=O)N1CCOc2c(C#N)cncc2C1] |
| 4-[4-fluoro-1-(5-fluoro-2-pyridyl)piperidine-4-carbonyl]-3,5-dihydro-2H-pyrido[3,4-f][1,4]oxazepine-9-carbonitrile | 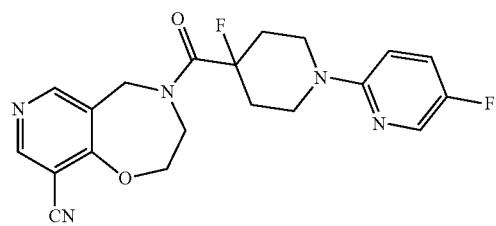 [SMILES: N#Cc1cncc2c1OCCN(C(=O)C1(F)CCN(c3ccc(F)cn3)CC1)C2] |

| Name | Structure |
|------|-----------|
| 4-[1-[5-(difluoromethyl)pyrimidin-2-yl]-4-fluoro-piperidine-4-carbonyl]-3,5-dihydro-2H-pyrido[3,4-f][1,4]oxazepine-9-carbonitrile | 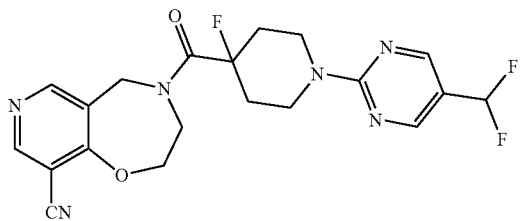 [SMILES: N#Cc1cncc2c1OCCN(C(=O)C1(F)CCN(c3ncc(C(F)F)cn3)CC1)C2] |
| 4-[1-(5-fluoro-2-pyridyl)-4-methoxy-piperidine-4-carbonyl]-3,5-dihydro-2H-pyrido[3,4-f][1,4]oxazepine-9-carbonitrile | 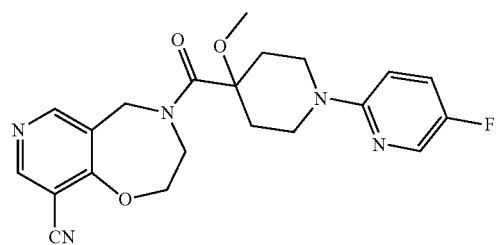 [SMILES: COC1(C(=O)N2CCOc3c(C#N)cncc3C2)CCN(c2ccc(F)cn2)CC1] |
| 4-[4-fluoro-1-(5-fluoro-4-methoxy-pyrimidin-2-yl)piperidine-4-carbonyl]-3,5-dihydro-2H-pyrido[3,4-f][1,4]oxazepine-9-carbonitrile | 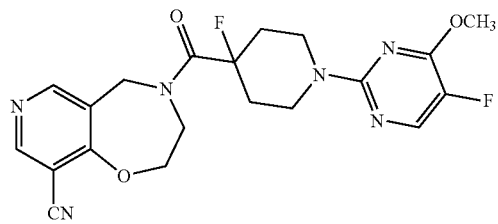 [SMILES: COc1nc(N2CCC(F)(C(=O)N3CCOc4c(C#N)cncc4C3)CC2)ncc1F] |
| 4-[1-(3,5-difluoro-2-pyridyl)-4-fluoro-piperidine-4-carbonyl]-3,5-dihydro-2H-pyrido[3,4-f][1,4]oxazepine-9-carbonitrile | 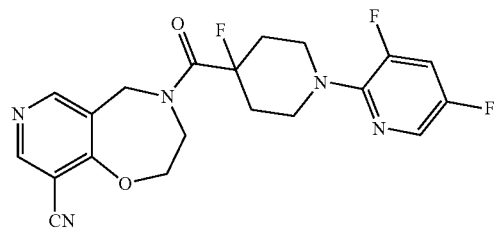 [SMILES: N#Cc1cncc2c1OCCN(C(=O)C1(F)CCN(c3ncc(F)cc3F)CC1)C2] |
| 4-[1-(5,6-difluoro-3-pyridyl)-4-fluoro-piperidine-4-carbonyl]-3,5-dihydro-2H-pyrido[3,4-f][1,4]oxazepine-9-carbonitrile | 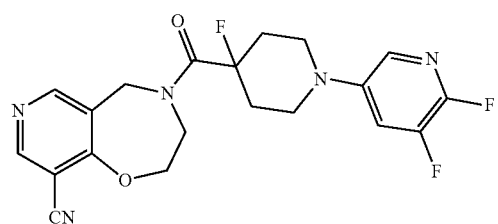 [SMILES: N#Cc1cncc2c1OCCN(C(=O)C1(F)CCN(c3cnc(F)c(F)c3)CC1)C2] |
| 4-[1-(5-fluoro-4-methoxy-pyrimidin-2-yl)-4-methoxy-piperidine-4-carbonyl]-3,5-dihydro-2H-pyrido[3,4-f][1,4]oxazepine-9-carbonitrile | 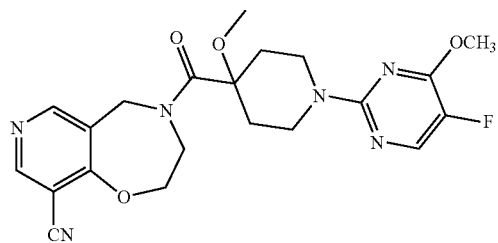 [SMILES: COc1nc(N2CCC(OC)(C(=O)N3CCOc4c(C#N)cncc4C3)CC2)ncc1F] |

-continued

| Name | Structure |
|---|---|
| 4-[1-(5-fluoro-4-methoxy-6-methyl-pyrimidin-2-yl)-4-methoxy-piperidine-4-carbonyl]-3,5-dihydro-2H-pyrido[3,4-f][1,4]oxazepine-9-carbonitrile | 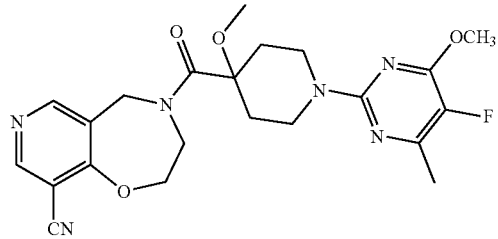 [SMILES: COc1nc(N2CCC(OC)(C(=O)N3CCOc4c(C#N)cncc4C3)CC2)nc(C)c1F] |
| 4-[4-fluoro-1-(5-fluoro-4-methoxy-6-methyl-pyrimidin-2-yl)piperidine-4-carbonyl]-3,5-dihydro-2H-pyrido[3,4-f][1,4]oxazepine-9-carbonitrile | 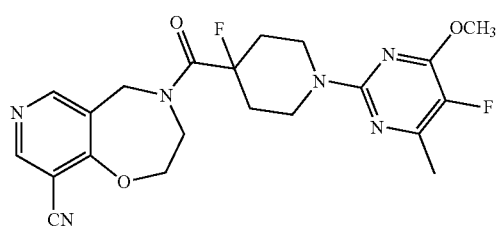 [SMILES: COc1nc(N2CCC(F)(C(=O)N3CCOc4c(C#N)cncc4C3)CC2)nc(C)c1F] |
| 4-[4-fluoro-1-(4-methoxyquinazolin-2-yl)piperidine-4-carbonyl]-3,5-dihydro-2H-pyrido[3,4-f][1,4]oxazepine-9-carbonitrile | 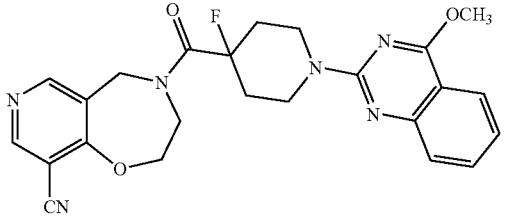 [SMILES: COc1nc(N2CCC(F)(C(=O)N3CCOc4c(C#N)cncc4C3)CC2)nc2ccccc12] |
| 4-(4-fluoro-1-quinoxalin-2-yl-piperidine-4-carbonyl)-3,5-dihydro-2H-pyrido[3,4-f][1,4]oxazepine-9-carbonitrile | 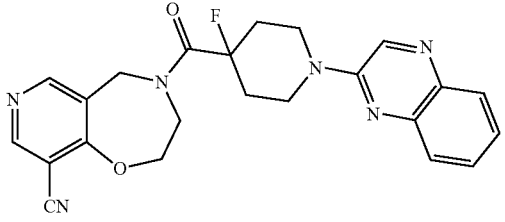 [SMILES: N#Cc1cncc2c1OCCN(C(=O)C1(F)CCN(c3cnc4ccccc4n3)CC1)C2] |
| 4-[4-fluoro-1-(3-isoquinolyl)piperidine-4-carbonyl]-3,5-dihydro-2H-pyrido[3,4-f][1,4]oxazepine-9-carbonitrile | 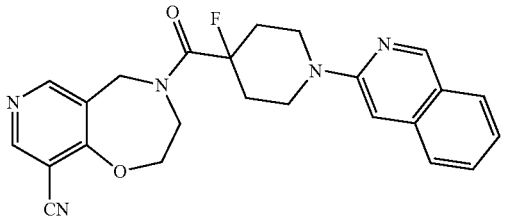 [SMILES: N#Cc1cncc2c1OCCN(C(=O)C1(F)CCN(c3cc4ccccc4cn3)CC1)C2] |
| 4-[4-fluoro-1-(2-quinolyl)piperidine-4-carbonyl]-3,5-dihydro-2H-pyrido[3,4-f][1,4]oxazepine-9-carbonitrile | 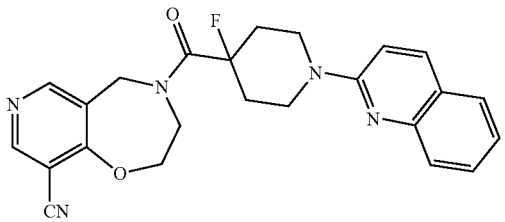 [SMILES: N#Cc1cncc2c1OCCN(C(=O)C1(F)CCN(c3ccc4ccccc4n3)CC1)C2] |

| Name | Structure |
|---|---|
| 4-[1-(4-cyclopropyl-5-fluoro-pyrimidin-2-yl)-4-fluoro-piperidine-4-carbonyl]-3,5-dihydro-2H-pyrido[3,4-f][1,4]oxazepine-9-carbonitrile | 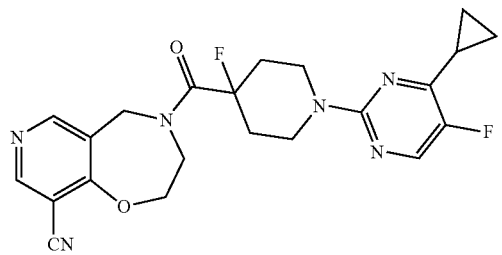 [SMILES: N#Cc1cncc2c1OCCN(C(=O)C1(F)CCN(c3ncc(F)c(C4CC4)n3)CC1)C2] |
| 4-[1-(2-chloro-5-fluoro-pyrimidin-4-yl)-4-fluoro-piperidine-4-carbonyl]-3,5-dihydro-2H-pyrido[3,4-f][1,4]oxazepine-9-carbonitrile | 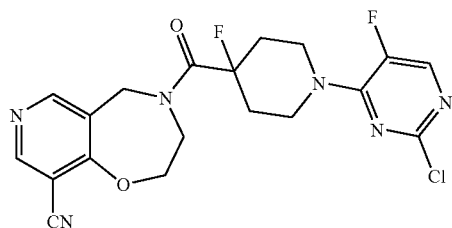 [SMILES: N#Cc1cncc2c1OCCN(C(=O)C1(F)CCN(c3nc(Cl)ncc3F)CC1)C2] |
| 4-[1-(8-fluoro-[1,2,4]triazolo[1,5-c]pyrimidin-5-yl)piperidine-4-carbonyl]-3,5-dihydro-2H-pyrido[3,4-f][1,4]oxazepine-9carbonitrile | 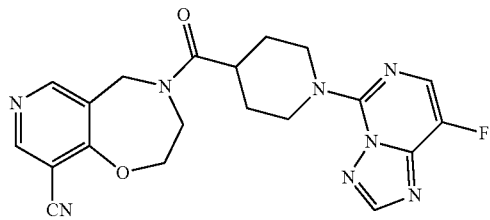 [SMILES: N#Cc1cncc2c1OCCN(C(=O)C1CCN(c3ncc(F)c4ncnn34)CC1)C2] |
| 4-(1-pyrazolo[1,5-a]pyrimidin-7-ylpiperidine-4-carbonyl)-3,5-dihydro-2H-pyrido[3,4-f][1,4]oxazepine-9-carbonitrile | 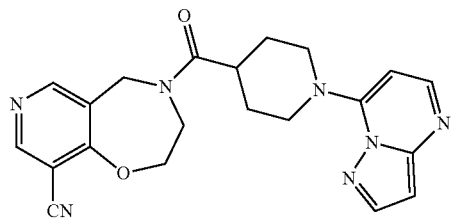 [SMILES: N#Cc1cncc2c1OCCN(C(=O)C1CCN(c3ccnc4ccnn34)CC1)C2] |
| 4-[4-fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile | 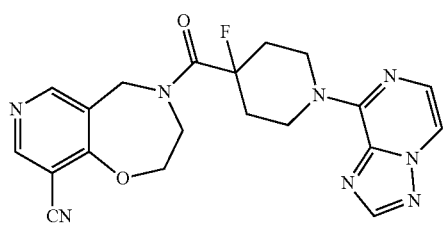 [SMILES: N#Cc1cncc2c1OCCN(C(=O)C1(F)CCN(c3nccn4ncnc34)CC1)C2] |
| 1-(9-fluoro-3,5-dihydro-2H-pyrido[3,4-f][1,4]oxazepin-4-yl)-2,2-dimethyl-butan-1-one | 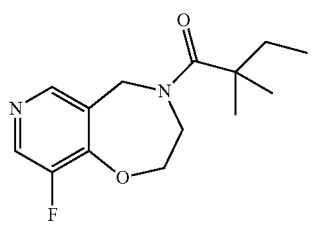 [SMILES: CCC(C)(C)C(=O)N1CCOc2c(F)cncc2C1] |

-continued

| Name | Structure |
|---|---|
| 4-[3-fluoro-1-(5-fluoropyrimidin-2-yl)-4-hydroxy-piperidine-4-carbonyl]-3,5-dihydro-2H-pyrido[3,4-f][1,4]oxazepine-9-carbonitrile | 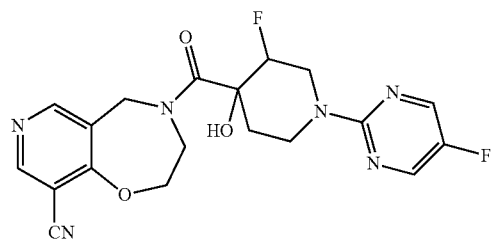 [SMILES: N#Cc1cncc2c1OCCN(C(=O)C1(O)CCN(c3ncc(F)cn3)CC1F)C2] |
| [1-[4-(2,2-difluoroethoxy)-1,3,5-triazin-2-yl]-4-methoxy-4-piperidyl]-(9-fluoro-3,5-dihydro-2H-pyrido[3,4-f][1,4]oxazepin-4-yl)methanone | 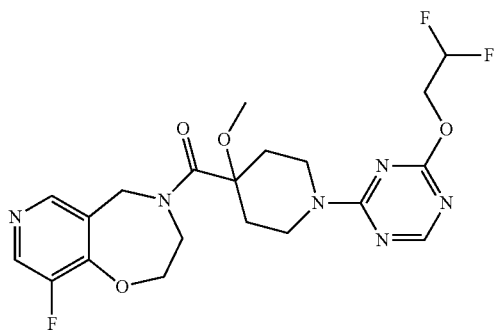 [SMILES: COC1(C(=O)N2CCOc3c(F)cncc3C2)CCN(c2ncnc(OCC(F)F)n2)CC1] |
| [1-[4-(2,2-difluoroethoxy)-1,3,5-triazin-2-yl]-4-piperidyl]-(9-fluoro-3,5-dihydro-2H-pyrido[3,4-f][1,4]oxazepin-4-yl)methanone | 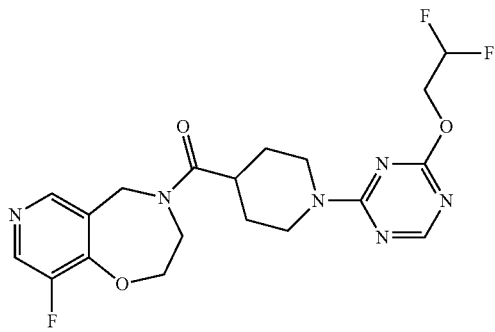 [SMILES: O=C(C1CCN(c2ncnc(OCC(F)F)n2)CC1)N1CCOc2c(F)cncc2C1] |
| 4-[1-(5-fluoropyrimidin-2-yl)-3-hydroxy-piperidine-4-carbonyl]-3,5-dihydro-2H-pyrido[3,4-f][1,4]oxazepine-9-carbonitrile | 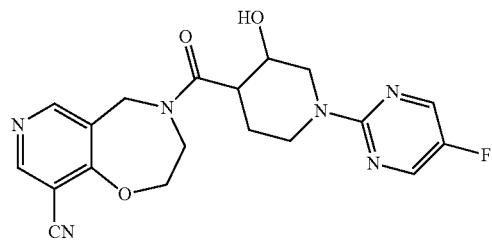 [SMILES: N#Cc1cncc2c1OCCN(C(=O)C1CCN(c3ncc(F)cn3)CC1O)C2] |
| 4-[4-fluoro-1-([1,2,4]triazolo[1,5-a]pyrimidin-7-yl)piperidine-4-carbonyl]-3,5-dihydro-2H-pyrido[3,4-f][1,4]oxazepine-9-carbonitrile | 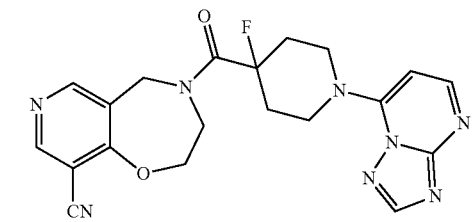 [SMILES: N#Cc1cncc2c1OCCN(C(=O)C1(F)CCN(c3ccnc4ncnn34)CC1)C2] |

| Name | Structure |
|------|-----------|
| 4-[3,3,4-trifluoro-1-(5-fluoropyrimidin-2-yl)piperidine-4-carbonyl]-3,5-dihydro-2H-pyrido[3,4-f][1,4]oxazepine-9-carbonitrile | 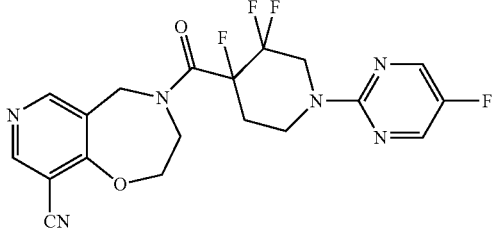 [SMILES: N#Cc1cncc2c1OCCN(C(=O)C1(F)CCN(c3ncc(F)cn3)CC1(F)F)C2] |
| 4-[3,3-difluoro-4-methyl-1-pyrimidin-2-yl-piperidine-4-carbonyl]-3,5-dihydro-2H-pyrido[3,4-f][1,4]oxazepine-9-carbonitrile | 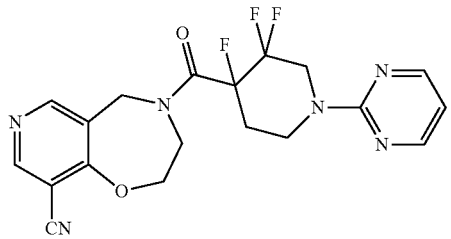 [SMILES: N#Cc1cncc2c1OCCN(C(=O)C1(F)CCN(c3ncccn3)CC1(F)F)C2] |
| 4-(1-(5-chloropyrimidin-2-yl)-3,3-difluoro-4-methylpiperidine-4-carbonyl)-2,3,4,5-tetrahydropyrido[3,4-f][1,4]oxazepine-9-carbonitrile | 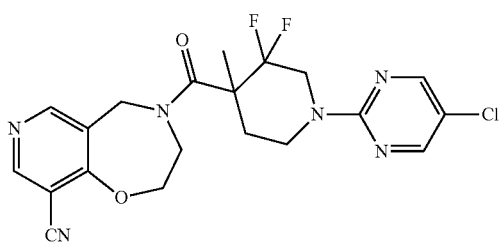 [SMILES: CC1(C(=O)N2CCOc3c(C#N)cncc3C2)CCN(c2ncc(Cl)cn2)CC1(F)F] |
| 4-[3,3-difluoro-1-(5-fluoro-6-oxo-1H-pyrimidin-2-yl)-4-methyl-piperidine-4-carbonyl]-3,5-dihydro-2H-pyrido[3,4-f][1,4]oxazepine-9-carbonitrile | 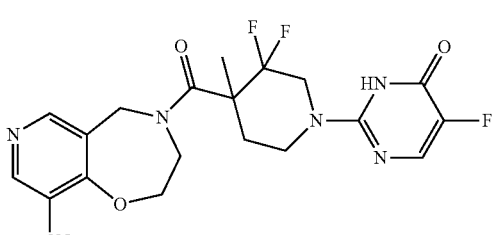 |
| 4-[3,3-difluoro-1-[5-fluoro-4-(2-methoxyethoxy)pyrimidin-2-yl]-4-methyl-piperidine-4-carbonyl]-3,5-dihydro-2H-pyrido[3,4-f][1,4]oxazepine-9-carbonitrile | 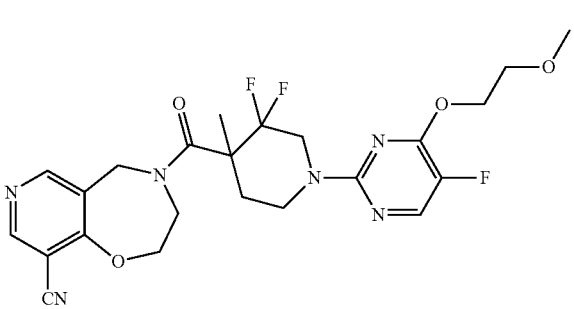 [SMILES: COCCOc1nc(N2CCC(C)(C(=O)N3CCOc4c(C#N)cncc4C3)C(F)(F)C2)ncc1F] |
| 4-(3,3-difluoro-1-(imidazo[2,1-f][1,2,4]triazin-4-yl)piperidine-4-carbonyl)-2,3,4,5-tetrahydropyrido[3,4-f][1,4]oxazepine-9-carbonitrile | 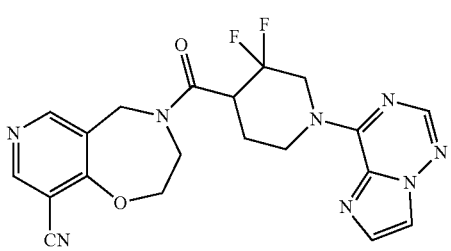 [SMILES: N#Cc1cncc2c1OCCN(C(=O)C1CCN(c3ncnn4ccnc34)CC1(F)F)C2] |

| Name | Structure |
|---|---|
| 4-[3,3-difluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile | 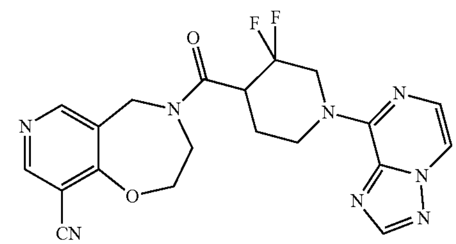 [SMILES: N#Cc1cncc2c1OCCN(C(=O)C1CCN(c3nccn4ncnc34)CC1(F)F)C2] |
| 4-(3,3-difluoro-1-pyrazolo[1,5-a][1,3,5]triazin-4-yl-piperidine-4-carbonyl)-3,5-dihydro-2H-pyrido[3,4-f][1,4]oxazepine-9-carbonitrile | 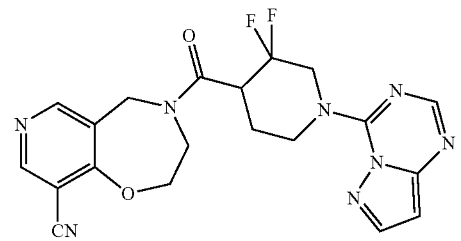 [SMILES: N#Cc1cncc2c1OCCN(C(=O)C1CCN(c3ncnc4ccnn34)CC1(F)F)C2] |
| 4-(3,3-difluoro-1-pyrazolo[1,5-a]pyrimidin-7-yl-piperidine-4-carbonyl)-3,5-dihydro-2H-pyrido[3,4-f][1,4]oxazepine-9-carbonitrile | 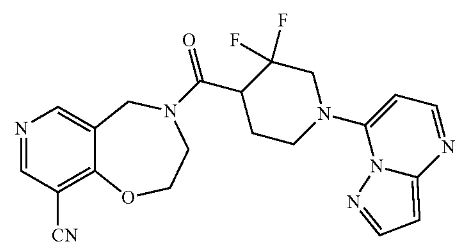 [SMILES: N#Cc1cncc2c1OCCN(C(=O)C1CCN(c3ccnc4ccnn34)CC1(F)F)C2] |
| 4-[3,3-difluoro-4-methyl-1-([1,2,4]triazolo[1,5-a]pyrazin-8-yl)piperidine-4-carbonyl]-3,5-dihydro-2H-pyrido[3,4-f][1,4]oxazepine-9-carbonitrile | 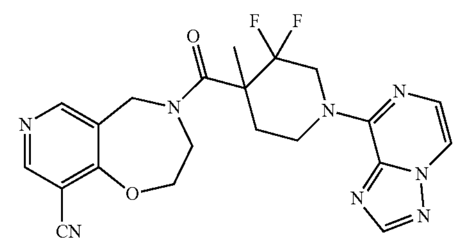 [SMILES: CC1(C(=O)N2CCOc3c(C#N)cncc3C2)CCN(c2nccn3ncnc23)CC1(F)F] |
| 4-[(3,4)-trans-3-fluoro-1-(5-fluoropyrimidin-2-yl)-4-methyl-piperidine-4-carbonyl]-3,5-dihydro-2H-pyrido[3,4-f][1,4]oxazepine-9-carbonitrile | 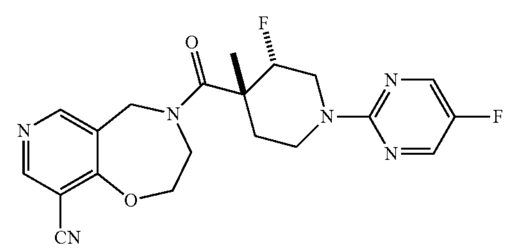 [SMILES: C[C@]1(C(=O)N2CCOc3c(C#N)cncc3C2)CCN(c2ncc(F)cn2)C[C@H]1F] |
| 4-[(3,4)-trans-3-fluoro-1-(2-methyl-3-oxo-pyridazin-4-yl)piperidine-4-carbonyl]-3,5-dihydro-2H-pyrido[3,4-f][1,4]oxazepine-9-carbonitrile | 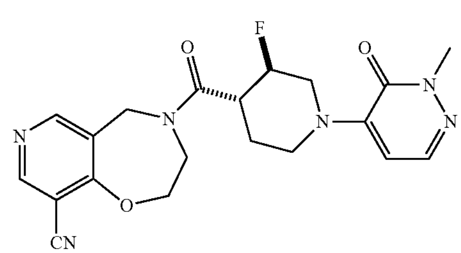 |

| Name | Structure |
|---|---|
| 4-[(3,4)-trans-3-fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile | 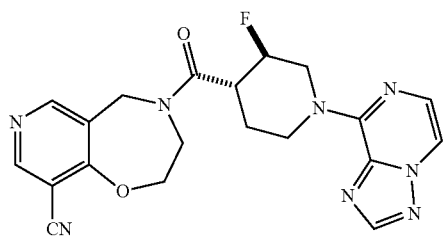 |
| 4-[(3,4)-trans-3-fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile | 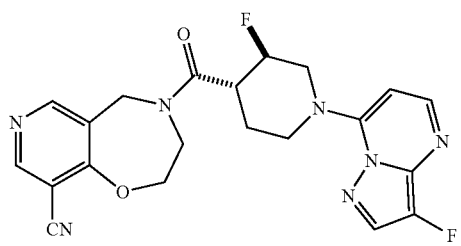 |
| 4-[1-(3-chloropyrazolo[1,5-a]pyrimidin-7-yl)-(3,4)-trans-3-fluoro-piperidine-4-carbonyl]-3,5-dihydro-2H-pyrido[3,4-f][1,4]oxazepine-9-carbonitrile | 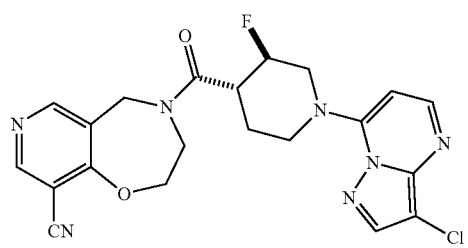 |
| 4-[1-(3-fluoropyrazolo[1,5-a]pyrimidin-7-yl)piperidine-4-carbonyl]-3,5-dihydro-2H-pyrido[3,4-f][1,4]oxazepine-9-carbonitrile | 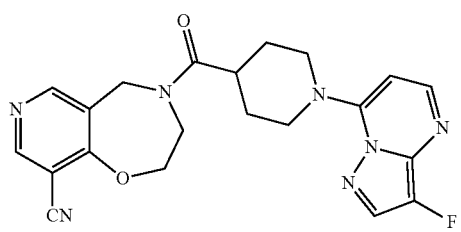 [SMILES: N#Cc1cncc2c1OCCN(C(=O)C1CCN(c3ccnc4c(F)cnn34)CC1)C2] |
| 4-[1-(3-chloropyrazolo[1,5-a]pyrimidin-7-yl)piperidine-4-carbonyl]-3,5-dihydro-2H-pyrido[3,4-f][1,4]oxazepine-9-carbonitrile | 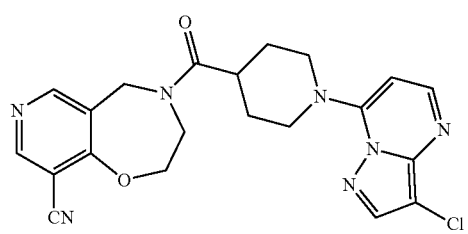 [SMILES: N#Cc1cncc2c1OCCN(C(=O)C1CCN(c3ccnc4c(Cl)cnn34)CC1)C2] |
| 4-[1-(5-fluoropyrimidin-2-yl)piperidine-4-carbonyl]spiro[2,5-dihydropyrido[3,4-f][1,4]oxazepine-3,1'-cyclopropane]-9-carbonitrile | 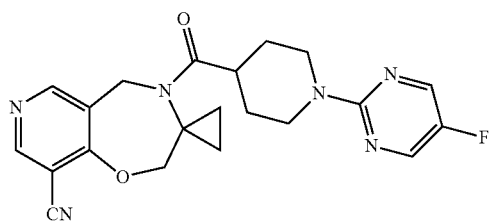 [SMILES: N#Cc1cncc2c1OCC1(CC1)N(C(=O)C1CCN(c3ncc(F)cn3)CC1)C2] |

-continued

| Name | Structure |
|------|-----------|
| 4-[4-(5-fluoropyrimidin-2-yl)-1,4-oxazepane-7-carbonyl]-3,5-dihydro-2H-pyrido[3,4-f][1,4]oxazepine-9-carbonitrile | 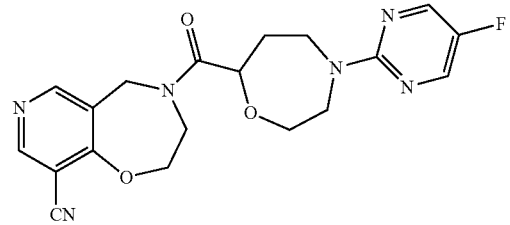 [SMILES: N#Cc1cncc2c1OCCN(C(=O)C1CCN(c3ncc(F)cn3)CCO1)C2] |
| 4-[4-fluoro-1-[4-methoxy-6-(trifluoromethyl)pyrimidin-2-yl]piperidine-4-carbonyl]-3,5-dihydro-2H-pyrido[3,4-f][1,4]oxazepine-9-carbonitrile | 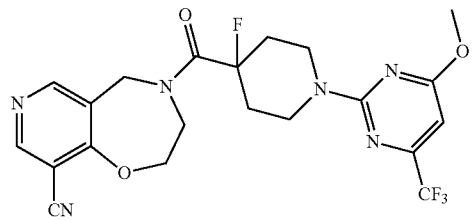 [SMILES: COc1cc(C(F)(F)F)nc(N2CCC(F)(C(=O)N3CCOc4c(C#N)cncc4C3)CC2)n1] |
| 4-[1-(4-cyclopropyl-5-fluoro-pyrimidin-2-yl)-4-methoxy-piperidine-4-carbonyl]-3,5-dihydro-2H-pyrido[3,4-f][1,4]oxazepine-9-carbonitrile | 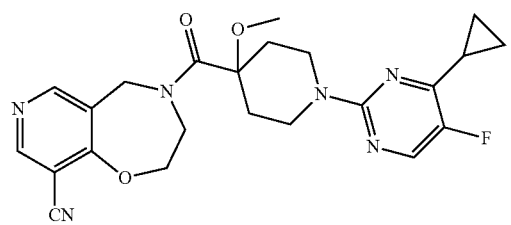 [SMILES: COC1(C(=O)N2CCOc3c(C#N)cncc3C2)CCN(c2ncc(F)c(C3CC3)n2)CC1] |
| 3,5-dihydro-2H-pyrido[3,4-f][1,4]oxazepin-4-yl-[1-(5-fluoropyrimidin-2-yl)-4-methoxy-4-piperidyl]methanone | 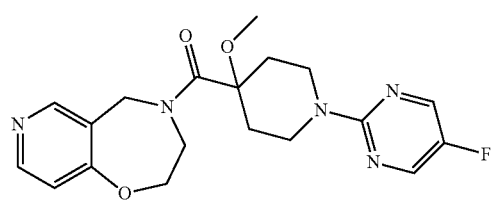 [SMILES: COC1(C(=O)N2CCOc3ccncc3C2)CCN(c2ncc(F)cn2)CC1] |
| 3,5-dihydro-2H-pyrido[3,4-f][1,4]oxazepin-4-yl41-(5-fluoro-4-methoxy-pyrimidin-2-yl)-4-methoxy-4-piperidyl]methanone | 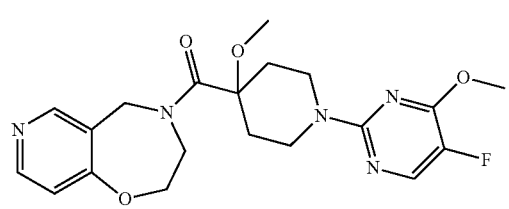 [SMILES: COc1nc(N2CCC(OC)(C(=O)N3CCOc4ccncc4C3)CC2)ncc1F] |
| (9-fluoro-3,5-dihydro-2H-pyrido[3,4-f][1,4]oxazepin-4-yl)-[1-(5-fluoro-4-methoxy-pyrimidin-2-yl)-4-piperidyl]methanone | 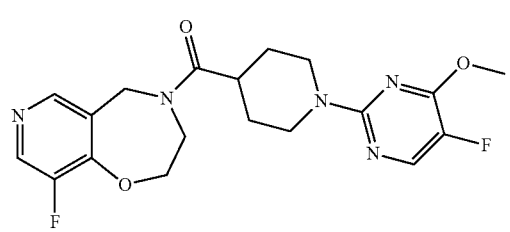 [SMILES: COc1nc(N2CCC(C(=O)N3CCOc4c(F)cncc4C3)CC2)ncc1F] |
| 3,5-dihydro-2H-pyrido[3,4-f][1,4]oxazepin-4-yl41-(5-fluoro-4-methoxy-pyrimidin-2-yl)-4-piperidyl]methanone | 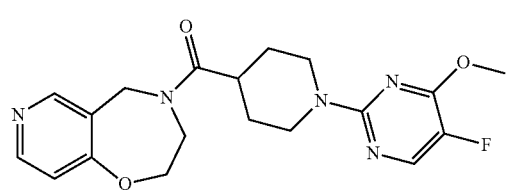 [SMILES: COc1nc(N2CCC(C(=O)N3CCOc4ccncc4C3)CC2)ncc1F] |

| Name | Structure |
|---|---|
| 4-(4-methoxy-1-pyrimidin-2-yl-piperidine-4-carbonyl)-3,5-dihydro-2H-pyrido[3,4-f][1,4]oxazepine-9-carbonitrile | 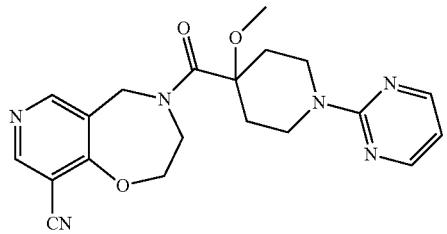 [SMILES: COC1(C(=O)N2CCOc3c(C#N)cncc3C2)CCN(c2ncccn2)CC1] |
| 4-(2-methyltetrahydropyran-2-carbonyl)-3,5-dihydro-2H-pyrido[3,4-f][1,4]oxazepine-9-carbonitrile | 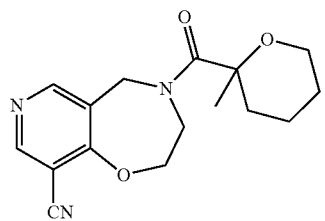 [SMILES: CC1(C(=O)N2CCOc3c(C#N)cncc3C2)CCCCO1] |
| 4-[(3,4)-cis-3-fluoro-1-(5-fluoropyrimidin-2-yl)piperidine-4-carbonyl]-3,5-dihydro-2H-pyrido[3,4-f][1,4]oxazepine-9-carbonitrile | 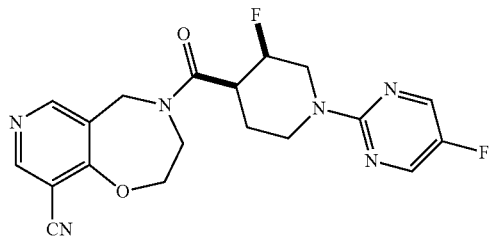 |
| 4-[(3,4)-trans-3-fluoro-1-(5-fluoropyrimidin-2-yl)piperidine-4-carbonyl]-3,5-dihydro-2H-pyrido[3,4-f][1,4]oxazepine-9-carbonitrile | 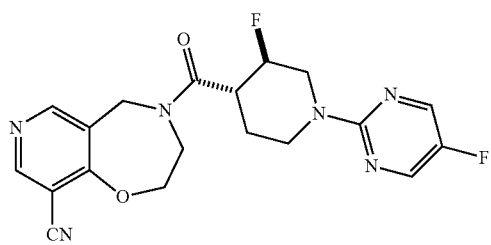 |
| 4-[3,3-difluoro-1-(5-fluoropyrimidin-2-yl)piperidine-4-carbonyl]-3,5-dihydro-2H-pyrido[3,4-f][1,4]oxazepine-9-carbonitrile | 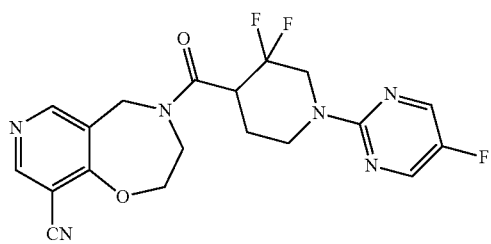 [SMILES: N#Cc1cncc2c1OCCN(C(=O)C1CCN(c3ncc(F)cn3)CC1(F)F)C2] |
| [3,3-difluoro-1-(5-fluoropyrimidin-2-yl)-4-methyl-4-piperidyl]-(3,5-dihydro-2H-pyrido[3,4-f][1,4]oxazepin-4-yl)methanone | 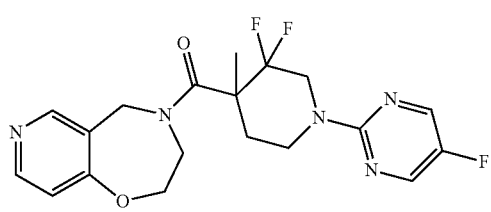 [SMILES: CC1(C(=O)N2CCOc3ccncc3C2)CCN(c2ncc(F)cn2)CC1(F)F] |

| Name | Structure |
|---|---|
| 4-[1-(5-fluoropyrimidin-2-yl)-3,6-dihydro-2H-pyridine-4-carbonyl]-3,5-dihydro-2H-pyrido[3,4-f][1,4]oxazepine-9-carbonitrile | 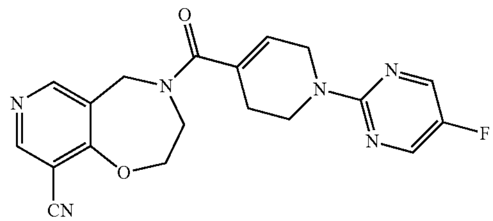 [SMILES: N#Cc1cncc2c1OCCN(C(=O)C1=CCN(c3ncc(F)cn3)CC1)C2] |
| 4-[3,3-difluoro-1-([1,2,4]triazolo[1,5-c]pyrimidin-5-yl)piperidine-4-carbonyl]-3,5-dihydro-2H-pyrido[3,4-f][1,4]oxazepine-9-carbonitrile | 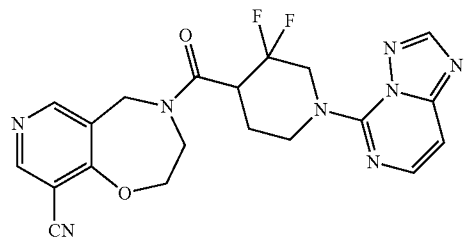 [SMILES: N#Cc1cncc2c1OCCN(C(=O)C1CCN(c3nccc4ncnn34)CC1(F)F)C2] |
| ((3R,4R)-3-fluoro-1-(5-fluoropyrimidin-2-yl)piperidin-4-yl)(9-fluoro-2,3-dihydropyrido[3,4-f][1,4]oxazepin-4(5H)-yl)methanone | |
| (9-fluoro-3,5-dihydro-2H-pyrido[3,4-f][1,4]oxazepin-4-yl)-[1-(5-fluoropyrimidin-2-yl)-3,6-dihydro-2H-pyridin-4-yl]methanone | 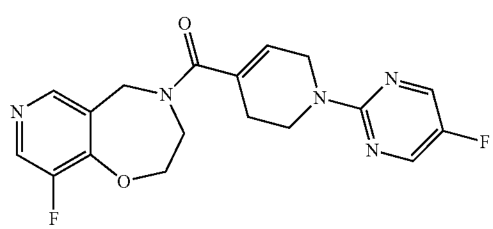 [SMILES: O=C(C1=CCN(c2ncc(F)cn2)CC1)N1CCOc2c(F)cncc2C1] |
| 4-[(3,4)-trans-3-fluoro-1-pyrazolo[1,5-a]pyrimidin-7-yl-piperidine-4-carbonyl]-3,5-dihydro-2H-pyrido[3,4-f][1,4]oxazepine-9-carbonitrile | |
| 4-[(3,4)-trans-3-fluoro-1-([1,2,4]triazolo[1,5-c]pyrimidin-5-yl)piperidine-4-carbonyl]-3,5-dihydro-2H-pyrido[3,4-f][1,4]oxazepine-9-carbonitrile | 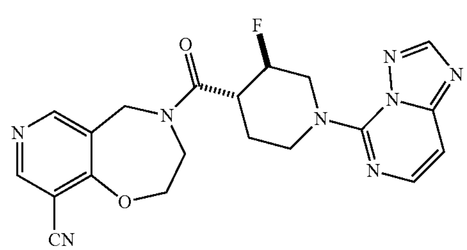 |

| Name | Structure |
|---|---|
| [3,3-difluoro-1-([1,2,4]triazolo[1,5-c]pyrimidin-5-yl)-4-piperidyl]-(9-fluoro-3,5-dihydro-2H-pyrido[3,4-f][1,4]oxazepin-4-yl)methanone | 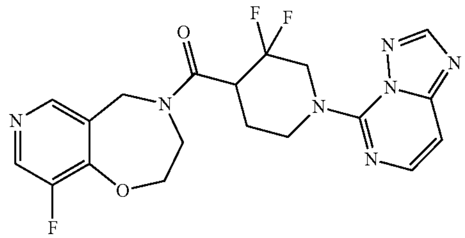 [SMILES: O=C(C1CCN(c2nccc3ncnn23)CC1(F)F)N1CCOc2c(F)cncc2C1] |
| (3,3-difluoro-1-pyrazolo[1,5-a]pyrimidin-7-yl-4-piperidyl)-(9-fluoro-3,5-dihydro-2H-pyrido[3,4-f][1,4]oxazepin-4-yl)methanone | |
| (9-fluoro-3,5-dihydro-2H-pyrido[3,4-f][1,4]oxazepin-4-yl)-[(3,4)-trans-3-fluoro-1-pyrazolo[1,5-a]pyrimidin-7-yl-4-piperidyl]methanone | 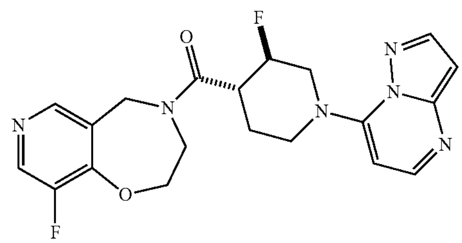 |
| 3,5-dihydro-2H-pyrido[3,4-f][1,4]oxazepin-4-yl-[(3,4)-trans-3-fluoro-1-(5-fluoropyrimidin-2-yl)-4-piperidyl]methanone | |
| (9-fluoro-3,5-dihydro-2H-pyrido[3,4-f][1,4]oxazepin-4-yl)-[(3,4)-trans-3-fluoro-1-([1,2,4]triazolo [1,5-c]pyrimidin-5-yl)-4-piperidyl]methanone | 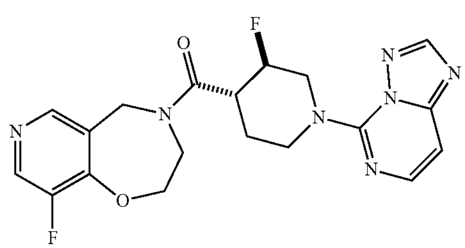 |
| (9-fluoro-3,5-dihydro-2H-pyrido[3,4-f][1,4]oxazepin-4-yl)-[(3,4)-trans-3-fluoro-1-(3-fluoropyrazolo[1,5-a]pyrimidin-7-yl)-4-piperidyl]methanone | 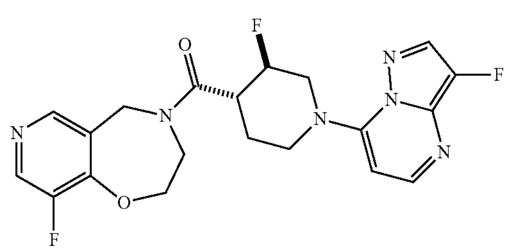 |

| Name | Structure |
|---|---|
| (9-fluoro-3,5-dihydro-2H-pyrido[3,4-f][1,4]oxazepin-4-yl)-[(3,4)-trans-3-fluoro-1-([1,2,4]triazolo[1,5-a]pyrazin-8-yl)-4-piperidyl]methanone | 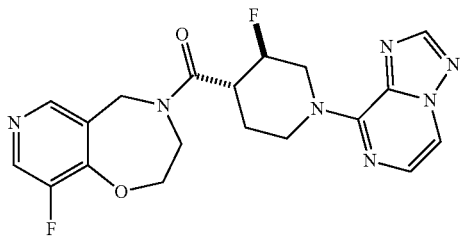 |
| 4-[((2S)-2-cyclopropyl-3,3-difluoro-2-methyl-propanoyl)]-3,5-dihydro-2H-pyrido[3,4-f][1,4]oxazepine-9-carbonitrile | 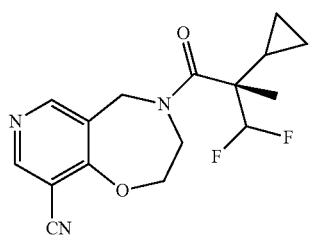 [SMILES: C[C@](C(=O)N1CCOc2c(C#N)cncc2C1)(C(F)F)C1CC1] |
| 4-[((2R)-2-cyclopropyl-3,3-difluoro-2-methyl-propanoyl)]-3,5-dihydro-2H-pyrido[3,4-f][1,4]oxazepine-9-carbonitrile | 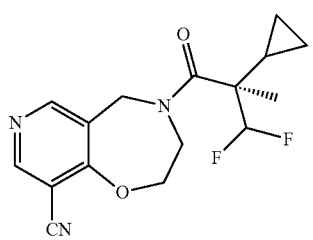 [SMILES: C[C@@](C(=O)N1CCOc2c(C#N)cncc2C1)(C(F)F)C1CC1] |
| 4-[((2S)-2-(difluoromethyl)-2-methylbutanoyl)]-2,3,4,5-tetrahydropyrido[3,4-f][1,4]oxazepine-9-carbonitrile | 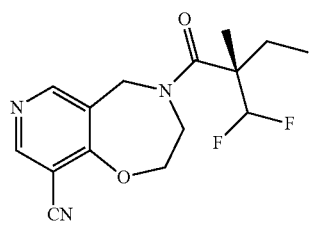 [SMILES: CC[C@@](C)(C(=O)N1CCOc2c(C#N)cncc2C1)C(F)F] |
| 4-[((2R)-2-(difluoromethyl)-2-methylbutanoyl)]-2,3,4,5-tetrahydropyrido[3,4-f][1,4]oxazepine-9-carbonitrile | 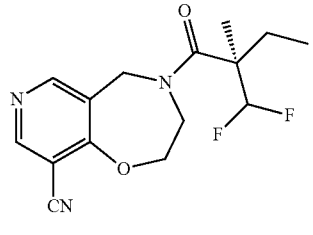 [SMILES: CC[C@](C)(C(=O)N1CCOc2c(C#N)cncc2C1)C(F)F] |
| 4-(3,3-difluoro-2,2-dimethyl-propanoyl)-8-methyl-3,5-dihydro-2H-pyrido[3,4-f][1,4]oxazepine-9-carbonitrile | 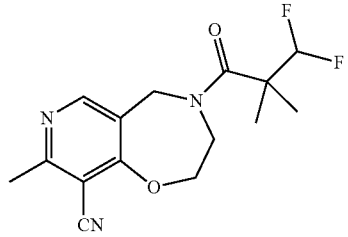 [SMILES: Cc1ncc2c(c1C#N)OCCN(C(=O)C(C)(C)C(F)F)C2] |

-continued

| Name | Structure |
|---|---|
| 2,2,3,3-tetradeuterio-4-(3,3-difluoro-2,2-dimethyl-propanoyl)-5H-pyrido[3,4-f][1,4]oxazepine-9-carbonitrile | 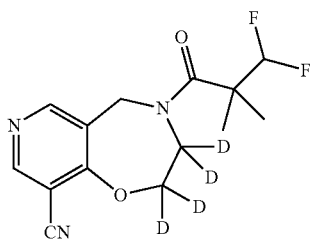 [SMILES: [2H]C1([2H])Oc2c(C#N)cncc2CN(C(=O)C(C)(C)C(F)F)C1([2H])[2H]] |
| 4-[(2S)-2-(cyanomethyl)-2-methyl-butanoyl]-3,5-dihydro-2H-pyrido[3,4-f][1,4]oxazepine-9-carbonitrile | 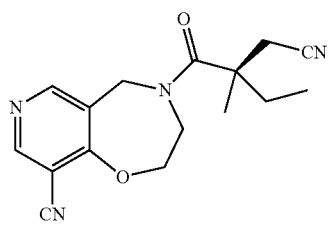 |
| 4-[(2R)-2-(cyanomethyl)-2-methyl-butanoyl]-3,5-dihydro-2H-pyrido[3,4-f][1,4]oxazepine-9-carbonitrile | 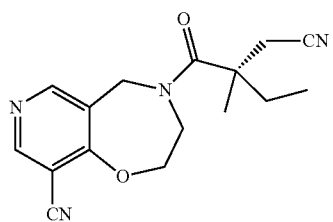 [SMILES: CC[C@](C)(CC#N)C(=O)N1CCOc2c(C#N)cncc2C1] |
| 4-[3,3-difluoro-2-(fluoromethyl)-2-methyl-propanoyl]-3,5-dihydro-2H-pyrido[3,4-f][1,4]oxazepine-9-carbonitrile | 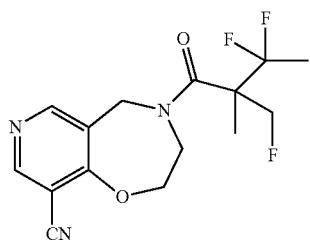 [SMILES: CC(F)(F)C(C)(CF)C(=O)N1CCOc2c(C#N)cncc2C1] |
| 4-[3,3-difluoro-2-(fluoromethyl)-2-methyl-butanoyl]-3,5-dihydro-2H-pyrido[3,4-f][1,4]oxazepine-9-carbonitrile | 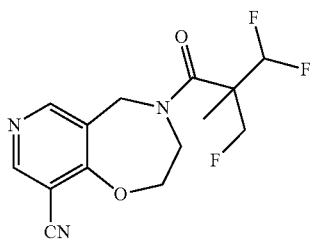 [SMILES: CC(CF)(C(=O)N1CCOc2c(C#N)cncc2C1)C(F)F] |
| 4-[2-(difluoromethyl)-3,3-difluoro-2-methyl-propanoyl]-3,5-dihydro-2H-pyrido[3,4-f][1,4]oxazepine-9-carbonitrile | 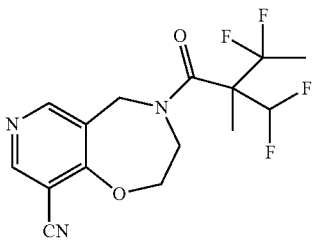 [SMILES: CC(F)(F)C(C)(C(=O)N1CCOc2c(C#N)cncc2C1)C(F)F] |

| Name | Structure |
|---|---|
| 4-[2-(difluoromethyl)-3,3-difluoro-2-methyl-butanoyl]-3,5-dihydro-2H-pyrido[3,4-f][1,4]oxazepine-9-carbonitrile | 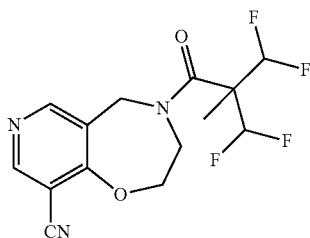 [SMILES: CC(C(=O)N1CCOc2c(C#N)cncc2C1)(C(F)F)C(F)F] |
| 4-(3-fluoro-2,2-dimethyl-butanoyl)-3,5-dihydro-2H-pyrido[3,4-f][1,4]oxazepine-9-carbonitrile | 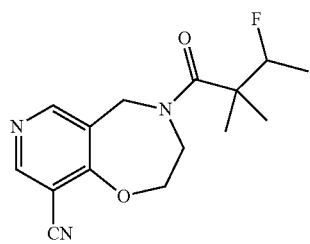 [SMILES: CC(F)C(C)(C)C(=O)N1CCOc2c(C#N)cncc2C1] |
| 4-(2,2-dimethylbut-3-enoyl)-3,5-dihydro-2H-pyrido[3,4-f][1,4]oxazepine-9-carbonitrile | 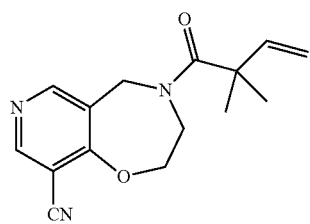 [SMILES: C=CC(C)(C)C(=O)N1CCOc2c(C#N)cncc2C1] |
| 4-[(3S)-3-fluoro-2,2-dimethyl-butanoyl]-3,5-dihydro-2H-pyrido[3,4-f][1,4]oxazepine-9-carbonitrile | 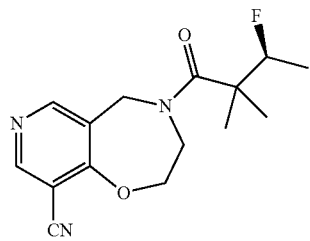 [SMILES: C[C@H](F)C(C)(C)C(=O)N1CCOc2c(C#N)cncc2C1] |
| 4-[(3R)-3-fluoro-2,2-dimethyl-butanoyl]-3,5-dihydro-2H-pyrido[3,4-f][1,4]oxazepine-9-carbonitrile | 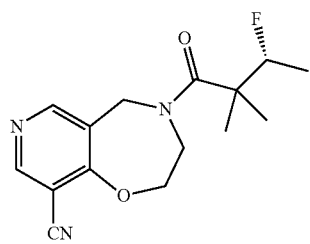 [SMILES: C[C@@H](F)C(C)(C)C(=O)N1CCOc2c(C#N)cncc2C1] |
| 4-(2-methyl-2-(2-((trifluoromethoxy)methyl)cyclopropyl)propanoyl)-2,3,4,5-tetrahydropyrido[3,4-f][1,4]oxazepine-9-carbonitrile | 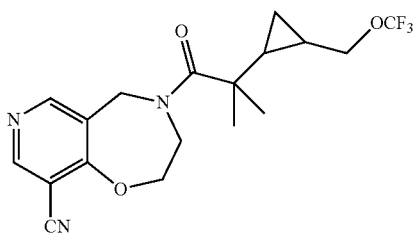 [SMILES: CC(C)(C(=O)N1CCOc2c(C#N)cncc2C1)C1CC1COC(F)(F)F] |

-continued

| Name | Structure |
|---|---|
| 4-[2-methyl-2-[3-(triazol-2-yl)cyclobutyl]propanoyl]-3,5-dihydro-2H-pyrido[3,4-f][1,4]oxazepine-9-carbonitrile | 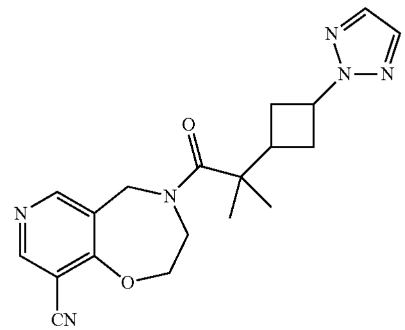 [SMILES: CC(C)(C(=O)N1CCOc2c(C#N)cncc2C1)C1CC(n2nccn2)C1] |
| 4-[2-methyl-2-[3-(triazol-1-yl)cyclobutyl]propanoyl]-3,5-dihydro-2H-pyrido[3,4-f][1,4]oxazepine-9-carbonitrile | 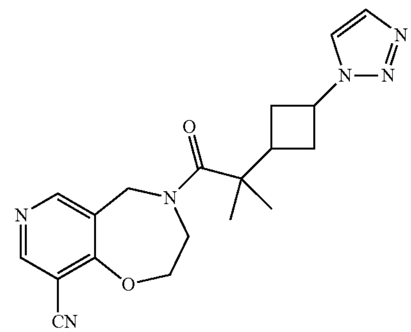 [SMILES: CC(C)(C(=O)N1CCOc2c(C#N)cncc2C1)C1CC(n2ccnn2)C1] |
| 4-[2-[3-(4-fluoropyrazol-1-yl)cyclobutyl]-2-methyl-propanoyl]-3,5-dihydro-2H-pyrido[3,4-f][1,4]oxazepine-9-carbonitrile | 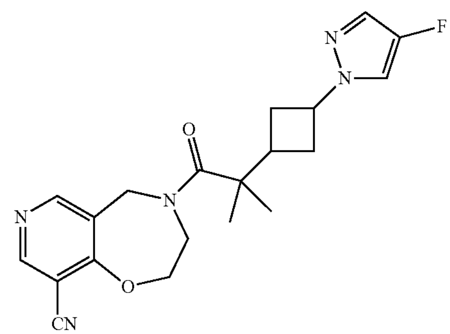 [SMILES: CC(C)(C(=O)N1CCOc2c(C#N)cncc2C1)C1CC(n2cc(F)cn2)C1] |
| 4-[2-(3-chlorocyclobutyl)-2-methyl-propanoyl]-3,5-dihydro-2H-pyrido[3,4-f][1,4]oxazepine-9-carbonitrile | 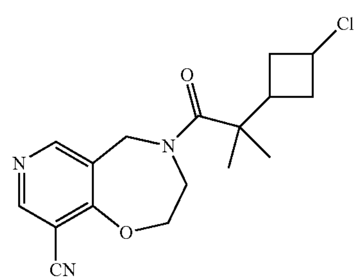 [SMILES: CC(C)(C(=O)N1CCOc2c(C#N)cncc2C1)C1CC(Cl)C1] |
| 4-[2-methyl-2-[3-(trifluoromethoxy)cyclobutyl]propanoyl]-3,5-dihydro-2H-pyrido[3,4-f][1,4]oxazepine-9-carbonitrile | 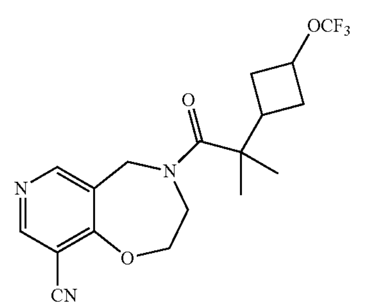 [SMILES: CC(C)(C(=O)N1CCOc2c(C#N)cncc2C1)C1CC(OC(F)(F)F)C1] |

| Name | Structure |
|---|---|
| 4-[2-[(3S)-1-(5-fluoropyrimidin-2-yl)pyrrolidin-3-yl]-2-methyl-propanoyl]-3,5-dihydro-2H-pyrido[3,4-f][1,4]oxazepine-9-carbonitrile | 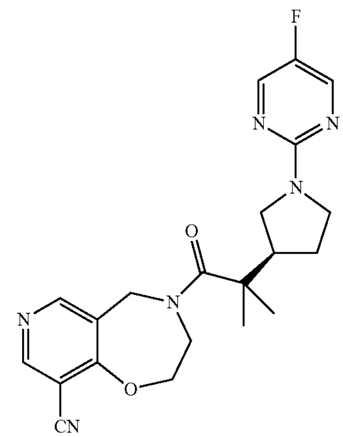 [SMILES: CC(C)(C(=O)N1CCOc2c(C#N)cncc2C1)[C@@H]1CCN(c2ncc(F)cn2)C1] |
| 4-[2-[(3R)-1-(5-fluoropyrimidin-2-yl)pyrrolidin-3-yl]-2-methyl-propanoyl]-3,5-dihydro-2H-pyrido[3,4-f][1,4]oxazepine-9-carbonitrile | 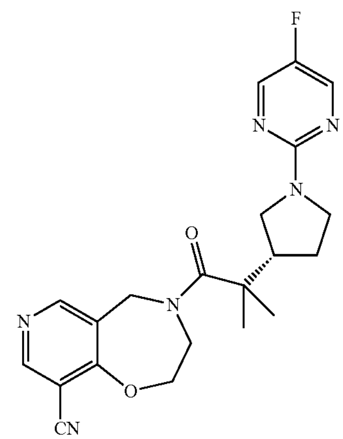 [SMILES: CC(C)(C(=O)N1CCOc2c(C#N)cncc2C1)[C@H]1CCN(c2ncc(F)cn2)C1] |
| 4-[(2S)-2-methoxy-2-methyl-butanoyl]-3,5-dihydro-2H-pyrido[3,4-f][1,4]oxazepine-9-carbonitrile | 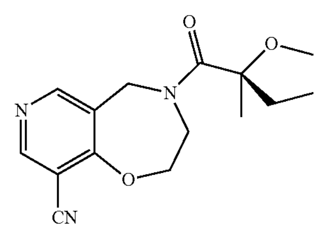 [SMILES: CC[C@](C)(OC)C(=O)N1CCOc2c(C#N)cncc2C1] |
| 4-[(2R)-2-methoxy-2-methyl-butanoyl]-3,5-dihydro-2H-pyrido[3,4-f][1,4]oxazepine-9-carbonitrile | 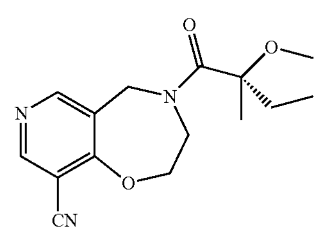 [SMILES: CC[C@@](C)(OC)C(=O)N1CCOc2c(C#N)cncc2C1] |
| 4-[(4R)-3,3-difluoro-1-(5-fluoropyrimidin-2-yl)-4-methyl-piperidine-4-carbonyl]-3,5-dihydro-2H-pyrido[3,4-f][1,4]oxazepine-9-carbonitrile | 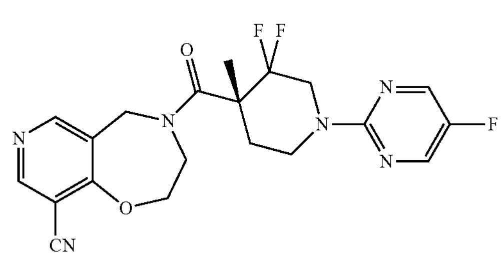 [SMILES: C[C@]1(C(=O)N2CCOc3c(C#N)cncc3C2)CCN(c2ncc(F)cn2)CC1(F)F] |

-continued

| Name | Structure |
|---|---|
| 4-[(4S)-3,3-difluoro-1-(5-fluoropyrimidin-2-yl)-4-methyl-piperidine-4-carbonyl]-3,5-dihydro-2H-pyrido[3,4-f][1,4]oxazepine-9-carbonitrile | 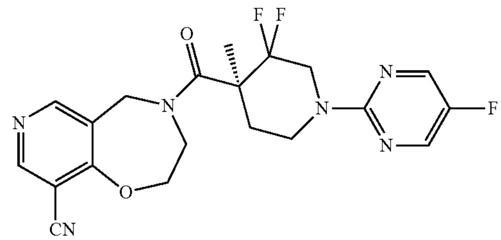 [SMILES: C[C@@]1(C(=O)N2CCOc3c(C#N)cncc3C2)CCN(c2ncc(F)cn2)CC1(F)F] |
| 4-[1-(6,7-dihydro-5H-pyrrolo[3,4-b]pyridin-2-yl)-4-fluoro-piperidine-4-carbonyl]-3,5-dihydro-2H-pyrido[3,4-f][1,4]oxazepine-9-carbonitrile | 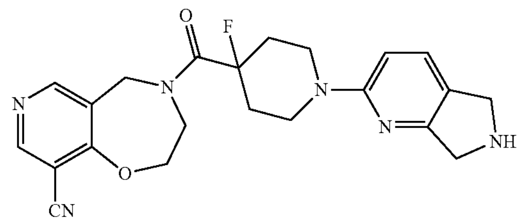 [SMILES: N#Cc1cncc2c1OCCN(C(=O)C1(F)CCN(c3ccc4c(n3)CNC4)CC1)C2] |
| 4-[1-(3,5-difluoro-6-methoxy-2-pyridyl)piperidine-4-carbonyl]-3,5-dihydro-2H-pyrido[3,4-f][1,4]oxazepine-9-carbonitrile | 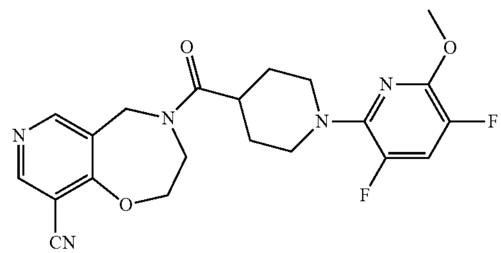 [SMILES: COc1nc(N2CCC(C(=O)N3CCOc4c(C#N)cncc4C3)CC2)c(F)cc1F] |
| 4-[1-(3,5,6-trifluoro-2-pyridyl)piperidine-4-carbonyl]-3,5-dihydro-2H-pyrido[3,4-f][1,4]oxazepine-9-carbonitrile | 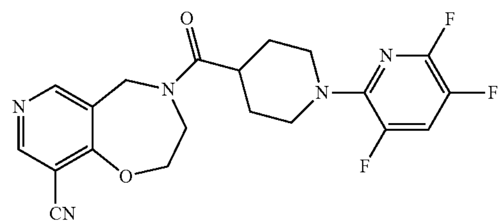 [SMILES: N#Cc1cncc2c1OCCN(C(=O)C1CCN(c3nc(F)c(F)cc3F)CC1)C2] |
| 4-[1-(3,5-difluoro-6-methoxy-2-pyridyl)-4-methoxy-piperidine-4-carbonyl]-3,5-dihydro-2H-pyrido[3,4-f][1,4]oxazepine-9-carbonitrile | |
| trans-4-[2-methyl-2-[3-(triazol-2-ylmethyl)cyclobutyl]propanoyl]-3,5-dihydro-2H-pyrido[3,4-f][1,4]oxazepine-9-carbonitrile | |

| Name | Structure |
|---|---|
| cis-4-[2-methyl-2-[3-(triazol-2-ylmethyl)cyclobutyl]propanoyl]-3,5-dihydro-2H-pyrido[3,4-][1,4]oxazepine-9-carbonitrile | 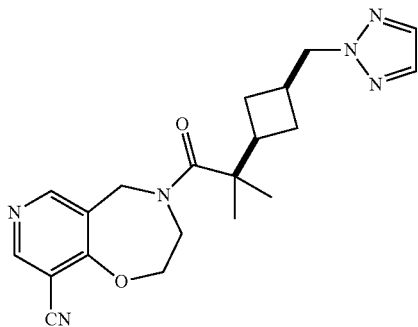 |
| trans-4-[2-methyl-2-[3-(triazol-1-ylmethyl)cyclobutyl]propanoyl]-3,5-dihydro-2H-pyrido[3,4-f][1,4]oxazepine-9-carbonitrile | 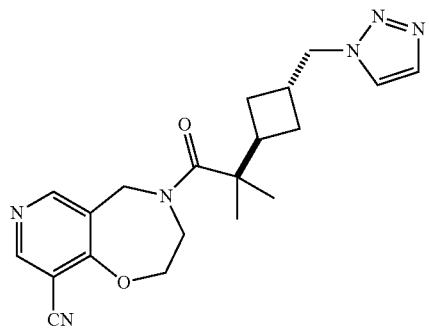 |
| cis-4-[2-methyl-2-[3-(triazol-1-ylmethyl)cyclobutyl]propanoyl]-3,5-dihydro-2H-pyrido[3,4-f][1,4]oxazepine-9-carbonitrile | 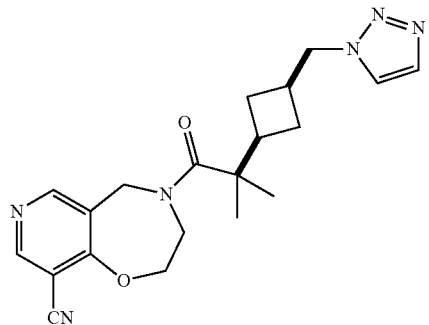 |
| 4-[4-fluoro-1-(5-fluoro-[1,2,4]triazolo[1,5-a]pyrazin-8-yl)piperidine-4-carbonyl]-3,5-dihydro-2H-pyrido[3,4-f][1,4]oxazepine-9-carbonitrile | 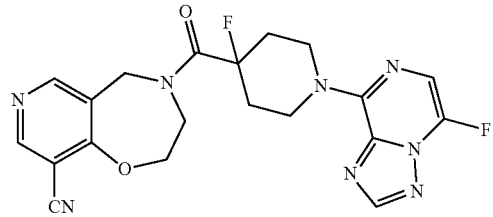 [SMILES: N#Cc1cncc2c1OCCN(C(=O)C1(F)CCN(c3ncc(F)n4ncnc34)CC1)C2] |
| 4-[(4S)-3,3,4-trifluoro-1-(5-fluoropyrimidin-2-yl)piperidine-4-carbonyl]-3,5-dihydro-2H-pyrido[3,4-f][1,4]oxazepine-9-carbonitrile | 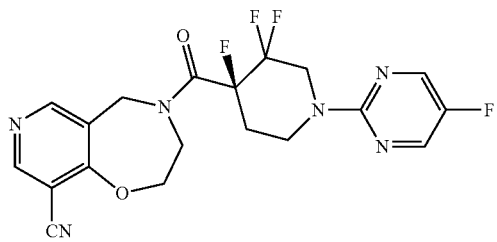 [SMILES: N#Cc1cncc2c1OCCN(C(=O)[C@@]1(F)CCN(c3ncc(F)cn3)CC1(F)F)C2] |

| Name | Structure |
|---|---|
| 4-[(4R)-3,3,4-trifluoro-1-(5-fluoropyrimidin-2-yl)piperidine-4-carbonyl]-3,5-dihydro-2H-pyrido[3,4-f][1,4]oxazepine-9-carbonitrile | 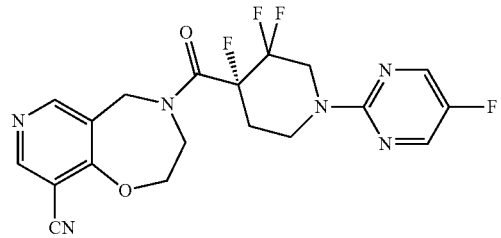 |
| 4-[(4R)-3,3-difluoro-4-methyl-pyrimidin-2-yl-piperidine-4-carbonyl]-3,5-dihydro-2H-pyrido[3,4-f][1,4]oxazepine-9-carbonitrile | 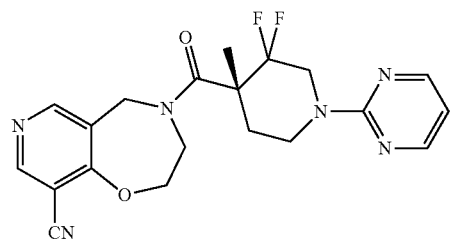 [SMILES: C[C@]1(C(=O)N2CCOc3c(C#N)cncc3C2)CCN(c2ncccn2)CC1(F)F] |
| 4-[(4S)-3,3-difluoro-4-methyl-1-pyrimidin-2-yl-piperidine-4-carbonyl]-3,5-dihydro-2H-pyrido[3,4-f][1,4]oxazepine-9-carbonitrile | 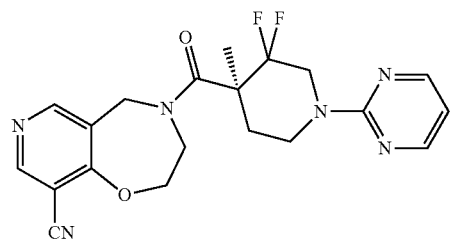 [SMILES: C[C@@]1(C(=O)N2CCOc3c(C#N)cncc3C2)CCN(c2ncccn2)CC1(F)F] |
| 4-[(3S,4R)-3-fluoro-1-(5-fluoropyrimidin-2-yl)-4-methyl-piperidine-4-carbonyl]-3,5-dihydro-2H-pyrido[3,4-]][1,4]oxazepine-9-carbonitrile | 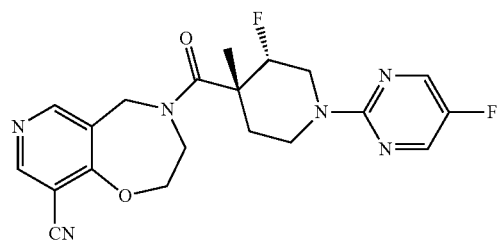 [SMILES: C[C@]1(C(=O)N2CCOc3c(C#N)cncc3C2)CCN(c2ncc(F)cn2)C[C@H]1F] |
| 4-[(3R,4S)-3-fluoro-1-(5-fluoropyrimidin-2-yl)-4-methyl-piperidine-4-carbonyl]-3,5-dihydro-2H-pyrido[3,4-]][1,4]oxazepine-9-carbonitrile | 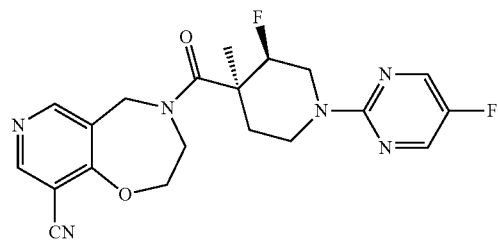 [SMILES: C[C@@]1(C(=O)N2CCOc3c(C#N)cncc3C2)CCN(c2ncc(F)cn2)C[C@@H]1F] |
| 4-[(3R,4R)-3-fluoro-([1,2,4]triazolo[1,5-a]pyrazin-8-yl)piperidine-4-carbonyl]-3,5-dihydro-2H-pyrido[3,4-]][1,4]oxazepine-9-carbonitrile | 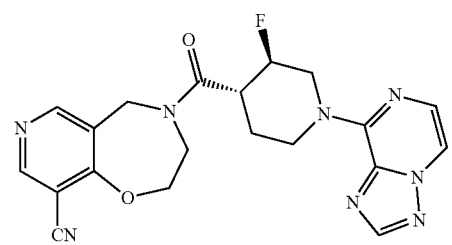 |

| Name | Structure |
|---|---|
| 4-[(3S,4S)-3-fluoro-1-([1,2,4]triazolo[1,5-a]pyrazin-8-yl)piperidine-4-carbonyl]-3,5-dihydro-2H-pyrido[3,4-f][1,4]oxazepine-9-carbonitrile | |
| 4-[(3R,4R)-3-fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile | 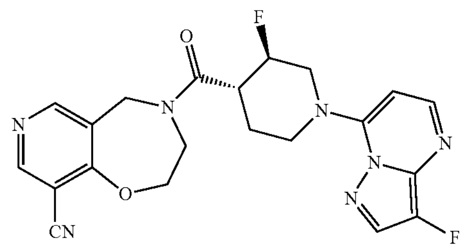 [SMILES: N#Cc1cncc2c1OCCN(C(=O)[C@H]1CCN(c3ccnc4c(F)cnn34)C[C@@H]1F)C2] |
| 4-[(3S,4S)-3-fluoro-1-(3-fluoropyrazolo[1,5-a]pyrimidin-7-yl)piperidine-4-carbonyl]-3,5-dihydro-2H-pyrido[3,4-f][1,4]oxazepine-9-carbonitrile | 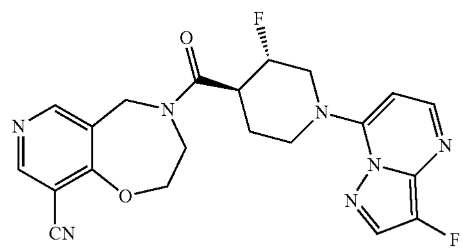 [SMILES: N#Cc1cncc2c1OCCN(C(=O)[C@@H]1CCN(c3ccnc4c(F)cnn34)C[C@H]1F)C2] |
| 4-[(3R,4R)-3-fluoro-1-(5-fluoropyrimidin-2-yl)piperidine-4-carbonyl]-3,5-dihydro-2H-pyrido[3,4-f][1,4]oxazepine-9-carbonitrile | 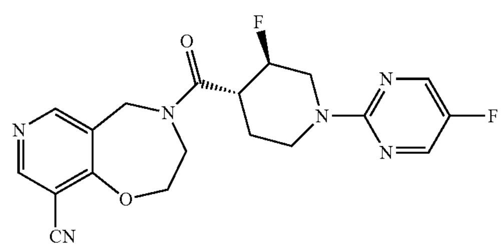 [SMILES: N#Cc1cncc2c1OCCN(C(=O)[C@H]1CCN(c3ncc(F)cn3)C[C@@H]1F)C2] |
| 4-[(3S,4S)-3-fluoro-1-(5-fluoropyrimidin-2-yl)piperidine-4-carbonyl]-3,5-dihydro-2H-pyrido[3,4-f][1,4]oxazepine-9-carbonitrile | 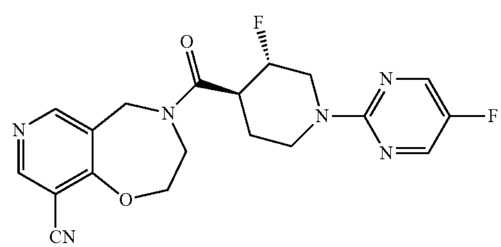 [SMILES: N#Cc1cncc2c1OCCN(C(=O)[C@@H]1CCN(c3ncc(F)cn3)C[C@H]1F)C2] |
| 4-[(4R)-3,3-difluoro-1-(5-fluoropyrimidin-2-yl)piperidine-4-carbonyl]-3,5-dihydro-2H-pyrido[3,4-f][1,4]oxazepine-9-carbonitrile | 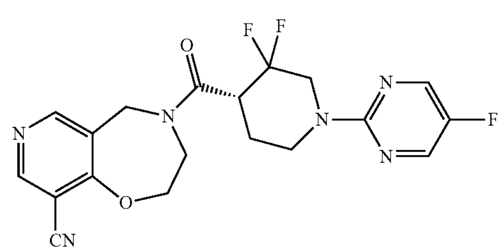 [SMILES: N#Cc1cncc2c1OCCN(C(=O)[C@H]1CCN(c3ncc(F)cn3)CC1(F)F)C2] |

| Name | Structure |
|---|---|
| 4-[(4S)-3,3-difluoro-1-(5-fluoropyrimidin-2-yl)piperidine-4-carbonyl]-3,5-dihydro-2H-pyrido[3,4-f][1,4]oxazepine-9-carbonitrile | 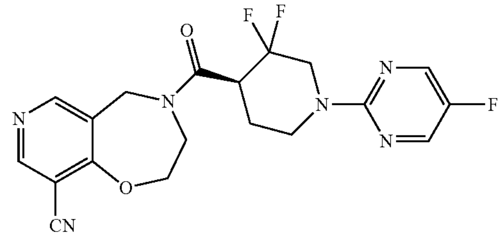 [SMILES: N#Cc1cncc2c1OCCN(C(=O)[C@@H]1CCN(c3ncc(F)cn3)CC1(F)F)C2] |
| 4-[1-(5-fluoropyrimidin-2-yl)-3-methoxy-piperidine-4-carbonyl]-3,5-dihydro-2H-pyrido[3,4-f][1,4]oxazepine-9-carbonitrile | | or a pharmaceutically acceptable salt, isotopic analog, or isomer thereof.

13. A pharmaceutical composition comprising a compound according to claim 1, and a pharmaceutically acceptable excipient.

14. A method for preparing a compound according to Formula A:

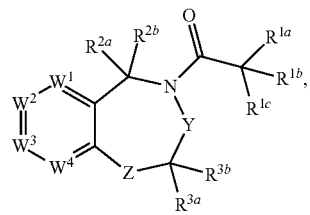

(A)

or a salt thereof, the method comprising:
contacting a compound according to Formula IIa

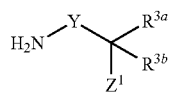

(IIa)

with a compound according to Formula IIb,

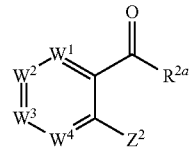

(IIb)

under conditions sufficient to form a compound according to Formula IIc

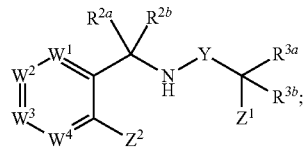

(IIc)

converting the compound of Formula IIc to a compound of Formula IId

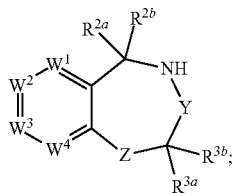

(IId)

and contacting the compound of Formula IId with a compound of Formula IIe

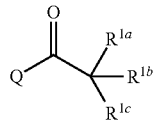

(IIe)

under conditions sufficient to form the compound of Formula A;
wherein:
$Z^1$ is an optionally protected first reactive group;
$Z^2$ is an optionally protected second reactive group;

Q is —OH or a leaving group; and $W^1$, $W^3$, and $W^4$ are independently $CR^7$;

$W^2$ is N;

$R^{1a}$, $R^{1b}$, and $R^{1c}$ are independently hydrogen, halogen, —CN, —$N_3$, —$NO_2$, —OH, —$SF_5$, —$SCF_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, $C_{1-8}$ haloalkoxy, 4- to 12-membered heterocyclyl, $C_{6-10}$ aryl, 5- to 12-membered heteroaryl, —$N(R^{1d})_2$, —C(O)$R^{1e}$, —C(O)O$R^{1d}$, —C(O)N($R^{1d})_2$, —$NR^{1d}$C(O)$R^{1e}$, —$NR^{1d}$C(O)N($R^{1d})_2$, —$NR^{1d}$C(O)O$R^{1d}$, —OC(O)N($R^{1d})_2$, —OC(O)O$R^{1d}$, —$SR^{1d}$, —S(O)$R^{1e}$, —S(O)$_2R^{1e}$, —S(O)$_3R^{1d}$, —S(O)N($R^{1d})_2$, —S(O)$_2$N($R^{1d})_2$, —$NR^{1d}$S(O)$R^{1e}$, —$NR^{1d}$S(O)$_2R^{1e}$, —$NR^{1d}$S(O)N($R^{1d})_2$, or —$NR^{1d}$S(O)$_2$N($R^{1d})_2$, wherein each of $R^{1a}$, $R^{1b}$, and $R^{1c}$ is optionally and independently substituted with one to eight $R^5$ and at least one of $R^{1a}$, $R^{1b}$, and $R^{1c}$ is other than hydrogen; or $R^{1b}$ and $R^{1c}$ are optionally taken together to form $C_{3-10}$ cycloalkyl or 4- to 12-membered heterocyclyl, each of which is optionally substituted with one to eight $R^5$; or $R^{1a}$, $R^{1b}$, and $R^{1c}$ are optionally taken together to form $C_{5-10}$ cycloalkyl or 5- to 12-membered heterocyclyl, each which is optionally substituted with one to eight $R^5$; or $R^{1a}$ is absent and $R^{1b}$ and $R^{1c}$ are taken together to form $C_{6-10}$ aryl or 5- to 12-membered heteroaryl or 5- to 12-membered heterocyclyl, each of which is optionally substituted with one to eight $R^5$;

each $R^{1d}$ is independently hydrogen, $C_{1-8}$ alkyl, $C_{1-8}$ haloalkyl, $C_{3-10}$ cycloalkyl, or 4- to 12-membered heterocyclyl, or two $R^{1d}$ on the same atom are optionally taken together to form a 4- to 8-membered heterocyclyl optionally substituted by oxo, halo, or $C_{1-6}$ alkyl, wherein said alkyl is optionally substituted with one to eight $R^5$;

each $R^{1e}$ is independently $C_{1-8}$ alkyl, $C_{1-8}$ haloalkyl, $C_{3-10}$ cycloalkyl, or 4- to 12-membered heterocyclyl;

$R^{2a}$ and $R^{2b}$ are independently hydrogen, halogen, $C_{1-8}$ alkyl, $C_{1-8}$ haloalkyl, $C_{2-8}$ alkenyl, or $C_{1-8}$ alkynyl, or $R^{2a}$ and $R^{2b}$ are optionally taken together to form $C_{3-6}$ cycloalkyl or 4- to 6-membered heterocyclyl, each of which is optionally substituted with one to eight $R^6$;

$R^{3a}$ and $R^{3b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one to eight $R^6$, or $R^{3a}$ and $R^{3b}$ are optionally taken together to form oxo, $C_{3-6}$ cycloalkyl, or 4- to 6-membered heterocyclyl, wherein said cycloalkyl and said heterocyclyl are optionally substituted with one to eight $R^6$;

Y is $CR^{4a}R^{4b}$;

$R^{4a}$ and $R^{4b}$ are independently hydrogen, halogen, $C_{1-8}$ alkyl, $C_{2-8}$ alkenyl, $C_{2-8}$ alkynyl, $C_{1-8}$ haloalkyl, $C_{3-6}$ cycloalkyl, or 4- to 6-membered heterocyclyl, wherein said cycloalkyl and said heterocyclyl are optionally substituted with one to eight $R^6$, or $R^{4a}$ and $R^{4b}$ are optionally taken together to form $C_{3-6}$ cycloalkyl or 4- to 6-membered heterocyclyl, wherein said cycloalkyl and said heterocyclyl are optionally substituted with one to eight $R^6$, or $R^{4a}$ and $R^{1b}$ are optionally taken together to form 4- to 12-membered heterocyclyl, which is optionally substituted with one to eight $R^6$, or $R^{4a}$ and $R^{3a}$ are optionally taken together to form $C_{3-8}$ cycloalkyl or 4- to 12-membered heterocyclyl, each of which is optionally substituted with one to eight $R^6$;

each $R^5$ is independently halogen, —CN, —OH, —$SF_5$, —$SCF_3$, $C_{1-8}$ alkyl, $C_{2-8}$ alkenyl, $C_{2-8}$ alkynyl, $C_{1-8}$ haloalkyl, $C_{1-8}$ heteroalkyl, $C_{3-8}$ cycloalkyl, $C_{1-8}$ haloalkyl, $C_{1-8}$ alkoxy, $C_{1-8}$ haloalkoxy, 4- to 12-membered heterocyclyl, $C_{6-10}$ aryl, 5- to 12-membered heteroaryl, (4- to 12-membered heterocyclyl)($C_{1-8}$ heteroalkyl), ($C_{6-10}$ aryl)($C_{1-8}$ heteroalkyl), (5- to 12-membered heteroaryl)($C_{1-8}$ heteroalkyl), —$N(R^{5a})_2$, —C(O)$R^{5b}$, —C(O)O$R^{5a}$, —C(O)N($R^{5a})_2$, —$NR^{5a}$C(O)$R^{5b}$, —$NR^{5a}$C(O)N($R^{5a})_2$, —$NR^{5a}$C(O)O$R^{5a}$, —OC(O)N($R^{5a})_2$, —OC(O)O$R^{5a}$, —$SR^{5a}$, —S(O)$R^{5b}$, —S(O)$_2R^{5b}$, —S(O)$_3R^{5a}$, —S(O)N($R^{5a})_2$, —S(O)$_2$N($R^{5a})_2$, —$NR^{5a}$S(O)$R^{5b}$, —$NR^{5a}$S(O)$_2R^{5b}$, —$NR^{5a}$S(O)N($R^{5a})_2$, or —$NR^{5a}$S(O)$_2$N($R^{5a})_2$, each of which is optionally substituted with one to eight $R^{5c}$, or two $R^5$ are optionally taken together to form oxo;

each $R^{5a}$ is independently hydrogen, $C_{1-8}$ alkyl, $C_{1-8}$ haloalkyl, $C_{3-10}$ cycloalkyl, or 4- to 12-membered heterocyclyl, and each $R^{5b}$ is independently $C_{1-8}$ alkyl, $C_{1-8}$ haloalkyl, $C_{3-10}$ cycloalkyl, 4- to 12-membered heterocyclyl, or 5- to 12-membered heteroaryl;

each $R^{5c}$ is independently halogen, cyano, $C_{1-8}$ haloalkyl, $C_{1-8}$ alkyl, $C_{1-8}$ alkoxy, $C_{1-8}$ haloalkoxy, ($C_{1-8}$ alkoxy)($C_{1-8}$ alkoxy), hydroxyl, $SR^{5d}$, $N(R^{5d})_2$, $N(R^{5d})_2$($C_{1-8}$ alkoxy), $C_{3-10}$ cycloalkyl, and 4- to 12-membered heterocyclyl, or two $R^{5c}$ are optionally taken together to form oxo;

each $R^{5d}$ is independently hydrogen, $C_{1-8}$ alkyl, or $C_{1-8}$ haloalkyl;

each $R^6$ is halogen, —CN, —OH, $C_{1-8}$ alkyl, $C_{1-8}$ heteroalkyl, $C_{3-8}$ cycloalkyl, $C_{1-8}$ haloalkyl, $C_{1-8}$ alkoxy, 4- to 12-membered heterocyclyl, $C_{6-10}$ aryl, 5- to 12-membered heteroaryl, —$N(R^{6a})_2$, —C(O)$R^{6b}$, —C(O)N($R^{6a})_2$, or —C(O)O$R^{6a}$, or two $R^6$ are taken together to form oxo;

each $R^{6a}$ is independently hydrogen, $C_{1-8}$ alkyl, or $C_{1-8}$ haloalkyl, or two $R^{6a}$ on the same atom are optionally taken together to form 4- to 6-membered heterocyclyl;

each $R^{6b}$ is independently $C_{1-8}$ alkyl or $C_{1-8}$ haloalkyl;

each $R^7$ is independently hydrogen, halogen, —CN, —$N_3$, —$NO_2$, —$SF_5$, —$SCF_3$, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, 4- to 12-membered heterocyclyl, $C_{6-10}$ aryl, 5- to 12-membered heteroaryl, —O$R^{7a}$, —C(O)$R^{7b}$, —N($R^{7a})_2$, —C(O)O$R^{7a}$, —C(O)N($R^{7a})_2$, —$NR^{7a}$C(O)$R^{7b}$, —$NR^{7a}$C(O)N($R^{7a})_2$, —$NR^{7a}$C(O)O$R^{7a}$, —OC(O)N($R^{7a})_2$, —OC(O)O$R^{7a}$, —$SR^{7a}$, —S(O)$R^{7b}$, —S(O)$_2R^{7b}$, —S(O)$_3R^{7a}$, —S(O)N($R^{7a})_2$, —S(O)$_2$N($R^{7a})_2$, —$NR^{7a}$S(O)$R^{7b}$, —$NR^{7a}$S(O)$_2R^{7b}$, —$NR^{7a}$S(O)N($R^{7a})_2$, or —$NR^{7a}$S(O)$_2$N($R^{7a})_2$, each of which is optionally and independently substituted with one to eight $R^8$;

each $R^{7a}$ is independently hydrogen, $C_{1-8}$ alkyl, $C_{1-8}$ haloalkyl, $C_{3-10}$ cycloalkyl, or 4- to 12-membered heterocyclyl, or two $R^{7a}$ on the same atom are optionally taken together to form a 4- to 8-membered heterocyclyl optionally substituted by oxo, halo, or $C_{1-6}$ alkyl, wherein said alkyl is optionally substituted with one to eight $R^8$;

each $R^{7b}$ is independently $C_{1-8}$ alkyl, $C_{1-8}$ haloalkyl, $C_{3-10}$ cycloalkyl, or 4- to 12-membered heterocyclyl;

each $R^8$ is halogen, —CN, —OH, $C_{1-8}$ alkyl, $C_{2-8}$ alkenyl, $C_{2-8}$ alkynyl, $C_{1-8}$ heteroalkyl, $C_{3-8}$ cycloalkyl, $C_{1-8}$ haloalkyl, $C_{1-8}$ alkoxy, 4- to 12-membered heterocyclyl, $C_{6-10}$ aryl, 5- to 12-membered heteroaryl, —N($R^{8a}$)$_2$, —C(O)$R^{8b}$, or —C(O)O$R^{8a}$, or two $R^8$ are optionally taken together to form oxo;

each $R^{8a}$ is independently hydrogen, $C_{1-8}$ alkyl, or $C_{1-8}$ haloalkyl;

each $R^{8b}$ is independently $C_{1-8}$ alkyl or $C_{1-8}$ haloalkyl; and Z is O.

15. A method of treating a receptor-interacting protein kinase 1-mediated disease or disorder comprising administering a therapeutically effective amount of a compound according to claim 1 to a subject in need thereof, wherein the receptor-interacting protein kinase 1-mediated disease or disorder is chosen from necrotizing enterocolitis, tuberous sclerosis, Tangier's Disease, Wohlman's Syndrome, inflammatory bowel disease, Crohn's disease, ulcerative colitis, psoriasis, retinal detachment, retinitis pigmentosa, macular degeneration, pancreatitis, atopic dermatitis, rheumatoid arthritis, psoriatic arthritis, spondyloarthritis, gout, SoJIA, systemic lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia ischemia reperfusion injury of solid organs, cerebral ischemia, sepsis, systemic inflammatory response syndrome, cerebrovascular accident, myocardial infarction, Huntington's disease, Alzheimer's disease, Parkinson's disease, asthma, atopic dermatitis, multiple sclerosis, type I diabetes, Wegener's granulomatosis, pulmonary sarcoidosis, Behçet's disease, interleukin-1 converting enzyme associated fever syndrome, chronic obstructive pulmonary disease, tumor necrosis factor receptor-associated periodic syndrome, periodontitis, bacterial infection, *staphylococcus* infection, *mycobacterium* infection, influenza, transplant rejection, hypoxia, stroke, cardiac infarction, lysosomal storage disease, Niemann-Pick disease, Gaucher's disease, Krabbe disease, amyotrophic lateral sclerosis (ALS/Lou Gehrig's Disease), HIV-associated dementia, encephalopathy, retinal degenerative disease, glaucoma, age-related macular degeneration, Friedreich's ataxia, Lewy body disease, diabetic neuropathy, polyglutamine (polyQ) diseases, Fahr disease, Menke's disease, Wilson's disease, a prion disorder, atherosclerosis, Guillain-Barre syndrome, chronic inflammatory demyelinating polyneuropathy, major depressive disorder, bipolar disorder, delirium, post-operative cognitive impairment, schizophrenia, or hidradenitis suppurativa.

16. A compound of claim 1, wherein the isomer is a stereoisomer.

17. A compound selected from

| Name | Structure |
|---|---|
| 4-(3,3-difluoro-2,2-dimethyl-propanoyl)-3,5-dihydro-2H-pyrido[3,4-f][1,4]oxazepine-9-carbonitrile | 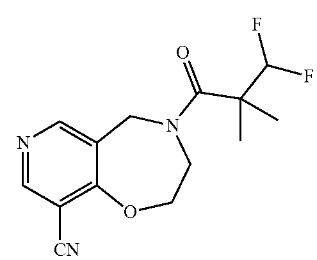 [SMILES: CC(C)(C(=O)N1CCOc2c(C#N)cncc2C1)C(F)F] |
| 4-(3-fluoro-2,2-dimethyl-propanoyl)-3,5-dihydro-2H-pyrido[3,4-f][1,4]oxazepine-9-carbonitrile | |
| 4-(2,2-dimethylpropanoyl)-3,5-dihydro-2H-pyrido[3,4-f][1,4]oxazepine-9-carbonitrile | 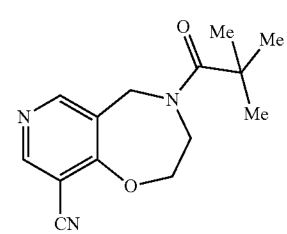 [SMILES: CC(C)(C)C(=O)N1CCOc2c(C#N)cncc2C1] |

-continued

| Name | Structure |
|---|---|
| 4-(3,3,3-trifluoro-2,2-dimethyl-propanoyl)-3,5-dihydro-2H-pyrido[3,4-f][1,4]oxazepine-9-carbonitrile | 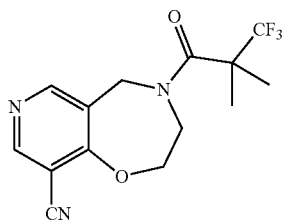 [SMILES: CC(C)(C(=O)N1CCOc2c(C#N)cncc2C1)C(F)(F)F] |
| 1-(9-fluoro-3,5-dihydro-2H-pyrido[3,4-f][1,4]oxazepin-4-yl)-2,2-dimethyl-propan-1-one | 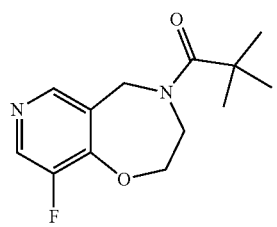 [SMILES: CC(C)(C)C(=O)N1CCOc2c(F)cncc2C1] |
| 4-[1-(5-fluoropyrimidin-2-yl)piperidine-4-carbonyl]-3,5-dihydro-2H-pyrido[3,4-f][1,4]oxazepine-9-carbonitrile | 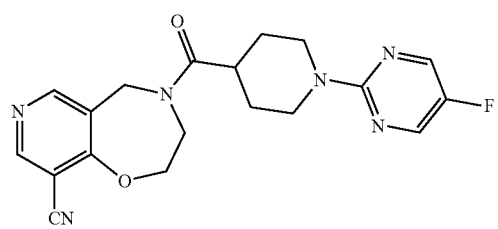 [SMILES: N#Cc1cncc2c1OCCN(C(=O)C1CCN(c3ncc(F)cn3)CC1)C2] |
| 4-[4-fluoro-1-(5-fluoropyrimidin-2-yl)piperidine-4-carbonyl]-3,5-dihydro-2H-pyrido[3,4-f][1,4]oxazepine-9-carbonitrile | 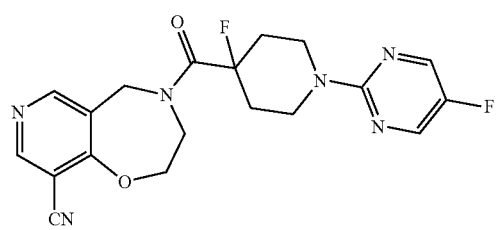 [SMILES: N#Cc1cncc2c1OCCN(C(=O)C1(F)CCN(c3ncc(F)cn3)CC1)C2] |
| (3R)-4-(2,2-dimethylpropanoyl)-3 methyl-3,5-dihydro-2H-pyrido[3,4-f][1,4]oxazepine-9-carbonitrile | 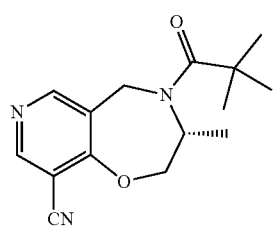 [SMILES: C[C@@H]1COc2c(C#N)cncc2CN1C(=O)C(C)(C)C] |
| 3,3,3-trifluoro-1-(9-fluoro-3,5-dihydro-2H-pyrido[3,4-f][1,4]oxazepin-4-yl)-2,2-dimethyl-propan-1-one | 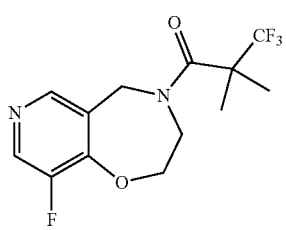 [SMILES: CC(C)(C(=O)N1CCOc2c(F)cncc2C1)C(F)(F)F] |
| 4-(3,3-difluoro-2,2-dimethyl-butanoyl)-3,5-dihydro-2H-pyrido[3,4-f][1,4]oxazepine-9-carbonitrile | 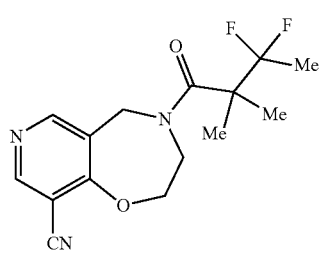 [SMILES: CC(F)(F)C(C)(C)C(=O)N1CCOc2c(C#N)cncc2C1] |

-continued

| Name | Structure |
|------|-----------|
| 1-(9-fluoro-3,5-dihydro-2H-pyrido[3,4-f][1,4]oxazepin-4-yl)-2,2-dimethyl-butan-1-one | 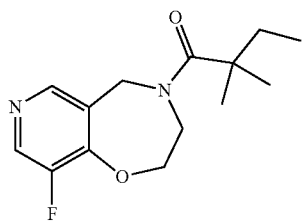 [SMILES: CCC(C)(C)C(=O)N1CCOc2c(F)cncc2C1] | or a pharmaceutically acceptable salt or isoptopic analog thereof.

18. A compound selected from

| Name | Structure |
|------|-----------|
| 4-(3,3-difluoro-2,2-dimethyl-propanoyl)-3,5-dihydro-2H-pyrido[3,4-f][1,4]oxazepine-9-carbonitrile | 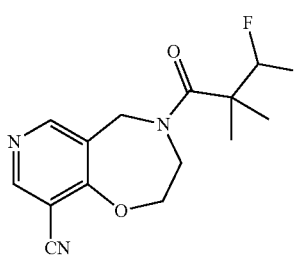 |

19. A compound selecte from

| Name | Structure |
|------|-----------|
| 4-(3,3,3-trifluoro-2,2-dimethyl-propanoyl)-3,5-dihydro-2H-pyrido[3,4-f][1,4]oxazepine-9-carbonitrile | 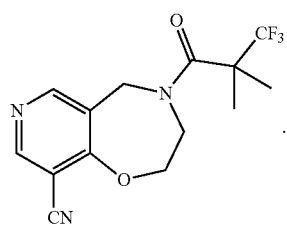 [SMILES: CC(C)(C(=O)N1CCOc2c(C#N)cncc2C1)C(F)(F)F] |

20. A compound selected from

| Name | Structure |
|------|-----------|
| 1-(9-fluoro-3,5-dihydro-2H-pyrido[3,4-f][1,4]oxazepin-4-yl)-2,2-dimethyl-propan-1-one | 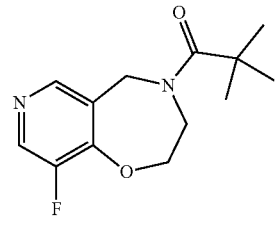 |

21. A compound selected from

| Name | Structure |
|------|-----------|
| (3R)-4-(2,2-dimethylpropanoyl)-3-methyl-3,5-dihydro-2H-pyrido[3,4-f][1,4]oxazepine-9-carbonitrile | 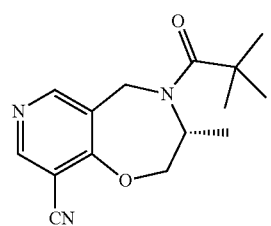 |

22. A compound selected from

| Name | Structure |
|------|-----------|
| 3,3,3-trifluoro-1-(9-fluoro-3,5-dihydro-2H-pyrido[3,4-f][1,4]oxazepin-4-yl)-2,2-dimethyl-propan-1-one | 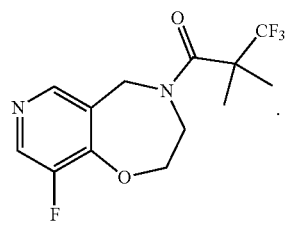 |

23. A compound selected from

| Name | Structure |
|------|-----------|
| 1-(9-fluoro-3,5-dihydro-2H-pyrido[3,4-f][1,4]oxazepin-4-yl)-2,2-dimethyl-butan-1-one | 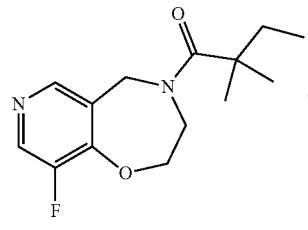 |

24. A compound selected from

| Name | Structure |
|---|---|
| 4-[4-fluoro-1-(5-fluoropyrimidin-2-yl)piperidine-4-carbonyl]-3,5-dihydro-2H-pyrido[3,4-f][1,4]oxazepine-9-carbonitrile | 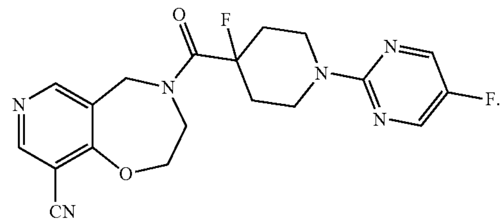 [SMILES: N#Cc1cncc2c1OCCN(C(=O)C1(F)CCN(c3ncc(F)cn3)CC1)C2] |

* * * * *

UNITED STATES PATENT AND TRADEMARK OFFICE
CERTIFICATE OF CORRECTION

PATENT NO. : 11,203,600 B2
APPLICATION NO. : 16/684340
DATED : December 21, 2021
INVENTOR(S) : Javier De Vicente Fidalgo et al.

It is certified that error appears in the above-identified patent and that said Letters Patent is hereby corrected as shown below:

In the Claims

1. In Claim 1, Column 228, Line 20:
"Y is $CR^{4a}R_{4b}$;"

Should be:
-- Y is $CR^{4a}R^{4b}$; --

2. In Claim 3, Column 230, Line 19:
"wherein $R^{1a}$, $R^{1b}$, $R^{2a}$, $R^{2b}$, $R^{3a}$, $R^{3b}$, $W^1$, $W^1$, $W^1$, Y, and Z"

Should be:
-- wherein $R^{1a}$, $R^{1b}$, $R^{1c}$, $R^{2a}$, $R^{2b}$, $R^{3a}$, $R^{3b}$, $W^1$, $W^2$, $W^3$, Y, and Z --

3. In Claim 8, Column 230, Line 41:
"wherein $R^{1a}$, and $R^{1c}$"

Should be:
-- wherein $R^{1a}$, $R^{1b}$, and $R^{1c}$ --

4. In Claim 8, Column 230, Line 42:
"form bicyclo[1.1.1[pentane,"

Should be:
-- form bicyclo[1.1.1]pentane, --

5. In Claim 8, Column 230, Line 43:
"[4.1.0[heptane,"

Signed and Sealed this
Sixteenth Day of May, 2023

Katherine Kelly Vidal
*Director of the United States Patent and Trademark Office*

Should be:
-- [4.1.0]heptane, --
6. In Claim 11, Column 230, Line 50:
"wherein $R^{3a}$ and $R^{ab}$ are"
Should be:
-- wherein $R^{3a}$ and $R^{3b}$ are --
7. In Claim 12, Column 244, 5th structure:
" 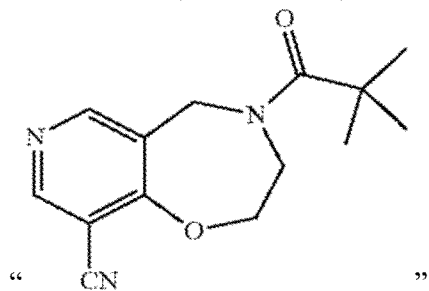 "
Should be:
-- 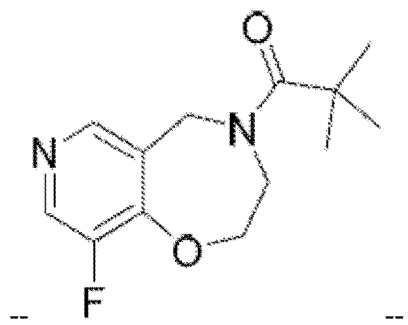 --
8. In Claim 12, Column 254, 1st structure:
" 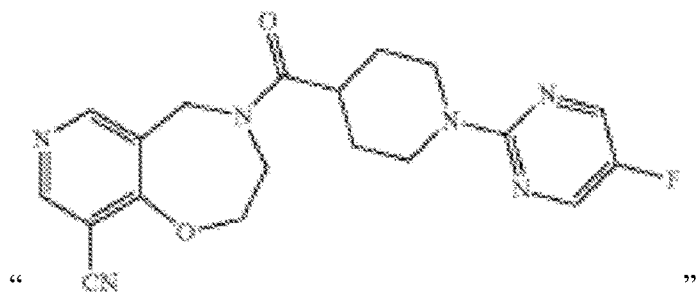 "

Should be:

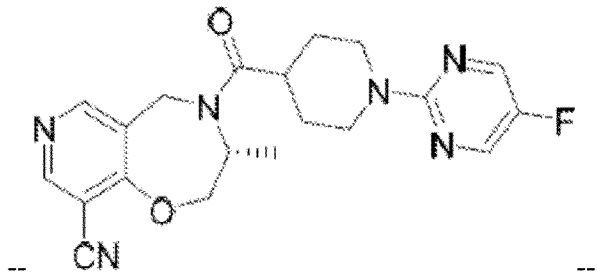

9. In Claim 12, Column 257, 5th name:
"(9-fluoro-3,5-dihydro-2H-pyrido[3,4-f][1,4]oxazepin-4-yl)-[1-(5 fluoropyrimidin-2-yl)-4-methoxy-4-piperidyl]methanone"

Should be:
-- (9-fluoro-3,5-dihydro-2H-pyrido[3,4-f][1,4]oxazepin-4-yl)-[1-(5-fluoropyrimidin-2-yl)-4-methoxy-4-piperidyl]methanone --

10. In Claim 12, Column 265, 2nd name:
"4-(1-(difluoromethyl)cyclopropane-1-carbonyl)-2,3,4,5-tetrahydropyrido]3,4-f][1,41oxazepine-9-carbonitrile"

Should be:
-- 4-(1-(difluoromethyl)cyclopropane-1-carbonyl)-2,3,4,5-tetrahydropyrido[3,4-f][1,4]oxazepine-9-carbonitrile --

11. In Claim 12, Column 277, 6th name:
"4-(3-((5-fluoropyrimidin-2-yl)thio)-2,2-dimethylpropanoyl)-2,3,4,5-tetrahydropyrido[3,4-f][1,41oxazepine-9-carbonitrile"

Should be:
-- 4-(3-((5-fluoropyrimidin-2-yl)thio)-2,2-dimethylpropanoyl)-2,3,4,5-tetrahydropyrido[3,4-f][1,4]oxazepine-9-carbonitrile --

CERTIFICATE OF CORRECTION (continued)
U.S. Pat. No. 11,203,600 B2

12. In Claim 12, Column 281, 6th name:
"4-[1-(5-fluoro-4-methoxy-pyrimidin-2-yl)-4-methoxy-piperidine-4-carbonyl] 3,5-dihydro-2H-pyrido[3,4-f][1,4]oxazepine-9-carbonitrile"

Should be:
-- 4-[1-(5-fluoro-4-methoxy-pyrimidin-2-yl)-4-methoxy-piperidine-4-carbonyl]-3,5-dihydro-2H-pyrido[3,4-f][1,4]oxazepine-9-carbonitrile --

13. In Claim 12, Column 285, 3rd name:
"4-[1-(8-fluoro-[1,2,4]triazolo[1,5-c]pyrimidin-5-yl)piperidine-4-carbonyl]-3,5-dihydro-2H-pyrido[3,4-f][1,4]oxazepine-9carbonitrile"

Should be:
-- 4-[1-(8-fluoro-[1,2,4]triazolo[1,5-c]pyrimidin-5-yl)piperidine-4-carbonyl]-3,5-dihydro-2H-pyrido[3,4-f] [1,4] oxazepine-9-carbonitrile --

14. In Claim 12, Column 289, 6th Name:
"4-(3,3-difluoro-1-(imidazo[2,1-f][1,2,4]triazin-4-yl)piperidine-4-carbonyl)-2,3,4,5-tetrahydropyridol3,4-f][1,4]oxazepine-9-carbonitrile"

Should be:
-- 4-(3,3-difluoro-1-(imidazo[2,1-f][1,2,4]triazin-4-yl)piperidine-4-carbonyl)-2,3,4,5-tetrahydropyrido[3,4-f][1,4]oxazepine-9-carbonitrile --

15. In Claim 12, Column 290, 2nd structure:

" 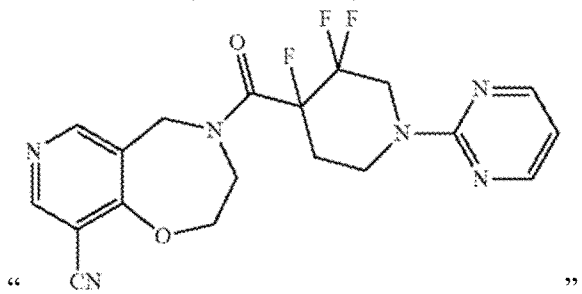 "

Should be:

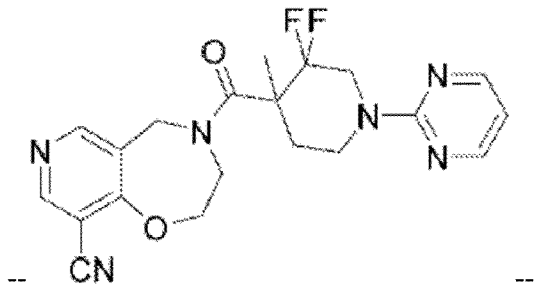

16. In Claim 12, Column 295, 5th name:
"3,5-dihydro-2H-pyrido[3,4-
f][1,4]oxazepin-4-yl41-(5-fluoro-4-
methoxy-pyrimidin-2-yl)-4-methoxy-4-
piperidyl]methanone"

Should be:
-- 3,5-dihydro-2H-pyrido[3,4-
f][1,4]oxazepin-4-yl-[1-(5-fluoro-4-
methoxy-pyrimidin-2-yl)-4-methoxy-4-
piperidyl]methanone --

17. In Claim 12, Column 295, 7th name:
"3,5-dihydro-2H-pyrido[3,4-
f][1,4]oxazepin-4-yl41-(5-fluoro-4-
methoxy-pyrimidin-2-yl)-4-
piperidyl]methanone"

Should be:
-- 3,5-dihydro-2H-pyrido[3,4-
f][1,4]oxazepin-4-yl-[1-(5-fluoro-4-
methoxy-pyrimidin-2-yl)-4-
piperidyl]methanone --

18. In Claim 12, Column 299, 3rd name:
"((3R,4R)-3-fluoro-1-(5-fluoropyrimidin-
2-yl)piperidin-4-yl)(9-fluoro-2,3-
dihydropyrido[3,4-f][1,41oxazepin-
4(5H)-yl)methanone"

Should be:
-- ((3R,4R)-3-fluoro-1-(5-fluoropyrimidin-
2-yl)piperidin-4-yl)(9-fluoro-2,3-
dihydropyrido[3,4-f][1,4]oxazepin-
4(5H)-yl)methanone --

19. In Claim 12, Column 301, 2nd name:
"(3,3-difluoro-1-pyrazolo[1,5-a]pyrimidin-7-yl-4-piperidy1)-(9-fluoro-3,5-dihydro-2H-pyrido[3,4-f][1,4]oxazepin-4-yl)methanone"

Should be:
-- (3,3-difluoro-1-pyrazolo[1,5-a]pyrimidin-7-yl-4-piperidyl)-(9-fluoro-3,5-dihydro-2H-pyrido[3,4-f][1,4]oxazepin-4-yl)methanone --

20. In Claim 12, Column 301, 5th name:
"(9-fluoro-3,5-dihydro-2H-pyrido[3,4-f][1,4]oxazepin-4-yl)-[(3,4)-trans-3-fluoro-1-([1,2,4]triazolo [1,5-c]pyrimidin-5-yl)-4-piperidyl]methanone"

Should be:
-- ((3R,4R)-1-([1,2,4]triazolo[1,5-c]pyrimidin-5-yl)-3-fluoropiperidin-4-yl)(9-fluoro-2,3-dihydropyrido[3,4-f][1,4]oxazepin-4(5H)-yl)methanone --

21. In Claim 12, Column 303, 1st name:
"(9-fluoro-3,5-dihydro-2H-pyrido[3,4-f][1,4]oxazepin-4-yl)-[(3,4)-trans-3-fluoro-1-([1,2,4]triazolo [1,5-a]pyrazin-8-yl)-4-piperidyl]methanone"

Should be:
-- ((3R,4R)-1-([1,2,4]triazolo[1,5-a]pyrazin-8-yl)-3-fluoropiperidin-4-yl)(9-fluoro-2,3-dihydropyrido[3,4-f][1,4]oxazepin-4(5H)-yl)methanone --

22. In Claim 12, Column 303, 5th name:
"4-[((2R)-2-(difluoromethyl)-2-methylbutanoyl]-2,3,4,5-tetrahydropyrido[3,4-f][1,4]oxazepine-9-carbonitrile"

Should be:
-- 4-[(2R)-2-(difluoromethyl)-2-methylbutanoyl]-2,3,4,5- tetrahydropyrido[3,4-f][1,4]oxazepine-9-carbonitrile --

23. In Claim 12, Column 309, 3rd name:
"4-[2-[3 -(4-fluoropyrazol-1-yl)cyclobutyl]-2-methyl-propanoyl]-3,5-dihydro-2H-pyrido[3,4-f][1,4]oxazepine-9-carbonitrile"

Should be:
-- 4-[2-[3-(4-fluoropyrazol-1-yl)cyclobutyl]-2-methyl-propanoyl]-3,5-dihydro-2H-pyrido[3,4-f][1,4]oxazepine-9-carbonitrile --

24. In Claim 12, Column 309, 5th name:
"4-[2-methyl-2- [3-(trifluoromethoxy)cyclobutyl]propanoyl]-3,5-dihydro-2H-pyrido[3,4-f][1,4]oxazepine-9-carbonitrile"

Should be:
-- 4-[2-methyl-2-[3-(trifluoromethoxy)cyclobutyl]propanoyl]-3,5-dihydro-2H-pyrido[3,4-f][1,4]oxazepine-9-carbonitrile --

25. In Claim 12, Column 313, 5th name:
"4-[1-(3,5-difluoro-6-methoxy-2-pyridyl)-4-methoxy-piperidine-4-carbonyl]-3,5-dihydro-2H-pyrido[3,4-][1,4]oxazepine-9-carbonitrile"

Should be:
-- 4-[1-(3,5-difluoro-6-methoxy-2-pyridyl)-4-methoxy-piperidine-4-carbonyl]-3,5-dihydro-2H-pyrido[3,4-f][1,4]oxazepine-9-carbonitrile --

26. In Claim 12, Column 313, 6th name:
"trans-4-[2-methyl-2-[3-(triazol-2-ylmethyl)cyclobutyl]propanoyl]-3,5-dihydro-2H-pyrido[3,4-] [1,4]oxazepine-9-carbonitrile"

Should be:
-- trans-4-[2-methyl-2-[3-(triazol-2-ylmethyl)cyclobutyl]propanoyl]-3,5-dihydro-2H-pyrido[3,4-f][1,4]oxazepine-9-carbonitrile --

27. In Claim 12, Column 315, 1st name:
"cis-4-[2-methyl-2-[3 -(triazol-2-ylmethyl)cyclobutyl]propanoyl]-3,5-dihydro-2H-pyrido[3,4-f][1,4]oxazepine-9-carbonitrile"

Should be:
-- cis-4-[2-methyl-2-[3-(triazol-2-ylmethyl)cyclobutyl]propanoyl]-3,5-dihydro-2H-pyrido[3,4-f][1,4]oxazepine-9-carbonitrile --

28. In Claim 12, Column 317, 2nd name:
"4-[(4R)-3,3 -difluoro-4-methyl-pyrimidin-2-yl-piperidine-4-carbonyl]-3,5-dihydro-2H-pyrido[3,4-f][1,4]oxazepine-9-carbonitrile"

Should be:
-- 4-[(4R)-3,3-difluoro-4-methyl-1-pyrimidin-2-yl-piperidine-4-carbonyl]-3,5-dihydro-2H-pyrido[3,4-f][1,4]oxazepine-9-carbonitrile --

29. In Claim 12, Column 317, 3rd name:
"4-[(4S)-3,3 -difluoro-4-methyl-1-pyrimidin-2-yl-piperidine-4-carbonyl]-3,5-dihydro-2H-pyrido[3,4-f][1,4]oxazepine-9-carbonitrile"

Should be:
-- 4-[(4S)-3,3-difluoro-4-methyl-1-pyrimidin-2-yl-piperidine-4-carbonyl]-3,5-dihydro-2H-pyrido[3,4-f][1,4]oxazepine-9-carbonitrile --

30. In Claim 12, Column 317, 4th name:
"4-[(3 S ,4R)-3-fluoro-1-(5-fluoropyrimidin-2-yl)-4-methyl-piperidine-4-carbonyl]-3,5-dihydro-2H- pyrido[3,4-][1,4]oxazepine-9-
carbonitrile"

Should be:
-- 4-[(3S,4R)-3-fluoro-1-(5-
fluoropyrimidin-2-yl)-4-methyl-
piperidine-4-carbonyl]-3,5-dihydro-2H-
pyrido[3,4-f][1,4]oxazepine-9-
carbonitrile --

31. In Claim 12, Column 317, 5th name:
"4-[(3R,4S)-3-fluoro-l-(5-
fluoropyrimidin-2-yl)-4-methyl-
piperidine-4-carbonyl]-3,5-dihydro-2H-
pyrido[3,4-][1,4]oxazepine-9-
carbonitrile"

Should be:
-- 4-[(3R,4S)-3-fluoro-1-(5-
fluoropyrimidin-2-yl)-4-methyl-
piperidine-4-carbonyl]-3,5-dihydro-2H-
pyrido[3,4-f][1,4]oxazepine-9-
carbonitrile --

32. In Claim 12, Column 317, 6th name:
"4-[(3R,4R)-3-fluoro-
([1,2,4]triazolo[1,5-a]pyrazin-8-
yl)piperidine-4-carbonyl]-3,5-dihydro-
2H-pyrido[3,4-][1,4]oxazepine-9-
carbonitrile"

Should be:
-- 4-[(3R,4R)-3-fluoro-1-
([1,2,4]triazolo[1,5-a]pyrazin-8-
yl)piperidine-4-carbonyl]-3,5-dihydro-
2H-pyrido[3,4-f][1,4]oxazepine-9-
carbonitrile --

33. In Claim 12, Column 319, 1st name:
"4-[(3 S ,4S)-3-fluoro-1-
([1,2,4]triazolo[1,5-a]pyrazin-8-
yl)piperidine-4-carbonyl]-3,5-dihydro-
2H-pyrido[3,4-][1,4]oxazepine-9-
carbonitrile"

CERTIFICATE OF CORRECTION (continued)
U.S. Pat. No. 11,203,600 B2

Should be:
-- 4-[(3S,4S)-3-fluoro-1-
([1,2,4]triazolo[1,5-a]pyrazin-8-
yl)piperidine-4-carbonyl]-3,5-dihydro-
2H-pyrido[3,4-f][1,4]oxazepine-9-
carbonitrile --

34. In Claim 14, Column 323, Line 42:
"$C_{1-8}$ haloalkyl, $C_{2-8}$ alkenyl, or $C_{1-8}$ alkynyl, or"

Should be:
-- $C_{1-8}$ haloalkyl, $C_{2-8}$ alkenyl, or $C_{2-8}$ alkynyl, or --

35. In Claim 14, Column 325, Lines 7-8:
"-$N(R^{8a})_2$, -$C(O)R^{8b}$, or -$C(O)OR^{8a}$, or two $R^8$ are optionally taken together to form oxo;"

Should be:
-- -$N(R^{8a})_2$, -$C(O)R^{8b}$, or -$C(O)OR^{8a}$, or two $R^8$ are optionally taken together to form oxo; --

36. In Claim 17, Column 327, 5th name:
"(3R)-4-(2,2-dimethylpropanoyl)-3
methyl-3,5-dihydro-2H-pyrido[3,4-
f][1,4]oxazepine-9-carbonitrile"

Should be:
-- (3R)-4-(2,2-dimethylpropanoyl)-3-
methyl-3,5-dihydro-2H-pyrido[3,4-
f][1,4]oxazepine-9-carbonitrile --

37. In Claim 19, Column 329, Line 35:
"A compound selecte from"

Should be:
-- A compound selected from --